(12) United States Patent
Andersen et al.

(10) Patent No.: US 8,101,640 B2
(45) Date of Patent: *Jan. 24, 2012

(54) ANTIBACTERIAL AGENTS

(75) Inventors: Niels H. Andersen, Seattle, WA (US); Jason Bowman, Quincy, IL (US); Alice Erwin, Seattle, WA (US); Eric Harwood, Emeryville, CA (US); Toni Kline, Seattle, WA (US); Khisimuzi Mdluli, Coppell, TX (US); Simon Ng, Walnut Creek, CA (US); Keith B. Pfister, San Ramon, CA (US); Ribhi Shawar, Bellevue, WA (US); Allan S. Wagman, Belmont, CA (US); Asha Yabannavar, Lafayette, CA (US)

(73) Assignees: Novartis Vaccines and Diagnostics, Inc., Emeryville, CA (US); University of Washington, Seattle, WA (US)

( * ) Notice: Subject to any disclaimer, the term of this patent is extended or adjusted under 35 U.S.C. 154(b) by 1093 days.

This patent is subject to a terminal disclaimer.

(21) Appl. No.: 11/981,279

(22) Filed: Oct. 31, 2007

(65) Prior Publication Data

US 2011/0172174 A1     Jul. 14, 2011

Related U.S. Application Data

(63) Continuation of application No. 11/837,327, filed on Aug. 10, 2007, now Pat. No. 7,989,660, which is a continuation of application No. 10/754,928, filed on Jan. 8, 2004, now abandoned.

(60) Provisional application No. 60/520,211, filed on Nov. 13, 2003, provisional application No. 60/466,974, filed on Apr. 30, 2003, provisional application No. 60/438,523, filed on Jan. 8, 2003.

(51) Int. Cl.
  *A61K 31/44* (2006.01)
  *C07D 213/56* (2006.01)

(52) U.S. Cl. ........................ 514/357; 546/332

(58) Field of Classification Search .................. 546/332; 514/357

See application file for complete search history.

(56) References Cited

U.S. PATENT DOCUMENTS

| | | | |
|---|---|---|---|
| 2,772,281 | A | 11/1956 | Holley et al. |
| 5,925,659 | A | 7/1999 | Patchett et al. |
| 6,218,389 | B1 | 4/2001 | Almstead et al. |
| 6,228,988 | B1 | 5/2001 | Floyd et al. |
| 6,281,245 | B1 | 8/2001 | Patel et al. |
| 6,358,987 | B1 | 3/2002 | Beckett et al. |
| 7,358,359 | B2 | 4/2008 | Andersen et al. |
| 2001/0053555 | A1 | 12/2001 | Patel et al. |
| 2004/0229955 | A1 | 11/2004 | Andersen et al. |
| 2006/0154988 | A1 | 7/2006 | Andersen et al. |
| 2007/0244197 | A1 | 10/2007 | Andersen et al. |
| 2008/0269221 | A1 | 10/2008 | Andersen et al. |
| 2009/0163496 | A1 | 6/2009 | Andersen et al. |
| 2010/0324025 | A1 | 12/2010 | Andersen et al. |

FOREIGN PATENT DOCUMENTS

| | | |
|---|---|---|
| WO | WO 96/26223 | 8/1996 |
| WO | WO 97/05105 | 2/1997 |
| WO | WO-97/05105 | 2/1997 |
| WO | WO 97/42179 | 11/1997 |
| WO | WO-98/15525 | 4/1998 |
| WO | WO 98/15525 | 4/1998 |
| WO | WO 98/18754 | 5/1998 |
| WO | WO 98/22494 | 5/1998 |
| WO | WO-98/22494 | 5/1998 |
| WO | WO-99/06340 | 2/1999 |
| WO | WO 99/39704 | 8/1999 |
| WO | WO 99/57097 | 11/1999 |
| WO | WO-00/02904 | 1/2000 |
| WO | WO-00/44373 | 8/2000 |
| WO | WO 00/44373 | 8/2000 |
| WO | WO-00/59874 | 10/2000 |
| WO | WO 00/61134 | 10/2000 |
| WO | WO 02/30873 | 4/2002 |
| WO | WO 02/50081 | 6/2002 |
| WO | WO-02/50081 | 6/2002 |
| WO | WO 03/004488 | 1/2003 |
| WO | WO-03/004488 | 1/2003 |
| WO | WO 2004/007444 | 1/2004 |
| WO | WO-2004/062601 | 7/2004 |

OTHER PUBLICATIONS

Second Office Action in Chinese Patent Application No. 200480005935.3 dated Jun. 19, 2009 (English translation only).
Examination Report in Israeli Patent Application No. 169475 dated Jul. 13, 2009 (English translation only).
Examining Division Communication in European Patent Application No. 04 700 887.5 dated Aug. 26, 2009.
Official Action in Mexican Patent Application No. Pa/a/2005/007394 received Sep. 1, 2009 (English translation only).
Angus, et al.; "Outer Membrane Permeability in *Pseudomonas aeruginosa*: Comparison of a Wild-type with an Antibiotic supersusceptible Mutant"; Antimocriob. Agents Chemother (1982); vol. 21(2), pp. 299-309.

(Continued)

*Primary Examiner* — Rebecca Anderson
(74) *Attorney, Agent, or Firm* — Foley & Lardner LLP

(57) ABSTRACT

Antibacterial compounds of formula I are provided:

$$E-L-D-G-Y-X-B-N(R_4)-C(A)(R_3)-(CH_2)_n-Q \quad I$$

As well as stereoisomers, pharmaceutically acceptable salts, esters, and prodrugs thereof; pharmaceutical compositions comprising such compounds; methods of treating bacterial infections by the administration of such compounds; and processes for the preparation of the compounds.

10 Claims, No Drawings

OTHER PUBLICATIONS

Bergeron, Raymond J., et al.; " Effects of C-4 Stereochemistry and C-4' Hydroxylation on the Iron Clearing Efficiency and Toxicity of Desferrithliocin Analogues"; J. Med. Chem. (1999); vol. 42, pp. 2432-2440.

Boyce, et al.; "Total Synthesis of Thiangazole, a Novel Naturally Occurring HIV-1 Inhibitor from Polyangium sp"; Tetrahedron (1995); Vo. 51(26), pp. 7321-7330.

Boyce, Richard J., et al.; "Total synthesis of Thiangazole, a Novel Naturally Occurring HIV-1 Inhibitor from Polyangium sp"; Tetrahedron (1995); vol. 51 No. 2, pp. 7321-7330.

Brooks & Summers; "Modulators of Leukotriene Biosynthesis and Receptor Activation"; J. Med. Chem. (1996) vol. 39(14), pp. 2629-2654.

Charette & Chua; "Mild Method for the Synthesis of Thiazolines from Secondary and Tertiary Amides"; J. Org. Chem. (1998); vol. 63, pp. 908-909.

Fernandez, et al.; "Novel Synthesis of 2-Thiazolines"; Tetrahedron Lett. (2000); vol. 41, pp. 3381-3384.

Galeotti, et al.; "Synthesis of Peptidyl Aldehydes from Thiazolidines"; Tetrahedron Lett. (1997); vol. 38(14), pp. 2459-2462.

Gilbert, S. Banker, et al., editor; Modern Pharmaceutics 3rd edition (1996); pp. 596; Marcel Dekker, Inc., NY.

Hyland, et al.; "Cloning, Expression and Purification of UDP-3-O-Acyl-GlcNAc Deacetylase from *Pseudomonas aeruginosa*: A metalloamidase of the Lipid A Biosynthesis Pathway"; J. Bacteriol. (1997); vol. 179(6), pp. 2029-2037.

International Preliminary Report on Patentability; PCT International Application No. PCT/US2004/000433; Applicant: Chiron Corp.; Issued: Jul. 8, 2005.

International Search Report; PCT International Patent Application No. PCT/US2004/000433; Applicant: Chiron Corp.; Issued: Jan. 19, 2005.

Ito, et al.; "Synthetic Reactions by Complex Catalysts XXXV. A Facile Synthetic Method of Cyclic Imino Ethers and Imino Thioethers"; Syn. Commun. (1974); vol. 4(2), pp. 97-103.

Ito, et al.; "Synthetic Reactions by Complex Catalysts, XXXI. A Novel and Versatile Method of Heterocycle Synthesis"; J. Am. Chem. Soc. (1973); vol. 95(13), pp. 4447-4448.

Jeng & Delombaert; "Endothelin Converting Enzyme Inhibitors"; Curr. Pharma. Design (1997); vol. 3, pp. 597-614.

Jones, R.N.; "Resistance Patterns Among Nosocomial Pathogens"; Chest (2001); vol. 119(2) (Supplement), pp. 397S-404S.

Manfred E. Wolff, editor; Burger's Medicinal Chemistry and Drug Discovery 5th edition (1995); vol. 1, pp. 975-977; John Wiley & Sons, NY.

Matsuda, et al.; "Nucleosides and Nucleotides. 95. Improved Synthesis of 1-(2-Azido-2-deoxy.beta.-D-arabinofuranosyl)cytosine (Cytarazid and -thymine, Inhibitory Spectrum of Cytarazid on the Growth of Various Human Tumor Cells in Vitro"; J. Med. Chem (1991); vol. 34, pp. 999-1002.

Nikaido, H.; "Antibiotic Resistance Caused by Gram-negative multidrug Efflux Pumps"; Clin. Infect. Dis. (1998); vol. 27 (Supplement 1), pp. S32-S41.

Notice of Allowance received for U.S. Appl. No. 11/837,327 dated Mar. 23, 2011.

Pattenden & Thom; "Naturally Occurring Linear Fused Thiazoline-thiazole Containing Metabolites: Total Synthesis of (-)-Didehydromirabazole A, a Cytotoxic Alkaloid from Blue-Green Algae"; J. Chem. Soc. Perkin Trans. (1993); pp. 1629-1636.

Pirrung, et al.; "High-throughput Catch-and-Release Synthesis of Oxazoline Hydroxamates, Structure-Activity Relationships in Novel Inhibitors of *Escherichia coli* Lpxc: In Vitro Enzyme Inhibition and Antibacterial Properties"; J. Am. Chem. Soc. (2003); vol. 125, pp. 1575-1586.

Raman, et al.; "Titanium IV-mediated Tandem Deprotection-Cyclodehydration of Protected Cysteine N-Amides: Biomimetic Syntheses of Thiazoline-and Thiazole-containing Heterocycles"; Org. Lett. (2000); vol. 2(21), pp. 3289-3292.

Righi, et al.; "Solution-and Solid-phase Synthesis of 4-Hydroxy-4,5-dihydroisoxazole Derivatives from Enantiomerically Pure N-Tosyl-2,3-aziridine Alcohols"; Org. Lett. (2002); vol. 4(4), pp. 497-500.

Sahm, et al.; "Evaluation of Current Activities of Fluoroquinolones Against Gram-negative Bacilli Using Centralized in Vitro Testing and Electronic Surveillance"; Antimicrob. Agents Chemother (2001); vol. 45(1), pp. 267-274.

Shen & Thomas; "Synthesis of 1,3-Diynes via Palladium-catalyzed Reaction of 1,1-Dibromo-1-alkenes"; Org. Lett. (2000); vol. 2(18), pp. 2857-2860.

Shen & Wang; "The Stille Reaction of 1,1-Dibromo-1-alkenes: Preparation of Trisubstituted Alkenes and Internal Alkynes"; J. Org. Chem. (1999); vol. 64, pp. 8873-8879.

Skotnicki, et al.; "Design Strategies for the Identification of MMP-13 and TACE Inhibitors"; Curr. Opin. Drug Dis. Dev. (2003); vol. 6(5), pp. 742-759.

Supplementary Partial European Search Report; European Patent Application No. 04700887.5; Issued: Sep. 21, 2006; (6 pgs.).

Wipf, et al.; "Thiolysis of Oxazolines: A New, Selective Method for the Direct Conversion of Peptide Oxazolines Into Thiazolines"; Tetrahedron Lett. (1995); vol. 36(36), pp. 6395-6398.

Witte & Seeliger; "Cyclische Imidsaureester aus Nitrilen und Aminoalkoholen"; Liebigs Ann. Chem. (1974); pp. 996-1009.

Written Opinion of the International Searching Authority; PCT International Application No. PCT/US2004/000433; Applicant: Chiron Corp.; Issued: Jan. 19, 2005.

Wyckoff, et al.; "Antibacterial and Anti-inflammatory Agents That Target Endotoxin"; Trends Microbiol. (1998); vol. 6(4), pp. 154-159.

Zask, et al.; "Inhibition of Matrix Metalloproteinases: Structure Based Design"; Curr. Pharma Design (1996); vol. 6, pp. 624-661.

Zhang, et al.; "Design, Combinatorial Chemical Synthesis and In vitro Characterization of Novel Urea Based Gelatinase Inhibitors"; Bioorg. Med. Chem. Lett. (1999); vol. 9, pp. 2823-2826.

Nicolaus, B. J. R., "Symbiotic Approach to Drug Design," in *Decision Making in Drug Research*, F. Gross (ed.) (1993), pp. 173-186; published by Raven Press, New York.

Chen, M. H., et al. "Carbohydroxamido-oxazolidines: antibacterial agents that target lipid A biosynthesis," Bioorg. Med. Chem. Lett., vol. 9, No. 3, Feb. 8, 1999, pp. 313-318.

Jackman et al., "Antibacterial agents that target lipid A biosynthesis in gram-negative bacteria. Inhibition of diverse UDP-3-O-(r-3-hydroxymyristoyl)-n-acetylglucosamine deacetylases by substrate analogs containing zinc binding motifs," J Biol Chem. Apr. 14, 2000;275(15):11002-9.

Non-final Office Action received for U.S. Appl. No. 11/837,327 dated Mar. 4, 2010.

Pirrung et al., "High-Throughput Catch-and-Release Synthesis of Oxazoline Hydroxamates. Structure-Activity Relationships in Novel Inhibitors of *Escherichia coli* LpxC: In Vitro Enzyme Inhibition and Antibacterial Properties," J. Am. Chem. Soc., vol. 125, No. 6, Feb. 12, 2003, pp. 1575-1586.

Pirrung et al., "A Convenient Procedure for the Preparation of Amino Acid Hydroxamates from Esters" J. Org. Chem. 60: 8084-8085, 1995.

Ngu et al., "A New and Efficient Solid Phase Synthesis of Hydroxamic Acids" J. Org. Chem. 62: 7088-7089; 1997.

Mellor et al., "N-Fmoc-Aminooxy-2-Chlorotrityl Polystyrene Resin: A Facile Solid-Phase Methodology for the Synthesis of Hydroxamic Acids" Tetrahedron Letters 38 (18): 3311-3314, 1997.

Khan et al., "A Facile and Convenient Solid-Phase Procedure for Synthesizing Nucleoside Hydroxamic Acids" Tetrahedron Letters 39: 8031-8034, 1998.

Jackman et al., "Antibacterial Agents that Target Lipid a Biosynthesis in Gram-Negative Bacteria" J. Biological Chemistry 275 (15): 11002-11009, 2000.

Pirrung et al., "Inhibition of the Antibacterial Target UDP-(3-O-acyl)-N-acetyglucosamine Deacetylase (LpxC) . . . " J. Med. Chem. 45: 4359-4370, 2002.

Kline et al., "Potent, Novel in Vitro Inhibitors of the *Pseudomonas aeruginosa* Deacetylase LpxC" J. Med. Chem. 45: 3112-3129, 2002.

Database CAPLUS on STN, Acc. No. 2002:429779, Kline et al., Journal of Medicinal Chemistry (2002), 45(14), p. 3112-3129 (abstract).
Database CAPLUS on STN, Acc. No. 1997:224101, Kleinman, WO 9705105 (Feb. 13, 2997) abstract.
Database CAPLUS on STN, Acc. No. 1997:746038, Patchett et al. WO 9742179 (Nov. 13, 1997) abstract.
Database CAPLUS on STN, Acc. No. 1999:113626, Almstead et al., WO 9906340 (Feb. 11, 1999) abstract.
Singapore Search Report for Singapore Patent Application No. 200705115-4 dated Apr. 1, 2009.
Nicolaus, B. J. R., "Symbiotic Approach to Drug Design," Decision Making in Drug Research, 1983, pp. 173-186.
Notice of Allowance received for U.S. Appl. No. 11/837,327 dated Dec. 17, 2010.
Final Office Action received for U.S. Appl. No. 11/837,327 dated Jul. 14, 2010.
Extended European Search Report received for EP 10179798.3 dated Jul. 4, 2011.
Notice of Allowance received for U.S. Appl. No. 11/928,122 dated Jul. 21, 2011.

ANTIBACTERIAL AGENTS

This application is a continuation of U.S. patent application Ser. No. 11/837,327, now U.S. Pat. No. 7,989,660, filed Aug. 10, 2007, which is a continuation of Ser. No. 10/754,928, filed Jan. 8, 2004, which claims benefit of priority to the following U.S. Provisional Patent Applications: U.S. Ser. No. 60/438,523, filed Jan. 8, 2003; U.S. Ser. No. 60/466,974, filed Apr. 30, 2003; and Ser. No. 60/520,211 filed Nov. 13, 2003; each of which is incorporated herein by reference in its entirety for any purpose.

FIELD OF THE INVENTION

This invention pertains generally to treating infections caused by gram-negative bacteria. More specifically, the invention described herein pertains to treating gram-negative infections by inhibiting activity of UDP-3-O—(R-3-hydroxydecanoyl)-N-acetylglucosamine deacetylase (LpxC). The present invention provides small molecule inhibitors of LpxC, pharmaceutical formulations containing such inhibitors, methods of treating patients with such pharmaceutical formulations, and to methods of preparing such pharmaceutical formulations and inhibitors. The inhibitors can be used to treat Gram-negative infections of patients alone and in combination with other antibacterials.

BACKGROUND OF THE INVENTION

Over the past several decades, the frequency of antimicrobial resistance and its association with serious infectious diseases have increased at alarming rates. The increasing prevalence of resistance among nosocomial pathogens is particularly disconcerting. Of the over 2 million nosocomial infections occurring each year in the United States, 50 to 60% are caused by antimicrobial-resistant strains of bacteria. This high rate of resistance increases the morbidity, mortality, and costs associated with nosocomial infections. In the United States, nosocomial infections are thought to contribute to or cause more than 77,000 deaths per year and cost approximately $5 to $10 billion annually. Among Gram-positive organisms, the most important resistant pathogens are methicillin-(oxacillin-) resistant *Staphylococcus aureus*, β-lactam-resistant and multidrug-resistant pneumococci, and vancomycin-resistant enterococci. Important causes of Gram-negative resistance include extended-spectrum β-lactamases (ESBLs) in *Klebsiella pneumoniae, Escherichia coli*, and *Proteus mirabilis*, high-level third-generation cephalosporin (Amp C) β-lactamase resistance among *Enterobacter* species and *Citrobacter freundii*, and multidrug-resistance genes observed in *Pseudomonas aeruginosa, Acinetobacter*, and *Stenotrophomonas maltophilia*. (Jones RN 2001 Chest 119 (supplement), 397S-404S: Resistance patterns among nosocomial pathogens: Trends over the past few years.)

The problem of antibacterial resistance is compounded by the existence of bacterial strains resistant to multiple antibacterials. For example, *Pseudomonas aeruginosa* isolates resistant to fluoroquinolones are virtually all resistant to additional antibacterials (Sahm D F et al 2001 Antimicrobial Agents and Chemotherapy 45, 267-274: Evaluation of current activities of fluoroquinolones against gram-negative bacilli using centralized in vitro testing and electronic surveillance.)

Thus there is a need for new antibacterials, particularly antibacterials with novel mechanisms of action. Most of the antibacterial discovery effort in the pharmaceutical industry is aimed at development of drugs effective against gram-positive bacteria. However, there is also a need for new gram-negative antibacterials. Gram-negative bacteria are in general more resistant to a large number of antibacterials and chemotherapeutic agents than are gram-positive bacteria. A survey of recently reported antibacterials of natural origin showed that over 90% lacked activity against *Escherichia coli*, although they were active against gram-positive bacteria. The outer membrane of gram-negative bacteria contributes to this intrinsic resistance by acting as an efficient permeability barrier, because the narrow porin channels limit the penetration of hydrophilic solutes and the low fluidity of the lipopolysaccharide leaflet slows down the inward diffusion of lipophilic solutes. A second mechanism contributes to the intrinsic resistance of gram-negative bacteria. Recent studies showed that multiple drug efflux pumps, sometimes with unusually broad specificity, act as this second factor to create the general intrinsic resistance of gram-negative bacteria. When their expression levels are elevated as a consequence of physiological regulation or genetic alteration, they can frequently produce impressive levels of resistance to a wide variety of antimicrobial agents. (Nikaido H 1998 Clinical Infectious Diseases 27 (Suppl 1), S32-41: Antibacterial resistance caused by gram-negative multidrug efflux pumps.)

Historically, most development of antimicrobial agents has been relatively empirical. Active compounds have generally been found via screening soil, sewage, water, and other natural substances to detect antimicrobial-producing organisms, or by screening various chemical compounds. Once a leading candidate has been found and its chemical structure determined, a series of analogs is made to identify an optimal compound for further clinical development. A more rational approach involves the defining of new targets, such as genes or enzymatic functions, responsible for a crucial cellular essential activity. Once this has been done, inhibitors or blockers of the function or gene product can be developed.

In order to identify potential targets for novel gram-negative antibacterial agents, studies aimed at identifying all essential and important genes in *Pseudomonas aeruginosa* have been performed. Among the essential genes identified was lpxC, that encodes the enzyme uridyldiphospho-3-O—(R-hydroxydecanoyl)-N-acetylglucosamine deacetylase (LpxC). This enzyme is the first committed step in the synthesis of lipid A, the lipid moiety of lipopolysaccharide, that is an essential component of all gram-negative bacteria. It therefore is an attractive target for novel antibacterials. In order to be useful as antibacterial agents, LpxC inhibitors would not only have to inhibit the enzymatic activity of LpxC from a variety of bacteria, but would have to defeat the intrinsic resistance mechanisms of gram-negative bacteria, as described above: they would have to penetrate the outer membrane and be relatively unsusceptible to multidrug efflux pumps.

Researchers have identified a few compounds with antibacterial activity that target lipid A biosynthesis. WO 97/42179 to Patchett et al. discloses compounds of the formula:

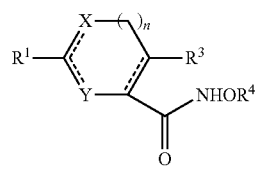

The compounds possess activity against certain gram-negative organisms, for example *Escherichia coli*, but are not active against other medically important gram-negative bacteria, for example *Pseudomonas aeruginosa*. Subsequent studies have found that the primary reason for their inactivity against particular, medically important gram-negative bacteria is their poor ability to inhibit *P. aeruginosa* LpxC; efflux by the major multidrug efflux pump or inability to penetrate the outer membrane were not the critical factors.

Jackman et al., in J. Biol. Chem. (vol. 275, no. 15, Apr. 14, 2000, pps. 11002-11009), discuss the mechanism of lipid A biosynthesis in the context of gram-negative bacteria and discloses a new class of hydroxamate-containing inhibitors of LpxC. Wyckoff et al., in Trends in Microbiology (vol. 6, no. 4, April 1998, pps. 154-159), discuss the role of LpxC in lipid A biosynthesis and its role in regulation. Wyckoff et al. disclose a few oxazoline hydroxamic acids that inhibit bacterial growth. However, Wyckoff et al. also discuss the shortcomings of the available deacetylase inhibitors as bactericidal agents against *Pseudomonas* and that more work is needed to be done in the area.

Thus, an increasing need exists for LpxC inhibitors that have activity as bactericidal agents against gram-negative bacteria. It is, accordingly, an object of this invention to provide compounds and combinations of such compounds for use in the preparation of antibacterials and other pharmaceuticals capable of inhibiting Gram-negative bacterial infections.

U.S. Patent Publication No. 2001/0053555 (U.S. patent application Ser. No. 08/958,638) published Dec. 20, 2001, corresponding to WO 98/18754 published May 7, 1998 discloses a combinatorial library of hydroxylamine, hydroxamic acid, hydroxyurea and hydroxylsulfonamide compounds purported to be potentially useful as inhibitors of metalloproteases. U.S. Pat. No. 6,281,245, a continuation in part of U.S. Ser. No. 08/958,638 claims a method of inhibiting a deformylase enzyme by administering one of the hydroxylamine compounds from the combinatorial library as disclosed in U.S. Patent Publication No. 2001/0053555 and the corresponding WO 98/18754. Related to the above disclosed patent publications is WO 99/57097, published Nov. 11, 1999, that discloses a method of solid phase synthesis of the hydroxylamine library of compounds. WO 00/61134 (to British Biotech Pharmaceuticals Limited), published Oct. 19, 2000, discloses compounds of the formula below:

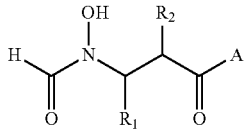

The compounds are useful as antimicrobial agents that are believed to have bactericidal activity at least in part to intracellular inhibition of bacterial polypeptide deformylase.

In an earlier to British Biotech Pharmaceuticals Limited, WO 99/39704, published Aug. 12, 1999, compounds of the formula below are disclosed:

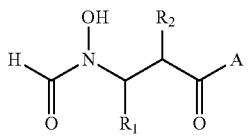

The compounds are useful as antimicrobial agents useful against gram-negative and gram positive bacteria.

Recently, De Novo Pharmaceuticals LTD disclosed in WO 02/50081, published Jun. 27, 2002, antibacterial and antiprotozoal agents having the formulae shown below:

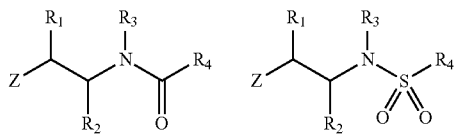

The patent publication discusses that the antibacterial activity is due, at least in part, to intracellular inhibition of bacterial polypeptide deformylase.

SUMMARY OF THE INVENTION

The present invention provides novel compounds, pharmaceutical formulations including the compounds, methods of inhibiting UDP-3-O—(R-3-hydroxydecanoyl)-N-acetylglucosamine deacetylase (LpxC), and methods of treating gram-negative bacterial infections.

In one embodiment, the present invention provides compounds of formula I:

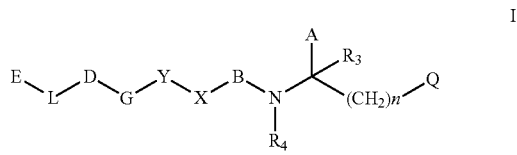

or stereoisomers, pharmaceutically acceptable salts, esters, and prodrugs thereof, wherein E is absent or selected from the group consisting of
  (1) H,
  (2) substituted or unsubstituted $C_1$-$C_6$-alkyl,
  (3) substituted or unsubstituted $C_2$-$C_6$-alkenyl,
  (4) substituted or unsubstituted $C_2$-$C_6$-alkynyl,
  (5) substituted or unsubstituted aryl,
  (6) substituted or unsubstituted heterocyclyl, and
  (7) substituted or unsubstituted heteroaryl;

L is absent or selected from the group consisting of
  (1) substituted or unsubstituted $C_1$-$C_6$-alkyl,
  (2) —$(NH)_{0-1}$—$(CH_2)_j$—$NR^{3L}$—$(CH_2)_k$—,
  (3) —$(NH)_{0-1}$—$C(R^{1L},R^{2L})$—$NR^{3L}$—$C(R^{1L},R^{2L})$—,
  (4) —$C(R^{1L},R^{2L})$—O—$C(R^{1L},R^{2L})$—,
  (5) —$(CH_2)_j$—$NR^{3L}$—$C(R^{1L},R^{2L})$—CONH—$(CH_2)_k$—,
  (6) —CO—$C(R^{1L},R^{2L})$—NHCO—,
  (7) —CONH—,
  (8) —NHCO—,
  wherein
  $R^{1L}$, $R^{2L}$, and $R^{3L}$ are independently selected from the group consisting of
    (a) H,
    (b) substituted or unsubstituted $C_1$-$C_6$-alkyl,
    (c) $C_1$-$C_6$-alkyl substituted with aryl,
    (d) $C_1$-$C_6$-alkyl substituted with heterocyclyl, and
    (e) $C_1$-$C_6$-alkyl substituted with heteroaryl,
  or $R^{1L}$ and $R^{31'''}$, together with the atoms to which they are attached can form a substituted or unsubstituted heterocyclic ring, having from 3 to 8 ring atoms, wherein 1-2 ring atoms of the heterocyclic ring system are selected from N, O and S;

j is an integer of 0-4;
k is an integer of 0-4;
D is absent or selected from the group consisting of
 (1) substituted or unsubstituted $C_3$-$C_8$-cycloalkyl,
 (2) substituted or unsubstituted aryl,
 (3) substituted or unsubstituted heterocyclyl, and
 (4) substituted or unsubstituted heteroaryl;
G is absent or selected from the group consisting of
 (1) —$(CH_2)_i$—O—$(CH_2)_i$—,
 (2) —$(CH_2)_i$—S—$(CH_2)_i$—,
 (3) —$(CH_2)_i$—$NR^g$—$(CH_2)_i$—,
 (4) —C(=O)—,
 (5) —NHC(=O)—,
 (6) —C(=O)NH—,
 (7) —$(CH_2)_i$NHCH$_2$C(=O)NH—,
 (8) —C≡C—,
 (9) —C≡C—C≡C—, and
 (10) —C=C—;
wherein
 Rg is H or substituted or unsubstituted $C_1$-$C_6$-alkyl;
 i is an integer of 0-4;
Y is selected from the group consisting of
 (1) substituted or unsubstituted $C_3$-$C_8$-cycloalkyl,
 (2) substituted or unsubstituted aryl,
 (3) substituted or unsubstituted heterocyclyl, and
 (4) substituted or unsubstituted heteroaryl;
X is selected from the group consisting of
 (1) —(C=O)—,
 (2) —$C_1$-$C_6$-alkyl-(C=O)—,
 (3) —$C_2$-$C_6$-alkenyl-(C=O)—,
 (4) —$C_2$-$C_6$-alkynyl-(C=O)—, and
 (5) —$CH_2$—;
 or when B is absent, X and A, together with the atoms to which they are attached can form a heterocyclic ring, having from 5 to 8 ring atoms, wherein 1-2 ring atoms of the heterocyclic ring system are selected from N, O and S;
B is a absent or

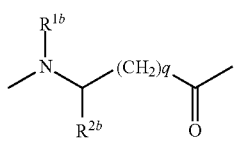

wherein $R^{1b}$ and $R^{2b}$, are independently selected from the group consisting of
 (a) H,
 (b) substituted or unsubstituted $C_1$-$C_6$-alkyl,
 (c) substituted or unsubstituted $C_2$-$C_6$-alkenyl,
 (d) substituted or unsubstituted $C_2$-$C_6$-alkynyl,
 (e) substituted or unsubstituted aryl,
 (f) substituted or unsubstituted heterocyclyl,
 (g) substituted or unsubstituted heteroaryl,
 (h) $C_1$-$C_6$-alkyl substituted with aryl,
 (i) $C_1$-$C_6$-alkyl substituted with heterocyclyl, and
 (j) $C_1$-$C_6$-alkyl substituted with heteroaryl,
 or $R^{1b}$ and $R^{2b}$, together with the atoms to which they are attached can form a substituted or unsubstituted heterocyclic ring, having from 5 to 8 ring atoms, wherein 1-2 ring atoms of the heterocyclic ring system are selected from N, O and S;
 q is an integer of 0-4;
$R_3$ is H or substituted or unsubstituted $C_1$-$C_6$-alkyl,
 or $R_3$ and A together with the atoms to which they are attached can form a substituted or unsubstituted 3-10 membered cycloalkyl or a heterocyclic ring system, wherein the heterocyclic ring system may have from 3 to 10 ring atoms, with 1 to 2 rings being in the ring system and contain from 1-4 heteroatoms selected from N, O and S;
$R_4$ is H or substituted or unsubstituted $C_1$-$C_6$-alkyl,
 or $R_4$ and A, together with the atoms to which they are attached can form a substituted or unsubstituted heterocyclic ring, having from 3 to 8 ring atoms, wherein 1-2 ring atoms of the heterocyclic ring system are selected from N, O and S;
n is an integer of 0-6;
A is selected from the group consisting of
 (1) H,
 (2) —$(CH_2)_r$C($R^{1a}$,$R^{2a}$)$(CH_2)_s$O$R^{3a}$,
 (3) —$(CH_2)_r$C($R^{1a}$,$R^{2a}$)N($R^{4a}$,$R^{5a}$),
 (4) —$(CH_2)_r$C($R^{1a}$,$R^{2a}$)N($R^{4a}$)CO$R^{3a}$,
 (5) —$(CH_2)_r$C($R^{1a}$,$R^{2a}$)NHCON($R^{4a}$,$R^{5a}$),
 (6) —$(CH_2)_r$C($R^{1a}$,$R^{2a}$)NHC(=NH)N($R^{4a}$,$R^{5a}$),
 (7) —CH($R^{1a}$,$R^{2a}$),
 (8) —C≡CH,
 (9) —$(CH_2)_r$C($R^{1a}$,$R^{2a}$)CN,
 (10) —$(CH_2)_r$C($R^{1a}$,$R^{2a}$)CO$_2$$R^{3a}$, and
 (11) —$(CH_2)_r$C($R^{1a}$,$R^{2a}$)CON($R^{4a}$,$R^{5a}$),
 wherein $R^{1a}$, $R^{2a}$, $R^{3a}$, $R^{4a}$, and $R^{5a}$ are independently selected from the group consisting of
 (a) H,
 (b) substituted or unsubstituted $C_1$-$C_6$-alkyl,
 (c) substituted or unsubstituted aryl,
 (d) substituted or unsubstituted heterocyclyl,
 (e) substituted or unsubstituted heteroaryl,
 (f) $C_1$-$C_6$-alkyl substituted with aryl,
 (g) $C_1$-$C_6$-alkyl substituted with heterocyclyl, and
 (h) $C_1$-$C_6$-alkyl substituted with heteroaryl,
 or $R^{4a}$ and $R^{5a}$ together with the N atom to which they are attached can form a substituted or unsubstituted heterocyclic ring, having from 5 to 8 ring atoms, wherein 1-2 ring atoms of the heterocyclic ring system are selected from N, O and S;
r is an integer of 0-4;
s is an integer of 0-4;
Q is absent or selected from the group consisting of
 (1) —C(=O)N($R_1$, $R_2$),
 (2) —NHC(=O)N($R_1$, $R_2$),
 (3) —N(OH)C(=O)N($R_1$, $R_2$),
 (4) —CH(OH)C(=O)N($R_1$, $R_2$),
 (5) —CH[N($R^{2q}$,$R^{3q}$)]C(=O)N($R_1$, $R_2$),
 (6) —CHR$_{1q}$C(=O)N($R_1$, $R_2$),
 (7) —CO$_2$H,
 (8) —C(=O)NHSO$_2$$R^{4q}$,
 (9) —SO$_2$NH$_2$,
 (10) —N(OH)C(=O)$R^{1q}$,
 (11) —N(OH)SO$_2$$R^{4q}$,
 (12) —NHSO$_2$$R^{4q}$,
 (13) —SH,
 (14) —CH(SH)(CH$_2$)$_{0-1}$C(=O)N($R_1$, $R_2$),
 (15) —CH(SH)(CH$_2$)$_{0-1}$CO$_2$H,
 (16) —CH(OH)(CH$_2$)$_{0-1}$CO$_2$H,
 (17) —CH(SH)CH$_2$CO$_2$$R^{1q}$,
 (18) —CH(OH)(CH$_2$)SO$_2$NH$_2$,
 (19) —CH(CH$_2$SH)NHCOR$^{1q}$,
 (20) —CH(CH$_2$SH)NHSO$_2$$R^{4q}$,
 (21) —CH(CH$_2$S$R^{5q}$)CO$_2$H,
 (22) —CH(CH$_2$SH)NHSO$_2$NH$_2$,
 (23) —CH(CH$_2$OH)CO$_2$H,

(24) —CH(CH₂OH)NHSO₂NH₂,
(25) —C(=O)CH₂CO₂H,
(26) —C(=O)(CH₂)₀₋₁CONH₂,
(27) —OSO₂NHR$^{5q}$,
(28) —SO₂NHNH₂,
(29) —P(=O)(OH)₂,

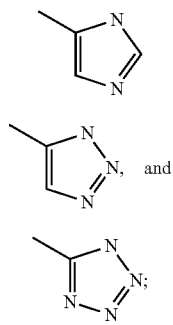

(30)

(31) and (32)

wherein
R₁ is selected from the group consisting of
  (1) H,
  (2) —OH,
  (3) —OC$_{1-6}$-alkyl,
  (4) —N(R$^{2q}$,R$^{3q}$), and
  (5) substituted or unsubstituted C$_{1-6}$-alkyl;
R₂ is selected from the group consisting of
  (1) H,
  (2) substituted or unsubstituted C₁-C₆-alkyl,
  (3) substituted or unsubstituted C₂-C₆-alkenyl,
  (4) substituted or unsubstituted C₂-C₆-alkenyl,
  (5) substituted or unsubstituted aryl,
  (6) substituted or unsubstituted heterocyclyl,
  (7) substituted or unsubstituted heteroaryl,
  (8) C₁-C₆-alkyl substituted with aryl,
  (9) C₁-C₆-alkyl substituted with heterocyclyl, and
  (10) C₁-C₆-alkyl substituted with heteroaryl,
  or R¹ and R², together with the N atom to which they are attached can form a substituted or unsubstituted heterocyclic ring, having from 3 to 10 ring atoms, wherein 1-4 ring atoms of the heterocyclic ring system are selected from N, O and S,
  or R² and R⁴, together with the N atoms to which they are attached can form a substituted or unsubstituted heterocyclic ring, having from 3 to 10 ring atoms, wherein 1-4 ring atoms of the heterocyclic ring system are selected from N, O and S;
R$^{1q}$, R$^{2q}$, R$^{3q}$, R$^{4q}$, and R$^{5q}$ are selected from H or C₁-C₆ alkyl,
wherein B is absent, or E, L, G, and B are absent, or E, L, and G are absent, or E, L, and B are absent, or E, L, D, G, and B are absent.

In one aspect, the invention provides a method of inhibiting a deacetylase enzyme in a gram-negative bacteria, thereby affecting bacterial growth, comprising administering to a patient in need of such inhibition a compound of formula I.

In another aspect, the invention provides a method of inhibiting LpxC, thereby modulating the virulence of a bacterial infection, comprising administering to a patient in need of such inhibition a compound of formula I.

In another aspect, the invention provides a method for treating a subject with a gram-negative bacterial infection comprising administering to the subject in need thereof an antibacterially effective amount of a compound of formula I with a pharmaceutically acceptable carrier. In a preferred embodiment of the method of treatment, the subject is a mammal and in some embodiments, a human.

In another aspect, the invention provides a method of administering an inhibitory amount of a compound of formula I to fermentative or non-fermentative gram-negative bacteria. In a preferred embodiment of the method of administering an inhibitory amount of a compound of formula I to fermentative or non-fermentative gram-negative bacteria, the gram-negative bacteria are selected from the group consisting of *Pseudomonas aeruginosa, Stenotrophomonas maltophila, Burkholderia cepacia, Alcaligenes xylosoxidans, Acinetobacter, Enterobacteriaceae, Haemophilus*, and *Neisseria* species.

In another embodiment, the invention provides a method of administering an inhibitory amount of a compound of formula I to gram-negative bacteria, such as *Enterobacteriaceae* which is selected from the group consisting of organisms such as *Serratia, Proteus, Klebsiella, Enterobacter, Citrobacter, Salmonella, Providencia, Morganella, Cedecea*, and *Edwardsiella* species and *Escherichia coli*.

Another embodiment of the invention provides a pharmaceutical composition comprising an effective amount of a compound of Formula I with a pharmaceutically acceptable carrier thereof.

Pharmaceutical formulations according to the present invention are provided which include any of the compounds described above in combination with a pharmaceutically acceptable carrier.

Another embodiment of the invention provides a method of co-administering the compound of formula I with other therapeutic agents that are selected for their particular usefulness against the condition that is being treated.

For example, the compound of formula I is useful in combination with other anti-bacterial agents. The compound of formula I augments the sensitivity of gram-negative bacteria to existing classes of antibacterials. Combinations of the presently disclosed compounds with other anti-bacterial agents are within the scope of the invention. Such anti-bacterial agents include, but are not limited to, erythromycin, rifampicin, Nalidixic acid, carbenicillin, bacitracin, cycloserine, fosfomycin, and vancomycin.

DETAILED DESCRIPTION

The present invention provides novel compounds, methods for inhibiting LpxC in gram-negative bacteria, and novel methods for treating bacterial infections. The compounds provided herein can be formulated into pharmaceutical formulations and medicaments that are useful in the methods of the invention. The invention also provides for the use of the compounds in preparing medicaments and pharmaceutical formulations, for use of the compounds in inhibiting LpxC, and for use of the compounds in treating bacterial infections in a subject.

The following abbreviations and definitions are used throughout this application:

"LpxC" is an abbreviation that stands for UDP-3-O—(R-3-hydroxydecanoyl)-N-acetylglucosamine deacetylase.

Generally, reference to a certain element such as hydrogen or H is meant to include all isotopes of that element. For example, if an R group is defined to include hydrogen or H, it also includes deuterium and tritium.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following that are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Thus the phrase alkyl groups includes primary alkyl groups, secondary alkyl groups, and tertiary alkyl groups. Preferred alkyl groups include straight and branched chain alkyl groups and cyclic alkyl groups having 1 to 12 carbon atoms.

The phrase "substituted alkyl" refers to an alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon(s) or hydrogen(s) atoms is replaced by a bond to an aryl, heterocyclyl group, or cycloalkyl group. Preferred substituted alkyl groups include, among others, alkyl groups in which one or more bonds to a carbon or hydrogen atom is/are replaced by one or more bonds to fluorine atoms. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Still other preferred substituted alkyl groups include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group.

The phrase "alkenyl" refers to straight and branched chain and cyclic groups such as those described with respect to alkyl groups as defined above, except that at least one double bond exists between two carbon atoms. Examples include, but are not limited to vinyl, —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, cyclohexenyl, cyclopentenyl, cyclohexadienyl, butadienyl, pentadienyl, and hexadienyl among others. The phrase "substituted alkenyl" has the same meaning with respect to alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "alkynyl" refers to straight and branched chain groups such as those described with respect to alkyl groups as defined above, except that at least one triple bond exists between two carbon atoms. Examples include, but are not limited to —C≡C(H), —C≡C(CH$_3$), —C≡C(CH$_2$CH$_3$), —C(H$_2$)C≡C(H), —C(H)$_2$O═C(CH$_3$), and —C(H)$_2$C≡C(CH$_2$CH$_3$) among others. The phrase "substituted alkynyl" has the same meaning with respect to alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "heterocyclyl" refers to both aromatic and non-aromatic ring compounds including monocyclic, bicyclic, and polycyclic ring compounds such as, but not limited to, quinuclidinyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to a heterocyclyl group as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, and 2-chloropyridyl among others.

The phrase "aryl" refers to aryl groups that do not contain heteroatoms. Thus the phrase includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others. Preferred substituents include straight and branched chain alkyl groups, —CH$_3$, —C$_2$H$_5$, —CH$_2$OH, —OH, —OCH$_3$, —OC$_2$H$_5$, —OCF$_3$, —CN, —NO$_2$, —CO$_2$H, —CO$_2$CH$_3$, —CONH$_2$, —NH$_2$, —F, —Cl, Br, —CF$_3$, —N(CH$_3$)$_2$, —NHSO$_2$CH$_3$, —NHCOCH$_3$.

The term "heteroaryl", as used herein, refers to a cyclic or bicyclic aromatic radical having from five to ten ring atoms in each ring of which one atom of the cyclic or bicyclic ring is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and naphthyridinyl, and the like.

The term "substituted heteroaryl" as used herein refers to a heteroaryl group as defined herein substituted by independent replacement of one, two or three of the hydrogen atoms thereon with Cl, Br, F, I, OH, CN, C$_1$-C$_3$-alkyl, C$_1$-C$_6$-alkoxy, C$_1$-C$_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group. Preferred substituents include straight and branched chain alkyl groups, —CH$_3$, —C$_2$H$_5$, —CH$_2$OH, —OH, —OCH$_3$, —OC$_2$H$_5$, —OCF$_3$, —CN, —NO$_2$, —CO$_2$H, —CO$_2$CH$_3$, —CONH$_2$, —NH$_2$, —F, —Cl, Br, —CF$_3$, —N(CH$_3$)$_2$, —NHSO$_2$CH$_3$, —NHCOCH$_3$.

The term "biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl)benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl)phenyl]acetamide, 1,4-diphenylbenzene, N-[4-(2-phenylethynyl)phenyl]-2-[benzylamino]acetamide, 2-amino-N-[4-(2-phenylethynyl)phenyl]propanamide, 2-amino-N-[4-(2-phenylethynyl)phenyl]acetamide, 2-(cyclopropylamino)-N-[4-(2-phenylethynyl)phenyl]acetamide, 2-(ethylamino)-N-[4-(2-phenylethynyl)phenyl]acetamide, 2-[(2-methylpropyl)amino]-N-[4-(2-phenylethynyl)phenyl]acetamide, 5-phenyl-2H-benzo[d]1,3-dioxolene, 2-chloro-1-methoxy-4-phenylbenzene, 2-[(imidazolylmethyl)amino]-N-[4-(2-phenylethynyl)phenyl]acetamide, 4-phenyl-1-phenoxybenzene, N-(2-aminoethyl)[4-(2-phenylethynyl)phenyl]carboxamide, 2-{[(4-fluorophenyl)methyl]amino}-N-[4-(2-phenylethynyl)phenyl]acetamide, 2-{[(4-methylphenyl)methyl]amino}-N-[4-(2-phenylethynyl)phenyl]acetamide, 4-phenyl-1-(trifluoromethyl)benzene, 1-butyl-4-phenylbenzene, 2-(cyclohexylamino)-N-[4-(2-phenylethynyl)phenyl]acetamide, 2-(ethylmethylamino)-N-[4-(2-phenylethynyl)phenyl]acetamide, 2-(butylamino)-N-[4-(2-phenylethynyl)phenyl]acetamide, N-[4-(2-phenylethynyl)phenyl]-2-(4-pyridylamino)acetamide, N-[4-(2-phenylethynyl)phenyl]-2-(quinuclidin-3-ylamino)acetamide, N-[4-(2-phenylethynyl)phenyl]pyrrolidin-2-ylcarboxamide, 2-amino-3-methyl-N-[4-(2-phenylethynyl)phenyl]butanamide, 4-(4-phenylbuta-1,3-diynyl)phenylamine, 2-(dimethylamino)-N-[4-(4-phenylbuta-1,3-diynyl)phenyl]acetamide, 2-(ethylamino)-N-[4-(4-phenylbuta-1,3-diynyl)phenyl]acetamide, 4-ethyl-1-phenylbenzene, 1-[4-(2-phenylethynyl)phenyl]ethan-1-one, N-(1-carbamoyl-2-hydroxypropyl)[4-(4-phenylbuta-1,3-diynyl)phenyl]carboxamide, N-[4-(2-phenylethynyl)phenyl]propanamide, 4-methoxyphenyl phenyl ketone, phenyl-N-benzamide, (tert-butoxy)-N-[(4-phenylphenyl)methyl]carboxamide, 2-(3-phenylphenoxy)ethanehydroxamic acid, 3-phenylphenyl propanoate, 1-(4-ethoxyphenyl)-4-methoxybenzene, and [4-(2-phenylethynyl)phenyl]pyrrole.

The term "heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl)pyridine, phenylpyrazole, 5-(2-phenylethynyl)-1,3-dihydropyrimidine-2,4-dione, 4-phenyl-1,2,3-thiadiazole, 2-(2-phenylethynyl)pyrazine, 2-phenylthiophene, phenylimidazole, 3-(2-piperazinylphenyl)furan, 3-(2,4-dichlorophenyl)-4-methylpyrrole, and the like. Preferred optionally substituted heteroarylaryl groups include: 5-(2-phenylethynyl)pyrimidine-2-ylamine, 1-methoxy-4-(2-thienyl)benzene, 1-methoxy-3-(2-thienyl)benzene, 5-methyl-2-phenylpyridine, 5-methyl-3-phenylisoxazole, 2-[3-(trifluoromethyl)phenyl]furan, 3-fluoro-5-(2-furyl)-2-methoxy-1-prop-2-enylbenzene, (hydroxyimino)(5-phenyl (2-thienyl))methane, 5-[(4-methylpiperazinyl)methyl]-2-phenylthiophene, 2-(4-ethylphenyl)thiophene, 4-methylthio-1-(2-thienyl)benzene, 2-(3-nitrophenyl)thiophene, (tert-butoxy)-N-[(5-phenyl(3-pyridyl))methyl]carboxamide, hydroxy-N-[(5-phenyl(3-pyridyl))methyl]amide, 2-(phenylmethylthio)pyridine, and benzylimidazole.

The term "heteroarylheteroaryl" refers to a biaryl group where both of the aryl groups is a heteroaryl group. Exemplary heteroarylheteroaryl groups include, for example, 3-pyridylimidazole, 2-imidazolylpyrazine, and the like. Preferred optionally substituted heteroarylheteroaryl groups include: 2-(4-piperazinyl-3-pyridyl)furan, diethyl(3-pyrazin-2-yl(4-pyridyl))amine, and dimethyl {2-[2-(5-methylpyrazin-2-yl) ethynyl](4-pyridyl)} amine.

"Optionally substituted" refers to the optional replacement of hydrogen with one or more monovalent or divalent radicals. Optionally substituted groups include those described herein, for each group in which a distinct definition for substitution is supplied. Additionally, suitable substitution groups include, for example, hydroxyl, nitro, amino, imino, cyano, halo, thio, thioamido, amidino, imidino, oxo, oxamidino, methoxamidino, imidino, guanidino, sulfonamido, carboxyl, formyl, alkyl, substituted alkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, benzyl, pyridyl, pyrazolyl, pyrrole, thiophene, imidazolyl, and the like.

Representative substituted amidino and heterocycloamidino groups include, for example, those shown below. These amidino and heterocycloamidino groups can be further substituted as will be apparent to those having skill in the organic and medicinal chemistry arts in conjunction with the disclosure herein.

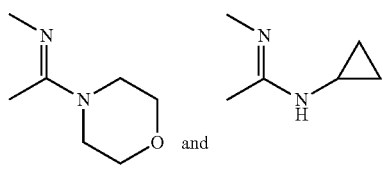

and

Representative substituted alkylcarbonylamino, alkyloxycarbonylamino, aminoalkyloxycarbonylamino, and arylcarbonylamino groups include, for example, those shown below. These groups can be further substituted as will be apparent to those having skill in the organic and medicinal chemistry arts in conjunction with the disclosure herein.

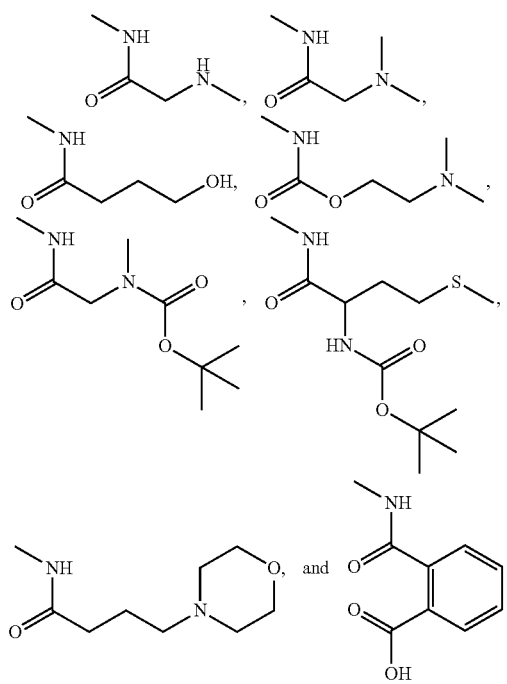

Representative substituted aminocarbonyl groups include, for example, those shown below. These can be further substituted by heterocyclo groups and heteroaryl groups as will be apparent to those having skill in the organic and medicinal chemistry arts in conjunction with the disclosure herein. Preferred aminocarbonyl groups include: N-(2-cyanoethyl)carboxamide, N-(3-methoxypropyl)carboxamide, N-cyclopropylcarboxamide, N-(2-hydroxy-isopropyl)carboxamide, methyl 2-carbonylamino-3-hydroxypropanoate, N-(2-hydroxypropyl)carboxamide, N-(2-hydroxy-isopropyl)carboxamide, N-[2-hydroxy-1-(hydroxymethyl)ethyl]carboxamide, N-(2-carbonylaminoethyl)acetamide, N-(2-(2-pyridyl) ethyl)carboxamide, N-(2-pyridylmethyl)carboxamide, N-(oxolan-2-ylmethyl)carboxamide, N-(4-hydroxypyrrolidin-2-yl)carboxamide, N-[2-(2-hydroxyethoxy)ethyl]carboxamide, N-(4-hydroxycyclohexyl)carboxamide, N-[2-(2-oxo-4-imidazolinyl)ethyl]carboxamide, N-(carbonylaminomethyl)acetamide, N-(3-pyrrolidinylpropyl)carboxamide, N-[1-(carbonylaminomethyl)pyrrolidin-3-yl]acetamide, N-(2-morpholin-4-ylethyl)carboxamide, N-[3-(2-oxopyrrolidinyl)propyl]carboxamide, 4-methyl-2-oxopiperazinecarbaldehyde, N-(2-hydroxy-3-pyrrolidinylpropyl)carboxamide, N-(2-hydroxy-3-morpholin-4-ylpropyl)carboxamide, N-{2-[(5-cyano-2-pyridyl)amino] ethyl}carboxamide, 3-(dimethylamino) pyrrolidinecarbaldehyde, N-[(5-methylpyrazin-2-yl)methyl] carboxamide, 2,2,2-trifluoro-N-(1-formylpyrrolidin-3-yl) acetamide,

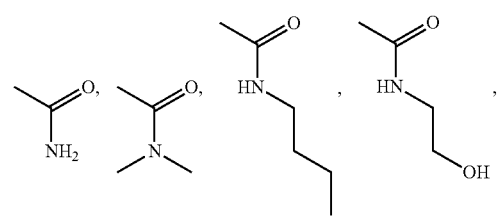

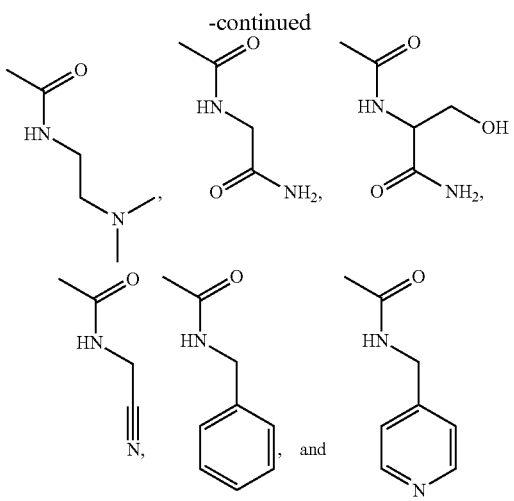

Representative substituted alkoxycarbonyl groups include, for example, those shown below. These alkoxycarbonyl groups can be further substituted as will be apparent to those having skill in the organic and medicinal chemistry arts in conjunction with the disclosure herein.

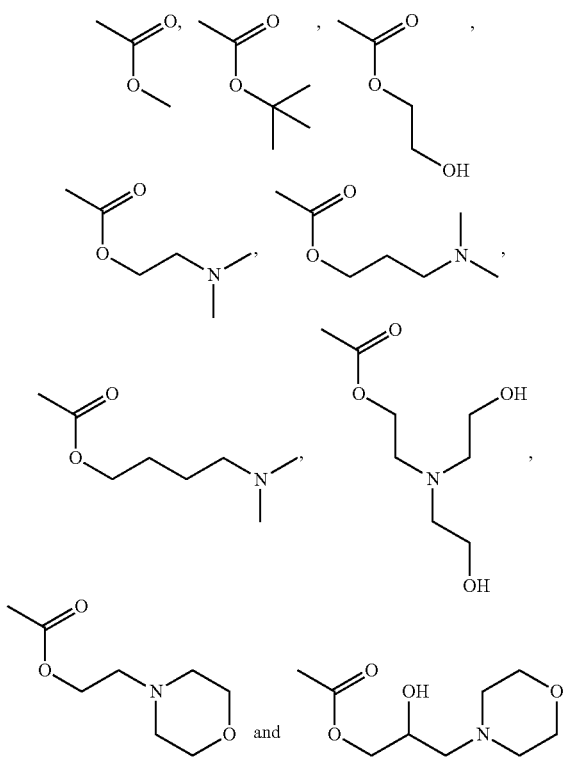

The term "protected" with respect to hydroxyl groups, amine groups, and sulfhydryl groups refers to forms of these functionalities that are protected from undesirable reaction with a protecting group known to those skilled in the art such as those set forth in Protective Groups in Organic Synthesis; Greene, T. W.; Wuts, P. G. M., John Wiley & Sons, New York, N.Y., (3rd Edition, 1999) that can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylhiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention that are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "antibacterial agent" refers to agents synthesized or modified in the laboratory that have either bactericidal or bacteriostatic activity. An "active" agent in this context will inhibit the growth of P. aeruginosa and other gram-negative bacteria. The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in uptake/efflux, solubility, half-life, etc. to compounds in order to correlate enzyme inhibition with growth inhibition. The activity of antibacterial agents is not necessarily limited to bacteria but may also encompass activity against parasites, virus, and fungi.

The subject invention also includes isotopically-labeled LpxC inhibitors, that are structurally identical to those disclosed above, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, prodrugs thereof, and pharmaceutically acceptable salts of said compounds and of said prodrugs that contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

The present invention provides novel compounds, pharmaceutical formulations including the compounds, methods of inhibiting UDP-3-O—(R-3-hydroxydecanoyl)-N-acetylglucosamine deacetylase (LpxC), and methods of treating gram-negative bacterial infections. In one embodiment, the present invention provides compounds of formula I:

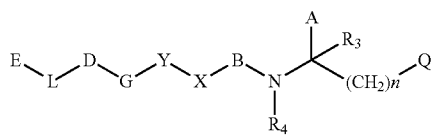

I or stereoisomers, pharmaceutically acceptable salts, esters, and prodrugs thereof, wherein
E is absent or selected from the group consisting of
(1) H,
(2) substituted or unsubstituted
(3) substituted or unsubstituted $C_2$-$C_6$-alkenyl,
(4) substituted or unsubstituted $C_2$-$C_6$-alkynyl,
(5) substituted or unsubstituted aryl,
(6) substituted or unsubstituted heterocyclyl, and
(7) substituted or unsubstituted heteroaryl;
L is absent or selected from the group consisting of
(1) substituted or unsubstituted $C_1$-$C_6$-alkyl,
(2) —(NH)$_{0-1}$—(CH$_2$)$_j$—NR$^{3L}$—(CH$_2$)$_k$—,
(3) —(NH)$_{0-1}$—C(R$^{1L}$,R$^{2L}$)—NR$^{3L}$—C(R$^{1L}$, R$^{2L}$)—,
(4) —C(R$^{1L}$,R$^{2L}$)—O—C(R$^{1L}$,R$^{2L}$)—,
(5) —(CH$_2$)$_j$—NR$^{3L}$—C(R$^{1L}$,R$^{2L}$)—CONH—(CH$_2$)$_k$—,
(6) —CO—C(R$^{1L}$,R$^{21}$)—NHCO—,
(7) —CONH—,
(8) —NHCO—,
wherein
R$^{1L}$, R$^{2L}$, and R$^{3L}$ are independently selected from the group consisting of
(a) H,
(b) substituted or unsubstituted
(c) $C_1$-$C_6$-alkyl substituted with aryl,
(d) $C_1$-$C_6$-alkyl substituted with heterocyclyl, and
(e) $C_1$-$C_6$-alkyl substituted with heteroaryl,
or R$^{1L}$ and R$^{3L}$, together with the atoms to which they are attached can form a substituted or unsubstituted heterocyclic ring, having from 3 to 8 ring atoms, wherein 1-2 ring atoms of the heterocyclic ring system are selected from N, O and S,
j is an integer of 0-4;
k is an integer of 0-4;
D is absent or selected from the group consisting of
(1) substituted or unsubstituted $C_3$-$C_8$-cycloalkyl,
(2) substituted or unsubstituted aryl,
(3) substituted or unsubstituted heterocyclyl, and
(4) substituted or unsubstituted heteroaryl;
G is absent or selected from the group consisting of
(1) —(CH$_2$)$_i$—O—(CH$_2$)$_i$—,
(2) —(CH$_2$)$_i$—S—(CH$_2$)$_i$—,
(3) —(CH$_2$)$_i$—NR$^g$—(CH$_2$)$_i$—,
(4) —C(=O)—,
(5) —NHC(=O)—,
(6) —C(=O)NH—,
(7) —(CH$_2$)$_i$NHCH$_2$C(=O)NH—,
(8) —C≡C—,
(9) —C≡C—C≡C—, and
(10) —C≡C—;
wherein
Rg is H or substituted or unsubstituted
i is an interger of 0-4;
Y is selected from the group consisting of
(1) substituted or unsubstituted $C_3$-$C_8$-cycloalkyl,
(2) substituted or unsubstituted aryl,
(3), substituted or unsubstituted heterocyclyl, and
(4) substituted or unsubstituted heteroaryl;
X is selected from the group consisting of
(1) —(C=O)—,
(2) —$C_1$-$C_6$-alkyl-(C=O)—,
(3) —$C_2$-$C_6$-alkenyl-(C=O)—,
(4) —$C_2$-$C_6$-alkynyl-(C=O)—, and
(5) —CH$_2$—;
or when B is absent, X and A, together with the atoms to which they are attached can form a heterocyclic ring, having from 5 to 8 ring atoms, wherein 1-2 ring atoms of the heterocyclic ring system are selected from N, O and S;

B is absent or

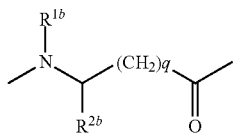

wherein $R^{1b}$ and $R^{2b}$, are independently selected from the group consisting of
(a) H,
(b) substituted or unsubstituted $C_1$-$C_6$-alkyl,
(c) substituted or unsubstituted $C_2$-$C_6$-alkenyl,
(d) substituted or unsubstituted $C_2$-$C_6$-alkynyl,
(e) substituted or unsubstituted aryl,
(f) substituted or unsubstituted heterocyclyl,
(g) substituted or unsubstituted heteroaryl,
(h) $C_1$-$C_6$-alkyl substituted with aryl,
(i) $C_1$-$C_6$-alkyl substituted with heterocyclyl, and
(j) $C_1$-$C_6$-alkyl substituted with heteroaryl,
or $R^{1b}$ and $R^{2b}$, together with the atoms to which they are attached can form a substituted or unsubstituted heterocyclic ring, having from 3 to 8 ring atoms, wherein 1-2 ring atoms of the heterocyclic ring system are selected from N, O and S;
q is an integer of 0-4;
$R_3$ is H or substituted or unsubstituted $C_1$-$C_6$-alkyl,
or $R_3$ and A, together with the atoms to which they are attached can form a substituted or unsubstituted 3-10 membered cycloalkyl or a heterocyclic ring system, wherein the heterocyclic ring system may have from 3 to 10 ring atoms, with 1 to 2 rings being in the ring system and contain from 1-4 heteroatoms selected from N, O and S;
$R_4$ is H or substituted or unsubstituted $C_1$-$C_6$-alkyl,
or $R_4$ and A, together with the atoms to which they are attached can form a substituted or unsubstituted heterocyclic ring, having from 3 to 8 ring atoms, wherein 1-2 ring atoms of the heterocyclic ring system are selected from N, O and S;
n is an integer of 0-2;
A is selected from the group consisting of
(1) H,
(2) —$(CH_2)_rC(R^{1a},R^{2a})(CH_2)_sOR^{3a}$,
(3) —$(CH_2)_rC(R^{1a},R^{2a})N(R^{4a},R^{5a})$,
(4) —$(CH_2)_rC(R^{1a},R^{2a})N(R^{4a})COR^{3a}$,
(5) —$(CH_2)_rC(R^{1a},R^{2a})NHCON(R^{4a},R^{5a})$,
(6) —$(CH_2)_rC(R^{1a},R^{2a})NHC(=NH)N(R^{4a},R^{5a})$,
(7) —$CH(R^{1a},R^{2a})$,
(8) —C≡CH,
(9) —$(CH_2)_rC(R^{1a},R^{2a})CN$,
(10) —$(CH_2)_rC(R^{1a},R^{2a})CO_2R^{3a}$, and
(11) —$(CH_2)_rC(R^{1a},R^{2a})CN(R^{4a},R^{5a})$,
wherein $R^{1a}$, $R^{2a}$, $R^{3a}$, $R^{4a}$, and $R^{5a}$ are independently selected from the group consisting of
(a) H,
(b) substituted or unsubstituted
(c) substituted or unsubstituted aryl,
(d) substituted or unsubstituted heterocyclyl,
(e) substituted or unsubstituted heteroaryl,
(f) $C_1$-$C_6$-alkyl substituted with aryl,
(g) $C_1$-$C_6$-alkyl substituted with heterocyclyl, and
(h) $C_1$-$C_6$-alkyl substituted with heteroaryl,
or $R^{4a}$ and $R^{5a}$ together with the N atom to which they are attached can form a substituted or unsubstituted heterocyclic ring, having from 3 to 8 ring atoms, wherein 1-2 ring atoms of the heterocyclic ring system are selected from N, O and S;
r is an integer of 0-4;
s is an integer of 0-4;
Q is absent or selected from the group consisting of
(1) —$C(=O)N(R_1, R_2)$,
(2) —$NHC(=O)N(R_1,R_2)$,
(3) —$N(OH)C(=O)N(R_1,R_2)$,
(4) —$CH(OH)C(=O)N(R_1,R_2)$,
(5) —$CH[N(R^{2q},R^{3q})]C(=O)N(R_1,R_2)$,
(6) —$CHR^{1q}C(=O)N(R_1,R_2)$,
(7) —$CO_2H$,
(8) —$C(=O)NHSO_2R^{4q}$,
(9) —$SO_2NH_2$,
(10) —$N(OH)C(=O)R^{1q}$,
(11) —$N(OH)SO_2R^{4q}$,
(12) —$NHSO_2R^{4q}$,
(13) —SH,
(14) —$CH(SH)(CH_2)_{0-1}C(=O)N(R_1, R_2)$,
(15) —$CH(SH)(CH_2)_{0-1}CO_2H$,
(16) —$CH(OH)(CH_2)_{0-1}CO_2H$,
(17) —$CH(SH)CH_2CO_2R^{1q}$,
(18) —$CH(OH)(CH_2)SO_2NH_2$,
(19) —$CH(CH_2SH)NHCOR^{1q}$,
(20) —$CH(CH_2SH)NHSO_2R^{4q}$,
(21) —$CH(CH_2SR^{5q})CO_2H$,
(22) —$CH(CH_2SH)NHSO_2NH_2$,
(23) —$CH(CH_2OH)CO_2H$,
(24) —$CH(CH_2OH)NHSO_2NH_2$,
(25) —$C(=O)CH_2CO_2H$,
(26) —$C(=O)(CH_2)_{0-1}CONH_2$,
(27) —$OSO_2NHR^{5q}$,
(28) —$SO_2NHNH_2$,
(29) —$P(=O)(OH)_2$,

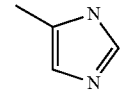 (30)

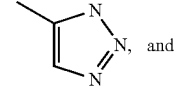 and (31)

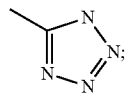 (32)

$R_1$ is selected from the group consisting of
(1) —H,
(2) —OH,
(3) —$OC_{1-6}$-alkyl,
(4) —$N(R^{2q},R^{3q})$, and
(5) substituted or unsubstituted $C_{1-6}$-alkyl;
$R_2$ is selected from the group consisting of
(1) H,
(2) substituted or unsubstituted
(3) substituted or unsubstituted $C_2$-$C_6$-alkenyl,
(4) substituted or unsubstituted $C_2$-$C_6$-alkenyl,
(5) substituted or unsubstituted aryl,
(6) substituted or unsubstituted heterocyclyl,
(7) substituted or unsubstituted heteroaryl,
(8) $C_1$-$C_6$-alkyl substituted with aryl, (9) $C_1$-$C_6$-alkyl substituted with heterocyclyl, and
(10) $C_1$-$C_6$-alkyl substituted with heteroaryl,
or $R^1$ and $R^2$, together with the N atom to which they are attached can form a substituted or unsubstituted heterocyclic ring, having from 3 to 10 ring atoms, wherein 1-4 ring atoms of the heterocyclic ring system are selected from N, O and S, $R^{1q}, R^{2q}, R^{3q}, R^{4q}$, and $R^{5q}$ are selected from H or $C_1$-$C_6$ alkyl, wherein B is absent, or E, L, G, and B are absent, or E, L, and G are absent, or E, L, and B are absent, or E, L, D, G, and B are absent.

In another embodiment, the present invention provides compounds of formula I:

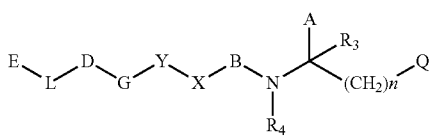

I or stereoisomers, pharmaceutically acceptable salts, esters, and prodrugs thereof, wherein E is absent or selected from the group consisting of
(1) H,
(2) substituted or unsubstituted $C_1$-$C_6$-alkyl,
(3) substituted or unsubstituted aryl,
(4) substituted or unsubstituted heterocyclyl, and
(5) substituted or unsubstituted heteroaryl;

L is absent or selected from the group consisting of
(1) —$(CH_2)_j$—$NR^{3L}$—$(CH_2)_k$—,
(2) —$C(R^{1L},R^{2L})_j$—$NR^{3L}$—$C(R^{1L},R^{2L})_k$—,
(3) —$C(R^{1L},R^{2L})_j$—O—$C(R^{1L},R^{2L})_k$—,
(4) —$(CH_2)_j$—$NR^{3L}$—$C(R^{1L},R^{2L})_k$—CONH—$(CH_2)_k$—,
(5) —CO—$C(R^{1L},R^{2L})$—NHCO—,
(6) —CONH—, and
(7) —NHCO—,
wherein
$R^{1L}, R^{2L}, R^{3L}$ are independently selected from the group consisting of
(a) H,
(b) substituted or unsubstituted $C_1$-$C_6$-alkyl,
(c) $C_1$-$C_6$-alkyl substituted with aryl,
(d) $C_1$-$C_6$-alkyl substituted with heterocyclyl,
(e) $C_1$-$C_6$-alkyl substituted with heteroaryl,
or $R^{1L}$ and $R^{3L}$, together with the atoms to which they are attached can form a substituted or unsubstituted heterocyclic ring, having from 5 to 8 ring atoms, wherein 1-2 ring atoms of the heterocyclic ring system are selected from N, O and S;
j is an integer of 0-4;
k is an integer of 0-4;

D is absent or selected from the group consisting of
(1) substituted or unsubstituted $C_3$-$C_8$-cycloalkyl,
(2) substituted or unsubstituted aryl,
(3) substituted or unsubstituted heterocyclyl,
(4) substituted or unsubstituted heteroaryl, and G is absent or selected from the group consisting of
(1) —C(=O)—,
(2) —NHC(=O)—,
(3) —C(=O)NH—,
(4) —$(CH_2)_i$NHCH$_2$C(=O)NH—,
(5) —C≡C—, and
(6) —C≡C—C≡C—,
wherein i is an integer of 0-4;

Y is selected from the group consisting of
(1) substituted or unsubstituted $C_3$-$C_8$-cycloalkyl,
(2) substituted or unsubstituted aryl,
(3) substituted or unsubstituted heterocyclyl, and
(4) substituted or unsubstituted heteroaryl;

X is selected from the group consisting of
(1) —(C=O)—,
(2) —$C_1$-$C_6$-alkyl-(C=O)—,
(3) —$C_2$-$C_6$-alkenyl-(C=O)—,
(4) —$C_2$-$C_6$-alkynyl-(C=O)—, and
(5) —$CH_2$—;
or when B is absent, X and A, together with the atoms to which they are attached can form a heterocyclic ring, having from 5 to 8 ring atoms, wherein 1-2 ring atoms of the heterocyclic ring system are selected from N, O and S;

B is absent or

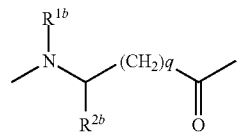

wherein $R^{1b}$ and $R^{2b}$ are independently selected from the group consisting of
(a) H,
(b) substituted or unsubstituted $C_1$-$C_6$-alkyl,
(c) substituted or unsubstituted $C_2$-$C_6$-alkenyl,
(d) substituted or unsubstituted $C_2$-$C_6$-alkenyl,
(e) substituted or unsubstituted aryl,
(f) substituted or unsubstituted heterocyclyl,
(g) substituted or unsubstituted heteroaryl,
(h) $C_1$-$C_6$-alkyl substituted with aryl,
(i) $C_1$-$C_6$-alkyl substituted with heterocyclyl, and
(j) $C_1$-$C_6$-alkyl substituted with heteroaryl,
or $R^{1b}$ and $R^{2b}$, together with the atoms to which they are attached can form a substituted or unsubstituted heterocyclic ring, having from 5 to 8 ring atoms, wherein 1-2 ring atoms of the heterocyclic ring system are selected from N, O and S;

q is an integer of 0-2;

$R_3$ is H or substituted or unsubstituted $C_1$-$C_6$-alkyl,
or $R_3$ and A, together with the atoms to which they are attached can form a substituted or unsubstituted 3-10 membered cycloalkyl or a heterocyclic ring system, wherein the heterocyclic ring system may have from 3 to 10 ring atoms, with 1 to 2 rings being in the ring system and contain from 1-4 heteroatoms selected from N, O and S;

$R_4$ is H or substituted or unsubstituted $C_1$-$C_6$-alkyl,
or $R_4$ and A, together with the atoms to which they are attached can form a substituted or unsubstituted heterocyclic ring, having from 5 to 8 ring atoms, wherein 1-2 ring atoms of the heterocyclic ring system are selected from N, O and S;

A is selected from the group consisting of
(1) H,
(2) —$(CH_2)_r C(R^{1a},R^{2a})(CH_2)_s OR^{3a}$,
(2) —$(CH_2)_r C(R^{1a},R^{2a})N(R^{4a},R^{5a})$,
(3) —$(CH_2)_r C(R^{1a},R^{2a})N(R^{4a},R^{5a})$,
(4) —$(CH_2)_r C(R^{1a},R^{2a})N(R^{4a})COR^{3a}$,
(5) —$(CH_2)_r C(R^{1a},R^{2a})NHCON(R^{4a},R^{5a})$,
(6) —$(CH_2)_r C(R^{1a},R^{2a})NHC(=NH)N(R^{4a},R^{5a})$, (7) —CH($R^{1a}$,$R^{2a}$),
(8) —C≡CH,
(9) —(CH$_2$)$_r$C($R^{1a}$,$R^{2a}$)CN, and
(10) —(CH$_2$)$_r$C($R^{1a}$,$R^{2a}$)CO$_2$$R^{3a}$,
  wherein $R^{1a}$,$R^{2a}$,$R^{3a}$,$R^{4a}$, and $R^{5a}$, are independently selected from the group consisting of
  (a) H,
  (b) substituted or unsubstituted $C_1$-$C_6$-alkyl,
  (c) $C_1$-$C_6$-alkyl substituted with aryl,
  (d) $C_1$-$C_6$-alkyl substituted with heterocyclyl, and
  (e) $C_1$-$C_6$-alkyl substituted with heteroaryl,
    or $R^{4a}$ and $R^{5a}$, together with the N atom to which they are attached can form a substituted or unsubstituted heterocyclic ring, having from 5 to 8 ring atoms, wherein 1-2 ring atoms of the heterocyclic ring system are selected from N, O and S;
  r is an integer of 0-4;
Q is absent or selected from the group consisting of
  (1) —C(=O)N($R_1$, $R_2$),
  (2) —NHC(=O)N($R_1$, $R_2$),
  (3) —N(OH)C(=O)N($R_1$, $R_2$),
  (4) —CH(OH)C(=O)N($R_1$, $R_2$),
  (5) —CH[N($R^{2q}$,$R^{3q}$)]C(=O)N($R_1$, $R_2$), and
  (6) —CHR$^{1q}$C(=O)N($R_1$, $R_2$),
$R_1$ is selected from the group consisting of
  (1) H,
  (2) OH,
  (3) OC$_{1-6}$-alkyl,
  (4) N($R^{2q}$,$R^{3q}$), and
  (5) substituted or unsubstituted $C_{1-6}$-alkyl;
$R_2$ is selected from the group consisting of
  (1) H,
  (2) substituted or unsubstituted $C_1$-$C_6$-alkyl,
  (3) substituted or unsubstituted aryl,
  (4) substituted or unsubstituted heterocyclyl,
  (5) substituted or unsubstituted heteroaryl,
  (6) $C_1$-$C_6$-alkyl substituted with aryl,
  (7) $C_1$-$C_6$-alkyl substituted with heterocyclyl, and
  (8) $C_1$-$C_6$-alkyl substituted with heteroaryl,
  or $R^1$ and $R^2$, together with the N atom to which they are attached can form a substituted or unsubstituted heterocyclic ring, having from 3 to 10 ring atoms, wherein 1-4 ring atoms of the heterocyclic ring system are selected from N, O and S,
$R^{1q}$,$R^{2q}$, and $R^{3q}$ are selected from H or $C_1$-$C_6$ alkyl,
wherein B is absent, or E, L, G, and B are absent, or E, L, and G are absent, or E, L, and B are absent, or E, L, D, G, and B are absent.

In another embodiment, the present invention provides compounds of formula II:

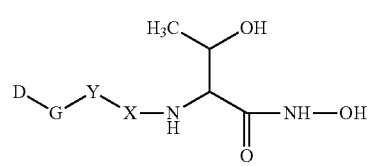

II or stereoisomers, pharmaceutically acceptable salts, esters, and prodrugs thereof, wherein D-G-Y taken together, is selected from the group consisting of

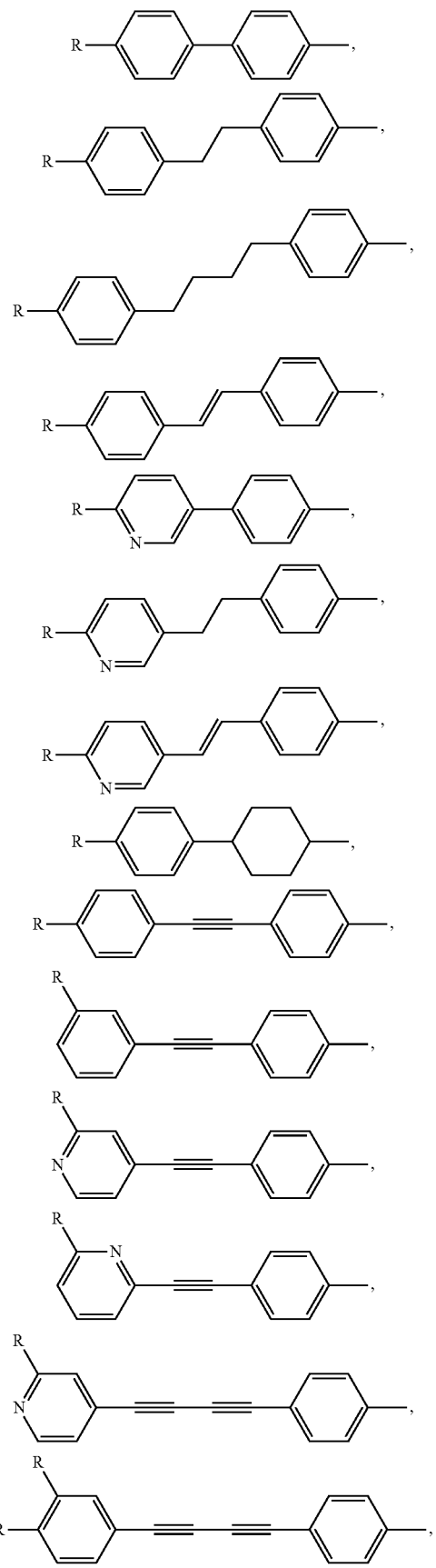

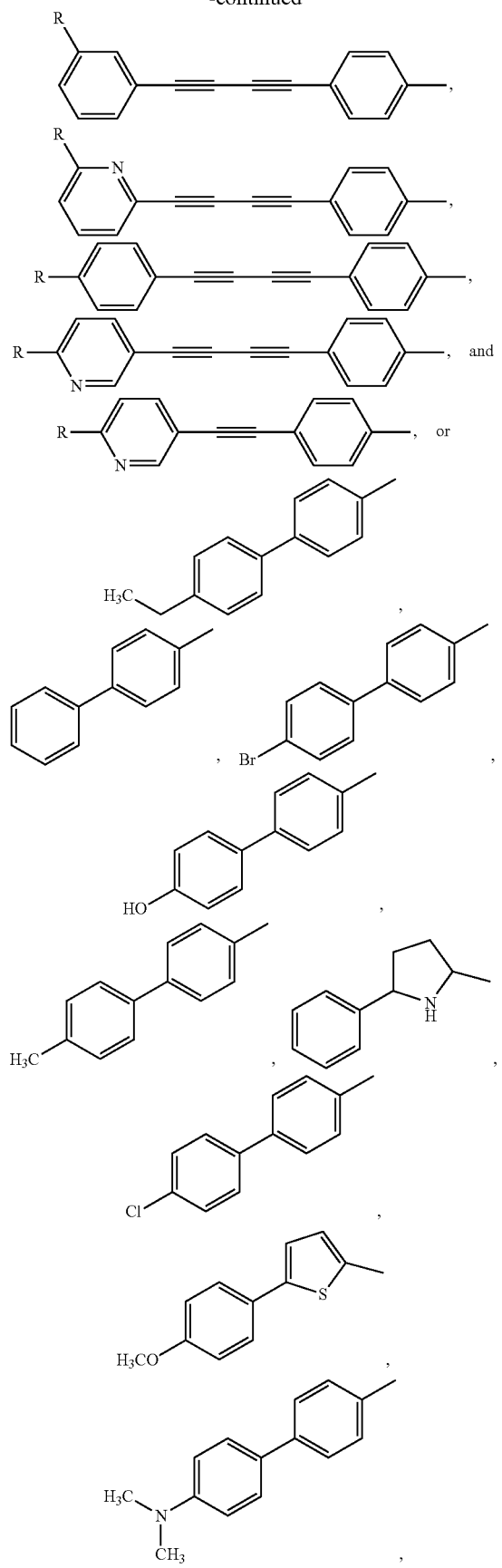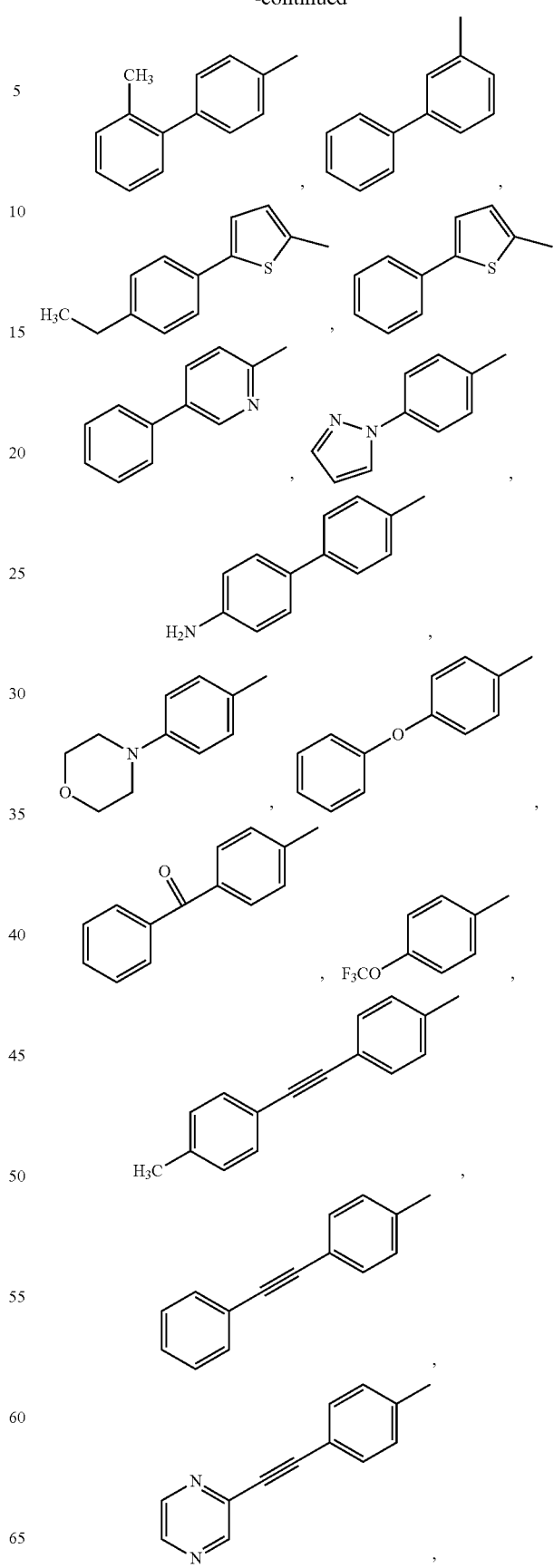

-continued

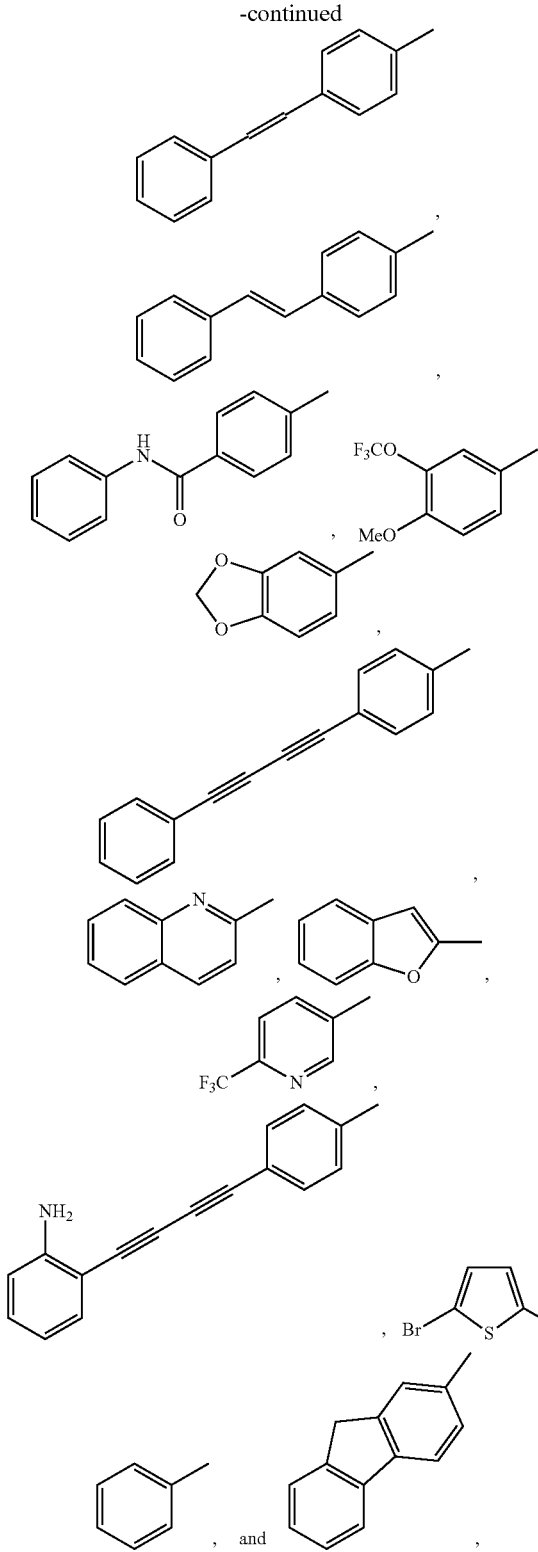

Wherein

R is selected from the group consisting of —CH$_3$, —C$_2$H$_5$, —CH$_2$OH, —OH, —OCH$_3$, —OC$_2$H$_5$, —OCF$_3$, —CN, —NO$_2$, —CO$_2$H, —CO$_2$CH$_3$, —CONH$_2$, —NH$_2$, —F, —Cl, —Br, —CF$_3$, —N(CH$_3$)$_2$, —NHSO$_2$CH$_3$, and —NHCOCH$_3$;

X is selected from the group consisting of
(1) —(C═O)—,
(2) —C$_1$-C$_6$-alkyl-(C═O)—, and
(3) —C$_2$-C$_6$-alkenyl-(C═O)—.

In another embodiment, the present invention provides compounds of formula III:

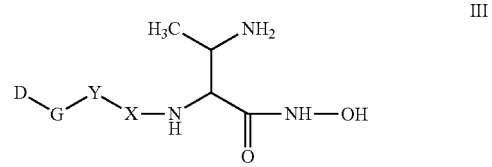

or stereoisomers, pharmaceutically acceptable salts, esters, and prodrugs thereof, wherein D-G-Y taken together, is selected from the group consisting of

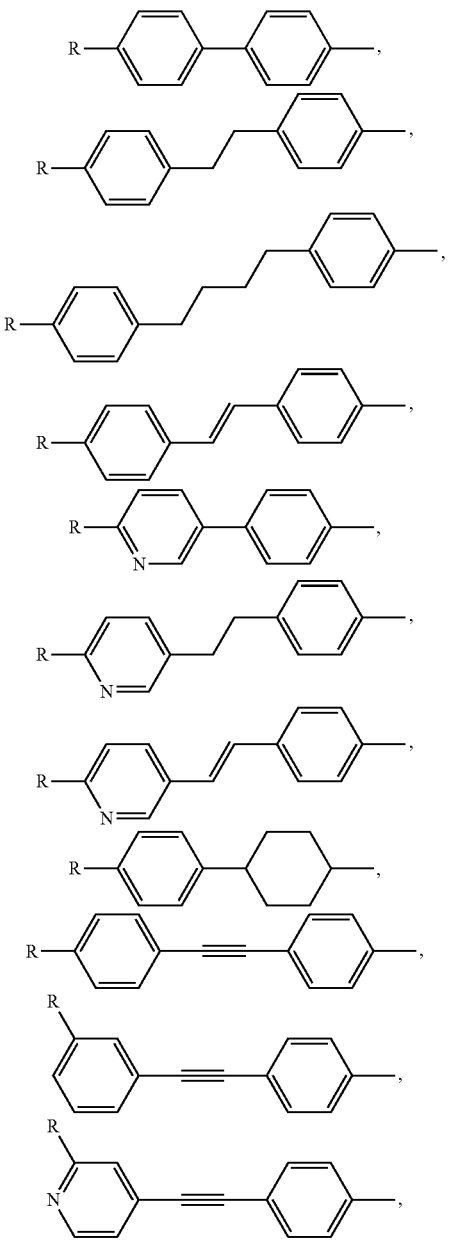

-continued
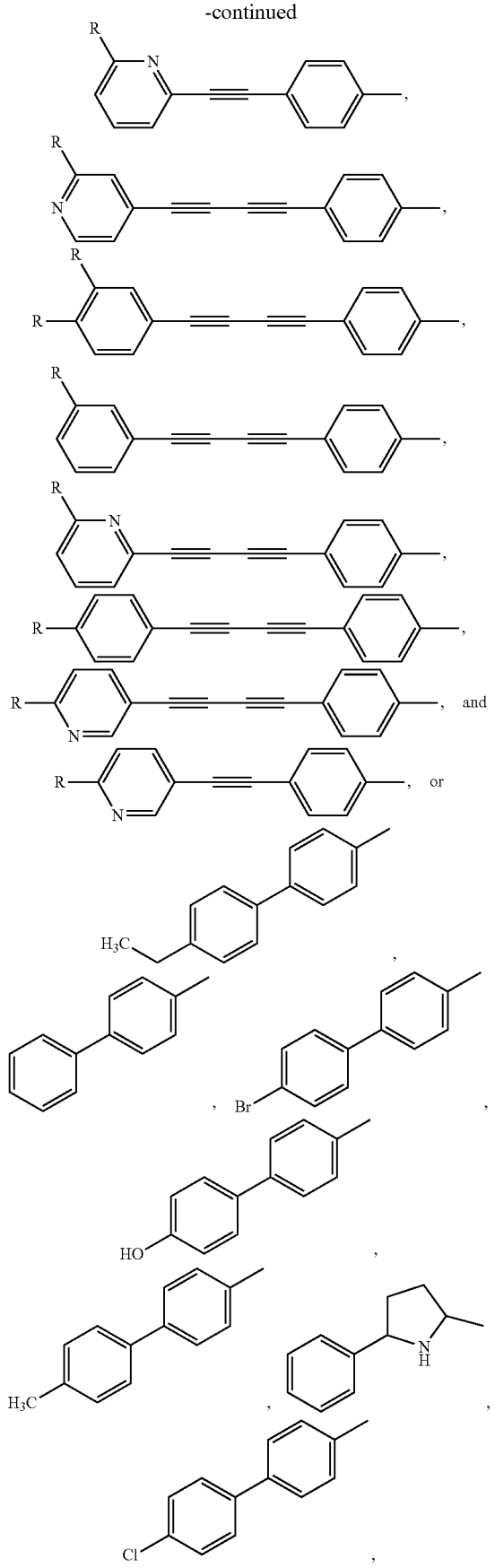
-continued
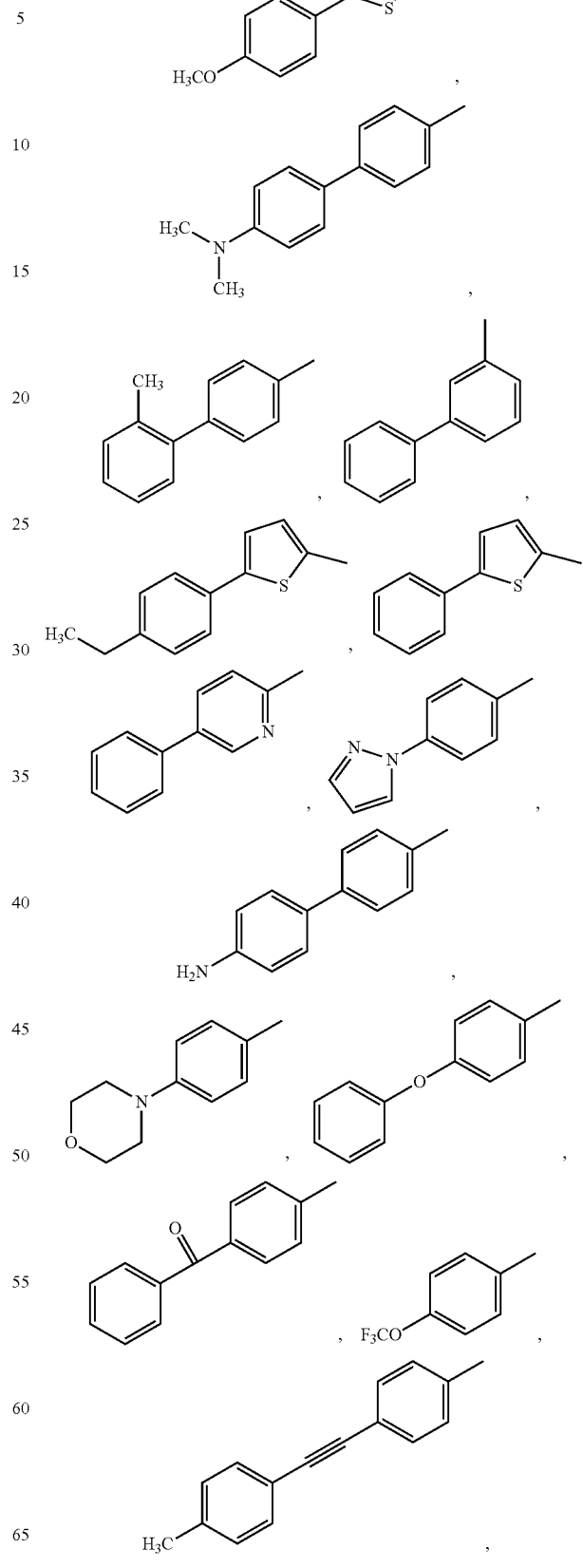

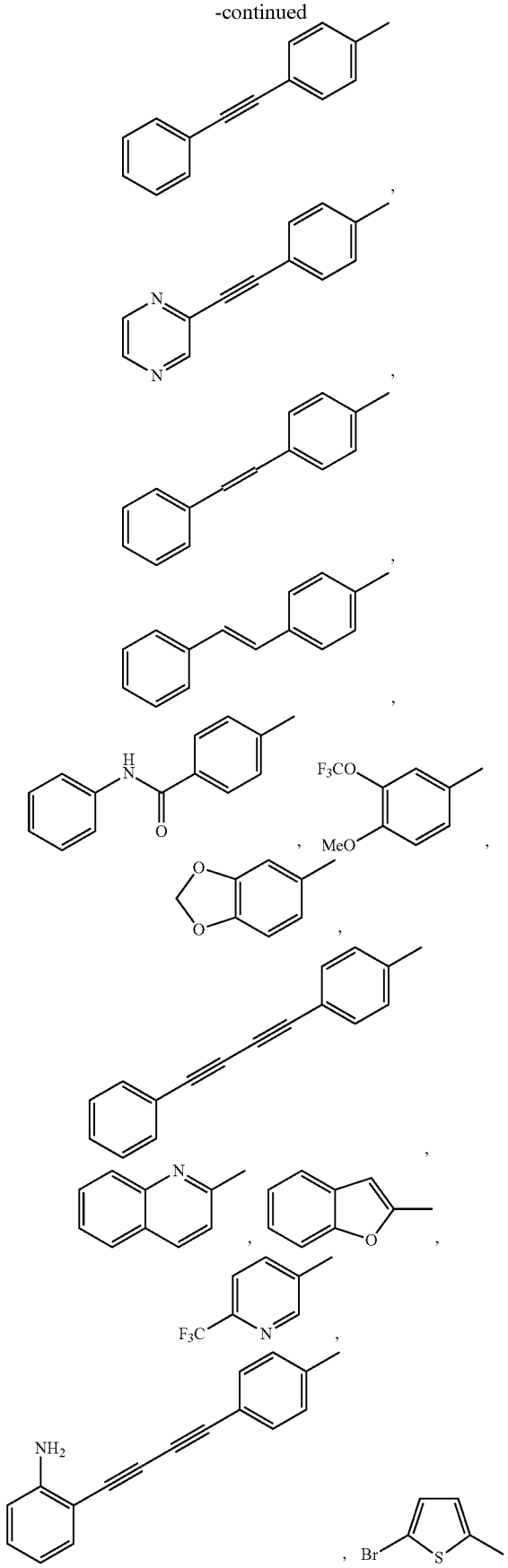

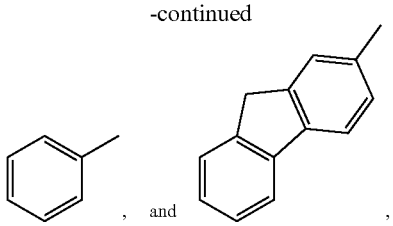

, and

Wherein

R is selected from the group consisting of —CH₃, —C₂H₅, —CH₂OH, —OH, —OCH₃, —OC₂H₅, —OCF₃, —CN, —NO₂, —CO₂H, —CO₂CH₃, —CONH₂, —NH₂, —F, —Cl, —Br, —CF₃, —N(CH₃)₂, —NHSO₂CH₃, and —NH-COCH₃;

X is selected from the groups consisting of
(1) —(C═O)—,
(2) —C₁-C₆-alkyl-(C═O)—, and
(3) —C₂-C₆-alkenyl-(C═O)—.

In another embodiment, the present invention provides compounds of formula IV:

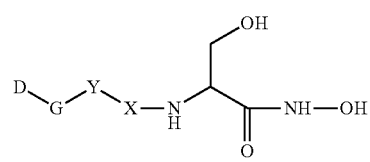

IV or stereoisomers, pharmaceutically acceptable salts, esters, and prodrugs thereof, wherein D-G-Y taken together, is selected from the group consisting of

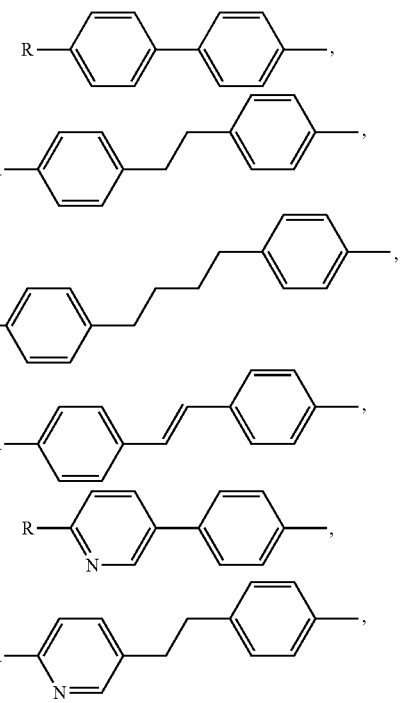

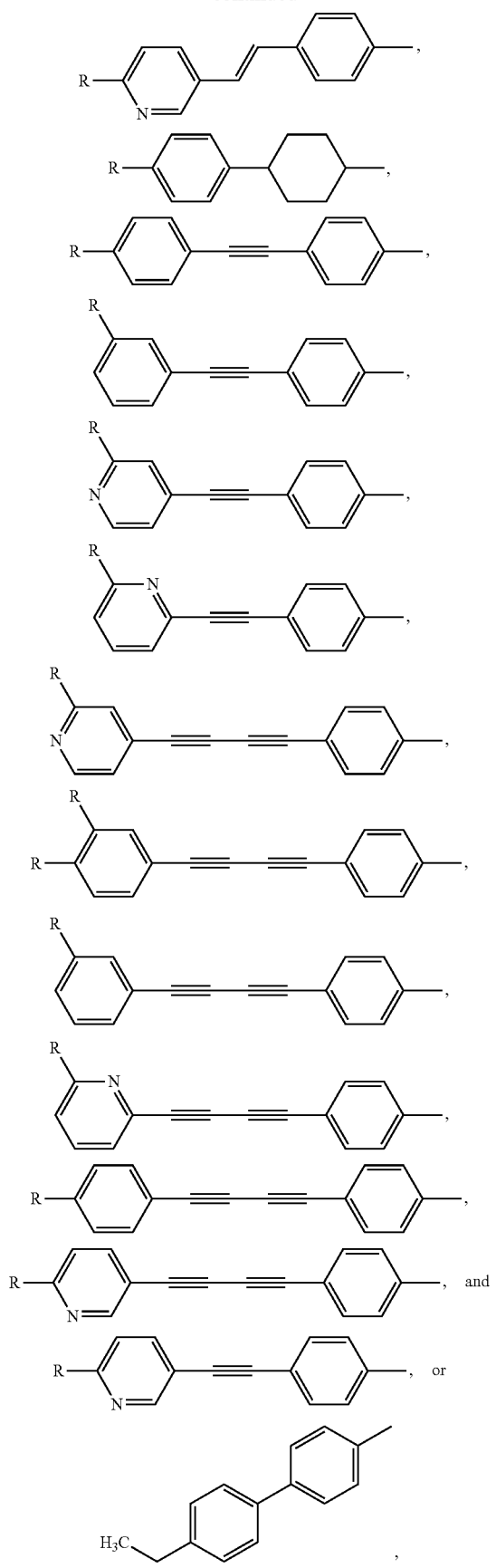
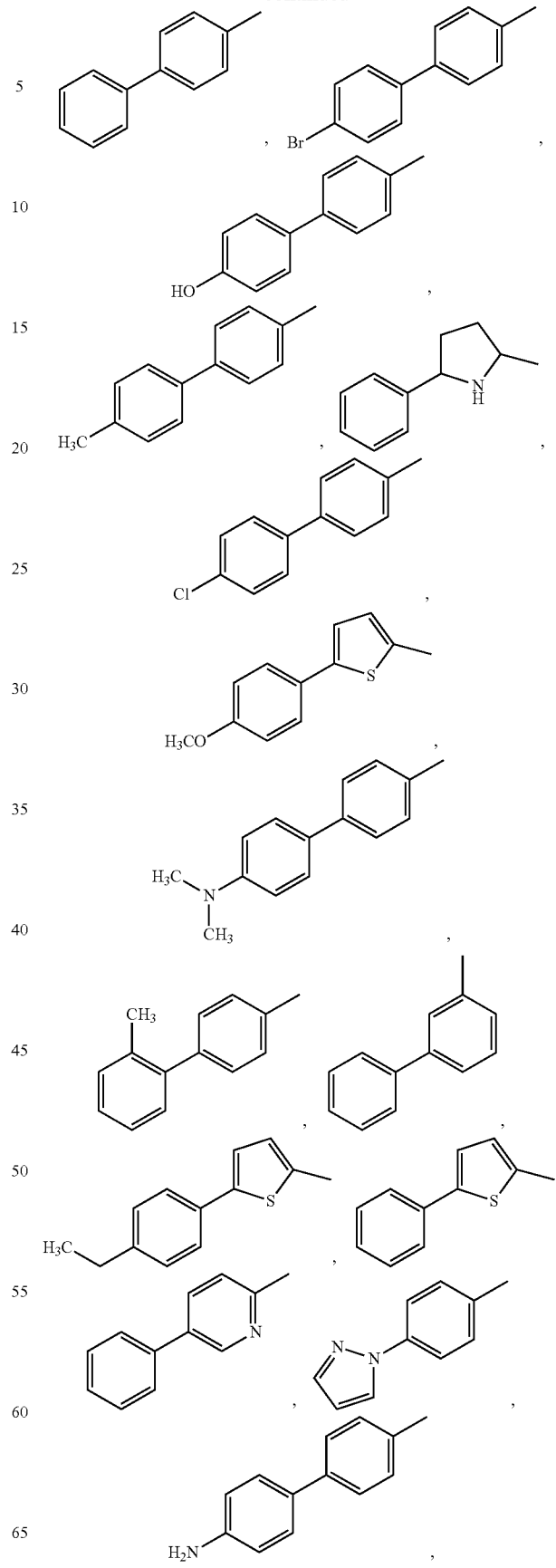

-continued

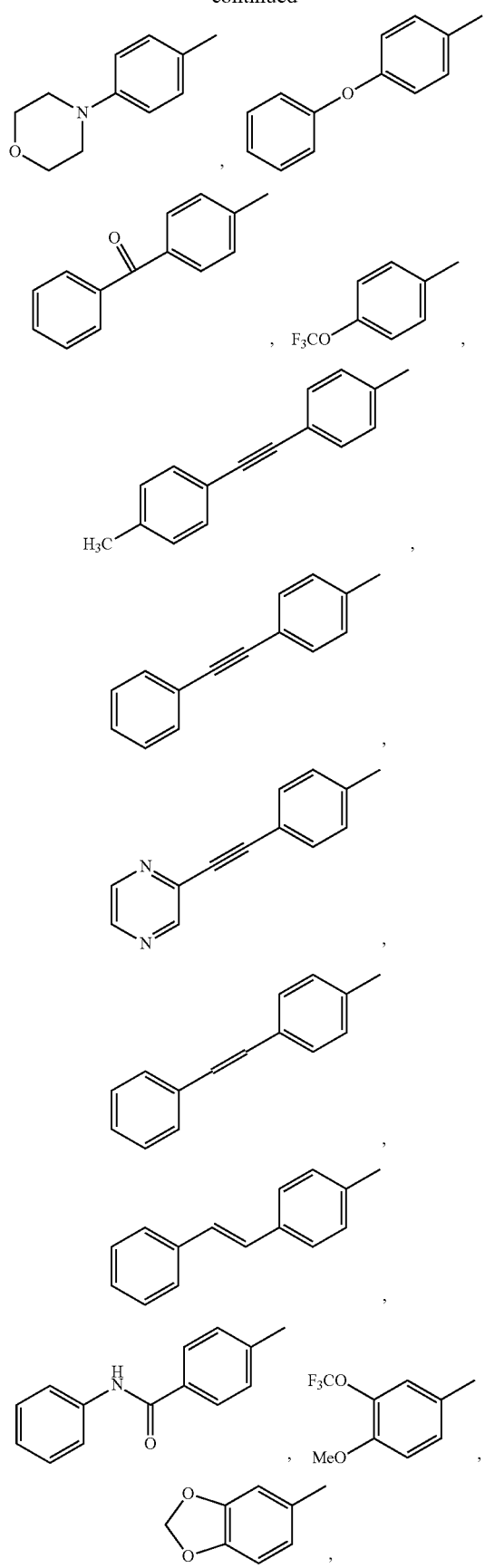

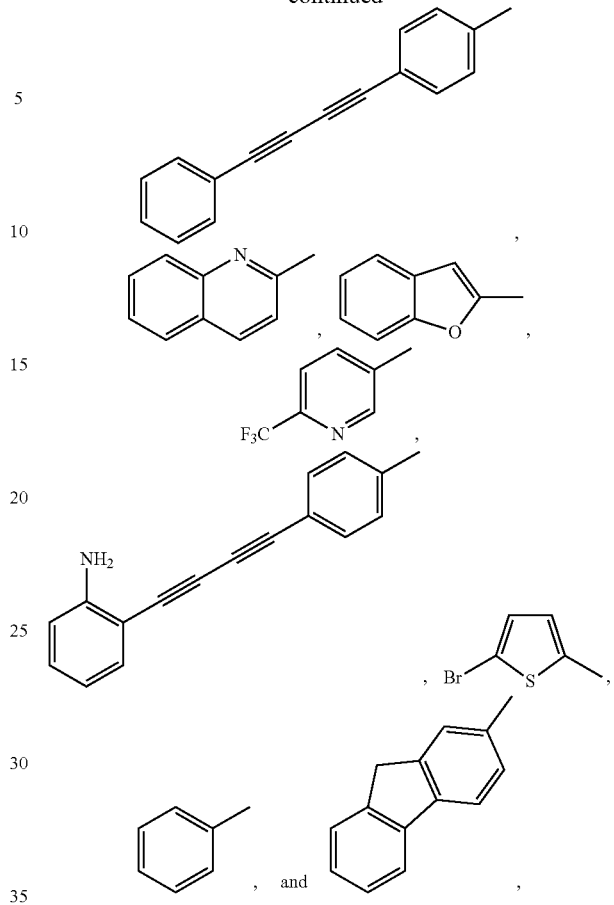

Wherein
R is selected from the group consisting of —CH$_3$, —C$_2$H$_5$, —CH$_2$OH, —OH, —OCH$_3$, —OC$_2$H$_5$, —OCF$_3$, —CN, —NO$_2$, —CO$_2$H, —CO$_2$CH$_3$, —CONH$_2$, —NH$_2$, —F, —Cl, —Br, —CF$_3$, —N(CH$_3$)$_2$; —NHSO$_2$CH$_3$, and —NH-COCH$_3$;
X is selected from the groups consisting of
(1) —(C═O)—,
(2) —C$_1$-C$_6$-alkyl-(C═O)—, and
(3) —C$_2$-C$_6$-alkenyl-(C═O)—.
In another embodiment, the present invention provides compounds of formula V:

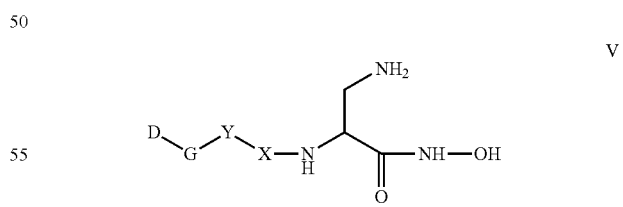

or stereoisomers, pharmaceutically acceptable salts, esters, and prodrugs thereof, wherein D-G-Y taken together, is selected from the group consisting of

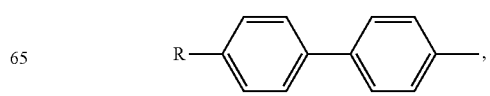

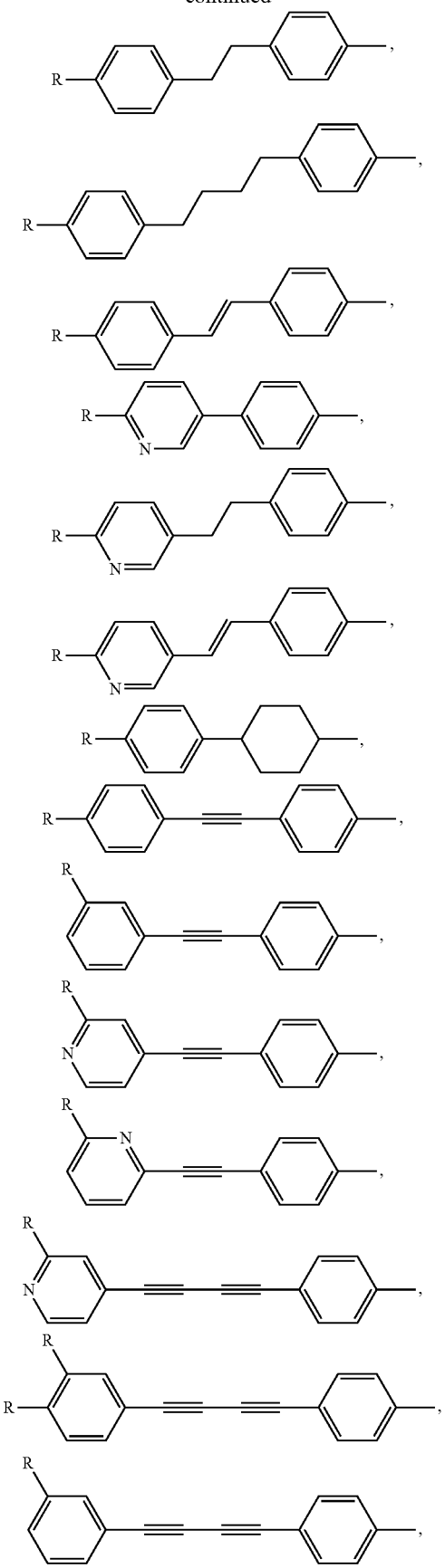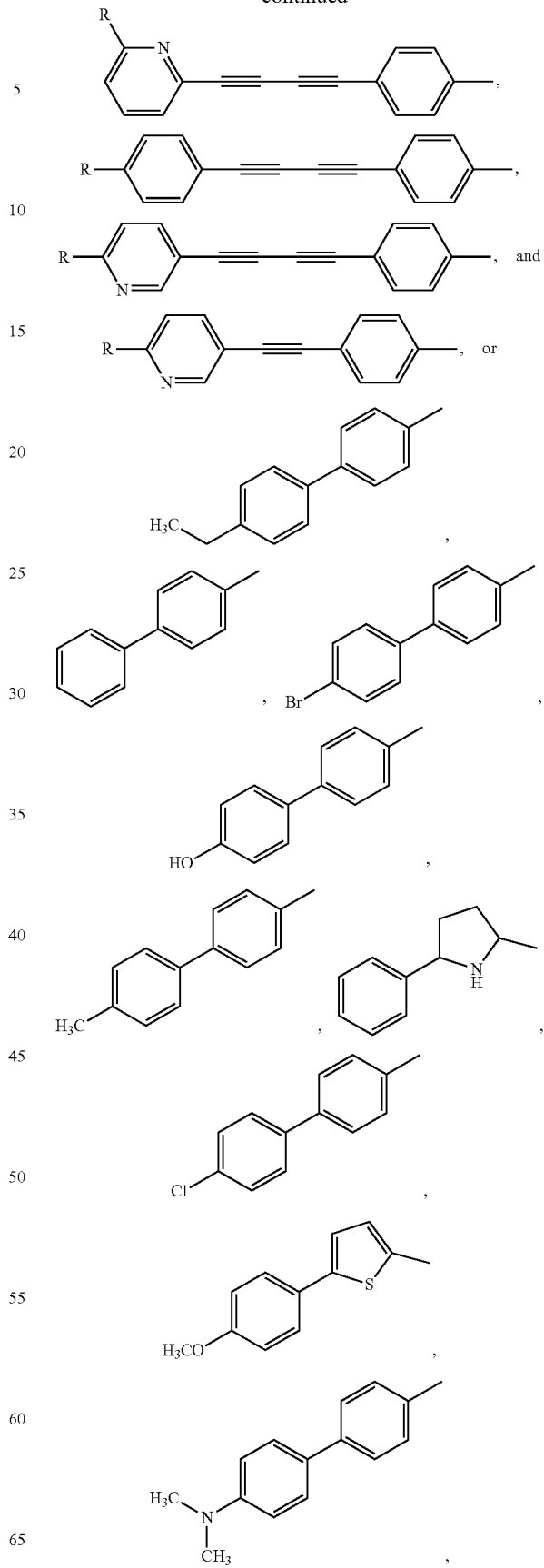

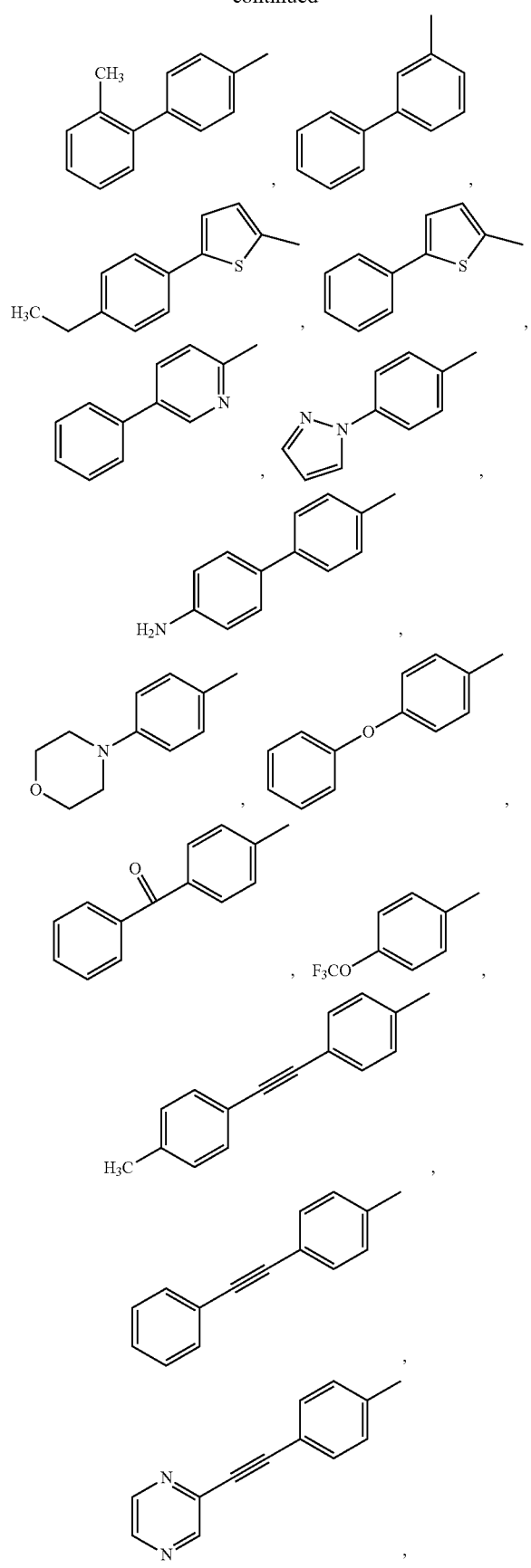
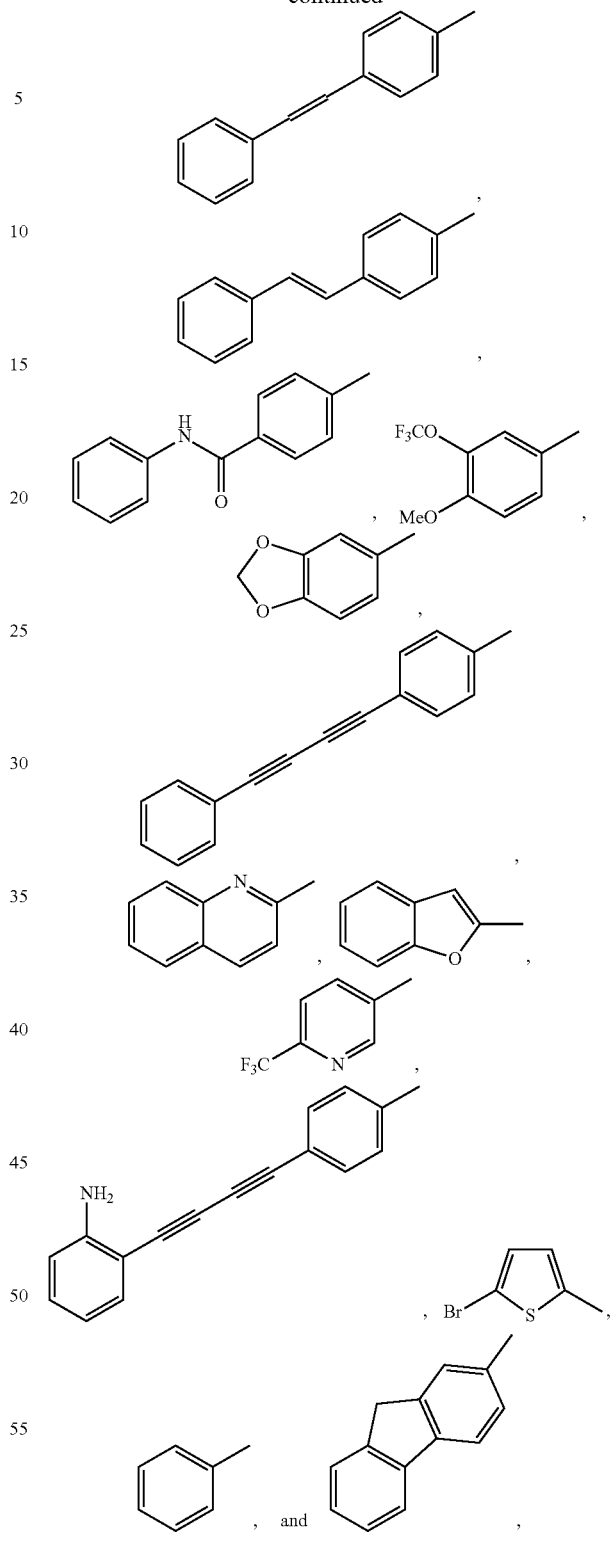
Wherein
R is selected from the group consisting of —CH₃, —C₂H₅, —CH₂OH, —OH, —OCH₃, —OC₂H₅, —OCF₃, —CN, —NO₂, —CO₂H, —CO₂CH₃, —CONH₂, —NH₂, —F, —Cl, —Br, —CF₃, —N(CH₃)₂)—NHSO₂CH₃, and —NH-COCH₃;

X is selected from the groups consisting of
(1) —(C=O)—,
(2) —$C_1$-$C_6$-alkyl-(C=O)—, and
(3) —$C_2$-$C_6$-alkenyl-(C=O)—.

In another embodiment, the present invention provides compounds of formula VI:

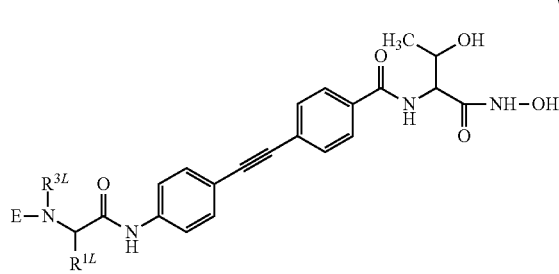

VI or stereoisomers, pharmaceutically acceptable salts, esters, and prodrugs thereof, wherein
E is absent or selected from the group consisting of
(1) H,
(2) substituted or unsubstituted $C_1$-$C_6$-alkyl,
(3) substituted or unsubstituted aryl,
(4) substituted or unsubstituted heterocyclyl, and
(5) substituted or unsubstituted heteroaryl,
or E and $R^{3L}$, together with the atoms to which they are attached can form a substituted or unsubstituted heterocyclic ring, having from 3 to 10 ring atoms, wherein 1-4 ring atoms of the heterocyclic ring system are selected from N, O and S,
$R^{1L}$,$R^{3L}$ are independently selected from the group consisting of
(1) H,
(2) substituted or unsubstituted $C_1$-$C_6$-alkyl,
(3) $C_1$-$C_6$-alkyl substituted with aryl,
(4) $C_1$-$C_6$-alkyl substituted with heterocyclyl, and
(5) $C_1$-$C_6$-alkyl substituted with heteroaryl,
or $R^{1L}$ and $R^{3L}$, together with the atoms to which they are attached can form a substituted or unsubstituted heterocyclic ring, having from 3 to 8 ring atoms, wherein 1-2 ring atoms of the heterocyclic ring system are selected from N, O and S.

In another embodiment, the present invention provides compounds of formula VII:

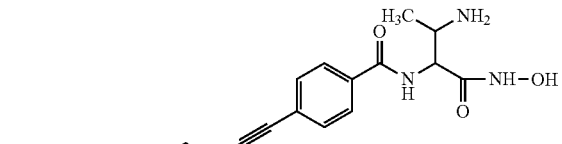

VII or stereoisomers, pharmaceutically acceptable salts, esters, and prodrugs thereof, wherein
E is absent or selected from the group consisting of
(1) H,
(2) substituted or unsubstituted $C_1$-$C_6$-alkyl,
(3) substituted or unsubstituted aryl,
(4) substituted or unsubstituted heterocyclyl, and
(5) substituted or unsubstituted heteroaryl,
or E and $R^{3L}$, together with the atoms to which they are attached can form a substituted or unsubstituted heterocyclic ring, having from 3 to 10 ring atoms, wherein 1-4 ring atoms of the heterocyclic ring system are selected from N, O and S;
$R^{1L}$,$R^{3L}$ are independently selected from the group consisting of
(1) H,
(2) substituted or unsubstituted $C_1$-$C_6$-alkyl,
(3) $C_1$-$C_6$-alkyl substituted with aryl,
(4) $C_1$-$C_6$-alkyl substituted with heterocyclyl, and
(5) $C_1$-$C_6$-alkyl substituted with heteroaryl,
or $R^{1L}$ and $R^{3L}$, together with the atoms to which they are attached can form a substituted or unsubstituted heterocyclic ring, having from 3 to 8 ring atoms, wherein 1-2 ring atoms of the heterocyclic ring system are selected from N, O and S.

In another embodiment, the present invention provides compounds of formula VIII:

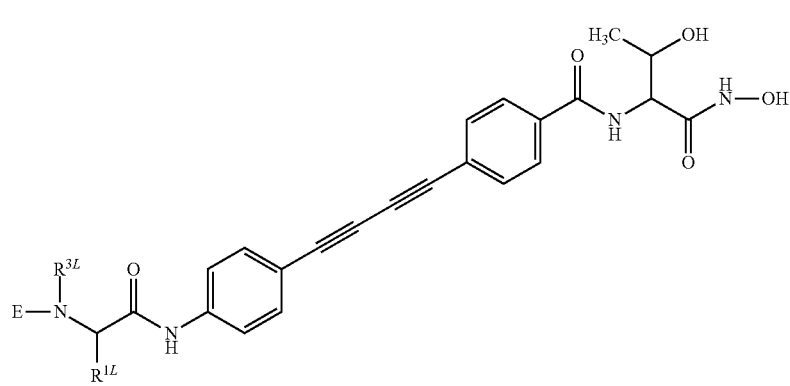

VIII or stereoisomers, pharmaceutically acceptable salts, esters, and prodrugs thereof, wherein
E is absent or selected from the group consisting of
(1) H,
(2) substituted or unsubstituted $C_1$-$C_6$-alkyl,
(3) substituted or unsubstituted aryl,
(4) substituted or unsubstituted heterocyclyl, and
(5) substituted or unsubstituted heteroaryl, or E and R³ᴸ, together with the atoms to which they are attached can form a substituted or unsubstituted heterocyclic ring, having from 3 to 10 ring atoms, wherein 1-4 ring atoms of the heterocyclic ring system are selected from N, O and S;

R¹ᴸ,R³ᴸ are independently selected from the group consisting of (1) H,
(2) substituted or unsubstituted $C_1$-$C_6$-alkyl,
(3) $C_1$-$C_6$-alkyl substituted with aryl,
(4) $C_1$-$C_6$-alkyl substituted with heterocyclyl, and
(5) $C_1$-$C_6$-alkyl substituted with heteroaryl, or R¹ᴸ and R³ᴸ, together with the atoms to which they are attached can form a substituted or unsubstituted heterocyclic ring, having from 3 to 8 ring atoms, wherein 1-2 ring atoms of the heterocyclic ring system are selected from N, O and S.

In another embodiment, the present invention provides compounds of formula IX:

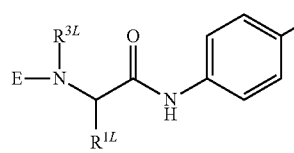
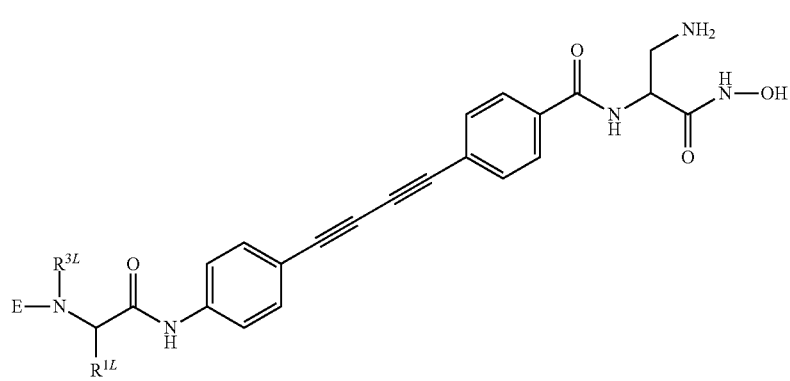

IX or stereoisomers, pharmaceutically acceptable salts, esters, and prodrugs thereof, wherein E is absent or selected from the group consisting of
(1) H,
(2) substituted or unsubstituted $C_1$-$C_6$-alkyl,
(3) substituted or unsubstituted aryl,
(4) substituted or unsubstituted heterocyclyl, and
(5) substituted or unsubstituted heteroaryl, or E and R³ᴸ, together with the atoms to which they are attached can form a substituted or unsubstituted heterocyclic ring, having from 3 to 10 ring atoms, wherein 1-4 ring atoms of the heterocyclic ring system are selected from N, O and S;

R¹ᴸ,R³ᴸ are independently selected from the group consisting of (1) H,
(2) substituted or unsubstituted $C_1$-$C_6$-alkyl,
(3) $C_1$-$C_6$-alkyl substituted with aryl,
(4) $C_1$-$C_6$-alkyl substituted with heterocyclyl, and
(5) $C_1$-$C_6$-alkyl substituted with heteroaryl, or R¹ᴸ and R³ᴸ, together with the atoms to which they are attached can form a substituted or unsubstituted heterocyclic ring, having from 3 to 8 ring atoms, wherein 1-2 ring atoms of the heterocyclic ring system are selected from N, O and S.

In another embodiment, the present invention provides compounds of formula X:

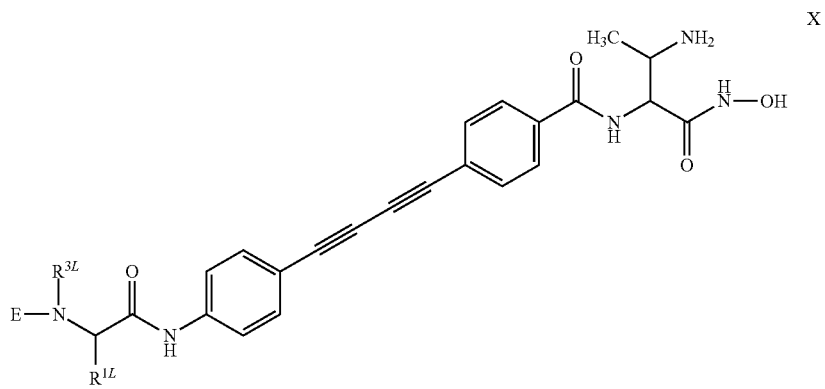

or stereoisomers, pharmaceutically acceptable salts, esters, and prodrugs thereof, wherein E is absent or selected from the group consisting of
  (1) H,
  (2) substituted or unsubstituted $C_1$-$C_6$-alkyl,
  (3) substituted or unsubstituted aryl,
  (4) substituted or unsubstituted heterocyclyl, and
  (5) substituted or unsubstituted heteroaryl,
  or E and $R^{3L}$, together with the atoms to which they are attached can form a substituted or unsubstituted heterocyclic ring, having from 3 to 10 ring atoms, wherein 1-4 ring atoms of the heterocyclic ring system are selected from N, O and S;

$R^{1L}$, $R^{3L}$ are independently selected from the group consisting of
  (1) H,
  (2) substituted or unsubstituted $C_1$-$C_6$-alkyl,
  (3) $C_1$-$C_6$-alkyl substituted with aryl,
  (4) $C_1$-$C_6$-alkyl substituted with heterocyclyl, and
  (5) $C_1$-$C_6$-alkyl substituted with heteroaryl,
  or $R^{1L}$ and $R^{3L}$, together with the atoms to which they are attached can form a substituted or unsubstituted heterocyclic ring, having from 3 to 8 ring atoms, wherein 1-2 ring atoms of the heterocyclic ring system are selected from N, O and S.

In another embodiment, the present invention provides compounds of formula XI:

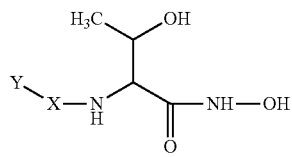

XI or stereoisomers, pharmaceutically acceptable salts, esters, and prodrugs thereof, wherein Y-X taken together, is selected from the group consisting of

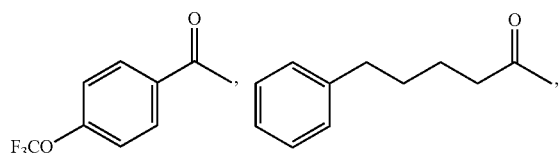

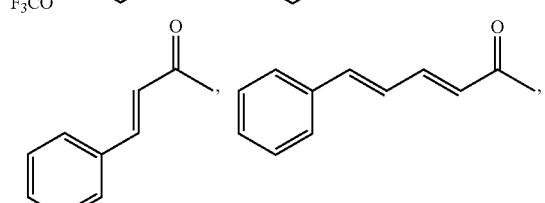

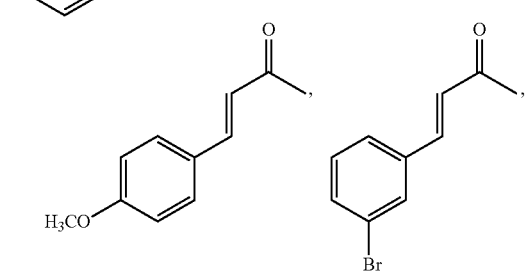

-continued

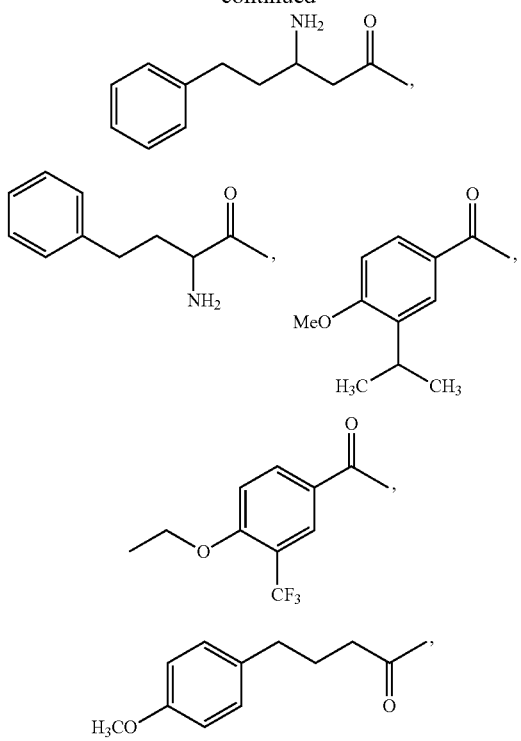

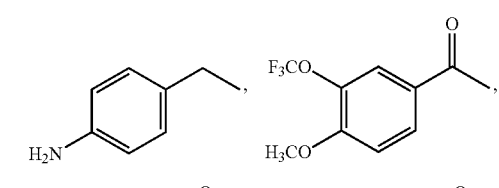

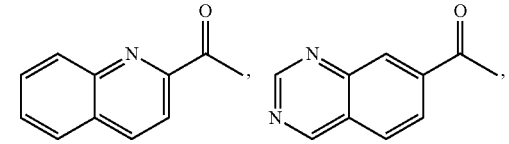

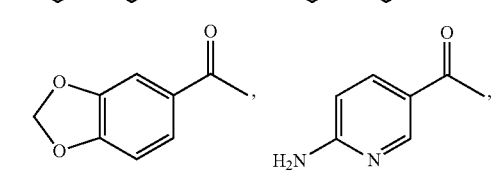

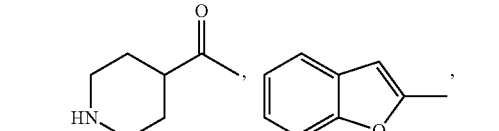

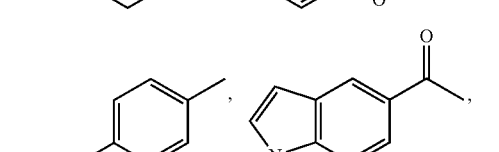

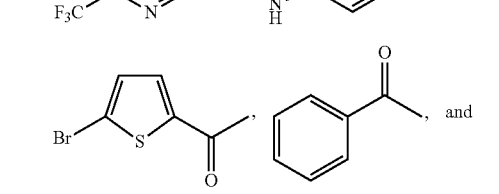

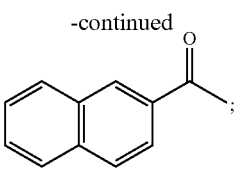

In another embodiment, the present invention provides compounds of formula XII:

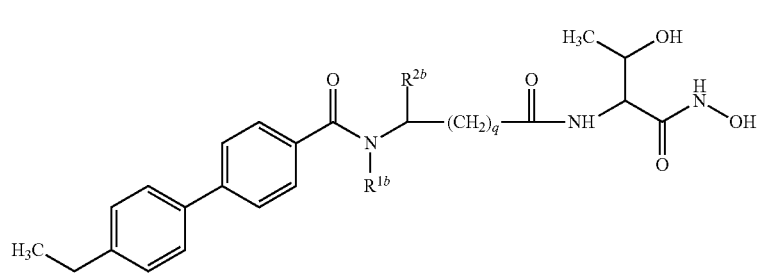

or stereoisomers, pharmaceutically acceptable salts, esters, and prodrugs thereof, wherein
$R^{1b}$ and $R^{2b}$ are independently selected from the group consisting of
(1) H,
(2) substituted or unsubstituted $C_1$-$C_6$-alkyl,
(3) substituted or unsubstituted $C_2$-$C_6$-alkenyl,
(4) substituted or unsubstituted $C_2$-$C_6$-alkenyl,
(5) substituted or unsubstituted aryl,
(6) substituted or unsubstituted heterocyclyl,
(7) substituted or unsubstituted heteroaryl,
(8) $C_1$-$C_6$-alkyl substituted with aryl,
(9) $C_1$-$C_6$-alkyl substituted with heterocyclyl, and
(10) $C_1$-$C_6$-alkyl substituted with heteroaryl;
q is an integer of 0-2;
In another embodiment, the present invention provides compounds of formula XIII:

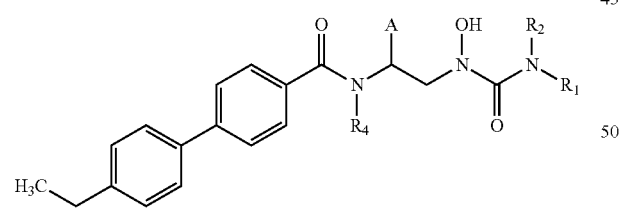

or stereoisomers, pharmaceutically acceptable salts, esters, and prodrugs thereof, wherein
$R_4$ is selected from the group consisting of
(1) H,
(2) substituted or unsubstituted $C_1$-$C_6$-alkyl,
(3) $C_1$-$C_6$-alkyl substituted with aryl,
(4) $C_1$-$C_6$-alkyl substituted with heterocyclyl, and
(5) $C_1$-$C_6$-alkyl substituted with heteroaryl;
A is H or —CH(CH$_3$)OH—;
$R_1$ is H or substituted or unsubstituted $C_{1-6}$-alkyl;
$R_2$ is selected from the group consisting of
(1) H,
(2) substituted or unsubstituted $C_1$-$C_6$-alkyl,
(3) substituted or unsubstituted aryl,
(4) substituted or unsubstituted heterocyclyl,
(5) substituted or unsubstituted heteroaryl,
(6) $C_1$-$C_6$-alkyl substituted with aryl,
(7) $C_1$-$C_6$-alkyl substituted with heterocyclyl,
(8) $C_1$-$C_6$-alkyl substituted with heteroaryl,
or $R^1$ and $R^2$ together with the N atom to which they are attached can form a substituted or unsubstituted heterocyclic ring, having from 3 to 10 ring atoms, wherein 1-2 ring atoms of the heterocyclic ring system are selected from N, O and S.

In another embodiment, the present invention provides compounds of formula XIV:

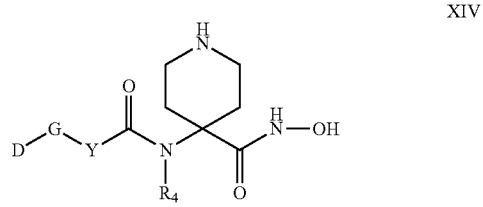

or stereoisomers, pharmaceutically acceptable salts, esters, and prodrugs thereof, wherein D-G-Y taken together is selected from the group consisting of

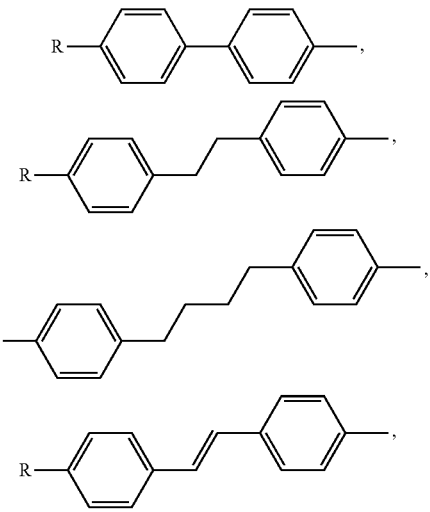

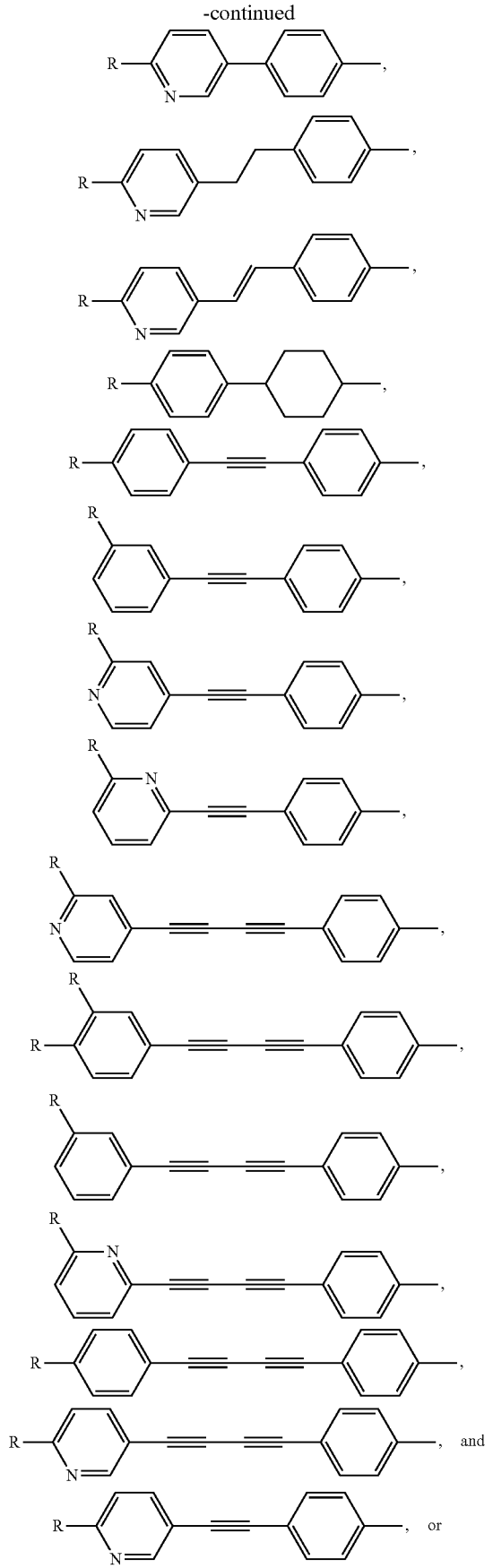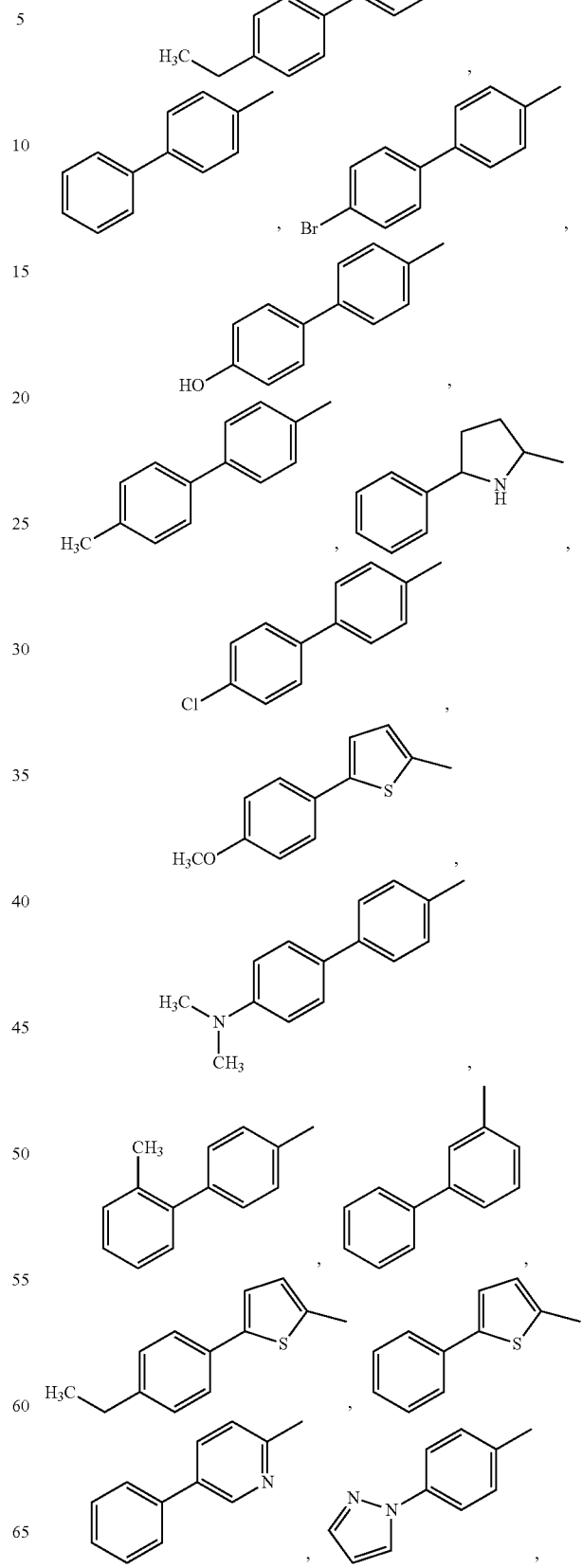

-continued

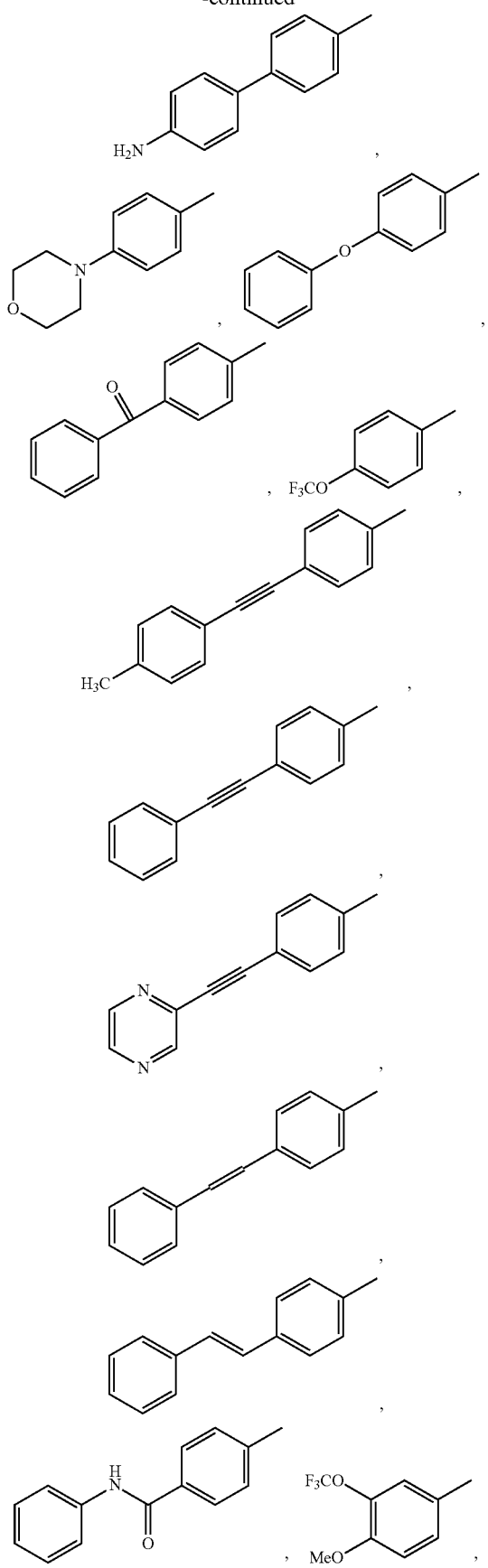

-continued

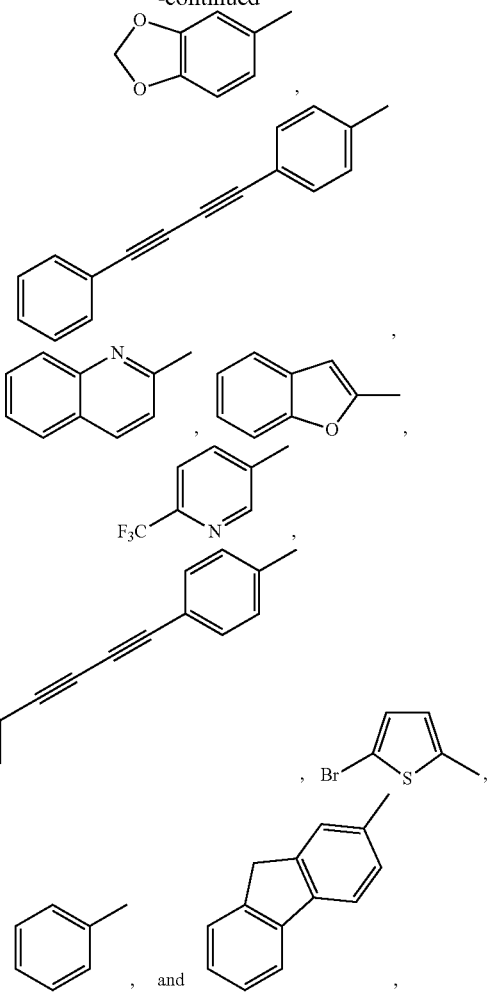

Wherein
R is selected from the group consisting of —CH$_3$, —C$_2$H$_5$, —CH$_2$OH, —OH, —OCH$_3$, —OC$_2$H$_5$, —OCF$_3$, —CN, —NO$_2$, —CO$_2$H, —CO$_2$CH$_3$, —CONH$_2$, —NH$_2$, —F, —Cl, —Br, —CF$_3$, —N(CH$_3$)$_2$, —NHSO$_2$CH$_3$, and —NHCOCH$_3$;
R$_4$ is selected from the group consisting of
 (1) H,
 (2) substituted or unsubstituted C$_1$-C$_6$-alkyl,
 (3) C$_1$-C$_6$-alkyl substituted with aryl,
 (4) C$_1$-C$_6$-alkyl substituted with heterocyclyl, and
 (5) C$_1$-C$_6$-alkyl substituted with heteroaryl.
In another embodiment, the present invention provides compounds of formula XV:

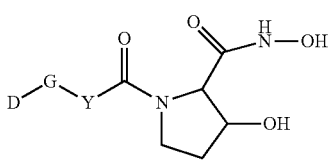

XV or stereoisomers, pharmaceutically acceptable salts, esters, and prodrugs thereof, wherein D-G-Y taken together, is selected from the group consisting of

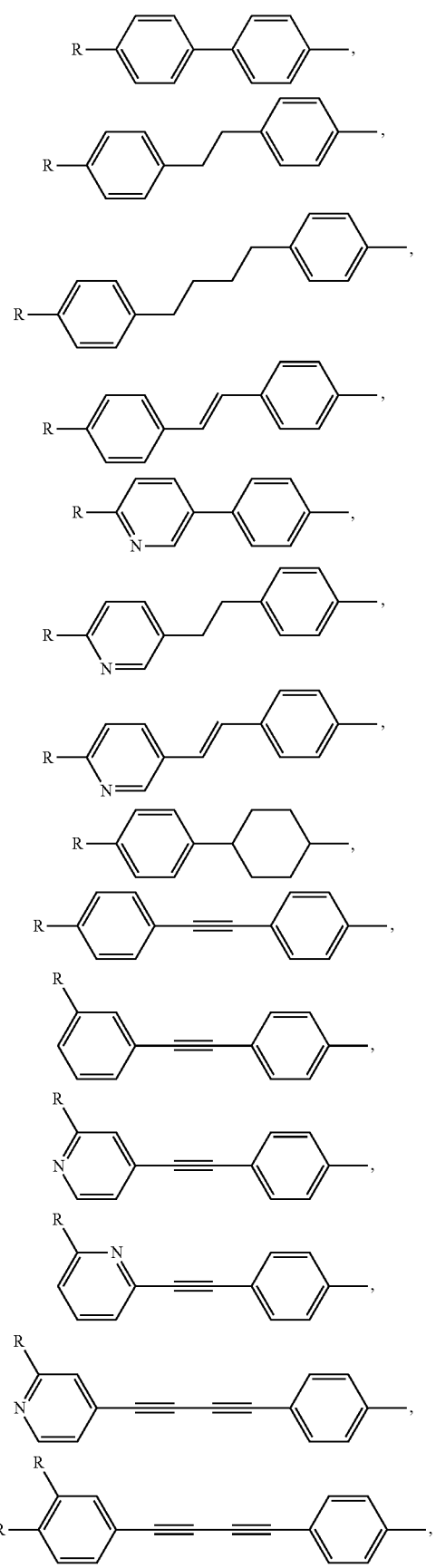
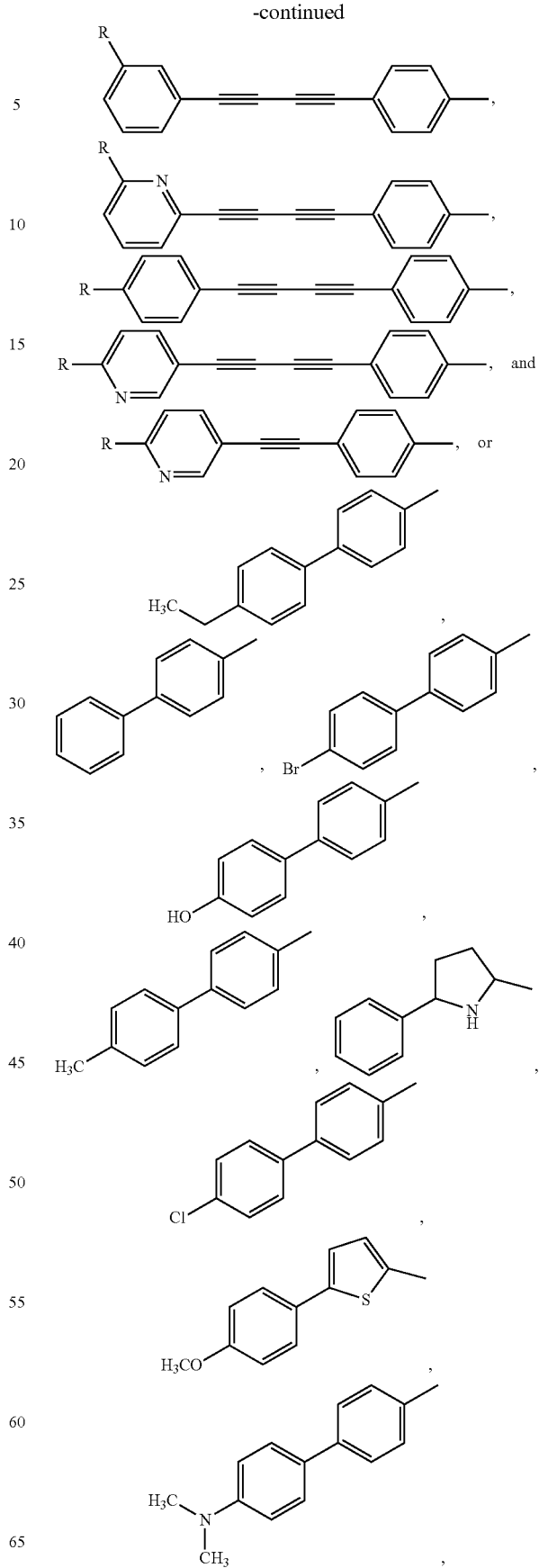

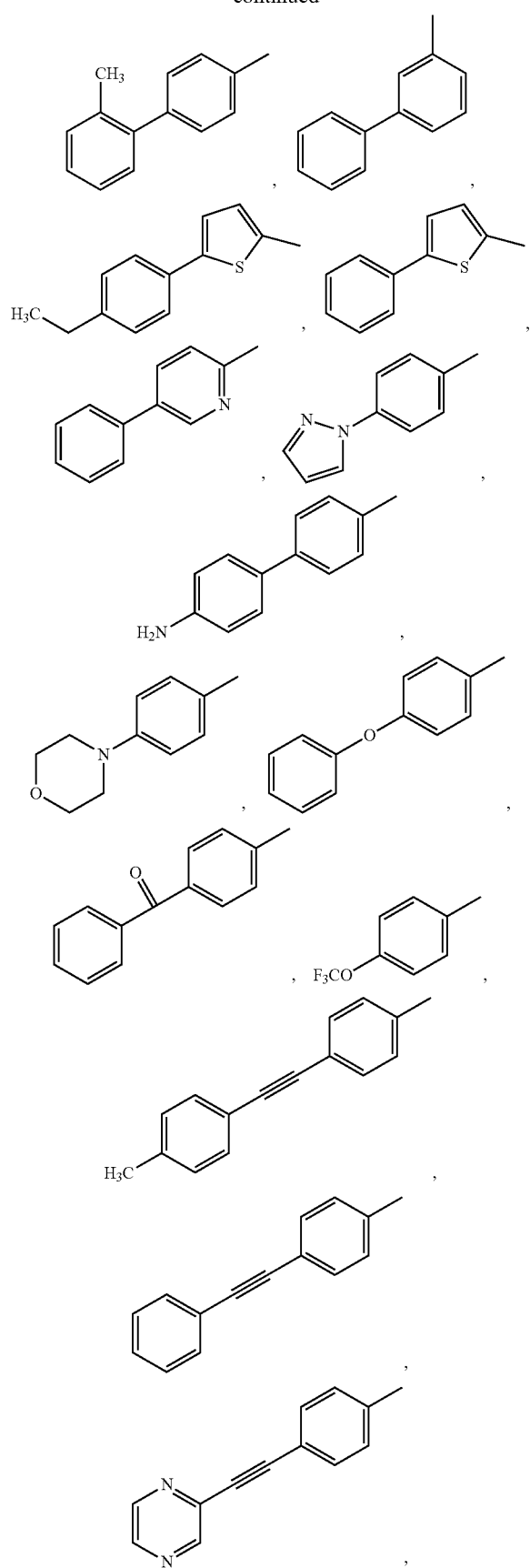
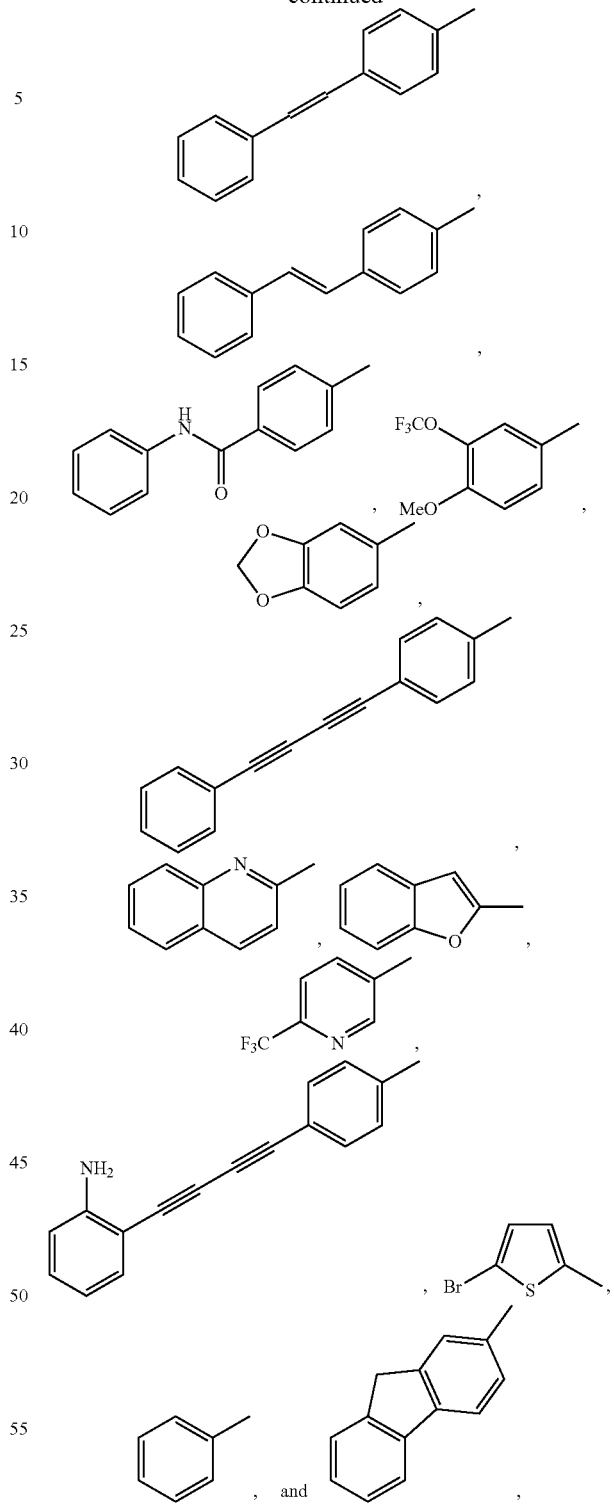
Wherein
R is selected from the group consisting of —CH$_3$, —C$_2$H$_5$, —CH$_2$OH, —OH, —OCH$_3$, —OC$_2$H$_5$, —OCF$_3$, —CN, —NO$_2$, —CO$_2$H, —CO$_2$CH$_3$, —CONH$_2$, —NH$_2$, —F, —Cl, —Br, —CF$_3$, —N(CH$_3$)$_2$, —NHSO$_2$CH$_3$, and —NH-COCH$_3$;
In another embodiment, the present invention provides compounds of formula XVI:

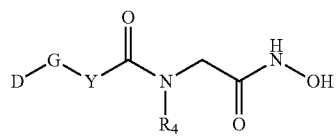
or stereoisomers, pharmaceutically acceptable salts, esters, and prodrugs thereof, wherein D-G-Y taken together, is selected from the group consisting of
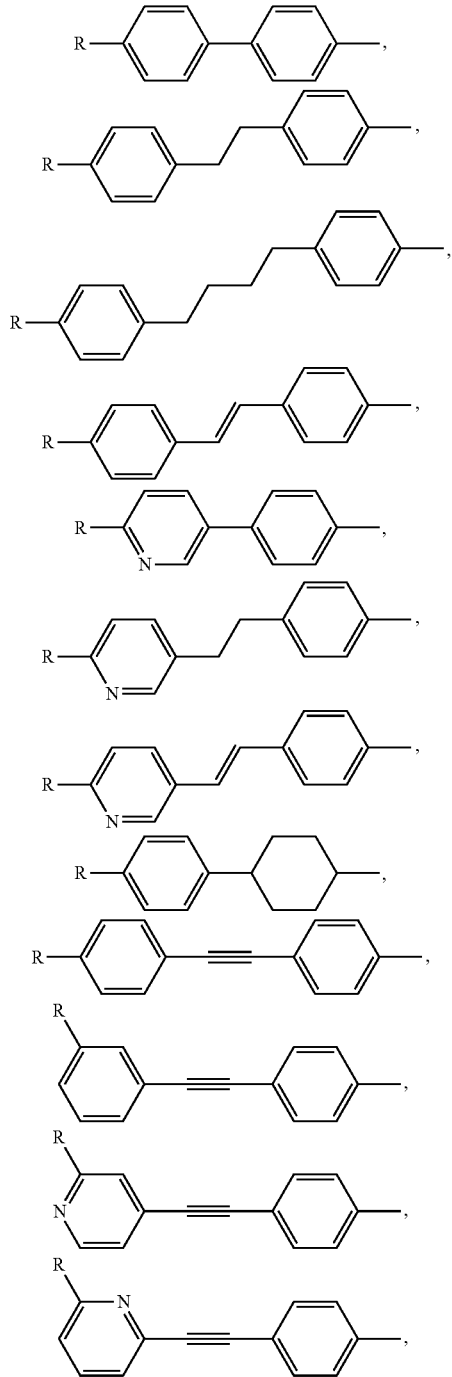
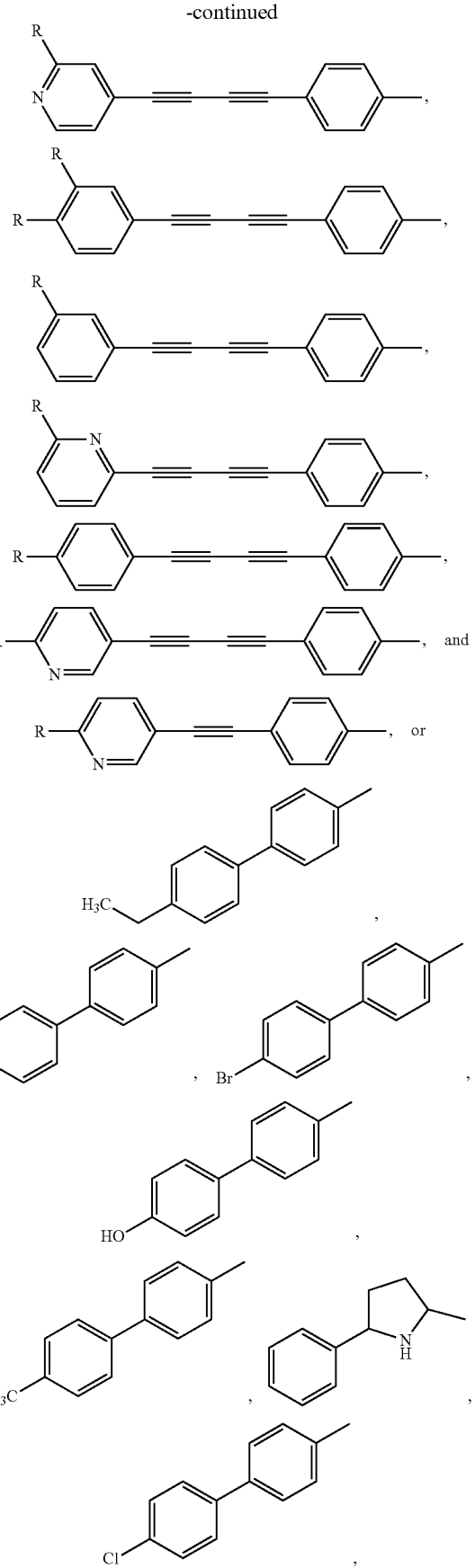

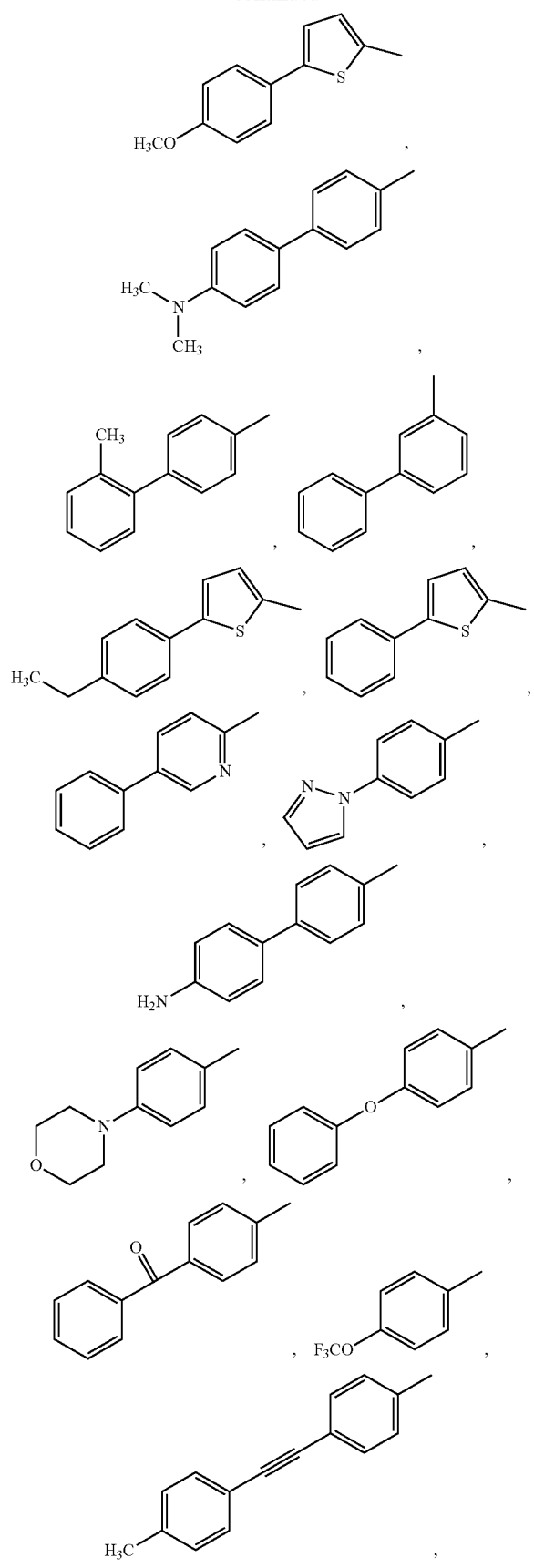
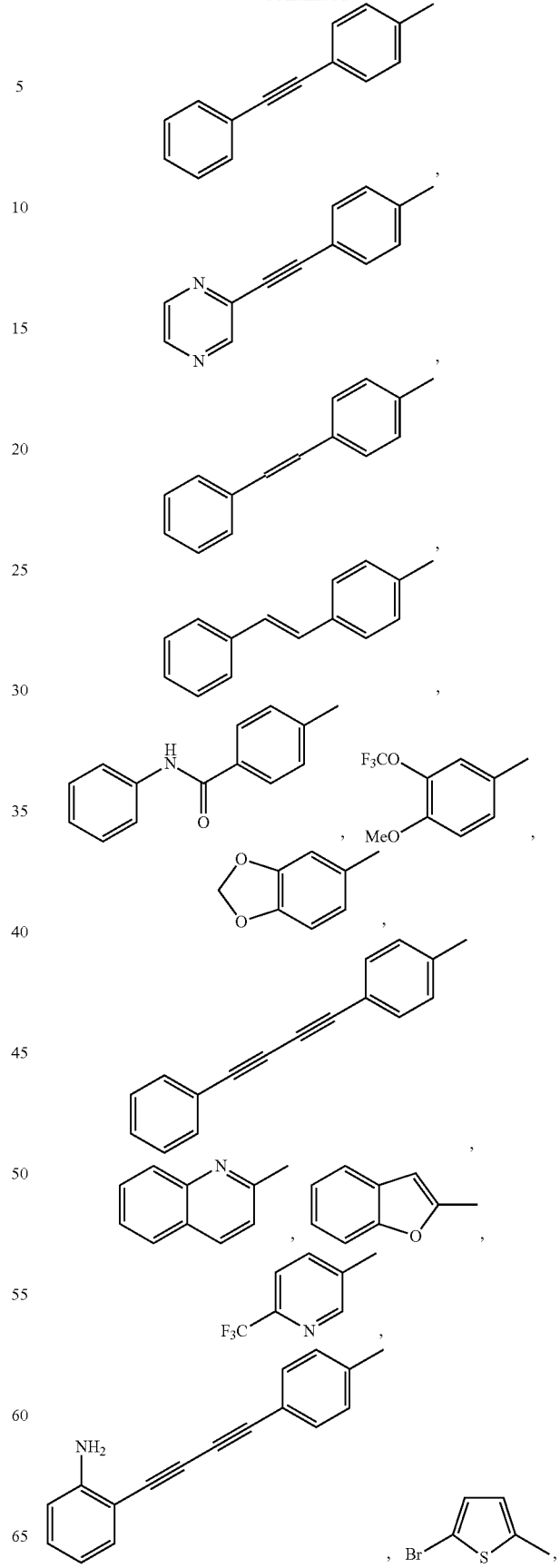

Wherein

R is selected from the group consisting of —CH$_3$, —C$_2$H$_5$, —CH$_2$OH, —OH, —OCH$_3$, —OC$_2$H$_5$, —OCF$_3$, —CN, —NO$_2$, —CO$_2$H, —CO$_2$CH$_3$, —CONH$_2$, —NH$_2$, —F, —Cl, —Br, —CF$_3$, —N(CH$_3$)$_2$, —NHSO$_2$CH$_3$, and —NH-COCH$_3$;

R$_4$ is selected from the group consisting of
(1) H,
(2) substituted or unsubstituted C$_1$-C$_6$-alkyl,
(3) C$_1$-C$_6$-alkyl substituted with aryl,
(4) C$_1$-C$_6$-alkyl substituted with heterocyclyl, and
(5) C$_1$-C$_6$-alkyl substituted with heteroaryl;

In another embodiment, the present invention provides compounds of formula XVII:

XVII or stereoisomers, pharmaceutically acceptable salts, esters, and prodrugs thereof, wherein D-G-Y taken together, is selected from the group consisting of

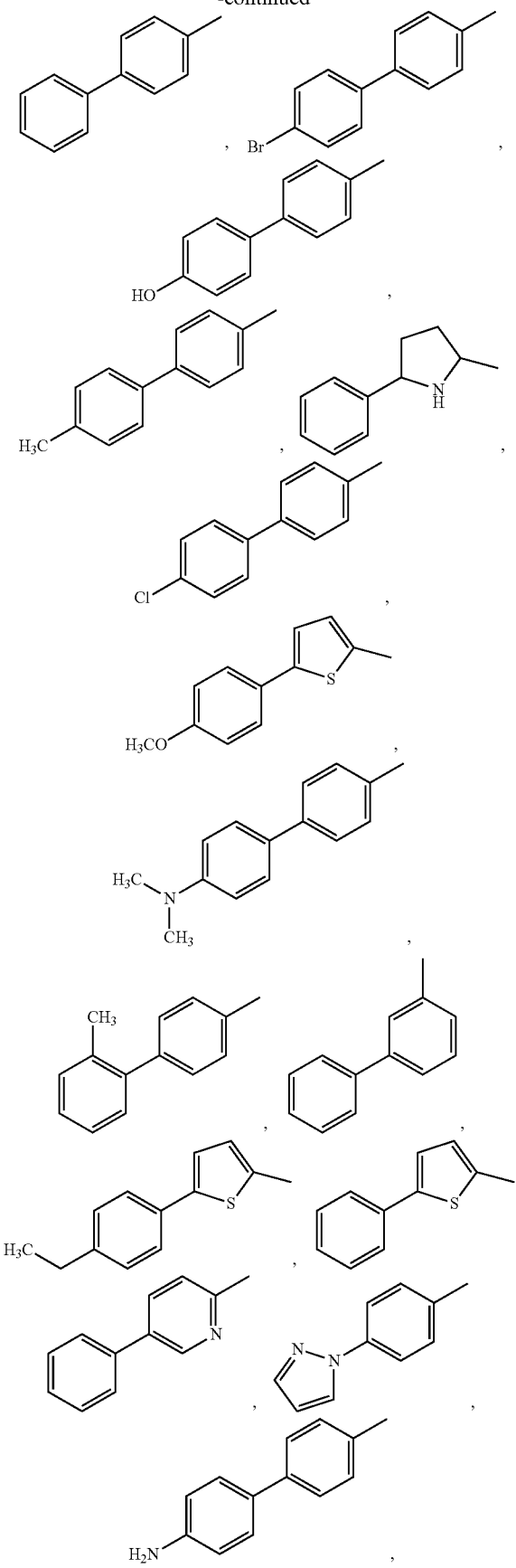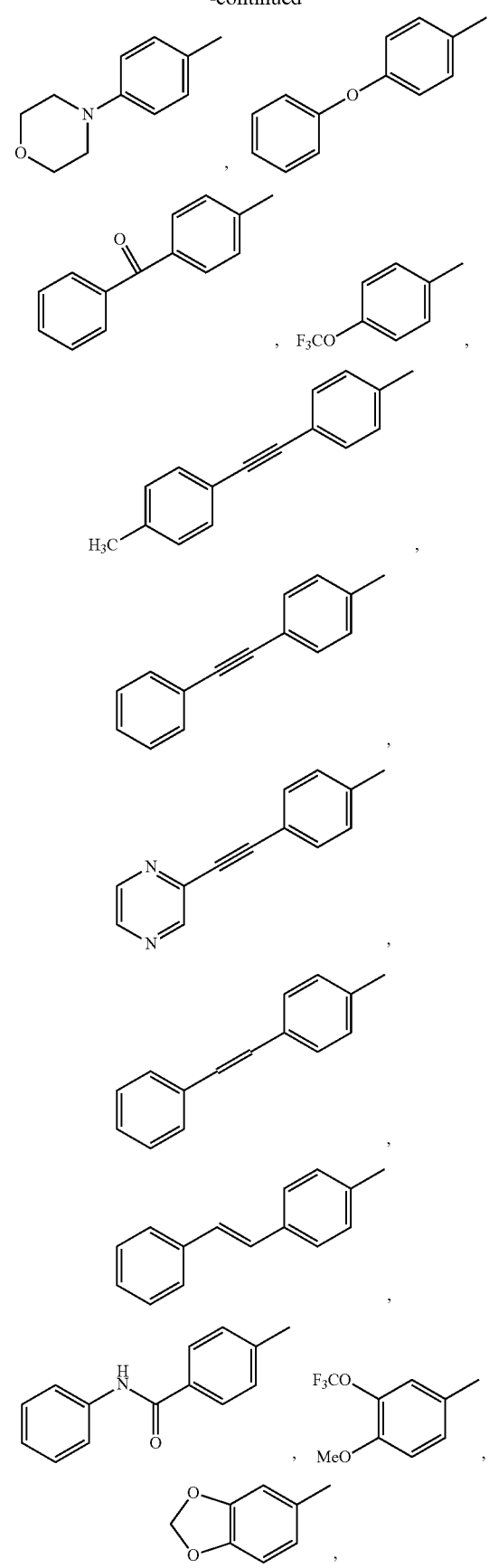

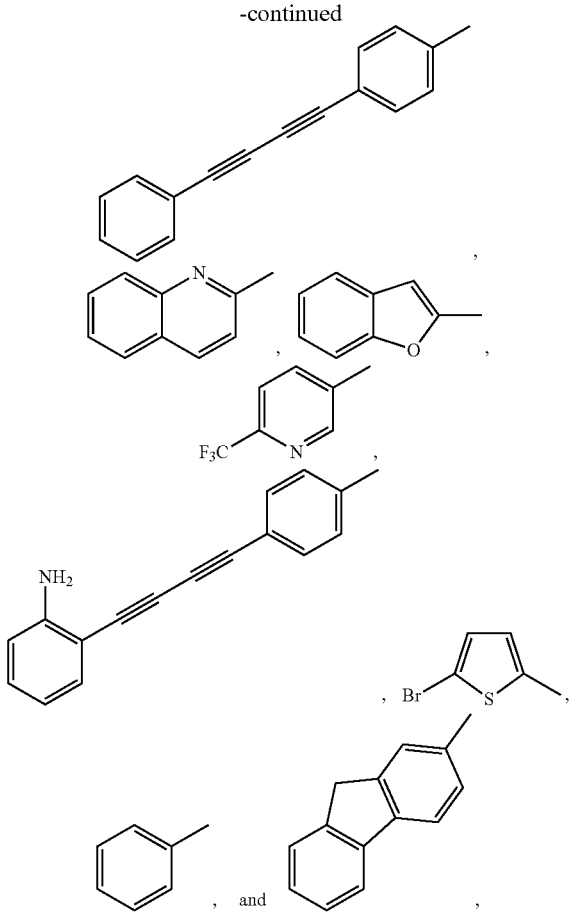

Wherein

R is selected from the group consisting of —CH$_3$, —C$_2$H$_5$, —CH$_2$OH, —OH, —OCH$_3$, —OC$_2$H$_5$, —OCF$_3$, —CN, —NO$_2$, —CO$_2$H, —CO$_2$CH$_3$, —CONH$_2$, —NH$_2$, —F, —Cl, —Br, —CF$_3$, —N(CH$_3$)$_2$, —NHSO$_2$CH$_3$, and —NHCOCH$_3$;

In one aspect, the invention provides a method of inhibiting a deacetylase enzyme in a gram-negative bacteria, thereby affecting bacterial growth, comprising administering to a patient in need of such inhibition a compound of formula I.

In another aspect, the invention provides a method of inhibiting LpxC, thereby modulating the virulence of a bacterial infection, comprising administering to a patient in need of such inhibition a compound of formula I.

In some embodiments of the method of inhibiting LpxC using a compound of formula I, the IC$_{50}$ value of the compound is less than or equal to 10 µM with respect to LpxC. In other such embodiments, the IC$_{50}$ value is less than or equal to 1 µM, is less than or equal to 0.1 µM, is less than or equal to 0.050 µM, is less than or equal to 0.030 µM, is less than or equal to 0.025 µM, or is less than or equal to 0.010 µM.

In one aspect of the invention, methods for treating a subject comprising administering to the subject an antibacterially effective amount of a compound of formula I, together with a pharmaceutically acceptable carrier is provided. In a preferred embodiment of the method of treatment, the subject is a mammal and some embodiments, a human.

In another aspect, the invention provides a method of administering an inhibitory amount of a compound of formula I to fermentative or non-fermentative gram-negative bacteria. In a preferred embodiment of the method of administering an inhibitory amount of a compound of formula I to fermentative or non-fermentative gram-negative bacteria, the gram-negative bacteria are selected from the group consisting of *Pseudomonas aeruginosa, Stenotrophomonas maltophila, Burkholderia cepacia, Alcaligenes xylosoxidans, Acinetobacter, Enterobacteriaceae, Haemophilus, Neisseria* species.

In another embodiment, the invention provides a method of administering an inhibitory amount of a compound of formula I to gram-negative bacteria, such as Enterobacteriaceae that is selected from the group consisting of organisms such as *Serratia, Proteus, Klebsiella, Enterobacter, Citrobacter, Salmonella, Providencia, Morganella, Cedecea,* and *Edwardsiella* species and *Escherichia coli*.

Another embodiment of the invention provides a pharmaceutical composition comprising an effective amount of a compound of Formula I with a pharmaceutically acceptable carrier thereof.

Pharmaceutical formulations according to the present invention are provided which include any of the compounds described above in combination with a pharmaceutically acceptable carrier.

Another embodiment of the invention provides a method of co-administering the compound of formula I with other therapeutic agents that are selected for their particular usefulness against the condition that is being treated.

For example, the compound of formula I is useful in combination with other anti-bacterial agents. The compound of formula I augments the sensitivity of gram-negative bacteria to existing classes of antibacterials. Combinations of the presently disclosed compounds with other anti-bacterial agents are within the scope of the invention. Such anti-bacterial agents include, but are not limited to, erythromycin, rifampicin, Nalidixic acid, carbenicillin, bacitracin, cycloserine, fosfomycin, and vancomycin.

A further aspect of the invention is the use of LpxC inhibitors for the treatment of an infection, particularly a bacterial infection. A bacterial infection treated with the compounds of the invention can be a primary infection or a co-infection caused by a species of bacteria and one or more additional infectious agents selected from the group consisting of bacteria, virus, parasite and fungus.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The compounds of the invention can be used for treating conditions caused by the bacterial production of endotoxin and, in particular, by gram-negative bacteria and bacteria that use LpxC in the biosynthesis of lipopolysaccharide (LPS) or endotoxin.

The compounds of the invention also are useful in the conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB). For these conditions, treatment includes the administration of a compound of the invention, or a combination of compounds of the invention, optionally with a second agent wherein the second agent is a second antibacterial agent or a second non-antibacterial agent.

For sepsis, septic shock, systemic inflammation, localized inflammation, chronic obstructive pulmonary disease (COPD) and acute exacerbations of chronic bronchitis (AECB), preferred second non-antibacterial agents include antiendotoxins including endotoxin receptor-binding antibodies, endotoxin-binding antibodies, antiCD14-binding protein antibodies antilipopolysaccharide-binding protein antibodies and tyrosine kinase inhibitors.

In treatment of serious or chronic respiratory tract infections, the compounds of the present invention may also be used with second non-antibacterial agents administered via inhalation. Preferred non-antibacterial agents used in this treatment include anti-inflammatory steroids, non-steroidal anti-inflammatory agents, bronchiodilators, mucolytics, anti-asthma therapeutics and lung fluid surfactants. In particular, the non-antibacterial agent may be selected from a group consisting of albuterol, salbuterol, budesonide, beclomethasone, dexamethasone, nedocromil, beclomethasone, fluticasone, flunisolide, triamcinolone, ibuprofin, rofecoxib, naproxen, celecoxib, nedocromil, ipratropium, metaproterenol, pirbuterol, salmeterol, bronchiodilators, mucolytics, calfactant, beractant, poractant alfa, surfaxin and pulmozyme (also called dornase alfa).

The compounds of the invention can be used, alone or in combination with a second antibacterial agent for the treatment of a serious or chronic respiratory tract infection including serious lung and nosocomial infections such as those caused by *Enterobacter aerogenes*, *Enterobacter cloacae*, *Escherichia coli*, *Klebsiella pneumoniae*, *Klebsiella oxytoca*, *Proteus mirabilis*, *Serratia marcescens*, *Stenotrophomonas maltophilia*, *Pseudomonas aeruginosa*, *Burkholderia cepacia*, *Acinetobacter calcoaceticus*, *Alcaligenes xylosoxidans*, *Flavobacterium meningosepticum*, *Providencia stuartii* and *Citrobacter freundi*, community lung infections such as those caused by *Haemophilus Influenzae*, *Legionella* species, *Moraxella catarrhalis*, *Branhamella catarrhalis*, *Enterobacter* species, *Acinetobacter* species, *Klebsiella* species, and *Proteus* species, and infections caused by other bacterial species such as *Neisseria* species, *Shigella* species, *Salmonella* species, *Helicobacter pylori*, *Vibrionaceae* and *Bordetella* species as well as the infections is caused by a *Brucella* species, *Francisella tularensis* and/or *Yersinia Pestis*.

When used for treating Gram-negative bacteria, the compounds of the present invention can be used to sensitize gram-negative bacteria to the effects of a second agent.

When the compounds of the present invention are used in combination with a second antibacterial agent, non-limiting examples of antibacterial agents may be selected from the following groups:

(1) Macrolides or ketolides such as erythromycin, azithromycin, clarithromycin and telithromycin;
(2) Beta-lactams including penicillin, cephalosporin, and carbapenems such as carbapenem, imipenem, and meropenem;
(3) Monobactams such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cefpirome, cefepime, and astreonam;
(4) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin;
(5) Antibacterial sulfonamides and antibacterial sulphanilamides, including para-aminobenzoic acid, sulfadiazine, sulfisoxazole, sulfamethoxazole and sulfathalidine;
(6) Aminoglycosides such as streptomycin, neomycin, kanamycin, paromycin, gentamicin, tobramycin, amikacin, netilmicin, spectinomycin, sisomicin, dibekalin and isepamicin;
(7) Tetracyclines such as tetracycline, chlortetracycline, demeclocycline, minocycline, oxytetracycline, methacycline, doxycycline;
(8) Rifamycins such as rifampicin (also called rifampin), rifapentine, rifabutin, bezoxazinorifamycin and rifaximin;
(9) Lincosamides such as lincomycin and clindamycin;
(10) Glycopeptides such as vancomycin and teicoplanin;
(11) Streptogramins such as quinupristin and daflopristin;
(12) Oxazolidinones such as linezolid;
(13) Polymyxin, colistin and colymycin;
(14) Trimethoprim and bacitracin.

The second antibacterial agent may be administered in combination with the compounds of the present inventions wherein the second antibacterial agent is administered prior to, simultaneously, or after the compound or compounds of the present invention. When simultaneous administration of a compound of the invention with a second agent is desired and the route of administration is the same, then a compound of the invention may be formulated with a second agent into the same dosage form. An example of a dosage form containing a compound of the invention and a second agent is a tablet or a capsule.

When used for treating a serious or chronic respiratory tract infections, the compounds of the invention may be used alone or in combination with a second antibacterial agent administered via inhalation. In the case of inhalation, a preferred second antibacterial agent is selected from a group consisting of tobramycin, gentamicin, aztreonam, ciprofloxacin, polymyxin, colistin, colymycin, azithromycin and clarithromycin.

Pharmaceutical Compositions

Pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials that can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions that can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution that, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions that are compatible with body tissues.

Compositions for rectal or vaginal administration are preferably suppositories that can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations of the invention may be delivered using an aerosol forming device, such as a jet, vibrating porous plate or ultrasonic nebulizer, preferably selected to allow the formation of a aerosol particles having with a mass medium average diameter predominantly between 1 to 5 µm. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5 µm. Predominantly in this application means that at least 70% but preferably more than 90% of all generated aerosol particles are 1 to 5 µm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb and AeroDose vibrating porous plate nebulizers (AeroGen, Inc., Sunnyvale, Calif.), Sidestream7 nebulizers (Medic-Aid Ltd., West Sussex, England), Pari LC7 and Pari LC Star7 jet nebulizers (Pari Respiratory Equipment, Inc., Richmond, Va.), and Aerosonic (DeVilbiss Medizinische Produkte (Deutschland) GmbH, Heiden, Germany) and UltraAire7 (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of the compound(s) of this invention per day in single or multiple doses.

Methods of formulation are well known in the art and are disclosed, for example, in Remington: The Science and Practice of Pharmacy, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

A "kit" as used in the instant application includes a container for containing the pharmaceutical compositions and may also include divided containers such as a divided bottle or a divided foil packet. The container can be in any conventional shape or form as known in the art that is made of a pharmaceutically acceptable material, for example a paper or cardboard box, a glass or plastic bottle or jar, a resealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil that is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It maybe desirable to provide a written memory aid, where the written memory aid is of the type containing information and/or instructions for the physician, pharmacist or other health care provider, or subject, e.g., in the form of numbers next to the tablets or capsules whereby the numbers correspond with the days of the regimen that the tablets or capsules so specified should be ingested or a card that contains the same type of information. Another example of such a memory aid is a calendar printed on the card e.g., as follows "First Week, Monday, Tuesday," . . . etc. . . . "Second Week, Monday, Tuesday, . . . ." etc. Other variations of memory aids will be readily apparent. A "daily dose" can be a single tablet or capsule or several tablets or capsules to be taken on a given day. When the kit contains separate compositions, a daily dose of one or more compositions of the kit can consist of one tablet or capsule while a daily dose of another one or more compositions of the kit can consist of several tablets or capsules.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter, that indicates the number of daily doses that has been dispensed. Another example of such a memory-aid is a battery-powered micro-chip memory coupled with a liquid crystal readout, or audible reminder signal that, for example, reads out the date that the last daily dose has been taken and/or reminds one when the next dose is to be taken.

The kits of the present invention may also include, in addition to LpxC inhibitors, one or more additional pharmaceutically active compounds. Preferably, the additional compound is another LpxC inhibitor or another compound useful to bacterial infections. The additional compounds may be administered in the same dosage form as the LpxC inhibitor or in different dosage forms. Likewise, the additional compounds can be administered at the same time as the LpxC inhibitor or at different times.

Compositions of the present compounds may also be used in combination with other known antibacterial agents of similar spectrum to (1) synergistically enhance treatment of severe Gram-negative infections covered by the spectrum of this compound or (2) add coverage in severe infections in which multiple organisms are suspected in which another agent of a different spectrum may be required in addition to this compound. Potential agents include members of the aminoglycosides, penicillins, cephalosporins, fluoroquinolones, macrolides, glycopeptides, lipopeptides and oxazolidinones. The treatment can involve administering a composition having both active agents or administration of the inventive compounds followed by or preceded by administration of an additional active antibacterial agent.

Characterization and Purification Methods

Referring to the examples that follow, compounds of the present invention were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburg, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). All masses are reported as those of the protonated parent ions.

GCMS analysis was performed on a Hewlet Packard instrument (HP6890 Series gas chromatograph with a Mass Selective Detector 5973; injector volume: 1 µL; initial column temperature: 50° C.; final column temperature: 250 C; ramp time: 20 minutes; gas flow rate: 1 mL/min; column: 5% phenyl methyl siloxane, Model #HP 190915-443, dimensions: 30.0 m×25 m×0.25 m).

Nuclear magnetic resonance (NMR) analysis was performed with a Varian 300 Mhz NMR (Palo Alto, Calif.). The spectral reference was either TMS or the known chemical shift of the solvent. Some compound samples were run at elevated temperatures (e.g. 75° C.) to promote increased sample solubility.

The purity of some of the invention compounds was assessed by elemental analysis (Desert Analytics, Tuscon, Ariz.)

Melting points were determined on a Laboratory Devices MeI-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, ethyl acetate, hexane, acetone, aqueous hydroxyamine and triethyl amine. Typical solvents employed for the reverse phase HPLC were varying concentrations of acetonitrile and water with 0.1% trifluoroacetic acid.

Compounds of the present invention can be readily synthesized using the methods described herein, or other methods, that are well known in the art. For example, the synthesis of hydroxamic acids or similar scaffolds having a wide variety of substituents are comprehensively reviewed in Kline T, Andersen N H, Harwood E A, Bowman J, Malanda A, Endsley S, Erwin A L, Doyle M, Fong S, Harris A L, Mendelsohn B, Mdluli K, Raetz C R, Stover C K, Witte P R, Yabannavar A, Zhu S., "Potent, novel in vitro inhibitors of the *Pseudomonas aeruginosa* deacetylase LpxC," *J Med Chem* 2002 Jul. 4; 45(14):3112-29; Patchett, A. A., Nargund, R., Chen, M.-H., Nishi, H. R., U.S. Pat. No. 5,925,659, 1999; Pirrung, M. C., Chau, J. H., "A Convenient Procedure for the Preparation of Amino Acid Hydroxamates from Esters," *J. Org. Chem.* 1995, 60, 8084-8085; Nhu, K., Patel, D. V., "A New and Efficient Solid Phase Synthesis of Hydroxamic Acids," *J. Org. Chem.* 1997, 62, 7088-7089; Patel, D., Nhu, K., "Methods for Solid-phase Synthesis of Hydroxylamine Compounds and Derivatives, and Combinatorial Libraries Thereof," PCT WO 98/18754, 1998, Mellor, S. L., McGuire, C., Chan, W. C., "N-Fmoc-aminoxy-2-chlortrityl Polystyrene Resin: A Facile Solid-phase Methodology for the Synthesis of Hydroxamic Acids," *Tetrahedron Lett.,* 1997, 38, 3311-3314; Khan, S. I., Grinstaff, M. W., "A Facile and Convenient Solid-phase Procedure for Synthesizing Nucleoside Hydroxamic Acids," *Terahedron. Lett.,* 1998, 39, 8031-8034; Zhang, Y., Li, D., Houtman, J. C., Witiak, D. T., Seltzer, J., Bertics, P. J., Lauhon, C. T., "Design, Combinatorial Chemical Synthesis, and in vitro Characterization of Novel Urea Based Gelatinase Inhibitors," *Bioorg. Med. Chem. Lett.,* 1999, 9, 2823-2826; Ito, Y., Inubushi, Y., Zenbayashi, M., Tomita, S., Saegusa, T., "Synthetic Reactions by Complex Catalysts. XXXI, A Novel and Versatile Method of Heterocycle Synthesis," *J. Am. Chem. Soc.,* 1973, 95, 4447-4448; Ito, Y., Ito, I., Hirao, T., Saegus, T., "Synthetic Reactions by Complex Catalysts XXXV," *Syn. Commun.* 1974, 4, 97-103; Witte, H., Seliger, W., "Cyclische Imidsaurester aus Nitrilen and Aminoalkoholen," *Liebigs Ann. Chem.,* 1974, 996-1009; Pattenden, G., Thom. S. M., "Naturally Occurring Linear Fused Thiazoline-Thiazole Containing Metabolites: Total Synthesis of (–) Didehydromirabazole A, a Cytotoxic Alkaloid from Blue-Green Algae," *J. Chem. Soc. Perkin Trans* 1, 1993, 1629-1636; Boyce, R. J., Mulqueen, G. C., Pattenden, G., "Total Synthesis of Thiangazole, A Novel Naturally Occurring HIV-1 Inhibitor from *Polyangium* sp." *Tetrahedron,* 1995, 51, 7321-7330; Galeotti, N., Plagnes, E., Jouin, P., "Synthesis of Peptidyl Aldehydes from Thiazolines," *Tetrahedron. Lett.* 1997, 38, 2459-2462; Charette, A. B., Chua, P., "Mild Method for the Synthesis of Thiazolines from Secondary and Tertiary Amides," *J. Org. Chem.,* 1998, 63, 908-909; Bergeron, R. J., Wiegand, J., McManis, J. S., McCosar, B. H., Weimar, W. R., Brittenham, G. M., Smith, R. E., "Effects of C-4 Stereochemistry and C-4' Hydroxylation on the Iron Clearing Efficiency and Toxicity of Desferrithiocin Analogues," *J. Med. Chem.* 1999, 42, 2432-2440; Raman, P., Razavik H., Kelly, J. W., "Titanium (IV)-mediated Tandem Deprotection-cyclodehydration of Protected Cysteine N-Amides: Biomimetic Synthesis of Thiazoline- and Thiazole-containing Heterocycles," *Org. Lett.,* 2000, 2, 3289-3292; Fernandez, X., Fellous, R., Dunach, E., "Novel Synthesis of 2-Thioazolines," *Tetrahedron Lett,* 2000, 41, 3381-3384. Wipf, P., Miller, C. P., Venkatraman, S., Fritch, P., "C. Thiolysis of Oxazolinenes: A New, Selective Method for the Direct Conversion of Peptide Oxazolines into Thiazolines," *Tetrahedron Lett.,* 1995, 36, 6395-6398, which are incorporated herein by reference.

The synthesis of other non-hydroxamates compounds or more generally zinc binding groups are reviewed in Pirrung, M. C., Tumey, L. N., Raetz, C. R. H., Jackman, J. E., Snehalatha, K., McClerren, A. L., Fierke, C. A., Gantt, S. L., Rusche, K. M., "Inhibition of the Antibacterial Target UDP-(3-O-acyl)-N-acetylglucosamine Deacetylase (LpxC): Isoxazoline Zinc Amidase Inhibitors Bearing Diverse Metal Binding Groups," Journal of Medicinal Chemistry (2002), 45(19), 4359-4370; Jackman, J. E., Fierke, C. A., Tumey, L. N., Pirrung, M., Uchiyama, T., Tahir, S. H., Hindsgaul, O., Raetz, C. R. H., "Antibacterial agents that target lipid A biosynthesis in gram-negative bacteria: inhibition of diverse UDP-3-O—(R-3-hydroxymyristoyl)-N-acetylglucosamine deacetylases by substrate analogs containing zinc binding motifs," Journal of Biological Chemistry (2000), 275(15), 11002-11009; Brooks, C. D. W., Summers, J. B., "Modulators of Leukotriene Biosynthesis and Receptor Activation," Journal of Medicinal Chemistry (1996), 39(14), 2629-2654; Jeng, A. Y., De Lombaert, S., "Endothelin converting enzyme inhibitors," Current Pharmaceutical Design (1997), 3(6), 597-614; Zask, A., Levin, J. I., Killar, L. M., Skotnicki, J. S., "Inhibition of matrix metalloproteinases: structure based design," Current Pharmaceutical Design (1996), 2(6), 624-661;

Skotnicki, J. S., DiGrandi, M. J., Levin, J. I., Chemical and Screening Sciences, Wyeth Research, New York, N.Y., USA. Current Opinion in Drug Discovery & Development (2003), 6(5), 742-759.

The foregoing may be better understood by reference to the following examples, that are presented for illustration and not to limit the scope of the inventive concepts.

EXAMPLES

The following are abbreviations used in the examples:
AcOH: Acetic acid
aq: Aqueous
ATP: Adenosine triphosphate
Boc: tert-butoxycarbonyl
Boc-Thr(OBn)-OH 3-(R)-Benzyloxy-2-(S)-tert-butoxycarbonylamino-butyric acid.
DAP or Dap: Diaminopropionate
DCM: 4-(Dicyanomethylene)-2-methyl-6-(4-dimethylaminostyryl)-4H-pyran
DEAD: Diethyl azodicarboxylate
DIEA: Diisopropylethylamine
DME: 1,2-dimethoxyethane
DMF: N,N-Dimethylformamide
DMSO: Dimethyl sulfoxide
DPPA: Diphenyl phosphoryl azide
$Et_3N$: Triethylamine
EDC: N-(3-Dimethylaminopropyl)-N'-ethylcarbodiimide
EDCI: 1-(3-dimethylaminopropyl)-3-ethylcarbodiimide
EtOAc: Ethyl acetate
EtOH: Ethanol
Fmoc: 9-fluorenylmethoxycarbonyl
Gly-OH: glycine
HATU: O-(7-azabenzotriaazol-1-yl)-N,N,N'N'=tetramethyluronium hexafluorophophate
HBTU: 2-(1H-benzotriazol-1-yl)-1,1,3,3-tetramethyluronium hexafluorophosphate
Hex: hexane
HOBt: butyl alcohol
HOBT: 1-Hydroxybenzotriazole
HPLC: High Pressure Liquid Chromatography
$IC_{50}$ value: The concentration of an inhibitor that causes a 50% reduction in a measured activity.
iPrOH: Isopropanol
LC/MS: Liquid Chromatography/Mass Spectrometry
LRMS: Low Resolution Mass Spectrometry
MeOH: Methanol
NaOMe: sodium methoxide
nm: Nanometer
NMP: N-Methylpyrrolidone
$PPh_3$: triphenyl phosphine
RP-HPLC: Reversed-phase high-pressure liquid chromatography
RT: Room temperature
sat: Saturated
TEA: Triethylamine
TFA: Trifluoroacetic acid
THF: Tetrahydrofuran Thr: Threonine
TLC: Thin Layer Chromatography
Trt-Br: Tert-butyl bromide
Nomenclature for the Example compounds was provided using ACD Name version 5.07 software (Nov. 14, 2001) available from Advanced Chemistry Development, Inc. Some of the compounds and starting materials were named using standard IUPAC nomenclature.

Synthesis of N-Aroyl Threonine Analogues and Formation of Hydroxamate

Example 1

Synthesis of 3-bromo-4-fluoro-N-{(1S,2R)-2-hydroxy-1-[(hydroxyamino) carbonyl]propyl}benzamide (3)

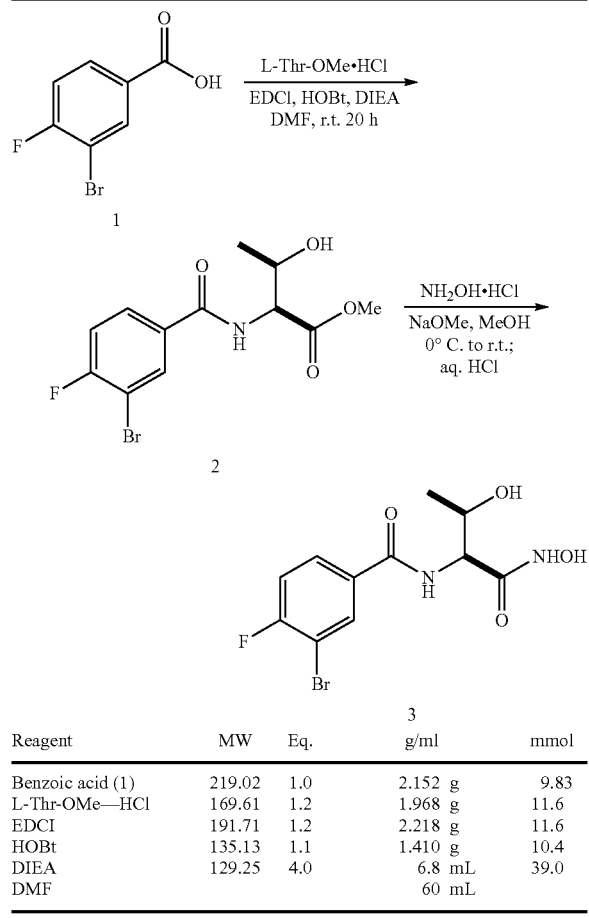

| Reagent | MW | Eq. | g/ml | mmol |
|---|---|---|---|---|
| Benzoic acid (1) | 219.02 | 1.0 | 2.152 g | 9.83 |
| L-Thr-OMe—HCl | 169.61 | 1.2 | 1.968 g | 11.6 |
| EDCI | 191.71 | 1.2 | 2.218 g | 11.6 |
| HOBt | 135.13 | 1.1 | 1.410 g | 10.4 |
| DIEA | 129.25 | 4.0 | 6.8 mL | 39.0 |
| DMF | | | 60 mL | |

Preparation of (2S,3R)-2-(3-bromo-4-fluoro-benzoylamino)-3-hydroxy-butyric acid methyl ester (2)

Diisopropylethylamine (6.8 mL, 39.0 mmol) was added to a stirred solution of 3-bromo-4-fluorobenzoic acid 1 (2.152 g, 9.83 mmol), L-threonine methyl ester hydrochloride (1.968 g, 11.6 mmol), EDCI (2.218 g, 11.6 mmol) and HOBt (1.410 g, 10.4 mmol) in anhydrous DMF (60 mL) at 0° C. under $N_2$. The solution was stirred at 0° C. for 1 h and at room temperature for 20 h. The solution was diluted with EtOAc (300 mL) and washed with 1.0 M HCl (2×80 mL), saturated $NaHCO_3$ (2×80 mL), $H_2O$ (4×80 mL), dried over $MgSO_4$, filtered and concentrated in vacuo to give a colorless syrup which solidified on standing to afford 3.280 g (100%) of (2S,3R)-2-(3-bromo-4-fluoro-benzoylamino)-3-hydroxy-butyric acid methyl ester 2 as a white solid, mp 73-74° C. MS (ES+) m/z 333.9 ($C_{12}H_{13}BrFNO_4$+H requires 334.00).

Preparation of 3-bromo-4-fluoro-N-{(1S,2R)-2-hydroxy-1-[(hydroxyamino)carbonyl]propyl}benzamide (3)

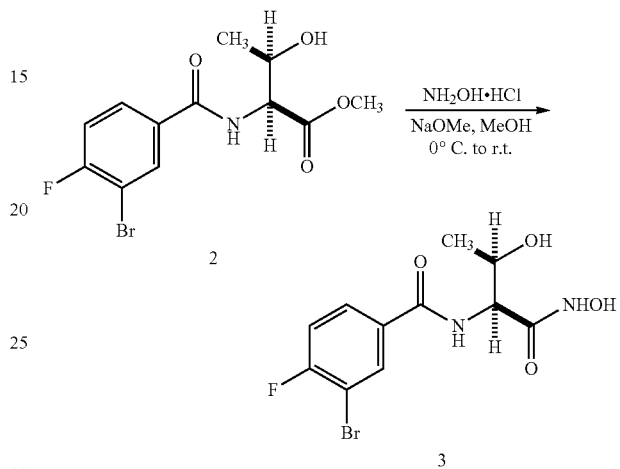

To a solution of hydroxylamine hydrochloride (66 mg, 0.95 mmol) in anhydrous MeOH (2.0 mL) at 0° C. under $N_2$ atmosphere was added sodium methoxide (25 wt % in MeOH, 360 mg, 1.67 mmol). A precipitate formed immediately and the cloudy white solution was stirred for 10 minutes at 0° C. A solution of methyl (2S,3R)-2-[(3-bromo-4-fluorophenyl)carbonylamino]-3-hydroxybutanoate (2) (284 mg, 0.850 mmol) in MeOH (2.0 mL) was added and the reaction stirred 2 h at 0° C. and then warmed gradually to room temperature overnight (17 h total). Aqueous 1.0 M HCl (10 mL) was added and the solution extracted with 4:1 chloroform/isopropyl alcohol (4×20 mL). The organic layers were combined, dried over $Na_2SO_4$ and concentrated to give a pink foam. The crude solid was triturated with diethyl ether (2×8 mL) and dried in vacuo to give 3-bromo-4-fluoro-N-{(1S,2R)-2-hydroxy-1-[(hydroxyamino)carbonyl]propyl}benzamide 3 as a white foam: mp 152-153° C. Rf (10:1 $CH_2Cl_2$/MeOH on silica gel)=0.53.

Preparation of Hydroxamates

Example 2

Synthesis of 4-benzoyl-N-{(1S,2R)-2-hydroxy-1-[(hydroxyamino) carbonyl]propyl}benzamide

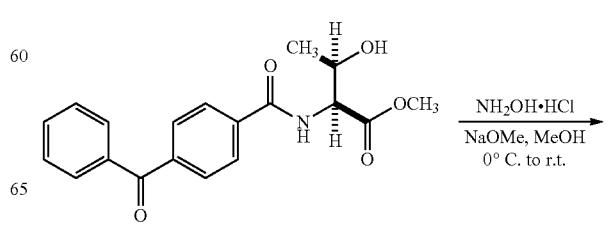

-continued

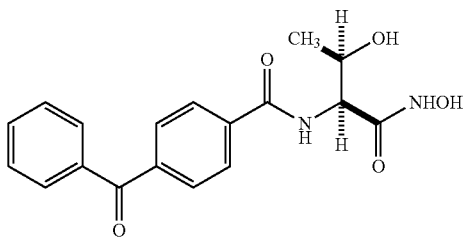

Procedure:

To a solution of hydroxylamine hydrochloride (121 mg, 1.74 mmol) in anhydrous MeOH (2.0 mL) at 0° C. under N2 atmosphere was added sodium methoxide (25 wt % in MeOH, 680 mg, 3.14 mmol). A precipitate was immediately observed and the cloudy white solution was stirred for 10 minutes at 0° C. A solution of methyl (2S,3R)-3-hydroxy-2-{[4-(phenylcarbonyl)phenyl]carbonylamino}butanoate (1) (534 mg, 1.56 mmol) in MeOH (3.0 mL) was added and the reaction stirred 3 h at 0° C., then warmed gradually to ambient temperature overnight (18 h total). Aqueous 0.5 M HCl (20 mL) was added and the solution extracted with 5:1 chloroform/isopropyl alcohol (4×40 mL). The organic layers were combined, dried over Na₂SO₄ and concentrated to give an orange foam. Purification by silica gel chromatography (increasing eluant polarity from 30:1 CH₂Cl₂/MeOH to 15:1 CH₂Cl₂/MeOH) afforded 228 mg (43%) of 4-benzoyl-N-{(1S,2R)-2-hydroxy-1-[(hydroxyamino)carbonyl]propyl}benzamide.

Example 3

Synthesis of (2R,3R)-3-hydroxy-1-{[4-(trifluoromethoxy)phenyl]carbonyl}pyrrolidine-2-carbohydroxamic acid Preparation of ((2R,3R)-3-hydroxy-1-{[4-(trifluoromethoxy)phenyl]carbonyl}pyrrolidin-2-yl)-N-(phenylmethoxy)carboxamide (2)

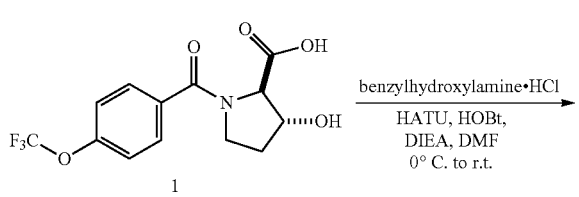

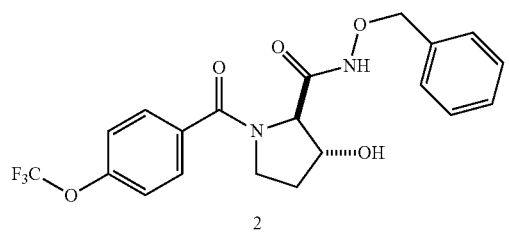

Procedure:

To a solution of (2R,3R)-3-hydroxy-1-{[4-(trifluoromethoxy)phenyl]carbonyl}pyrrolidine-2-carboxylic acid (1) (405 mg, 1.27 mmol), benzylhydroxylamine hydrochloride (243 mg, 1.52 mmol), HATU (556 mg, 1.46 mmol), and HOBt (178 mg, 1.32 mmol) in DMF (10 mL) at 0° C. was added diisopropylethylamine (710 µL, 4.07 mmol) with stirring. The cooling bath was removed after one hour and the reaction mixture stirred at ambient temperature for 18 h and then diluted with EtOAc (200 mL). The organic layer was washed with 1.0 M HCl (2×60 mL), sat. NaHCO₃ (2×60 mL) and H₂O (5×60 mL), dried over MgSO₄ and concentrated to give 493 mg (92%) of ((2R,3R)-3-hydroxy-1-{[4-(trifluoromethoxy)phenyl]carbonyl}pyrrolidin-2-yl)-N-(phenylmethoxy)carboxamide (2), a colorless oil that slowly crystallized upon standing. Rf (25:1 CH₂Cl₂/MeOH)=0.35.

Preparation of (2R,3R)-3-hydroxy-1-{[4-(trifluoromethoxy)phenyl]carbonyl}pyrrolidine-2-carbohydroxamic acid (2)

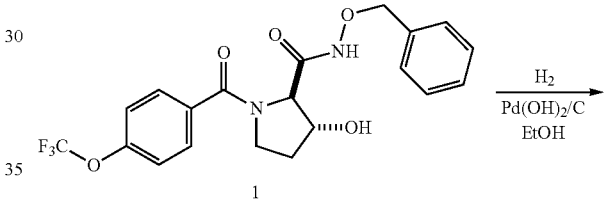

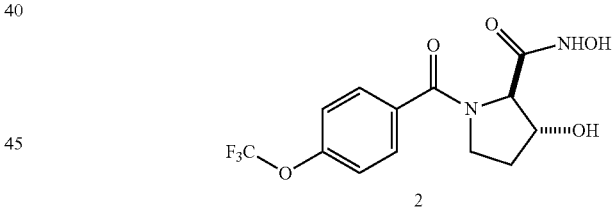

Procedure:

To a solution of ((2R,3R)-3-hydroxy-1-{[4-(trifluoromethoxy)phenyl]carbonyl}pyrrolidin-2-yl)-N-(phenylmethoxy)carboxamide (1) (143 mg, 0.337 mmol) in EtOH (10 mL) was added 20% Pd(OH)₂/C (50 mg). The solution was purged with hydrogen gas (approx. 0.5 L from a 1 L balloon) and then stirred under an atmosphere of H₂ (balloon pressure). TLC analysis showed no starting material after one hour. The solution was diluted with EtOAc (10 mL) and filtered through celite, washing with 20:1 EtOAc/EtOH (50 mL). The solution was concentrated and dried in vacuo to afford 90 mg (80%) of (2R,3R)-3-hydroxy-1-{[4-(trifluoromethoxy)phenyl]carbonyl}pyrrolidine-2-carbohydroxamic acid (2) as a sticky white foam: mp 64-65° C. Rf (10:1 CH₂Cl₂/MeOH)=0.29.

Synthesis of N-Benzyl Threonine Analogues by Reductive Amination

Example 4

Synthesis of (2S,3R)-3-hydroxy-2-{[(4-phenylphenyl)methyl]amino}butanehydroxamic acid (3)

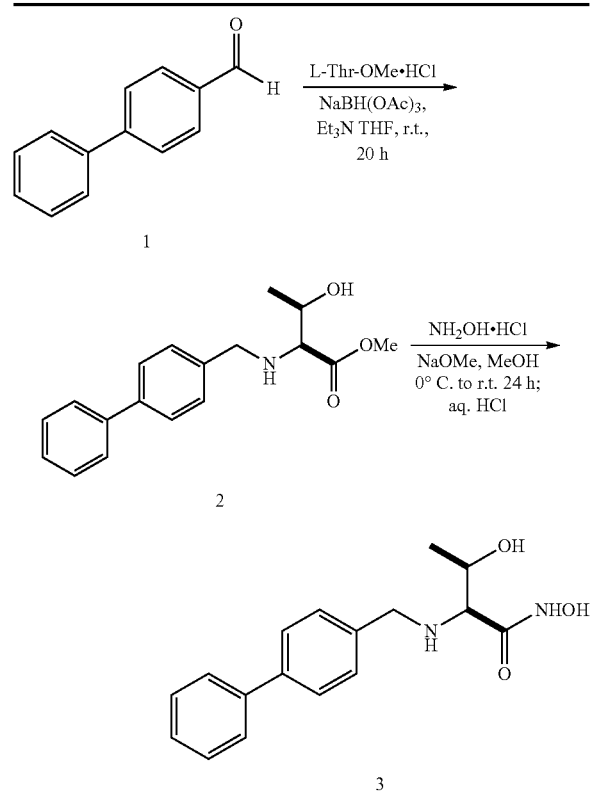

| Reagent | MW | Eq. | g/ml | mmol |
|---|---|---|---|---|
| 4-biphenylcarboxaldehyde | 182.22 | 1.0 | 1.104 g | 6.06 |
| L-Thr-OMe—HCl | 169.61 | 1.0 | 1.030 g | 6.07 |
| NaBH(OAc)$_3$ | 211.94 | 1.4 | 1.800 g | 8.49 |
| Et$_3$N | 101.19 | 2.0 | 1.70 mL | 12.1 |
| THF | | | | 25 mL |

Triethylamine (1.70 mL, 12.1 mmol) was added to a stirred suspension of L-threonine methyl ester hydrochloride (1.030 g, 6.07 mmol) and 4-biphenylcarboxaldehyde (1.104 g, 6.06 mmol) in THF (25 mL). After 20 min, NaBH(OAc)$_3$ was added and the suspension stirred for 20 h. The reaction was monitored by TLC (50:1 DCM/MeOH, R$_f$=0.4). The reaction mixture was quenched with saturated NaHCO$_3$ (50 mL), extracted with EtOAc (2×120 mL), dried over MgSO$_4$, filtered and concentrated to give a yellow oil. Purification by silica gel chromatography (150:1 DCM/MeOH) afforded 1.220 g (67% yield, 98% pure) of (2S, 3R)-2-[(biphenyl-4-ylmethyl)-amino]-3-hydroxy-butyric acid methyl ester 2 as a pale yellow oil.

HPLC (260 nm, 34 min run) 14.2 min; LRMS (ES+) m/z 299.9 (C$_{18}$H$_{21}$NO$_3$+H requires 300.10). Compound 3 was then formed by the addition of NH$_2$OH in MeOH/NaOMe at 0° C., warming to ambient temperature of the period of several hours. LCMS MH+ 301.15.

General Methods for Making Phenyl-benzoic acids and Phenyl-benzoate esters (see Example 5 below)

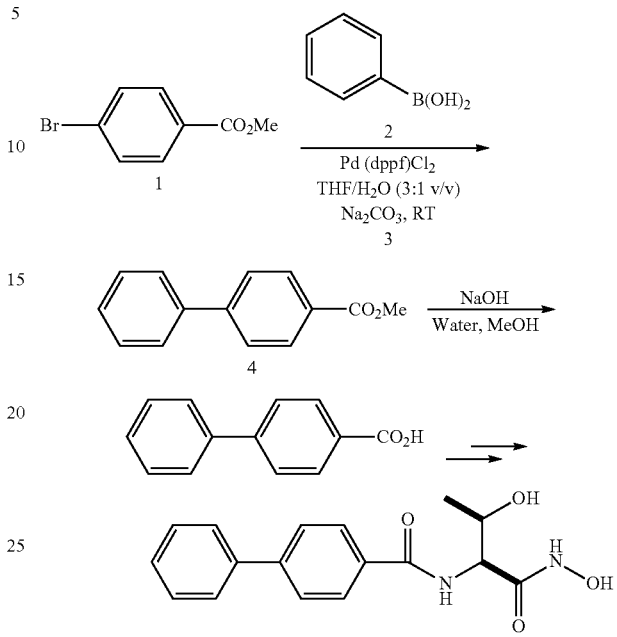

Suzuki Procedures Using Pd(dppt)Cl$_2$-DCM Catalyst and a THF/H$_2$O Mixture

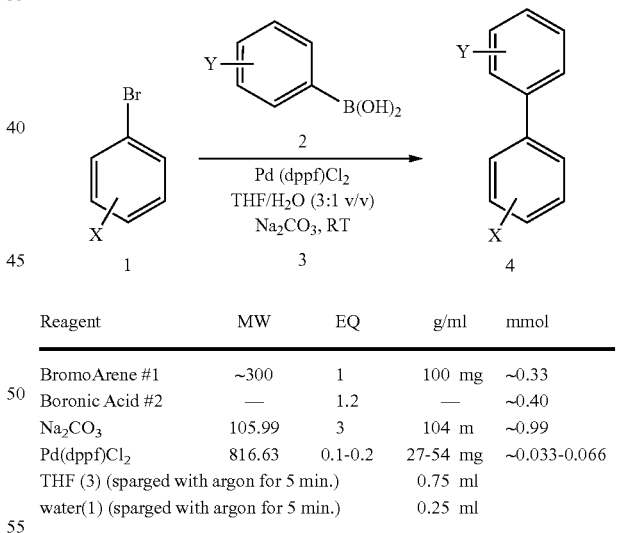

| Reagent | MW | EQ | g/ml | mmol |
|---|---|---|---|---|
| BromoArene #1 | ~300 | 1 | 100 mg | ~0.33 |
| Boronic Acid #2 | — | 1.2 | — | ~0.40 |
| Na$_2$CO$_3$ | 105.99 | 3 | 104 m | ~0.99 |
| Pd(dppf)Cl$_2$ | 816.63 | 0.1-0.2 | 27-54 mg | ~0.033-0.066 |
| THF (3) (sparged with argon for 5 min.) | | | 0.75 ml | |
| water(1) (sparged with argon for 5 min.) | | | 0.25 ml | |

Standard Procedure 1 eq aryl halide (1) was added to 1.2 eq. (2) and Pd(dppf)Cl$_2$ in THF, followed by addition of water and stirred 8 hours at RT. Upon completion (usually over night), the reactions are diluted with ethyl acetate (5-10 ml) and water (1 ml). The organic layer is separated and washed with NaHCO$_3$ (2×3 ml), water (1×3 ml), brine (1×3 ml), dried with Na$_2$SO$_4$, filtered and concentrated in an 8 ml glass vial. The residue is dissolved in DMSO and injected on a preparatory HPLC reverse phase column to afford >80% yield.

Suzuki Procedures Using Pd(dppf)Cl$_2$-DCM Catalyst and DMF Solvent

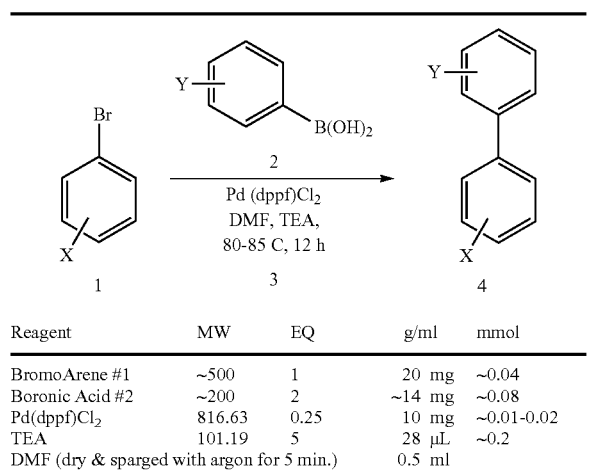

| Reagent | MW | EQ | g/ml | mmol |
|---|---|---|---|---|
| BromoArene #1 | ~500 | 1 | 20 mg | ~0.04 |
| Boronic Acid #2 | ~200 | 2 | ~14 mg | ~0.08 |
| Pd(dppf)Cl$_2$ | 816.63 | 0.25 | 10 mg | ~0.01-0.02 |
| TEA | 101.19 | 5 | 28 µL | ~0.2 |
| DMF (dry & sparged with argon for 5 min.) | | | 0.5 ml | |

Standard Procedure

The haloarene 1 and boronic acid 2 were weighed out and placed in the reaction flask. The DMF was sparged with argon for 5-10 minutes, followed by TEA addition, and the reaction was lightly bubbled with argon. The solid Pd(dppf)Cl$_2$ catalyst was added in one portion. The vial was flushed with argon, capped tight and stirred or shaken at ~80° C. Upon reaching completion (over night), the reaction was filtered and injected on a preparatory HPLC reverse phase column (80% yield).

Synthesis of Methyl DAP Analogues

Example 5

3-(R)-Amino-2-(S)-[(4'-ethyl-biphenyl-4-carbonyl)-amino]-butyl-hydroxamic acid (8)

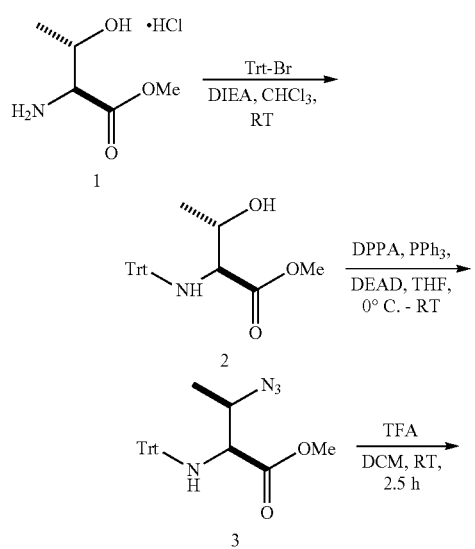

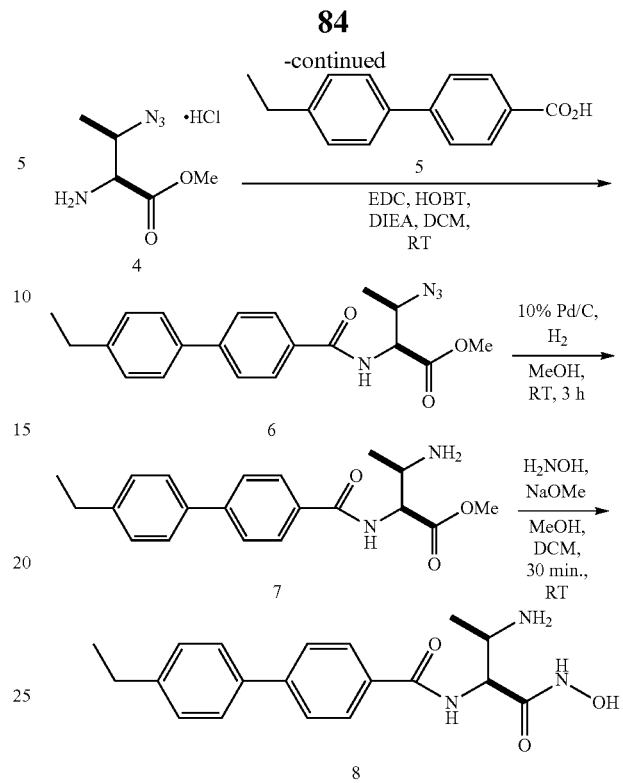

Preparation of N-triphenylmethyl allo-threonine methyl ester (2)

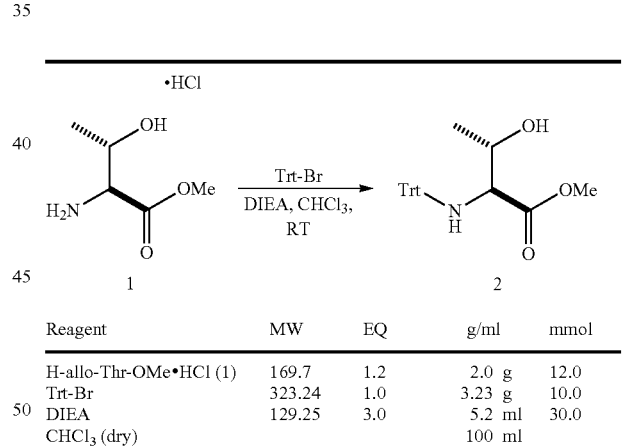

| Reagent | MW | EQ | g/ml | mmol |
|---|---|---|---|---|
| H-allo-Thr-OMe•HCl (1) | 169.7 | 1.2 | 2.0 g | 12.0 |
| Trt-Br | 323.24 | 1.0 | 3.23 g | 10.0 |
| DIEA | 129.25 | 3.0 | 5.2 ml | 30.0 |
| CHCl$_3$ (dry) | | | 100 ml | |

For similar procedures see: Righi, P.; Scardovi, N.; Marotta, E.; ten Holte, P.; Zwanenburg, B. Organic Letters 2002, 4(4), 497-500.

A solution of trityl bromide (3.2 g, 10.0 mmol) in CHCl$_3$ (40 ml) was added dropwise to a stirred solution of allo-threonine methyl ester HCl salt (1) (2.0 g, 12.0 mmol) and DIEA (5.2 ml, 30.0 mmol) in CHCl$_3$ (60 ml) at rt under N$_2$. The reaction could be followed by TLC eluting with EtOAc/Hex (40:60) (Rf=0.3). After stirring 12 h, the reaction was concentrated to a brown oil. The crude product was diluted with EtOAc (170 ml) and washed with 0.2 N citric acid (2×50 ml), water (2×50 ml), brine (50 ml), dried (Na$_2$SO$_4$), filtered and concentrated under reduced pressure to yield 3.73 g (85% yield, 95% pure) of a yellow solid.

HPLC (220 nm, 41 min. run) 30.90 min.; HPLC (220 nm, 17 min. run) 14.86 min.; LCMS: LC (214 nm) 3.06 min., MS (ES+) m/z 376.2 ($C_{24}H_{25}NO_3$+H requires 376.18).

Preparation of 3-(R)-Azido-2-(S)-(trityl-amino)-butyric acid methyl ester (3)

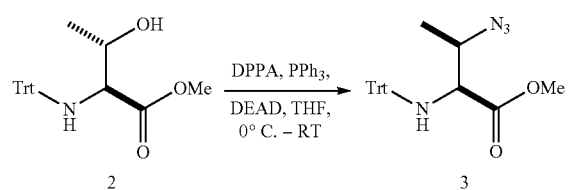

| Reagent | MW | Eq. | g/ml | mmol |
|---|---|---|---|---|
| Trt-allo-Thr-OMe (2) | 375.46 | 1.0 | 4.08 g | 10.88 |
| $PPh_3$ | 262.29 | 1.0 | 2.85 g | 10.88 |
| DEAD (neat) | 174.16 | 1.6 | 2.93 ml | 17.82 |
| DPPA | 275.7 | 2.7 | 6.40 ml | 29.7 |
| THF (dry) | | | 50 ml | |

For similar procedures see: Matsuda, A.; Yasuoka, J.; Sasaki, T.; Ueda, T. J. Med. Chem. 1991, 34, 999-1002.

A solution of pure DEAD (2.9 ml, 17.8 mmol) in THF (5 ml) was added slowly dropwise to a stirred solution of trt-allo-threonine methyl ester (2) (4.1 g, 10.9 mmol) and $PPh_3$ (2.9 g, 10.9 mmol) in THF (40 ml) at 0° C. under $N_2$. After 3 min., a solution of DPPA (6.4 ml, 29.7 mmol) in THF (5 ml) was added to the orange-yellow reaction solution at 0° C. After 1 h, the reaction was allowed to warm to rt. After 40 h, the reaction had reached completion by TLC (Hexane/DCM/EtOAc (64:20:16) (Rf=0.6)) and LCMS. The yellow solution was concentrated to give 18 g of crude material that was purified by column chromatography eluting with Hexane/EtOAc (88:12) giving 3.5 g of 70% pure product after evaporation. The product was purified again (to remove trityl alcohol and a crotyl side-product formed during the reaction by elimination) by column chromatography eluting with Hexane/DCM/EtOAc (76:20:4) giving 1.65 g (38% yield) of a pale yellow oil after concentration and drying in vacuo. Note that the trityl protecting group would hydrolyze when exposed to TFA while running the sample on HPLC.

Alternately, the reaction could be carried out in dry DCM. A reaction using 5.44 g (14.5 mmol) of trt-allo-threonine methyl ester (2) in DCM (100 ml) with $PPh_3$ (3.8 g, 14.5 mmol), pure DEAD (3.4 ml, 21.8 mmol) in DCM (5 ml) and DPPA (6.3 ml, 24.0 mmol) in DCM (10 ml) were combined following the procedure above. After 3 days, the reaction did not progress further by TLC and LCMS. After the same work up, 2.97 g of the product was obtained in 51% yield.

HPLC (220 nm, 41 min. run) 40.5 min.; HPLC (220 nm, 17 min. run) 16.32 min.; LCMS: LC (214 nm) 3.7 min., MS (ES+) m/z 401.2 ($C_{24}H_{25}N_3O_2$+H requires 401.15).

Preparation of 2-(S)-Amino-3-(R)-azido-butyric acid methyl ester HCl Salt (4)

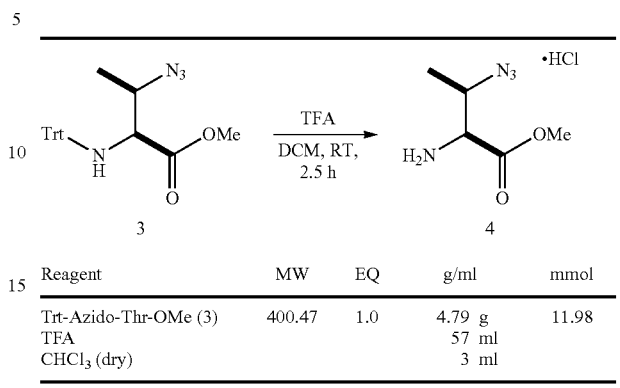

| Reagent | MW | EQ | g/ml | mmol |
|---|---|---|---|---|
| Trt-Azido-Thr-OMe (3) | 400.47 | 1.0 | 4.79 g | 11.98 |
| TFA | | | 57 ml | |
| $CHCl_3$ (dry) | | | 3 ml | |

A solution of Trt-Azido-Thr-OMe (3) (4.8 g, 12.0 mmol) was dissolved in a 95% TFA/DCM solution (60 ml) at rt with stirring. After 2.5 h, the reaction was complete by LCMS. The bright yellow solution was diluted with 0.5 N aq. HCl (300 ml). The aqueous layer was extracted with DCM (2×30 ml) and then lyophilized to dryness. The white solid was dissolved in AcCN/water (50:50) (100 ml) and again lyophilized to dryness to produce a consistent powder and remove as much of the TFA as possible. The azido-Thr product (4), 2.26 g (97% yield, 95% pure) of a white solid, was obtained as the HCl salt.

HPLC (220 nm, 41 min. run) 7.91 min.; HPLC (220 nm, 17 min.run) 3.36 min; LCMS: LC (214 nm) 0.48 min., MS (ES+) m/z 159.3 ($C_5H_{10}N_4O_2$+H requires 159.08).

Preparation of 3-(R)-Azido-2-(S)-[(4'-ethyl-biphenyl-4-carbonyl)-amino]-butyric acid methyl ester (6)

| Reagent | MW | EQ | g/ml | mmol |
|---|---|---|---|---|
| Azido-Thr-OMe•HCl (4) | 194.62 | 1.0 | 195 mg | 1.0 |
| Biphenyl Acid (5) | 226.27 | 1.0 | 226 mg | 1.0 |
| HOBT | 153 | 1.0 | 158 mg | 1.0 |
| EDC•HCl | 191.17 | 1.3 | 249 mg | 1.3 |
| DIEA | 129.25 | 2.5 | 0.44 ml | 2.5 |
| DCM (dry) | | | 10 ml | |

A EDC.HCl (249 mg, 1.3 mmol) was added to a stirred colorless solution of azido-Thr-OMe.HCl (4) (195 mg, 1.0 mmol), HOBT (158 mg, 1.0 mmol), 4'-Ethyl-biphenyl-4-carboxylic acid (5) (226 mg, 1.0 mmol) and DIEA (0.44 ml, 2.5 mmol) in DCM (10 ml) at rt under $N_2$. After 24 h, the reaction had reached completion by TLC (Hexane/EtOAc (60:40) (Rf=0.3)) and LCMS. The reaction was evaporated under reduced pressure to a brown tar. The crude product was dissolved in EtOAc (100 ml) and washed with 0.2N aq. HCl (2×50 ml), aq. sat. $NaHCO_3$ (50 ml), brine (50 ml), dried ($Na_2SO_4$), filtered and concentrated under reduced pressure to yield a crude brown solid. The crude material was further purified by column chromatography eluting with Hexane/EtOAc (70:30) giving 245 mg (67% yield) of pure product after evaporation and drying in vacuo.

HPLC (220 nm, 41 min. run) 33.87 min.; HPLC (220 nm, 17 min. run) 15.61 min; LCMS: LC (214 nm) 3.25 min., MS (ES+) m/z 367.2 ($C_{20}H_{22}N_4O_3$+H requires 367.17).

Preparation of 3-(R)-Amino-2-(S)-[(4'-ethyl-biphenyl-4-carbonyl)-amino]-butyric acid methyl ester (7)

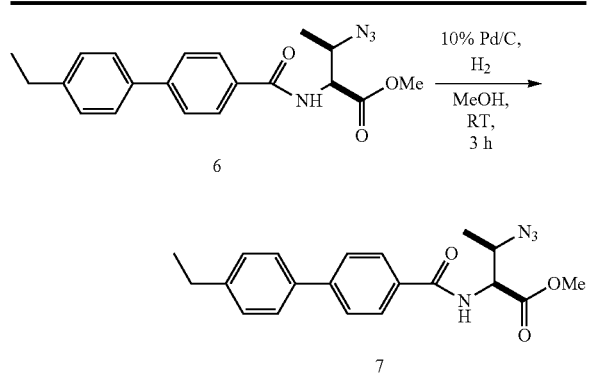

| Reagent | MW | EQ | g/ml | mmol |
|---|---|---|---|---|
| Biphenyl Azido-Thr (6) | 366.41 | 1.0 | 244 mg | 0.67 |
| 10% Pd/C | | | 200 mg | |
| $H_2$ (gas) | | | 12" balloon | |
| MeOH (dry) | | | 10 ml | |

A solution of biphenyl azido-Thr methyl ester (6) (244 mg, 0.67 mmol) in MeOH (10 ml) was made by sonicating until the milky precipitate cleared. After bubbling nitrogen through the reaction solution for 30 sec., 10% Pd/C was added in one portion. The reaction was stirred under nitrogen at RT. The reaction was exposed to aspirator vacuum to remove the nitrogen and then opened to the hydrogen gas at balloon pressure (~1 atm). The reaction stirred for 3 h at which time the hydrogen was exchanged for nitrogen. The reaction was filtered through a pad of celite to remove the palladium. The celite pad was washed with MeOH (30 ml). The combined fractions of MeOH were evaporated under reduced pressure and dried in vacuo to give 225 mg (99% yield) of pure produce (7) as a white solid.

HPLC (220 nm, 17 min. run) 10.79 min.; LCMS: LC (214 nm) 2.21 min., MS (ES+) m/z 341.2 ($C_{20}H_{24}N_2O_2$+H requires 341.18).

Preparation of 3-(R)-Amino-2-(S)-[(4'-ethyl-biphenyl-4-carbonyl)-amino]-butyl-hydroxamic acid (8)

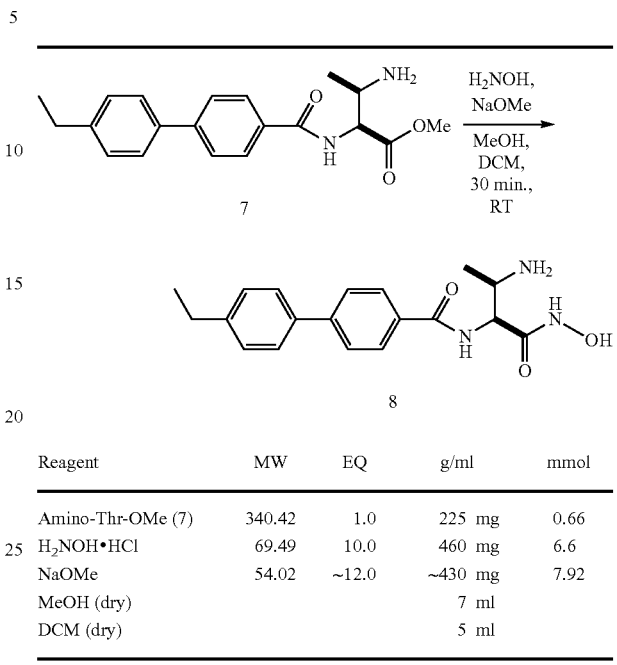

| Reagent | MW | EQ | g/ml | mmol |
|---|---|---|---|---|
| Amino-Thr-OMe (7) | 340.42 | 1.0 | 225 mg | 0.66 |
| $H_2$NOH•HCl | 69.49 | 10.0 | 460 mg | 6.6 |
| NaOMe | 54.02 | ~12.0 | ~430 mg | 7.92 |
| MeOH (dry) | | | 7 ml | |
| DCM (dry) | | | 5 ml | |

To a stirred suspension of biphenyl-amino-Thr methyl ester (7) (225 mg, 0.6 mmol) and hydroxylamine HCl salt (460 mg, 6.6 mmol) in MeOH (7 ml) and DCM (5 ml) was added fresh solid NaOMe powder (430 mg, 7.92 mmol) in one portion. After stirring for 2 min. at rt under nitrogen, the pH of the reaction on wet pH paper was approximately 7-8. The suspension had change from larger particles of white solid to a finely-divided milky consistency. The pH of the reaction was checked after adding small portions of NaOMe (50-100 mg) and allowing 2 min. for the reaction to equilibrate. The pH of the reaction reached a stable 11-12 after the final portion of NaOMe was added (250 mg total). The reaction was initiated at pH 11 and proceeded quickly. After 30 min., the reaction reached 85% completion as determined by LCMS, and the reaction was placed in a −10° C. bath. The cold mixture filtered over fine filter paper on a Büchner funnel. The white residue was washed with MeOH (15 ml). The organic fractions were collected and concentrated under reduced pressure to give crude product (750 mg). The crude product (only one 150 mg portion) was dissolved in DMSO (1 ml), AcCN (100 µl) and water (100 µl), passed through a Teflon syringe filter, and the clear filtrate was injected on a preparative HPLC. The purification used a 20×50 mm Ultro 120 C18 column running a 22 ml/min 2% gradient (AcCN/water, 0.1% TFA) for 16 min. The purified fractions were lyophilized to dryness. The product as the TFA salt was dissolved in AcCN/water (50:50) (5 ml), 1N aq. HCl (1 equivalent) and lyophilized again to give 11.5 mg of white powder as an HCl salt (23% yield).

HPLC (220 nm, 41 min. run) 19.31 min.; HPLC (220 nm, 17 min. run) 9.39 min; LCMS: LC (214 nm) 1.98 min., MS (ES+) m/z 342.2 ($C_{19}H_{23}N_3O_3$+H requires 342.17).

Synthesis of 4'Benzamide Biphenyl Threonine Hydroxamic Acid
Example 6
Biphenyl-4,4'-dicarboxylic acid 4'-[(3-Boc-amino-propyl)-amide]-4-[((2R)-hydroxy-(1S)-hydroxycarbamoyl-propyl)-amide] (6), and
Example 7
Biphenyl-4,4'-dicarboxylic acid 4'-[(3-amino-propyl)-amide]-4-[((2R)-hydroxy-(1S)-hydroxycarbamoyl-propyl)-amide](7)
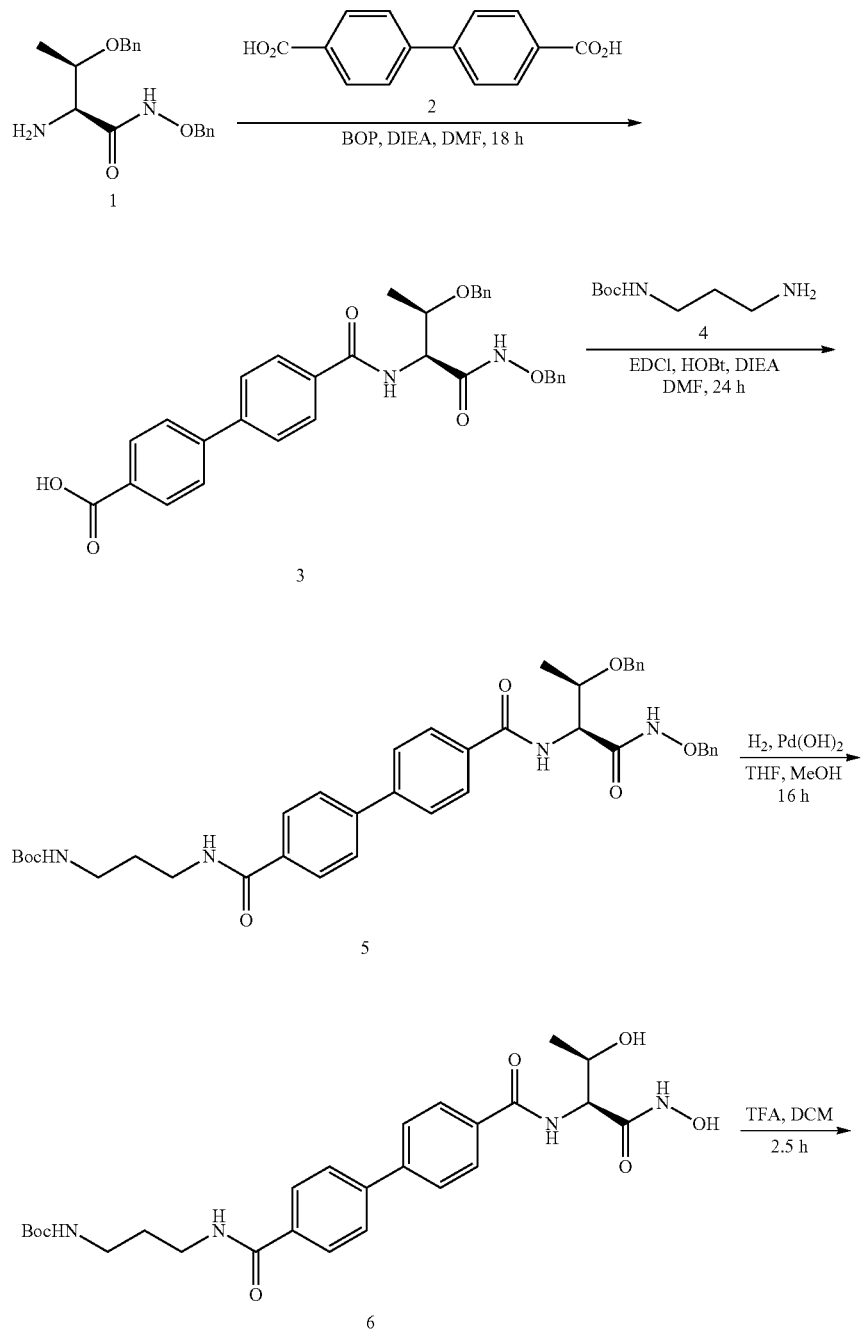

-continued

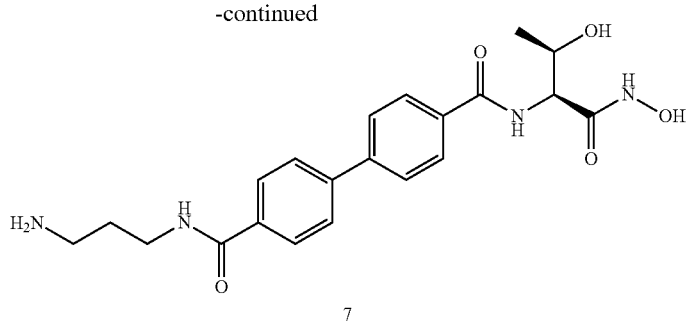

7

Synthesis of (2S,3R)-2-amino-3-(phenylmethoxy)-N-(phenylmethoxy)butanamide (1)

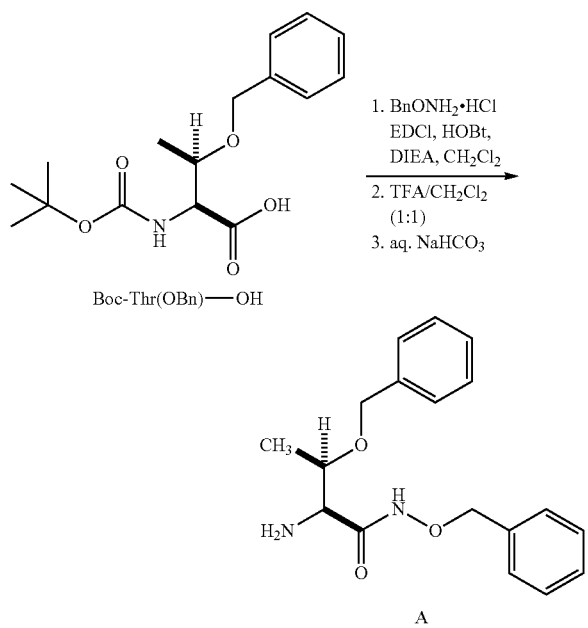

Procedure:

To a suspension of benzylhydroxylamine hydrochloride (8.310 g, 52.06 mmol), Boc-Thr(OBn)-OH (14.01 g, 45.28 mmol), EDCI (10.01 g, 52.21 mmol), and HOBt (6.90 g, 51.06 mmol) in $CH_2Cl_2$ (300 mL) at 0° C. was added diisopropylethylamine (28.3 mL, 162 mmol) with stirring. The cooling bath was removed after one hour and the reaction mixture stirred at ambient temperature for 20 h and was then diluted with $CH_2Cl_2$ (300 mL). The organic layer was washed with 1.0 M HCl (2×200 mL), sat. $NaHCO_3$ (2×200 mL) and brine (200 mL), dried over $MgSO_4$ and concentrated to give 14.5 g of a white solid. The crude solid was treated with a solution of trifluoroacetic acid (90 mL) in $CH_2Cl_2$ (90 mL) and stirred for 2.5 h. The reaction mixture was concentrated by rotary evaporation and then diluted with $CH_2Cl_2$ (600 mL). The organic layer was washed with sat. $NaHCO_3$ (2×200 mL), dried over $MgSO_4$ and concentrated to give a dark orange oil. Purification by silica gel chromatography (50:1 $CH_2Cl_2$/MeOH) afforded (2S,3R)-2-amino-3-(phenylmethoxy)-N-(phenylmethoxy) butanamide (A) (8.9 g,) as a pale yellow oil. Rf (50:1 $CH_2Cl_2$/MeOH on silica gel)=0.2.

Preparation of (1S,2R)-4'-(2-benzyloxy-1-benzyloxycarbamoyl-propylcarbamoyl)-biphenyl-4-carboxylic acid (3)

| Reagent | MW | Eq. | g/mL | mmol |
|---|---|---|---|---|
| Amine (1) | 314.38 | 1.0 | 0.944 g | 3.00 |
| Dicarboxylic acid (2) | 242.23 | 1.9 | 1.360 g | 5.61 |
| BOP | 442.3 | 1.5 | 2.007 g | 4.54 |
| DIEA | 129.25 | 3.3 | 1.7 mL | 9.76 |
| DMF | | | 200 mL | |

To a suspension of 4,4'-biphenyldicarboxylic acid 2 (1.360 g, 5.61 mmol) in DMF (180 mL) was added BOP (2.007 g, 4.54 mmol) and DIEA (1.7 mL, 9.8 mmol). A solution of (1S,2R)-2-amino-3,N-bis-benzyloxy-butyramide 1 (944 mg, 3.00 mmol) in DMF (20 mL) was added and the reaction stirred for 18 h. The solution was diluted with EtOAc (250 mL) and washed with 1.0 M HCl (500 mL). The aqueous layer was extracted with EtOAc (250 mL) and the organic layers combined. The organic layer was washed with 1.0 M HCl (250 mL), dried over $MgSO_4$, and concentrated to give a crude yellow solid. Purification by silica gel chromatography (60:1 $CH_2Cl_2$/MeOH) gave 210 mg (1 S,2R)-4'-(2-benzyloxy-1-benzyloxycarbamoyl-propylcarbamoyl)-biphenyl-4-carboxylic acid 3. (13% yield) as a yellow solid. $R_f$=0.80 (10:1 $CH_2Cl_2$/MeOH); LRMS (ES+) m/z 539.1 ($C_{32}H_{30}N_2O_6$+H requires 539.22).

Preparation of biphenyl-4,4'-dicarboxylic acid 4'-[(3-(Boc)-amino-propyl)-amide]-4-[(2R)-benzyloxy-(1S)-benzyloxycarbamoyl-propyl)-amide] (5)

| Reagent | MW | Eq. | g/mL | mmol |
|---|---|---|---|---|
| Biphenylcarboxylic acid (3) | 538.59 | 1.0 | 0.200 g | 0.371 |
| Amine (4) | 174.24 | 1.1 | 0.071 g | 0.407 |
| EDCI | 191.71 | 1.1 | 0.078 g | 0.407 |
| HOBt | 135.13 | 1.0 | 0.052 g | 0.385 |
| DIEA | 129.25 | 2.7 | 180 µL | 1.0 |
| DMF | | | 2 mL | |

To a solution of biphenylcarboxylic acid 3 (200 mg, 0.371 mmol), EDCI (78 mg, 0.407 mmol), and HOBt (52 mg, 0.385 mmol) in DMF (2 mL) was added t-Butyl N-(3-aminopropyl) carbamate 4 (71 mg, 0.407 mmol) and DIEA (180 µL, 1.0 mmol). The reaction mixture was stirred 24 h, diluted with EtOAc (150 mL), washed with 1.0 M HCl (2×60 mL), saturated NaHCO$_3$ (2×60 mL), H$_2$O (3×60 mL), dried over MgSO$_4$ and concentrated to give a crude white solid. Purification by silica gel chromatography (25:1 CH$_2$Cl$_2$/MeOH) afforded 194 mg (75% yield) of biphenyl-4,4'-dicarboxylic acid 4'-[(3-(Boc)-amino-propyl)-amide]-4-[(2R)-benzyloxy-(1S)-benzyloxycarbamoyl-propyl)-amide] 5 as a white solid. R$_{f=0.15}$ (50:1 CH$_2$Cl$_2$/MeOH); LRMS (ES+) m/z 695.2 (C$_{40}$H$_{46}$N$_4$O$_7$+H requires 695.35).

Preparation of Biphenyl-4,4'-dicarboxylic acid 4'-[(3-Boc-amino-propyl)-amide]-4-[((2R)-hydroxy-(1S)-hydroxycarbamoyl-propyl)-amide] (6)

| Reagent | MW | Eq. | g/mL | mmol |
|---|---|---|---|---|
| Biphenyl diamide (5) | 694.82 | 1.00 | 0.190 g | 0.273 |
| Pd(OH)$_2$ (20%/C) | 106.42 | 0.15 | 0.020 g | 0.040 |
| H$_2$ (g) | | | balloon | |
| THF | | | 5.0 mL | |
| MeOH | | | 3.0 mL | |

A solution of dibenzyl-protected threonine hydroxamic acid 5 (190 mg, 0.273 mmol) in THF (5 mL) and MeOH (3 mL) was charged with Pd(OH)$_2$ (20%/C, 20 mg, 0.04 mmol) and stirred under a hydrogen atmosphere (balloon pressure) for 16 h. The crude mixture was filtered through a plug of celite eluting with 2:1 MeOH/THF (15 mL) and concentrated to give an orange syrup. Purification by silica gel chromatography (5:1:1 THF/MeOH/CH$_2$Cl$_2$) afforded 110 mg (78% yield) of biphenyl-4,4'-dicarboxylic acid 4'-[(3-Boc-amino-propyl)-amide] 4-[((2R)-hydroxy-(1S)-hydroxycarbamoyl-propyl)-amide] as a white foam, mp 75-77° C. R$_f$=0.20 (10:1 CH$_2$Cl$_2$/MeOH); LRMS (ES+) m/z 515.4 (C$_{26}$H$_{34}$N$_4$O$_7$+H requires 515.26).

Preparation of Biphenyl-4,4'-dicarboxylic acid 4'-[(3-amino-propyl)-amide]-4-[((2R)-hydroxy-(1S)-hydroxycarbamoyl-propyl)-amide] (7)

| Reagent | MW | Eq. | g/mL | mmol |
|---|---|---|---|---|
| Boc-protected amine (6) | 514.57 | 1.00 | 0.080 g | 0.155 |
| TFA | | | 3.0 mL | |
| CH$_2$Cl$_2$ | | | 3.0 mL | |

A flask containing Boc-protected amine 6 (80 mg, 0.155 mmol) was treated with 50% TFA/CH$_2$Cl$_2$ (6.0 mL) and stirred for 2.5 h. The reaction mixture was concentrated by rotary evaporation to give a brown syrup. Purification by RP-HPLC (C$_{18}$ column, CH$_3$CN gradient 5-70%, 0.1% TFA, UV analysis 300 nm, 36 min) and lyophilization of the collected fractions afforded 14 mg (21% yield) of biphenyl-4,4'-dicarboxylic acid 4'-[(3-amino-propyl)-amide]-4-[((2R)-hydroxy-(1S)-hydroxycarbamoyl-propyl)-amide] as a white solid. LRMS (ES+) m/z 415.3 (C$_{21}$H$_{26}$N$_4$O$_5$+H requires 415.20); RP-HPLC (300 nm, 36 min run) 18.2 min.

Example 8

Synthesis of N-(2-(N-hydroxycarbamoyl)(2S)-2-{[4-(4-ethylphenyl)phenyl]carbonylamino}ethyl)acetamide (4)

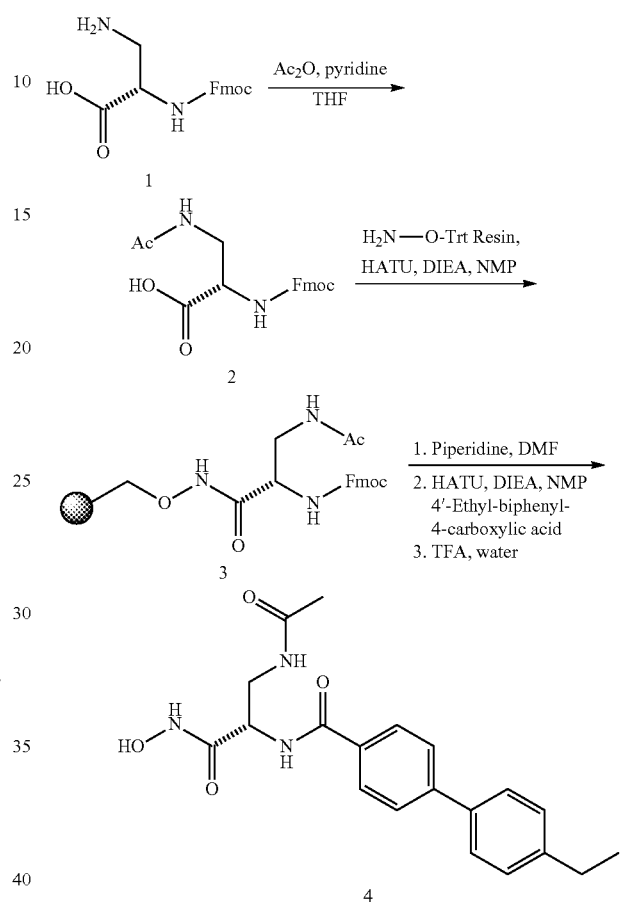

Preparation of 3-Acetylamino-2-(9H-fluoren-9-yl-methoxycarbonylamino)-propionic acid (2)

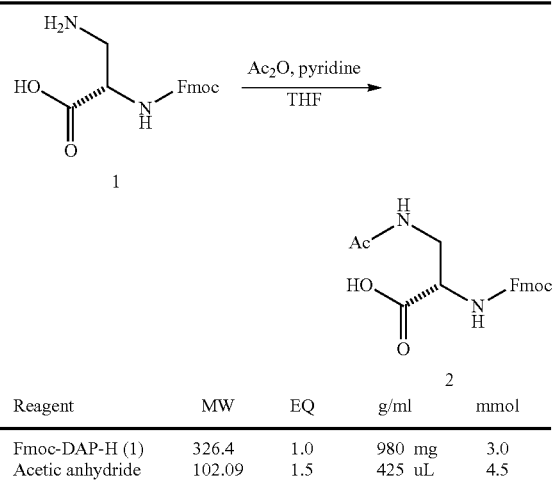

| Reagent | MW | EQ | g/ml | mmol |
|---|---|---|---|---|
| Fmoc-DAP-H (1) | 326.4 | 1.0 | 980 mg | 3.0 |
| Acetic anhydride | 102.09 | 1.5 | 425 uL | 4.5 |

-continued

| | | | | |
|---|---|---|---|---|
| Pyridine | 79.1 | 2.0 | 483 uL | 6.0 |
| THF | | | 20 ml | |

Acetic anhydride in THF (5 ml) was added to a cloudy mixture of Fmoc-DAP-H (1) (980 mg, 3.0 mmol) and pyridine (483 uL, 6.0 mmol) in THF (15 ml) with stirring at rt. After 4 hours, the clear pale yellow solution had reacted completely by LCMS. The reaction was evaporated under reduced pressure. The residue was dissolved in EtOAc (150 ml) and washed with 0.1M NaHSO$_4$ (50 ml), water (50 ml), sat. brine (50 ml), dried with Na$_2$SO$_4$, filtered and concentrated under reduced pressure to give 1.1 g of crude product as a white solid. The crude product was purified by prep. HPLC to give 0.99 g (90% yield) of acyl-DAP (2).

Preparation of (2-Acetylamino-1-hydroxycarbamoyl-ethyl)-carbamic acid 9H-fluoren-9-ylmethyl ester trityl resin (3)

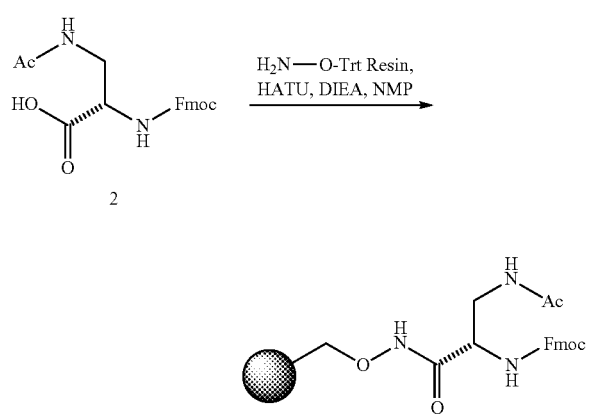

| Reagent | MW | EQ | g/ml | mmol |
|---|---|---|---|---|
| H$_2$N—O-Trt Resin | | 1.0 | 120 mg | 0.113 |
| Fmoc-DAP(Ac)—H (1) | 368.4 | 5.0 | 980 mg | 0.564 |
| HATU | 380 | 5.0 | 0.146 g | 0.564 |
| DIEA | 129.25 | 10.0 | 196 ul | 1.13 |
| NMP | | | 1.7 ml | |

A solution of Fmoc-DAP(Ac)-H (1) (980 mg, 0.56 mmol), HATU (0.146 g, 0.56 mmol) in NMP (1.7 ml) was made. After 2 min. of shaking, the activated acid was added to the deprotected H$_2$N—O-Trt Resin (120 mg, 0.113 mmol) at rt with shaking. [Deprotection of the Fmoc group from the resin was accomplished using 20% piperizine in DMF (4 ml) for 2 hours twice. The resin was drained and washed with DMF (2×5 ml) and DCM (2×5 ml).] After shaking for 20 hours, the reaction was drained and washed with DMF (2×5 ml) and DCM (2×5 ml). The resin was dried and used as is in the next reaction.

Preparation of N-(2-(N-hydroxycarbamoyl)(2S)-2-{[4-(4-ethylphenyl)phenyl]carbonylamino}ethyl)acetamide (4)

Preparation of (2-Acetylamino-1-hydroxycarbamoyl-ethyl)-carbamic acid 9H-fluoren-9-ylmethyl ester trityl resin (3)

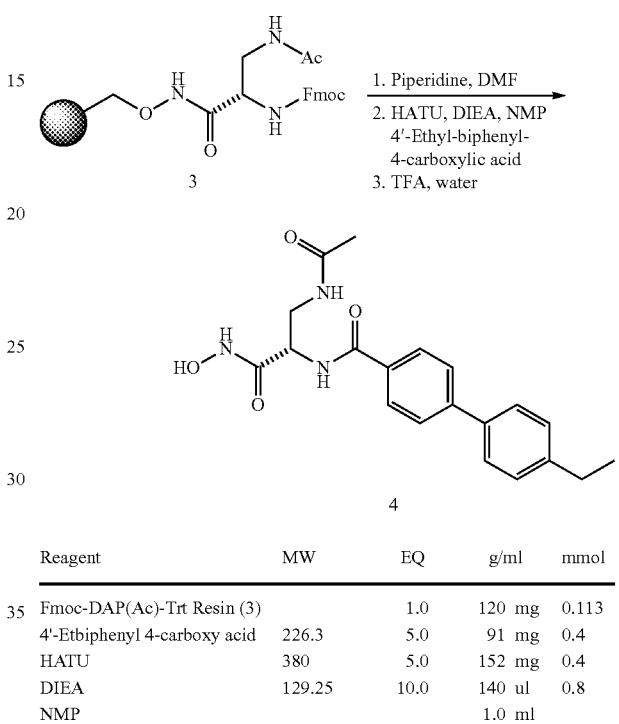

| Reagent | MW | EQ | g/ml | mmol |
|---|---|---|---|---|
| Fmoc-DAP(Ac)-Trt Resin (3) | | 1.0 | 120 mg | 0.113 |
| 4'-Etbiphenyl 4-carboxy acid | 226.3 | 5.0 | 91 mg | 0.4 |
| HATU | 380 | 5.0 | 152 mg | 0.4 |
| DIEA | 129.25 | 10.0 | 140 ul | 0.8 |
| NMP | | | 1.0 ml | |

The resin was treated with 20% piperizine in DMF (4 ml) for 2 hours twice. The resin was drained and washed with DMF (2×5 ml) and DCM (2×5 ml). The resin was dried in vacuo. A solution of 4'-Ethyl-biphenyl-4-carboxylic acid (91 mg, 0.4 mmol), HATU (152 g, 0.4 mmol) in NMP (1.0 ml) was made. After 2 min. of shaking, the activated acid was added to the deprotected H-DAP(Ac)-Trt resin (120 mg, 0.113 mmol) at rt with shaking. After shaking for 18 hours, the reaction was drained and washed with DMF (2×5 ml) and DCM (2×5 ml). The resin was dried in vacuo. The product was cleaved from the resin through treatment with a solution of TFA (500 uL), DCM (500 uL) and water (50 uL) for 25 min. The resin was filtered and washed with fresh DCM (2 ml). The combined TFA and DCM fractions are evaporated under reduced pressure. The residue was diluted with CH$_3$CN/water (1:1) (10 ml) and lyophilized. The crude product was purified by prep. HPLC. The crude product was dissolved in DMSO (1 ml), passed through a Teflon syringe filter, and the clear filtrate was injected on a preparative HPLC. The purification used a 20×50 mm Ultro 120 C18 column running a 22 ml/min 2% gradient (AcCN/water, 0.1% TFA) for 16 min. The purified fractions were lyophilized to dryness. The solid residue was lyophilized again from CH$_3$CN/water (1:1) (5 ml) give 8.6 mg of pure product (4) (~21% yield).

Example 9

Synthesis of 4'-Ethyl-biphenyl-4-carboxylic acid (1-hydroxycarbamoyl-2-methanesulfonylamino-ethyl)-amide (3)

Preparation of 4'-Ethyl-biphenyl-4-carboxylic acid (2-amino-1-hydroxycarbamoyl-ethyl)-amide trityl resin (2)

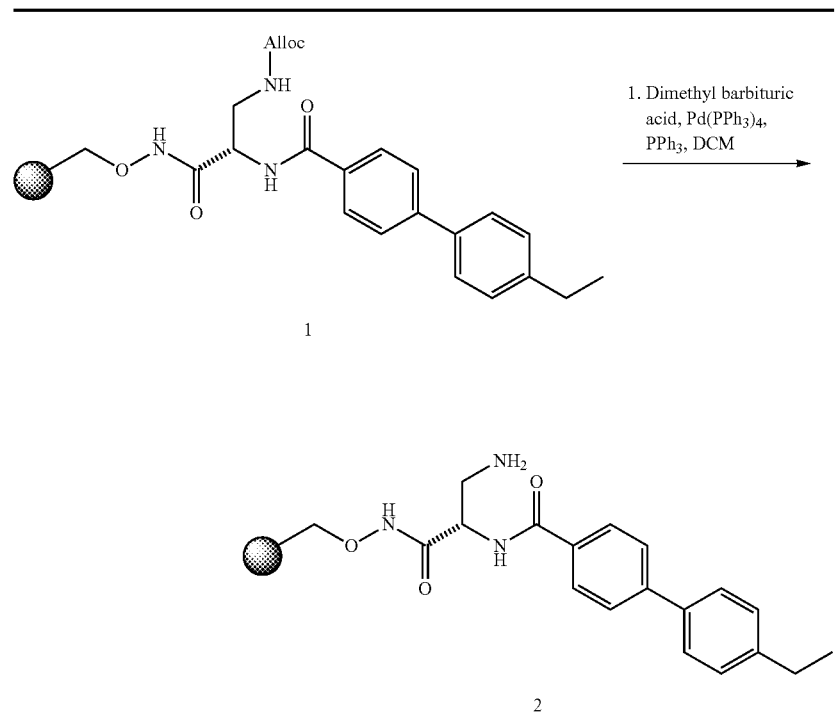

| Reagent | MW | EQ | g/ml | mmol |
|---|---|---|---|---|
| Biphenyl-DAP(Alloc)-Trt Resin (1) | | 1.0 | 500 mg | 0.35 |
| Dimethyl barbituric acid | 156.14 | 10.0 | 600 mg | 3.5 |
| Pd(PPh$_3$)$_4$ | 1135.6 | 1.0 | 438 mg | 0.35 |
| PPh$_3$ | 262.3 | 2.0 | 202 mg | 0.7 |
| DCM | | | 11.0 ml | |

Pd(PPh$_3$)$_4$ (438 mg, 0.35 mmol) was added to a vial containing biphenyl-DAP(Alloc)-Trt Resin (1) (500 mg, 0.35 mmol), Dimethyl barbituric acid (600 mg, 3.5 mmol) and PPh$_3$ (438 mg, 0.35 mmol) in DCM (11 ml) at rt under argon. The mixture was sparged with argon and shaken for 16 hours. The bright yellow mixture was drained and washed with DMF (8×10 ml) and DCM (8×10 ml). The resin was dried in vacuo to give the deprotected DAP resin 2.

Preparation of 4'-Ethyl-biphenyl-4-carboxylic acid (1-hydroxycarbamoyl-2-methane sulfonylamino-ethyl)-amide (3)

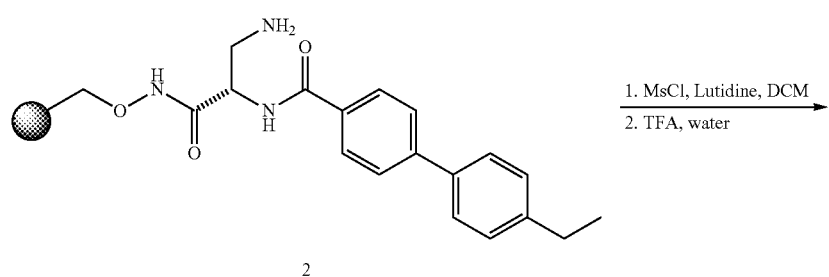

2

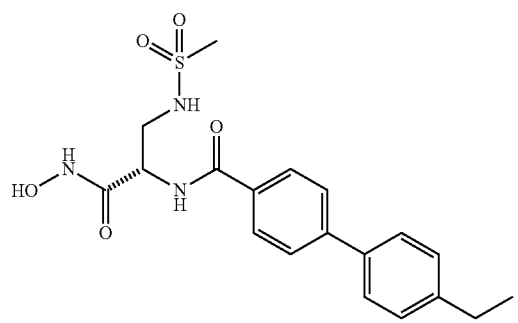

3

| Reagent | MW | EQ | g/ml | mmol |
|---|---|---|---|---|
| Biphenyl-DAP-Trt Resin (2) | | 1.0 | 160 mg | 0.11 |
| Methanesulfonyl chloride | 114.55 | 10.0 | 85 uL | 1.1 |
| Lutidine | 107.16 | 15.0 | 190 uL | 1.6 |
| DCM | | | 1.5 ml | |

Methanesulfonyl chloride (85 uL, 1.1 mmol) was added to a mixture of deprotected DAP resin (2) (160 mg, 0.11 mmol) and lutidine (190 uL, 1.6 mmol) in DCM (1.5 ml). After shaking for 16 hours, the mixture was drained and washed with DMF (10×2 ml) and DCM (5×2 ml). The product was cleaved from the resin through treatment with TFA/water (4:1) (1.5 ml). After shaking for 45 min., the TFA solution was collected from the resin by filtration, and the resin was washed with TFA (1 ml) and TFA/water (1:1) (10 ml). The combined TFA fractions were concentrated under reduced pressure to a reddish-brown solid. The product, identified by LCMS, was purified by prep. HPLC using a 20×50 mm Ultro 120 C18 column running a 22 ml/min 4% gradient (AcCN/water, 0.1% TFA) for 16 min. The purified fractions were lyophilized to dryness. The solid residue was lyophilized again from $CH_3CN$/water (1:1) (5 ml) give 4 mg of pure product as a white solid (3) (~9% yield).

Example 10

Synthesis of 4'-Ethyl-biphenyl-4-carboxylic acid [2-(3,3-dimethyl-ureido)-1-hydroxycarbamoyl-ethyl]-amide (3) (Continued from compound 2 of Example 9 above)

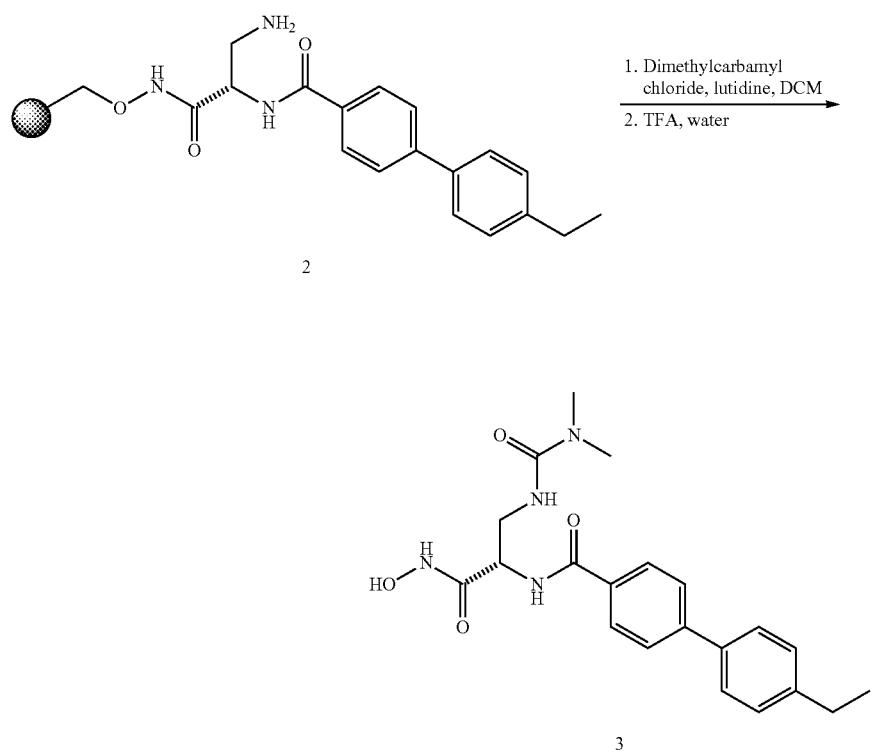

| Reagent | MW | EQ | g/ml | mmol |
|---|---|---|---|---|
| Biphenyl-DAP-Trt Resin (2) | | 1.0 | 125 mg | 0.096 |
| Dimethylcarbamyl chloride | 107.5 | 10.0 | 103 mg | 0.96 |
| Lutidine | 107.16 | 20.0 | 225 uL | 1.92 |
| DCM | | | 1.5 ml | |

Dimethylcarbamyl chloride (103 mg, 0.96 mmol) was added to a mixture of deprotected DAP resin (2) (125 mg, 0.096 mmol) and lutidine (225 uL, 1.92 mmol) in DCM (1.5 ml). After shaking at rt for 5 hours, the mixture was drained and washed with DCM (5×2 ml), DMF (5×2 ml) and DCM (5×2 ml). The product was cleaved from the resin through treatment with TFA/water (4:1) (1.5 ml). After shaking for 45 min., the TFA solution was collected from the resin by filtration, and the resin was washed with TFA/water (1:1) (2 ml). The combined TFA fractions were concentrated under reduced pressure to a reddish-brown solid. The product, identified by LCMS, was purified by prep. HPLC using a 20×50 mm Ultro 120 C18 column running a 22 ml/min 4% gradient (AcCN/water, 0.1% TFA) for 16 min. The purified fractions were lyophilized to dryness. The solid residue was lyophilized again from $CH_3CN$/water (1:1) (5 ml) give 5 mg of pure product as a white solid (3) (~13% yield).

Example 11

Synthesis of 4'-Ethyl-biphenyl-4-carboxylic acid [2-(2-amino-ethylamino)-1-hydroxycarbamoyl-ethyl]-amide (2)

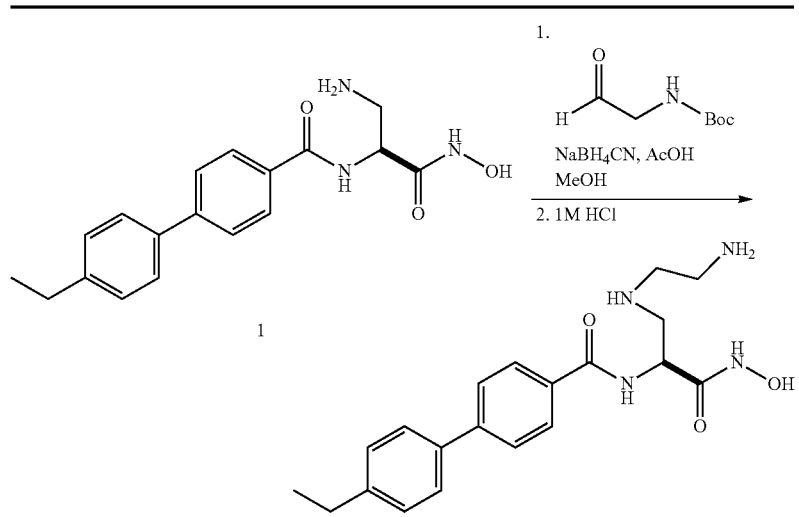

| Reagent | MW | EQ | g/ml | mmol |
|---|---|---|---|---|
| Biphenyl-DAP-hydroxamate (1) | 327.4 | 1.0 | 20 mg | 0.096 |
| Boc-amino-acetaldehyde | 159.19 | 4.0 | 6.4 mg | 0.4 |
| NaBH$_3$CN | 62.84 | 10.0 | 3.1 mg | 0.05 |
| Acetic acid | 60.05 | 20.0 | 6 uL | 1.00 |
| DCM | | | 1.5 ml | |

NaBH$_3$CN (3.1 mg, 0.05 mmol) followed by acetic acid (6 uL, 1.0 mmol) were sequentially added to a stirred suspension of biphenyl-DAP-hydroxamate (1) (20 mg, 0.096 mmol) and Boc-amino-acetaldehyde (6.4 mg, 0.4 mmol) in MeOH (1.5 ml) in a 4 ml vial. The reaction was followed by LCMS. After stirring 12 hours, the cloudy reaction was only 50% complete. The reaction was concentrated under reduced pressure to a thick slurry that was dissolved in DMSO. The product was purified by prep. HPLC using a 20×50 mm Ultro 120 C18 column running a 22 ml/min 3% gradient (AcCN/water, 0.1% TFA) for 16 min. The purified fractions were lyophilized to dryness. The dried powder was dissolved in CH$_3$CN/water (1:1) (1 ml) and 1M HCl (700 uL). After heating at 50° C. for 75 min., the reaction mixture was again lyophilized to dryness to produce 7.1 mg of product (2) as a 2×HCl salt white powder (~17% yield).

Example 12

Synthesis of N-(1-(N-hydroxycarbamoyl)(1S,2R)-2-hydroxypropyl)[4-(2-phenylethynyl)phenyl]carboxamide

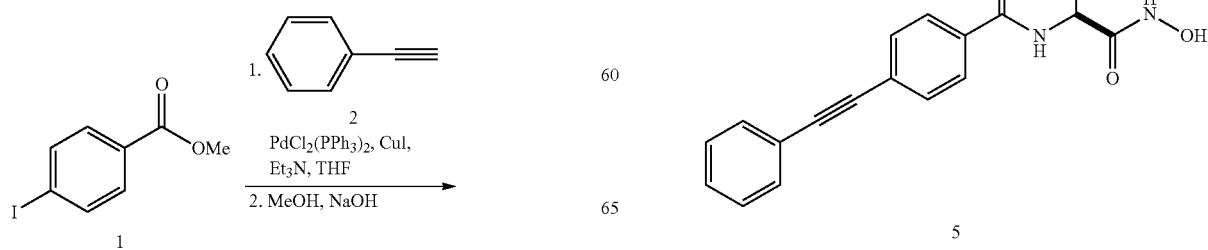

Preparation of 4-Phenylethynyl-benzoic acid (3)

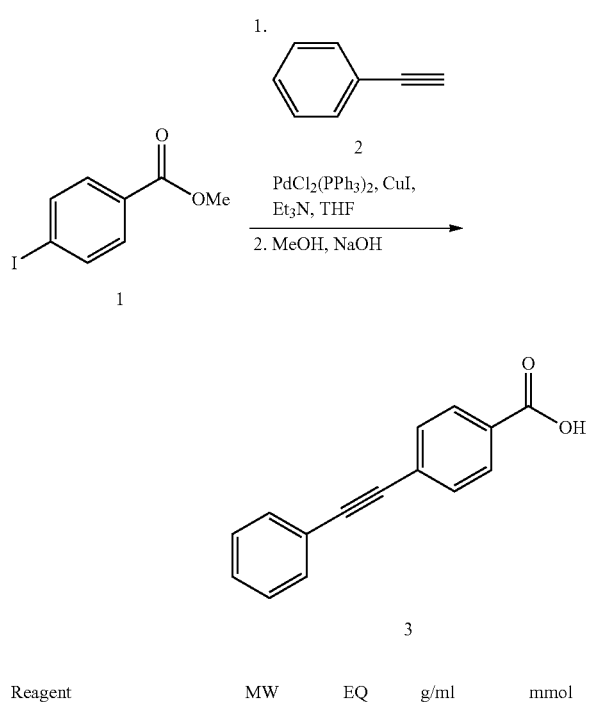

| Reagent | MW | EQ | g/ml | mmol |
|---|---|---|---|---|
| Iodo-benzoate 1 | 262 | 1.0 | 20.0 g | 76.34 |
| Ethynyl-benzene 2 | 102 | 1.1 | 8.56 g | 83.96 |
| $PdCl_2(PPh_3)_2$ | 702 | 0.012 | 0.65 g | 0.92 |
| CuI | 190 | 0.024 | 0.35 g | 1.83 |
| TEA | 101 | 1.5 | 16 ml | 114.5 |
| THF (dry & sparged with argon for 5 min.) | | | 110 ml | | d = 0.726

The 4-iodo-benzoic acid methyl ester 1 (20.0 g, 76.34 mmol), ethynyl-benzene 2 (8.56 g, 83.96 mmol), $PdCl_2(PPh_3)_2$ (0.65 g, 0.92 mmol), and CuI (0.35 g, 1.83 mmol) were mixed with THF (110 ml) in a round bottom under argon. The dry THF was sparged with dry, oxygen-free argon for at least 5 min. immediately before use. The reaction was cooled to 10° C. and TEA (16 ml) was added. The cooling bath was removed and the reaction was stirred at RT under argon. After 2.5 h, the reaction was diluted with EtOAc (400 ml) and the solids were filtered off through a pad of celite. The organic filtrate was washed with 1M HCl (60 ml), sat. aq. $NaHCO_3$ (60 ml), water (60 ml), brine (60 ml), dried with $Na_2SO_4$, filtered and concentrated under reduced pressure. The crude solid methyl ester was dissolved in MeOH (400 ml), 6M NaOH (30 ml) and water (50 ml). The reaction was stirred at 70° C. until a clear solution was formed (about 1 h). The reaction could be followed by LCMS. The reaction was cooled and diluted with water (500 ml) and hexane (100 ml). The pH was adjusted to pH 6-7. The white solid that formed was collected and washed with water (3×60 ml) and hexane (3×60 ml). The solid 3 was dried in vacuo yielding 17.3 g (approximately quantitative yield in 99% purity).

Preparation of 3-Hydroxy-2-(4-phenylethynyl-benzoylamino)-butyric acid methyl ester (4)

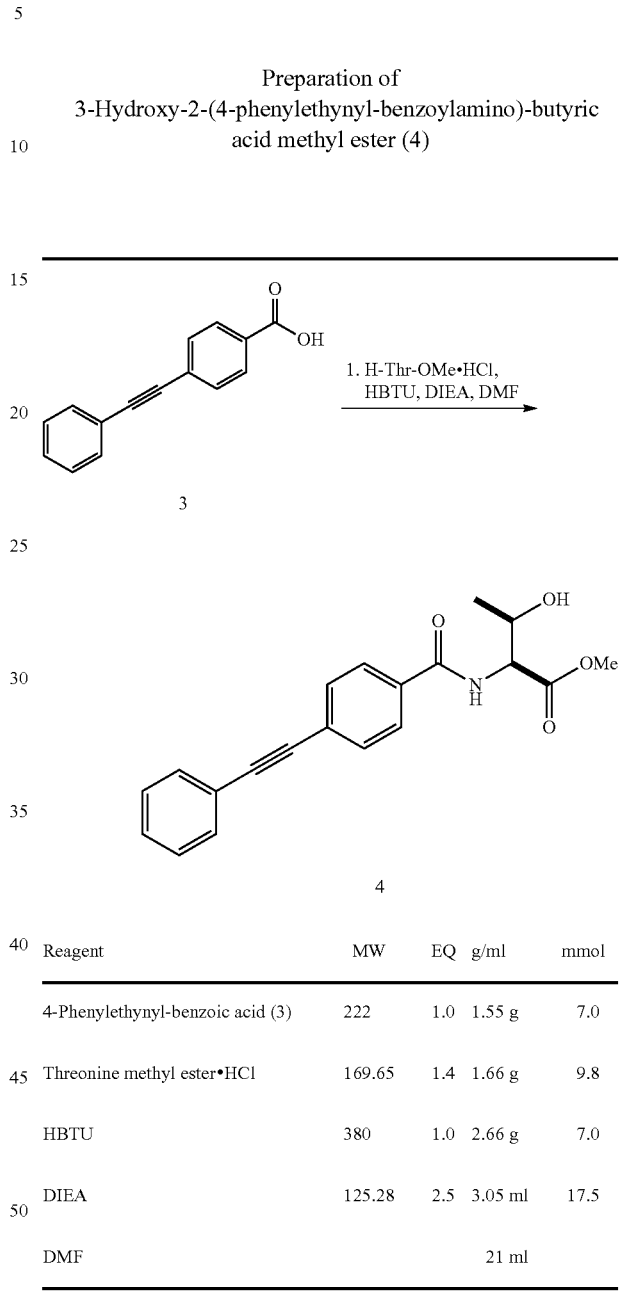

| Reagent | MW | EQ | g/ml | mmol |
|---|---|---|---|---|
| 4-Phenylethynyl-benzoic acid (3) | 222 | 1.0 | 1.55 g | 7.0 |
| Threonine methyl ester•HCl | 169.65 | 1.4 | 1.66 g | 9.8 |
| HBTU | 380 | 1.0 | 2.66 g | 7.0 |
| DIEA | 125.28 | 2.5 | 3.05 ml | 17.5 |
| DMF | | | 21 ml | |

A solution of threonine (1.66 g, 9.8 mmol) and DIEA (1.53 ml, 8.8 mmol) in DMF (10 ml) was added to a stirred solution of 4-phenylethynyl-benzoic acid 3 (1.55 g, 7.0 mmol) and DIEA (1.53 ml, 8.8 mmol) in DMF (11 ml) at rt. After 12 h, the reaction was diluted with EtOAc (300 ml) and washed with 0.5M HCl (2×60 ml), sat. aq. $NaHCO_3$ (60 ml), 50% diluted brine (60 ml), sat. brine (60 ml), dried with $Na_2SO_4$, filtered and concentrated under reduced pressure. Upon drying in vacuo, 2.34 g of white solid was obtained (approximately quantitative yield in 99% purity).

Preparation of N-(2-Hydroxy-1-hydroxycarbamoyl-propyl)-4-phenylethynyl-benzamide (5)

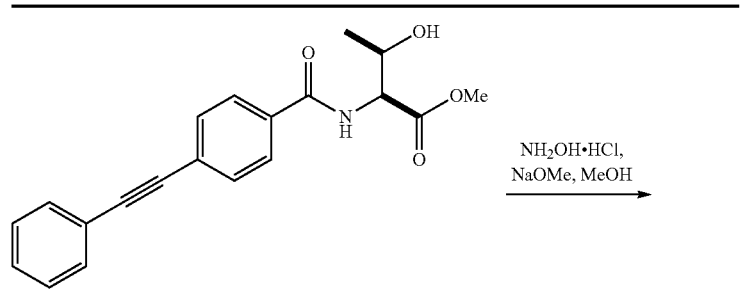

| Reagent | MW | EQ | g/ml | mmol |
|---|---|---|---|---|
| Tolanoic-Thr-OMe (4) | 340.42 | 1.0 | 2.34 g | 7.0 |
| H₂NOH•HCl | 69.49 | 10.0 | 4.81 g | 70.0 |
| NaOMe | 54.02 | >11.0 | >4.16 g | >77.0 |
| MeOH (dry) | | | 50 ml | |
| DCM (dry) | | | 30 ml | |

A solution of tolanoic-Thr methyl ester (4) (2.34 g, 7.0 mmol) in MeOH (20 ml) and DCM (30 ml) was added to a cooled (−10° C. bath) suspension of hydroxylamine HCl salt (4.81 g, 70.0 mmol) and NaOMe (4.16 g, 77.0 mmol) in MeOH (30 ml). Follow reaction by LCMS. After stirring for 2 hours, the reaction seems to stall at 50% completion. Add an additional 1 equivalent of NaOMe (0.416 g). After 3 hours, the reaction was 75% complete. Add an additional 0.5 equivalent of NaOMe (0.21 g). After 4 hours, the reaction was 90% complete. Add an additional 0.15 equivalent of NaOMe (0.064 g) for a total of 12.65 equivalents of NaOMe. The pH of the reaction was between 11-12 and had reacted about 95% completion. The reaction was diluted with EtOAc (500 ml) and washed with sat. aq. NaHCO₃ (2×60 ml), 50% diluted brine (60 ml), sat. brine (60 ml), dried with Na₂SO₄, filtered and concentrated under reduced pressure. The residue was dissolved in minimal DMA. The product was purified by prep. HPLC using a reverse phase Ultro 120 C18 column running a 2% gradient (AcCN/water, 0.1% TFA). The purified fractions were lyophilized to dryness. The product as the TFA salt was dissolved in AcCN/water (50:50) (80 ml), 1N aq. HCl (13 equivalent) and lyophilized again to give 1.3 g of white powder in 55% yield and >97% purity.

Example 13

Synthesis of 3-(R)-Amino-2-(S)-(3-phenylethynyl-benzoylamino)-butyl-hydroxamic acid (10)

Preparation of 3-(R)-Azido-2-(S)-(3-phenylethynyl-benzoylamino)-butyric acid methyl ester (9)

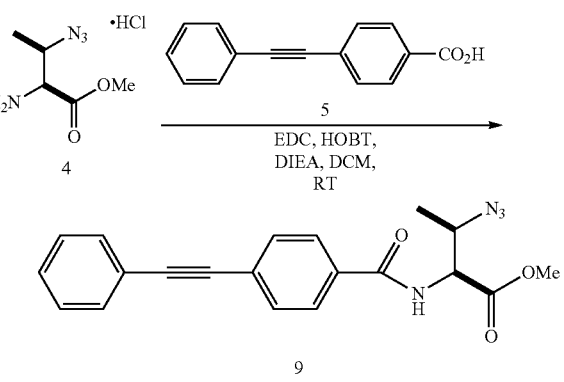

The synthesis of compound 4 is described above. The tolanyl compound (9) was made by the same procedures as for compound (6). The product (9) was obtained in 92% yield (952 mg).

HPLC (220 nm, 41 min. run) 32.64 min.; HPLC (220 nm, 17 min. run) 15.08 min LCMS: LC (214 nm) 3.16 min., MS (ES+) m/z 363.1 ($C_{20}H_{18}N_4O_3$+H requires 363.14).

Preparation of 3-(R)-Amino-2-(S)-(3-phenylethynyl-benzoylamino)-butyl-hydroxamic acid (10)

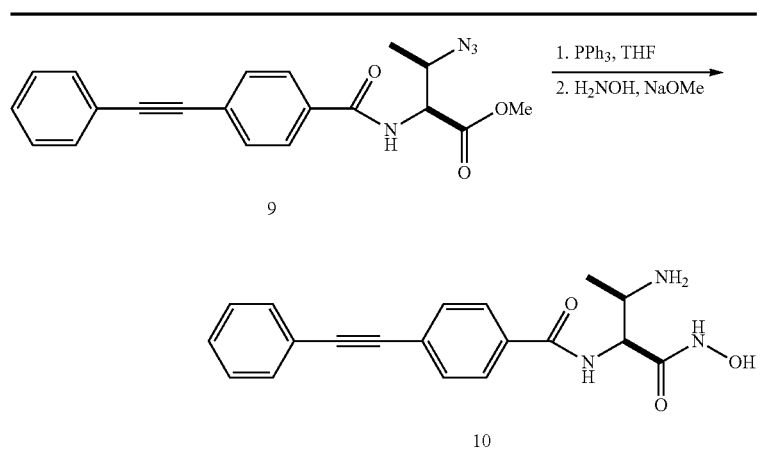

| Reagent | MW | Eq. | g/ml | mmol |
| --- | --- | --- | --- | --- |
| Amino-Thr-OMe (9) | 362.38 | 1.0 | 726 mg | 2.0 |
| PPh₃ | 262.29 | 1.0 | 526 mg | 2.0 |
| H₂NOH•HCl | 69.49 | 10.0 | 1.4 g | 20.0 |
| NaOMe | 54.02 | ~12.0 | 1.3 g | 24.0 |
| THF (dry) | | | 20 ml | |
| MeOH (dry) | | | 20 ml | |

Triphenylphosphine (526 mg, 2.0 mmol) was added to a stirred solution of tolanyl-azido-Thr methyl ester (9) (726 mg, 2.0 mmol) at rt. After 3 days the reaction reached completion as judged by TLC (EtOAc/Hex (2:1)) and LCMS. The reaction was concentrated under reduced pressure to give an ivory colored solid. The crude amino-phosphine was dissolved in MeOH (20 ml) to give a pale yellow solution. To the solution of amino-phosphine was added sequentially hydroxylamine HCl salt (1.4 g, 20.0 mmol) followed by fresh solid NaOMe powder (1.3 g, 24.0 mmol) to make a milky pH 10 suspension. After 36 h, the reaction was complete by LCMS. The reaction was evaporated under reduced pressure to give a yellow solid that was dried in vacuo. The crude product (2.75 g) was triturated with ether (3×50 ml) to remove impurities (P(O)Ph₃) and then was dissolved in abs. EtOH (120 ml) with sonication for 15 min. A fine white powder was suction filtered off, and the clear yellow ethanolic portion was concentrated to a small volume. The crude product was dissolved in DMSO (8 ml) and purified by preparative HPLC (Ultro 120 C18 75×300 mm column) running a gradient (AcCN/water, 0.1% TFA) from 5 to 70% for 55 min. The purified fractions were pooled together and lyophilized to dryness. The product as the TFA salt was dissolved in AcCN/water (50:50) (100 ml), 1N aq. HCl (1 equivalent) and lyophilized again to give 325 mg of light yellow powder as the HCl salt (43% yield).

HPLC (220 nm, 41 min.run) 18.31 min.; HPLC (220 nm, 17 min.run) 9.11 min; LCMS: LC (214 nm) 1.91 min., MS (ES+) m/z 338.1 ($C_{19}H_{19}N_3O_3$+H requires 338.14).

Synthesis of 4'-(N-Acylamino)-Tolan Dap Analogs
Example 14
Synthesis of 4-({4-[(aminoacetyl)amino]phenyl}ethynyl)-N-[(1S)-1-(aminomethyl)-2-(hydroxyamino)-2-oxoethyl]benzamide
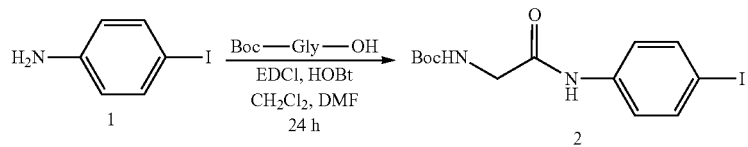
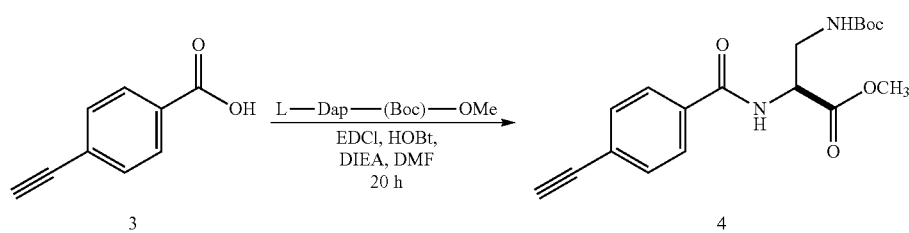
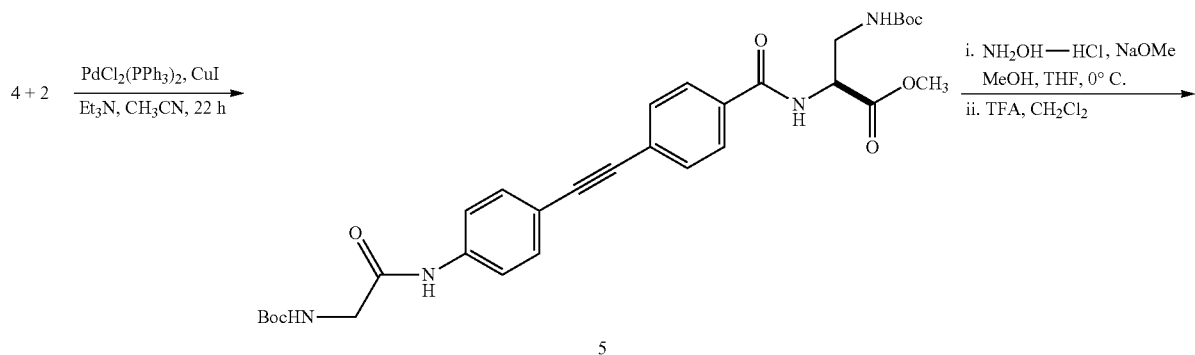
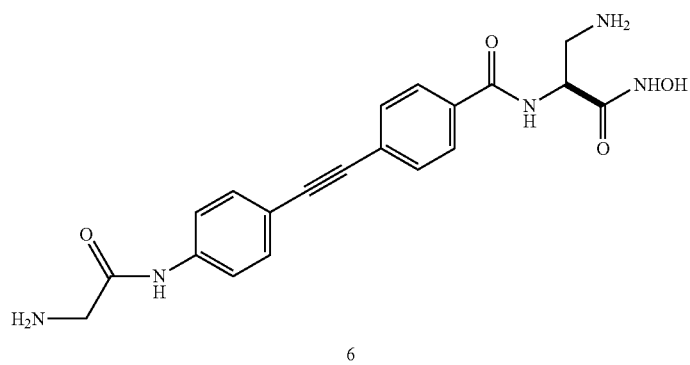

Preparation of 2-N-Boc-amino-N-(4-iodo-phenyl)-acetamide (2)

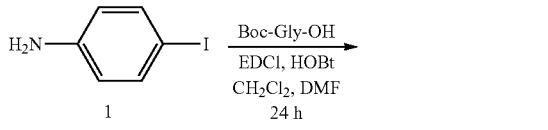

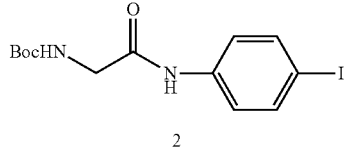

| Reagent | MW | Eq. | g/ml | mmol |
|---|---|---|---|---|
| Boc-Gly-OH | 175.19 | 1.00 | 1.752 g | 10.0 |
| 4-Iodoaniline (1) | 219.03 | 1.04 | 2.290 g | 10.4 |
| EDCI | 191.71 | 1.04 | 1.994 g | 10.4 |
| HOBt | 135.13 | 1.00 | 1.351 g | 10.0 |
| DCM | | | 18 mL | |
| DMF | | | 1 mL | |

A solution of Boc-Gly-OH (1.752 g, 10.0 mmol) in DCM (18 mL) and DMF (1 mL) was treated with EDCI (1.994 g, 10.4 mmol) and HOBt (1.351 g, 10.0 mmol). After stirring 15 min, 4-iodoaniline 1 (2.290 g, 10.4 mmol) was added and the reaction monitored by TLC (25:1 DCM/MeOH ($R_f$=0.6)). After 24 h the solution was diluted with EtOAc (250 mL), washed with 1.0 M HCl (3×100 mL), sat. NaHCO$_3$ (3×100 mL), brine (3×100 mL), dried over MgSO$_4$, filtered and concentrated in vacuo to afford 2.900 g (77% yield) of a white solid.

Preparation of (2S)-3-N-Boc-amino-(4-ethynyl-benzoylamino)-propionic acid methyl ester (4)

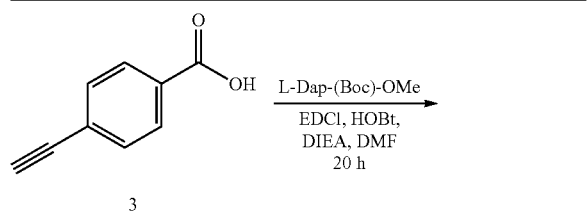

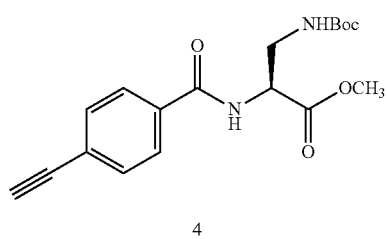

| Reagent | MW | Eq. | g/mL | mmol |
|---|---|---|---|---|
| 4-Ethynylbenzoic acid (3) | 146.14 | 1.0 | 0.910 g | 6.22 |
| H-Dap(Boc)-OMe—HCl | 254.71 | 1.2 | 1.903 g | 7.47 |
| EDCI | 191.71 | 1.2 | 1.432 g | 7.47 |
| HOBt | 135.13 | 1.1 | 0.910 g | 6.73 |
| DIEA | 129.25 | 3.2 | 3.5 mL | 20.0 |
| DMF | | | 50 mL | |

Triethylamine (3.5 mL, 20.0 mmol) was added to a stirred solution of 4-ethynylbenzoic acid 3 (910 mg, 6.22 mmol), H-Dap(Boc)-OMe hydrochloride (1.903 g, 7.47 mmol), EDCI (1.432 g, 7.47 mmol), and HOBt (910 mg, 6.73 mmol) in DMF (50.0 mL). After stirring 20 h, the reaction mixture was diluted with EtOAc (400 mL), washed with 1.0 M HCl (2×100 mL), saturated NaHCO$_3$ (2×100 mL), H$_2$O (4×100 mL), dried over MgSO$_4$, filtered and concentrated in vacuo to give 2.140 g (99% yield) of a tan solid, mp=110-111° C. LRMS (ES+) m/z 346.9 (C$_{18}$H$_{22}$N$_2$O$_5$+H requires 347.10).

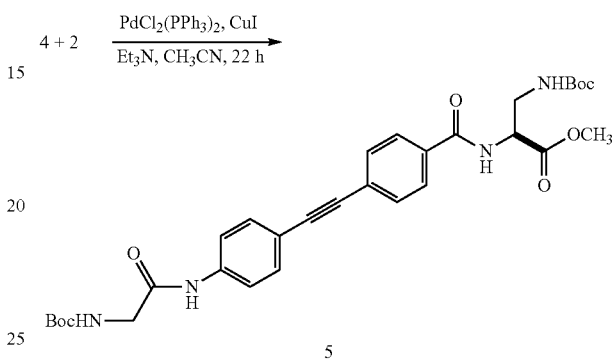

To a suspension of methyl (2S)-3-[(tert-butoxy)carbonylamino]-2-[(4-ethynylphenyl)carbonylamino]propanoate (4) (200 mg, 0.577 mmol) and 2-[(tert-butoxy)carbonylamino]-N-(4-iodophenyl)acetamide (2) (476 mg, 1.26 mmol) was added Et$_3$N (350 µL, 2.5 mmol). The solution was purged with a stream of N$_2$ for several minutes and PdCl$_2$(PPh$_3$)$_2$ (20 mg, 0.028 mmol) and CuI (10.6 mg, 0.055 mmol) were added. The reaction mixture was stirred at ambient temperature for 22 h and then concentrated by rotary evaporation. The crude black residue was chromatographed twice by silica gel chromatography (30:1 CH$_2$Cl$_2$/MeOH) to give 285 mg (83%) of methyl (2S)-3-[(tert-butoxy)carbonylamino]-2-({4-[2-(4-{2-[(tert-butoxy)carbonylamino]acetylamino}phenyl)ethynyl]phenyl}carbonylamino) propanoate (5) as a yellow foam.

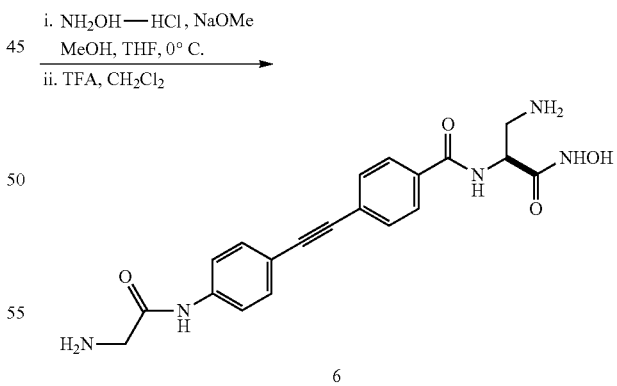

To a solution of hydroxylamine hydrochloride (98 mg, 1.41 mmol) in MeOH (1.3 mL) at 0° C. was added 25 wt % NaOMe (460 mg, 2.13 mmol). The solution was stirred at 0° C. for 15 min and then charged with a solution of methyl (2S)-3-[(tert-butoxy)carbonylamino]-2-({4-[2-(4-{2-[(tert-butoxy)carbonylamino]acetylamino}phenyl)ethynyl]phenyl}carbonylamino)propanoate (4) (279 mg, 0.469 mmol) in THF (1.5 mL) and MeOH (0.6 mL). The reaction was stirred at 0° C. for 30 min and at room temperature for 2.5 h. The reaction mixture was diluted with 4:1 CHCl₃/iPrOH (50 ml) and washed with 0.1 M HCl (30 mL). The layers were separated and the aqueous layer extracted once more with 4:1 CHCl₃/iPrOH (30 ml). The organic layers were combined, dried over Na₂SO₄, filtered and concentrated. The crude residue was suspended in 10:1 CH₂Cl₂/MeOH (4 mL), filtered, and washed with 50:1 CH₂Cl₂/MeOH (2 mL) and Et₂O (10 mL) to afford 180 mg (64%) of N-(4-{2-[4-(N-{1-(N-hydroxycarbamoyl)(1S)-2-[(tert-butoxy)carbonylamino]ethyl}carbamoyl) phenyl]ethynyl}phenyl)-2-[(tert-butoxy)carbonylamino]acetamide (6) as a white powder.

To an oven-dried flask containing N-(4-{2-[4-(N-{1-(N-hydroxycarbamoyl)(1S)-2-[(tert-butoxy)carbonylamino]ethyl}carbamoyl)phenyl]ethynyl}phenyl)-2-[(tert-butoxy)carbonylamino]acetamide (6) (130 mg, 0.218 mmol) was added 1:1 TFA/CH₂Cl₂ (2.5 mL). The resulting pink solution was stirred for 2 h and concentrated to give a pink gum. The crude residue was rinsed with CH₂Cl₂ (4 mL), concentrated by rotary evaporation and dissolved in THF (2 mL) and MeOH (0.4 mL). A solution of 4 M HCl in dioxane (200 µL) was added and the resulting precipitate filtered and washed with Et₂O (10 mL) to afford 90 mg of 4-({4-[(aminoacetyl)amino]phenyl}ethynyl)-N-[(1S)-1-(aminomethyl)-2-(hydroxyamino)-2-oxoethyl]benzamide as a pale tan powder.

Reaction of Iodoaniline with Bromoacetyl Bromide

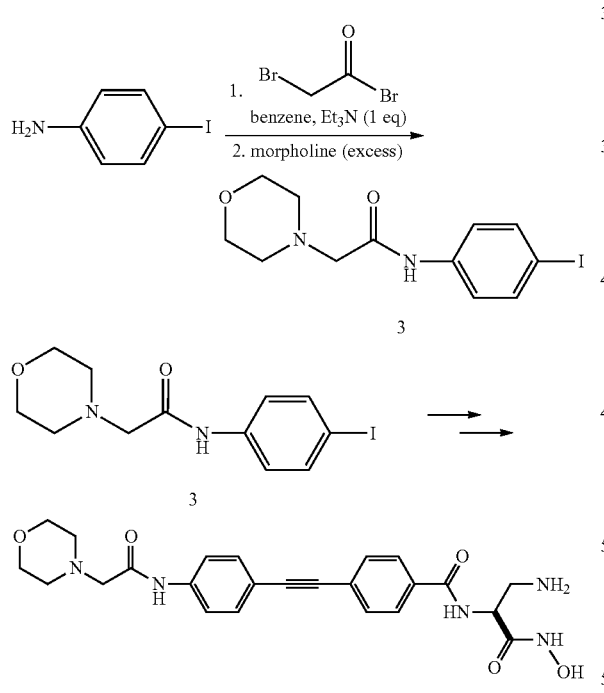

Bromoacetyl bromide (175 µL, 2.00 mmol) was added dropwise over 5 minutes to a solution of 4-iodoaniline (438 mg, 2.00 mmol) and Et₃N (280 µL, 2.00 mmol) in benzene (5 mL). The reaction was stirred 1 hour, treated with morpholine (1.0 mL, 11.5 mmol) and stirred overnight. The reaction mixture was diluted with EtOAc (200 mL), washed with aqueous 0.1 M KOH (50 mL), H₂O (50 mL), dried over MgSO₄ and concentrated to give a yellow oil. Purification by silica gel chromatography (100:1 CH₂Cl₂/MeOH) afforded 630 mg (91%) of N-(4-iodophenyl)-2-morpholin-4-ylacetamide as a waxy tan solid. This product was converted to analogues in a similar manner as Example 14.

Example A

Preparation of 4-[4-(6-Chloro-pyridin-3-yl)-buta-1,3-diynyl]-benzoic acid methyl ester

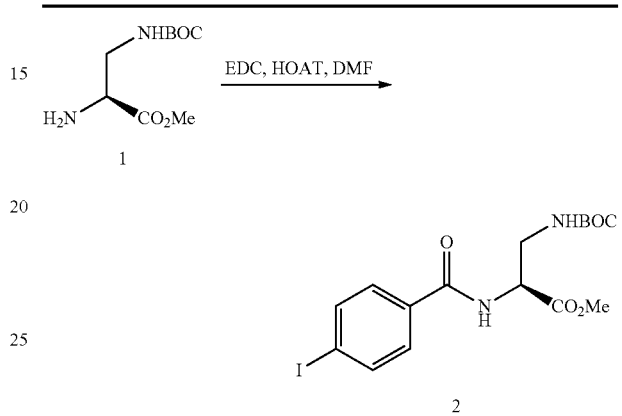

| Reagent | MW | EQ | g/ml | mmol |
|---|---|---|---|---|
| H-DAP(Boc)-OMe (1) | 254 | 1.05 | 5.93 g | 23.3 |
| 4-Iodo-benzoic acid | 248 | 1.0 | 5.49 g | 22.2 |
| HOAT | 136.1 | 1.02 | 3.08 g | 22.6 |
| EDC | 191.71 | 1.02 | 4.33 g | 22.6 |
| DIEA | 129.25 | 2.5 | 9.7 ml | 55.1 |
| DMF | | | 85 ml | |

DIEA (9.7 ml, 55.1 mmol) was added to a stirred solution of 4-iodo-benzoic acid (5.49 g, 22.2 mmol), HOAT (3.08 g, 22.6 mmol), EDC (4.33 g, 22.6 mmol) in DMF (85 ml). After 2 min., the H-DAP(Boc)-OMe (1) was added in one portion. After 12 hours, the reaction was found complete by LCMS. The reaction was diluted with EtOAc/hexane (1:1) (500 ml). The organic phase was washed with 1N HCl (2×80 ml), 1N NaOH (2×80 ml), water (2×80 ml), sat. brine (80 ml), dried with Na₂SO₄, filtered and concentrated under reduced pressure to give crude product. The residue was filtered through a filter plug of silica eluting with EtOAc/hexane (1:1). The fractions with product were evaporated to give 9.3 g of product (3-tert-Butoxycarbonylamino-2-(4-iodo-benzoylamino)-propionic acid methyl ester) in 93% yield. This product was converted to analogues in a similar manner as the aforementioned Examples.

Example 15
N-(1-(N-hydroxycarbamoyl)(1S,2R)-2-hydroxypropyl)(4-{2-[4-(morpholin-4-ylmethyl)phenyl]ethynyl}phenyl)carboxamide (5)
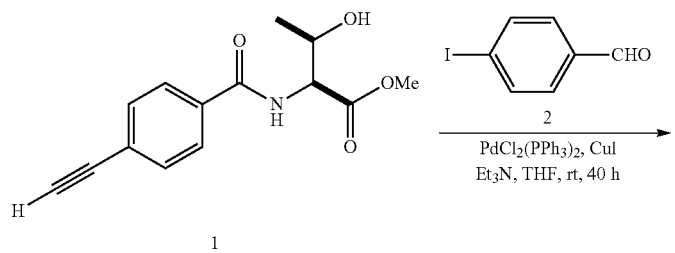
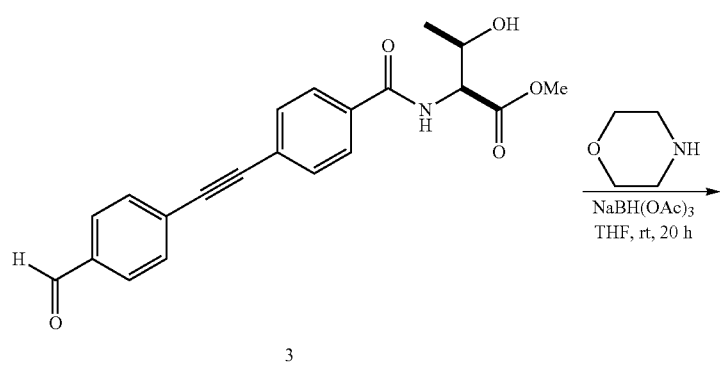
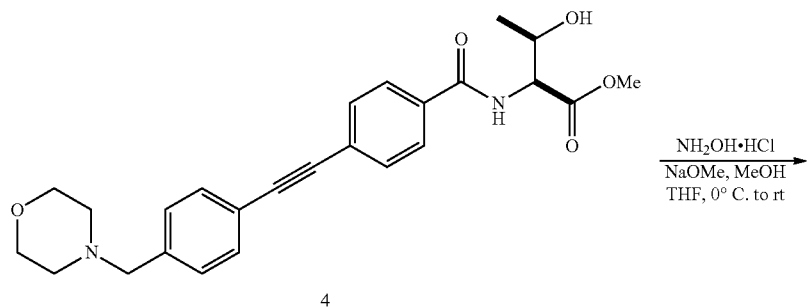
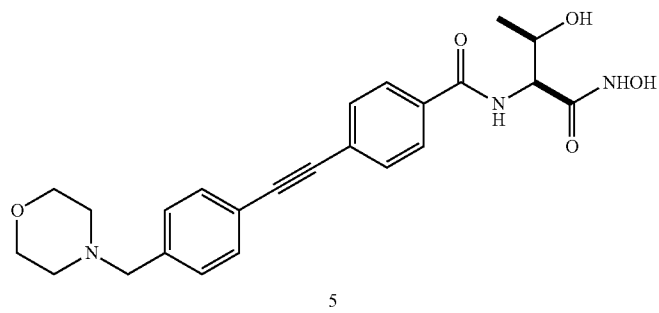

Preparation of (2S,3R)-2-[4-(4-formyl-phenylethynyl)-benzoylamino]-3-hydroxy-butyric acid methyl ester (3)

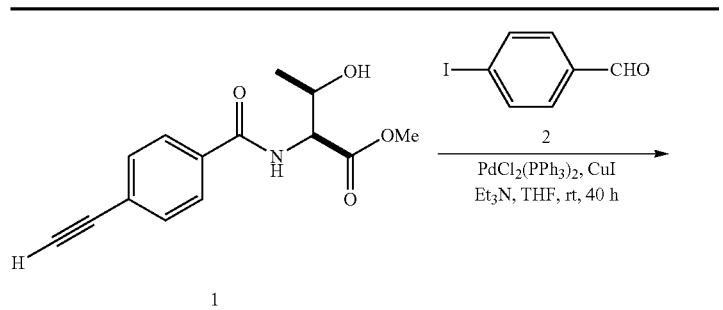

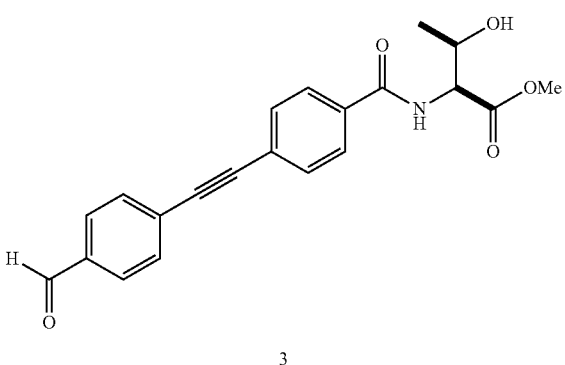

| Reagent | MW | Eq. | g/ml | mmol |
| --- | --- | --- | --- | --- |
| Ethynylbenzene (1) | 261.27 | 1.0 | 0.745 g | 2.85 |
| 4-Iodobenzaldehyde (2) | 232.00 | 1.4 | 0.902 g | 3.89 |
| $PdCl_2(PPh_3)_2$ | 701.89 | 0.03 | 0.070 g | 0.10 |
| CuI | 190.44 | 0.06 | 0.034 g | 0.18 |
| $Et_3N$ | 101.19 | 2.3 | 0.90 mL | 6.5 |
| THF | | | 50 mL | |

A solution of alkyne 1 (745 mg, 2.85 mmol), 4-iodobenzaldehyde 2 (902 mg, 3.89 mmol), and $Et_3N$ (900 μL, 6.5 mmol) in THF (50 mL) was purged with a stream of $N_2$ for two minutes and then treated with $PdCl_2(PPh_3)_2$ (70 mg, 0.10 mmol) and CuI (34 mg, 0.18 mmol). The reaction mixture was stirred 40 h, concentrated by rotary evaporation and purified by silica gel chromatography (40:1 DCM/MeOH) to give 0.833 g (80% yield) of (2S,3R)-2-[4-(4-formyl-phenylethynyl)-benzoylamino]-3-hydroxy-butyric acid methyl ester 3 as a pale yellow powder, mp= 143-144° C. $R_f$=0.3 (25:1 DCM/MeOH); LRMS (ES+) m/z 366.1 ($C_{21}H_{19}NO_5$+H requires 366.13); HPLC (300 nm, 47 min) 15.3 min.

Preparation of (2S,3R)-3-Hydroxy-2-[4-(4-morpholin-4-ylmethyl-phenylethynyl)-benzoylamino]-butyric acid methyl ester (4)

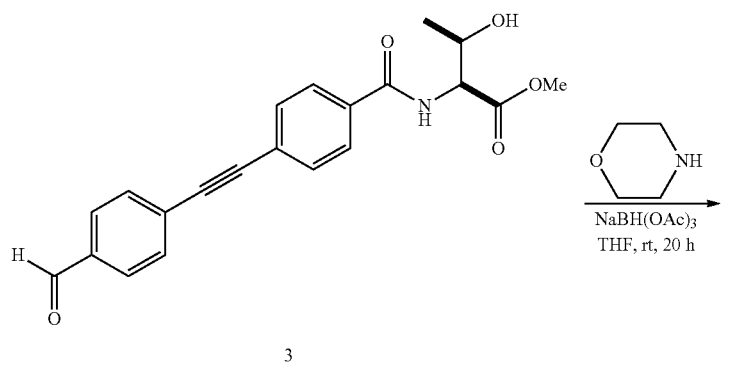

3

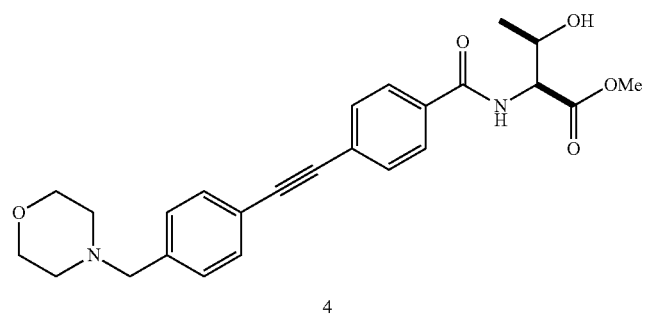

4

| Reagent | MW | Eq. | g/ml | mmol |
|---|---|---|---|---|
| Tolanylaldehyde (3) | 365.38 | 1.0 | 0.822 g | 2.25 |
| Morpholine | 87.12 | 1.3 | 0.260 mL | 2.97 |
| NaBH(OAc)$_3$ | 211.94 | 1.4 | 0.670 g | 3.16 |
| THF | | | | 15 ml |

Sodium triacetoxyborohydride (0.670 g, 3.16 mmol) was added to a solution of benzaldehyde 3 (0.822 g, 2.25 mmol) and morpholine (260 μL, 2.97 mmol) in THF (15 mL) under $N_2$ atmosphere and the reaction monitored by TLC (25:1 DCM/MeOH, $R_f$=0.2). After stirring 4 h, the reaction mixture was quenched with saturated $NaHCO_3$ (150 mL), extracted with EtOAc (3×100 mL), dried over $MgSO_4$, filtered and concentrated to give a yellow syrup. Purification by silica gel chromatography (35:1 DCM/MeOH) afforded 0.844 g (86% yield) of 4 as a sticky white foam.

Preparation of (2S,3R)—N-(2-Hydroxy-1-hydroxy-carbamoyl-propyl)-4-(4-morpholin-4-ylmethyl-phenylethynyl)-benzamide (5)

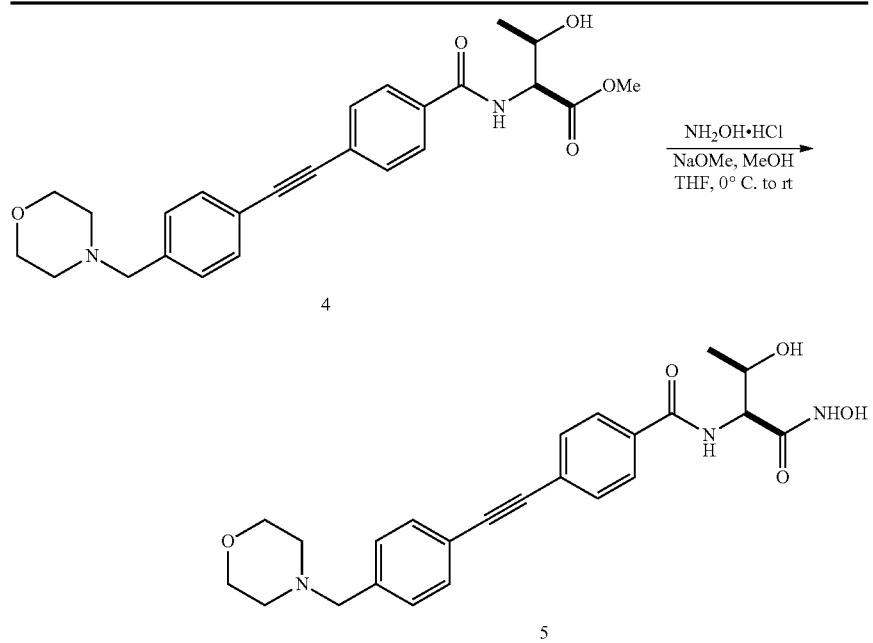

| Reagent | MW | Eq. | g/ml | mmol |
|---|---|---|---|---|
| Methyl ester (4) | 436.50 | 1.0 | 0.829 g | 1.90 |
| NH₂OH—HCl | 69.49 | 3.0 | 0.400 g | 5.76 |
| NaOMe (25 wt %) | 54.02 | 4.5 | 1.860 g | 8.60 |
| MeOH | | | 8 mL | |
| THF | | | 3 mL | |

Sodium methoxide (25 wt % in MeOH, 1.860 g, 8.60 mmol) was added to a stirred solution of hydroxylamine hydrochloride (400 mg, 5.76 mmol) in anhydrous MeOH (5 mL) at 0° C. under $N_2$ atmosphere. After stirring 20 min, a solution of methyl ester 4 (829 mg, 1.90 mmol) in 1:1 MeOH/THF (6 mL) was added and the reaction mixture stirred at 0° C. for 1 h and at room temperature for 4 h. The reaction was quenched with 1.0 M HCl (6 mL), concentrated by rotary evaporation to remove organic solvents, and diluted with DMSO (4 mL). Analytical RP-HPLC ($C_{18}$ column, $CH_3CN$ gradient 5-35%, 0.1% TFA, UV analysis 300 nm, 16 min) indicated a purity of 85% for the crude product mixture. Purification by preparative RP-HPLC and lyophilization of the collected fractions gave 701 mg (81%) of 5 as a fluffy white solid. LRMS (ES₊) m/z 438.1 ($C_{24}H_{27}N_3O_5$+H requires 438.20); RP-HPLC (300 nm, 16 min run) 8.7 min.

Resin Procedures for Synthesizing Tolanyl Hydroxamates

Example 16

Synthesis of 4-[(4-{[(benzylamino)acetyl]amino}phenyl)ethynyl]-N-{(1S,2R)-2-hydroxy-1-[(hydroxyamino)carbonyl]propyl}benzamide

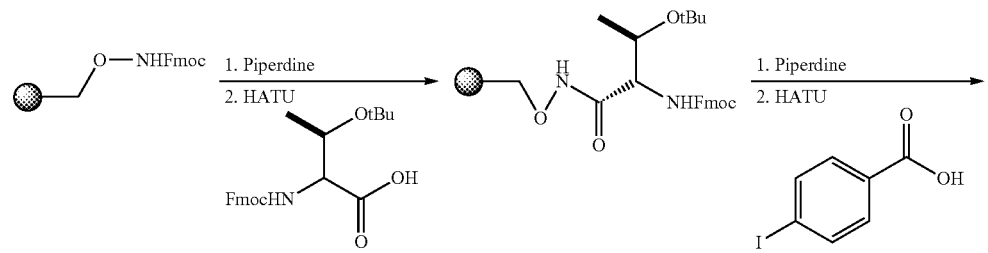

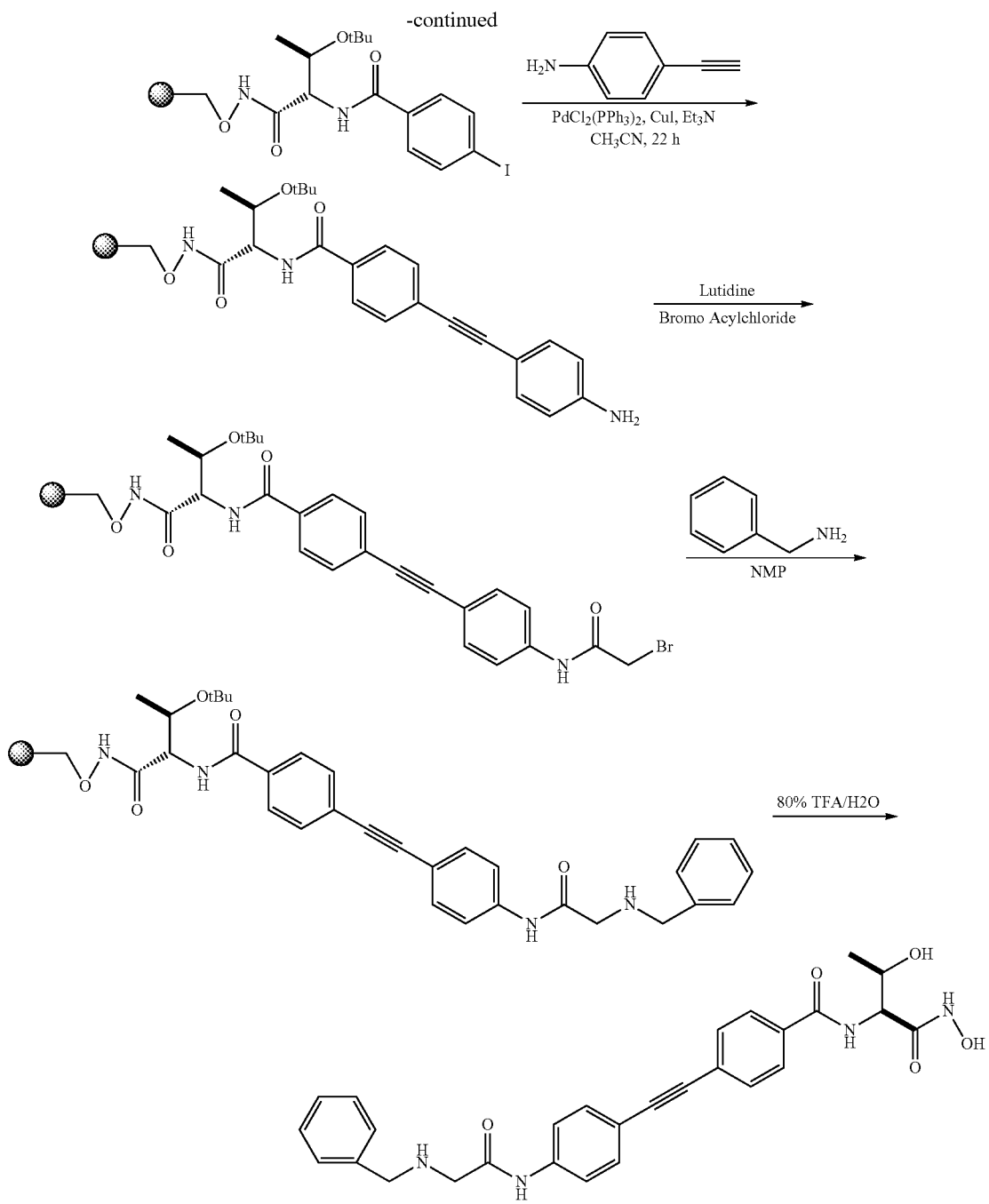

1. Coupling to Fmoc Hydroxylamine Resin

The resin was pre-swelled by adding DCM and shaking for 30 min. The resin was drained, 20% piperidine was added in DMF, the resin was shaken 1.25 hours, and finally drained and washed in 2×DMF and 2×DCM. After draining completely, 20% piperidine in DMF was added to attain cleavage in 1.25 hours. The resin was washed 4×DMF, 4×DCM and drained completely. In a separate flask, the amino acid (Fmoc-Thr tBu-OH, or Fmoc-DAP Boc-OH, 4 eq) was mixed, HATU (4 eq), DMF (60 ml) and Hunig's (8 eq) base were added and stirred for 2-3 min. The mixture was added to the resin and shaken 20-24 hours. Subsequently, the resin was drained and run with a standard wash (1×DCM, 4×DMF and 4×DCM). The Fmoc was removed from the amino acid by adding 20% piperidine in DMF and shaken 1.25 hours, drained, and given the standard wash (1×DCM, 4×DMF and 4×DCM).

2. Coupling of 4-iodobenzoic Acid to Amino Acid Resin

A mixture of 4-iodobenzoic acid (4 eq), HBTU (4 eq), DMF (60 ml) was shaken for several minutes. Hünig's base (8 eq) was subsequently added and the mixture was shaken further for 2-3 min. The pre-activated mixture was then added to the prepared Thr or DAP resin (Fmoc removed, 7.5 g, 5.775 mmol). The reaction is shaken 12-16 hours followed by the standard wash (1×DCM, 4×DMF and 4×DCM).

3. Alkyne Coupling on Resin

To the 4-iodobenzoic resin (4 g, 3.08 mmol) was added 4-aminophenylacetylene (3 eq), Pd(PPh$_3$)$_2$Cl$_2$ (0.04 eq), CuI (0.08 eq) and THF (purged with Argon). After mixing for 1 min., TEA (4.5 eq) was added and the reaction was shaken 12 hours at RT under argon.

4. Aniline Coupling with Bromoacetyl Chloride on Resin

To aniline resin (4 g, 3.08 mmol) was added DCM (30 ml) lutidine (10 eq) and shaken for 1 min. Bromoacetyl chloride (8 eq) in DCM (5 ml) was added slowly. After the addition, the slurry was shaken for 1.5 to 1.75 hours. Subsequent draining and a wash with 2×DCM, 4×DMF and 4×DCM was then performed.

5. Displacement with Amines on Resin

To the bromoacetyl resin (125 mg), was added NMP (1.5 ml) followed by amine (0.2 g or ml, ie excess) and the slurry was shaken for 12-16 hours at RT. To neutralize the salt, TEA was added. The imidazole was heated at 38° C. for 24 h (in the case of anilines, they were heated at 38° C. for 48 h). The reaction mixture was drained and washed 4×DMF and 4×DCM.

6. Cleavage from Resin and Deprotection of Thr tBu and DAP Boc

The resin (125 mg) was soaked in TFA/water (80:20 v/v) (1.5 ml) at RT for 45 min. Upon cleavage the solution was collected and the resin was washed with more TFA/water mixture (0.75 ml). To the TFA/product solution was added acetonitrile/water solution (1:1 v/v, 10 ml) and pure water (2.5 ml). The mixture was frozen in liquid nitrogen for ~15 min and lyophilized. The dry residue was dissolved in the acetonitrile/water solution (1:1 v/v, 10 ml) again followed by addition of 1M aq. HCl (1.2 eq per basic nitrogen), frozen, and lyophilized to a powder.

Synthesis of 3'-Nitro-Tolan Threonine Hydroxamic Acid

Example 17

(1S,2R)—N-(2-hydroxy-1-hydroxycarbamoyl-propyl)-4-(3-nitro-phenylethynyl)-benzamide

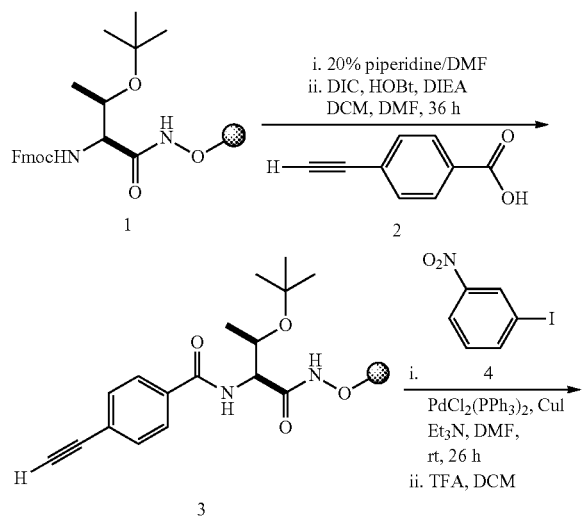

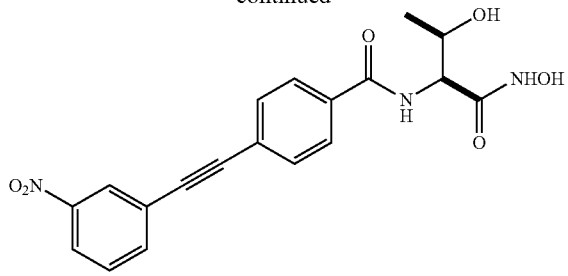

Preparation of (1S,2R)—N-(2-tert-butoxy-1-hydroxycarbamoyl-propyl)-4-ethynyl-benzamide on hydroxylamine 2-chlorotrityl resin (3)

| Reagent | MW | Eq. | g/mL | mmol |
|---|---|---|---|---|
| Fmoc-threonine/resin (1) | 0.70 mmol/g | 1.0 | 0.522 g | 0.365 |
| 4-Ethynylbenzoic acid (2) | 146.14 | 3.0 | 0.160 g | 1.10 |
| DIC | 126.20 | 4.9 | 0.28 mL | 1.79 |
| HOBt | 135.13 | 3.0 | 0.148 g | 1.10 |
| DIEA | 129.25 | 6.3 | 0.40 mL | 2.30 |
| DCM | | | 1.0 mL | |
| DMF | | | 3.0 mL | |

The resin 1 (0.522 g, 0.365 mmol, 0.70 mmol/g) was swelled in DCM (5 mL) for 2 h and drained. The resin was treated with 20% piperidine in DMF (6 mL) for 1 hour, washed with DMF (4×6 mL) and DCM (4×6 mL) and drained completely. In a separate flask, 4-ethynylbenzoic acid 2 (0.160 g, 1.10 mmol), DIC (0.280 mL, 1.79 mmol), HOBt (0.148 g, 1.10 mmol) and DIEA (0.4 mL, 2.30 mmol) were dissolved in DCM (1 mL) and DMF (4 mL), stirred 15 min and added to the resin. After shaking for 36 h, the mixture was drained, washed with DMF (4×6 mL) and DCM (4×6 mL) and dried in vacuo to give 0.495 g of a yellow resin.

Preparation of (1S,2R)—N-(2-hydroxy-1-hydroxycarbamoyl-propyl)-4-(3-nitro-phenylethynyl)-benzamide (5)

| Reagent | MW | Eq. | g/mL | mmol |
|---|---|---|---|---|
| Alkyne on resin (3) | 0.70 mmol/g | 1.0 | 100 mg | 0.070 |
| 1-Iodo-3-nitrobenzene (4) | 249.01 | 5.0 | 87.1 mg | 0.350 |
| PdCl$_2$(PPh$_3$)$_2$ | 701.89 | 0.2 | 10.0 mg | 0.014 |
| CuI | 190.44 | 0.5 | 7.0 mg | 0.036 |
| Et$_3$N | 101.19 | 15 | 150 µL | 1.10 |
| DMF | | | 1.5 mL | |

Resin 3 (100 mg, 0.070 mmol) was swelled in DCM (2 mL) for 1 h and drained. A solution of 1-iodo-3-nitrobenzene 4 (87.1 mg, 0.350 mmol) and Et$_3$N (150 µL, 1.10 mmol) in DMF (1.5 mL) was purged with a stream of N$_2$ bubbles for two minutes and added to the resin. After mixing for 5 min, PdCl$_2$(PPh$_3$)$_2$ (10.0 mg, 0.014 mmol) and CuI (7.0 mg, 0.036 mmol) were added and the mixture shaken for 26 h. The resin was drained, washed with DMF (3×2 mL), DCM (3×2 mL) and cleaved with 10% TFA/DCM (1.5 mL) for 20 min. The solution was collected and the resin was rinsed with additional 10% TFA/DCM (1.0 mL). The cleavage fractions were combined, treated with neat TFA (2.0 mL), stirred for 1 h at rt and concentrated by rotary evaporation to give a crude brown residue. Purification by RP-HPLC ($C_{18}$ column, $CH_3CN$ gradient 5-65%, 0.1% TFA, UV analysis 300 nm, 28 min) and lyophilization of the collected fractions afforded 6.0 mg (22% yield) of (1S,2R)—N-(2-hydroxy-1-hydroxycarbamoyl-propyl)-4-(3-nitro-phenylethynyl)-benzamide as a white foam. LRMS (ES+) m/z 384.2 ($C_{19}H_{17}N_3O_6$+H requires 384.15); RP-HPLC (300 nm, 28 min run) 15.2 min.

Synthesis of 4'-Trifluoromethoxy-Tolan Dap Hydroxamic Acid

Example 18

(1S)—N-(2-amino-1-hydroxycarbamoyl-ethyl)-4-(4-trifluoromethoxy-phenylethynyl)-benzamide (5)

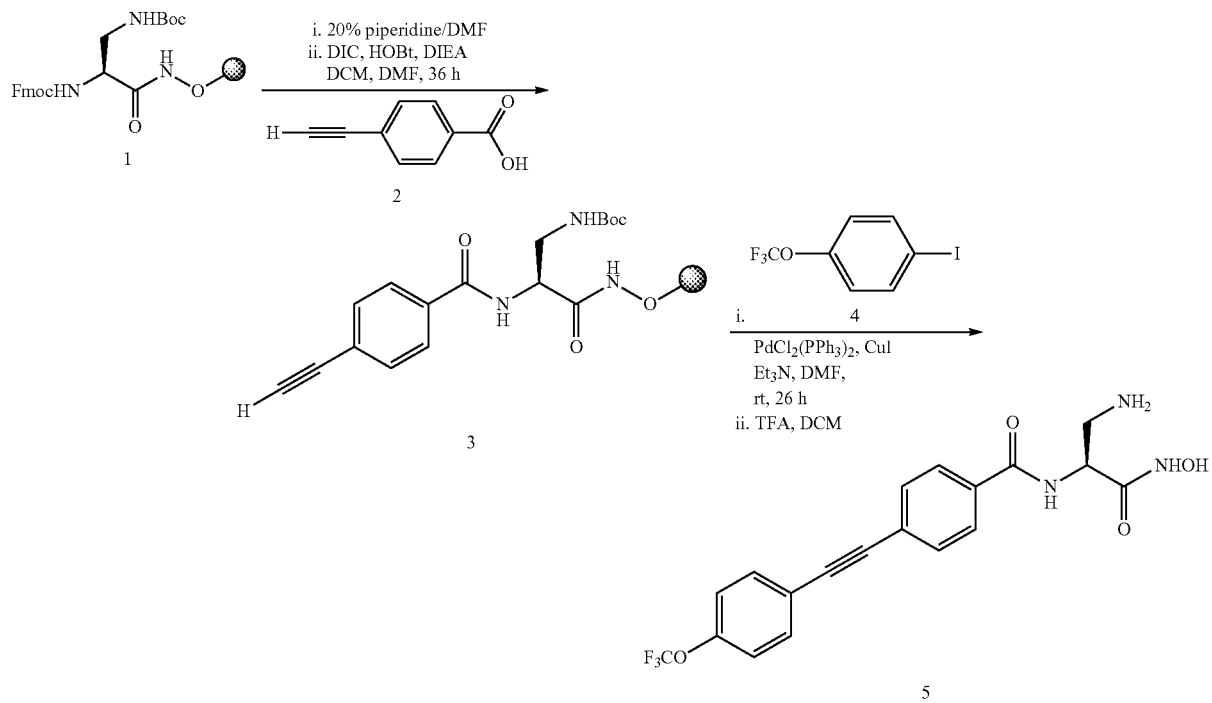

Preparation of (1S)—N-(2-(Boc)-amino-1-hydroxycarbamoyl-ethyl)-4-ethynyl-benz-amide on hydroxylamine 2-chlorotrityl resin (3)

| Reagent | MW | Eq. | g/mL | mmol |
|---|---|---|---|---|
| Fmoc-Dap/resin (1) | 0.70 mmol/g | 1.0 | 1.330 g | 0.931 |
| 4-Ethynylbenzoic acid (2) | 146.14 | 3.0 | 0.408 g | 2.793 |
| DIC | 126.20 | 4.8 | 0.70 mL | 4.470 |
| HOBt | 135.13 | 3.0 | 0.377 g | 2.793 |
| DIEA | 129.25 | 6.2 | 1.0 mL | 5.7 |
| DCM | | | 10.0 mL | |
| DMF | | | 2.0 mL | |

The resin 1 (1.330 g, 0.931 mmol, 0.70 mmol/g) was swelled in DCM (15 mL) for 2 h and drained. The resin was treated with 20% piperidine in DMF (20 mL) for 1 hour, washed with DMF (3×15 mL) and DCM (3×15 mL) and drained completely. In a separate flask, 4-ethynylbenzoic acid 2 (0.408 g, 2.793 mmol), DIC (0.70 mL, 4.470 mmol), HOBt (0.377 g, 2.793 mmol) and DIEA (1.0 mL, 5.7 mmol) were dissolved in DCM (10 mL) and DMF (2 mL), stirred 15 min and added to the resin. After shaking for 36 h, the mixture was drained, washed with DMF (3×15 mL) and DCM (3×15 mL) and dried in vacuo to give 1.290 g of a yellow resin.

Preparation of (1S)—N-(2-amino-1-hydroxycarbamoyl-ethyl)-4-(4-trifluoromethoxy-phenylethynyl)-benzamide (5)

| Reagent | MW | Eq. | g/mL | mmol |
|---|---|---|---|---|
| Alkyne on resin (3) | 0.70 mmol/g | 1.0 | 120 mg | 0.084 |
| 4-$CF_3O$-iodobenzene (4) | 287.99 | 4.0 | 96.8 mg | 0.336 |
| $PdCl_2(PPh_3)_2$ | 701.89 | 0.3 | 18.0 mg | 0.025 |

-continued

| Reagent | MW | Eq. | g/mL | mmol |
|---|---|---|---|---|
| CuI | 190.44 | 0.5 | 8.0 mg | 0.042 |
| $Et_3N$ | 101.19 | 13 | 150 µL | 1.10 |
| DMF | | | 2.0 mL | |

Resin 3 (120 mg, 0.084 mmol) was swelled in DCM (2 mL) for 1 h and drained. A solution of 4-(trifluoromethoxy)iodobenzene 4 (96.8 mg, 0.336 mmol) and $Et_3N$ (150 µL, 1.10 mmol) in DMF (2.0 mL) was purged with a stream of $N_2$ bubbles for two minutes and added to the resin. After mixing for 5 min, $PdCl_2(PPh_3)_2$ (18.0 mg, 0.025 mmol) and CuI (8.0 mg, 0.042 mmol) were added and the mixture shaken for 24 h. The resin was drained, washed with DMF (3×2 mL), DCM (3×2 mL) and cleaved with 10% TFA/DCM (2.0 mL) for 20 min. The solution was collected and the resin was rinsed with additional 10% TFA/DCM (1.0 mL). The cleavage fractions were combined, treated with neat TFA (3.0 mL), stirred for 1 h at rt and concentrated by rotary evaporation to give a crude brown residue. Purification by RP-HPLC (C$_{18}$ column, CH$_3$CN gradient 5-55%, 0.1% TFA, UV analysis 300 nm, 28 min) and lyophilization of the collected fractions afforded 9.0 mg (25% yield) of (1S)—N-(2-amino-1-hydroxycarbamoyl-ethyl)-4-(4-trifluoromethoxy-phenylethynyl)-benzamide as a white solid. LRMS (ES$_+$) m/z 408.0 (C$_{19}$H$_{16}$F$_3$N$_3$O$_4$+H requires 408.11); RP-HPLC (300 nm, 28 min run) 18.0 min.

Example 19

Synthesis of N-(1-(N-hydroxycarbamoyl)(1S,2R)-2-hydroxypropyl)[4-(4-phenylbuta-1,3-diynyl)phenyl]carboxamide

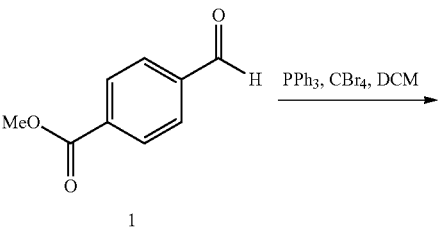

1

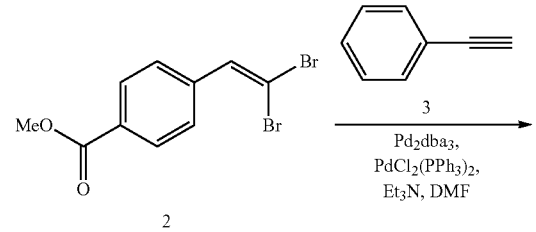

2

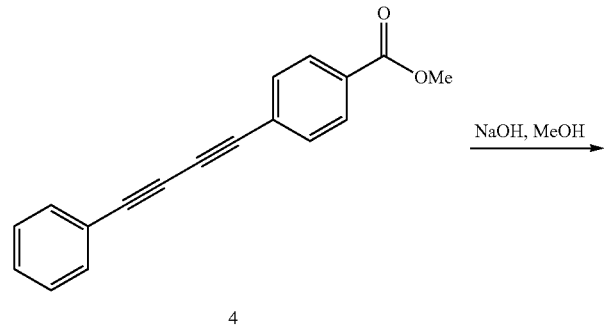

4

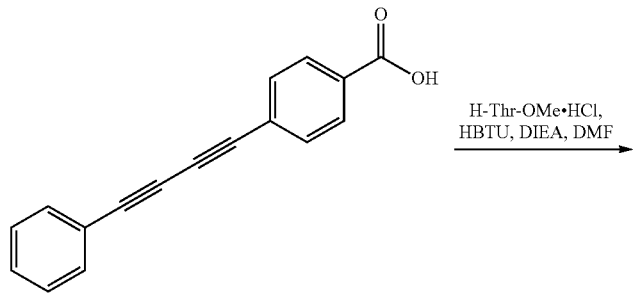

5

-continued

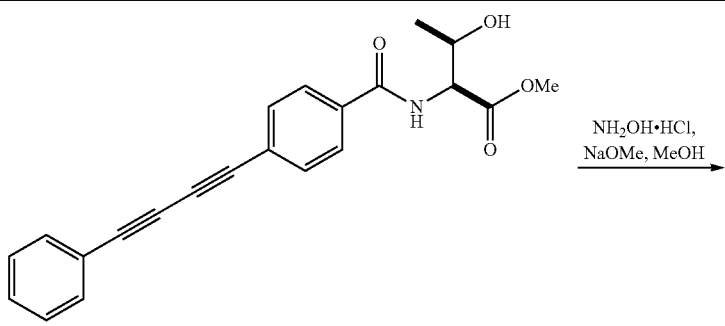

6

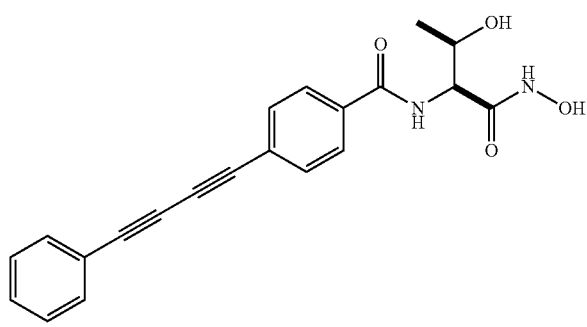

7

| Reagent | MW | EQ | g/ml | mmol |
|---|---|---|---|---|
| Dibromovinylbenzoic acid (2) | 320 | 1.0 | 5.76 g | 18.0 |
| Ethynyl-benzene | 102 | 1.4 | 2.57 g | 25.2 |
| Pd$_2$dba$_3$ | 915 | 0.01 | 164 mg | 0.18 (1% cat.) |
| TMPP | 352 | 0.04 | 253 mg | 0.72 (4%) |
| TEA | 101 | 3.0 | 7.5 ml | 54.0 |
| DMF | | | 60 ml | degassed with argon |

The 4-(2,2-Dibromo-vinyl)-benzoic acid methyl ester (2) was made by the method of Wang Shen and Le Wang in J. Org. Chem. 1999, 64, 8873-8879.

A solution of 4-(2,2-dibromo-vinyl)-benzoic acid methyl ester (2) (5.76 g, 18.0 mmol), ethynyl-benzene (2.57 g, 25.2 mmol), Pd$_2$ dba$_3$ (164 mg, 0.18 mmol), tris(4-methoxyphenyl) phosphine (TMPP) (253 mg, 0.72 mmol) were dissolved in argon sparged (5 min.) DMF (60 ml). The reaction was sparged with argon for 1 min. TEA (7.5 ml, 54.0 mmol) was added to the stirred reaction mixture that was then heated under argon at 85° C. for 3.5 hours. The reaction was found complete by LCMS. The reaction was cooled to rt and diluted with EtOAc/hexane (1:1) (300 ml). The organic phase was washed with 1M HCl (2×50 ml), 1M NaOH (3×50 ml), water (2×50 ml), sat. brine (50 ml), dried with Na$_2$SO$_4$, filtered and concentrated under reduced pressure to obtain 5.25 g of crude product as an oil. The oil was treated with approximately 20 ml of a solution of 20% EtOAc/hexane that was heated to dissolve the residue. The walls of the flask were washed with the 20% EtOAc/hexane solution (5 ml) that upon cooling gave 1.45 g of pure product (31% yield) as a white solid. The balance of the crude reaction product was purified by flash chromatography using EtOAc (8%)/hexane as eluant. The pure fractions were evaporated and dried in vacuo to give addition product typically 25-30% addition yield.

4-(4-Phenyl-buta-1,3-diynyl)-benzoic acid methyl ester (4) was made according to the method of Wang Shen and Sheela A. Thomas in Org. Lett. 2000, 2(18), 2857-2860.

Preparation of 4-(4-Phenyl-buta-1,3-diynyl)-benzoic acid (5)

A 3M aq. solution of NaOH (20 ml) was added to a stirred solution of methyl ester 4 (1.45 g, 5.6 mmol) in MeOH (100 ml) at rt. The reaction solution was heated to reflux for 45 min. until the reaction turned clear. All of the starting material was gone by TLC and HPLC. The reaction was cooled to rt and some MeOH (~50 ml) was removed by evaporation under reduced pressure. Water (100 ml) was added to the mixture. Conc. HCl was added dropwise to the stirred solution until acidic by pH paper (pH2). The white precipitate that formed was collected by suction filtration. The solid was washed with water (3×20 ml) and hexane (2×20 ml) to give after drying 1.35 g of product acid 5 in 99% yield.

Subsequent conversion of compound 5 to compound 7 was performed according to the method described in Example 12 for the synthesis of N-(2-Hydroxy-1-hydroxycarbamoyl-propyl)-4-phenylethynyl-benzamide (compound 5). LCMS MH+ 363.13.

Example B

Synthesis of N-[(1S)-1-(aminomethyl)-2-(hydroxyamino)-2-oxoethyl]-4-[4-(4-aminophenyl)buta-1,3-diynyl]benzamide 5

Preparation of 2-{4-[4-(4-Amino-phenyl)-buta-1,3-diynyl]-benzoylamino}-3-tert-butoxycarbonylamino-propionic acid methyl ester (2)

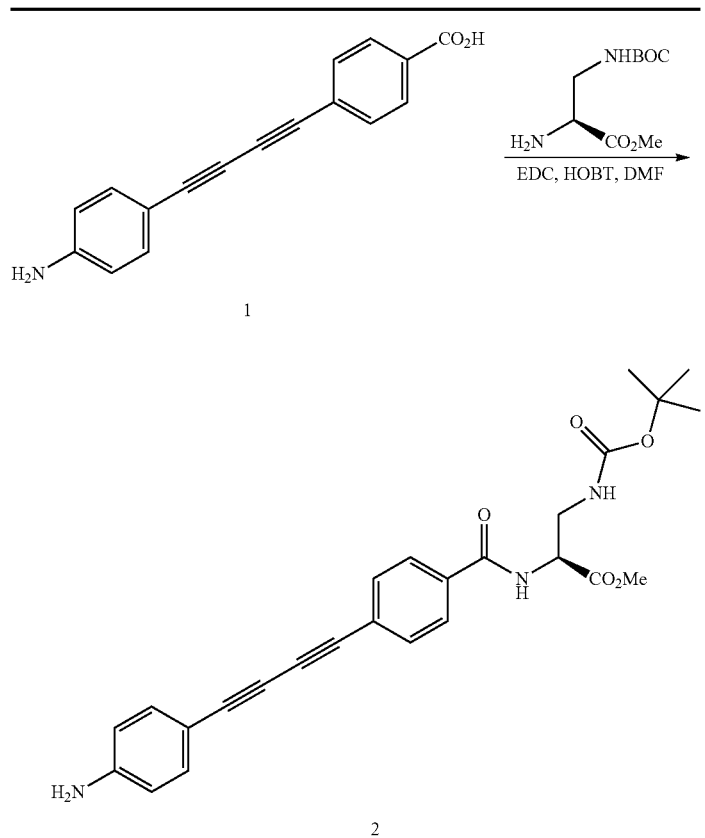

| Reagent | MW | EQ | g/ml | mmol |
|---|---|---|---|---|
| H-DAP(Boc)-OMe | 254 | 1.05 | 5.12 g | 20.1 |
| 1,3-diynyl benzoic acid (1) | 261.3 | 1.0 | 5.0 g | 19.1 |
| HOBT | 135.1 | 1.05 | 2.72 g | 20.1 |
| EDC | 191.71 | 1.05 | 3.85 g | 20.1 |
| DIEA | 129.25 | 3.0 | 10.5 ml | 60.3 |
| DMF | | | 80 ml | |

DIEA (10.5 ml, 60.3 mmol) was added to a stirred solution of 4-[4-(4-Amino-phenyl)-buta-1,3-diynyl]-benzoic acid (1) (5.0 g, 19.1 mmol), HOBT (2.72 g, 20.1 mmol), EDC (3.85 g, 20.1 mmol) in DMF (80 ml). After 2 min., the H-DAP(Boc)-OMe was added in one portion. After 12 hours at rt, the reaction was found complete by LCMS. The reaction was diluted with EtOAc/hexane (4:1) (500 ml). The organic phase was washed with 1N NaOH (2×80 ml), water (2×80 ml), sat. brine (80 ml), dried with $Na_2SO_4$, filtered and concentrated under reduced pressure to give crude product. The residue was filtered through a filter plug of silica eluting with EtOAc/hexane (4:1). The fractions with product were evaporated to give 8.02 g of product in 91% yield.

Subsequent conversion of compound 2 to the final hydroxamic acid (for example, Example 892) was performed according to the method described in Example 12 for the synthesis of N-(2-Hydroxy-1-hydroxycarbamoyl-propyl)-4-phenylethynyl-benzamide (compound 5).

Synthesis of 4-(Buta-1,3-diynyl)-benzoic Acid (4) for making 1,3-diynyl analogues (such as Example 20 below)

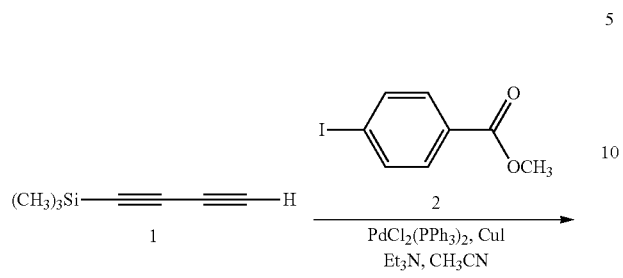

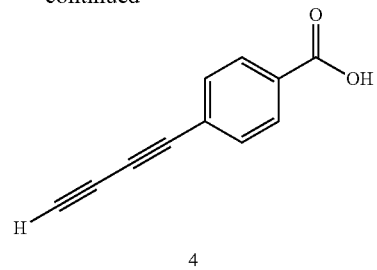

Preparation of 4-(4-trimethylsilanyl-buta-1,3-diynyl)-benzoic acid methyl ester (3)

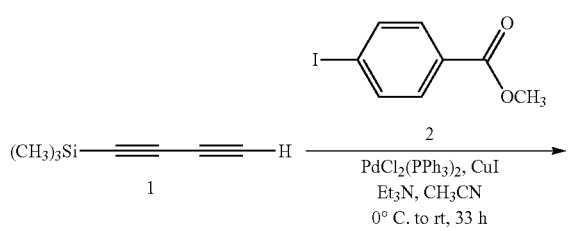

| Reagent | MW | Eq. | g/ml | mmol |
|---|---|---|---|---|
| Methyl 4-iodobenzoate (2) | 262.04 | 1.0 | 4.510 g | 17.2 |
| Trimethylsilylbutadiyne (1) | 122.24 | 2.5 | 5.240 g | 42.8 |
| $PdCl_2(PPh_3)_2$ | 701.89 | 0.04 | 0.483 g | 0.690 |
| CuI | 190.44 | 0.08 | 0.262 g | 1.37 |
| $Et_3N$ | 101.19 | 3.0 | 7.2 mL | 52.0 |
| $CH_3CN$ | | | 50 mL | |

A solution of methyl 4-iodobenzoate 2 (4.510 g, 17.2 mmol), $PdCl_2(PPh_3)_2$ (483 mg, 0.690 mmol), and CuI (262 mg, 1.37 mmol) in $CH_3CN$ (50 mL) was cooled to 0° C. under $N_2$ atmosphere in the absence of light. Triethylamine (7.2 mL, 52.0 mmol) was added, followed by trimethylsilyl-1,3-butadiyne 1 (5.240 g, 42.8 mmol) and the reaction stirred 3 h at 0° C. and 30 h at ambient temperature. Removal of solvent by rotary evaporation afforded a crude black residue that was purified by silica gel chromatography (95:5 hexanes/EtOAc) to give 3.450 g (79% yield) of 4-(4-trimethylsilanyl-buta-1,3-diynyl)-benzoic acid methyl ester 3 as a brown solid, mp=67-68° C.

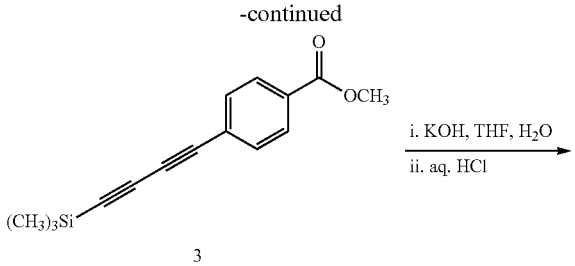

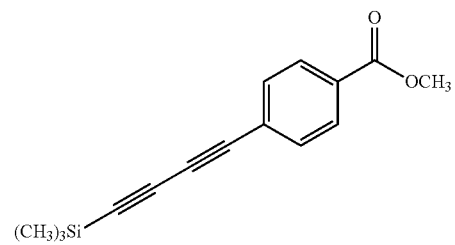

Preparation of 4-(buta-1,3-diynyl)-benzoic acid (4)

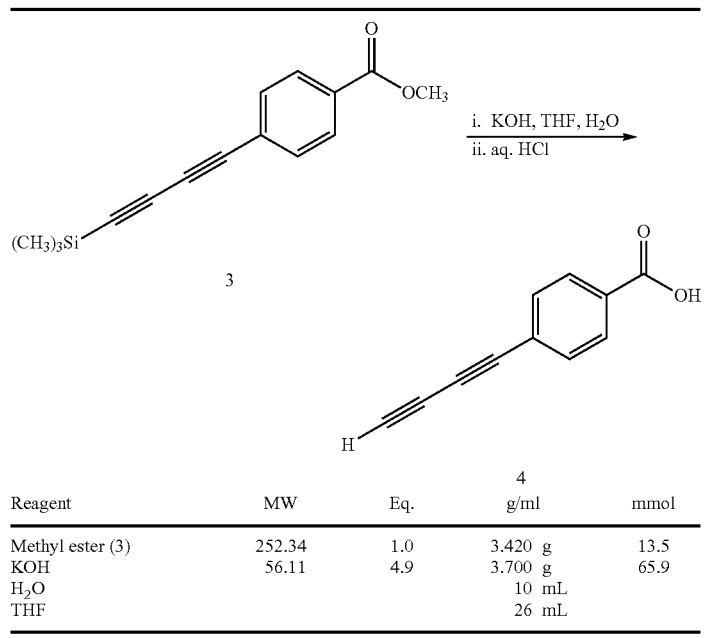

| Reagent | MW | Eq. | g/ml | mmol |
|---|---|---|---|---|
| Methyl ester (3) | 252.34 | 1.0 | 3.420 g | 13.5 |
| KOH | 56.11 | 4.9 | 3.700 g | 65.9 |
| H$_2$O | | | 10 mL | |
| THF | | | 26 mL | |

Potassium hydroxide (3.700 g, 65.9 mmol) was dissolved in H$_2$O (10 mL) and added to a solution of 4-(4-trimethylsilanyl-buta-1,3-diynyl)-benzoic acid methyl ester 3 (3.420 g, 13.5 mmol) in THF (26 mL) in the absence of light. After stirring 16 h, the reaction was quenched with 1.0 M HCl (120 mL) and the resulting precipitate was filtered, washed with 1:1 hexanes/benzene (150 mL) and dried in vacuo to afford 2.100 g (91% yield, 98% pure) of 4-(buta-1,3-diynyl)-benzoic acid 4 as a brown solid, mp>230° C. Although diyne 4 was found to be unstable at room temperature it could be stored for several weeks at 0° C. with only small amounts of decomposition observed by TLC. R$_f$=0.2 (4:1 Hexanes/EtOAc); HPLC (300 nm, 28 min run) 16.0 min; LRMS (ES+) m/z 171.0 (C$_{11}$H$_6$O$_2$+H requires 171.04).

Synthesis of a 3'-Nitrophenyl-Diacetylenic-Dap Hydroxamic Acid

Example 20

N-(1-(N-hydroxycarbamoyl)(1S)-2-aminoethyl){4-[4-(3-nitrophenyl)buta-1,3-diynyl]phenyl}carboxamide (6)

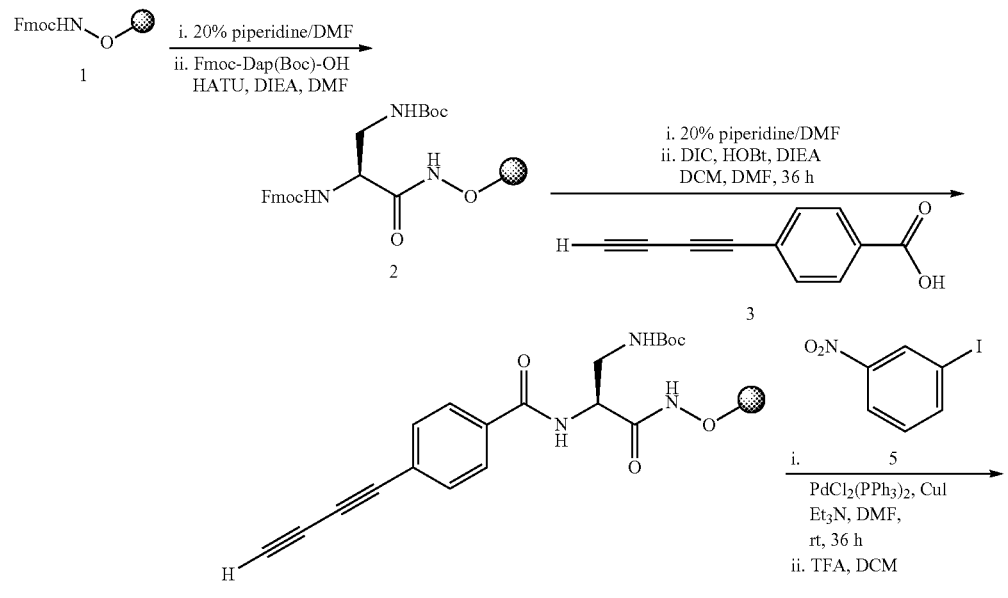

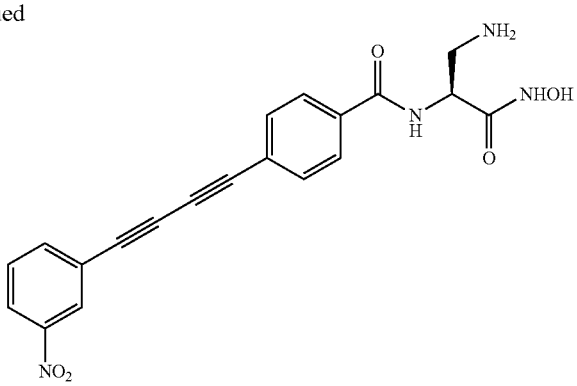

6

Preparation of Fmoc-Dap(Boc)-NHOH on hydroxylamine 2-chlorotrityl resin (2)

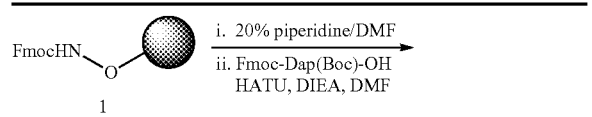

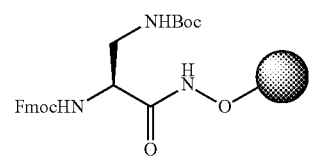

| Reagent | MW | Eq. | g/mL | mmol |
|---|---|---|---|---|
| Hydroxylamine resin (1) | 0.77 mmol/g | 1.0 | 3.288 g | 2.53 |
| Fmoc-Dap(Boc)-OH | 426.47 | 3.0 | 3.175 g | 7.44 |
| HATU | 380.25 | 3.0 | 2.829 g | 7.44 |
| DIEA | 129.25 | 10.0 | 4.3 mL | 24.7 |
| DMF | | | 35 mL | |

A suspension of N-Fmoc-hydroxylamine 2-chlorotrityl resin (3.288 g, 2.53 mmol, 0.77 mmol/g, Novabiochem) in DCM (40 mL) was shaken for 2 h and drained. The resin was treated with 20% piperidine in DMF (40 mL) for 1 hour, washed with DMF (2×40 mL), treated a second time with 20% piperidine in DMF (40 mL), washed with DMF (3×40 mL) and DCM (3×40 mL) and drained completely. In a separate flask, Fmoc-Dap(Boc)-OH (3.175 g, 7.44 mmol), HATU (2.829 g, 7.44 mmol) and DIEA (4.3 mL, 24.7 mmol) were dissolved in DMF (35 mL), stirred three minutes and added to the resin. After shaking for 48 h, the mixture was drained, washed with DMF (4×40 mL) and DCM (4×40 mL) and dried in vacuo to give 3.530 g of a yellow resin.

Preparation of (S)—N-(2-N-Fmoc-amino-1-hydroxycarbamoyl-ethyl)-4-buta-1,3-diynyl-benzamide on hydroxylamine 2-chlorotrityl resin (4)

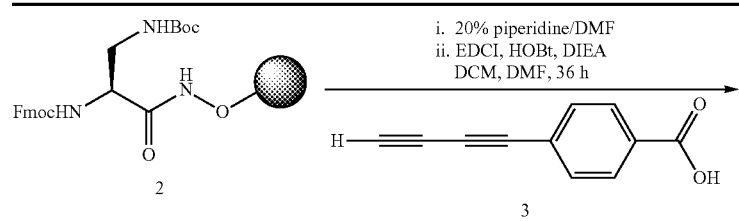

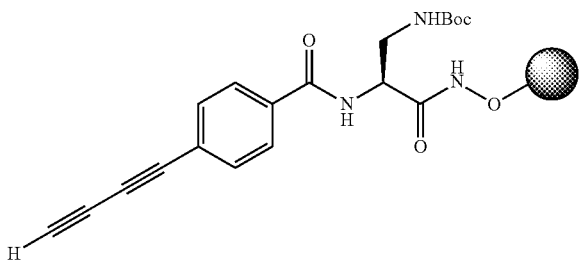

| Reagent | MW | Eq. | g/mL | mmol |
|---|---|---|---|---|
| Fmoc-Dap(Boc)/resin (2) | 0.71 mmol/g | 1.0 | 3.530 g | 2.53 |
| Butadiynyl benzoic acid (3) | 170.16 | 2.5 | 1.076 g | 6.32 |

| | -continued | | | |
|---|---|---|---|---|
| EDCI | 191.71 | 3.0 | 1.457 g | 7.60 |
| HOBt | 135.13 | 3.0 | 1.048 g | 7.75 |
| DIEA | 129.25 | 5.0 | 2.2 mL | 12.6 |
| DCM | | | 25 mL | |
| DMF | | | 5 mL | |

The resin 2 (3.530 g, 2.53 mmol, 0.71 mmol/g) was swelled in DCM (40 mL) for 2 h and drained. The resin was treated with 20% piperidine in DMF (40 mL) for 1 hour, washed with DMF (4×40 mL) and DCM (4×40 mL) and drained completely. In a separate flask, 4-buta-1,3-diynyl-benzoic acid 3 (1.076 g, 6.32 mmol), EDCI (1.457 g, 7.60 mmol), HOBt (1.048 g, 7.75 mmol) and DIEA (2.2 mL, 12.6 mmol) were dissolved in DCM (25 mL) and DMF (5 mL), stirred 45 min and added to the resin. After shaking for 48 h, the mixture was drained, washed with DMF (4×40 mL) and DCM (4×40 mL) and dried in vacuo to give 3.35 g of a pale brown resin.

Preparation of (S)—N-(2-amino-1-hydroxycarbamoyl-ethyl)-4-[4-(3-nitro-phenyl)-buta-1,3-diynyl]-benzamide (6)

Resin 4 (176 mg, 0.135 mmol) was swelled in DCM (3 mL) for 1 h and drained. A solution of 1-iodo-3-nitrobenzene 5 (118 mg, 0.474 mmol) and $Et_3N$ (200 μL, 1.43 mmol) in DMF (3.0 mL) was purged with a stream of $N_2$ bubbles for two minutes and added to the resin. After mixing for 5 min, $PdCl_2(PPh_3)_2$ (6.0 mg, 0.009 mmol) and CuI (10.0 mg, 0.052 mmol) were added and the mixture shaken for 36 h. The resin was drained, washed with DMF (4×3 mL), DCM (4×3 mL) and cleaved with 10% TFA/DCM (2 mL) for 20 min. The solution was collected and the resin was rinsed with additional 10% TFA/DCM (2 mL). The cleavage fractions were combined, treated with neat TFA (4.0 mL), stirred for 1 h at rt and concentrated by rotary evaporation to give a crude brown residue. Purification by RP-HPLC ($C_{18}$ column, $CH_3CN$ gradient 5-65%, 0.1% TFA, UV analysis 300 nm, 30 min) and lyophilization of the collected fractions afforded 12.0 mg (22%) of 470 as a white solid. LRMS ($ES_+$) m/z 392.9 ($C_{20}H_{16}N_4O_5$+H requires 393.11); RP-HPLC (300 nm, 30 min run) 14.9 min.

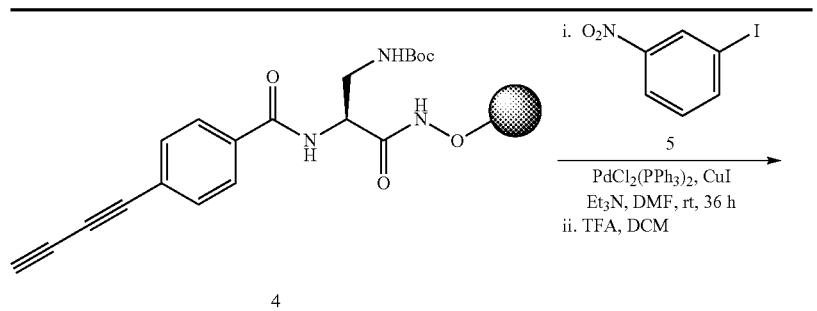

4

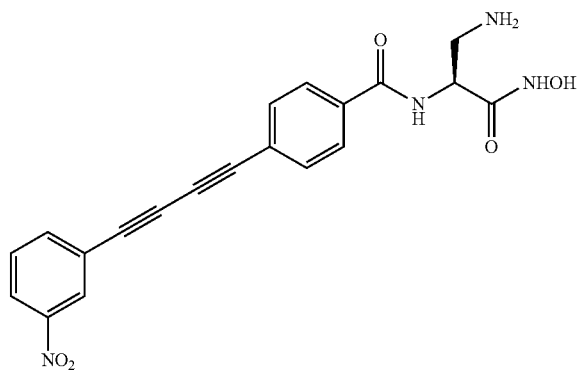

6

| Reagent | MW | Eq. | g/mL | mmol |
|---|---|---|---|---|
| Diacetylene on resin (4) | 0.77 mmol/g | 1.0 | 176 mg | 0.135 |
| 1-Iodo-3-nitrobenzene (5) | 249.01 | 3.5 | 118 mg | 0.474 |
| $PdCl_2(PPh_3)_2$ | 701.89 | 0.07 | 6.0 mg | 0.009 |
| CuI | 190.44 | 0.38 | 10.0 mg | 0.052 |
| $Et_3N$ | 101.19 | 10.6 | 200 μL | 1.43 |
| DMF | | | 3.0 mL | |

Synthesis of 4'-Benzamide Diacetylene Dap Hydroxamic Acid

Example 21

N-((2S)-amino-1-hydroxycarbamoyl-ethyl)-4-{4-[4-(2-amino-ethylcarbamoyl)-phenyl]-buta-1,3-diynyl}-benzamide (3)

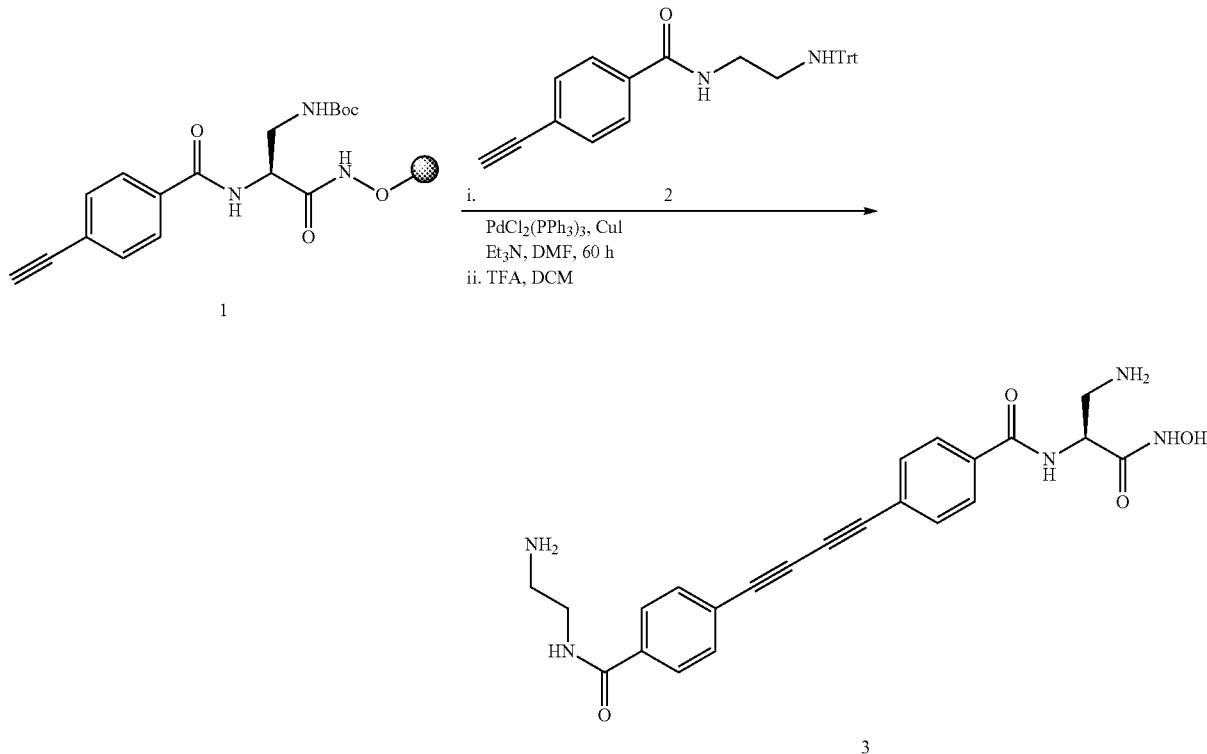

Preparation of N-((2S)-amino-1-hydroxycarbamoyl-ethyl)-4-{4-[4-(2-amino-ethylcarbamoyl)-phenyl]-buta-1,3-diynyl}-benzamide (3)

| Reagent | MW | Eq. | g/mL | mmol |
|---|---|---|---|---|
| Alkyne on resin (1) | 0.77 mmol/g | 1.0 | 145 mg | 0.111 |
| 4-Ethynylbenzamide (2) | 430.54 | 2.6 | 124 mg | 0.288 |
| $PdCl_2(PPh_3)_2$ | 701.89 | 0.3 | 21 mg | 0.030 |
| CuI | 190.44 | 1.0 | 22 mg | 0.110 |
| $Et_3N$ | 101.19 | 6.5 | 100 µL | 0.72 |
| DMF | | | 2.0 mL | |

Resin 1 (145 mg, 0.111 mmol) was swelled in DCM (2 mL) for 1 h and drained. A solution of 4-ethynylbenzamide 2 (124 mg, 0.288 mmol) and $Et_3N$ (100 µL, 0.72 mmol) in DMF (2.0 mL) was added and the resin agitated for 5 min. A mixture of $PdCl_2(PPh_3)_2$ (21 mg, 0.030 mmol) and CuI (22 mg, 0.110 mmol) was added and the resin was agitated for 60 h. The resin was drained, washed with DMF (3×2 mL), DCM (3×2 mL) and cleaved with 10% TFA/DCM (1.5 mL) for 20 min. The solution was collected and the resin was rinsed with additional 10% TFA/DCM (1.0 mL). The cleavage fractions were combined, treated with neat TFA (2.0 mL), stirred for 1 h at rt and concentrated by rotary evaporation to give a crude brown residue. Purification by RP-HPLC ($C_{18}$ column, $CH_3CN$ gradient 5-55%, 0.1% TFA, UV analysis 300 nm, 26 min) and lyophilization of the collected fractions afforded 2.6 mg (5% yield) of N-((2S)-amino-1-hydroxycarbamoyl-ethyl)-4-{4-[4-(2-amino-ethylcarbamoyl)-phenyl]-buta-1,3-diynyl}-benzamide. LRMS (ES+) m/z 434.0 ($C_{23}H_{23}N_5O_4$+H requires 434.19); RP-HPLC (300 nm, 26 min run) 15.3 min.

Synthesis of N-[4-Butadiynyl-benzoyl]-Thr(tBu) on Resin (Continued to Make Examples 22 and 23)

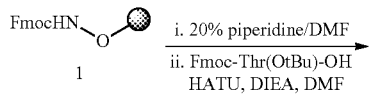

i. 20% piperidine/DMF
ii. Fmoc-Thr(OtBu)-OH
HATU, DIEA, DMF

-continued

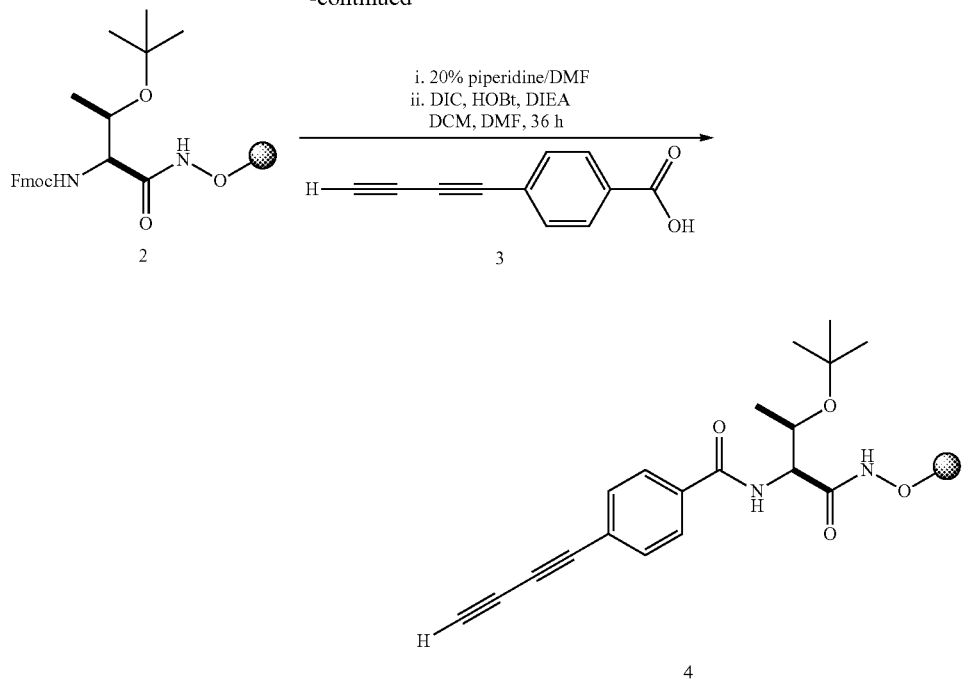

Preparation of (2S,3R)-2-N-Fmoc-amino-3-tert-butoxy-N-hydroxy-butyramide on hydroxylamine 2-chlorotrityl resin (2)

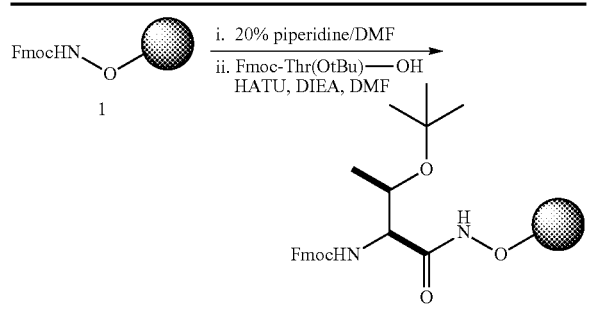

| Reagent | MW | Eq. | g/mL | mmol |
|---|---|---|---|---|
| Hydroxylamine resin (1) | 0.77 mmol/g | 1.0 | 3.188 g | 2.45 |
| Fmoc-Thr(tBu)—OH | 397.50 | 3.0 | 2.927 g | 7.36 |

-continued

| | | | | |
|---|---|---|---|---|
| HATU | 380.25 | 3.0 | 2.798 g | 7.36 |
| DIEA | 129.25 | 10.0 | 4.3 mL | 24.6 |
| DMF | | | 40 mL | |

A suspension of N-Fmoc-hydroxylamine 2-chlorotrityl resin (3.188 g, 2.45 mmol, 0.77 mmol/g, Novabiochem) in DCM (40 mL) was shaken for 2 h and drained. The resin was treated with 20% piperidine in DMF (40 mL) for 1 hour, washed with DMF (2×40 mL), treated a second time with 20% piperidine in DMF (40 mL), washed with DMF (3×40 mL) and DCM (3×40 mL) and drained completely. In a separate flask, Fmoc-Thr(tBu)-OH (2.927 g, 7.36 mmol), HATU (2.798 g, 7.36 mmol) and DIEA (4.3 mL, 24.6 mmol) were dissolved in DMF (40 mL), stirred three minutes and added to the resin. After shaking for 24 h, the mixture was drained, washed with DMF (4×40 mL) and DCM (4×40 mL) and dried in vacuo to give 3.500 g of a yellow resin.

Preparation of 4-buta-1,3-diynyl-N-(2-tert-butoxy-1-hydroxycarbamoyl-propyl)-benzamide on hydroxylamine 2-chlorotrityl resin (4)

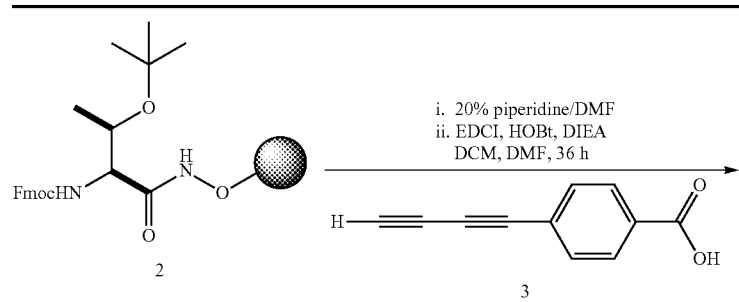

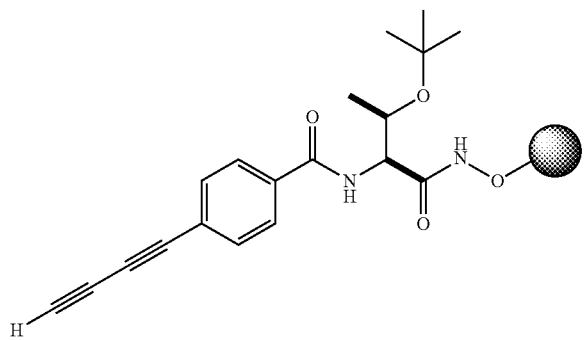

4

| Reagent | MW | Eq. | g/mL | mmol |
|---|---|---|---|---|
| Fmoc-threonine/resin (2) | 0.77 mmol/g | 1.0 | 2.030 g | 1.56 |
| Butadiynyl benzoic acid (3) | 170.16 | 2.3 | 0.617 g | 3.63 |
| EDCI | 191.71 | 2.8 | 0.834 g | 4.35 |
| HOBt | 135.13 | 2.8 | 0.588 g | 4.35 |
| DIEA | 129.25 | 3.7 | 1.0 mL | 5.7 |
| DCM | | | 15 mL | |
| DMF | | | 4 mL | |

The resin 2 (2.030 g, 1.56 mmol, 0.77 mmol/g) was swelled in DCM (20 mL) for 2 h and drained. The resin was treated with 20% piperidine in DMF (20 mL) for 1 hour, washed with DMF (4×20 mL) and DCM (4×20 mL) and drained completely. In a separate flask, 4-buta-1,3-diynyl-benzoic acid 3 (0.617 g, 3.63 mmol), EDCI (0.834 g, 4.35 mmol), HOBt (0.588 g, 4.35 mmol) and DIEA (1.0 mL, 5.7 mmol) were dissolved in DCM (15 mL) and DMF (4 mL), stirred 45 min and added to the resin. After shaking for 36 h, the mixture was drained, washed with DMF (4×20 mL) and DCM (4×20 mL) and dried in vacuo to give 1.900 g of a pale brown resin.

Synthesis of Diacetylenic Threonine Hydroxamic Acids

Example 22

(2S,3R)-4-[4-(3-aminomethyl-phenyl)-buta-1,3-diynyl]-N-(2-hydroxy-1-hydroxycarbamoyl-propyl)-benzamide (3)

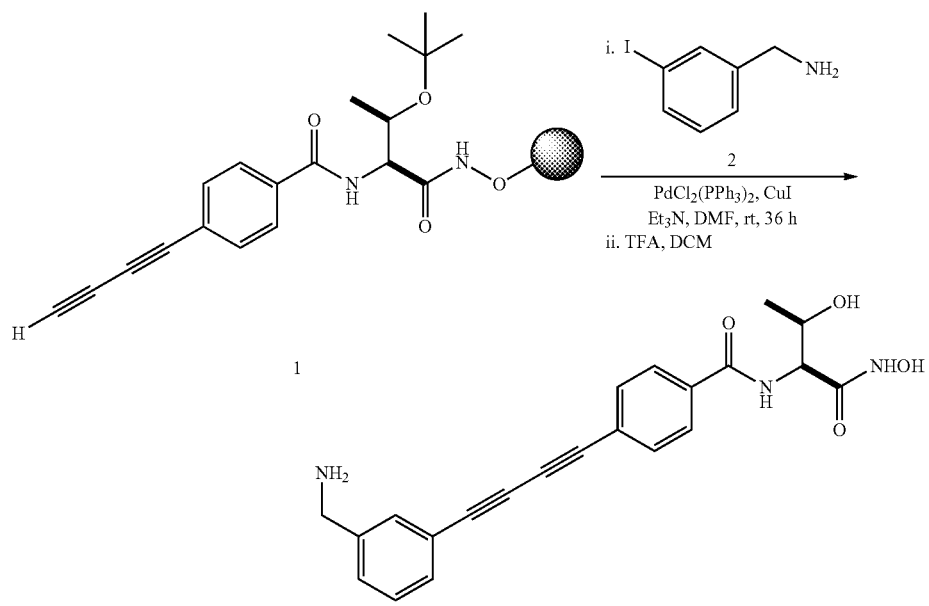

| Reagent | MW | Eq. | g/mL | mmol |
|---|---|---|---|---|
| Diacetylene on resin (1) | 0.77 mmol/g | 1.0 | 100 mg | 0.077 |
| 3-Iodobenzylamine HCl (2) | 269.51 | 4.0 | 83.0 mg | 0.308 |

| | | | | |
|---|---|---|---|---|
| -continued | | | | |
| PdCl$_2$(PPh$_3$)$_2$ | 701.89 | 0.2 | 11.0 mg | 0.016 |
| CuI | 190.44 | 0.5 | 7.0 mg | 0.037 |
| Et$_3$N | 101.19 | 23 | 250 μL | 1.80 |
| DMF | | | 1.5 mL | |

Resin 1 (obtained from previous synthesis) (100 mg, 0.077 mmol) was swelled in DCM (2 mL) for 1 h and drained. A solution of 3-iodobenzylamine hydrochloride 2 (83.0 mg, 0.308 mmol) and Et$_3$N (250 μL, 1.80 mmol) in DMF (1.5 mL) was purged with a stream of N$_2$ bubbles for two minutes and added to the resin. After mixing for 5 min, PdCl$_2$(PPh$_3$)$_2$ (11.0 mg, 0.016 mmol) and CuI (7.0 mg, 0.037 mmol) were added and the mixture shaken for 36 h. The resin was drained, washed with DMF (4×2 mL), DCM (4×2 mL) and cleaved with 10% TFA/DCM (1.5 mL) for 20 min. The solution was collected and the resin was rinsed with additional 10% TFA/DCM (1.5 mL). The cleavage fractions were combined, treated with neat TFA (3.0 mL), stirred for 1 h at rt and concentrated by rotary evaporation to give a crude brown residue. Purification by RP-HPLC (C$_{18}$ column, CH$_3$CN gradient 5-65%, 0.1% TFA, UV analysis 300 nm, 28 min) and lyophilization of the collected fractions afforded 4.3 mg (14%) of (2S,3R)-4-[4-(3-aminomethyl-phenyl)-buta-1,3-diynyl]-N-(2-hydroxy-1-hydroxycarbamoyl-propyl)-benzamide as a white solid. LRMS (ES+) m/z 392.0 (C$_{22}$H$_{21}$N$_3$O$_4$+H requires 392.15); RP-HPLC (300 nm, 28 min run) 10.0 min.

Synthesis of Diacetylenic Benzylamine Analogues

Example 23

(1S,2R)—N-2-hydroxy-1-hydroxycarbamoyl-propyl)-4-[4-(4-morpholin-4-ylmethyl-phenyl)-buta-1,3-diynyl]-benzamide (4)

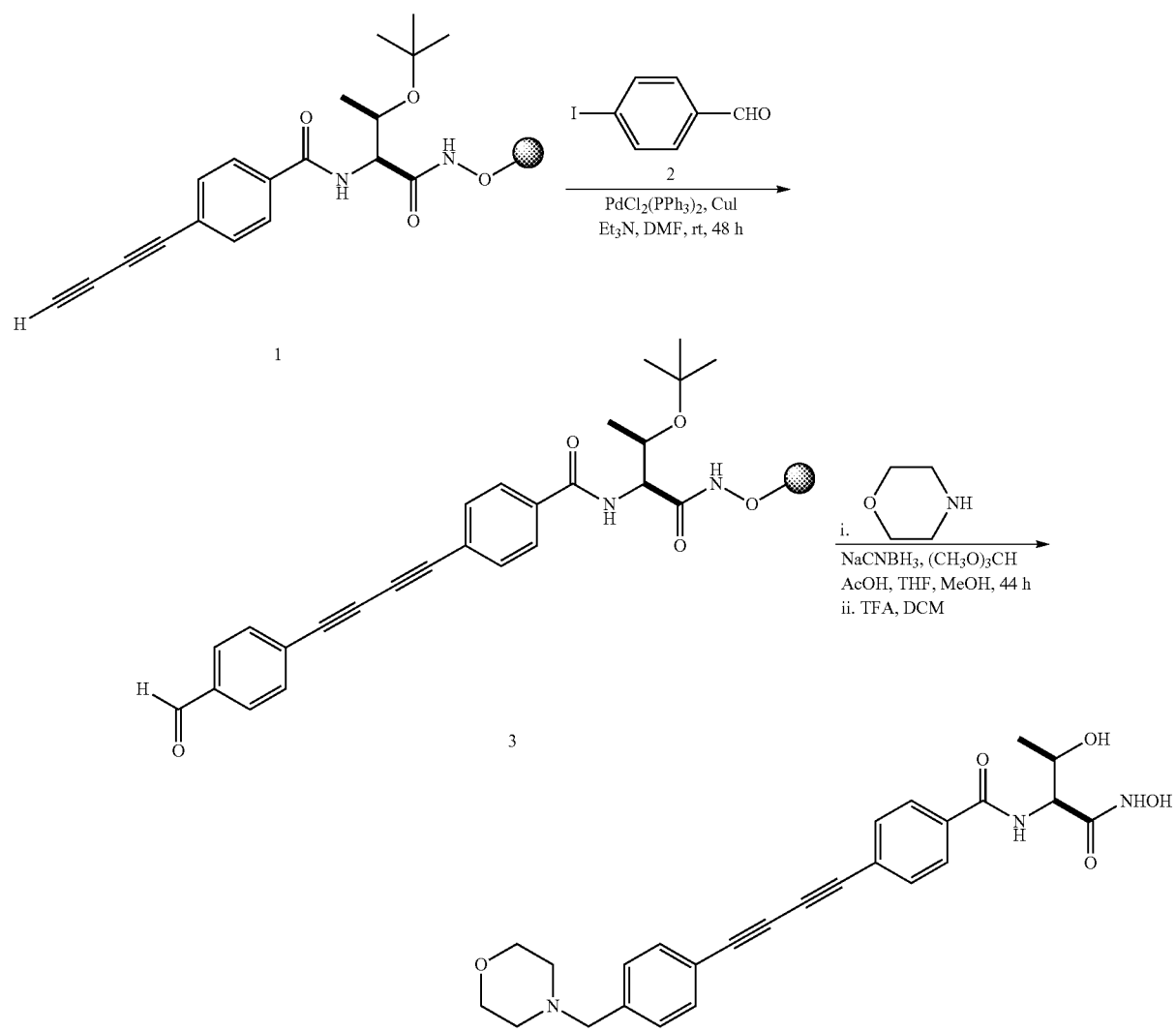

Preparation of Threonine Diacetylenic Benzaldehyde on Resin (3)

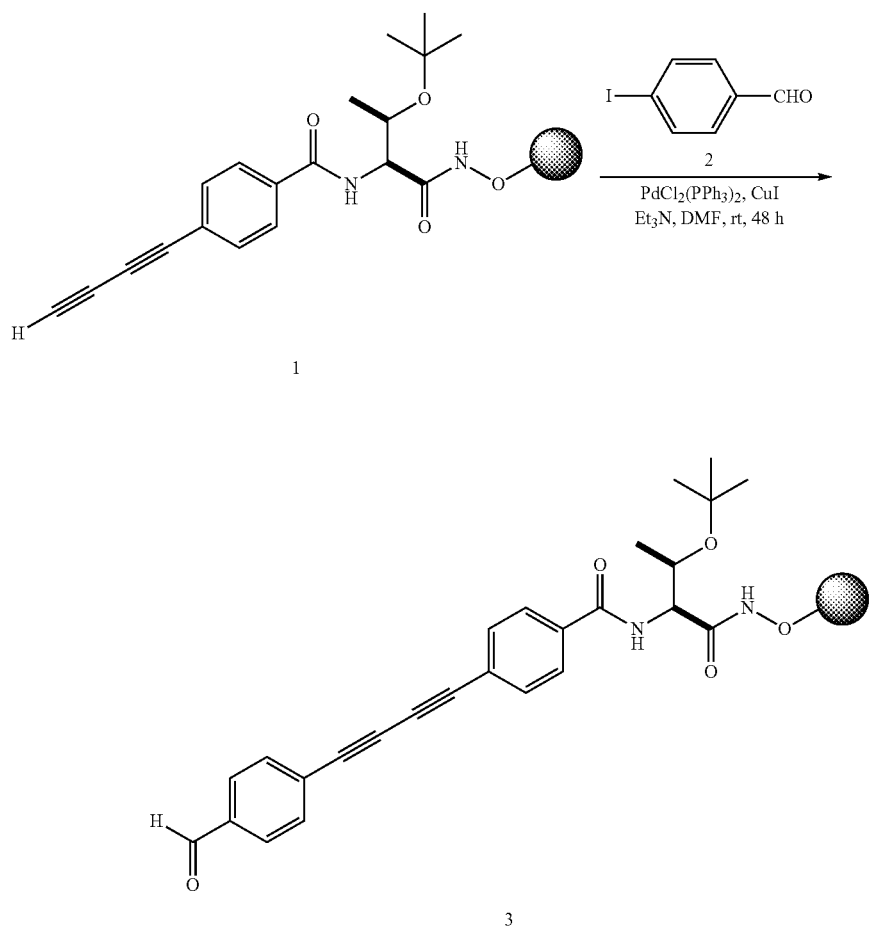

| Reagent | MW | Eq. | g/mL | mmol |
|---|---|---|---|---|
| Diacetylene on resin (1) | 0.77 mmol/g | 1.0 | 1.00 g | 0.770 |
| 4-Iodobenzaldehyde | 232.00 | 4.0 | 715 mg | 3.081 |
| $PdCl_2(PPh_3)_2$ | 701.89 | 0.07 | 40.0 mg | 0.057 |
| CuI | 190.44 | 0.13 | 19.0 mg | 0.100 |
| $Et_3N$ | 101.19 | 9.3 | 1.00 mL | 7.17 |
| DMF | | | 20.0 mL | |

Resin 1 (1.00 g, 0.77 mmol) was pre-swelled in DCM (25 mL) for 14 h and drained. A solution of 4-iodobenzaldehyde 2 (715 mg, 3.08 mmol) and $Et_3N$ (1.00 mL, 7.17 mmol) in DMF (20 mL) was purged with $N_2$ for two minutes and added to the resin. After mixing for 5 min, $PdCl_2(PPh_3)_2$ (40.0 mg, 0.057 mmol) and CuI (19.0 mg, 0.100 mmol) were added and the reaction shaken for 48 h. The resin was drained, washed with DMF (4×20 mL), DCM (4×20 mL) and dried in vacuo to give 1.100 g of a dark yellow resin.

Preparation of (1S,2R)—N-2-hydroxy-1-hydroxycarbamoyl-propyl)-4-[4-(4-morpholin-4-ylmethyl-phenyl)-buta-1,3-diynyl]-benzamide (4)

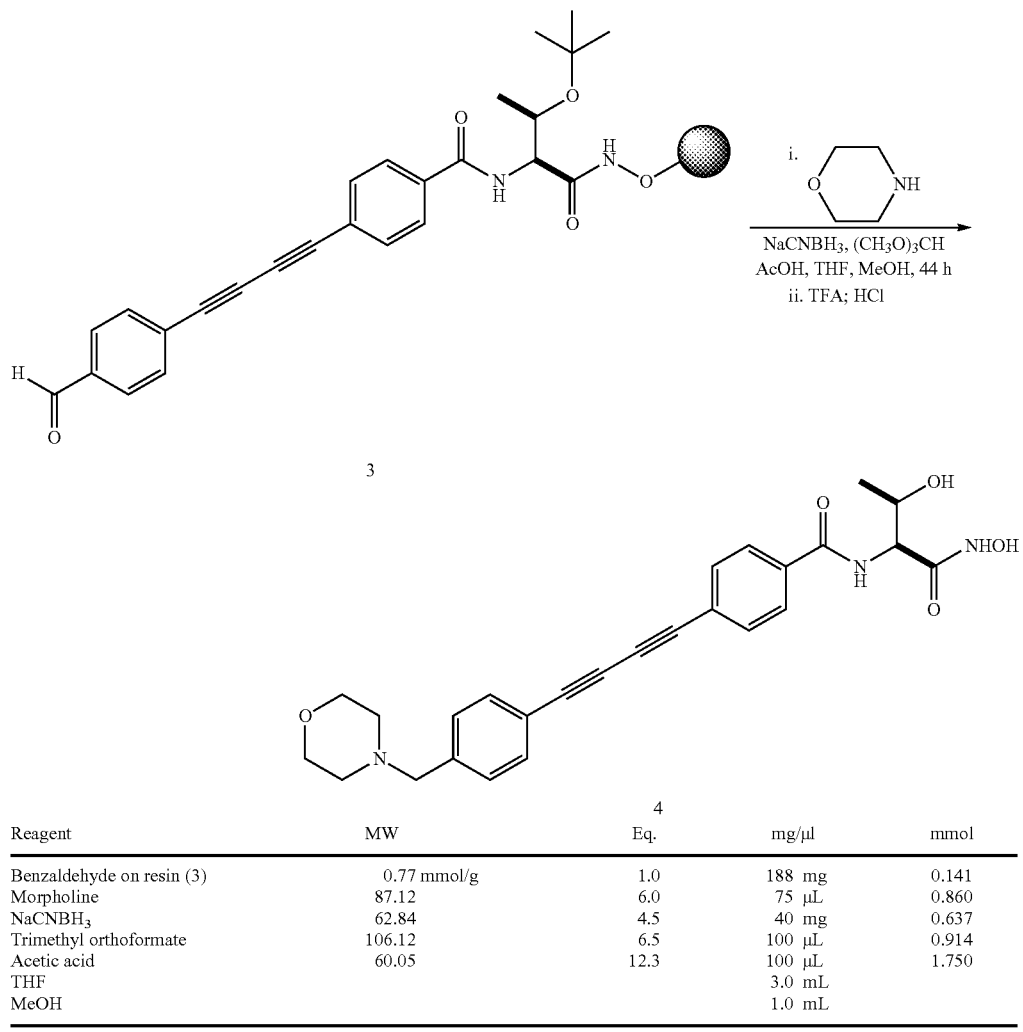

| Reagent | MW | Eq. | mg/μl | mmol |
|---|---|---|---|---|
| Benzaldehyde on resin (3) | 0.77 mmol/g | 1.0 | 188 mg | 0.141 |
| Morpholine | 87.12 | 6.0 | 75 μL | 0.860 |
| NaCNBH₃ | 62.84 | 4.5 | 40 mg | 0.637 |
| Trimethyl orthoformate | 106.12 | 6.5 | 100 μL | 0.914 |
| Acetic acid | 60.05 | 12.3 | 100 μL | 1.750 |
| THF | | | 3.0 mL | |
| MeOH | | | 1.0 mL | |

A solution of morpholine (75 μL, 0.860 mmol) and trimethyl orthoformate (100 μL, 0.914 mmol) in THF (3.0 mL) was added to a Teflon-lined screw-capped vial containing the resin-bound diacetylenic benzaldehyde 3. The resin was agitated for 10 min, treated successively with acetic acid (100 μL, 1.75 mmol) and a solution of NaCNBH₃ (40.0 mg, 0.637 mmol) in MeOH (1.0 mL) and shaken for 44 h. The resin was filtered, washed with DMF (3×3 mL) and DCM (3×3 mL) and drained. Cleavage from the resin was achieved by treatment with 10% TFA/DCM (2.0 mL) and shaking 20 min. The solution was collected and the resin was rinsed with additional 10% TFA/DCM (2.0 mL). The cleavage fractions were combined, treated with neat TFA (3.0 mL), stirred for 1 h at rt and concentrated by rotary evaporation to give a crude yellow residue. Purification by RP-HPLC ($C_{18}$ column, $CH_3CN$ gradient 5-35%, 0.1% TFA, UV analysis 300 nm, 18 min) and lyophilization of the collected fractions afforded 19.0 mg (29%) of 472 as a fluffy yellow solid. LRMS (ES+) m/z 462.0 ($C_{26}H_{27}N_3O_5$+H requires 462.10); HPLC (300 nm, 18 min run) 10.3 min.

Synthesis of 4'-Benzamide Diacetylene Threonine Hydroxamic Acid

Example 24

(1S,2R)—N-(2-hydroxy-1-hydroxycarbamoyl-propyl)-4-{4-[4-(2-amino-ethylcarbamoyl)-phenyl]-buta-1,3-diynyl}-benzamide (5)

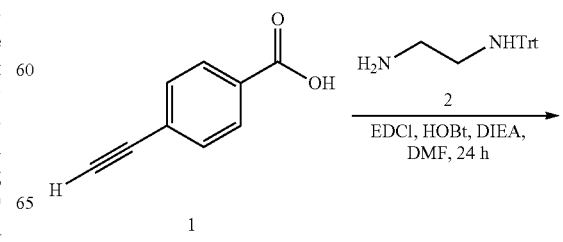

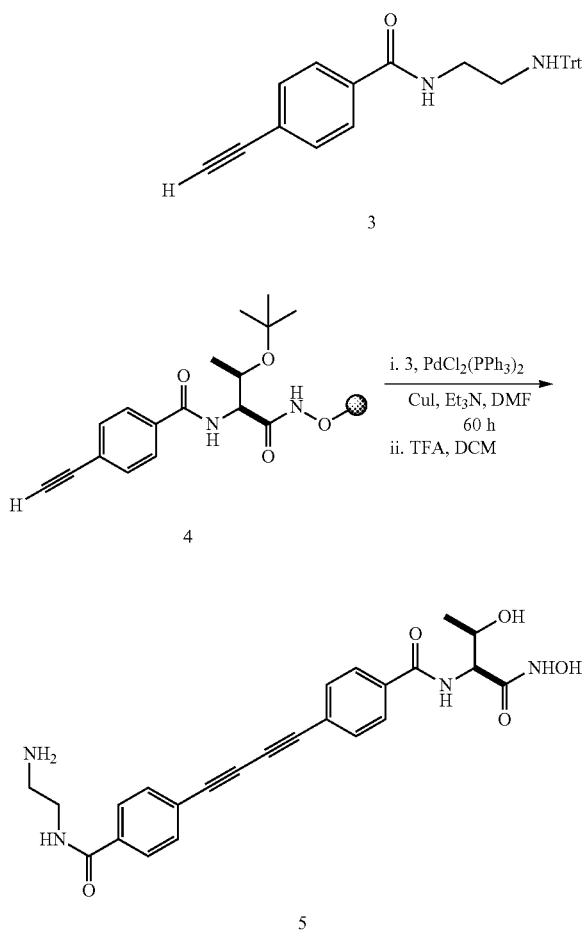

Preparation of N-(2-trityl-amino-ethyl)-4-ethynyl-benzamide (3)

| Reagent | MW | Eq. | g/mL | mmol |
|---|---|---|---|---|
| 4-Ethynylbenzoic acid (1) | 146.14 | 1.0 | 0.292 g | 2.00 |
| N-Trityl ethylenediamine | 302.41 | 1.3 | 0.810 g | 2.67 |
| EDCI | 191.71 | 1.0 | 0.382 g | 2.00 |
| HOBt | 135.13 | 3.0 | 0.270 g | 2.00 |
| DIEA | 129.25 | 4.0 | 1.40 mL | 8.00 |
| DMF | | | 10.0 mL | |

To a solution of 4-ethynylbenzoic acid 1 (292 mg, 2.00 mmol), EDCI (382 mg, 2.00 mmol), and HOBt (270 mg, 2.00 mmol) in DMF (10 mL) was added N-trityl ethylenediamine 2 (810 mg, 2.67 mmol) and DIEA (1.4 mL, 8.0 mmol). The reaction mixture was stirred 24 h, diluted with EtOAc (200 mL), washed with 0.5 M HCl (60 mL), saturated NaHCO$_3$ (2×60 mL), H$_2$O (4×60 mL), dried over MgSO$_4$ and concentrated to give 836 mg (97% yield) of N-(2-trityl-amino-ethyl)-4-ethynyl-benzamide 3 as a white solid, mp 50-51° C. R$_f$=0.40 (1:1 Hexanes/EtOAc).

Preparation of (1S,2R)—N-(2-hydroxy-1-hydroxycarbamoyl-propyl)-4-{4-[4-(2-amino-ethylcarbamoyl)-phenyl]buta-1,3-diynyl}-benzamide (5)

| Reagent | MW | Eq. | g/mL | mmol |
|---|---|---|---|---|
| Alkyne on resin (4) | 0.77 mmol/g | 1.00 | 150 mg | 0.116 |
| 4-Ethynylbenzamide (3) | 430.54 | 3.00 | 151 mg | 0.350 |
| PdCl$_2$(PPh$_3$)$_2$ | 701.89 | 0.25 | 21 mg | 0.030 |
| CuI | 190.44 | 1.25 | 28 mg | 0.147 |
| Et$_3$N | 101.19 | 9.50 | 150 μL | 1.10 |
| DMF | | | 2.0 mL | |

Resin 4 (150 mg, 0.116 mmol) was swelled in DCM (2 mL) for 1 h and drained. A solution of 4-ethynylbenzamide 3 (151 mg, 0.350 mmol) and Et$_3$N (150 μL, 1.10 mmol) in DMF (2.0 mL) was added and the resin agitated for 5 min. A mixture of PdCl$_2$(PPh$_3$)$_2$ (21 mg, 0.030 mmol) and CuI (28 mg, 0.147 mmol) was added and the resin was agitated for 60 h. The resin was drained, washed with DMF (3×2 mL), DCM (3×2 mL) and cleaved with 10% TFA/DCM (1.5 mL) for 20 min. The solution was collected and the resin was rinsed with additional 10% TFA/DCM (1.0 mL). The cleavage fractions were combined, treated with neat TFA (2.0 mL), stirred for 1 h at rt and concentrated by rotary evaporation to give a crude brown residue. Purification by RP-HPLC (C$_{18}$ column, CH$_3$CN gradient 5-65%, 0.1% TFA, UV analysis 300 nm, 26 min) and lyophilization of the collected fractions afforded 2.0 mg (4% yield) of (1S,2R)—N-(2-hydroxy-1-hydroxycarbamoyl-propyl)-4-{4-[4-(2-amino-ethylcarbamoyl)-phenyl]-buta-1,3-diynyl}-benzamide. LRMS (ES+) m/z 449.1 (C$_{24}$H$_{24}$N$_4$O$_5$+H requires 449.18); RP-HPLC (300 nm, 26 min run) 17.0 min.

Synthesis of 3'-Pyridine Diacetylene Threonine Hydroxamic Acid

Example 25

N-((2R)-hydroxy-(1S)-hydroxycarbamoyl-propyl)-4-(4-pyridin-3-yl-buta-1,3-diynyl)-benzamide (3)

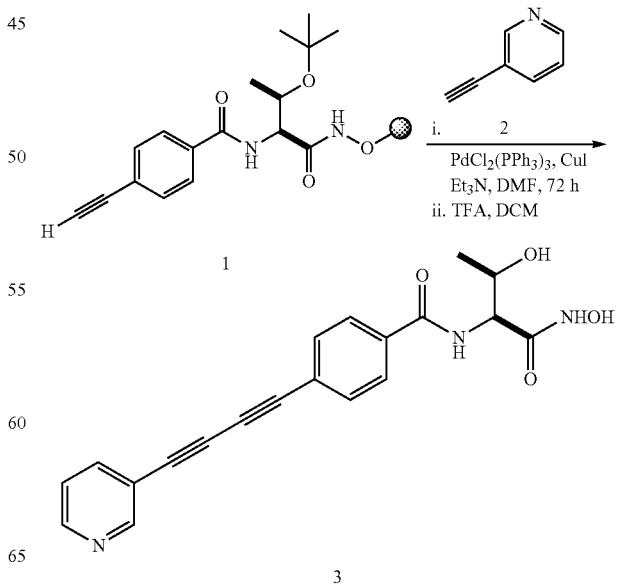

Preparation of N-((2R)-hydroxy-(1S)-hydroxycarbamoyl-propyl)-4-(4-pyridin-3-yl-buta-1,3-diynyl)-benzamide (3)

| Reagent | MW | Eq. | g/mL | mmol |
|---|---|---|---|---|
| Alkyne on resin (1) | 0.77 mmol/g | 1.0 | 142 mg | 0.109 |
| 3-Ethynylpyridine (2) | 103.12 | 3.4 | 38 mg | 0.368 |
| $PdCl_2(PPh_3)_2$ | 701.89 | 0.3 | 22 mg | 0.031 |
| CuI | 190.44 | 1.2 | 25 mg | 0.131 |
| $Et_3N$ | 101.19 | 13 | 200 μL | 1.40 |
| DMF |  |  | 2.0 mL |  |

Resin 1 (142 mg, 0.109 mmol) was swelled in DCM (2 mL) for 1 h and drained. A solution of 3-ethynylpyridine 2 (38 mg, 0.368 mmol) and $Et_3N$ (200 μL, 1.4 mmol) in DMF (2 mL) was added and the resin agitated for 5 min. A mixture of $PdCl_2(PPh_3)_2$ (22 mg, 0.031 mmol) and CuI (25 mg, 0.131 mmol) was added and the resin was agitated for 72 h. The resin was drained, washed with DMF (3×2 mL), DCM (3×2 mL) and cleaved with 10% TFA/DCM (1.5 mL) for 20 min. The solution was collected and the resin was rinsed with additional 10% TFA/DCM (1.0 mL). The cleavage fractions were combined, treated with neat TFA (2.0 mL), stirred for 1 h at rt and concentrated by rotary evaporation to give a crude brown residue. Purification by RP-HPLC ($C_{18}$ column, $CH_3CN$ gradient 5-65%, 0.1% TFA, UV analysis 300 nm, 24 min) and lyophilization of the collected fractions afforded 4.4 mg (11% yield) of N-((2R)-hydroxy-(1S)-hydroxycarbamoyl-propyl)-4-(4-pyridin-3-yl-buta-1,3-diynyl)-benzamide. LRMS (ES+) m/z 364.0 ($C_{20}H_{17}N_3O_4$+H requires 364.13); RP-HPLC (300 nm, 24 min run) 11.2 min.

Example 26

Synthesis of N-(1-(N-hydroxycarbamoyl)(1S,2R)-2-hydroxy propyl){4-[4-(6-morpholin-4-yl(3-pyridyl))buta-1,3-diynyl]phenyl}carboxamide (5)

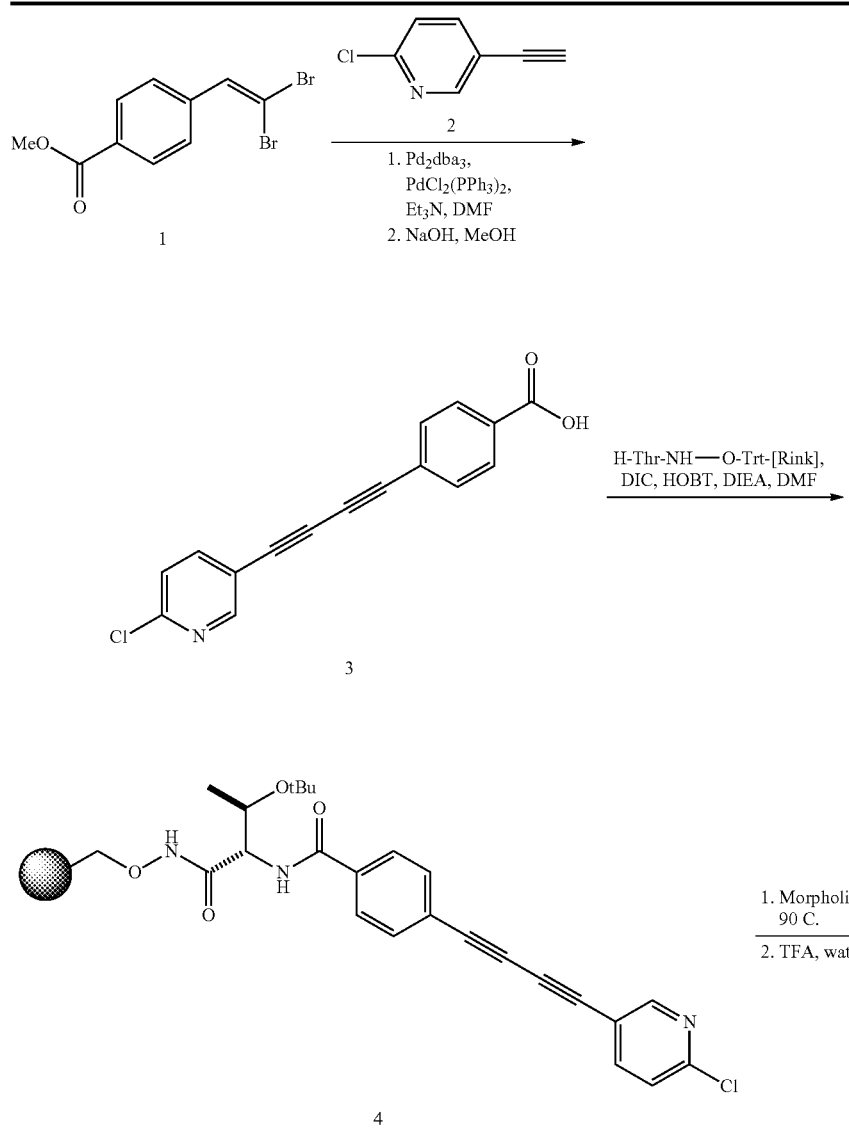

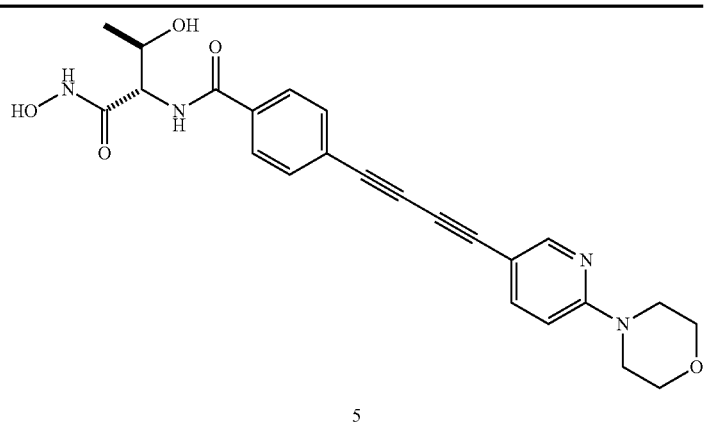

| Reagent | MW | EQ | g/ml | mmol |
|---|---|---|---|---|
| Dibromovinylbenzoic acid (1) | 320 | 1.0 | 9.6 g | 30.0 |
| 2-Chloro-5-ethynyl-pyridine | 138 | 1.3 | 5.43 g | 39.0 |
| $Pd_2dba_3$ | 915 | 0.01 | 274 mg | 0.3 (1% cat.) |
| TMPP | 352 | 0.04 | 422 mg | 1.2 (4%) |
| TEA | 101 | 3.0 | 12.5 ml | 90.0 |
| DMF | | | 90 ml | degassed with argon |

Preparation of 4-[4-(6-Chloro-pyridin-3-yl)-buta-1,3-diynyl]-benzoic acid methyl ester

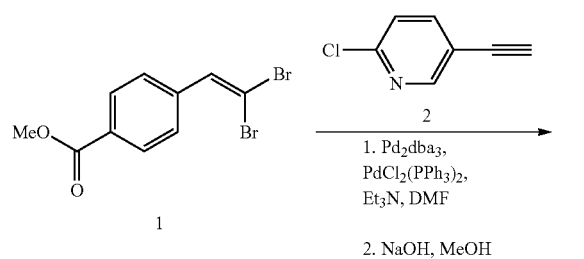

4-[4-(6-Chloro-pyridin-3-yl)-buta-1,3-diynyl]-benzoic acid was made according to the method of Wang Shen and Sheela A. Thomas in Org. Lett. 2000, 2(18), 2857-2860.

A solution of 4-(2,2-dibromo-vinyl)-benzoic acid methyl ester (1) (9.6 g, 30.0 mmol), ethynyl-pyridine (2) (5.43 g, 39.0 mmol), $Pd_2 dba_3$ (274 mg, 0.3 mmol), tris(4-methoxyphenyl) phosphine (TMPP) (422 mg, 1.2 mmol) were dissolved in argon sparged (5 min.) DMF (60 ml). The reaction was sparged with argon for 1 min. TEA (12.5 ml, 90.0 mmol) was added to the stirred reaction mixture that was then heated under argon at 85° C. for 3 hours. The reaction was found complete by LCMS. The reaction was cooled to rt and diluted with EtOAc/hexane (1:1) (500 ml). The organic phase was washed with 1M NaOH (2×80 ml), water (2×80 ml), sat. brine (80 ml), dried with $Na_2SO_4$, filtered and concentrated under reduced pressure to give crude product. The residue was filtered through a filter plug of silica eluting with EtOAc/hexane (1:1). The fractions with product were evaporated to give 9.06 g of product in good purity (~96% pure). The material was taken on without further purification.

Preparation of 4-[4-(6-Chloro-pyridin-3-yl)-buta-1,3-diynyl]-benzoic acid (3)

A 6M aq. solution of NaOH (15 ml) was added to a stirred solution of 4-[4-(6-Chloro-pyridin-3-yl)-buta-1,3-diynyl]-benzoic acid methyl ester. (9.06 g, 30 mmol) in MeOH (350 ml) at rt. The reaction solution was heated to reflux for 3 hours. The reaction stayed a mixture and did not turn clear. HPLC and LCMS indicated that the reaction was forming side products. The reaction was cooled to rt and some MeOH (~200 ml) was removed by evaporation under reduced pressure. Water (400 ml) was added to the mixture. Conc. HCl was added dropwise to the stirred solution until acidic by pH paper (pH2). The yellow precipitate that formed was collected by suction filtration. The solid was washed with water (3×20 ml) and hexane (2×20 ml) to give the crude product. HPLC indicated that there was approximately 40% product in the mixture. The crude reaction product was purified by flash chromatography using EtOAc (8-10%)/hexane as eluant. The pure fractions were evaporated and dried in vacuo to give 4.2 g of product 3 in 50% yield.

Preparation of [4-[4-(6-chloro-pyridin-3-yl)-buta-1, 3-diynyl]-benzoyl]-HN-Thr(OtBu)-hydroxamic acid trityl resin (4)

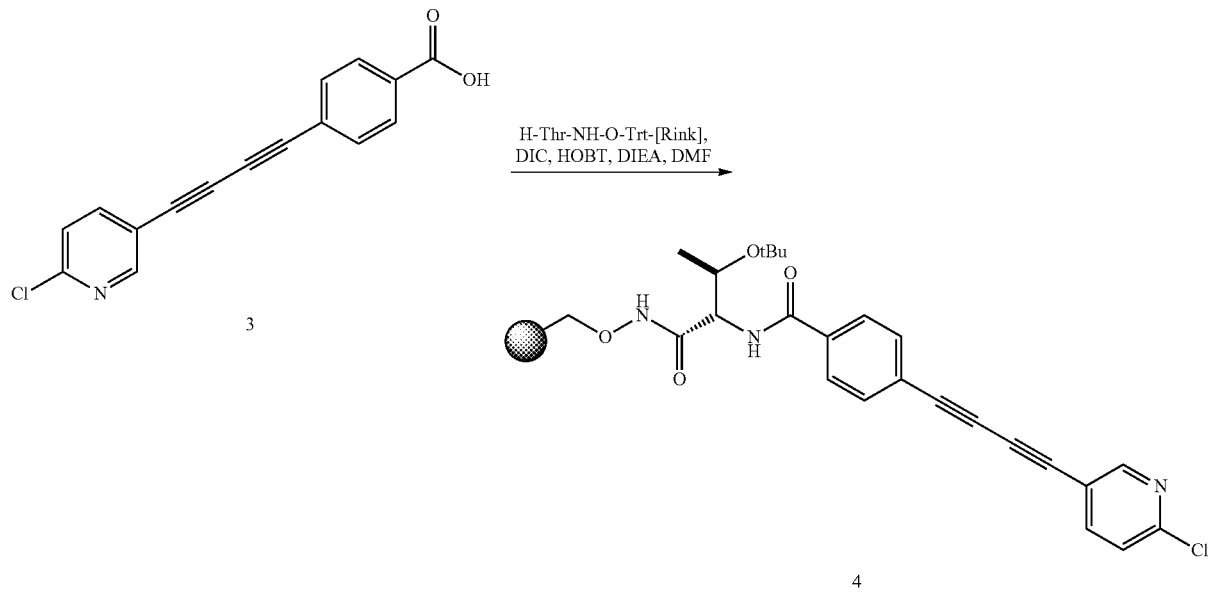

4-[4-(6-Chloro-pyridin-3-yl)-buta-1,3-diynyl]-benzoic acid (3) was coupled to a tert-butyl protected threonine pre-loaded on hydroxylamine 2-chlorotrityl resin following the same procedure as used for Example 26. The coupling employed DIC and HOBT. [N-Fmoc-hydroxylamine 2-chlorotrityl resin was purchased from Novabiochem cat. #01-64-0165.]

Preparation of N-(2-Hydroxy-1-hydroxycarbamoyl-propyl)-4-[4-(6-morpholin-4-yl-pyridin-3-yl)-buta-1,3-diynyl]-benzamide (5)

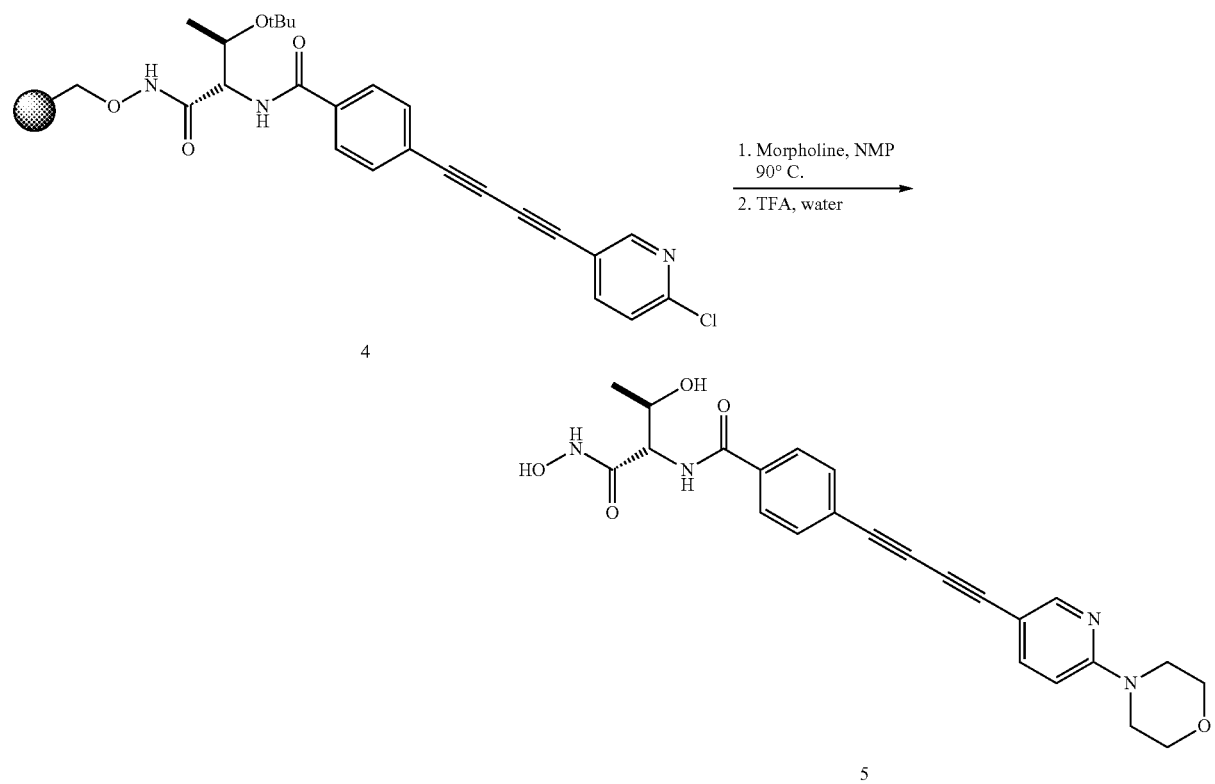

A solution of morpholine (300 uL) in NMP (1 ml) was added to a vial containing the 2-cloropyridine resin (4) (150 mg, 0.12 mmol). The reaction mixture was purged with argon and heated to 85-90° C. for 24 hours. The resin was drained and washed with DMF and DCM alternately several times. The product was cleaved from the resin through treatment with a TFA/water solution (80:20) (1.5 ml) for 45 min. The resin was filtered and washed with fresh TFA/water solution (80:20) (0.5 ml). The combined TFA and organic fractions were diluted with CH3CN/water (1:1) (10 ml), water (2 ml) and lyophilized. The crude product was purified by prep. HPLC. The crude product was dissolved in DMSO (1 ml), passed through a Teflon syringe filter, and the clear filtrate was injected on a preparative HPLC. The purification used a 20×50 mm Ultro 120 C18 column running a 22 ml/min 2% gradient (AcCN/water, 0.1% TFA) for 16 min. The purified fractions were lyophilized to dryness to give 2.2 mg of pure product as the TFA salt (~32% yield).

Example 27

Synthesis of 4-[4-(4-Amino-phenyl)-buta-1,3-diynyl]-N-(2-hydroxy-1-hydroxycarbamoyl-propyl)-benzamide (4)

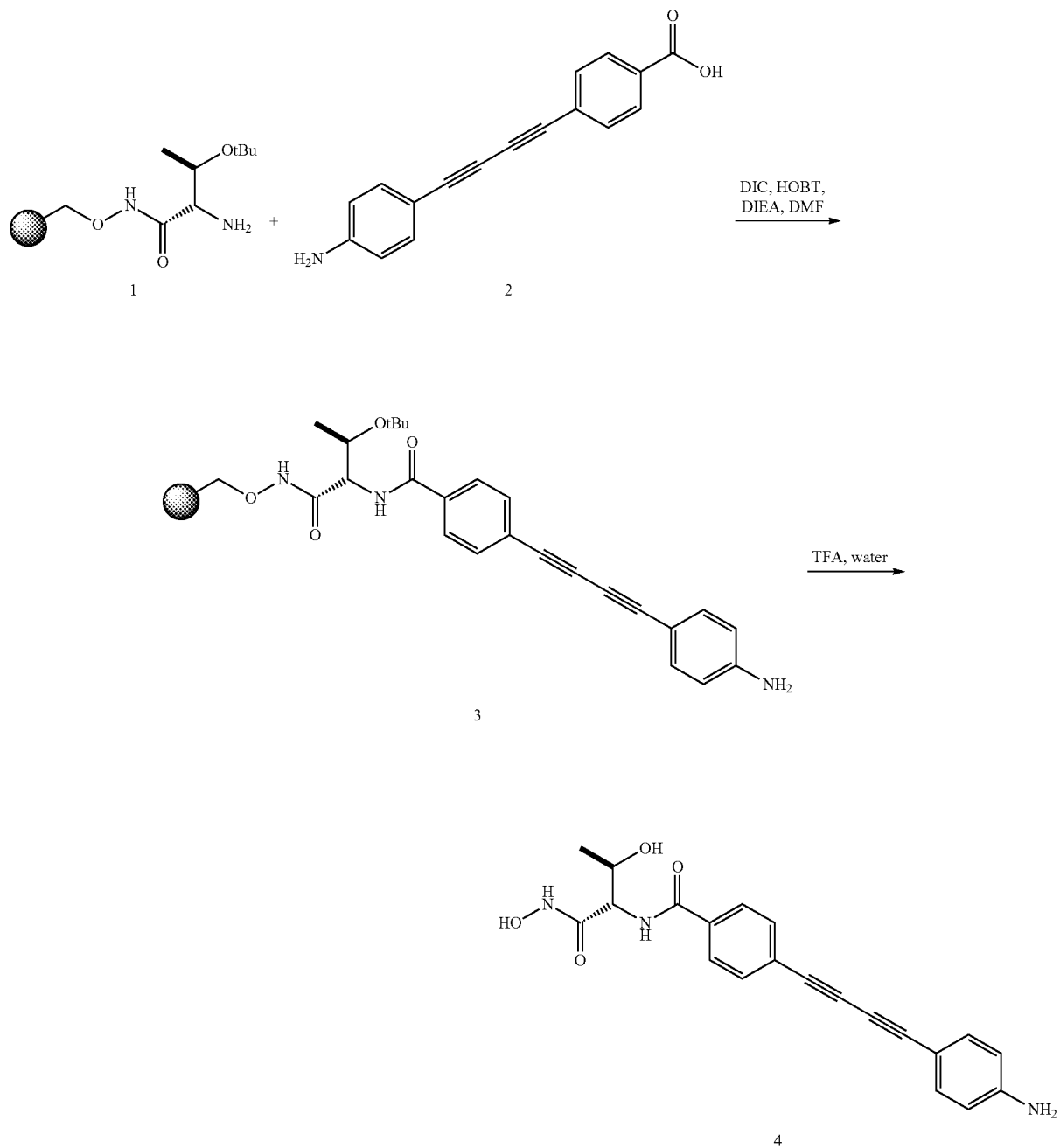

Preparation of 2-{4-[4-(4-Amino-phenyl)-buta-1,3-diynyl]-benzoylamino}-3-tert-butoxycarbonyloxy-butyric hydroxamic acid trityl resin (3)

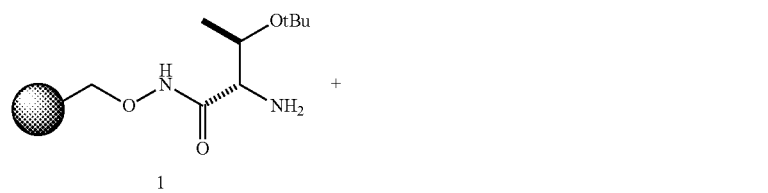

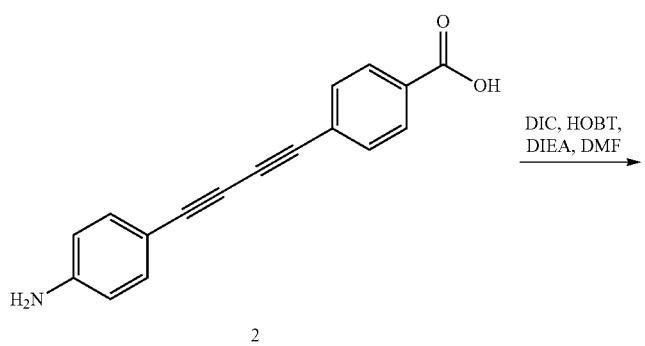

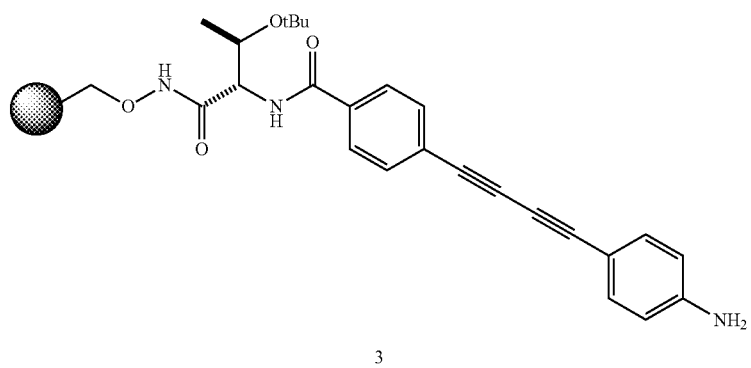

| Reagent | MW | EQ | g/ml | mmol |
| --- | --- | --- | --- | --- |
| H-Thr(Boc)-NHO-Trt Resin (1) | | 1.0 | 5.8 g | 4.47 |
| 1,3-diynyl benzoic acid (2) | 261.3 | 1.4 | 1.64 g | 6.25 |
| HOBT | 135.1 | 1.4 | 0.85 g | 6.25 |
| DIC | 126.2 | 1.4 | 0.98 ml | 6.25 |
| DIEA | 129.25 | 3.5 | 2.7 ml | 15.6 |
| DMF | | | 50 ml | |

DIEA (2.7 ml, 15.6 mmol) was added to a stirred solution of 4-[4-(4-Amino-phenyl)-buta-1,3-diynyl]-benzoic acid (2) (1.64 g, 6.3 mmol), HOBT (0.85 g, 6.3 mmol), DIC (0.98 ml, 6.3 mmol) in DMF (50 ml). After 2 min., the Thr hydroxylamine resin (5.8 g, 4.5 mmol) was added in one portion. [N-Fmoc-hydroxylamine 2-chlorotrityl resin was purchased from Novabiochem cat. #01-64-0165.] After 12 hours at rt, the reaction was found complete by LCMS. The resin was drained and washed with DMF and DCM alternately 3 times each. The product on resin 3 was used as is in subsequent reactions without further treatment.

Preparation of 4-[4-(4-Amino-phenyl)-buta-1,3-diynyl]-N-(2-hydroxy-1-hydroxy carbamoyl-propyl)-benzamide (4)

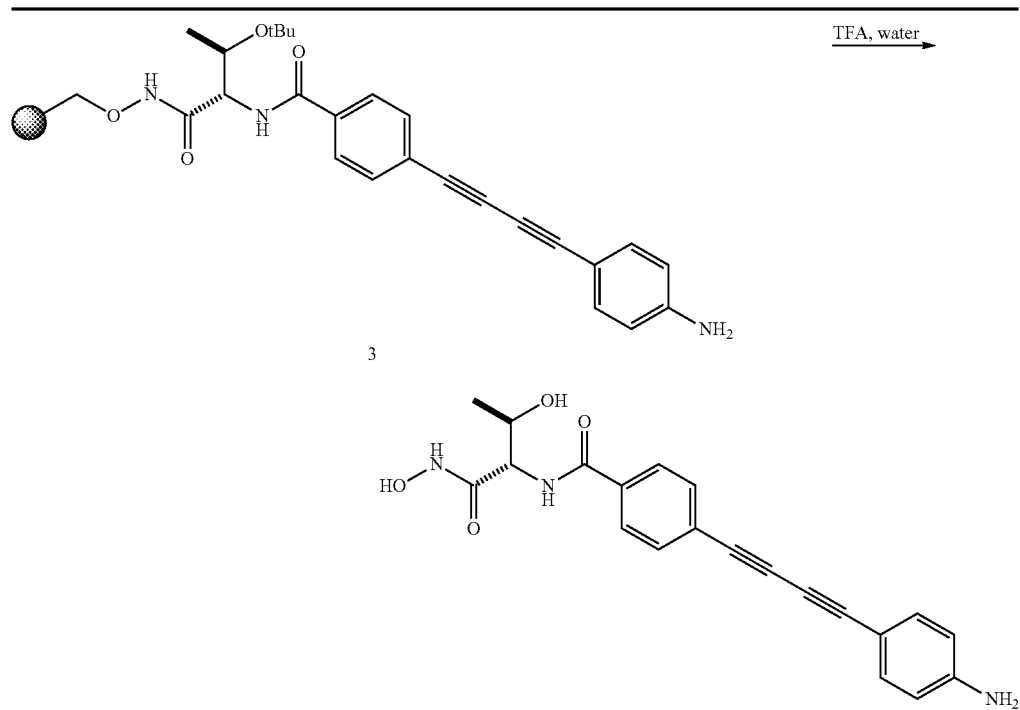

| Reagent | MW | EQ | g/ml | mmol |
|---|---|---|---|---|
| 1,3-diynyl benzoic Thr Resin (3) | | 1.0 | 120 mg | 0.09 |
| TFA/water (80:20) | | | 1.5 ml | |

The product (4) (120 mg, 0.09 mmol) was cleaved from the resin through treatment with a TFA/water solution (80:20) (1.5 ml) for 45 min. The resin was filtered and washed with fresh TFA/water solution (80:20) (0.5 ml). The combined TFA and organic fractions were diluted with CH3CN/water (1:1) (10 ml), water (2 ml) and lyophilized. The crude product was purified by prep. HPLC. The crude product was dissolved in DMSO (1 ml), passed through a Teflon syringe filter, and the clear filtrate was injected on a preparative HPLC. The purification used a 20×50 mm Ultro 120 C18 column running a 22 ml/min 2% gradient (AcCN/water, 0.1% TFA) for 16 min. The purified fractions were lyophilized to dryness to give 2.2 mg of pure product as the TFA salt. The product (4) was lyophilized again from CH₃CN/water with 10 equivalents of HCl to remove most of the TFA to yield 2 mg of product as the HCl salt (~53% yield).

Example 28

Synthesis of 4-{4-[4-(2-Dimethylamino-acetylamino)-phenyl]-buta-1,3-diynyl}-N-(2-hydroxy-1-hydroxycarbamoyl-propyl)-benzamide (6) (Continued from compound 3 of Example 27 Above)

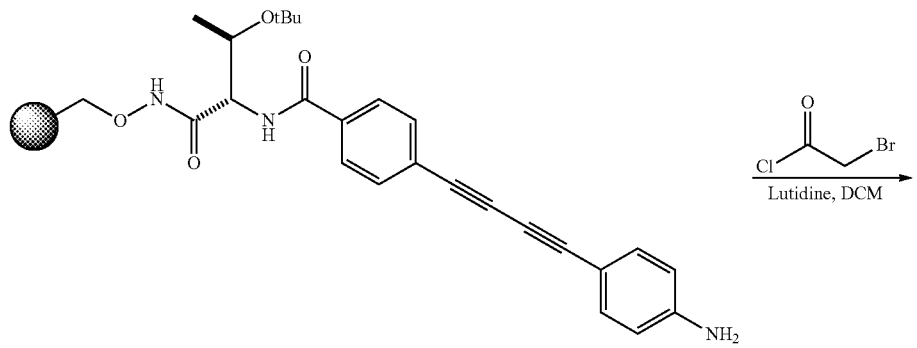

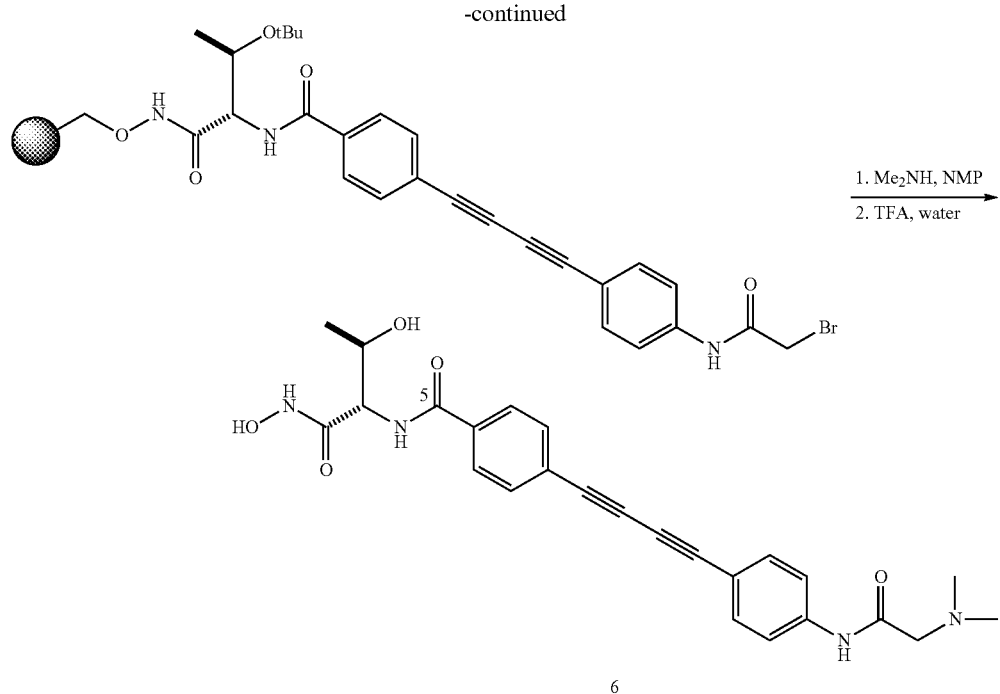
Preparation of 2-(4-{4-[4-(2-Bromo-acetylamino)-phenyl]-buta-1,3-diynyl}-benzoylamino)-3-tert-butoxycarbonyloxy-butyric acid hydroxamate trityl resin (5)
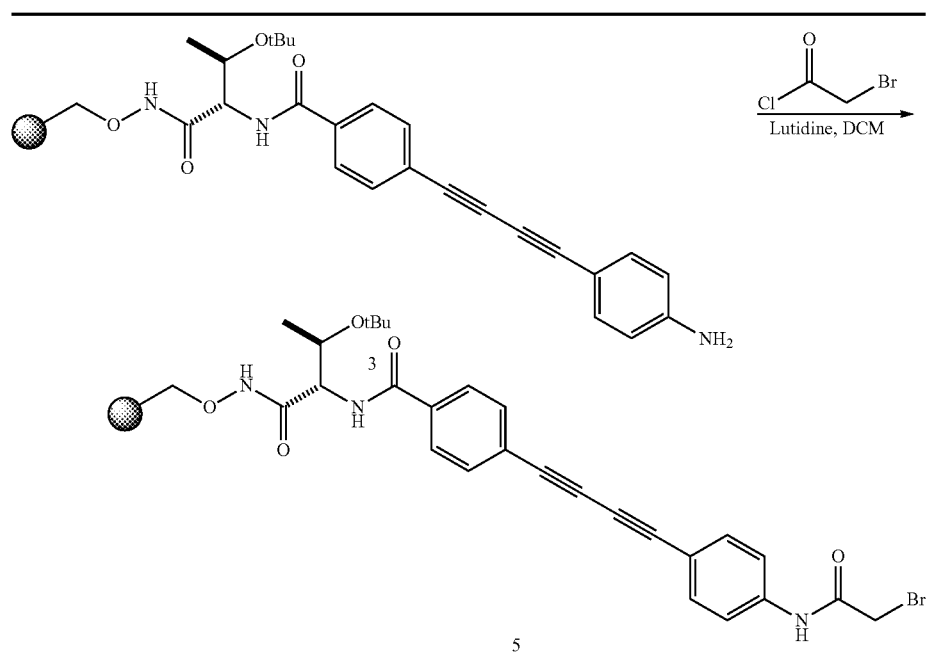
| Reagent | MW | EQ | g/ml | mmol |
|---|---|---|---|---|
| Amino 1,3-diynyl benzoic Thr Trt Resin (3) | | 1.0 | 0.75 g | 0.578 |
| Bromo-acetyl chloride | 157.4 | 8.0 | 0.728 g | 4.62 |
| Lutidine | 107 | 10.0 | 1.07 ml | 9.24 |
| DMF | | | 6 ml | |

A solution of bromo-acetyl chloride (0.75 g, 0.58 mmol) in DCM (2 ml) was added to a mixture of 2-{4-[4-(4-Aminophenyl)-buta-1,3-diynyl]-benzoylamino}-3-tert-butoxycarbonyloxy-butyric acid hydroxamate Trt Resin (3) (0.75 g, 0.58 mmol), lutidine (1.1 ml, 9.2 mmol) and DCM (4 ml) at rt with shaking. After shaking for 1.5 hours, the reaction was found complete by LCMS. The resin was drained and washed with DCM (2×10 ml), DMF (3×10 ml) and DCM (3×10 ml) again. The resin was drained and dried in vacuo. The product on resin 5 was used as is in subsequent reactions without further treatment.

Preparation of 4-{4-[4-(2-Dimethylamino-acetylamino)-phenyl]-buta-1,3-diynyl}-N-(2-hydroxy-1-hydroxycarbamoyl-propyl)-benzamide (6)

A solution of dimethyl amine (0.2 ml) in NMP (1.2 ml) was added to bromo acetic Thr Trt Resin (5) (125 mg, 0.09 mmol) at rt with shaking. After shaking for 12 hours, the reaction was found complete by LCMS. The resin was drained and washed with DCM (2×10 ml), DMF (3×10 ml) and DCM (3×10 ml) again. The product (6) was cleaved from the resin through treatment with a TFA/water solution (80:20) (1.5 ml) for 45 min. The resin was filtered and washed with fresh TFA/water solution (80:20) (0.5 ml). The combined TFA and organic fractions were diluted with CH3CN/water (1:1) (10 ml), water (2 ml) and lyophilized. The crude product was purified by prep. HPLC. The crude product was dissolved in DMSO (1 ml), passed through a Teflon syringe filter, and the clear filtrate was injected on a preparative HPLC. The purification used a 20×50 mm Ultro 120 C18 column running a 22 ml/min 2% gradient (AcCN/water, 0.1% TFA) for 16 min. The purified fractions were lyophilized to dryness to give 2 mg of pure product as the TFA salt (~37% yield).

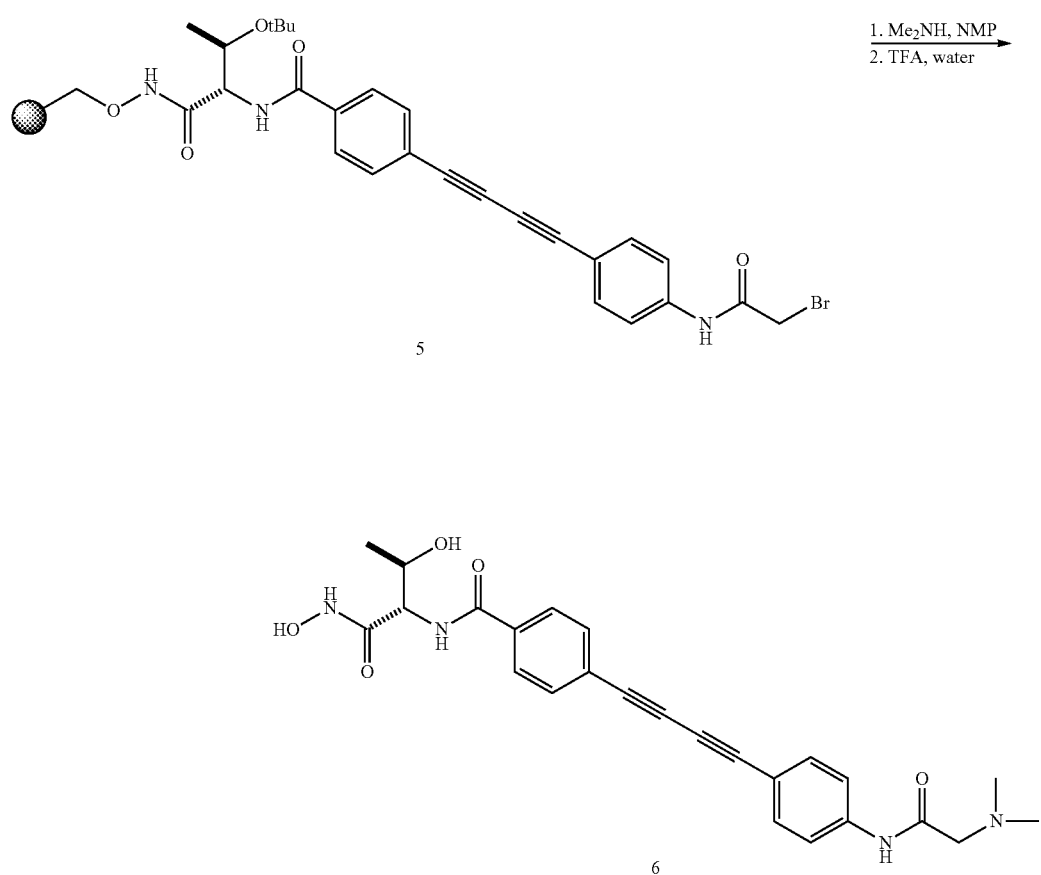

| Reagent | MW | EQ | g/ml | mmol |
|---|---|---|---|---|
| Bromo acetic Thr Trt Resin (5) | | 1.0 | 125 mg | 0.093 |
| Dimethyl amine | 45.08 | | 0.2 ml | excess |
| NMP | | | 1.2 ml | |

Example 29

Synthesis of 4-{4-[4-(2-Amino-4-methyl-pentanoylamino)-phenyl]-buta-1,3-diynyl}-N-(2-hydroxy-1-hydroxycarbamoyl-propyl)-benzamide (7) (Continued from Compound 3 of Example 27 Above)

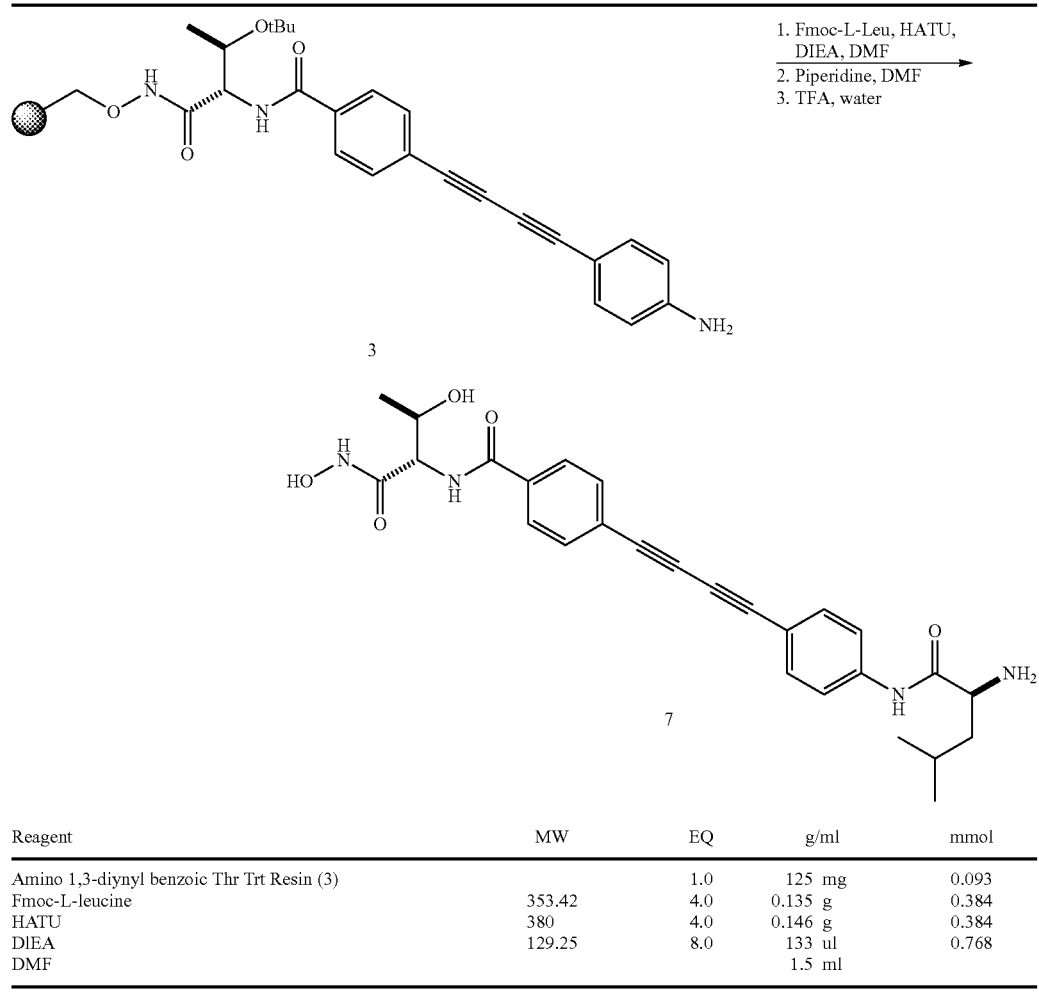

| Reagent | MW | EQ | g/ml | mmol |
|---|---|---|---|---|
| Amino 1,3-diynyl benzoic Thr Trt Resin (3) |  | 1.0 | 125 mg | 0.093 |
| Fmoc-L-leucine | 353.42 | 4.0 | 0.135 g | 0.384 |
| HATU | 380 | 4.0 | 0.146 g | 0.384 |
| DIEA | 129.25 | 8.0 | 133 ul | 0.768 |
| DMF |  |  | 1.5 ml |  |

A solution of Fmoc-L-leucine (0.135 g, 0.38 mmol), HATU (0.146 g, 0.38 mmol) in DMF (1.5 ml) was made. After 2 min. of shaking, the activated acid was added to the amino 1,3-diynyl benzoic Thr Trt Resin (3) (125 mg, 0.09 mmol) at rt with shaking. After shaking for 36 hours, the reaction was drained and washed with DCM (2×4 ml), DMF (3×4 ml) and DCM (3×4 ml) again. The resin was treated with 20% piperizine in DMF (4 ml) for 2 hours twice. The resin was drained and washed with DMF and DCM alternately several times. The product was cleaved from the resin through treatment with a TFA/water solution (80:20) (1.5 ml) for 45 min. The resin was filtered and washed with fresh TFA/water solution (80:20) (0.5 ml). The combined TFA and organic fractions were diluted with CH3CN/water (1:1) (10 ml), water (2 ml) and lyophilized. The crude product was purified by prep. HPLC. The crude product was dissolved in DMSO (1 ml), passed through a Teflon syringe filter, and the clear filtrate was injected on a preparative HPLC. The purification used a 20×50 mm Ultro 120 C18 column running a 22 ml/min 2% gradient (AcCN/water, 0.1% TFA) for 16 min. The purified fractions were lyophilized to dryness to give 1.7 mg of pure product (7) as the TFA salt (~30% yield).

Examples 30-1307 of Table 1 were Synthesized According to the Synthetic Schemes Described Above Biological Protocols and Data
*P. aeruginosa* LpxC Inhibition Assay The assay followed the general method of Hyland et al (Journal of Bacteriology 1997 179, 2029-2037: Cloning, expression and purification of UDP-3-O-acyl-GlcNAc deacetylase from *Pseudomonas aeruginosa*: a metalloamidase of the lipid A biosynthesis pathway) and the radiolabeling procedure is according to Kline et al. supra. Briefly, samples were incubated with 2 nM *P. aeruginosa* LpxC and 150 nM [3H-Ac]-UDP-3-O—(R-3-hydroxydecanoyl)-GlcNAc in a total volume of 50 uL for 90 min at room temperature. Reactions were carried out in 96-well polypropylene plates in 50 mM sodium phosphate buffer, pH 7.5, containing 1 mg/mL BSA. Reactions were stopped by the addition of 180 uL of a 3% suspension of activated charcoal powder in 100 mM sodium acetate, pH 7.5. Supernatants were clarified by centrifugation. A portion of the clarified supernatant, containing the enzymatically released [3H]-acetate, was transferred to opaque white 96-well plates containing scintillation fluid. The radioactivity was measured in a Perkin-Elmer/Wallac Trilux Microbeta counter. Control reactions to which 5 mM EDTA had been added were included with each run to determine nonspecific tritium release.

Bacterial Screens and Cultures

Bacterial isolates were cultivated from −70° C. frozen stocks by two consecutive overnight passages at 35° C. in ambient air on 5% blood agar (Remel, Lenexa, Kans.). Clinical isolates tested were from a collection composed of isolates collected during clinical trials and recent clinical isolates obtained from various geographically diverse hospitals in the US. Quality control and primary panel strains were from the American Type Culture Collection (ATCC; Rockville, Md.), with the exception of *P. aeruginosa* PAO200, a strain with a deletion of the mexABoprM genes that was received from Dr. H. Schweizer. This strain does not express the principal multidrug efflux pump and is hypersusceptible to many antibacterials. Strain Z61 (ATCC 35151) is also hypersusceptible to antibacterials. It is thought that the hypersusceptibility of this strain is the result of increased permeability of its outer membrane (Angus B L et al, Antimicrobial Agents and Chemotherapy 1982 21, 299-309: Outer membrane permeability in *Pseudomonas aeruginosa*: Comparison of a wild-type with an antibacterial-supersusceptible mutant).

Susceptibility Testing

Minimum Inhibitory Concentrations (MICs) were determined by the broth microdilution method in accordance with the National Committee for Clinical Laboratory Standards (NCCLS) guidelines. In brief, organism suspensions were are adjusted to a 0.5 McFarland standard to yield a final inoculum between $3\times10^5$ and $7\times10^5$ colony-forming units (CFU)/mL. Drug dilutions and inocula were made in sterile, cation adjusted Mueller-Hinton Broth (Remel). An inoculum volume of 100 µl was added to wells containing 100 µl of broth with 2-fold serial dilutions of drug. All inoculated microdilution trays were incubated in ambient air at 35° C. for 18-24 hours. Following incubation, the lowest concentration of the drug that prevented visible growth was recorded as the MIC. Performance of the assay was monitored by the use of laboratory quality-control strains against tobramycin, that has a defined MIC spectrum, in accordance with NCCLS guidelines.

Efficacy in Mouse Model of Systemic *Pseudomonas aeruginosa* Infection

Female Balb/c mice were injected intraperitoneally with 0.5 ml of a bacterial suspension containing approximately 100 times the dose that would kill 50% of animals ($LD_{50}$) of *P. aeruginosa* strain PAO1 or *E. coli* ATCC 25922. At one and five hours post infection, the test compound was injected intravenously in doses ranging from 5 mg/kg to 100 mg/kg, five mice per group. Mice were observed for 5 days, and the dose of compound resulting in survival of 50% of mice ($ED_{50}$) was calculated.

Drug Combination (Synergy) Studies

I. Principle

Checkerboard experiments can be performed to assess potential interactions between primary drug of interest (#1) and other related antibacterials (#2). *P. aeruginosa* ATCC 27853, *S. aureus* ATCC 29213 and other organisms can be used as challenge strains as well as selected clinical isolates. Broth microdilution format can be used to assess the activity of drug #1 and test compound alone and in combination. Two-fold dilutions of the two compounds to be tested (each bracketing the expected MIC value) are used. The fractional inhibitory concentration (FIC) was calculated as the MIC of compound #1 in combination with a second compound, divided by the MIC of compound #1 alone. A summation FIC (ΣFIC) was computed for each drug combination as the sum of the individual FICs of compound #1 and #2. Synergy was defined as an ΣFIC≦0.5, indifference as an ΣFIC between 0.5 and 4, and antagonism as ΣFIC>4. The lowest ΣFIC was used for the final interpretation of drug combination studies.

Interpretation of Summation (ΣFIC)
 a) Synergism, x≦50.5
 b) Indifference, 0.5<x≦4.
 c) Antagonism, x>4

TABLE 2

Demonstration of Antibacterial activity of Select Compounds from Table 1
Enzyme inhibitory activity

| Compound Example # | $IC_{50}$ (nM) |
|---|---|
| 12 | <100 nM |
| 572 | <100 nM |
| 481 | <100 nM |
| 19 | <100 nM |
| 516 | <100 nM |
| 280 | <100 nM |
| 366 | <100 nM |
| 777 | <100 nM |
| 315 | <100 nM |
| 779 | <100 nM |
| 860 | <100 nM |
| 801 | <100 nM |
| 13 | <100 nM |

TABLE 3

Antibacterial activity vs standard panel of organisms (MIC, µg/ml).

| Compound Example # | Bacterial strain: | | | | |
|---|---|---|---|---|---|
| | *P. aeruginosa* 27853 | *E. coli* 25922 | *S. aureus* 29213 | hyper-permeable *P. aerug.* 35151 | *P. aeruginosa* PAO200 mexAB |
| 12 | A | A | C | A | A |
| 572 | A | A | C | A | A |
| 481 | A | A | C | A | A |
| 19 | A | A | B | A | A |
| 516 | A | A | C | A | A |
| 280 | A | A | C | A | A |

TABLE 3-continued

Antibacterial activity vs standard panel of organisms (MIC, µg/ml).

| Compound Example # | P. aeruginosa 27853 | E. coli 25922 | S. aureus 29213 | hyper-permeable P. aerug. 35151 | P. aeruginosa PAO200 mexAB |
|---|---|---|---|---|---|
| 366 | A | A | C | A | A |
| 777 | A | A | C | A | A |
| 315 | A | A | C | A | A |
| 779 | A | A | C | A | A |
| 860 | A | A | C | A | A |
| 801 | A | A | C | A | A |
| 13 | A | A | C | AA | A |

MIC Key
MIC's of 6.25 ug/ml or less = A
MIC's of greater than 6.25 ug/ml to 50 ug/ml = B
MIC's of greater than 50 ug/ml = C

TABLE 4

Antibacterial activity vs cystic fibrosis isolates of *Pseudomonas aeruginosa* (MIC, µg/ml).
Strains have the following phenotypes: 3198 and 3236, sensitive to most antibacterials;
2196, resistant to ciprofloxacin; 3224, resistant to ceftazidime; 3317, resistant to aztreonam;
1145 and 3206, multi-drug resistant.

| Strain number: Phenotype: | 3198 Sensitive | 3236 Sensitive | 2196 Cipro R | 3224 Tobra R | 3232 Ceftaz. R | 3317 Aztr. R | 1145 MDR | 3206 MDR |
|---|---|---|---|---|---|---|---|---|
| LpxC inhibitors | | | | | | | | |
| 12 | A | A | B | A | A | A | A | A |
| 481 | A | A | A | A | A | A | A | A |
| 19 | A | A | A | A | A | A | A | A |
| 516 | A | A | A | A | A | A | A | A |
| 280 | A | A | B | A | A | A | A | A |
| 366 | A | A | A | A | A | A | A | A |
| 777 | A | A | A | A | A | A | A | A |
| 315 | A | A | A | A | A | A | A | A |
| 779 | A | A | A | A | A | A | A | A |
| 801 | A | A | A | A | A | A | A | A |
| 13 | A | A | A | A | A | A | A | A |
| Comparator antibacterials | | | | | | | | |
| Tobramycin | 2 | 0.5 | 2 | 64 | 1 | 2 | 8-32 | 64 |
| Aztreonam | 1 | 0.5 | 1 | 1 | 1 | 64 | >128 | >128 |
| Ceftazidime | 2 | 0.25 | 2 | 2 | 64 | 4 | >128 | >128 |
| Cefepime | 4 | 2 | 2 | 8 | 2 | 8 | >128 | 32 |
| Ciprofloxacin | 1 | 0.06 | >8 | 2 | 2 | 0.5 | 4 | >8 |

MIC Key
MIC's of 6.25 ug/ml or less = A
MIC's of greater than 6.25 ug/ml to 50 ug/ml = B
MIC's of greater than 50 ug/ml = C

TABLE 5

Antibacterial activity vs non-CF clinical isolates of *P. aeruginosa* and vs other gram-
negative pathogens. Set 1: non-fermenting organisms. P. aer., P. aeruginosa; Acinet. calc.,
Acinetobacter calcoaceticus; Alcal. xyl., Alcaligenes xylosoxidans; B. cep., Burkholderia cepacia;
S. malt., Stenotrophomonas maltophilia

| Species: | P. aer 27853 | P. aer. PAO1 | P. aer 12307 | P. aer psa-6b | Acinet. calc. | Alcal. xyl | B. cepacia | S. malt. |
|---|---|---|---|---|---|---|---|---|
| LpxC inhibitors | | | | | | | | |
| 12 | A | A | A | A | A | A | B | A |
| 481 | A | A | A | A | C | C | B | C |
| 19 | A | A | A | A | A | B | B | B |
| 516 | A | | A | A | C | C | C | C |
| 280 | A | A | A | A | C | B | B | B |
| 366 | A | A | A | B | C | A | B | B |
| 777 | A | | A | B | A | B | A | C |
| 315 | A | A | A | A | C | B | A | A |
| 779 | A | A | | A | C | A | A | B |

TABLE 5-continued

Antibacterial activity vs non-CF clinical isolates of *P. aeruginosa* and vs other gram-negative pathogens. Set 1: non-fermenting organisms. *P. aer.*, *P. aeruginosa*; *Acinet. calc.*, *Acinetobacter calcoaceticus*; *Alcal. xyl.*, *Alcaligenes xylosoxidans*; *B. cep.*, *Burkholderia cepacia*; *S. malt.*, *Stenotrophomonas maltophilia*

| Species: | *P. aer* 27853 | *P. aer.* PAO1 | *P. aer* 12307 | *P. aer* psa-6b | *Acinet. calc.* | *Alcal. xyl* | *B. cepacia* | *S. malt.* |
|---|---|---|---|---|---|---|---|---|
| 801 | A | A |  | A | B | C | B | C |
| 13 | A | A |  | A | C | A | A | B |
| Comparator antibacterials |  |  |  |  |  |  |  |  |
| Tobramycin |  |  | 8 | 2 | 2 | 64 | 64/>128 | 0.5 |
| Aztreonam |  |  | 16 | 32 | 32 | 32 | 64 | >128/16 |
| Ceftazidime |  |  | 4 | 64 | 16 | 1 | 8/4 | 1 |
| Cefepime |  |  | 2 | 8 | 8 | 8 | 32/16 | 8/1 |
| Meropenem |  |  | 0.5 | 0.25 | 4 | 0.5 | 4 | 64 |
| Pip/Tazo |  |  | 4 | >128 | 8 | 1 | 64 | 16 |
| Ciprofloxacin |  |  |  |  | 0.5 | 2 | 0.5 | 0.5 |

MIC Key
MIC's of 6.25 ug/ml or less = A
MIC's of greater than 6.25 ug/ml to 50 ug/ml = B
MIC's of greater than 50 ug/ml = C

TABLE 6

Antibacterial activity vs non-CF clinical isolates of *P. aeruginosa* and vs other gram-negative pathogens, continued. Set 2: enteric organisms. *E. aer.*, *Enterobacter aerogenes*; *E. clo.*, *Enterobacter cloacae*; *E. coli*, *Escherichia coli*; *K. pneu.*, *Klebsiella pneumoniae*; *K. oxy.*, *Klebsiella oxytoca*; *P. mir*, *Proteus mirabilis*; *S. marc.*, *Serratia marcescens*.

| Species: | *E. aer.* | *E. clo.* | *E. coli* 1619 | *E. coli* 2788 | *K. pneu.* | *K. oxy.* | *P. mir.* | *S. marc.* |
|---|---|---|---|---|---|---|---|---|
| LpxC inhibitors |  |  |  |  |  |  |  |  |
| 12 | C | A | A | A | A | A | A | A |
| 481 | C | A | A | A | A | A | A | A |
| 19 | A | A | A | A | A | A | A | A |
| 516 | C | B | A | B | C | C | C | A |
| 280 | C | A | A | A | B | C | B | B |
| 366 | C | A | A | A | B | B | A | A |
| 777 | B | A | A | A | A | A | A | A |
| 315 | C | A | A | A | C | C | C | B |
| 779 | C | A | A | A | B | B | B | A |
| 801 | B | A | A | A | A | A | A | A |
| 13 | C | A | A | A | A | A | A | A |
| Comparator antibacterials |  |  |  |  |  |  |  |  |
| Tobramycin | 64 | 0.06 | 16/64 | 0.06/2 | 64 | 1 | 2 | 2 |
| Aztreonam |  | <=0.13 | 128/64 | <=0.13/0.25 | 2 | 0.5 | <=0.13 | <=0.13 |
| Ceftazidime | 32 | 0.25 | >128 | 0.25/<=0.13 | 8 | 0.25 | <=0.13 | 0.25 |
| Cefepime |  | <=0.13 | 4/<=0.13 | <=0.13 | 8 | <=0.13 | <=0.13 | <=0.13 |
| Meropenem | 2 | <=0.06 | 0.25/0.13 | <=0.06 | 0.13 | <=0.06 | 0.5 | 0.13 |
| Pip/Tazo |  | 2 | >128 | 1 | >128 | 2 | 0.25 | 1 |
| Ciprofloxacin | >8 | 0.015 | 2 | 0.03 | 0.06 | 0.03 | 0.03 | 0.25 |

MIC Key
MIC's of 6.25 ug/ml or less = A
MIC's of greater than 6.25 ug/ml to 50 ug/ml = B
MIC's of greater than 50 ug/ml = C

TABLE 7

Drug Combination (Synergy) Studies Result

|  | Erythromycin | LpxC inhibitor 925 |
|---|---|---|
| LpxC inhibitor 925 only | — | 6.25 |
| Erythromycin only | 128 | — |
| LpxC inhibitor 925 + erythromycin | 2 | 0.78 |

Minimum Concentration (mg/ml) required to inhibit growth of *E. coli* 25922

Each of the Example compounds of Table 1 was synthesized and assayed as described above. Many of the Example compounds 1-1307 displayed an $IC_{50}$ value of less than 10 µM with respect to LpxC. Many of these compounds displayed an $IC_{50}$ value of less than or equal to 1 µM or less than or equal to 0.1 µM. Many of these compounds exhibited $IC_{50}$ values of less than or equal to 0.050 µM, less than or equal to 0.030 µM, less than or equal to 0.025 µM, or less than or equal to 0.010 µM.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

TABLE 1
| Example | Structure |
|---|---|
| 30 | 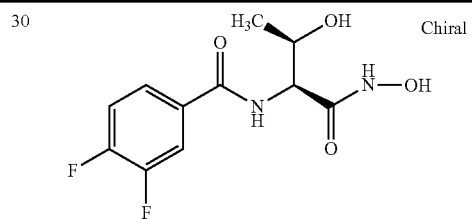 |
| 31 | 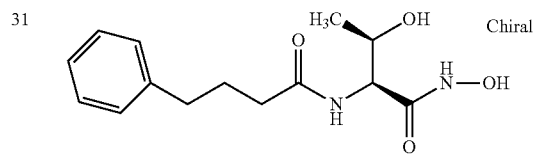 |
| 32 | 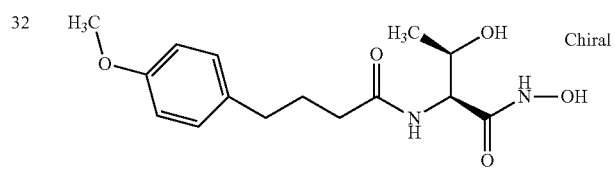 |
| 33 | 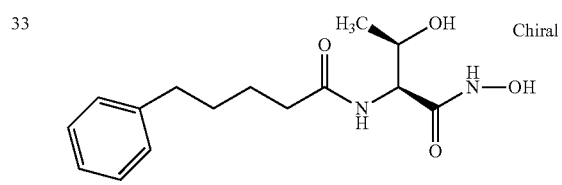 |
| 34 | 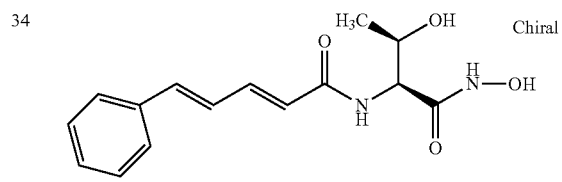 |
| 35 | 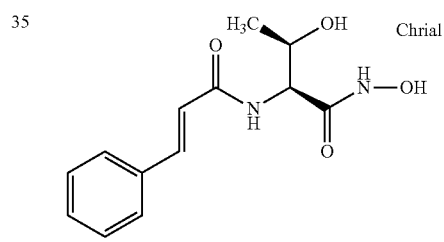 |
| 36 | 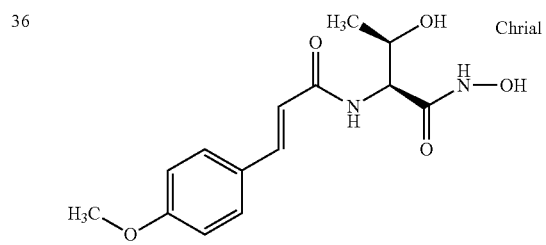 |
| 37 | 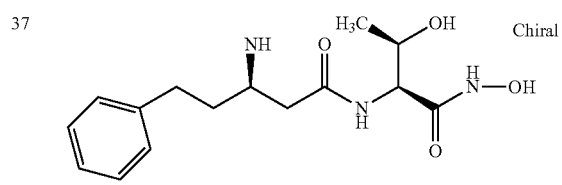 |

TABLE 1-continued
| 38 | 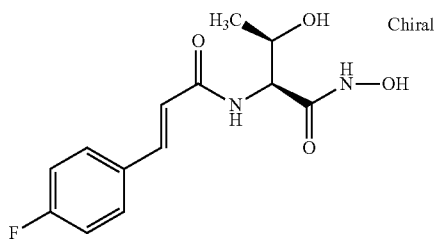 |
| 39 | 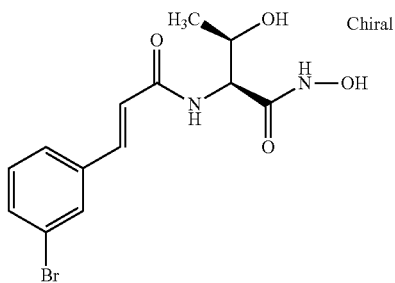 |
| 40 | 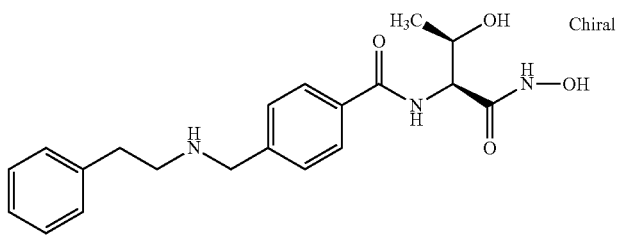 |
| 41 | 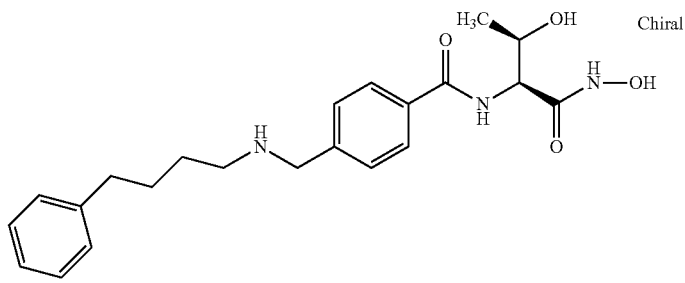 |
| 42 | 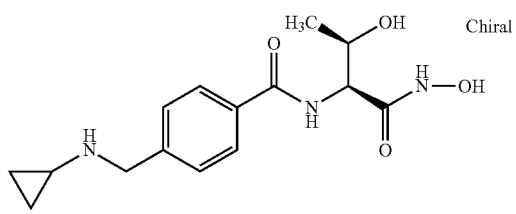 |
| 43 | 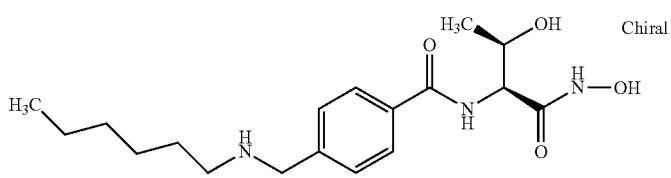 |

TABLE 1-continued

| # | Structure |
|---|---|
| 44 | 2-(pyridin-2-yl)ethylamino-methyl-benzamide-threonine-hydroxamic acid (Chiral) |
| 45 | 4-(4-methylpiperazin-1-yl)benzamide-threonine-hydroxamic acid (Chiral) |
| 46 | 4-(piperidin-1-ylmethyl)benzamide-threonine-hydroxamic acid (Chiral) |
| 47 | 4-(morpholinomethyl)benzamide-threonine-hydroxamic acid (Chiral) |
| 48 | 4-((3-(2-oxopyrrolidin-1-yl)propylamino)methyl)benzamide-threonine-hydroxamic acid (Chiral) |
| 49 | 4-((3-phenylpropylamino)methyl)benzamide-threonine-hydroxamic acid (Chiral) |
| 50 | 5-phenylpyrrolidine-2-carboxamide-threonine-hydroxamic acid (Chiral) |

TABLE 1-continued
| 51 | 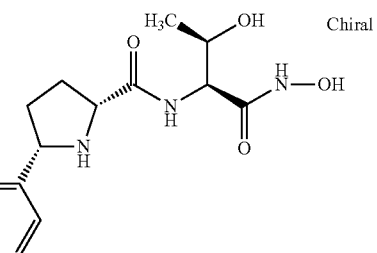 |
| 52 | 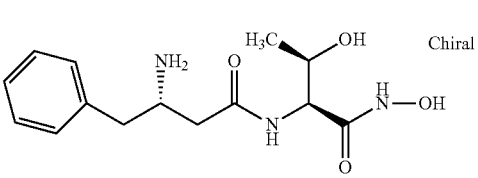 |
| 53 | 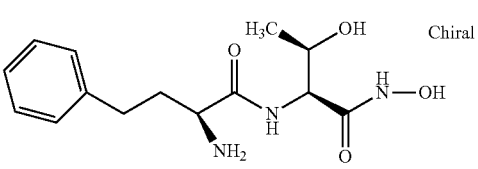 |
| 54 | 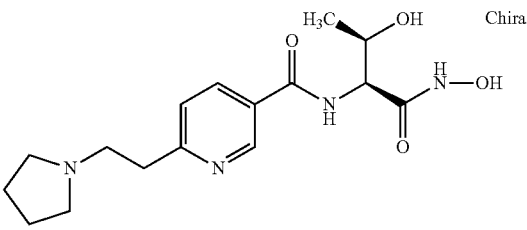 |
| 55 | 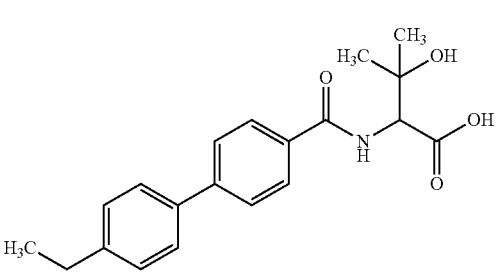 |
| 56 | 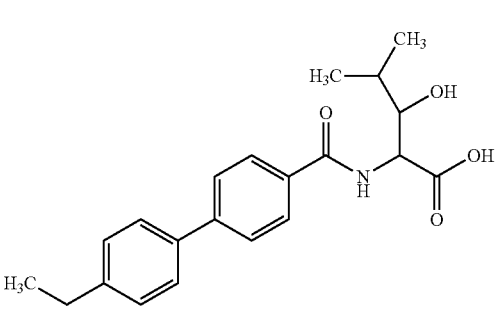 |
| 57 | 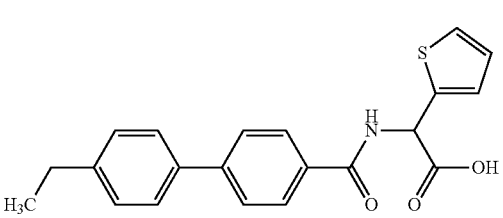 |

TABLE 1-continued
58 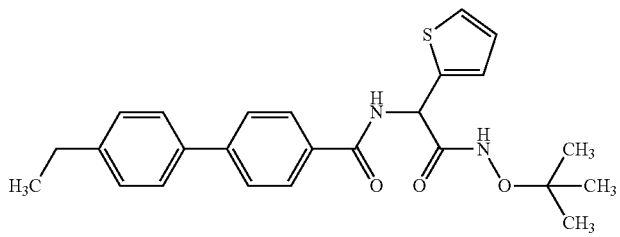
59 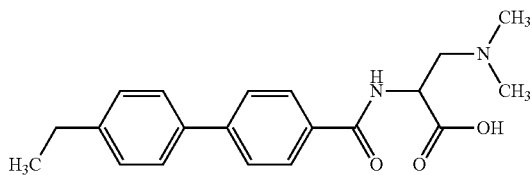
60 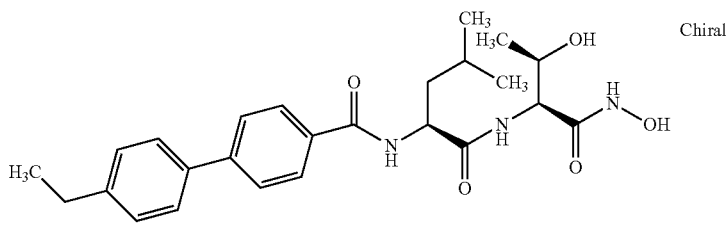
61 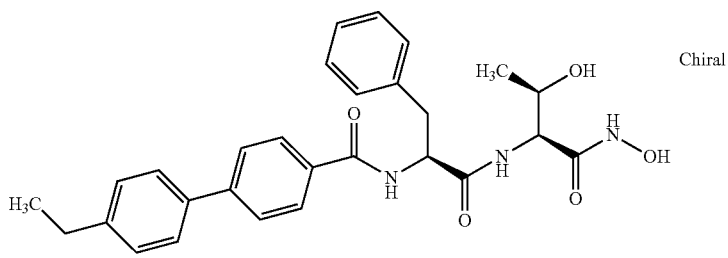
62 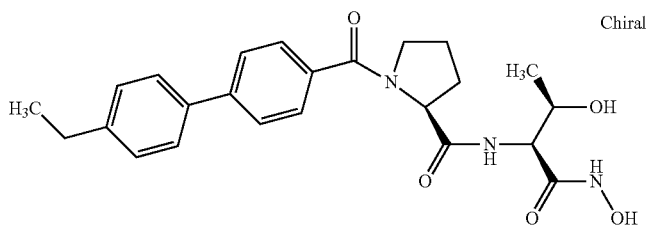
63 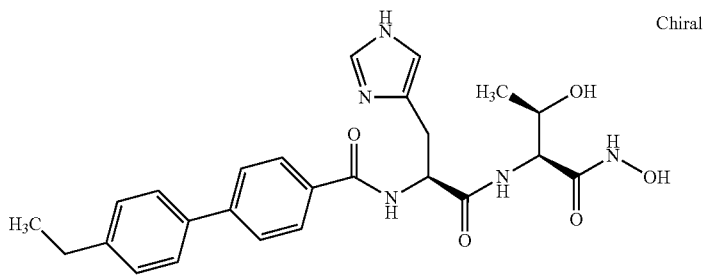

TABLE 1-continued
| 64 | 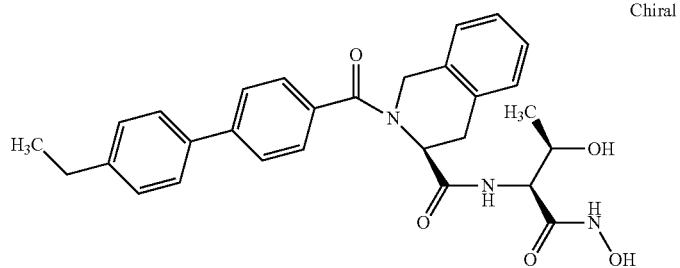 | Chiral |
| 65 | 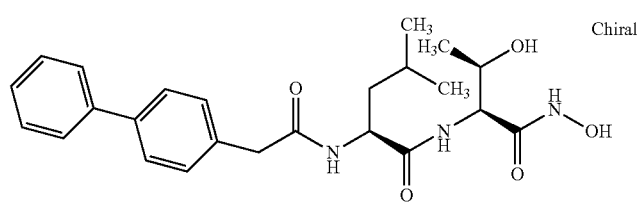 | Chiral |
| 66 | 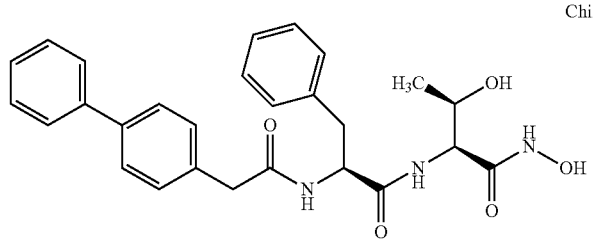 | Chiral |
| 67 | 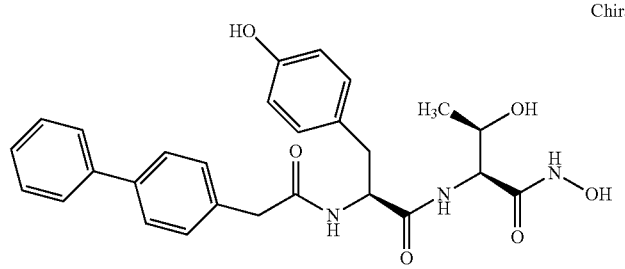 | Chiral |
| 68 | 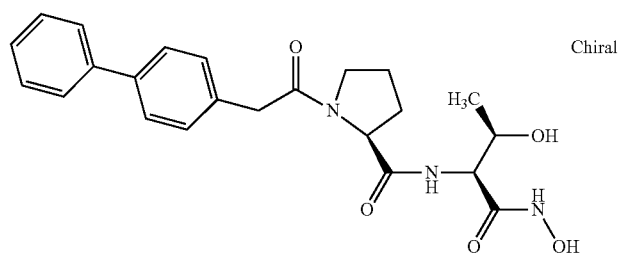 | Chiral |
| 69 | 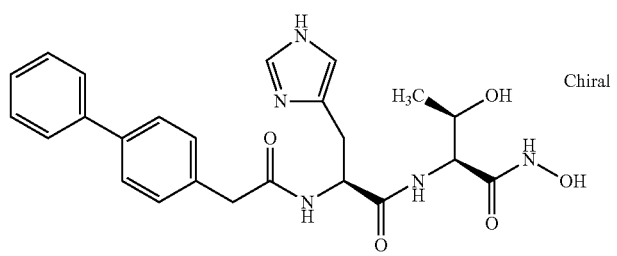 | Chiral |

TABLE 1-continued
| 70 | 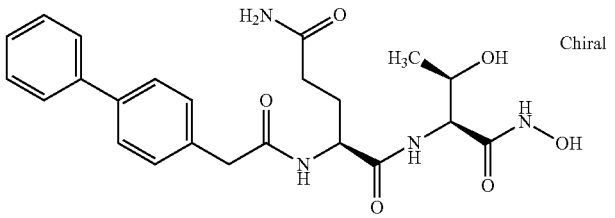 |
| --- | --- |
| 71 | 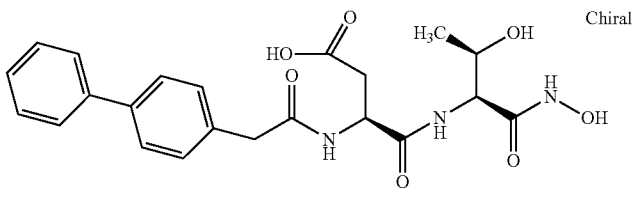 |
| 72 | 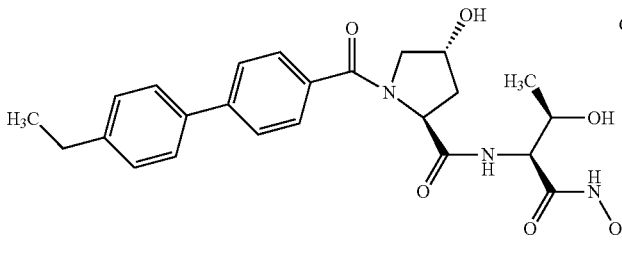 |
| 73 | 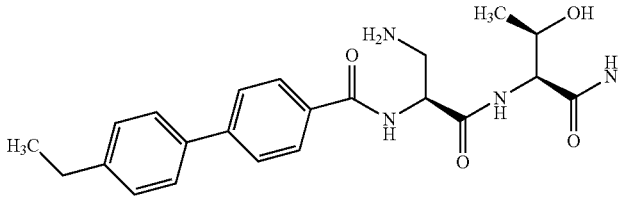 |
| 74 | 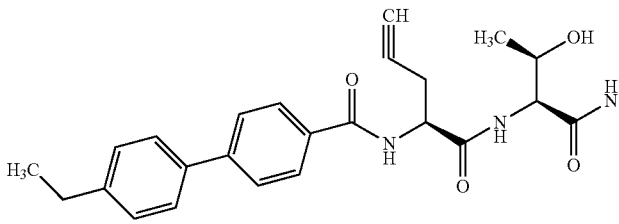 |
| 75 | 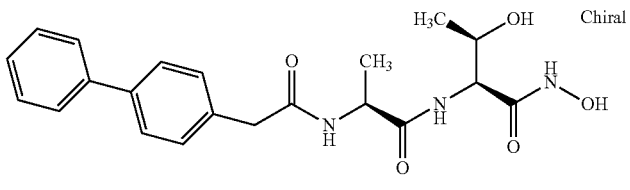 |
| 76 | 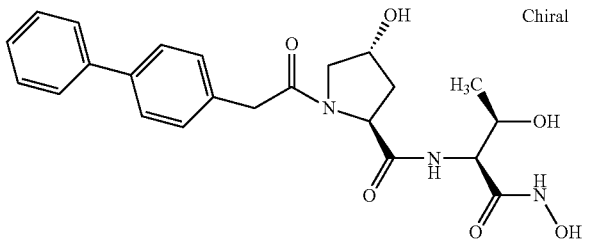 |

| | | |
|---|---|---|
| 77 | 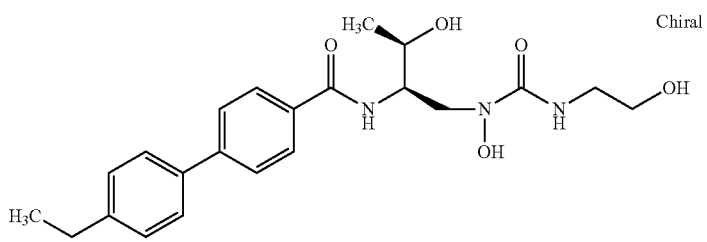 | Chiral |
| 78 | 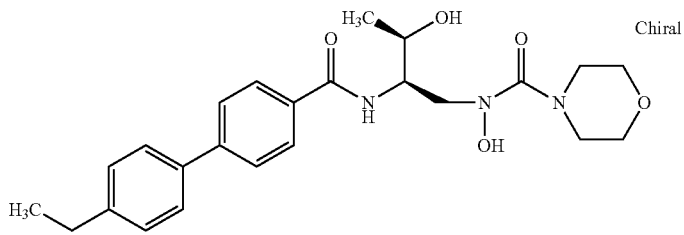 | Chiral |
| 79 | 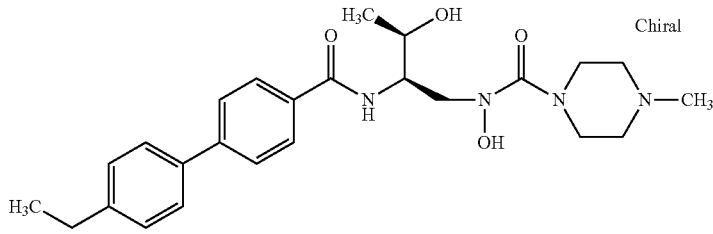 | Chiral |
| 80 | 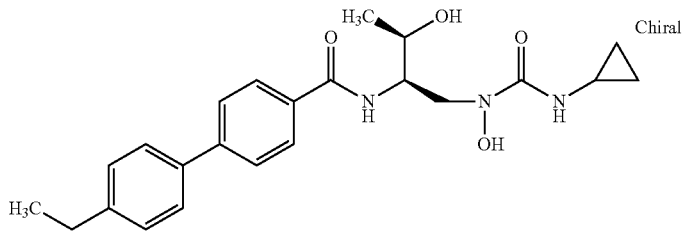 | Chiral |
| 81 | 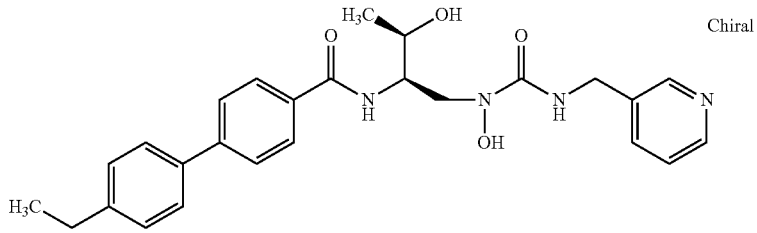 | Chiral |
| 82 | 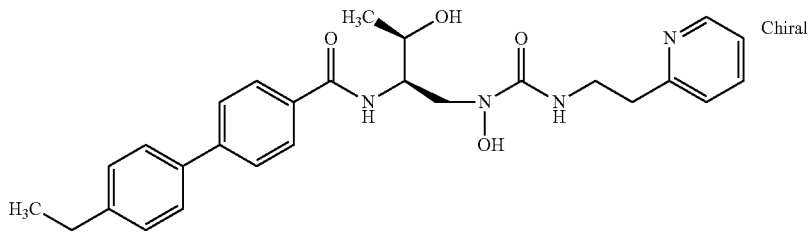 | Chiral |

TABLE 1-continued
| | | |
|---|---|---|
| 83 | 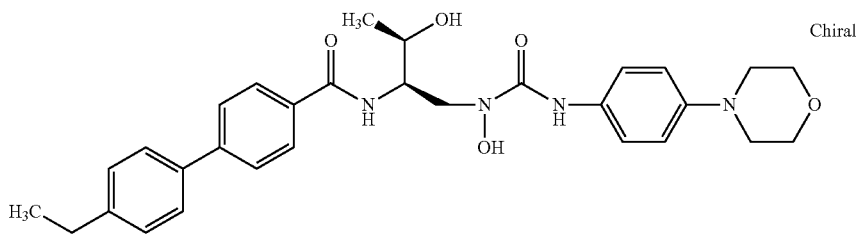 | Chiral |
| 84 | 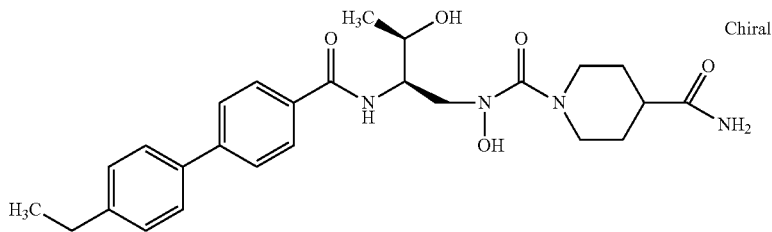 | Chiral |
| 85 | 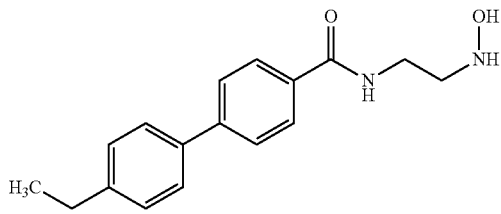 | |
| 86 | 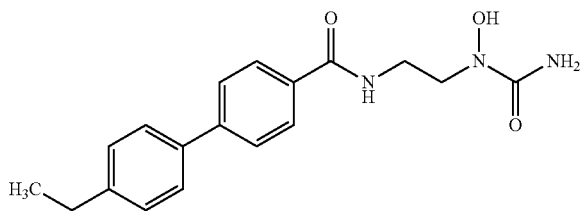 | |
| 87 | 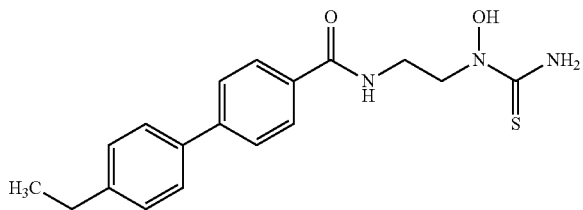 | |
| 88 | 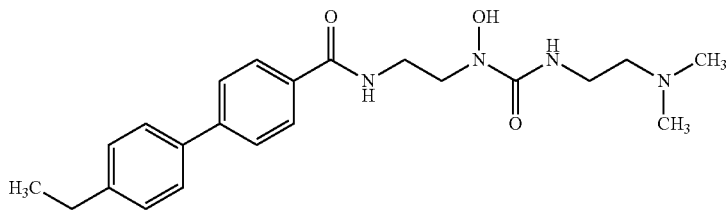 | |
| 89 | 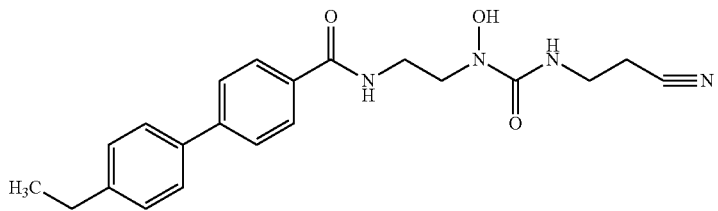 | |

TABLE 1-continued
| 90 |  |
| 91 |  |
| 92 |  |
| 93 |  |
| 94 |  |
| 95 | 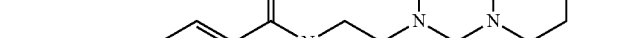 |
| 96 |  |

TABLE 1-continued
| 97 | 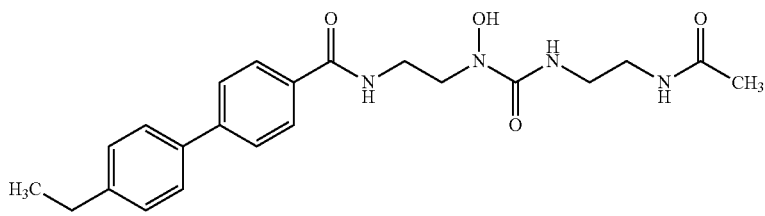 |
| 98 | 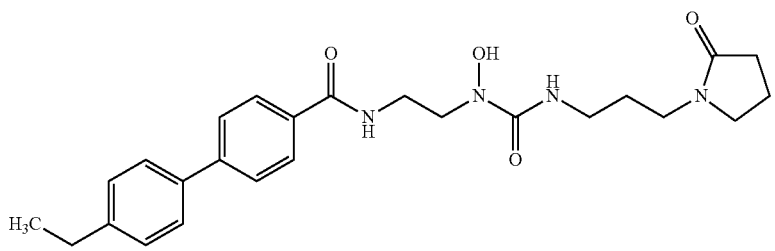 |
| 99 | 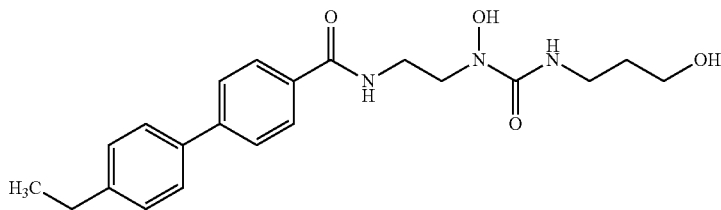 |
| 100 | 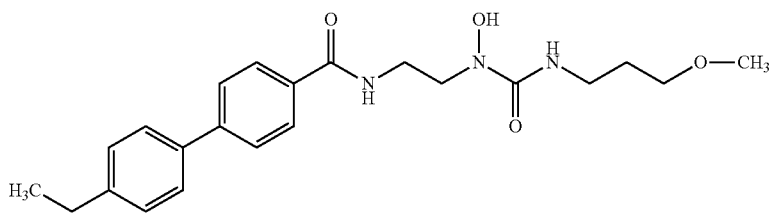 |
| 101 | 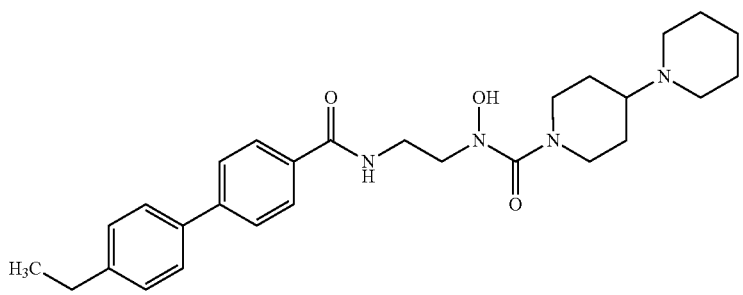 |
| 102 | 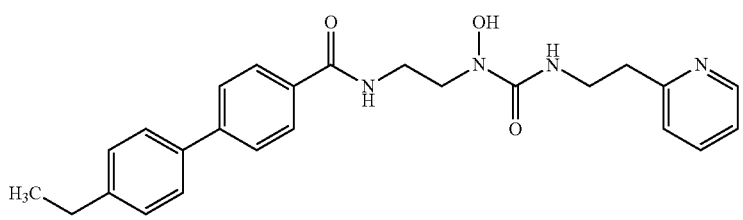 |

TABLE 1-continued
103
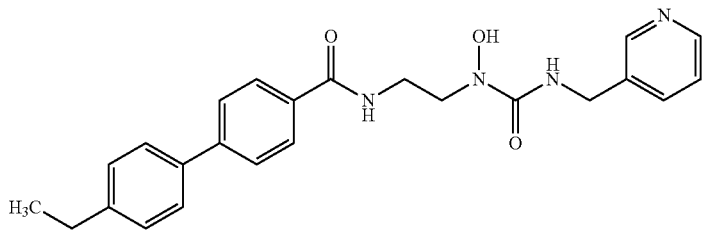
104
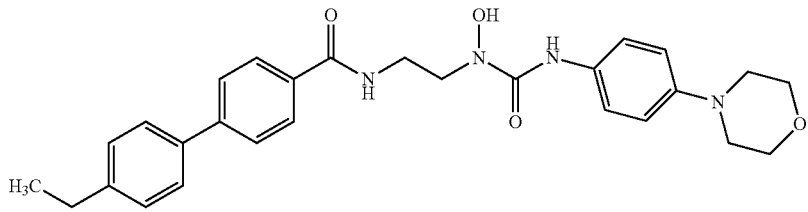
105
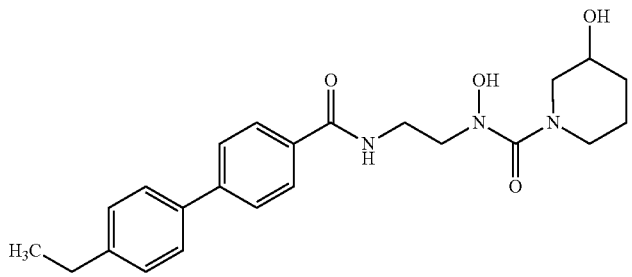
106
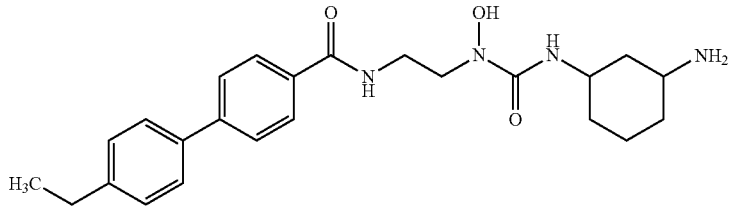
107
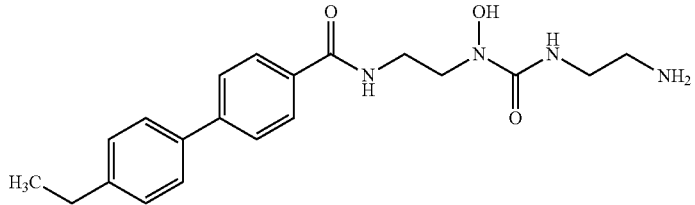
108
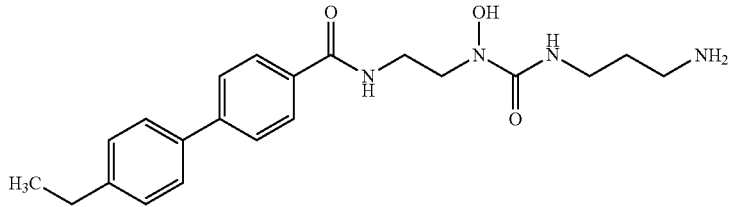
109
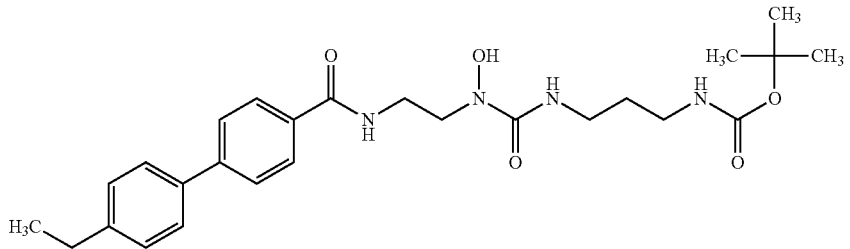

TABLE 1-continued
110 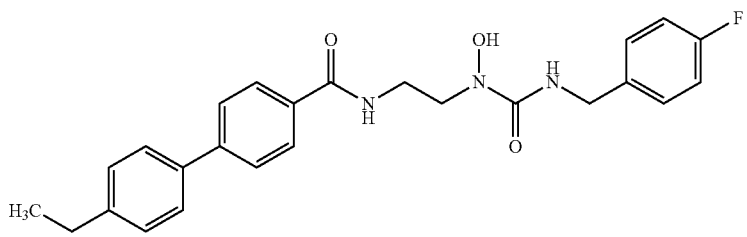
111 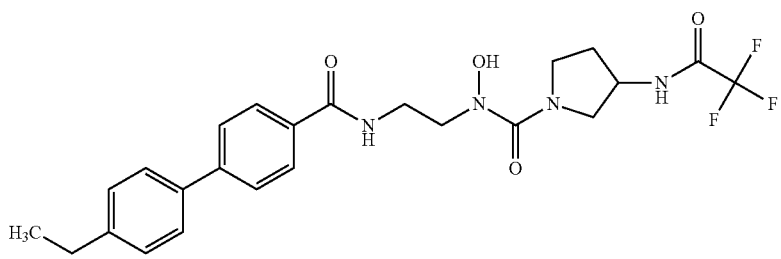
112 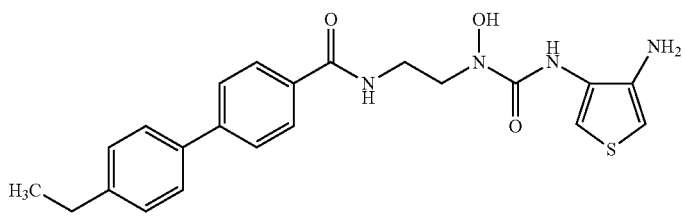
113 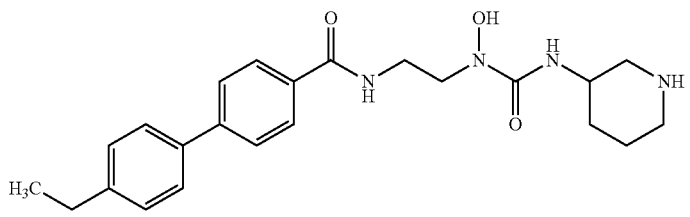
114 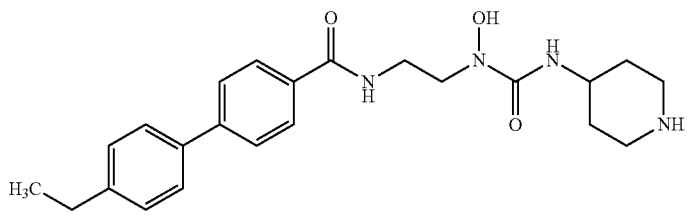
115 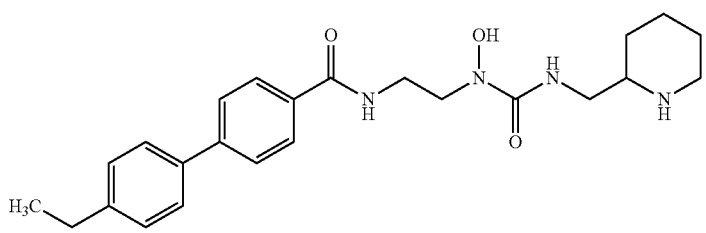
116 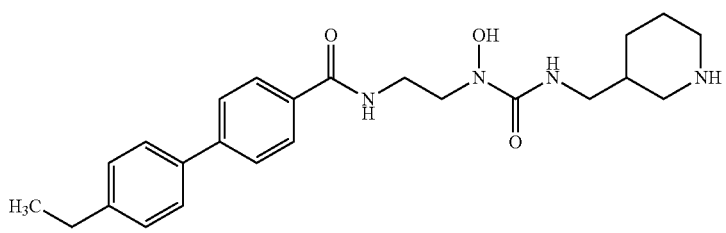

TABLE 1-continued
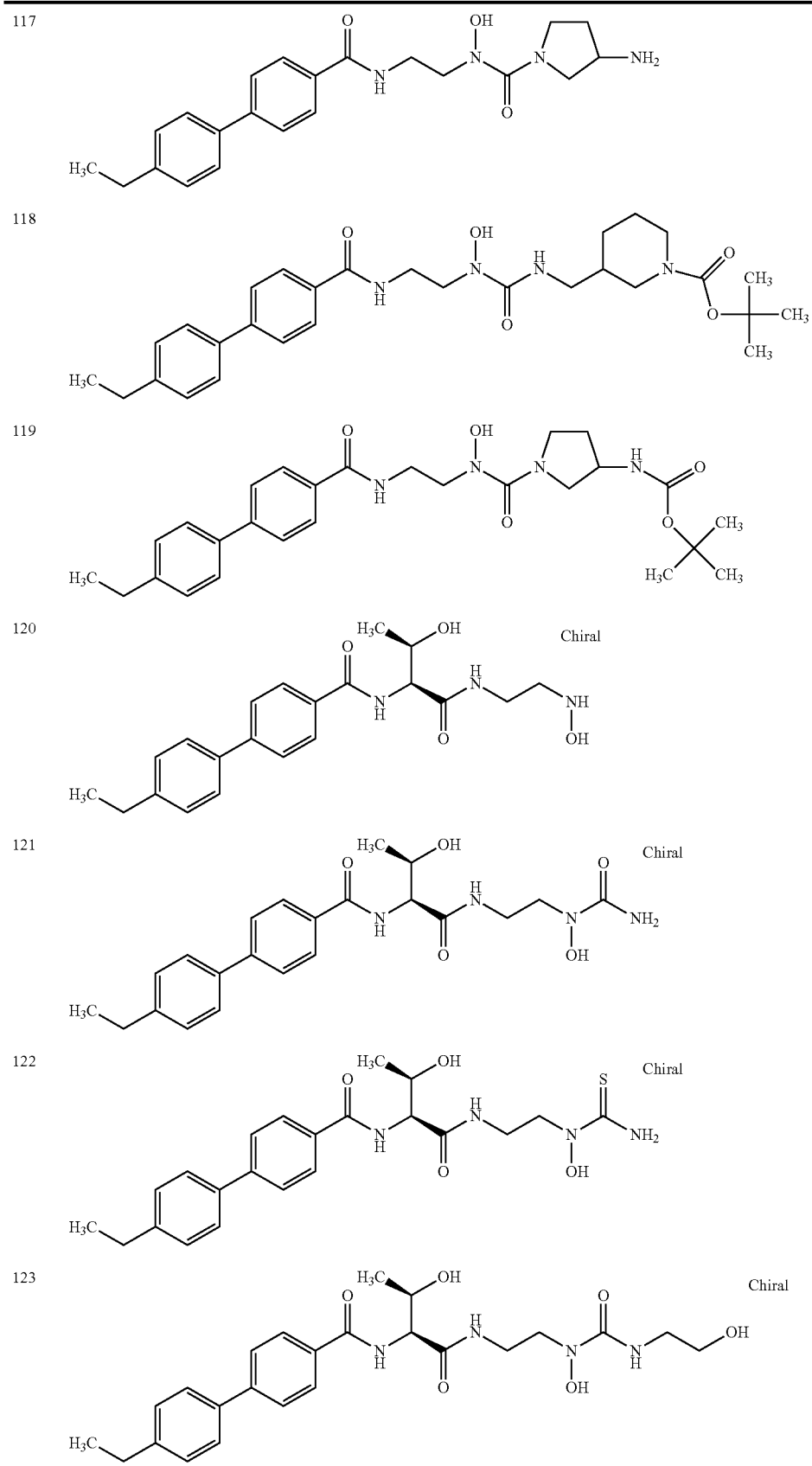

TABLE 1-continued
| 124 | 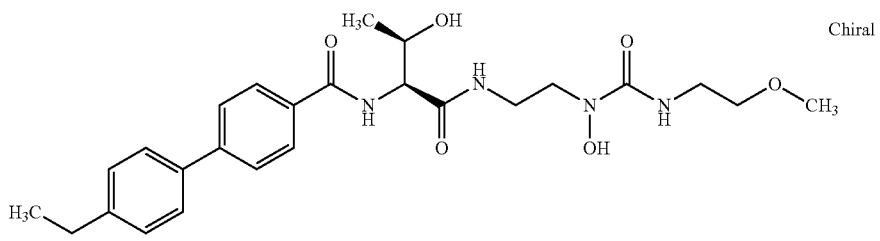 | Chiral |
| 125 | 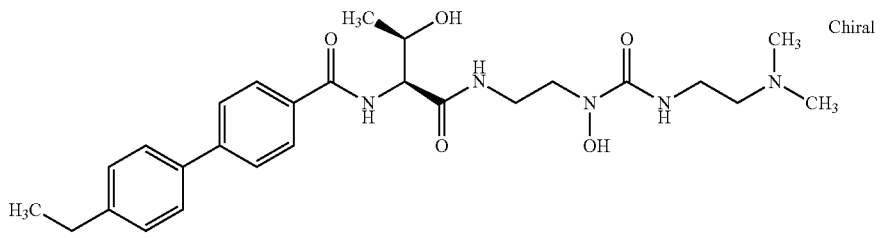 | Chiral |
| 126 | 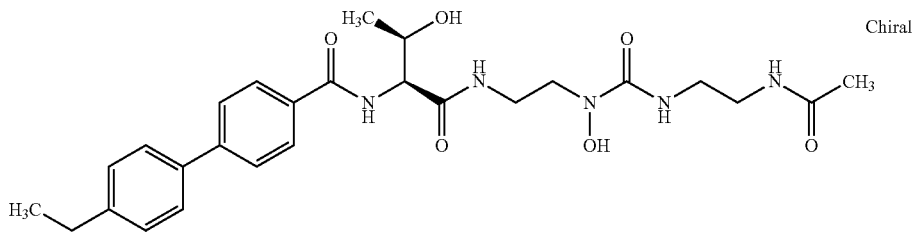 | Chiral |
| 127 | 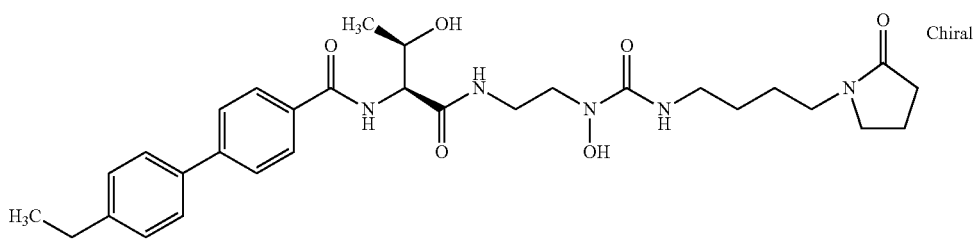 | Chiral |
| 128 | 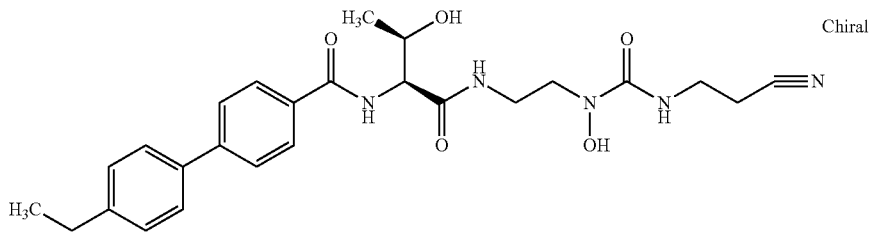 | Chiral |
| 129 | 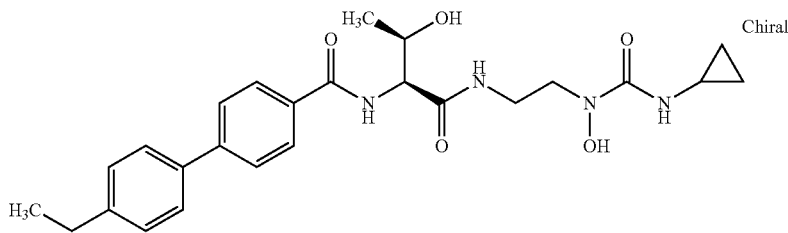 | Chiral |

TABLE 1-continued
| 130 | 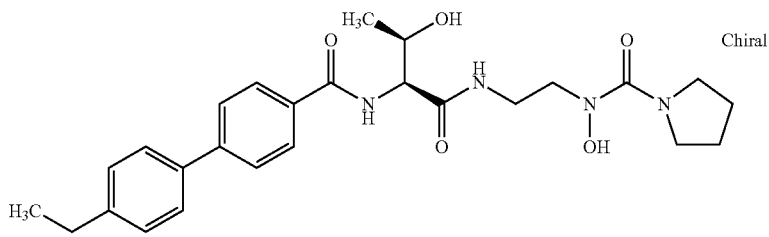 Chiral |
| 131 | 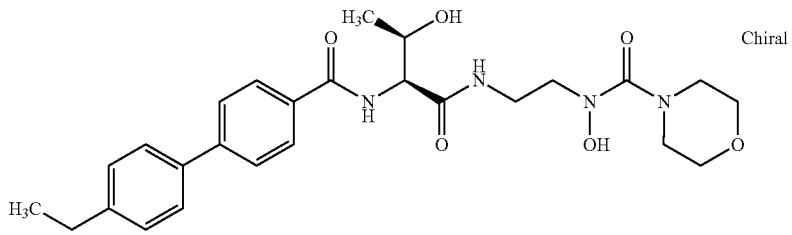 Chiral |
| 132 | 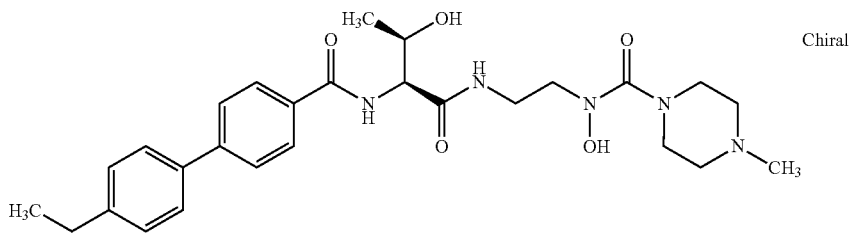 Chiral |
| 133 | 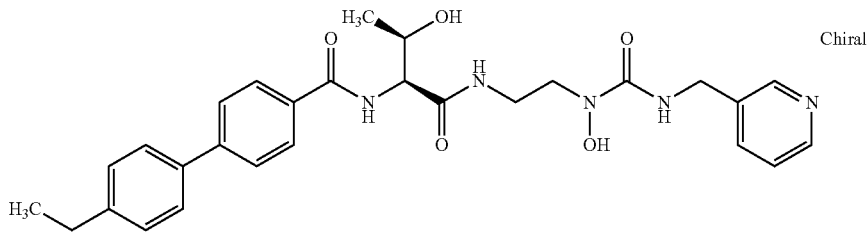 Chiral |
| 134 | 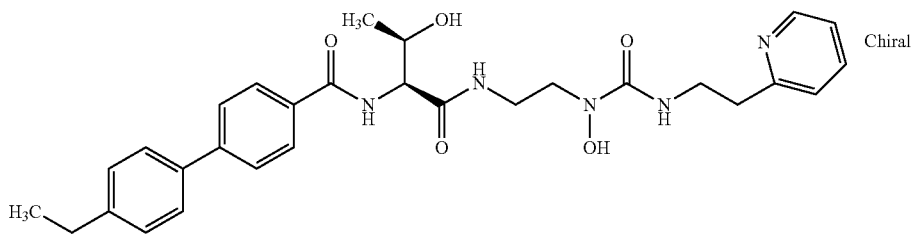 Chiral |
| 135 | 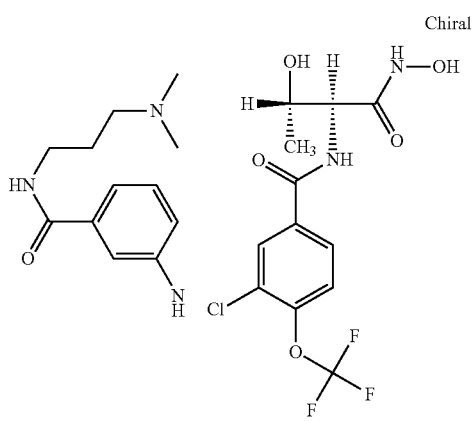 Chiral |

TABLE 1-continued
| 136 | 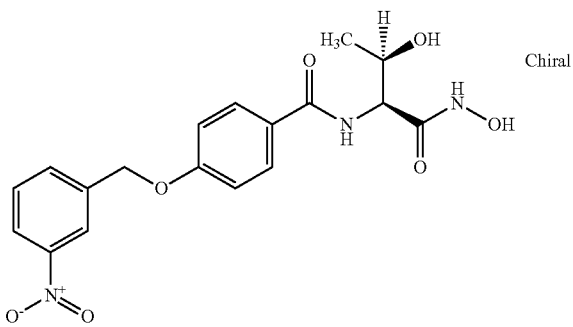 Chiral |
| --- | --- |
| 137 | 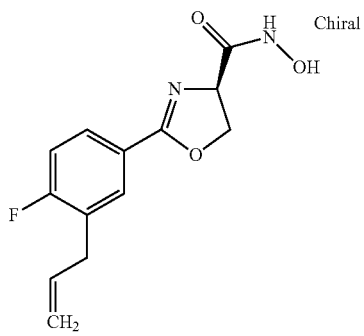 Chiral |
| 138 | 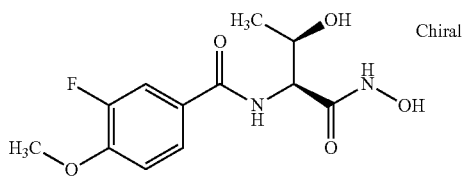 Chiral |
| 139 | 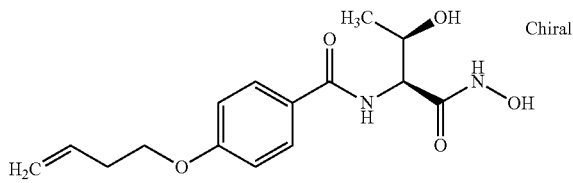 Chiral |
| 140 | 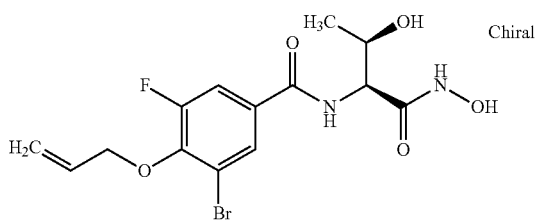 Chiral |
| 141 | 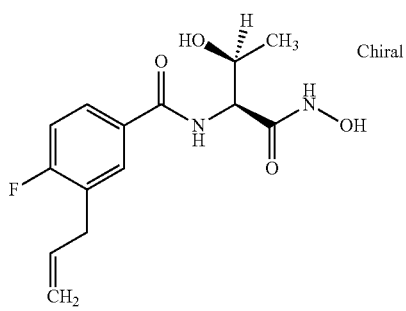 Chiral |

TABLE 1-continued
| 142 | 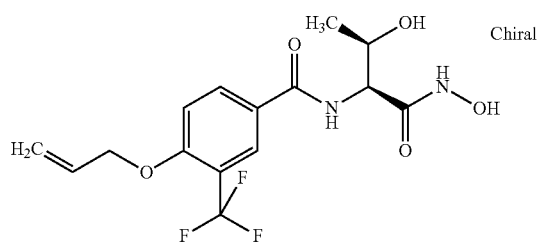 |
| 143 | 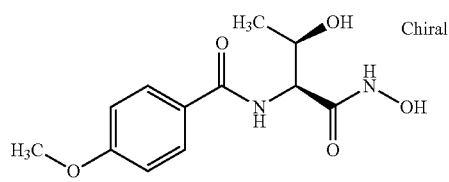 |
| 144 | 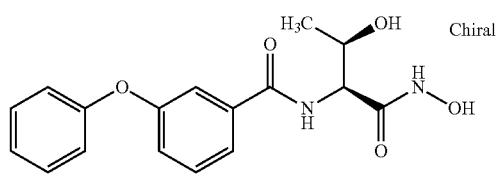 |
| 145 | 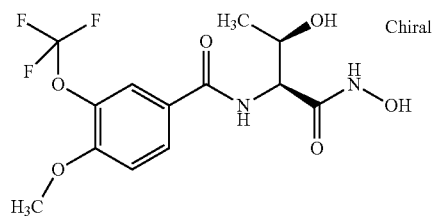 |
| 146 | 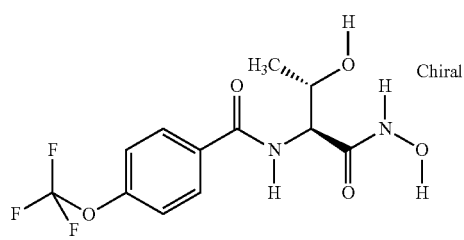 |
| 147 | 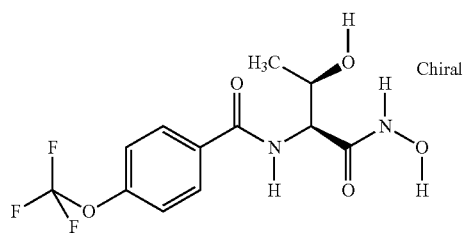 |
| 148 | 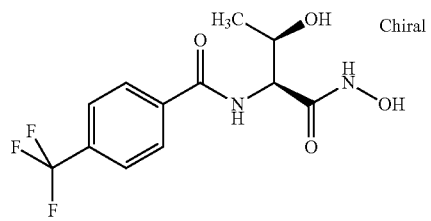 |

TABLE 1-continued

| | | |
|---|---|---|
| 149 | 3,4-difluorobenzoyl-Thr-NHOH | Chiral |
| 150 | 4-methoxybenzoyl-Thr-NHOH | Chiral |
| 151 | 4'-propyl-biphenyl-4-carbonyl-Thr-NHOH | Chiral |
| 152 | 4'-propyl-biphenyl-4-carbonyl-Thr-NHOH | Chiral |
| 153 | 4-(pentafluoro-λ6-sulfanylmethyl)benzoyl-Thr-NHOH | Chiral |
| 154 | benzoyl-Thr-NHOH | Chiral |
| 155 | biphenyl-4-carbonyl-Thr-NHOH | Chiral |

TABLE 1-continued
| | |
|---|---|
| 156 | 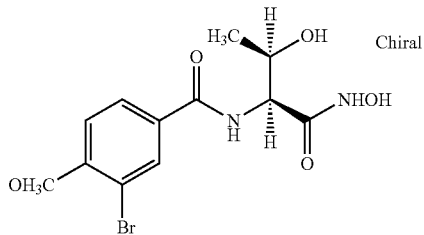 |
| 157 | 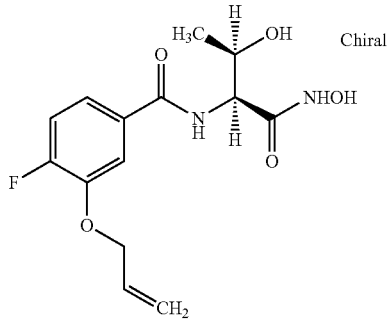 |
| 158 | 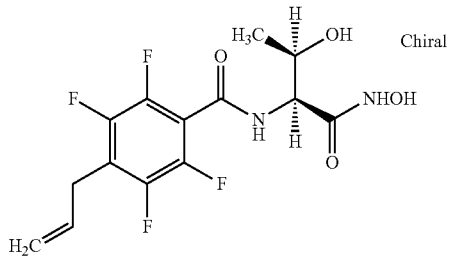 |
| 159 | 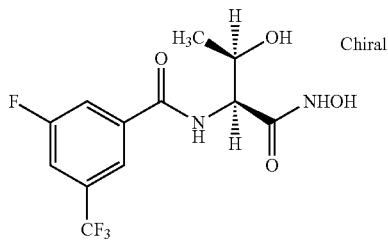 |
| 160 | 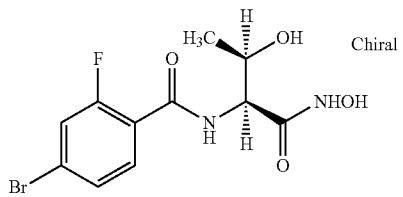 |
| 161 | 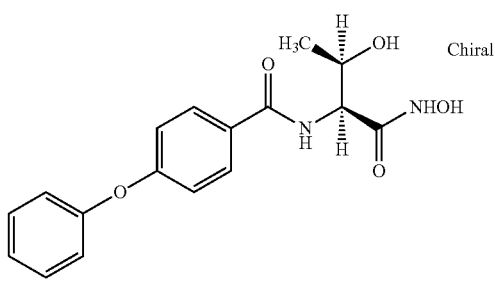 |

TABLE 1-continued
| 162 | 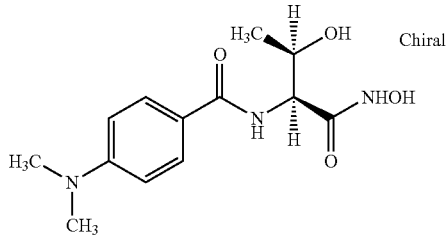 |
| 163 | 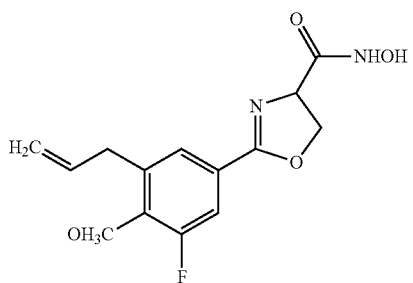 |
| 164 | 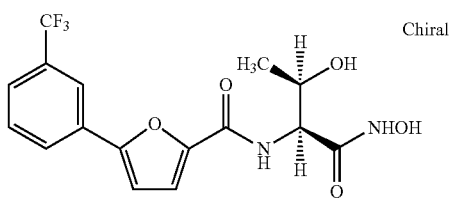 |
| 165 | 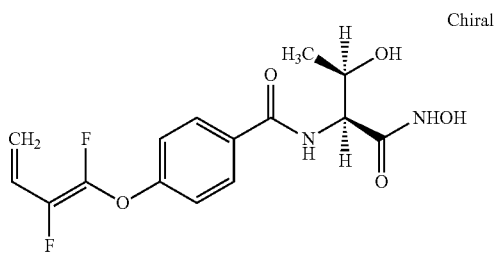 |
| 166 | 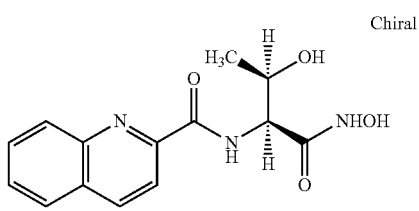 |
| 167 | 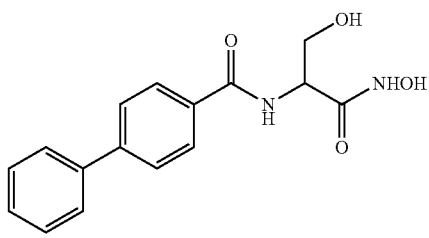 |

TABLE 1-continued
168 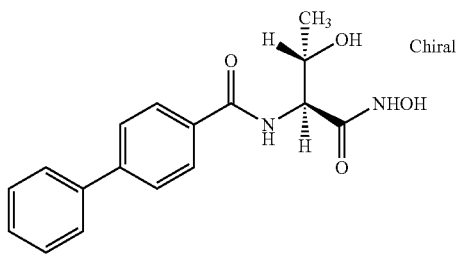
169 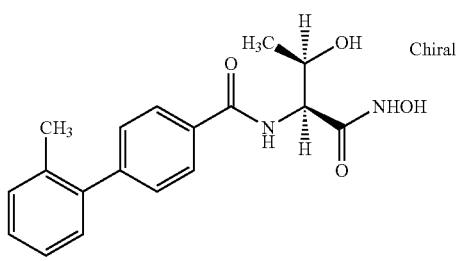
170 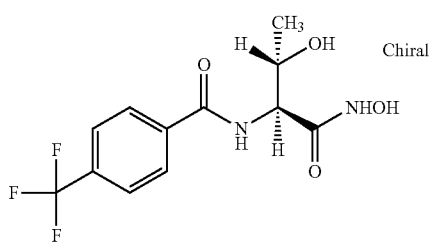
171 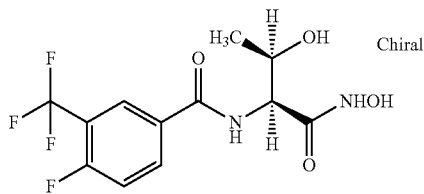
172 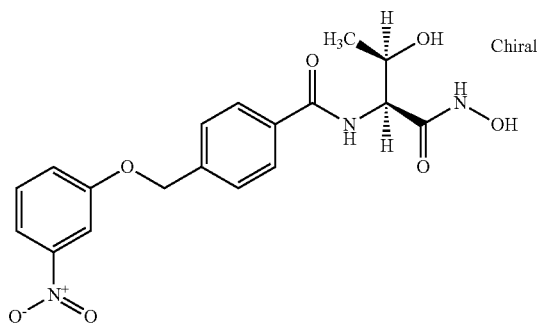
173 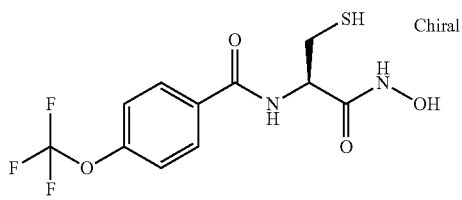

TABLE 1-continued
| 174 | 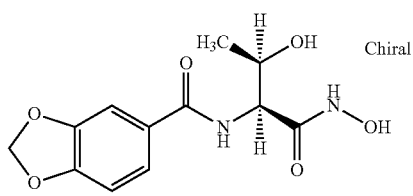 |
| --- | --- |
| 175 | 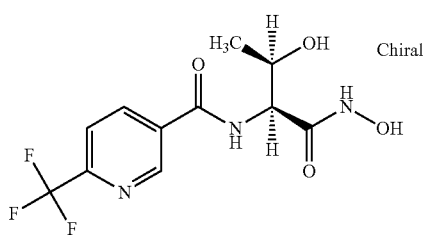 |
| 176 | 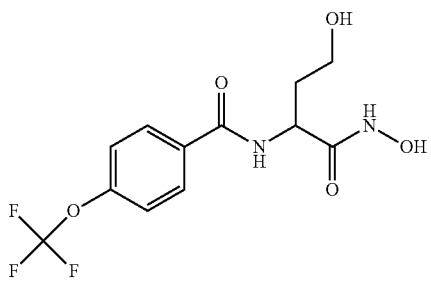 |
| 177 | 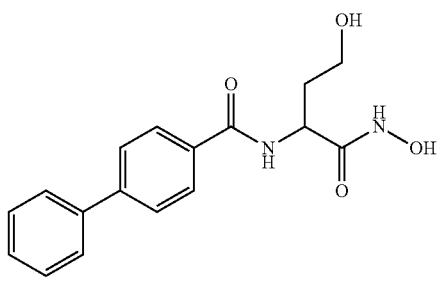 |
| 178 | 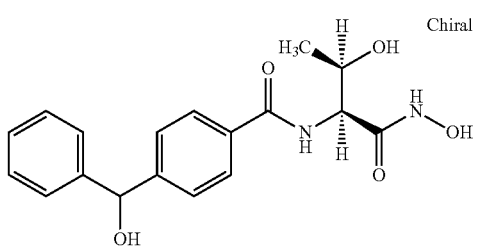 |
| 179 | 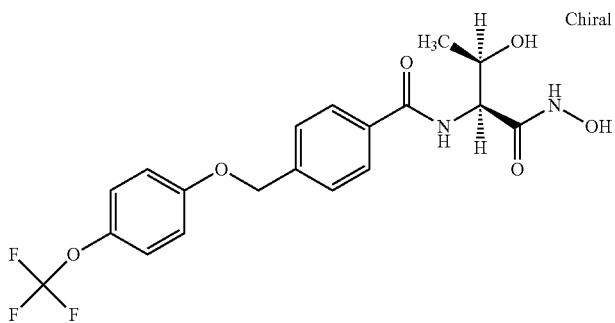 |

| | |
|---|---|
| 180 | 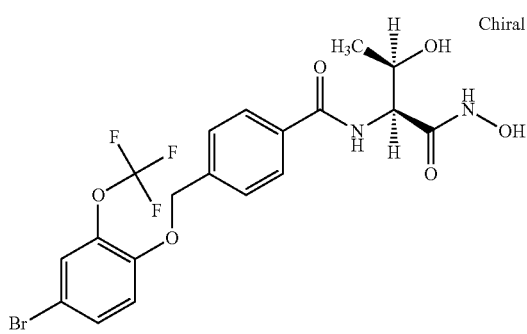 |
| 181 | 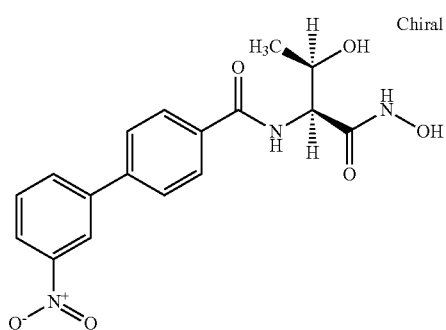 |
| 182 | 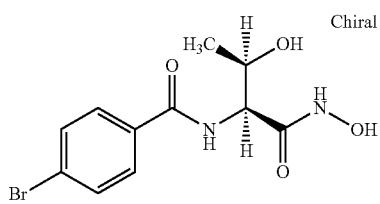 |
| 183 | 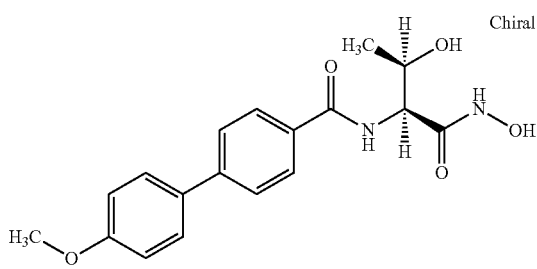 |
| 184 | 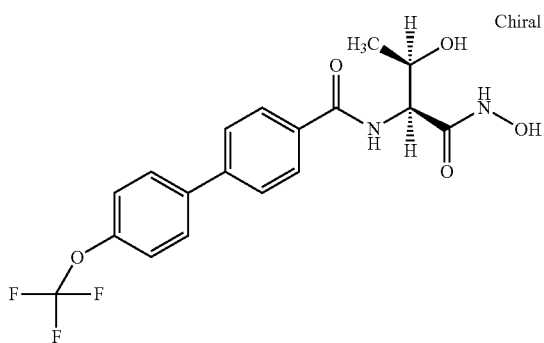 |

| | |
|---|---|
| 185 | 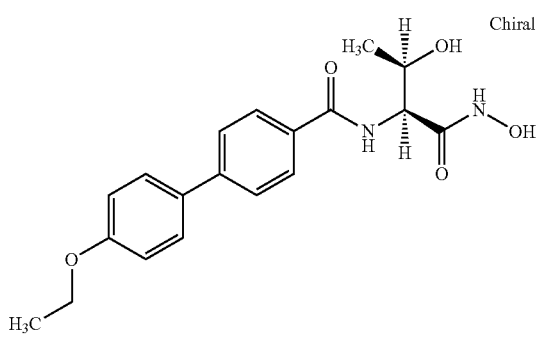 |
| 186 | 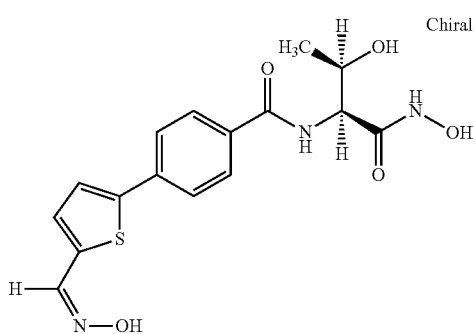 |
| 187 | 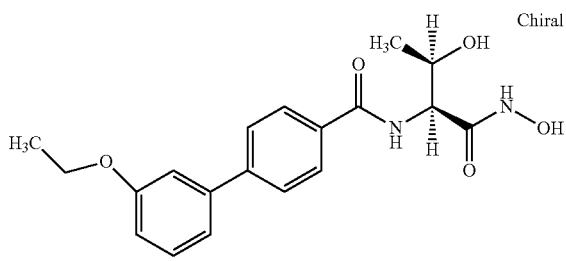 |
| 188 | 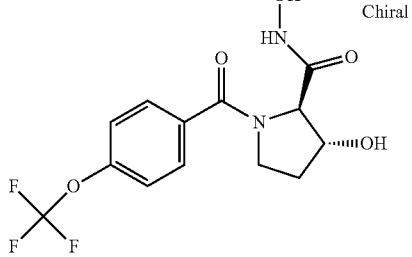 |
| 189 | 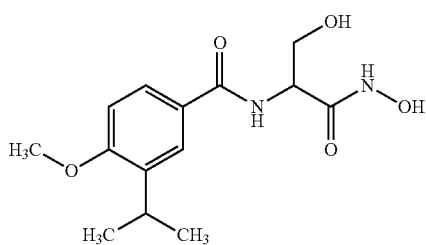 |

TABLE 1-continued
| | |
|---|---|
| 190 | 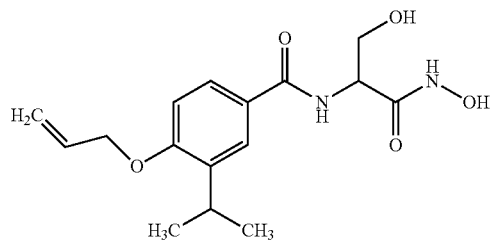 |
| 191 | 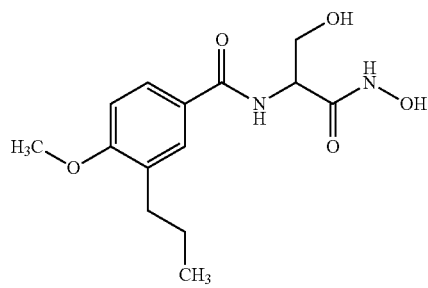 |
| 192 | 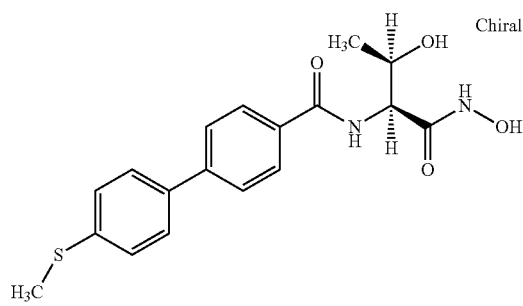 |
| 193 | 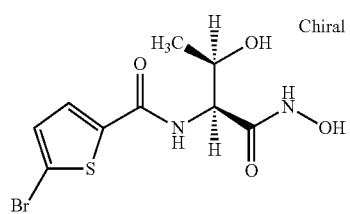 |
| 194 | 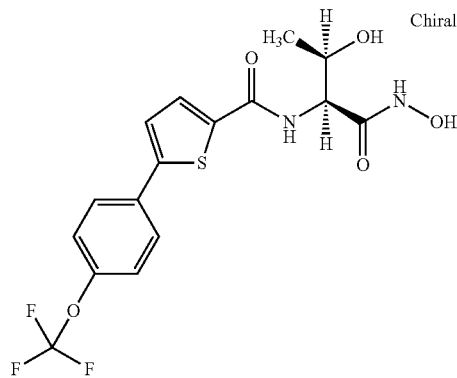 |
| 195 | 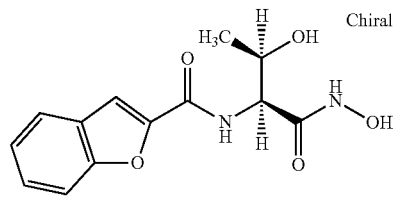 |

TABLE 1-continued
| 196 | 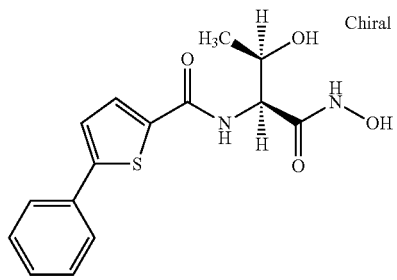 |
| 197 | 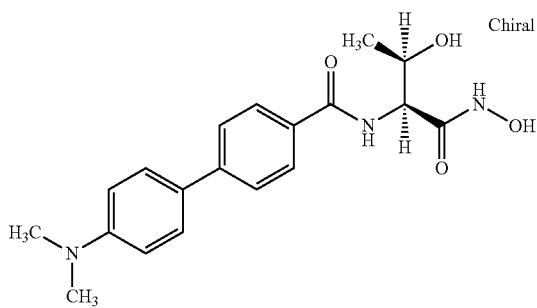 |
| 198 | 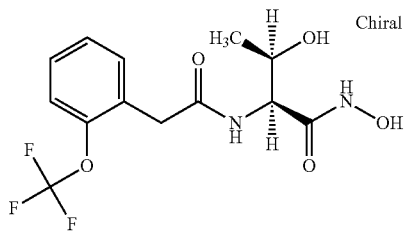 |
| 199 | 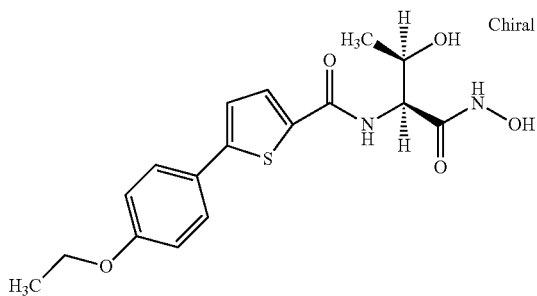 |
| 200 | 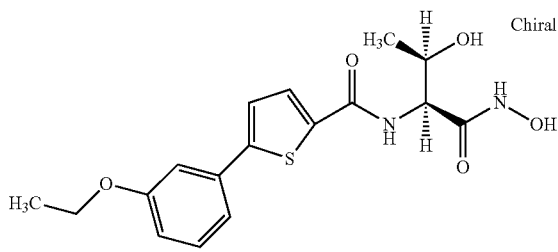 |

TABLE 1-continued
| 201 | 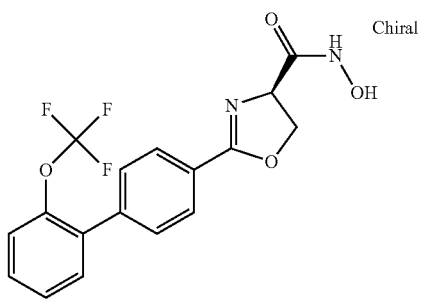 |
| --- | --- |
| 202 | 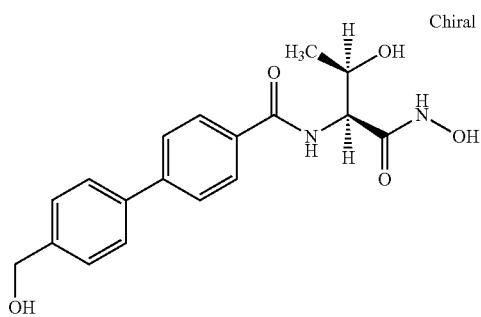 |
| 203 | 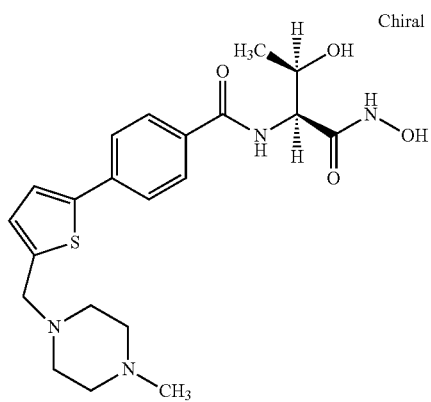 |
| 204 | 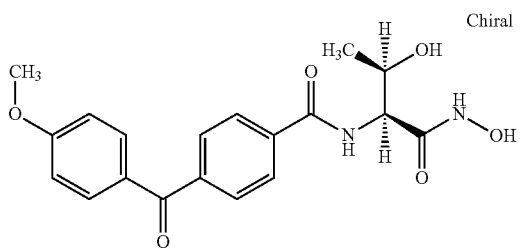 |
| 205 | 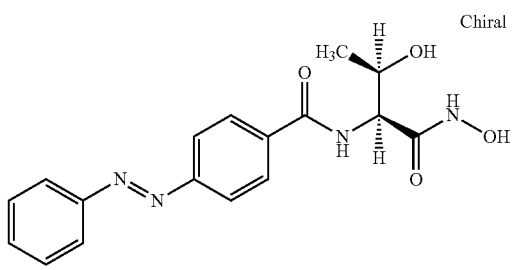 |

TABLE 1-continued
206 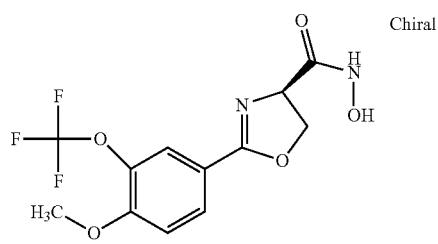
207 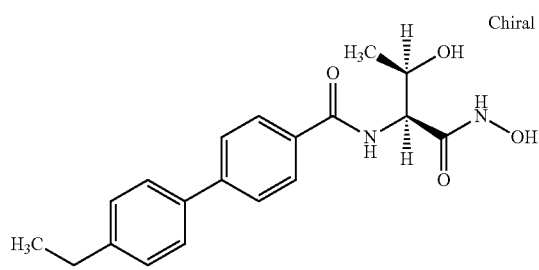
208 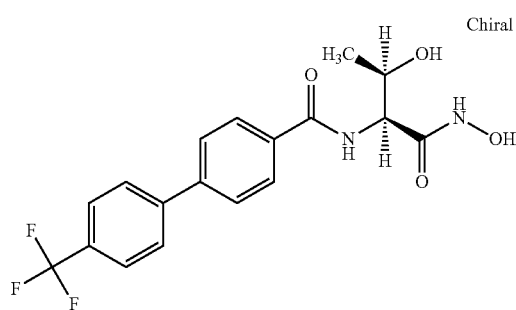
209 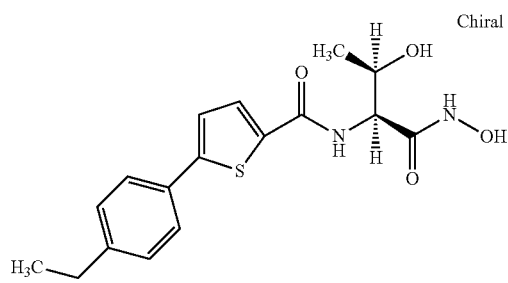
210 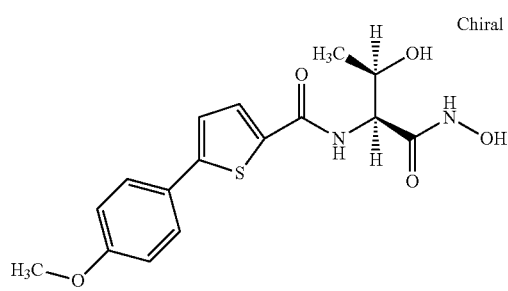

TABLE 1-continued
| 211 | 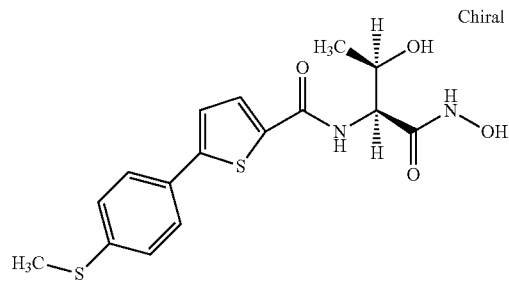 |
| 212 | 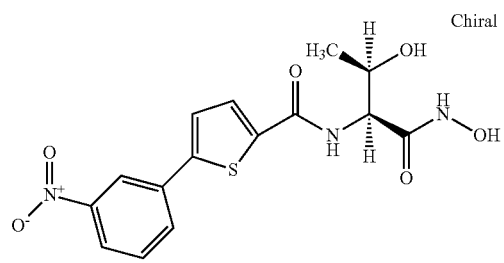 |
| 213 | 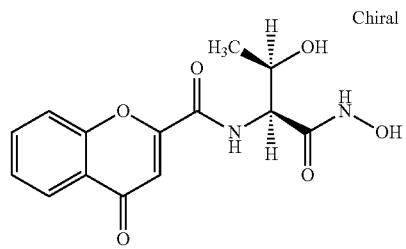 |
| 214 | 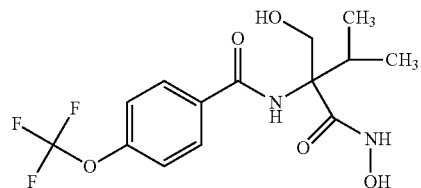 |
| 215 | 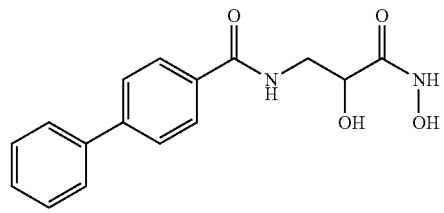 |
| 216 | 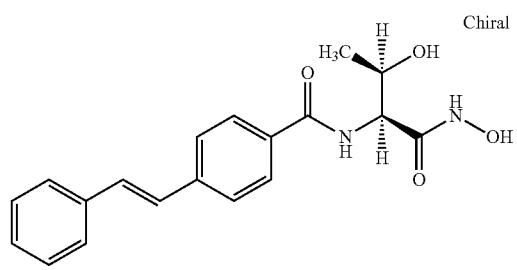 |

TABLE 1-continued
217 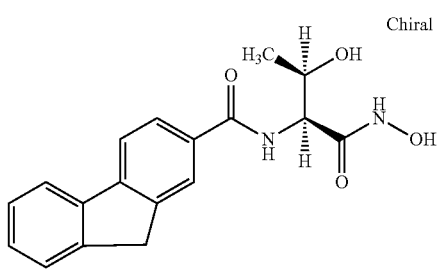
218 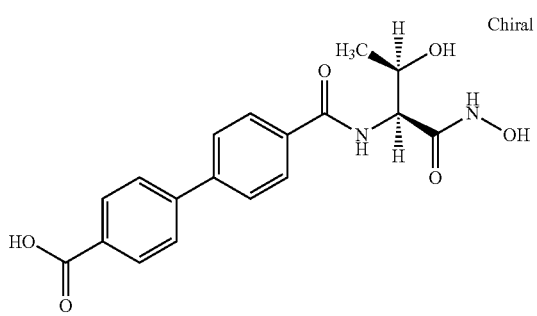
219 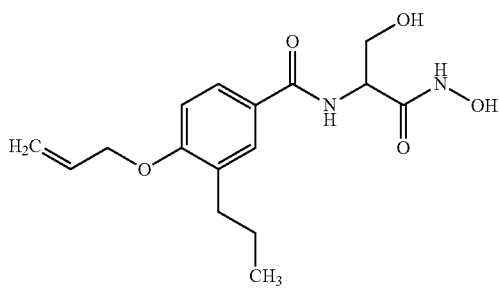
220 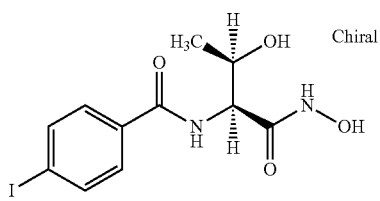
221 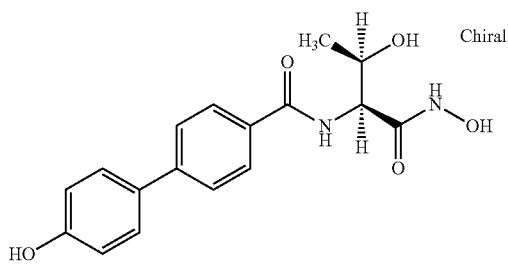
222 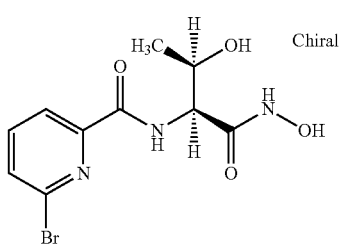

TABLE 1-continued
223 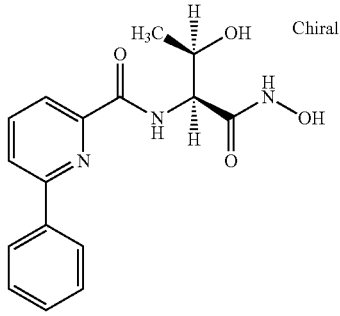
224 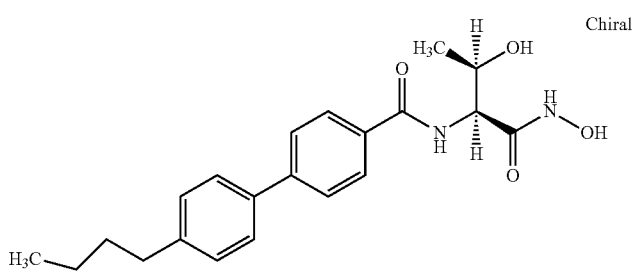
225 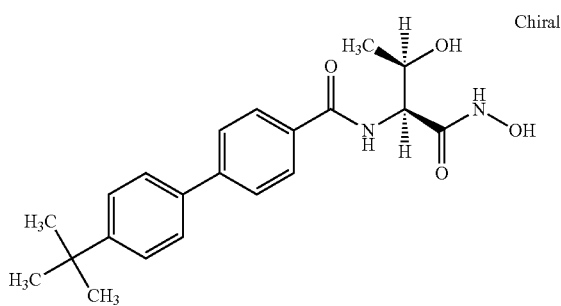
226 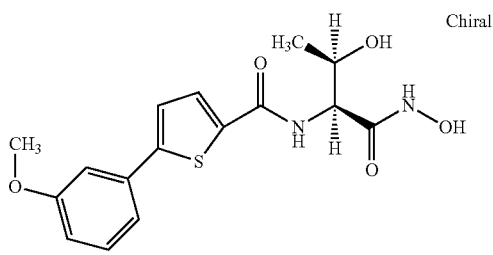
227 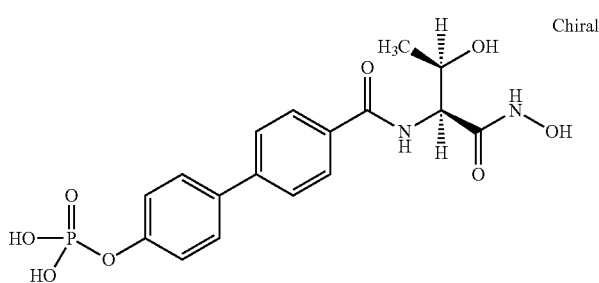

TABLE 1-continued
228 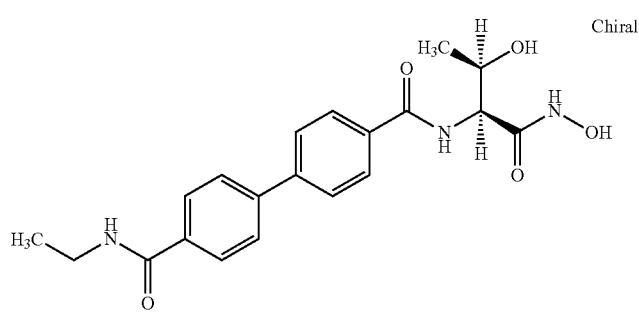
229 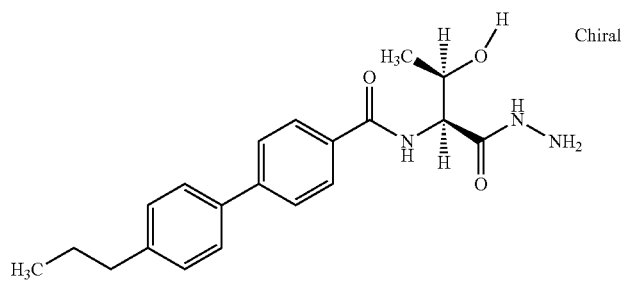
230 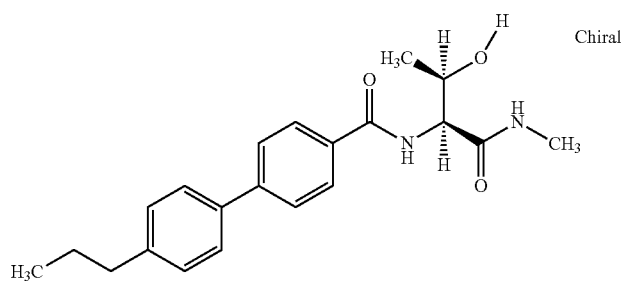
231 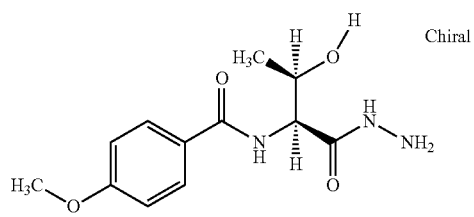
232 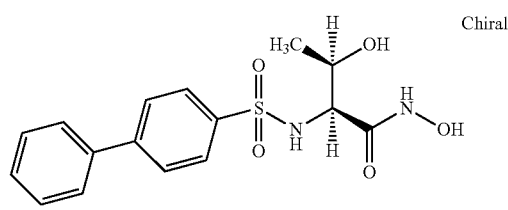
233 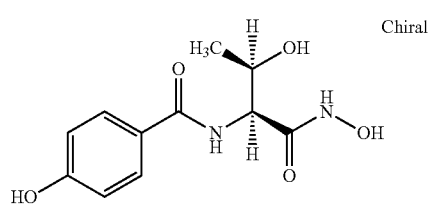

TABLE 1-continued
234 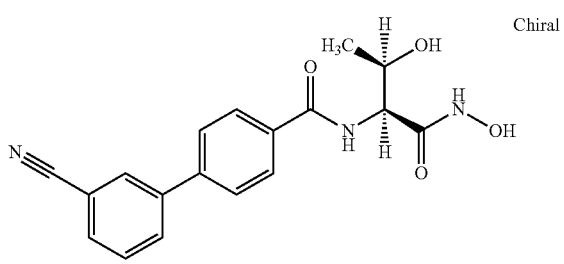 Chiral
235 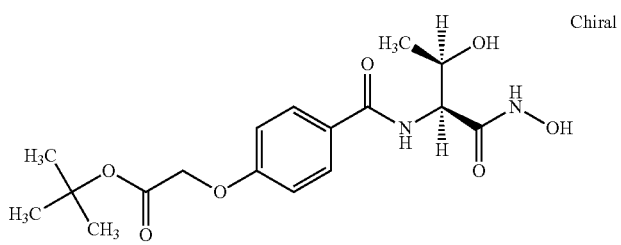 Chiral
236 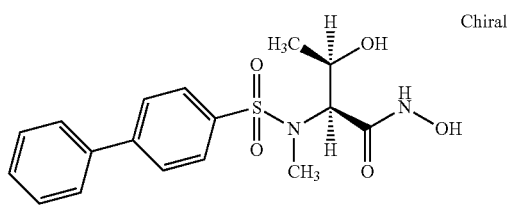 Chiral
237 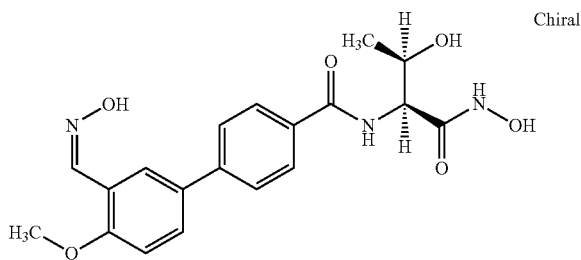 Chiral
238 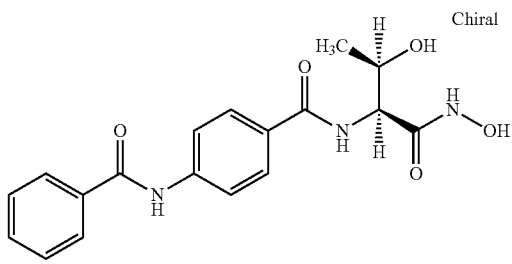 Chiral
239 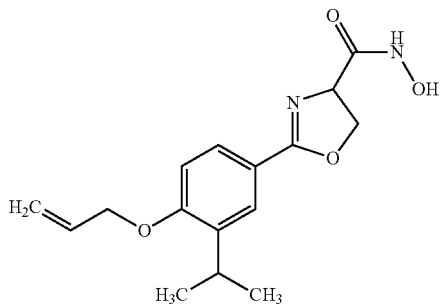

TABLE 1-continued
240 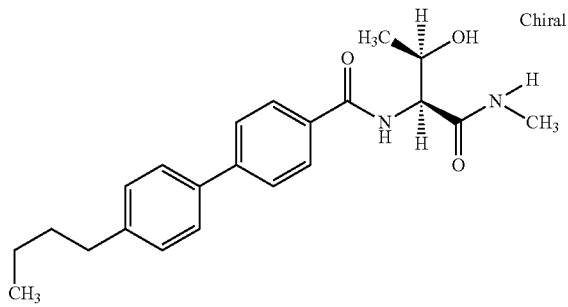
241 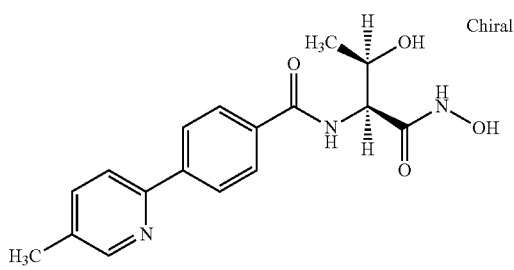
242 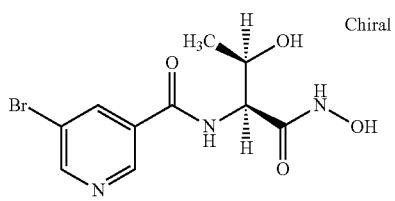
243 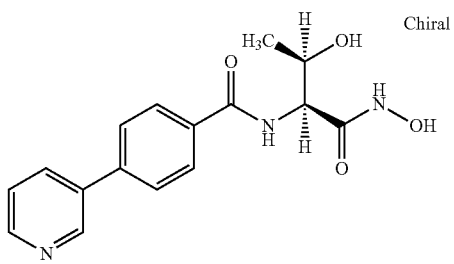
244 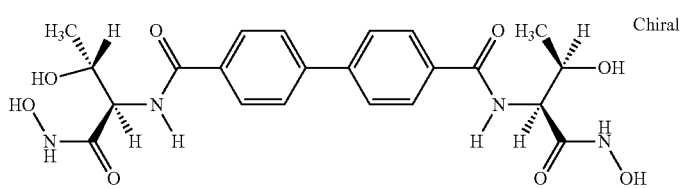
245 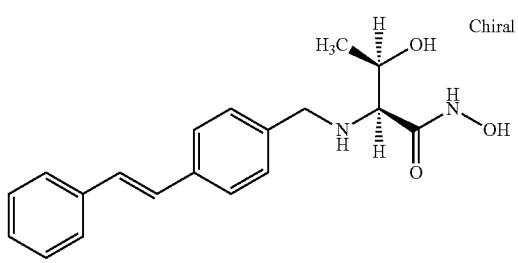

TABLE 1-continued
246 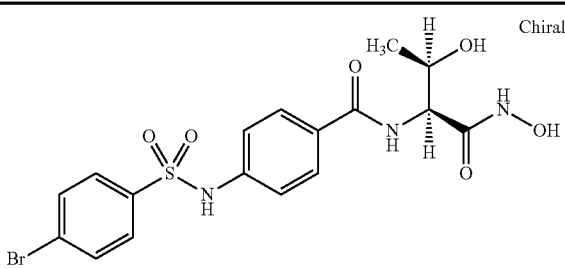
247 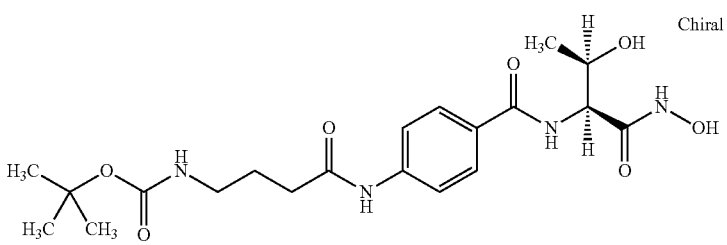
248 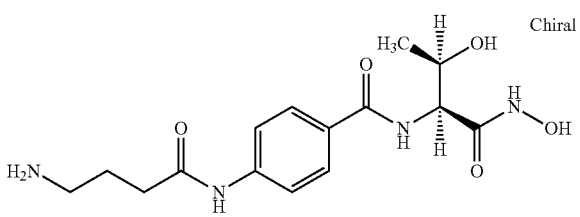
249 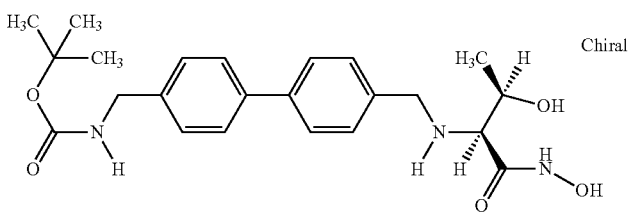
250 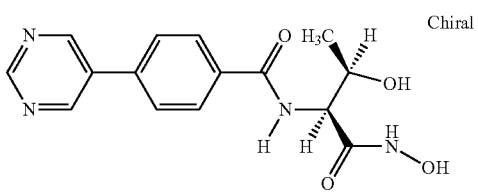
251 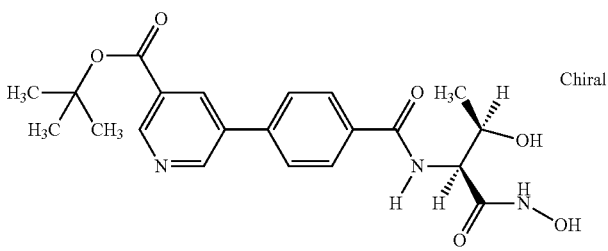
252 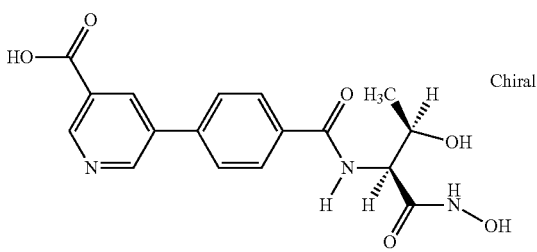

TABLE 1-continued
| | | |
|---|---|---|
| 253 | 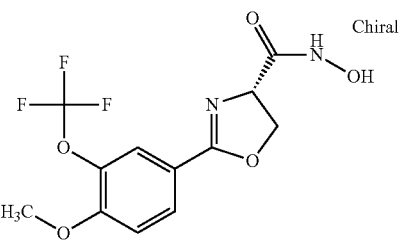 | |
| 254 | 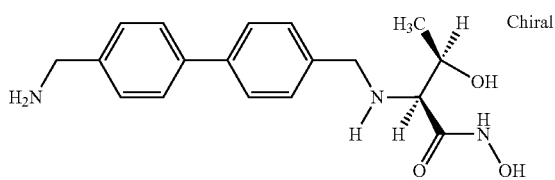 | |
| 255 | 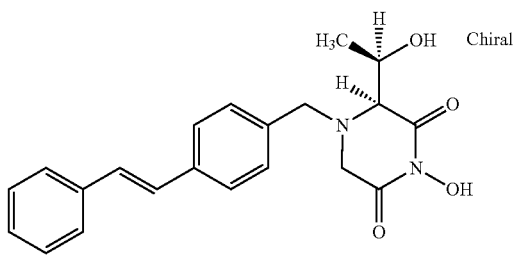 | |
| 256 | 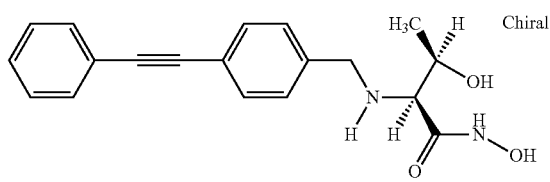 | |
| 257 | 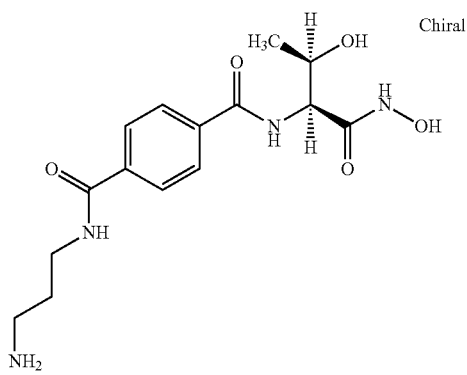 | |
| 258 | 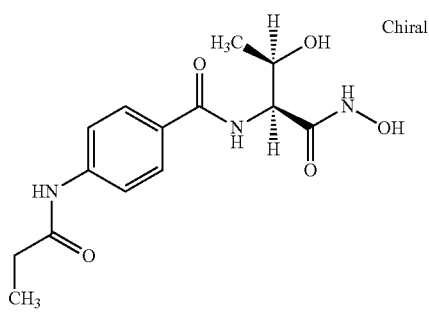 | |

TABLE 1-continued
| 259 | 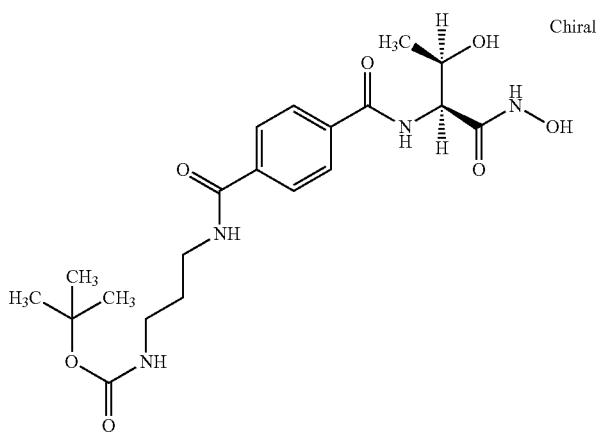 |
| 260 | 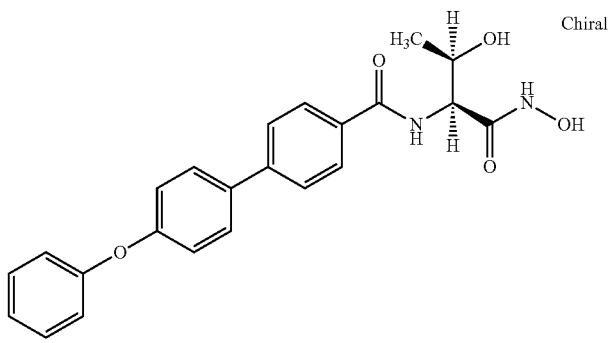 |
| 261 | 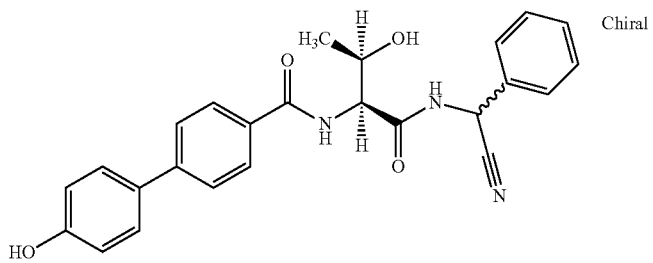 |
| 262 | 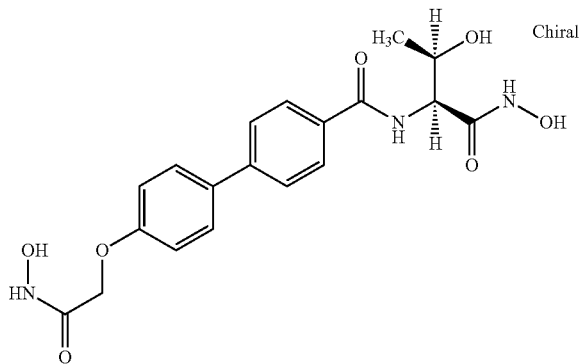 |

TABLE 1-continued
263
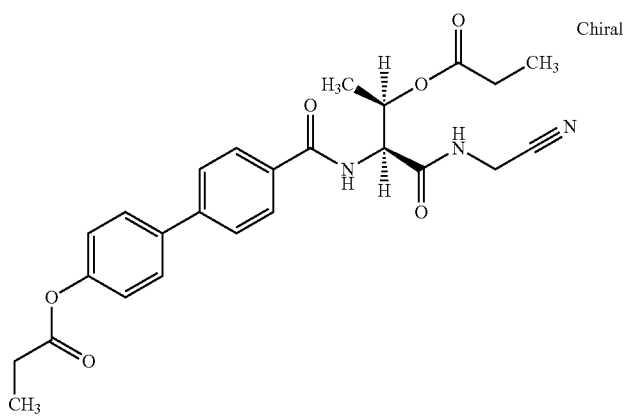
264
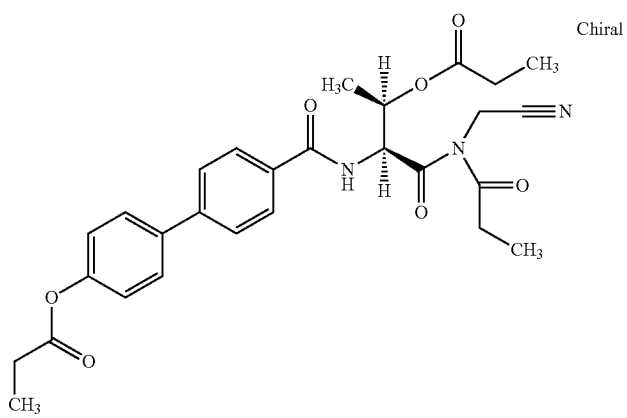
265
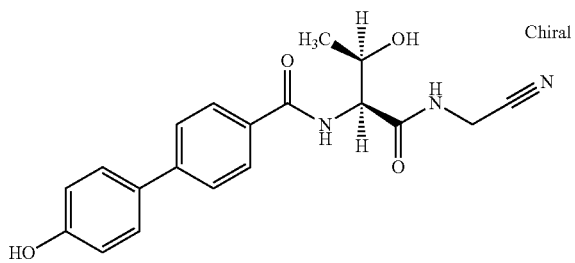
266
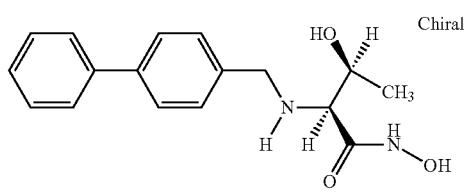
267
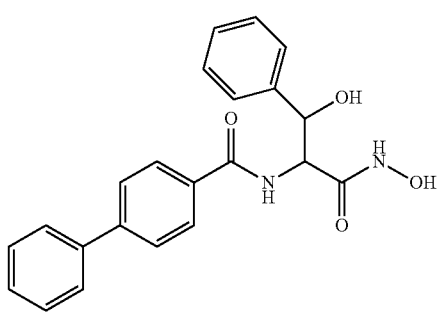

TABLE 1-continued
| 268 | 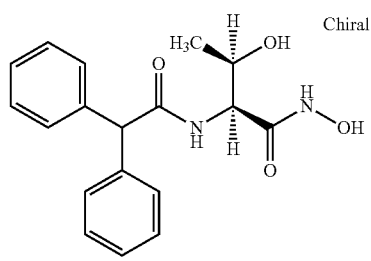 |
| --- | --- |
| 269 | 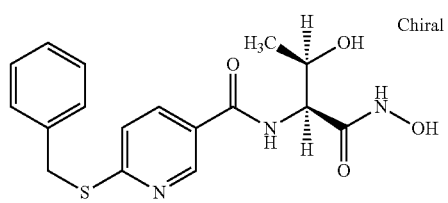 |
| 270 | 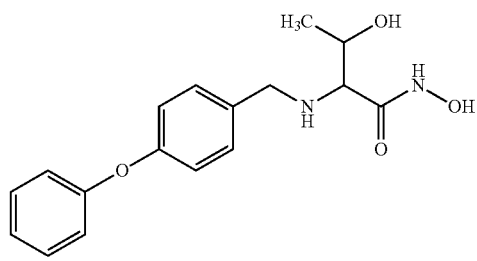 |
| 271 | 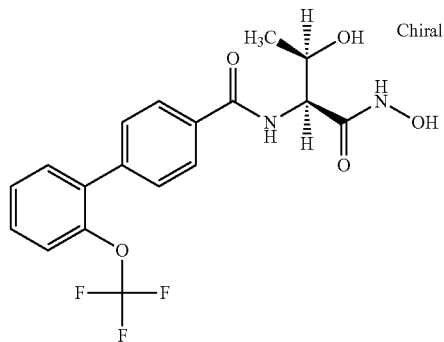 |
| 272 | 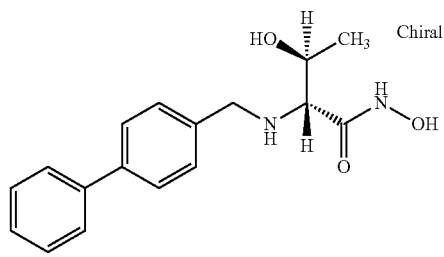 |
| 273 | 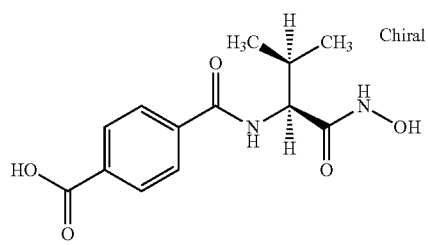 |

TABLE 1-continued
| 274 | 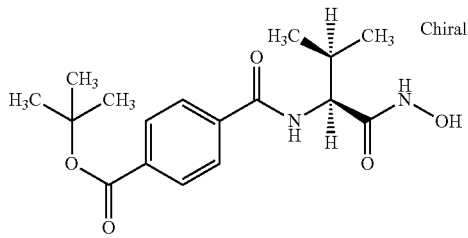 |
| --- | --- |
| 275 | 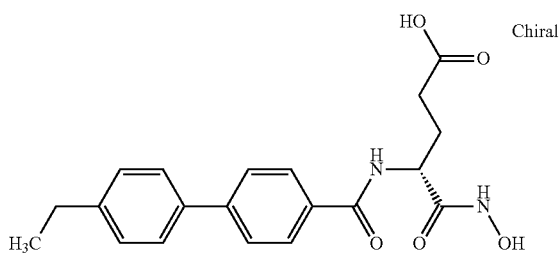 |
| 276 | 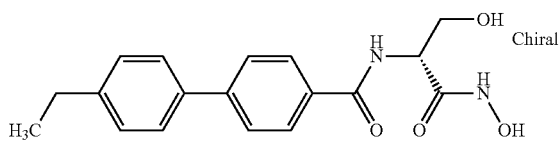 |
| 277 | 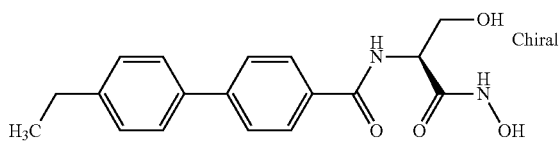 |
| 278 | 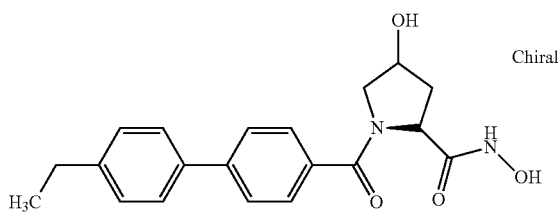 |
| 279 | 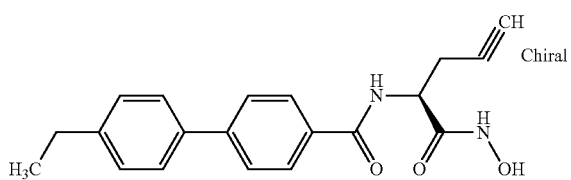 |
| 280 | 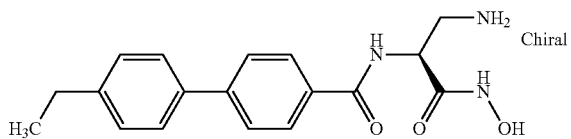 |
| 281 | 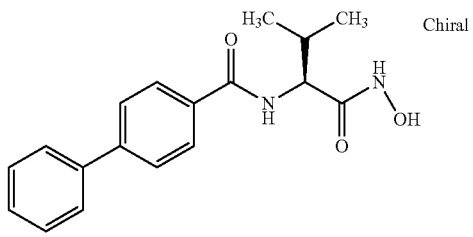 |

TABLE 1-continued
| 282 | 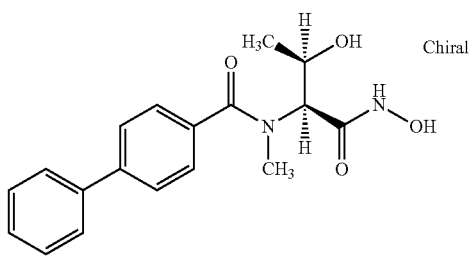 |
| --- | --- |
| 283 | 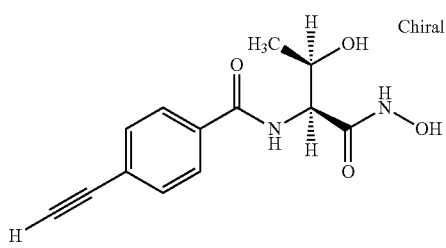 |
| 284 | 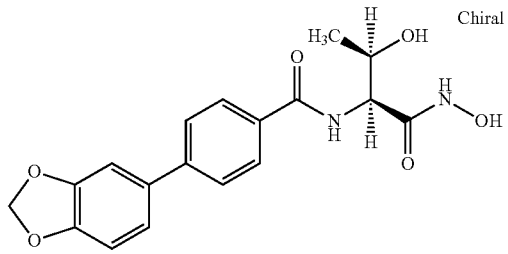 |
| 285 | 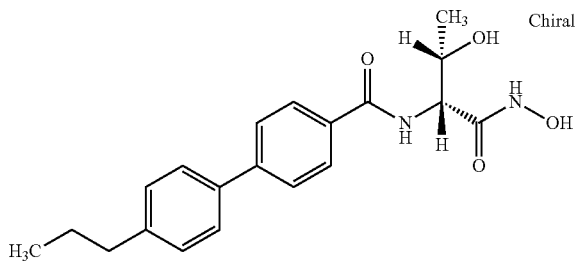 |
| 286 | 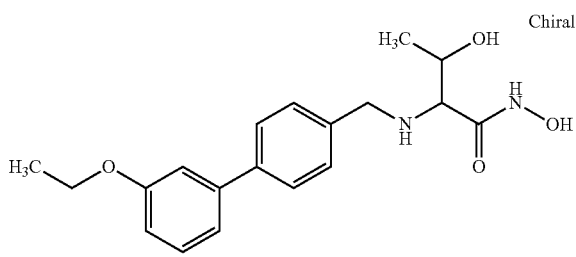 |
| 287 | 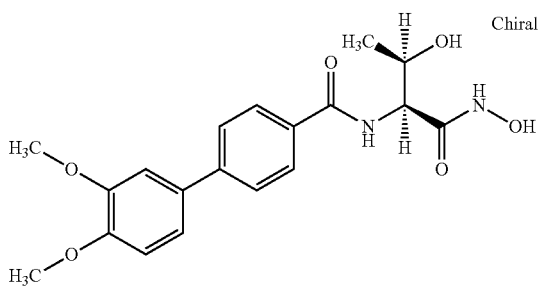 |

TABLE 1-continued
| | |
|---|---|
| 288 | 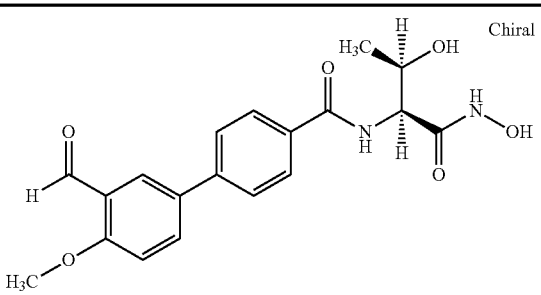 |
| 289 | 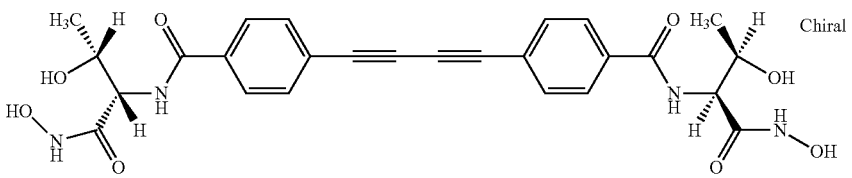 |
| 290 | 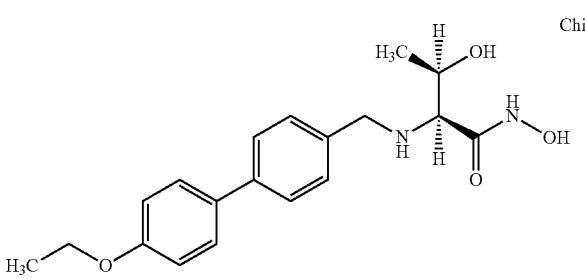 |
| 291 | 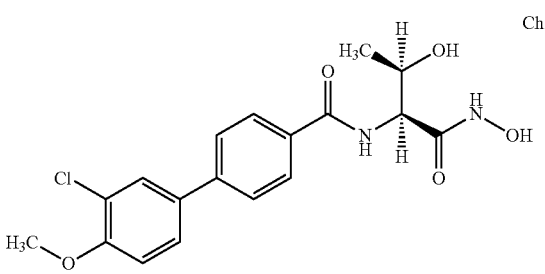 |
| 292 | 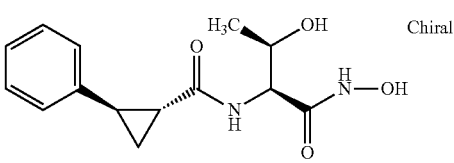 |
| 293 | 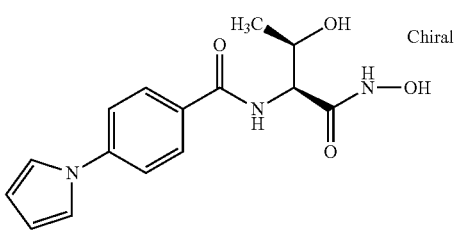 |
| 294 | 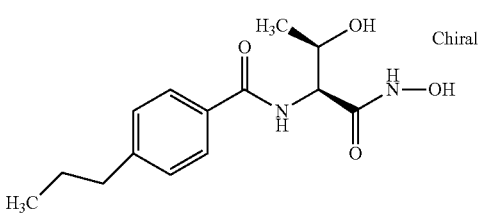 |

TABLE 1-continued
| 295 | 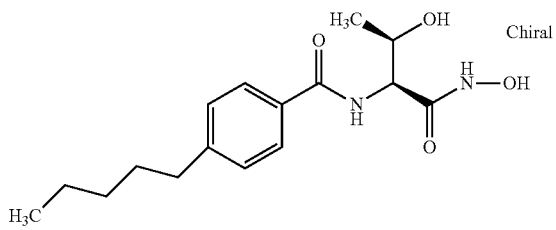 |
| --- | --- |
| 296 | 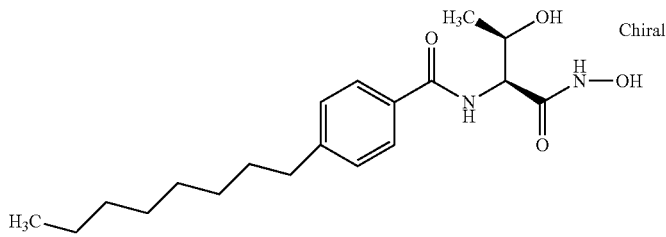 |
| 297 | 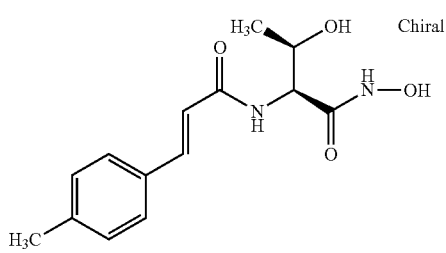 |
| 298 | 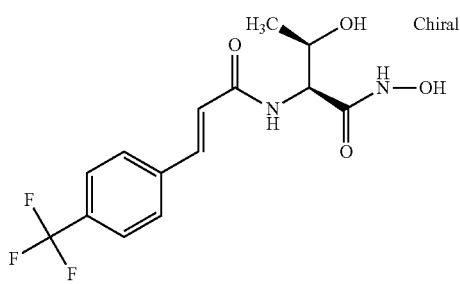 |
| 299 | 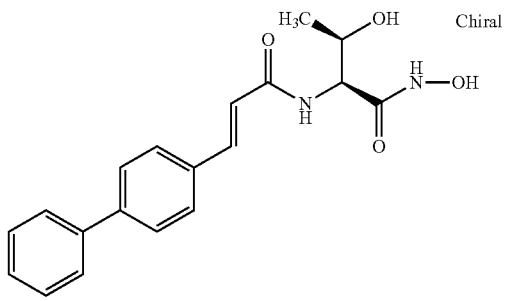 |
| 300 | 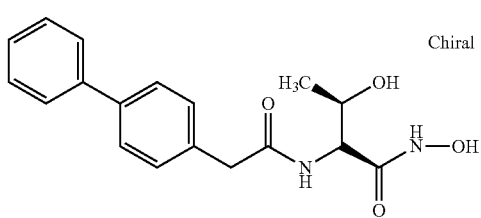 |

TABLE 1-continued
301 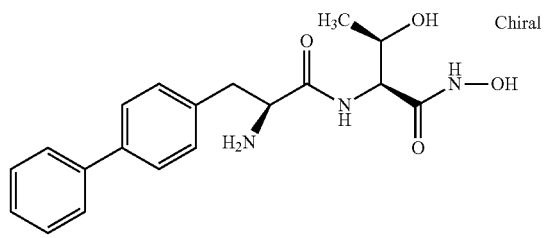
302 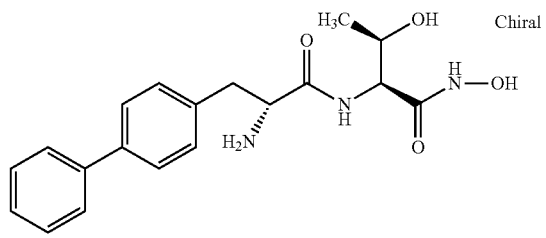
303 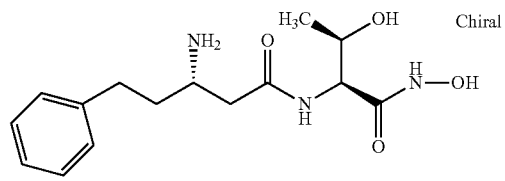
304 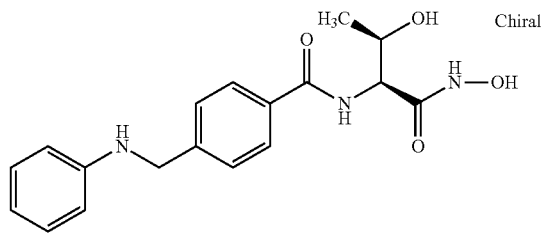
305 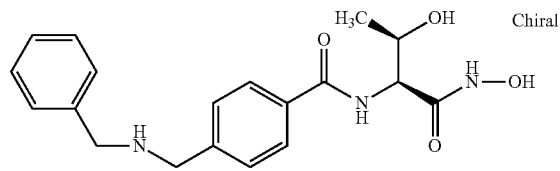
306 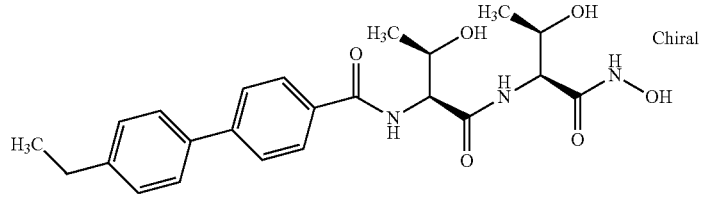
307 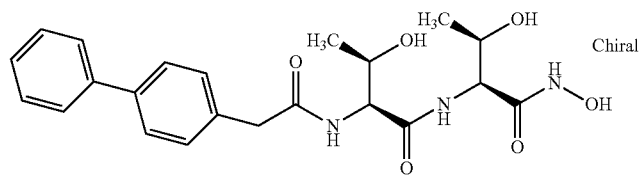

TABLE 1-continued
| | | |
|---|---|---|
| 308 | 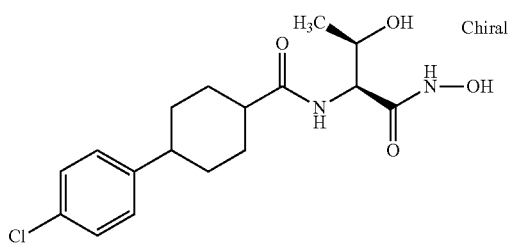 | Chiral |
| 309 | 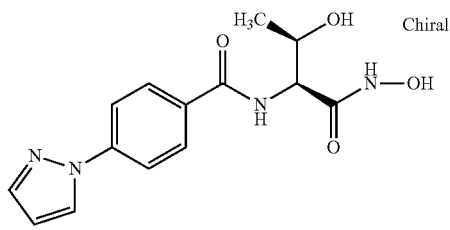 | Chiral |
| 310 | 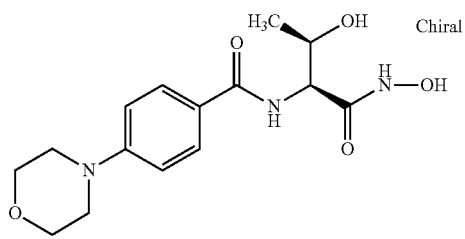 | Chiral |
| 311 | 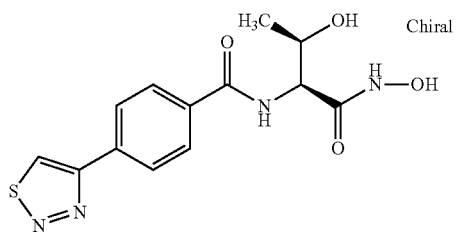 | Chiral |
| 312 | 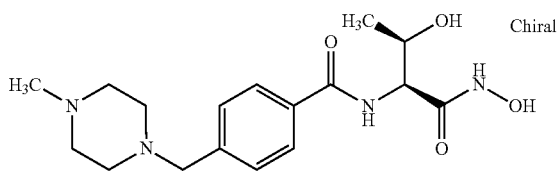 | Chiral |
| 313 | 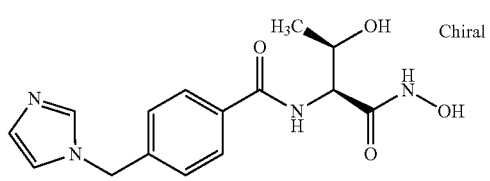 | Chiral |
| 314 | 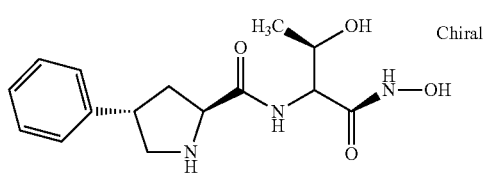 | Chiral |

TABLE 1-continued
| 315 | 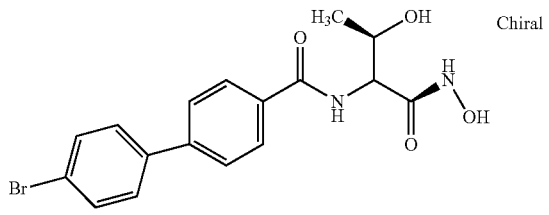 |
| 316 | 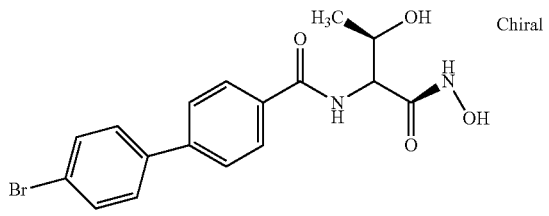 |
| 317 | 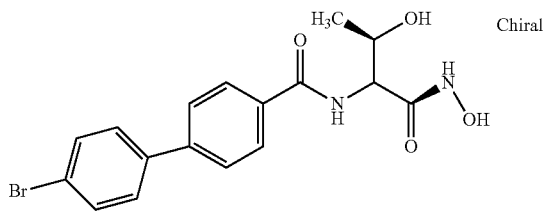 |
| 318 | 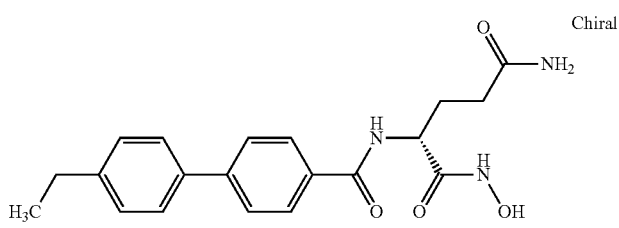 |
| 319 | 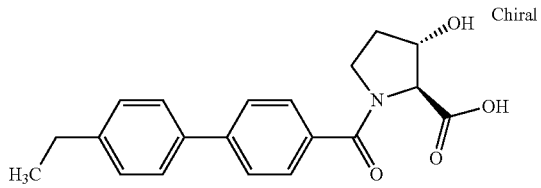 |
| 320 | 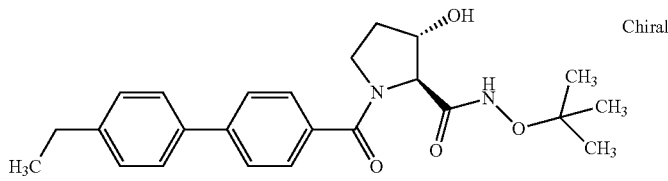 |
| 321 | 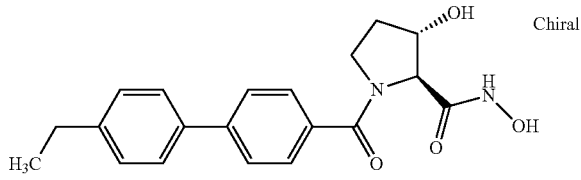 |

TABLE 1-continued
322 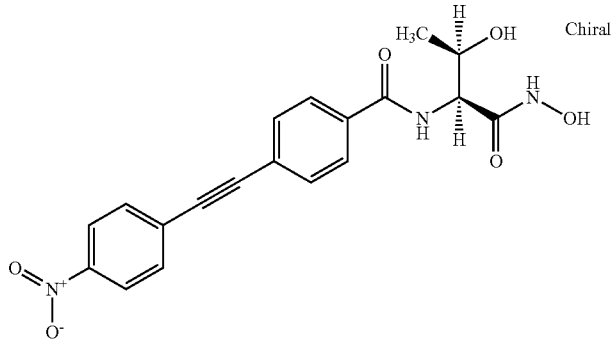
323 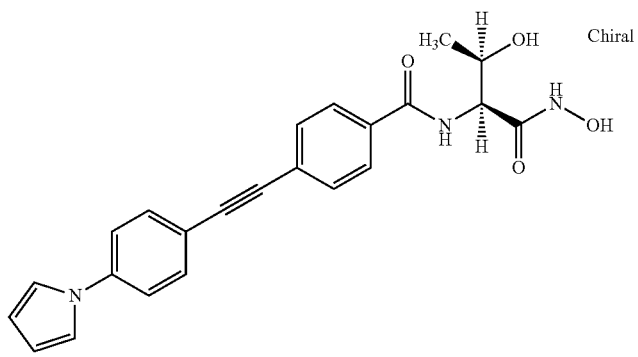
324 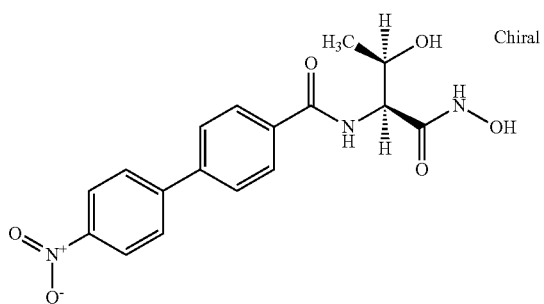
325 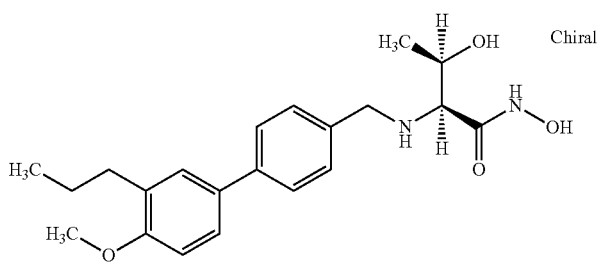
326 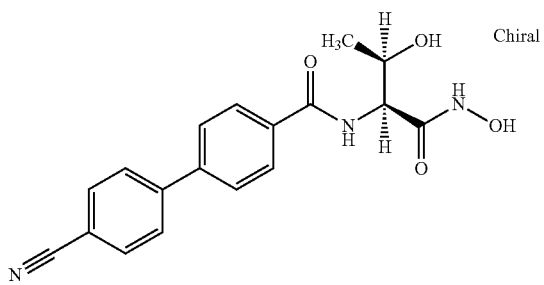

TABLE 1-continued
| 327 | 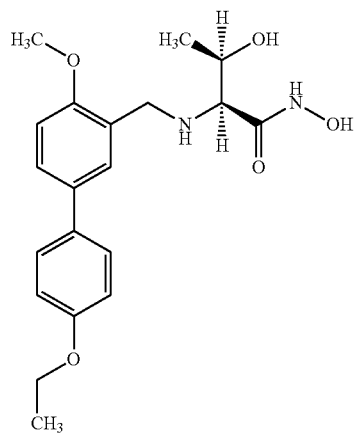 |
| 328 | 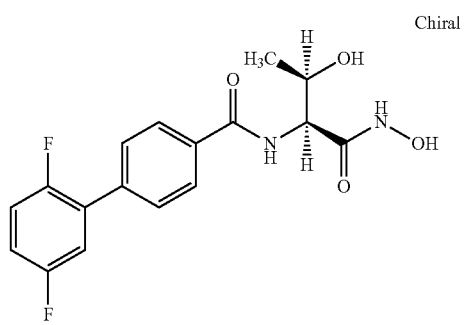 |
| 329 | 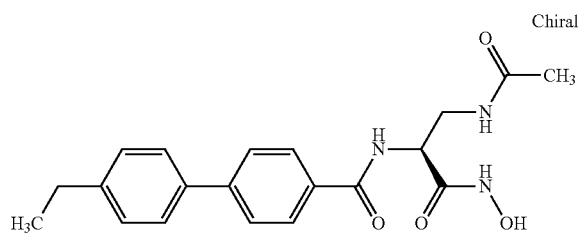 |
| 330 | 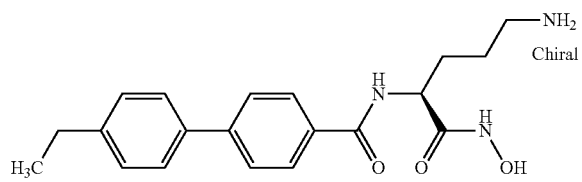 |
| 331 | 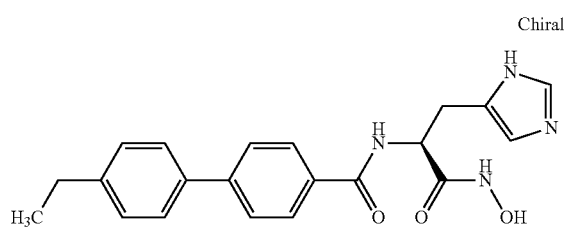 |

TABLE 1-continued
| | | |
|---|---|---|
| 332 | 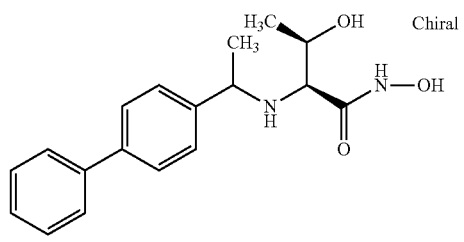 | Chiral |
| 333 | 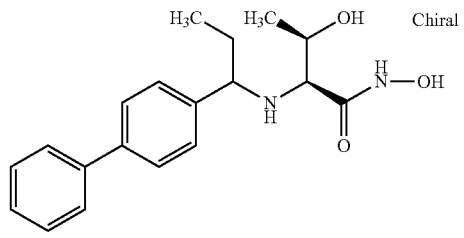 | Chiral |
| 334 | 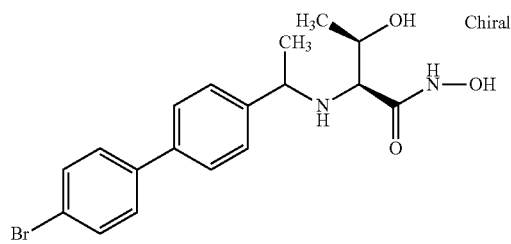 | Chiral |
| 335 | 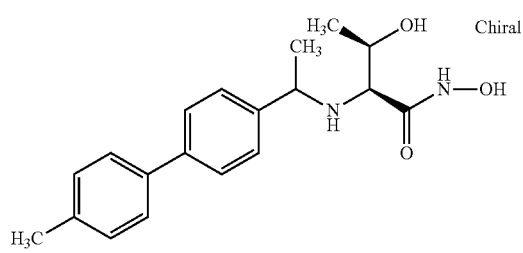 | Chiral |
| 336 | 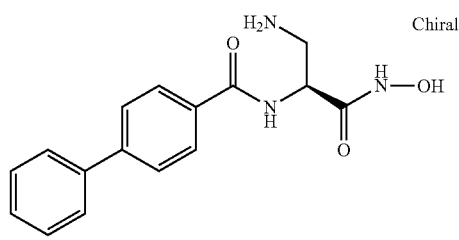 | Chiral |
| 337 | 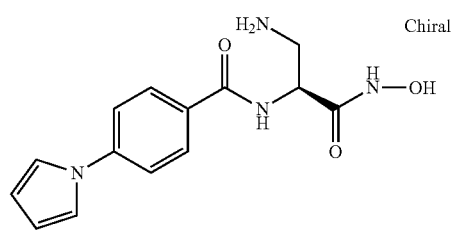 | Chiral |

TABLE 1-continued
| 338 | 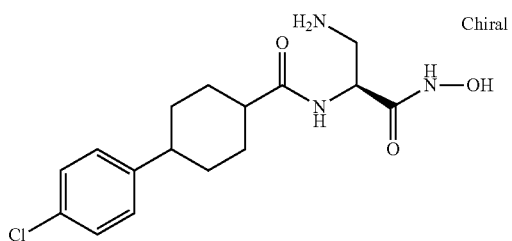 |
| 339 | 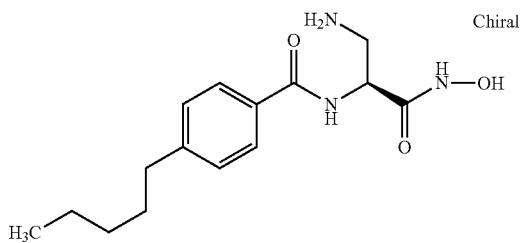 |
| 340 | 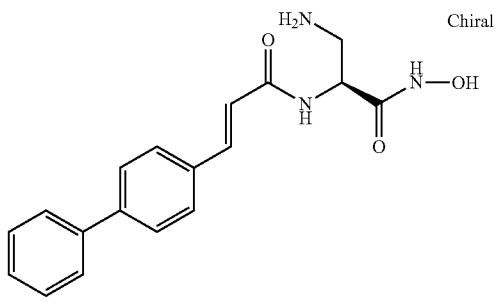 |
| 341 | 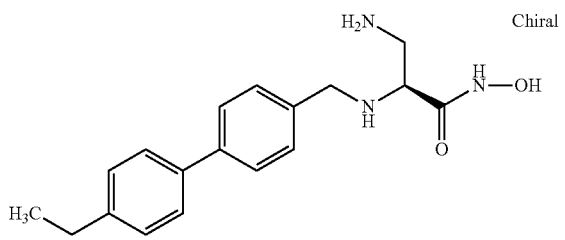 |
| 342 | 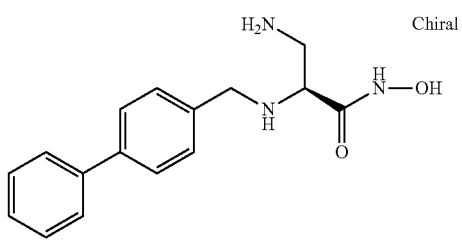 |
| 343 | 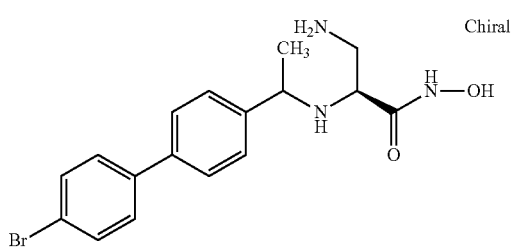 |

TABLE 1-continued
344 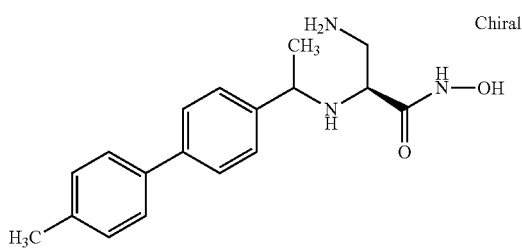
345 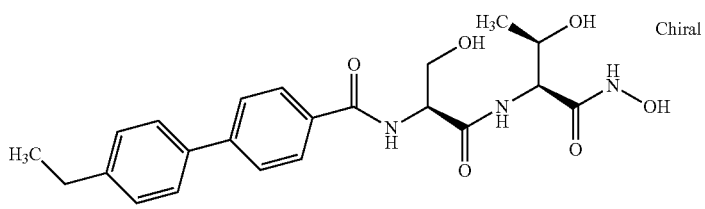
346 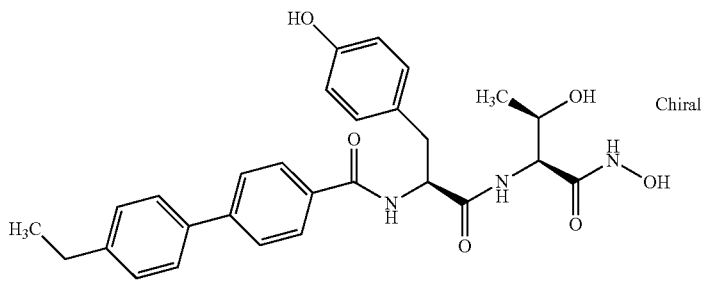
347 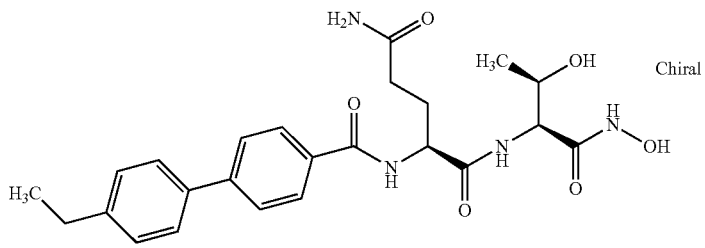
348 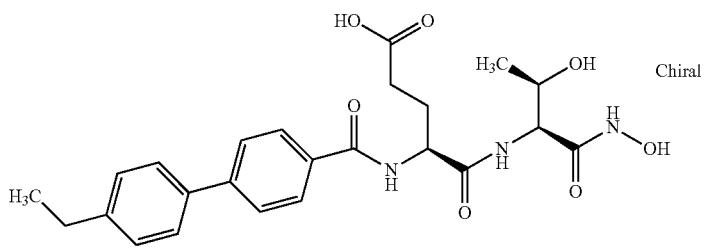
349 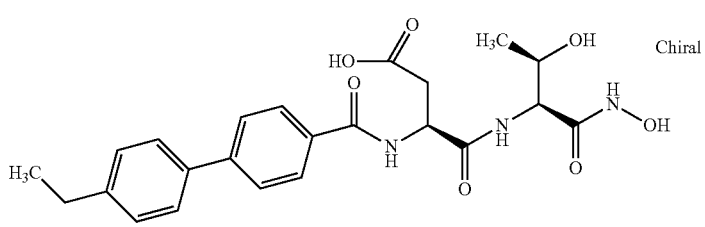

TABLE 1-continued

TABLE 1-continued
| 357 | 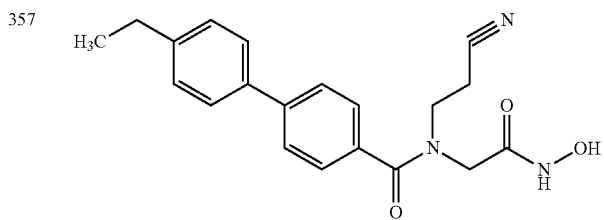 |
| 358 | 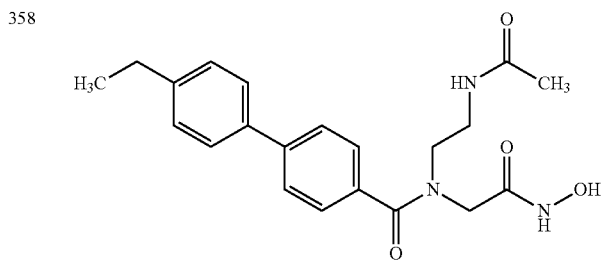 |
| 359 | 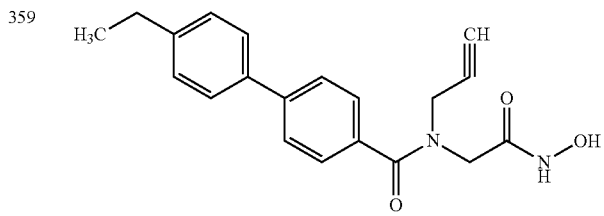 |
| 360 | 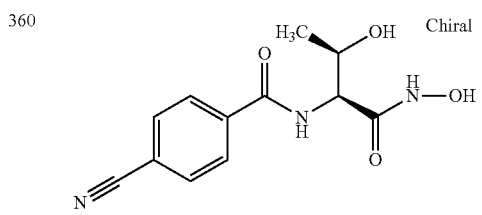 |
| 361 | 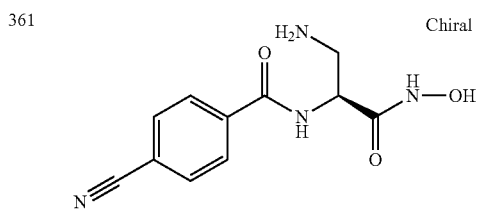 |
| 362 | 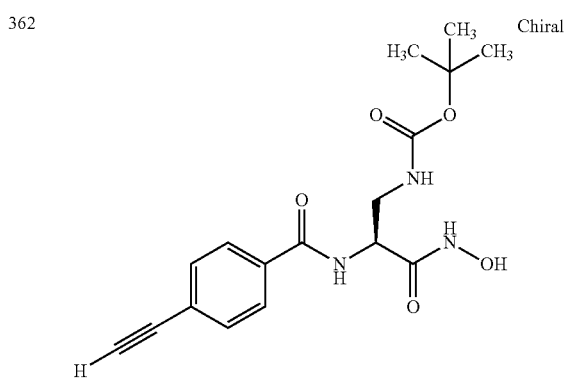 |

TABLE 1-continued
| 363 | 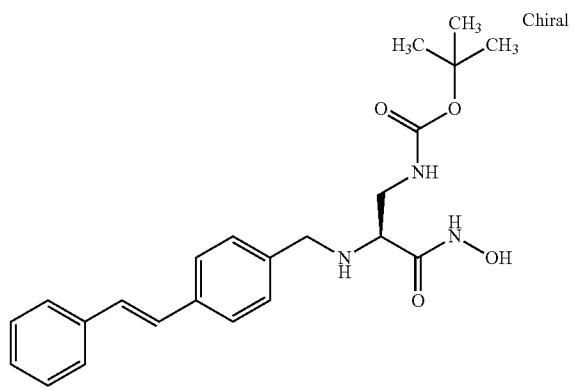 |
| --- | --- |
| 364 | 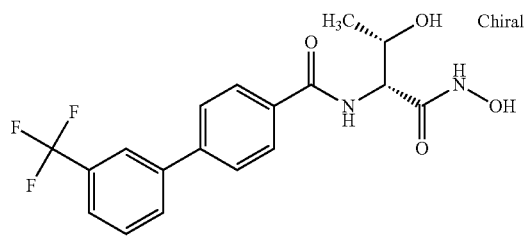 |
| 365 | 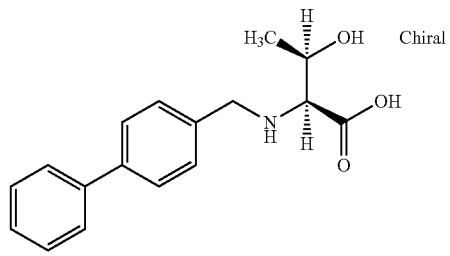 |
| 366 | 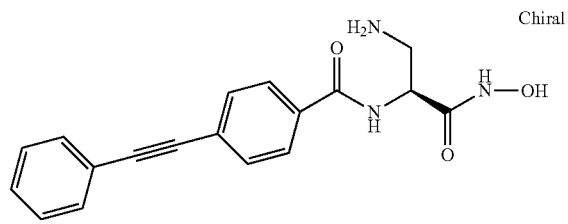 |
| 367 | 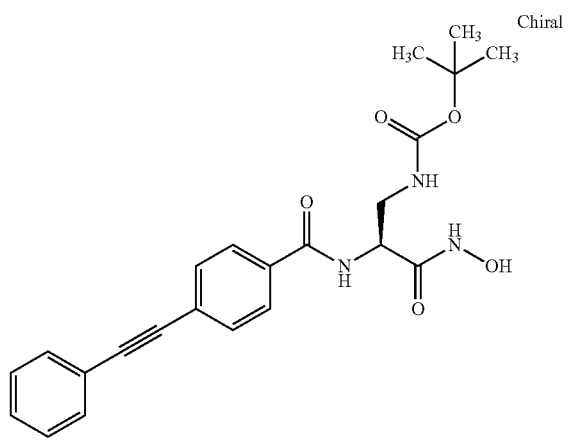 |

TABLE 1-continued
| 368 | 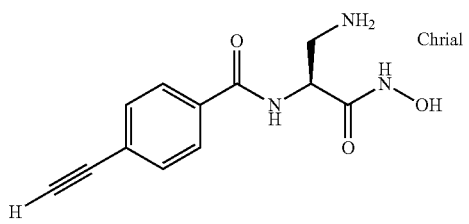 |
| 369 | 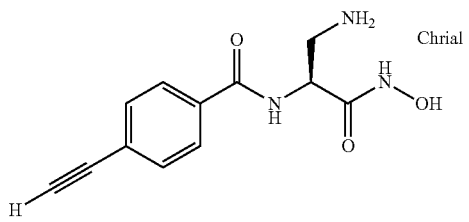 |
| 370 | 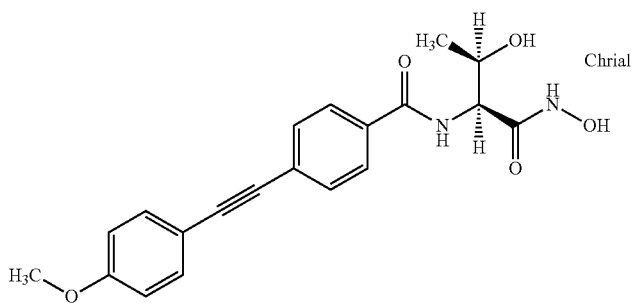 |
| 371 | 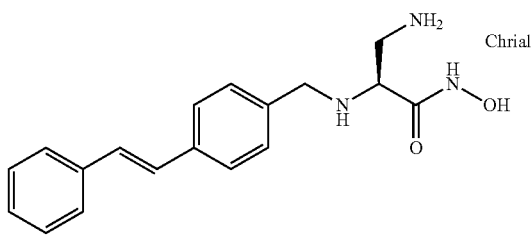 |
| 372 | 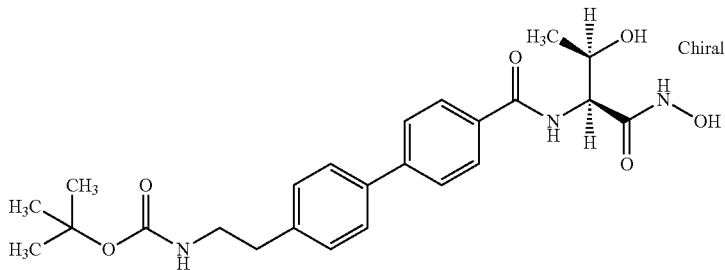 |
| 373 | 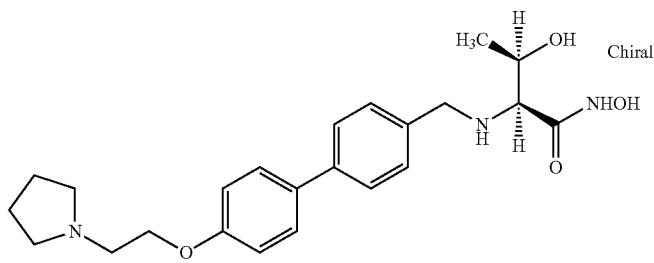 |

TABLE 1-continued
| 374 | 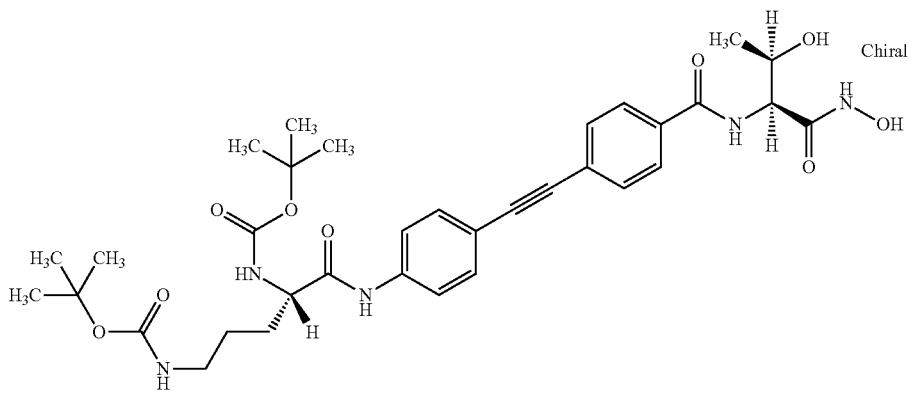 |
| 375 | 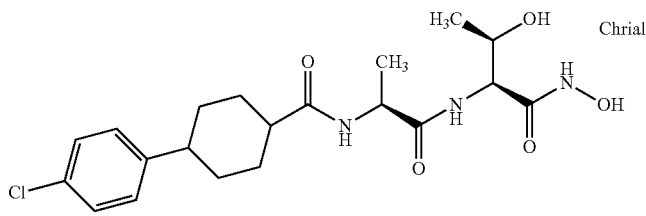 |
| 376 | 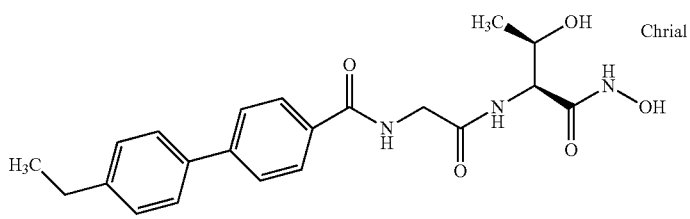 |
| 377 | 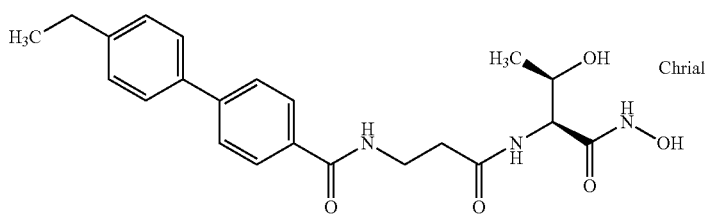 |
| 378 | 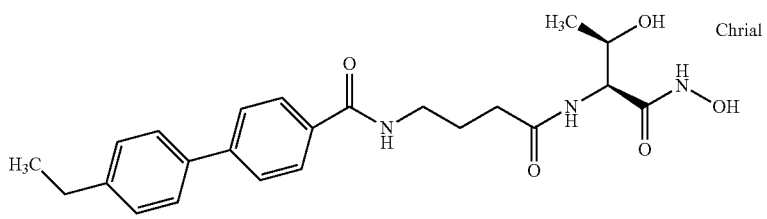 |
| 379 | 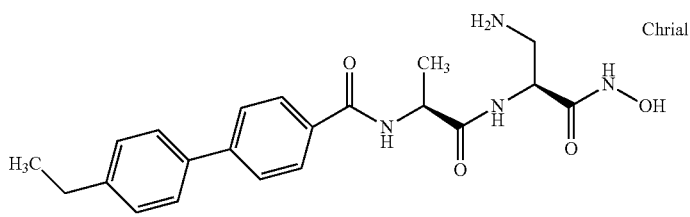 |

TABLE 1-continued
| 380 | 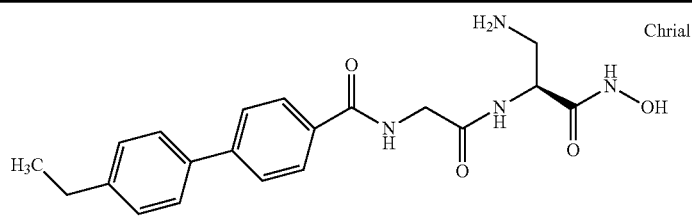 |
| --- | --- |
| 381 | 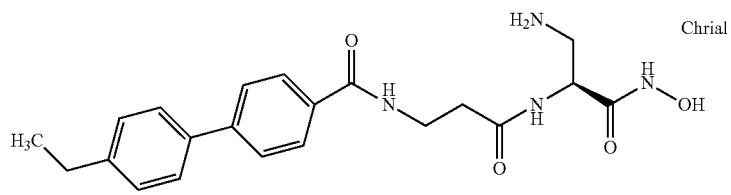 |
| 382 | 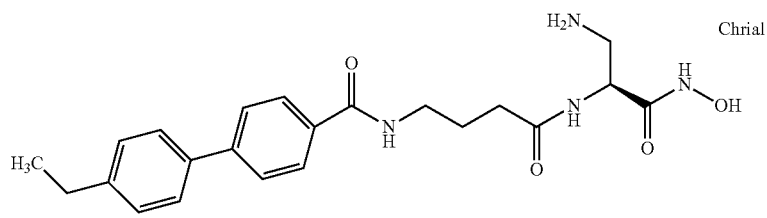 |
| 383 | 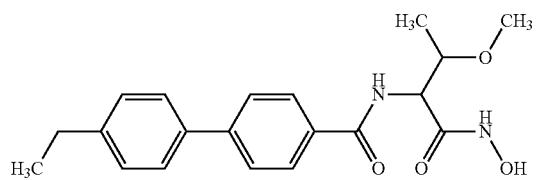 |
| 384 | 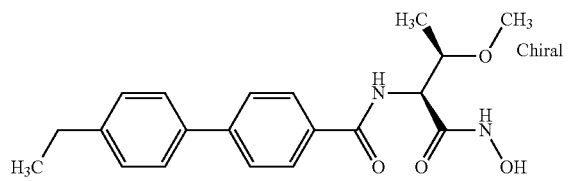 |
| 385 | 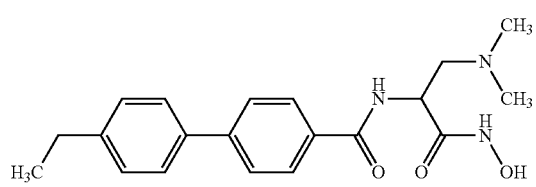 |
| 386 | 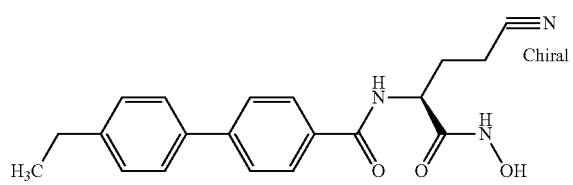 |
| 387 | 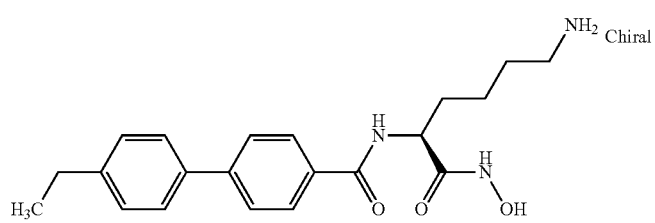 |

TABLE 1-continued
388 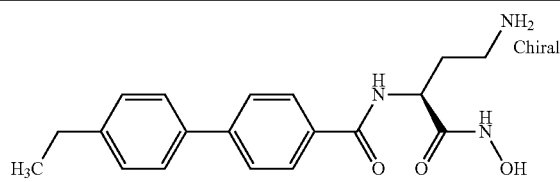
389 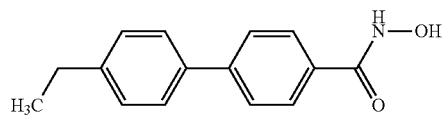
390 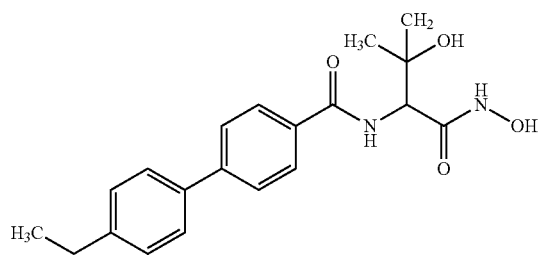
391 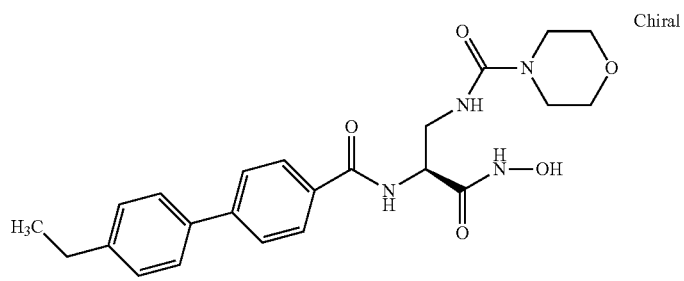
392 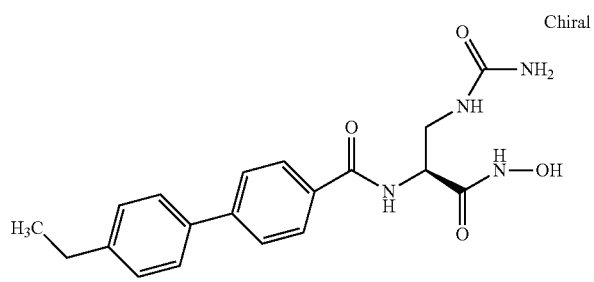
393 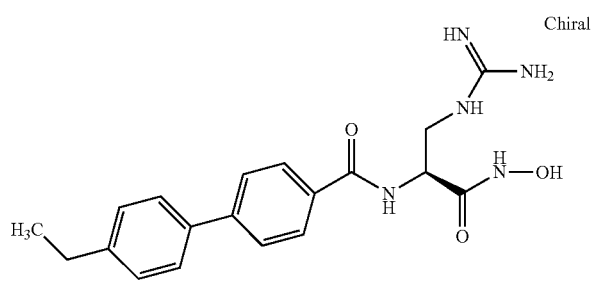
394 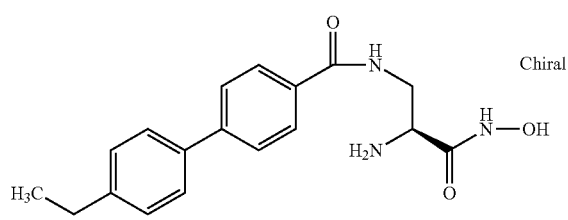

395 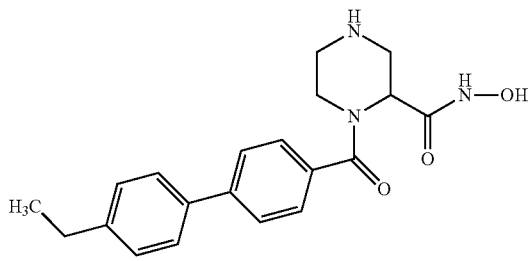
396 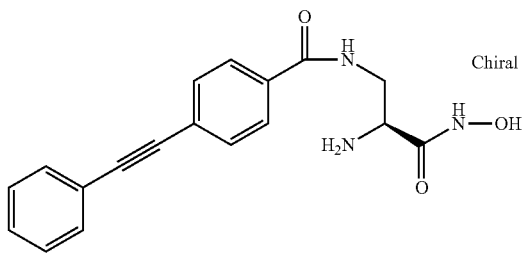
397 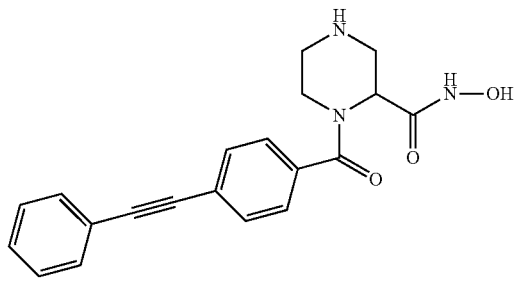
398 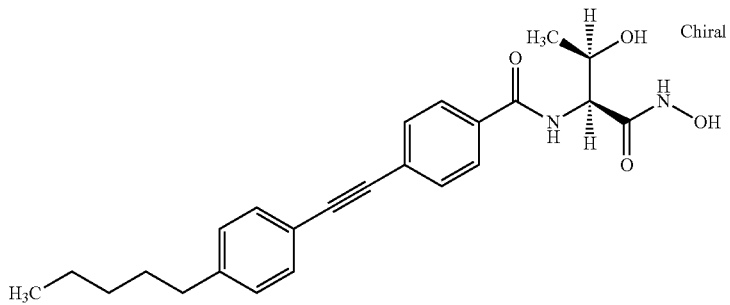
399 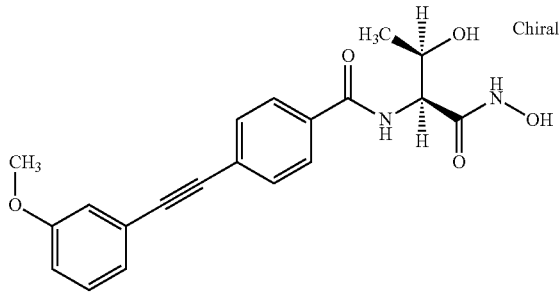

TABLE 1-continued
| 400 | 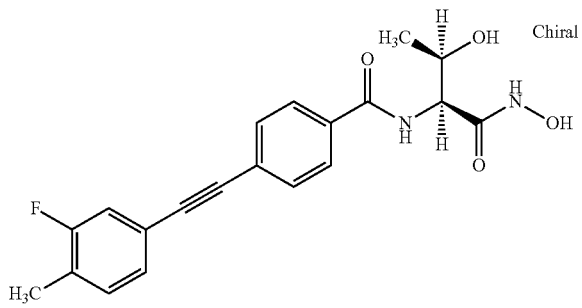 |
| 401 | 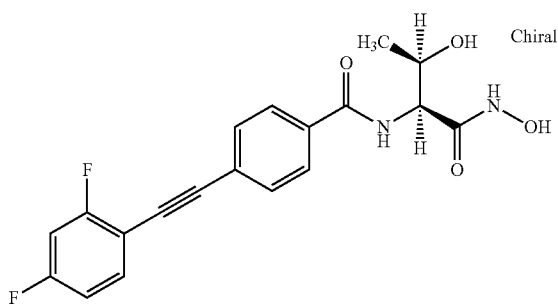 |
| 402 | 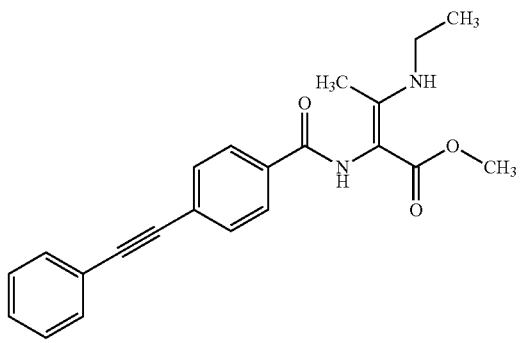 |
| 403 | 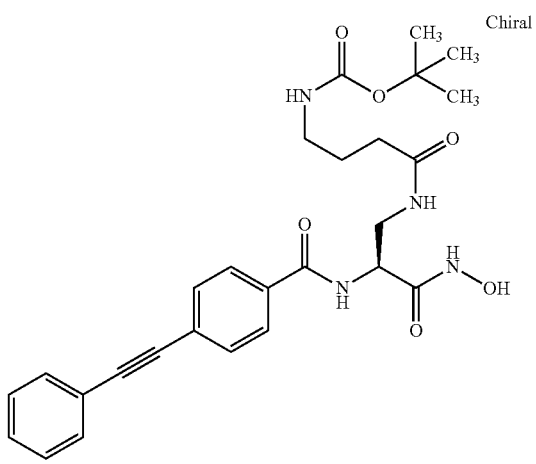 |

TABLE 1-continued
| 404 | 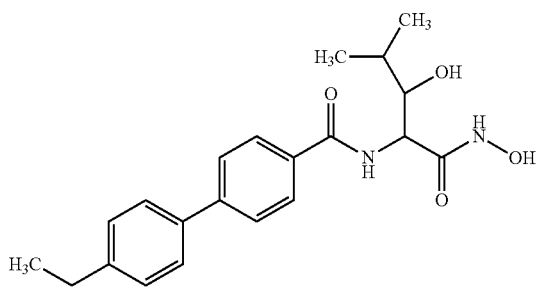 |
| 405 | 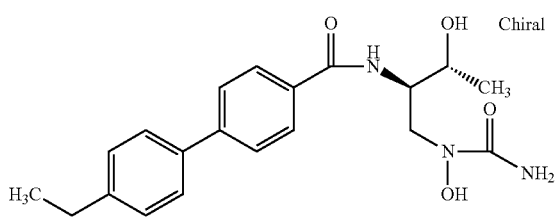 |
| 406 | 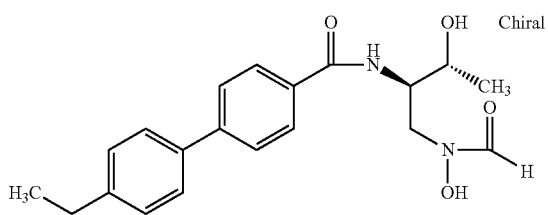 |
| 407 | 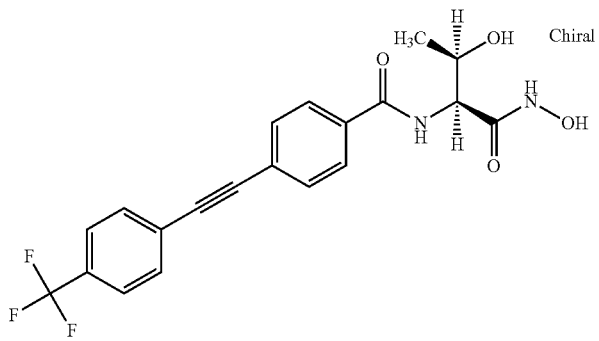 |
| 408 | 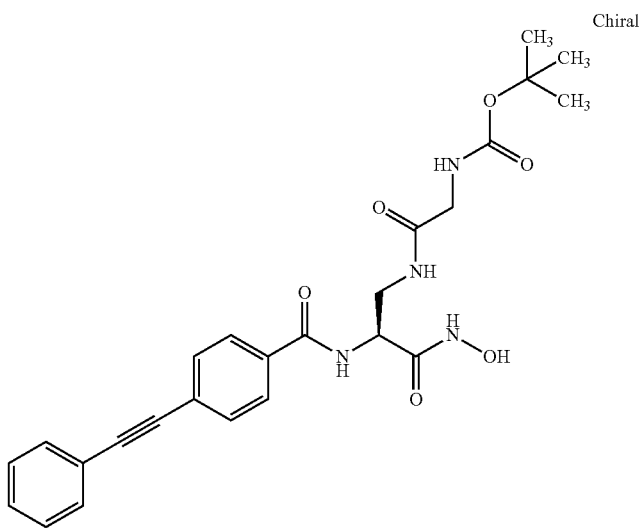 |

TABLE 1-continued
409
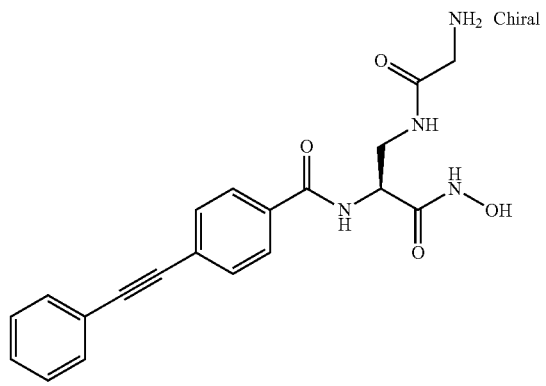
410
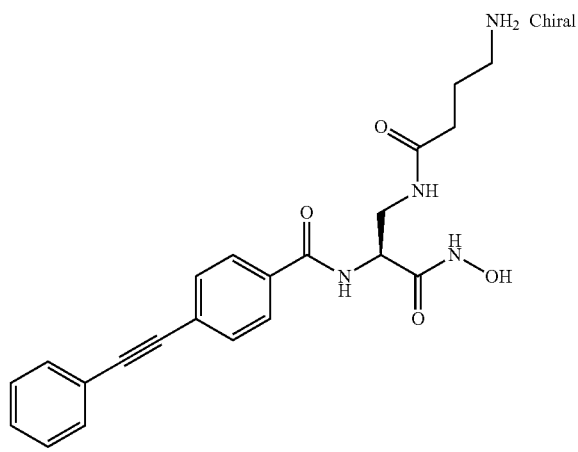
411
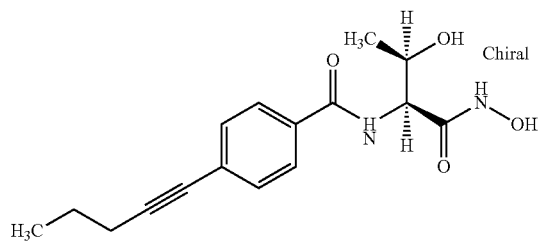
412
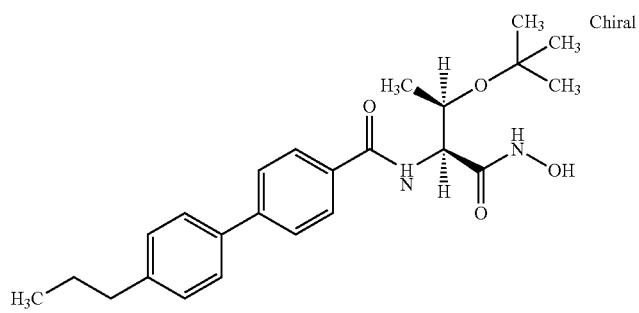

TABLE 1-continued
| 413 | 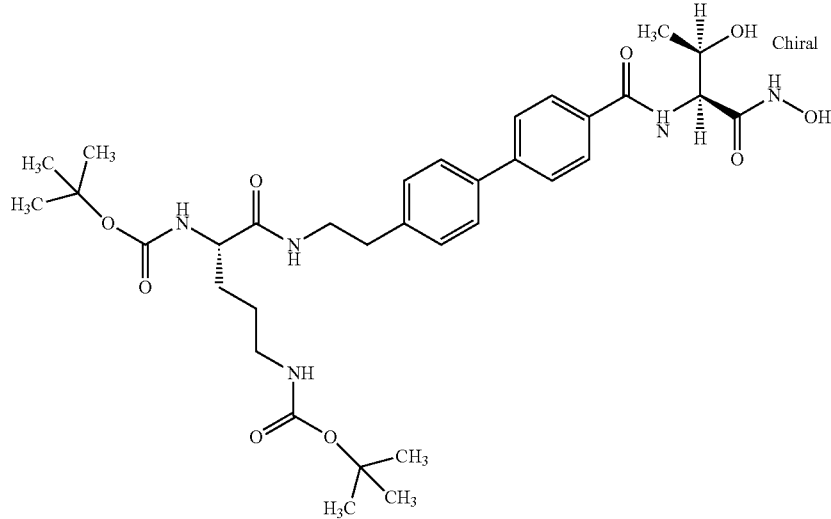 |
| 414 | 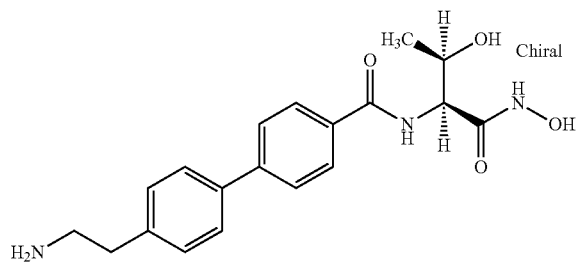 |
| 415 | 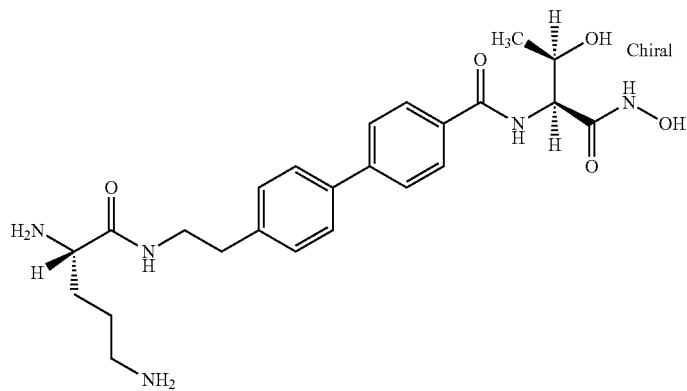 |
| 416 | 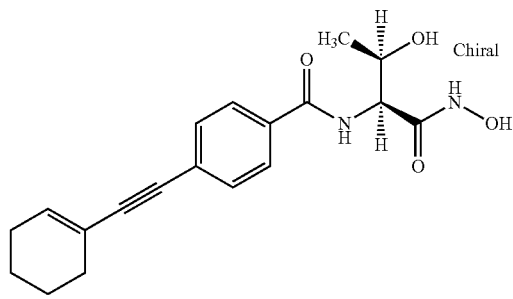 |

TABLE 1-continued
417 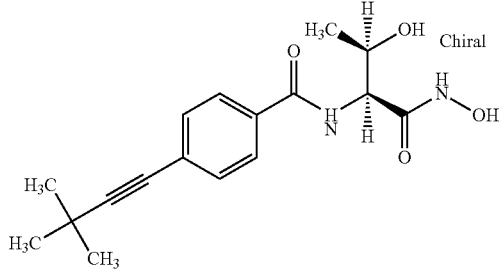
418 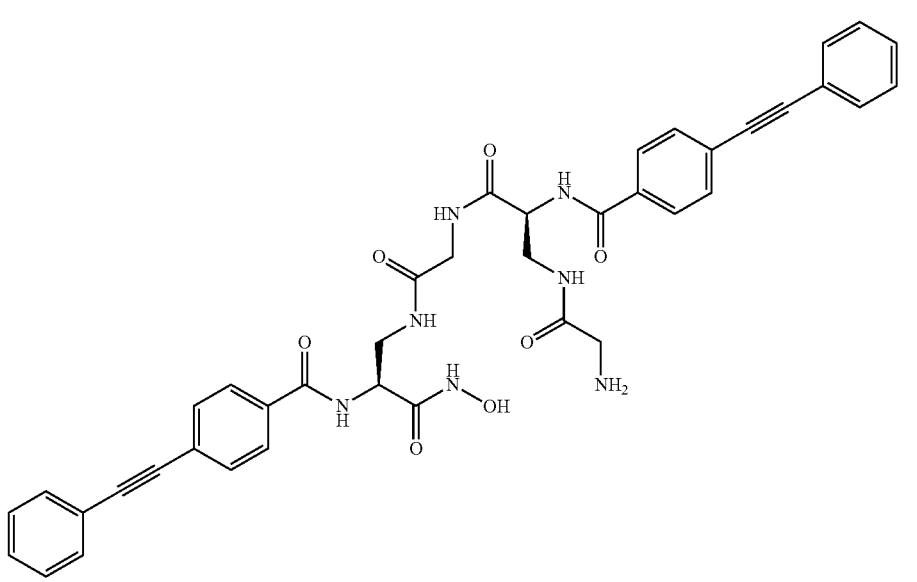
419 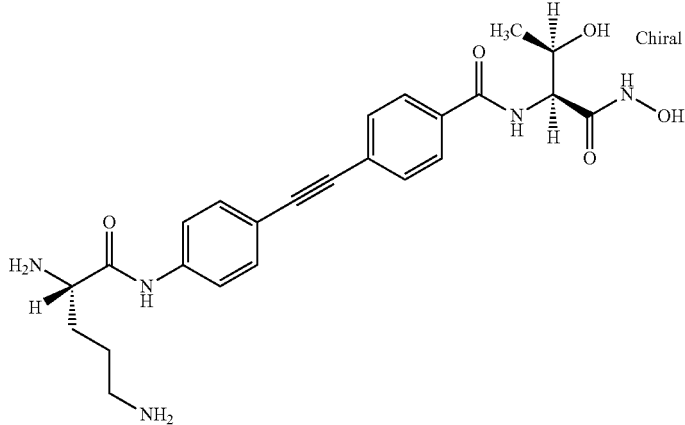
420 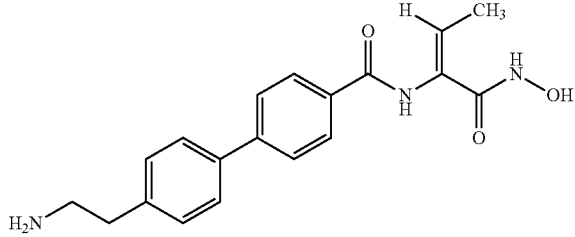

TABLE 1-continued
421
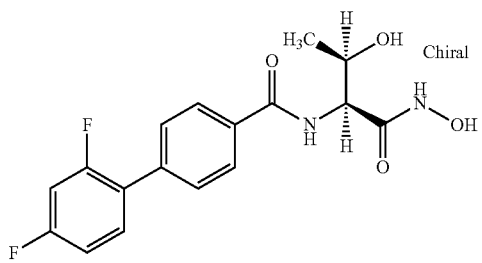
422
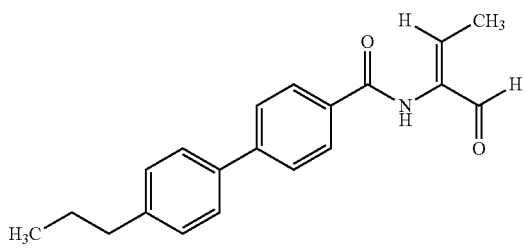
423
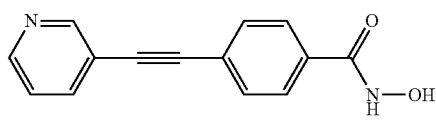
424
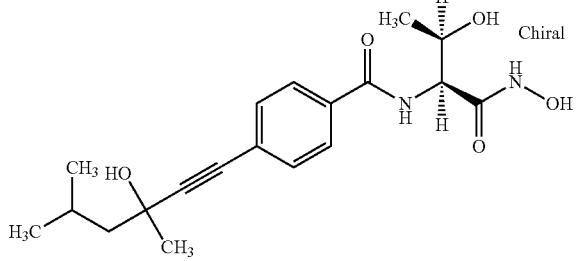
425
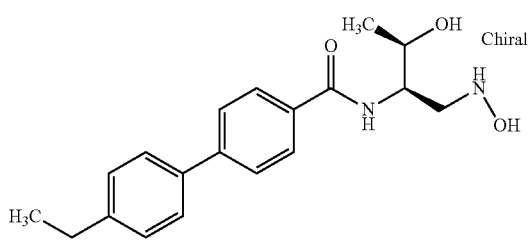
426
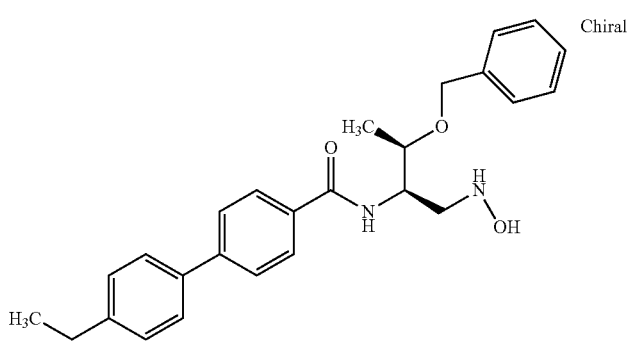

TABLE 1-continued
| 427 | 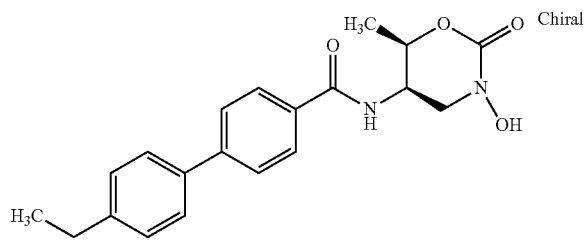 |
| --- | --- |
| 428 | 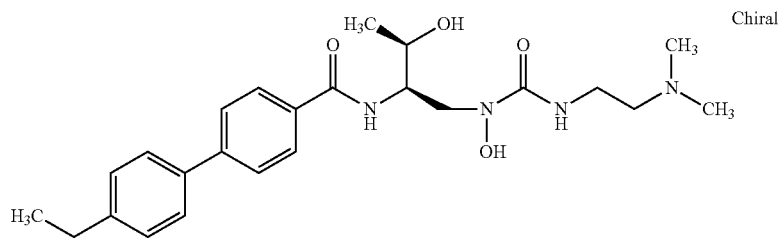 |
| 429 | 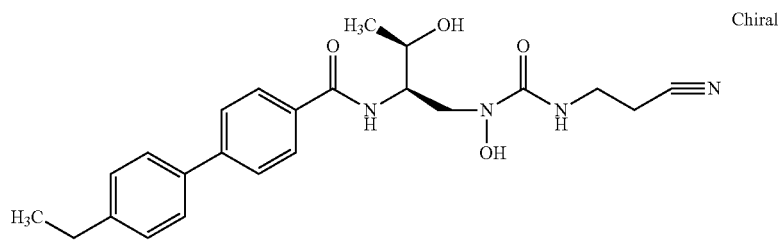 |
| 430 | 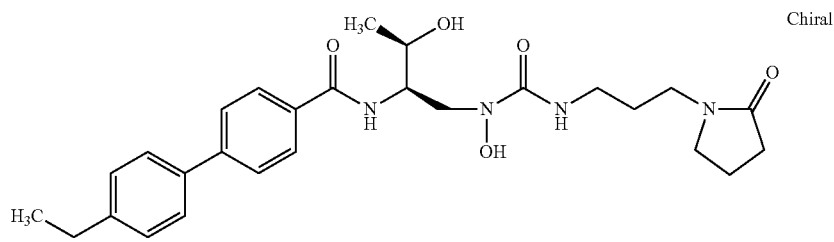 |
| 431 | 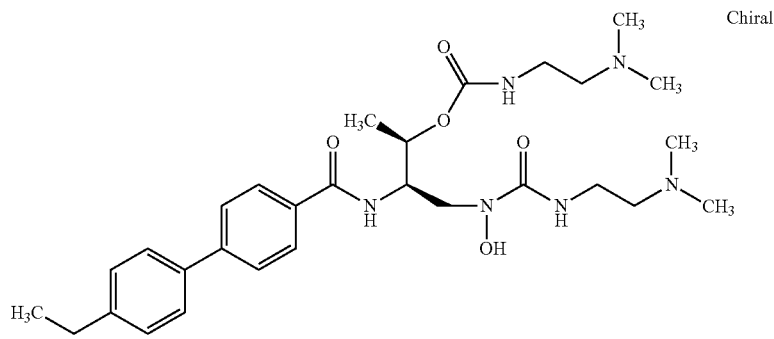 |

TABLE 1-continued
| 432 | 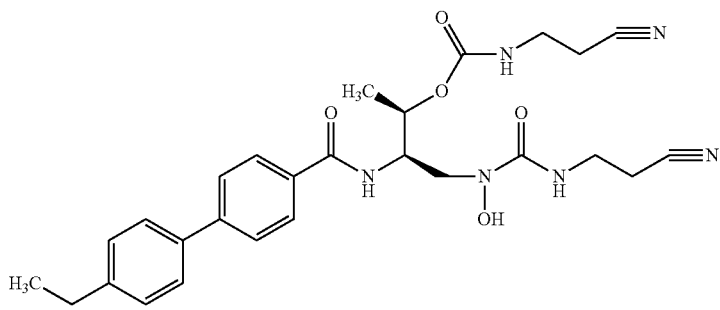 Chiral |
| 433 | 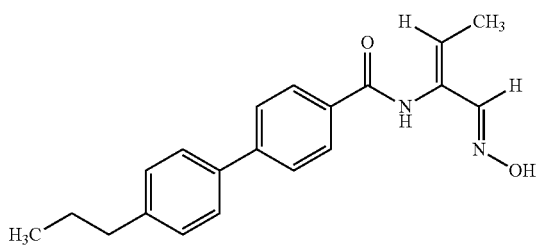 |
| 434 | 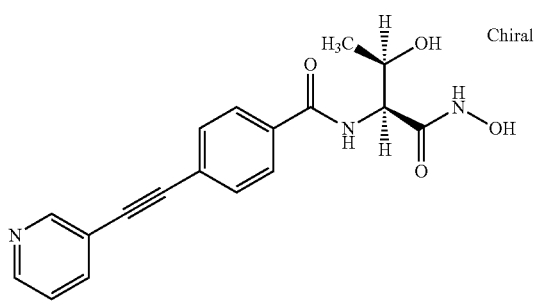 Chiral |
| 435 | 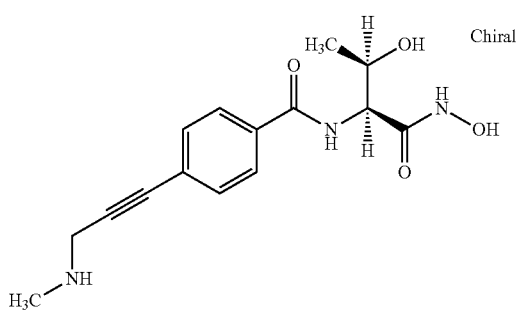 Chiral |
| 436 | 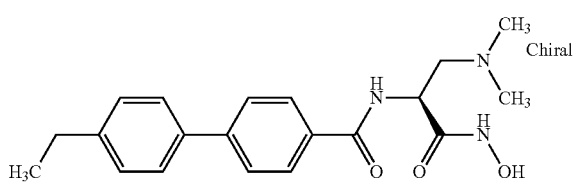 Chiral |
| 437 | 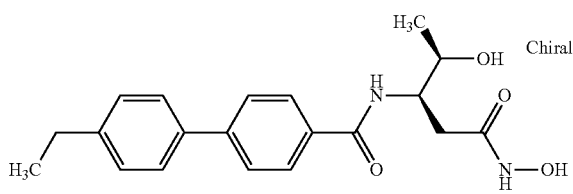 Chiral |

TABLE 1-continued
| 438 | 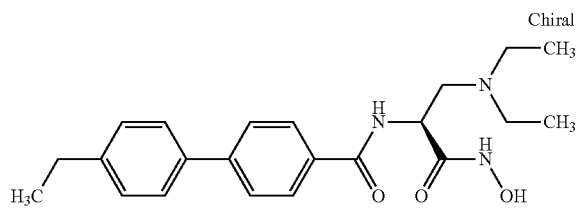 |
| --- | --- |
| 439 | 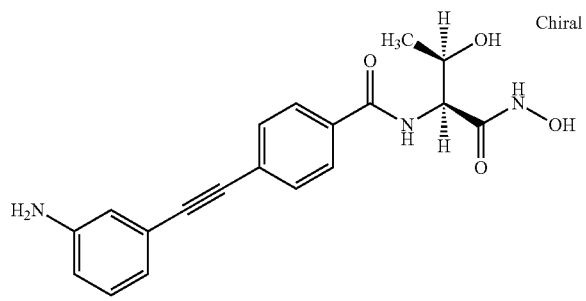 |
| 440 | 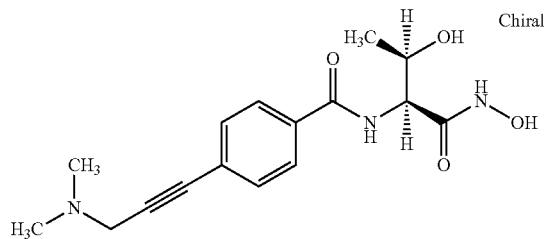 |
| 441 | 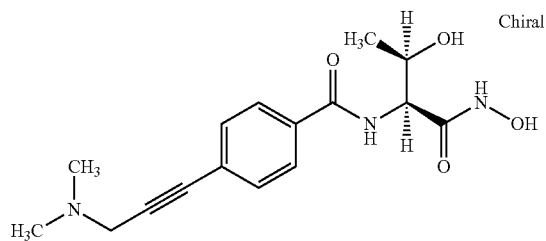 |
| 442 | 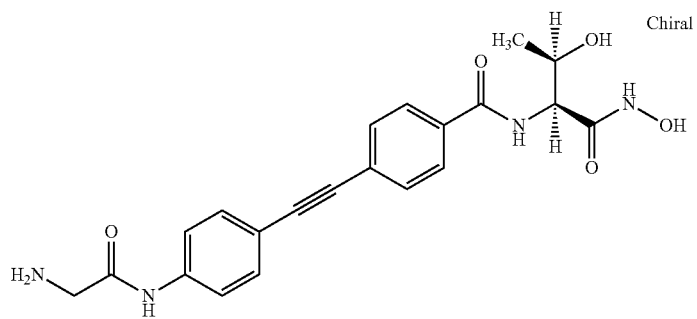 |
| 443 | 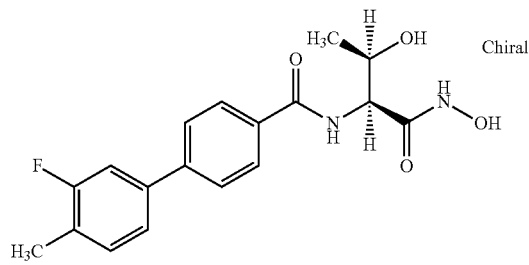 |

TABLE 1-continued
444
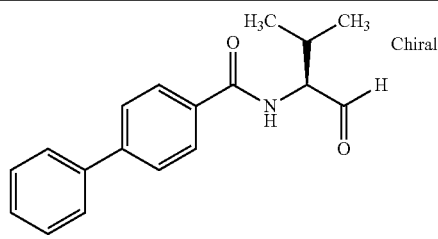
445
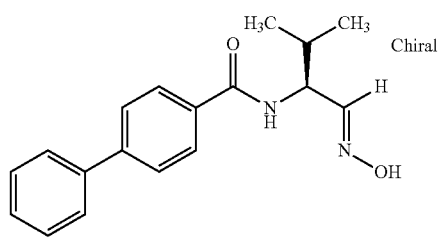
446
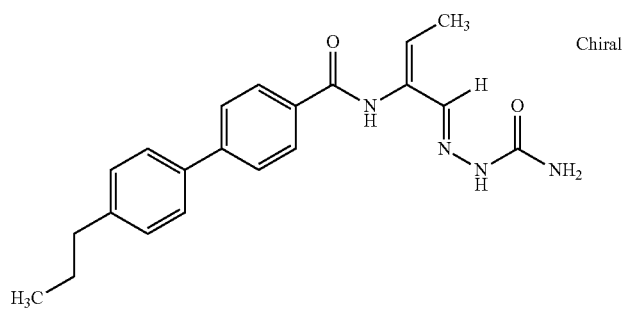
447
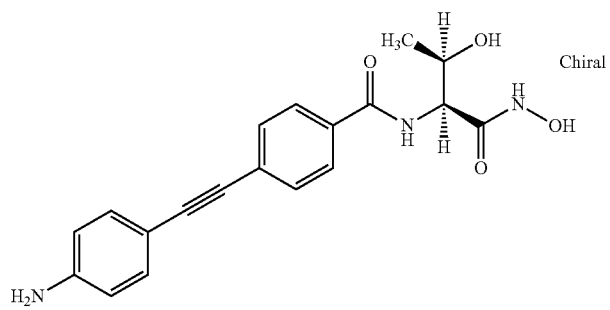
448
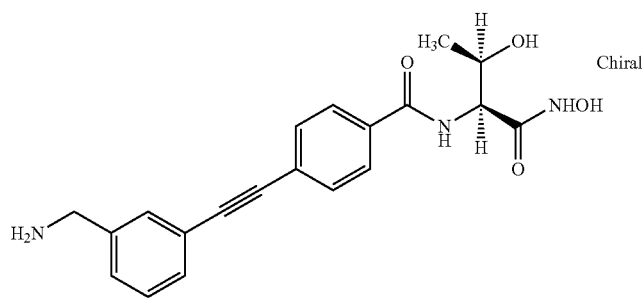

TABLE 1-continued
449
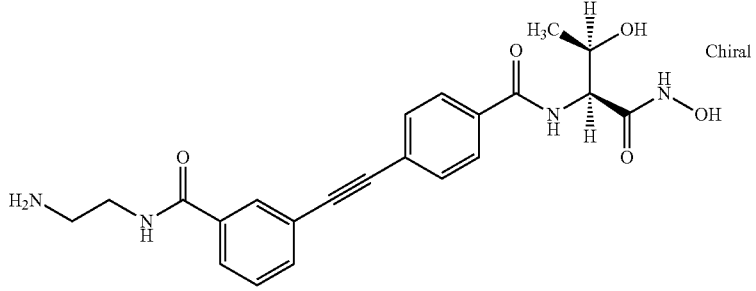
450
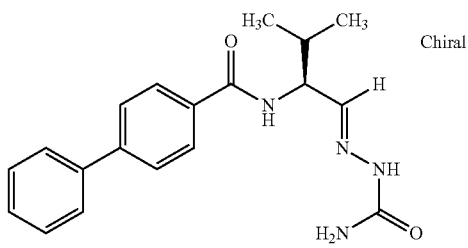
451
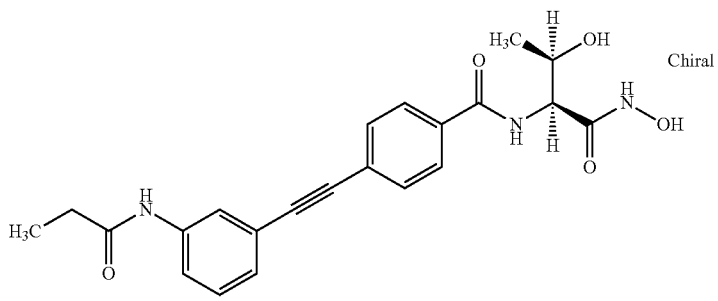
452
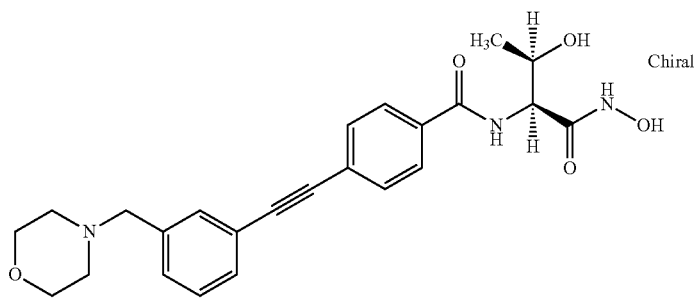
453
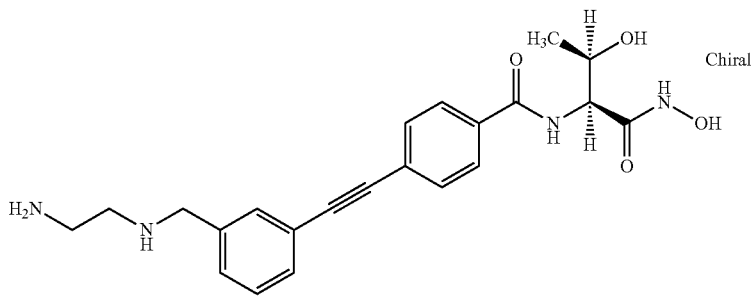

TABLE 1-continued
454 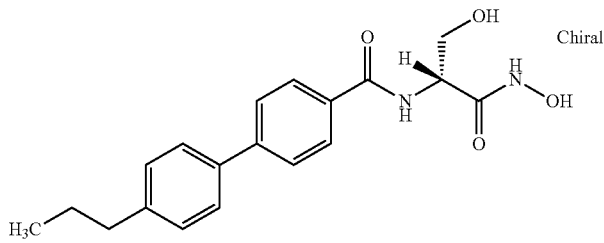
455 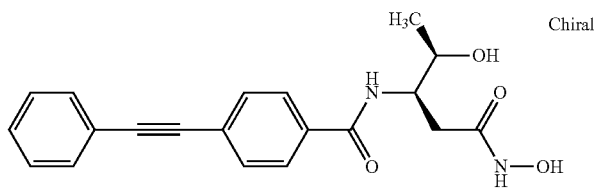
456 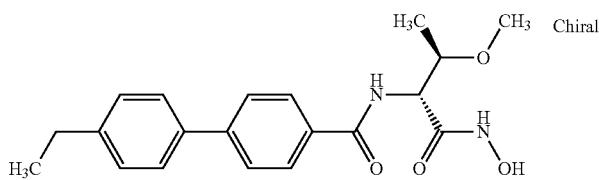
457 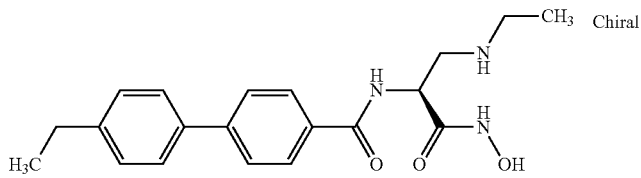
458 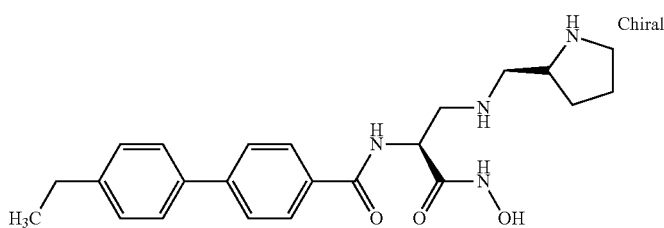
459 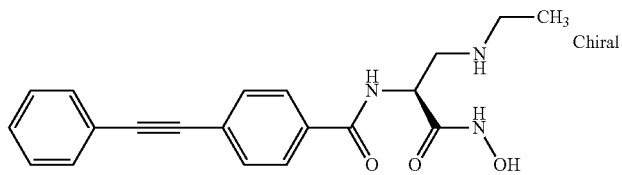
460 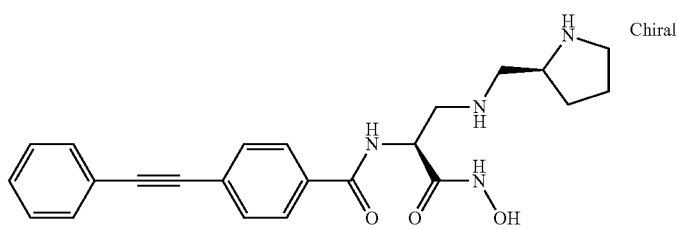

US 8,101,640 B2
327                                                                                                                                 328
TABLE 1-continued
461 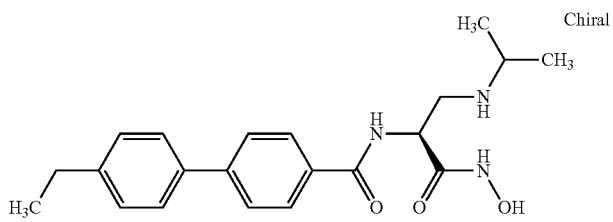
462 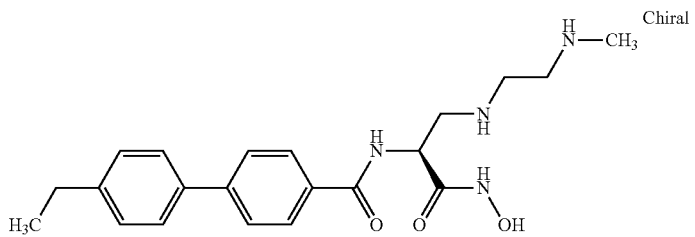
463 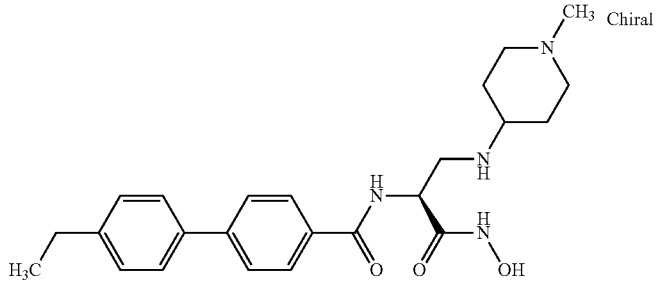
464 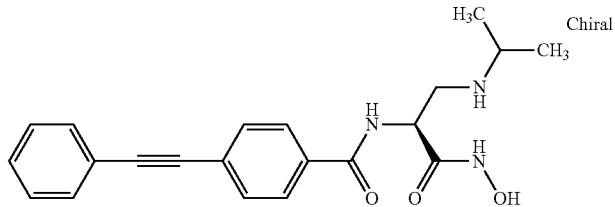
465 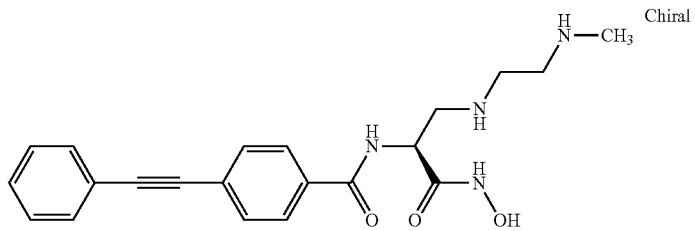
466 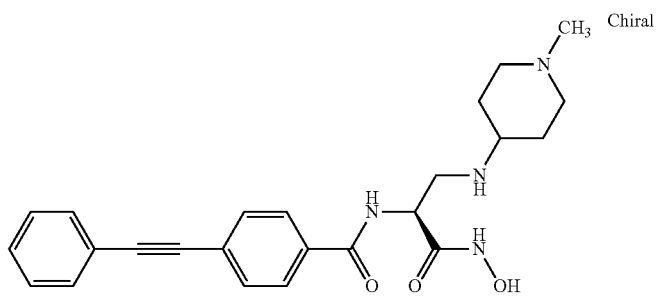

TABLE 1-continued
| 467 | 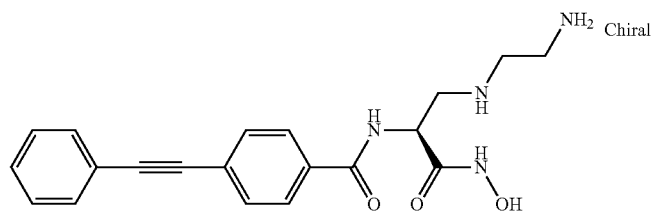 |
| --- | --- |
| 468 | 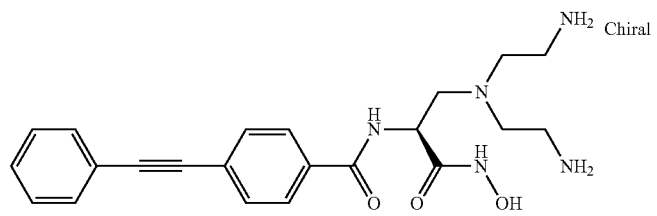 |
| 469 | 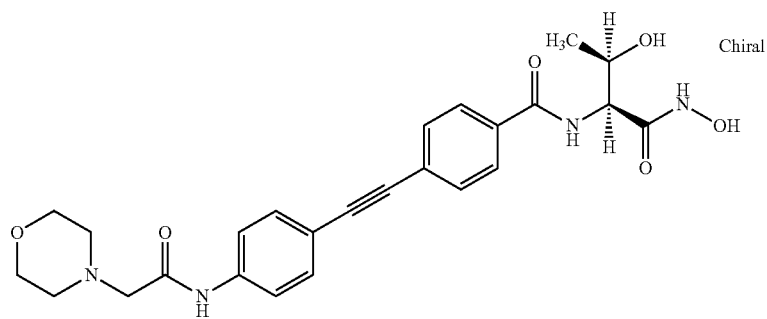 |
| 470 | 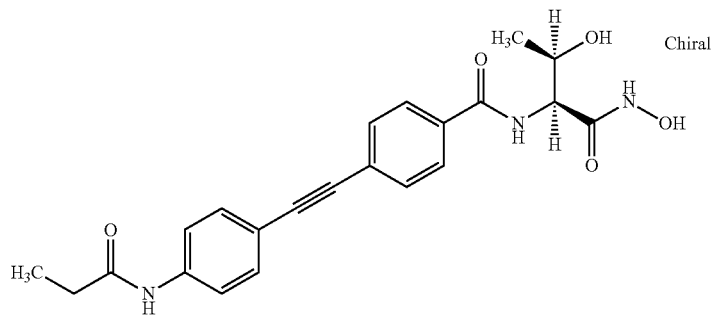 |
| 471 | 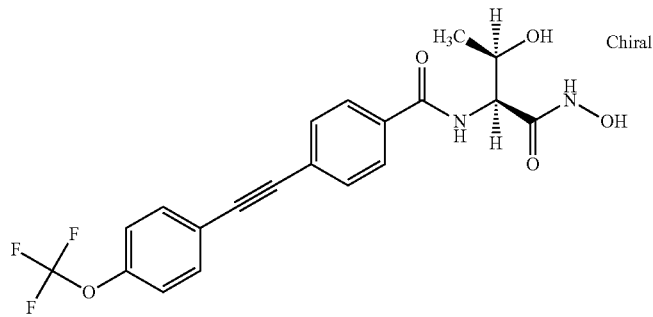 |

TABLE 1-continued
| 472 | 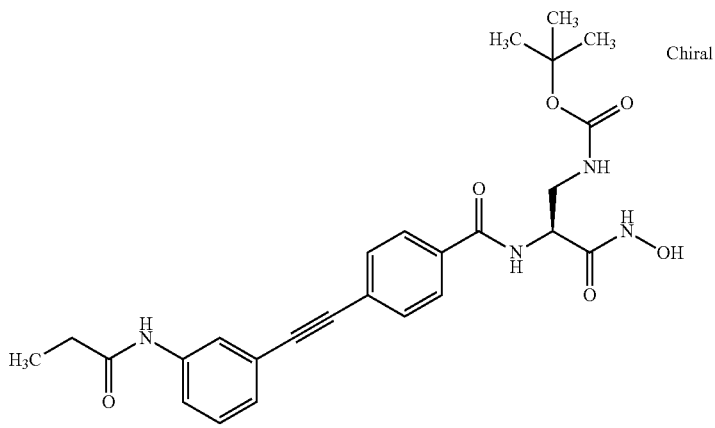 |
| --- | --- |
| 473 | 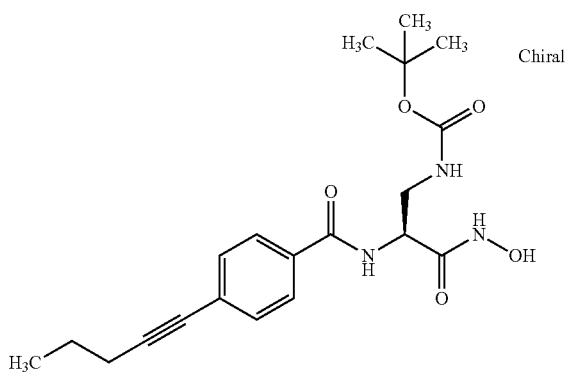 |
| 474 | 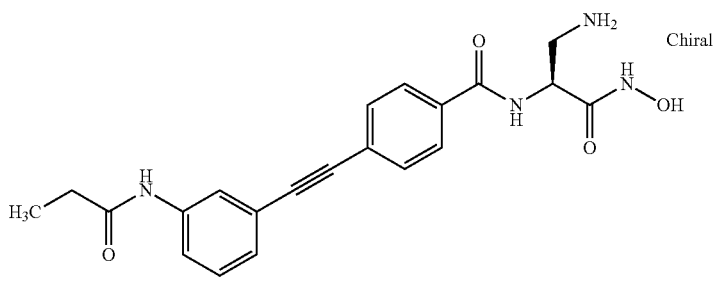 |
| 475 | 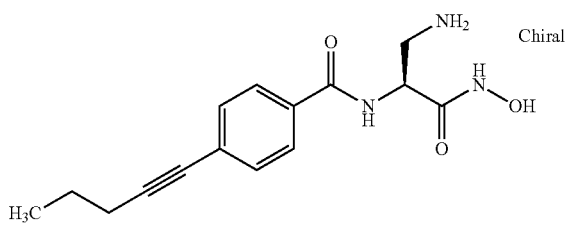 |
| 476 | 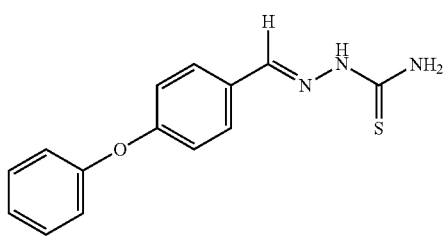 |

TABLE 1-continued
477 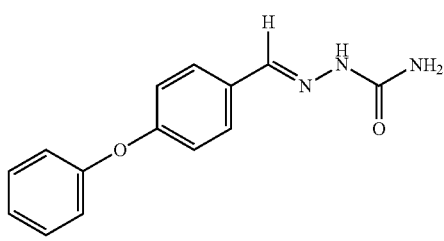
478 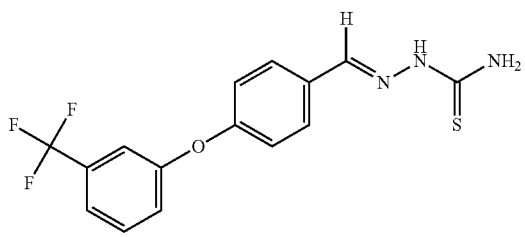
479 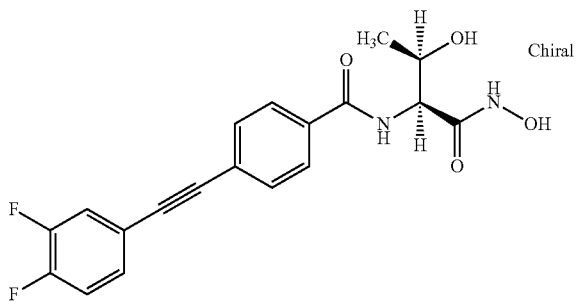
480 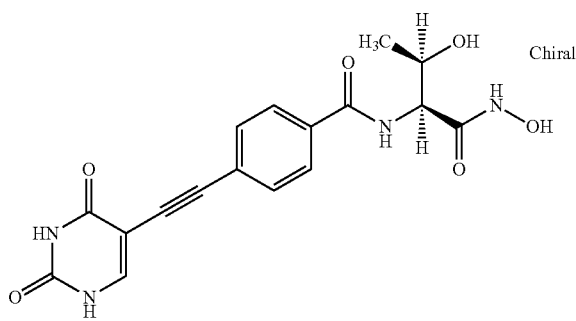
481 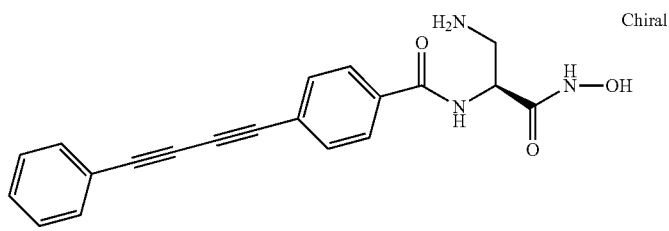
482 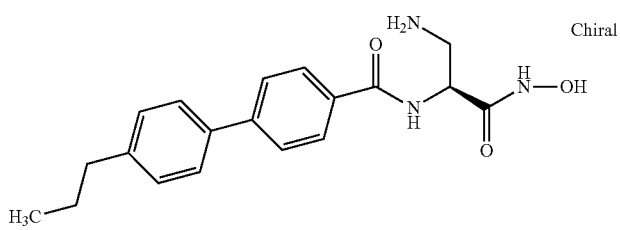

TABLE 1-continued
| 483 | 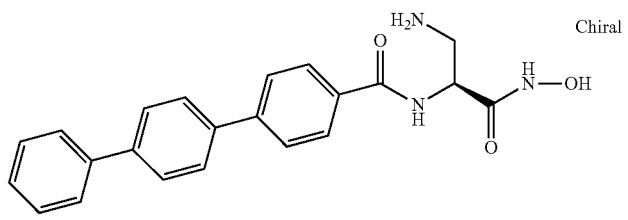 |
| --- | --- |
| 484 | 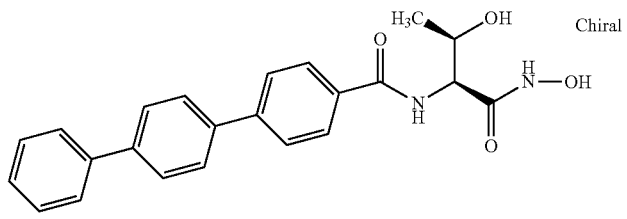 |
| 485 | 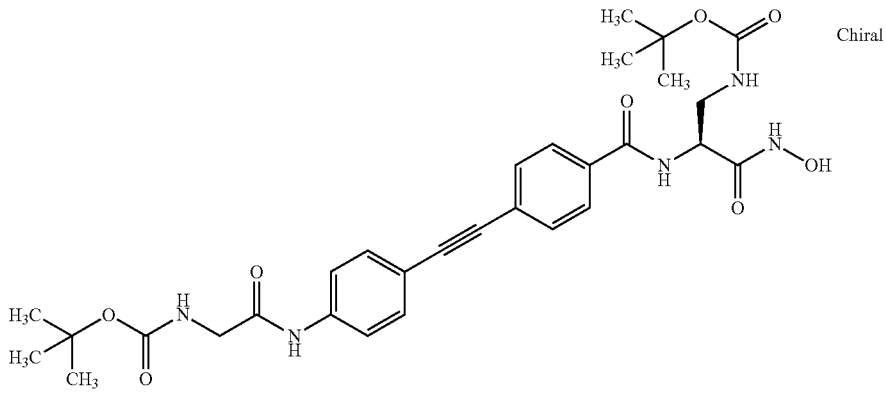 |
| 486 | 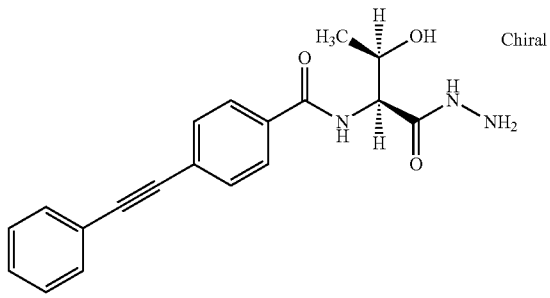 |
| 487 | 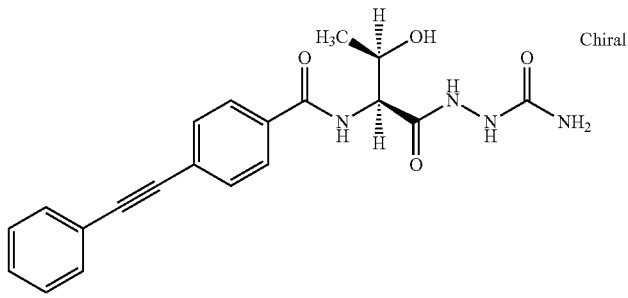 |

TABLE 1-continued
488
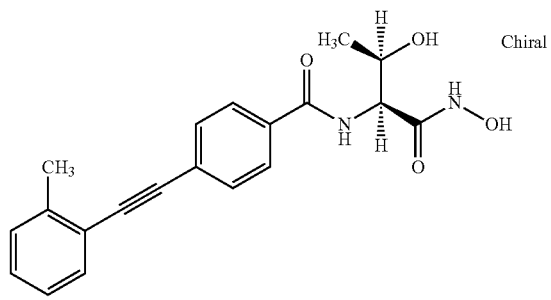
489
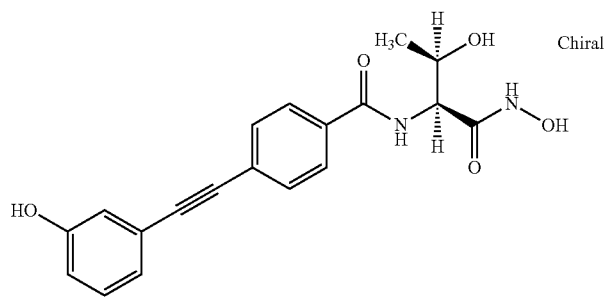
490
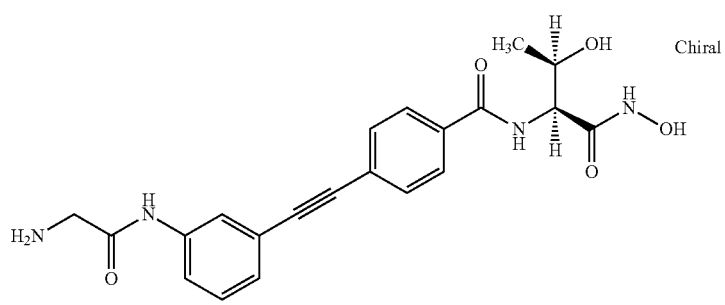
491
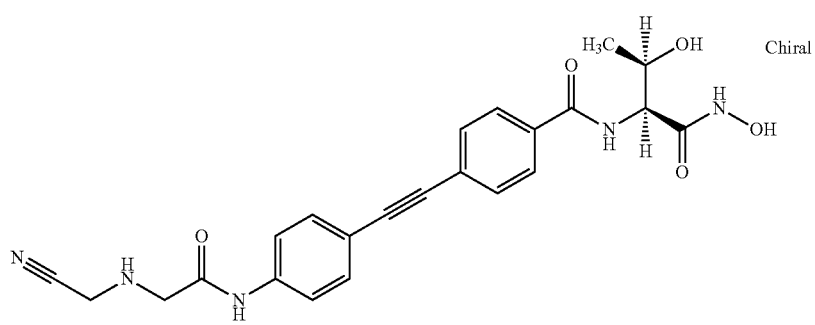
492
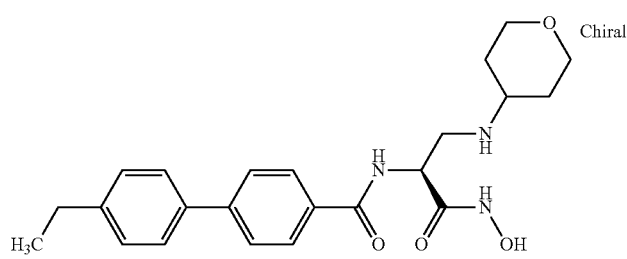

TABLE 1-continued
| 493 | 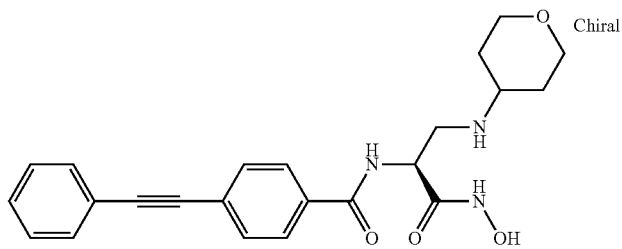 |
| --- | --- |
| 494 | 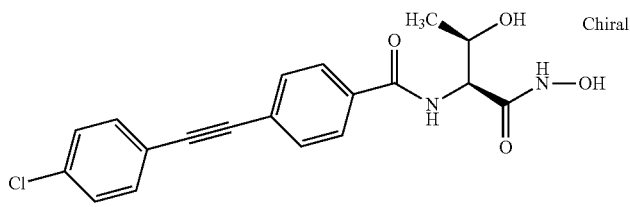 |
| 495 | 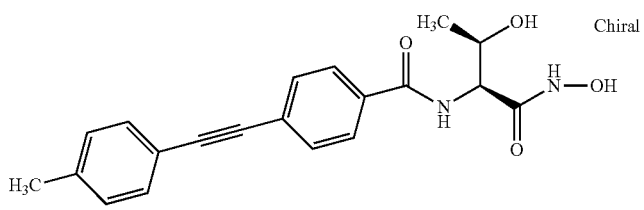 |
| 496 | 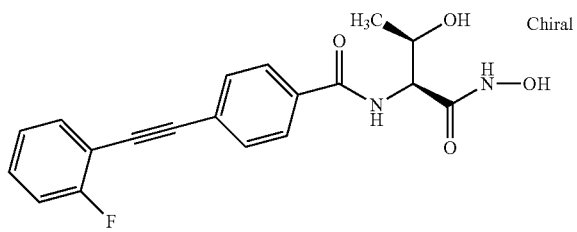 |
| 497 | 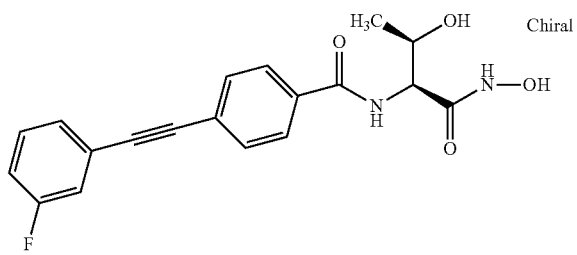 |
| 498 | 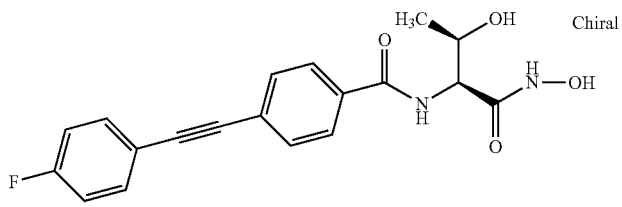 |
| 499 | 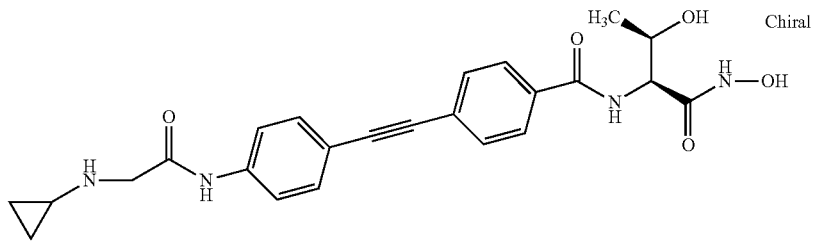 |

US 8,101,640 B2
TABLE 1-continued
| 500 | 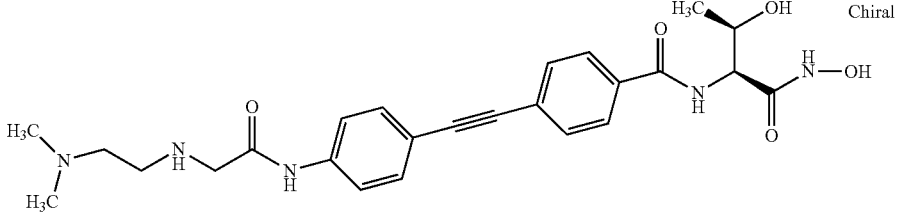 |
| 501 | 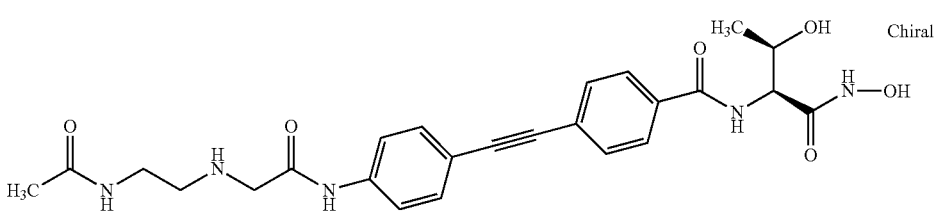 |
| 502 | 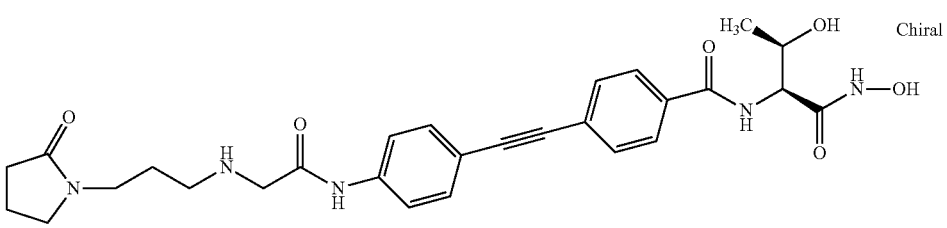 |
| 503 | 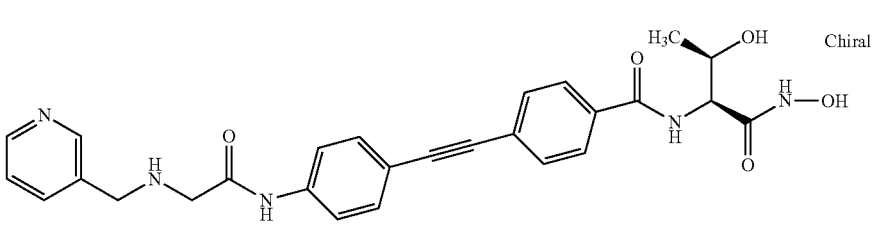 |
| 504 | 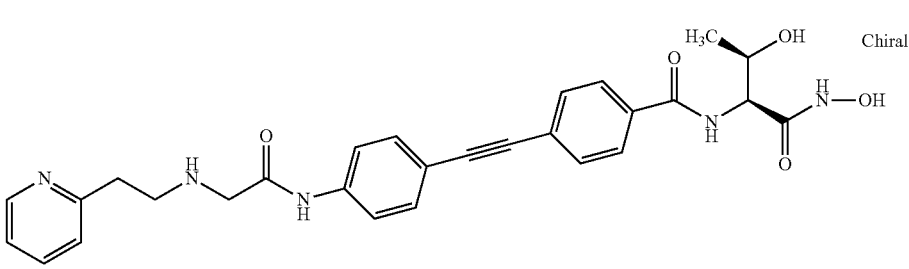 |
| 505 | 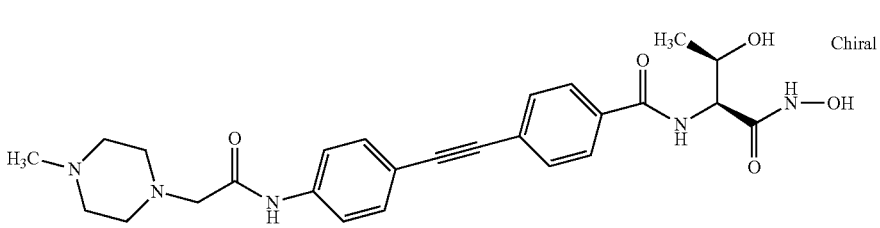 |
| 506 | 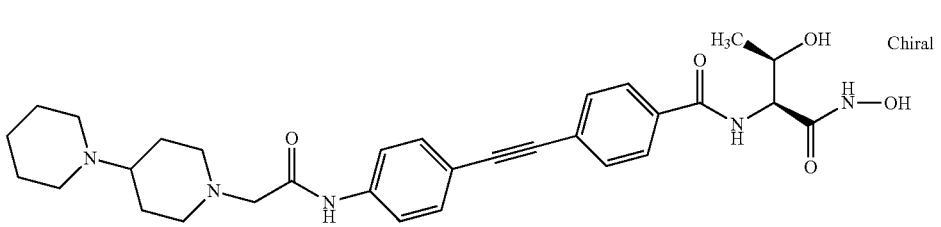 |

TABLE 1-continued
| 507 | 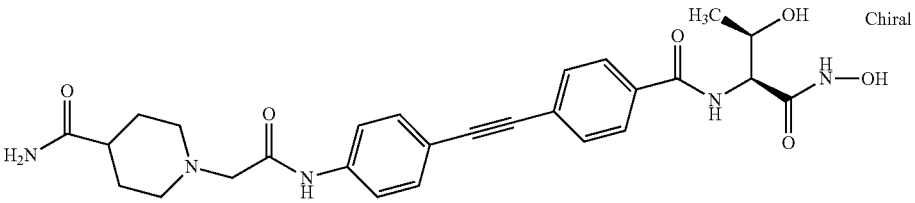 |
| 508 | 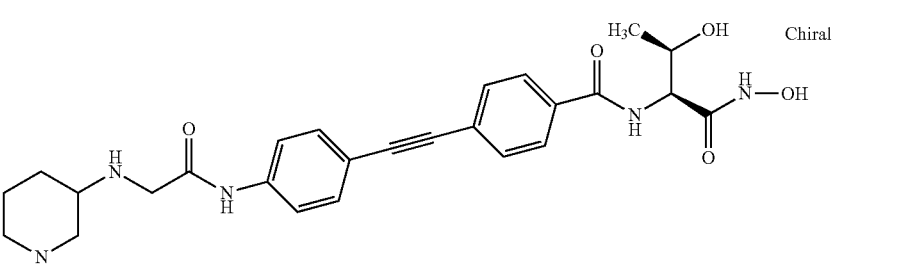 |
| 509 | 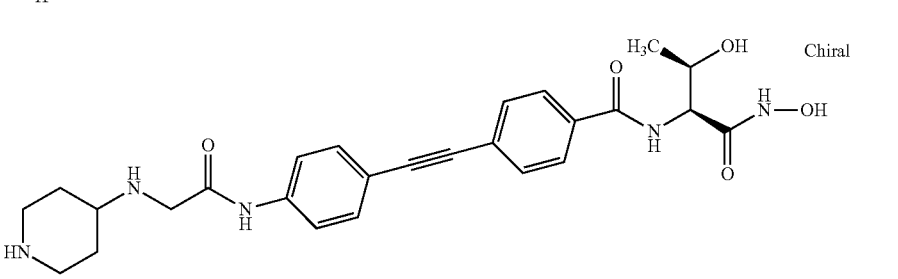 |
| 510 | 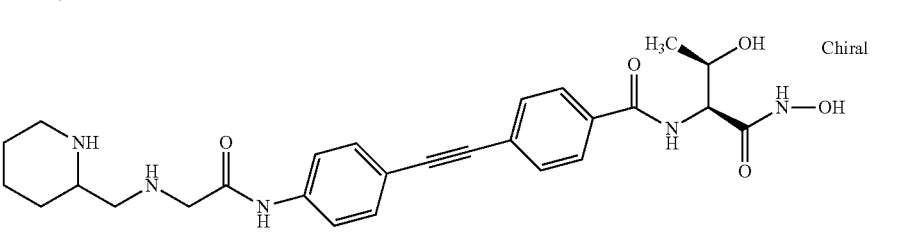 |
| 511 | 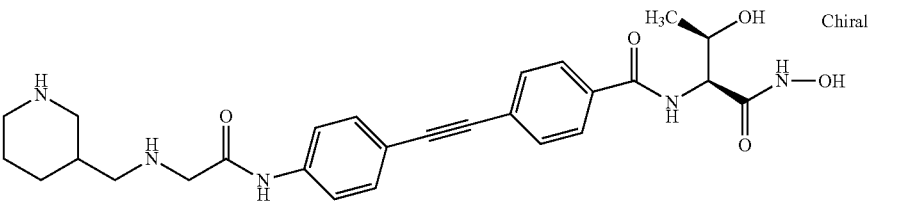 |
| 512 | 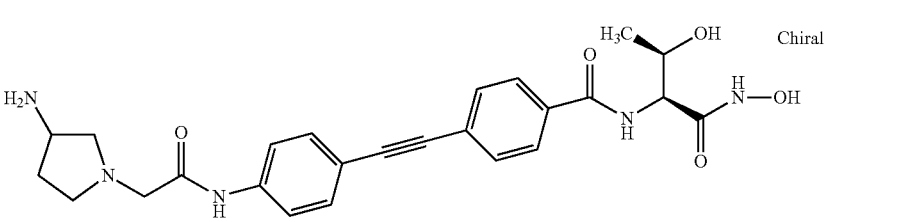 |
| 513 | 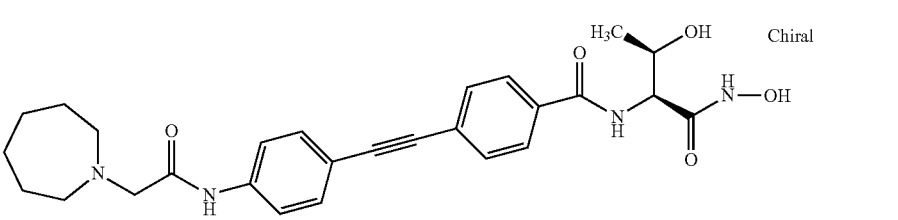 |

TABLE 1-continued
| 514 | 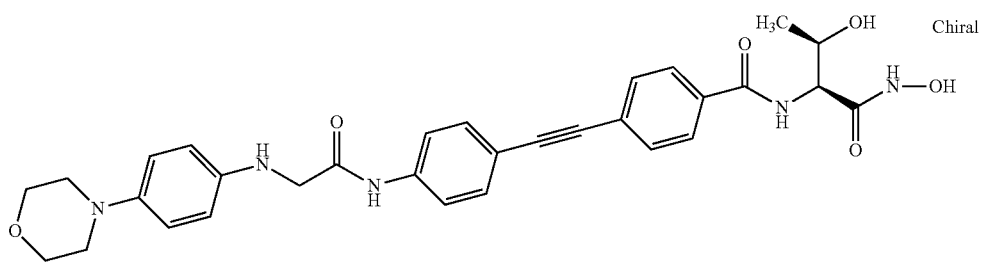 |
| 515 | 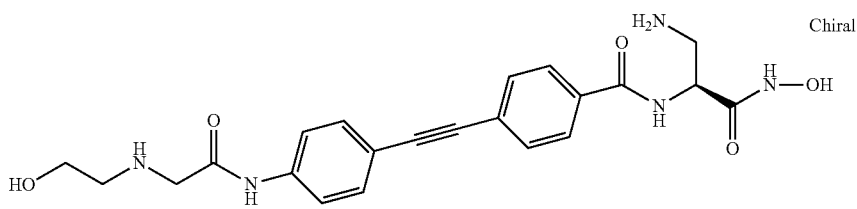 |
| 516 | 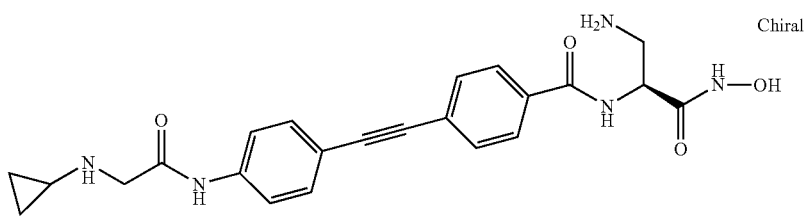 |
| 517 | 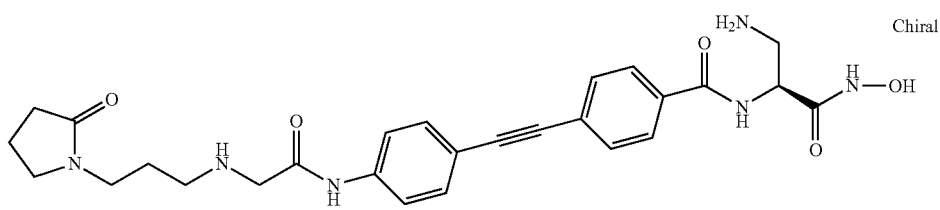 |
| 518 | 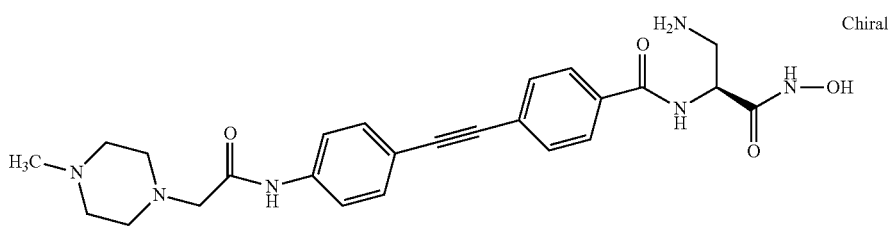 |
| 519 | 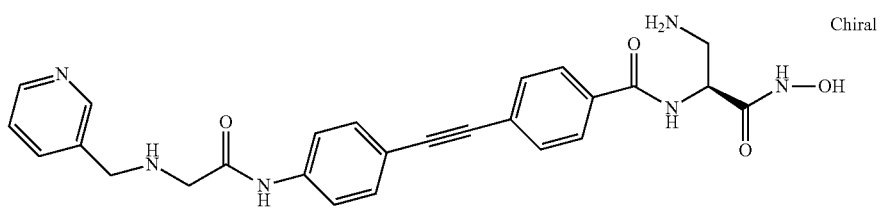 |
| 520 | 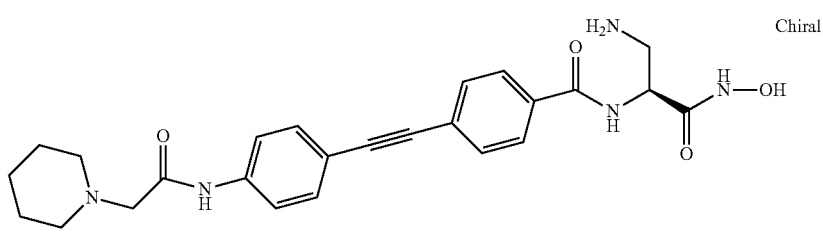 |

TABLE 1-continued
| 521 | 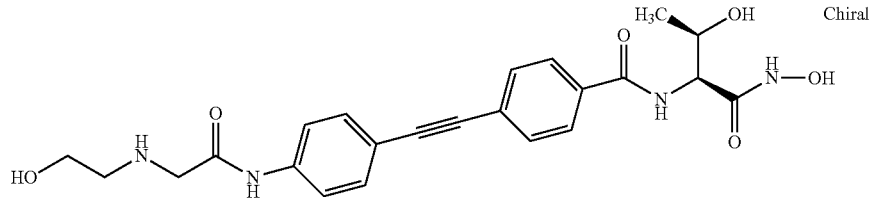 |
| 522 | 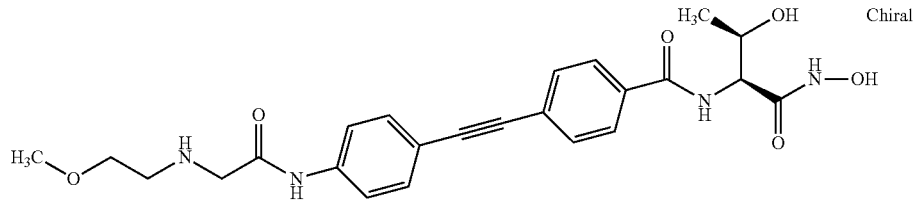 |
| 523 | 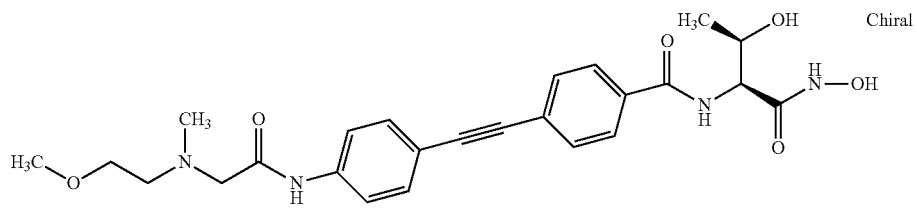 |
| 524 | 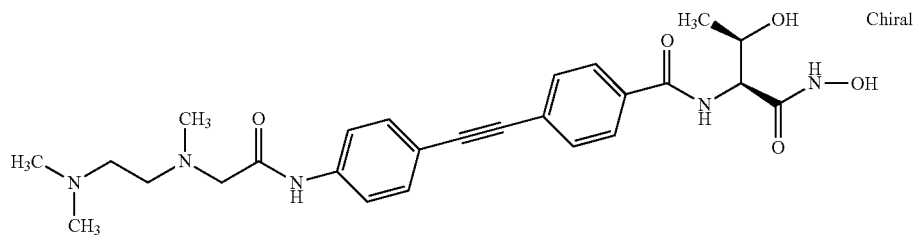 |
| 525 | 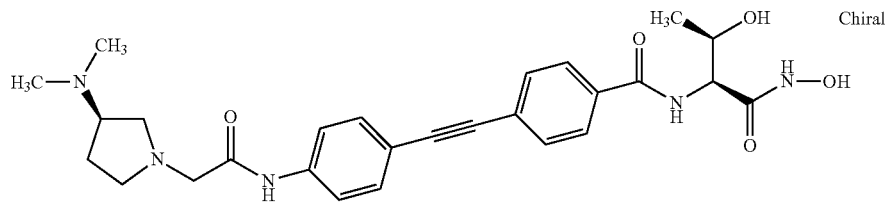 |
| 526 | 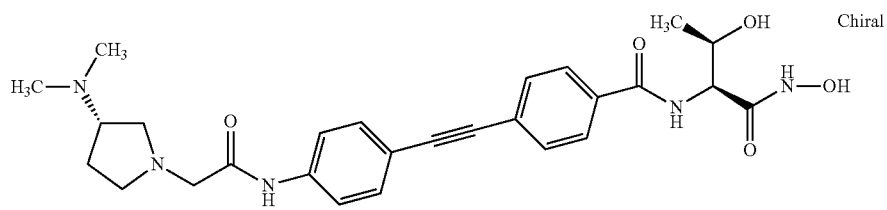 |
| 527 | 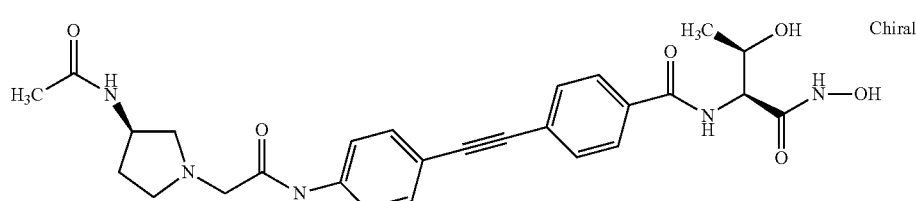 |

TABLE 1-continued
| 528 | 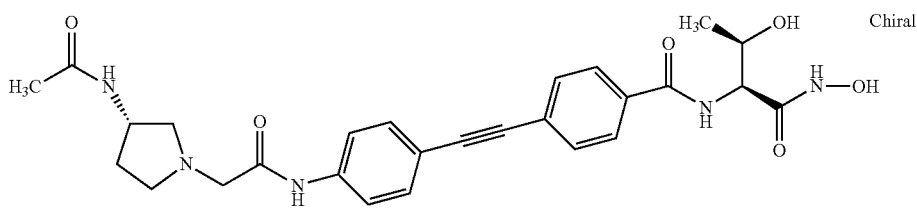 |
| 529 | 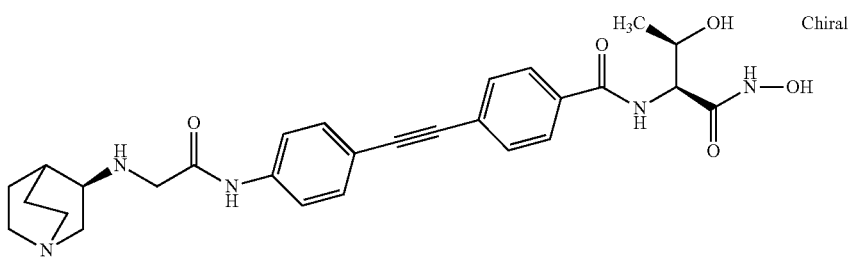 |
| 530 | 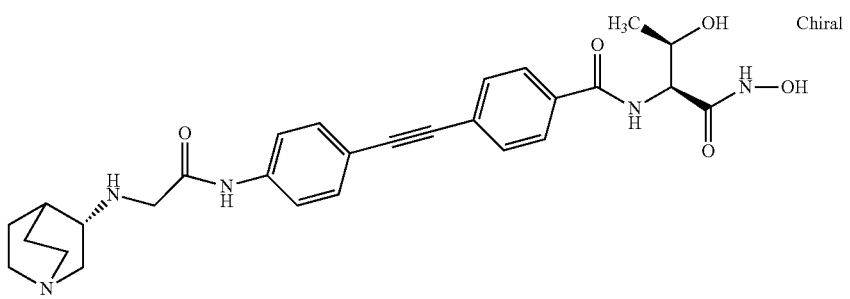 |
| 531 | 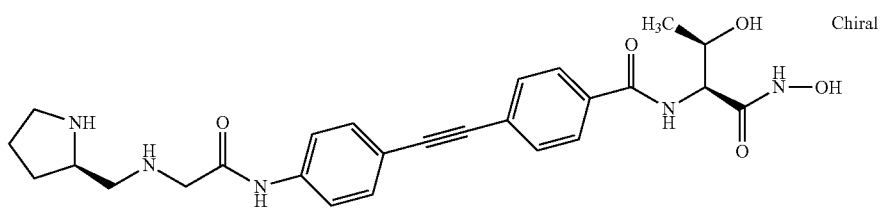 |
| 532 | 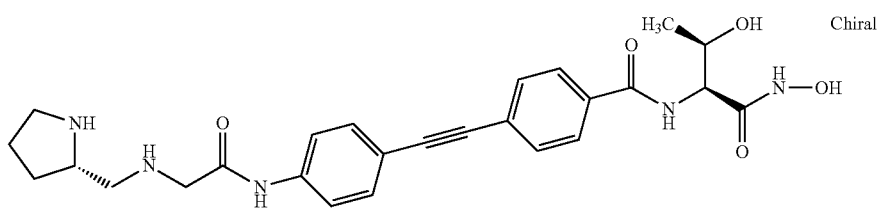 |
| 533 | 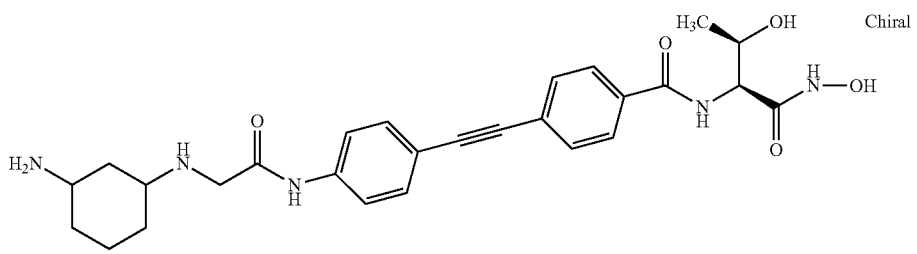 |

US 8,101,640 B2
TABLE 1-continued
534 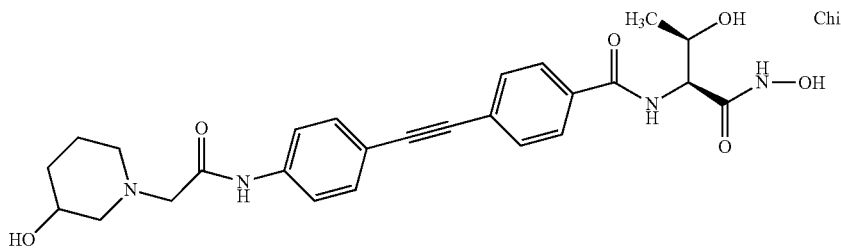
535 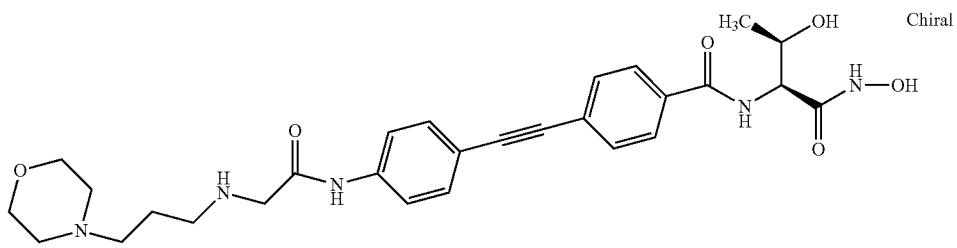
536 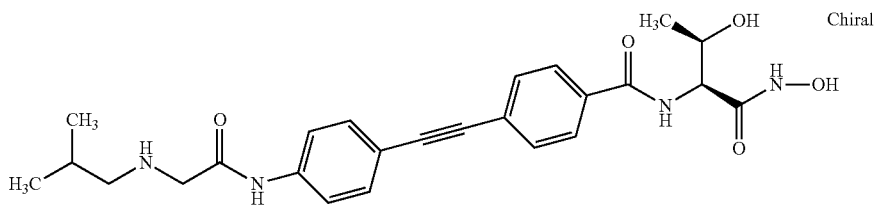
537 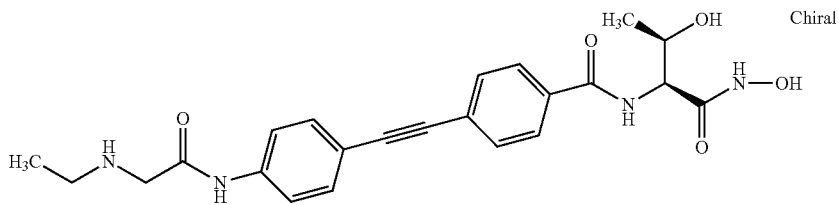
538 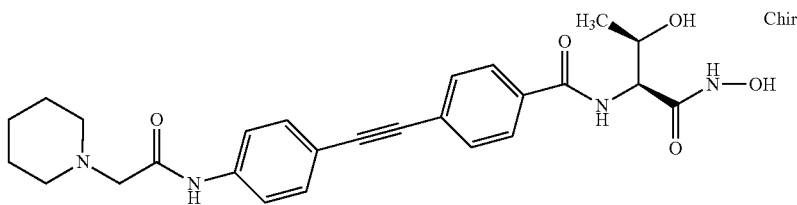
539 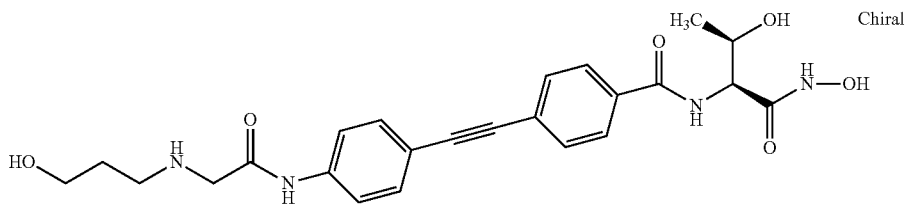
540 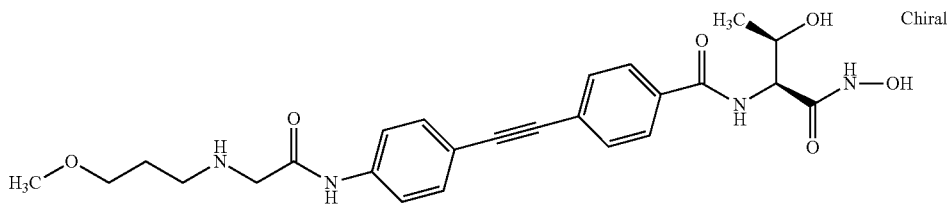

TABLE 1-continued
| 541 | 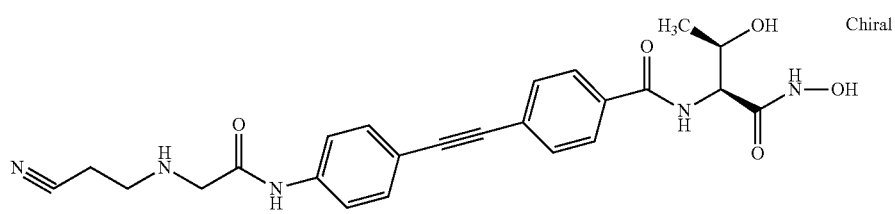 |
| 542 | 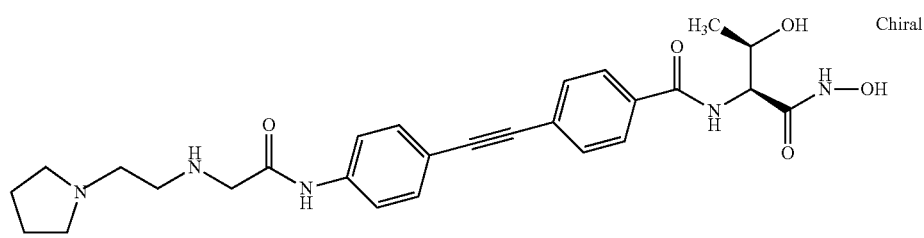 |
| 543 | 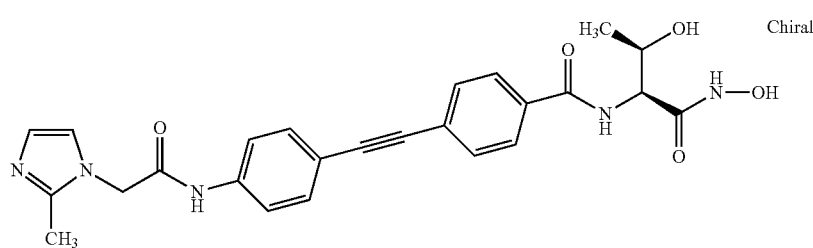 |
| 544 | 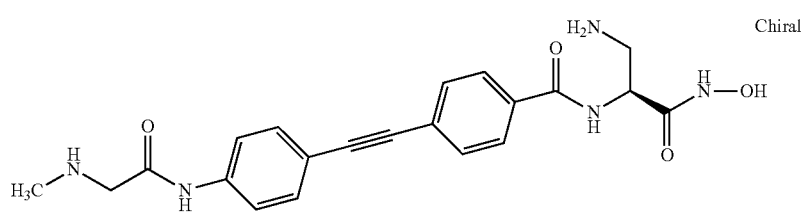 |
| 545 | 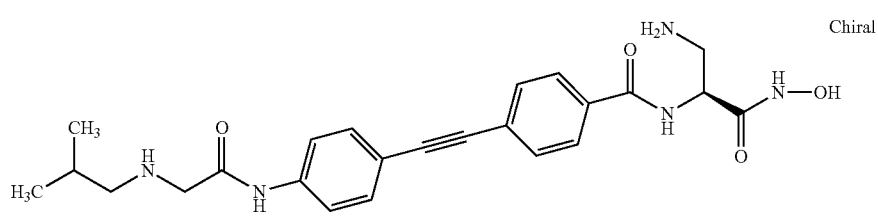 |
| 546 | 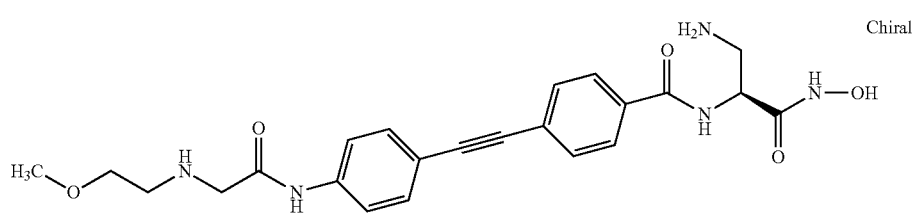 |
| 547 | 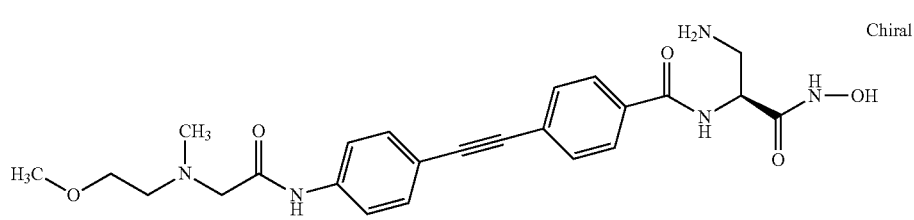 |

TABLE 1-continued
| 548 | 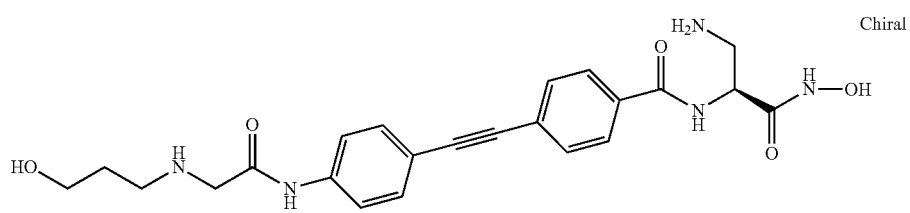 Chiral |
| 549 | 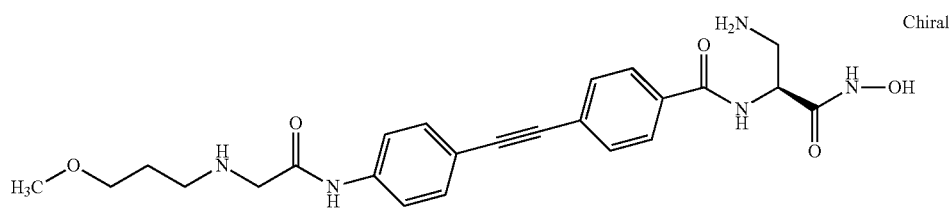 Chiral |
| 550 | 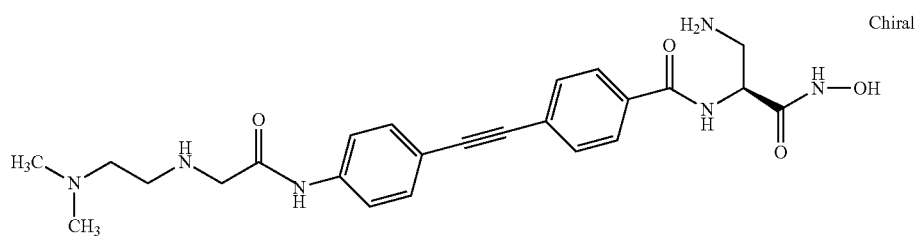 Chiral |
| 551 | 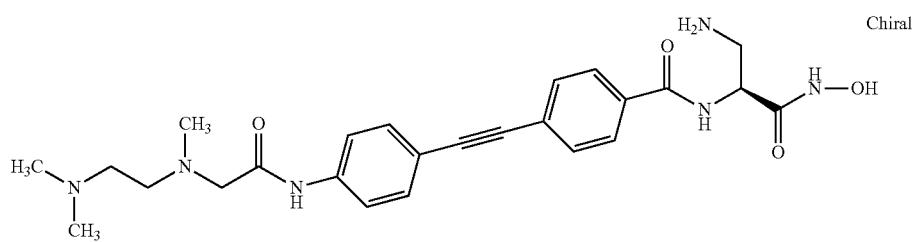 Chiral |
| 552 | 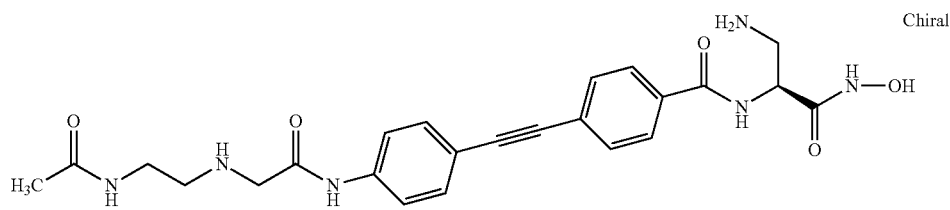 Chiral |
| 553 | 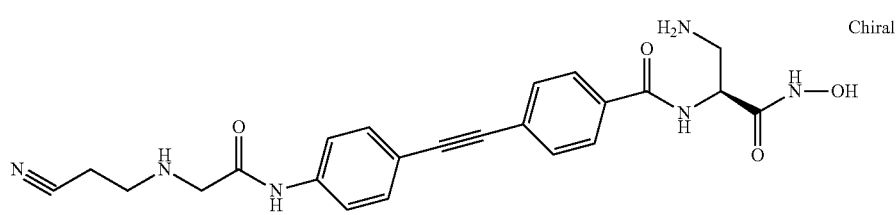 Chiral |
| 554 | 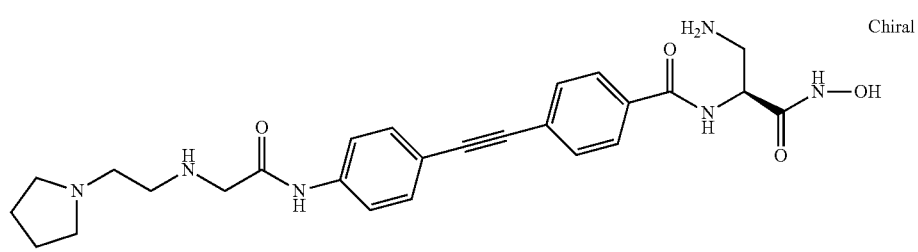 Chiral |

TABLE 1-continued
| 556 | 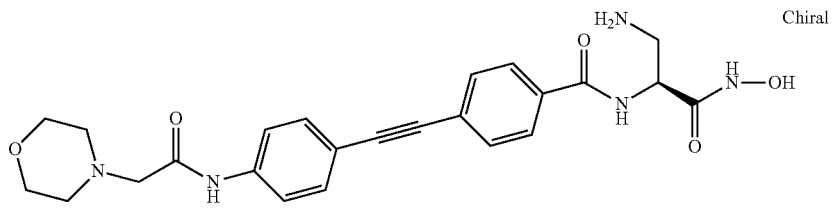 | Chiral |
| 557 | 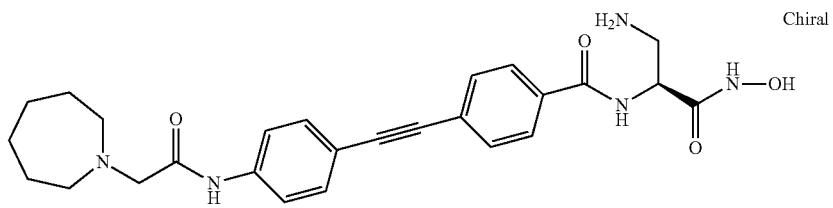 | Chiral |
| 558 | 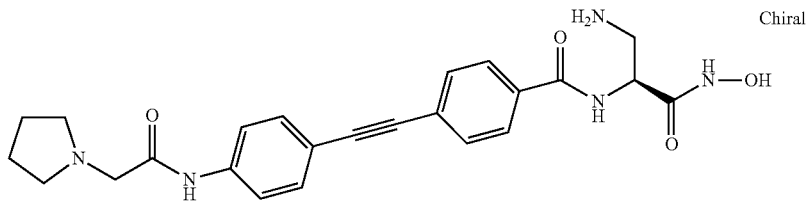 | Chiral |
| 559 | 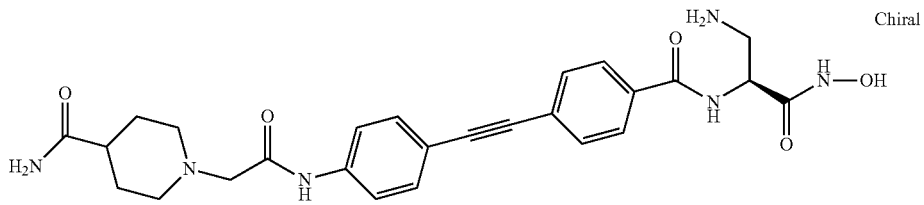 | Chiral |
| 560 | 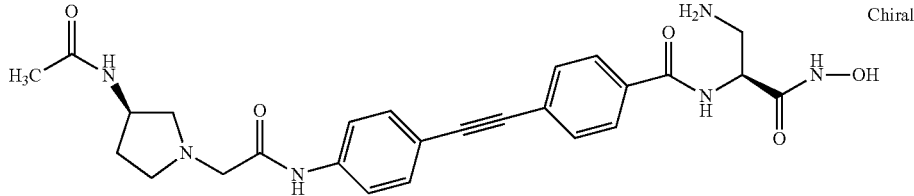 | Chiral |
| 561 | 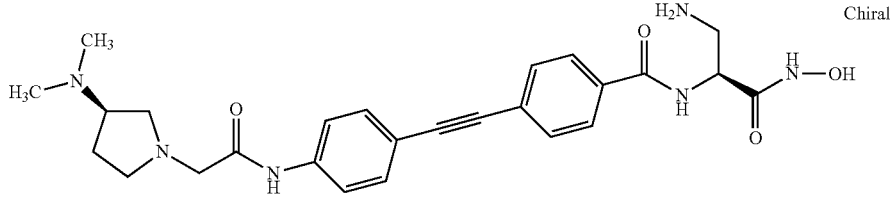 | Chiral |
| 562 | 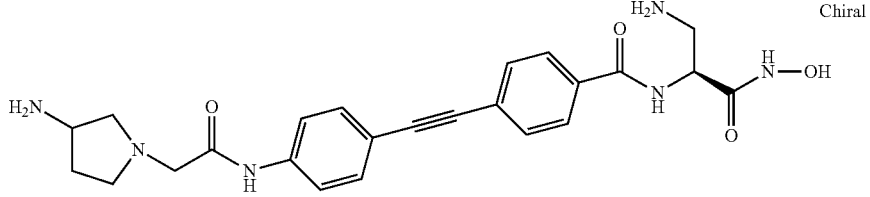 | Chiral |

TABLE 1-continued
| 563 | 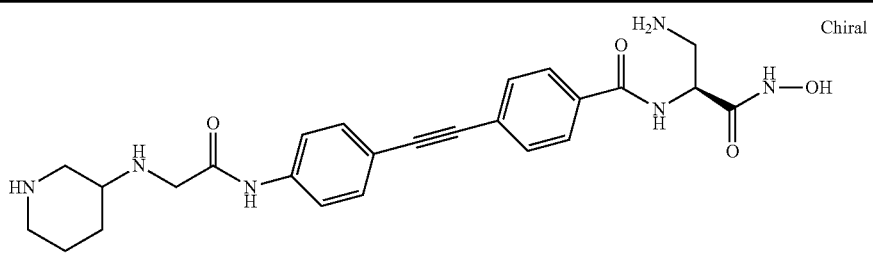 | Chiral |
| --- | --- | --- |
| 564 | 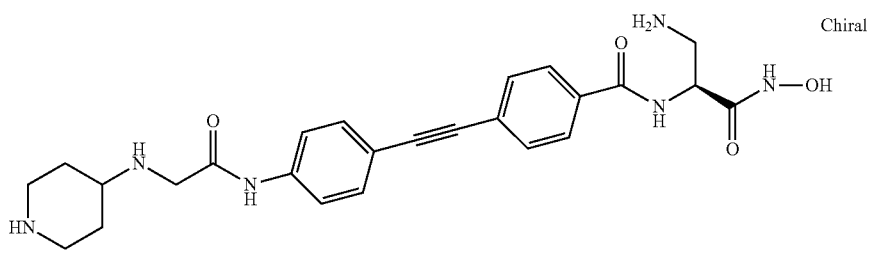 | Chiral |
| 565 | 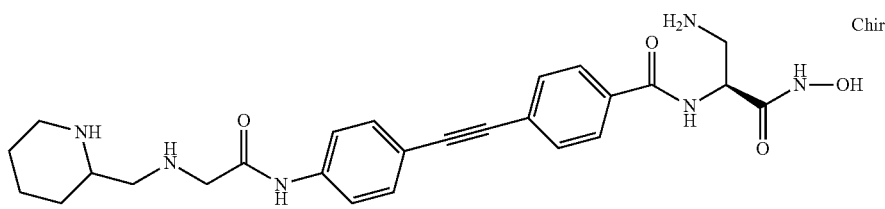 | Chiral |
| 566 | 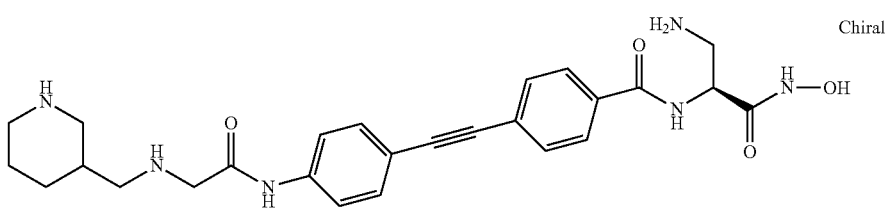 | Chiral |
| 567 | 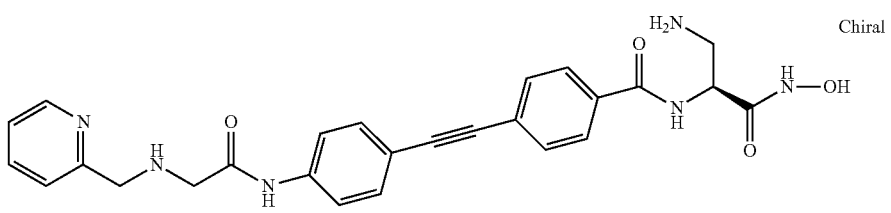 | Chiral |
| 568 | 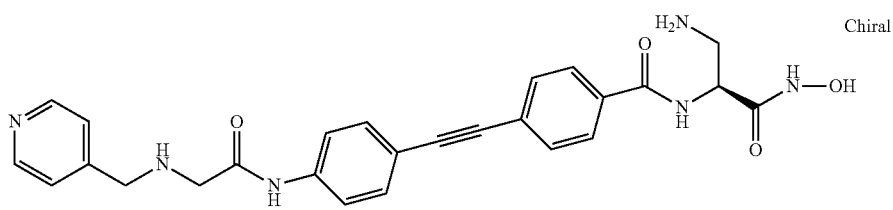 | Chiral |
| 569 | 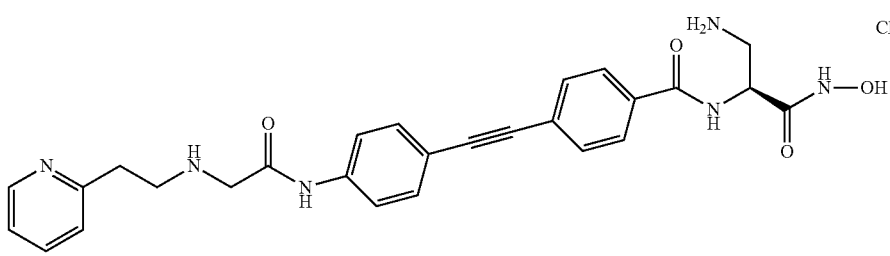 | Chiral |

TABLE 1-continued
| 570 | 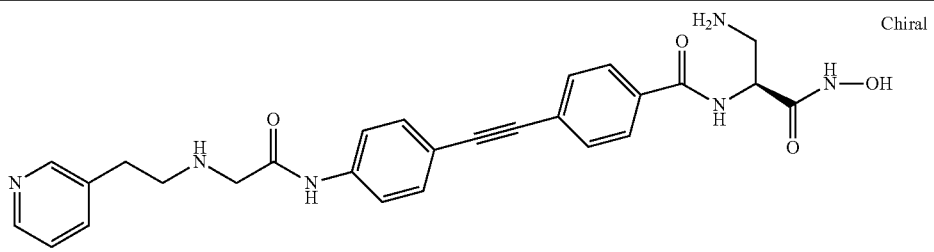 |
| 571 | 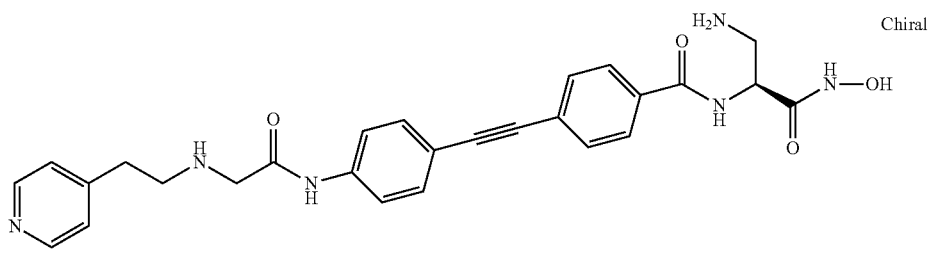 |
| 572 | 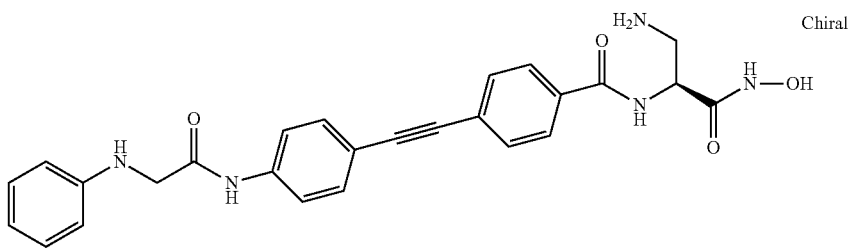 |
| 573 | 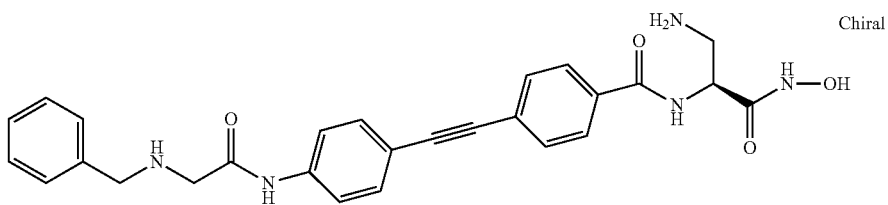 |
| 574 | 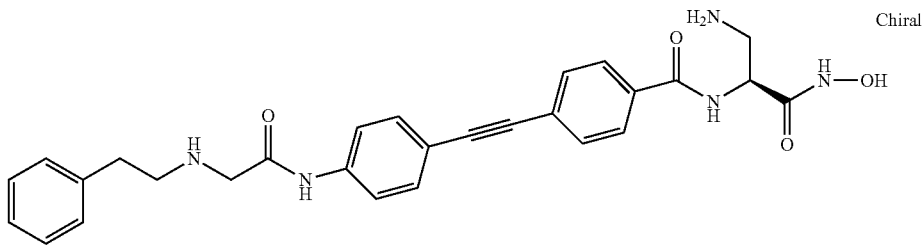 |
| 575 | 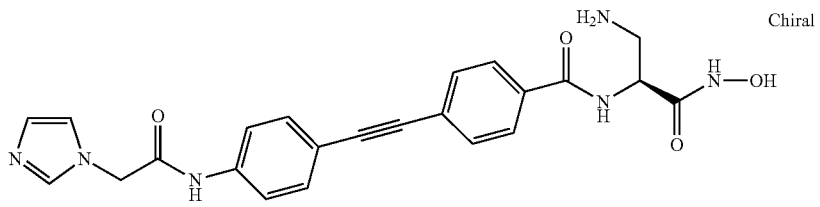 |
| 576 | 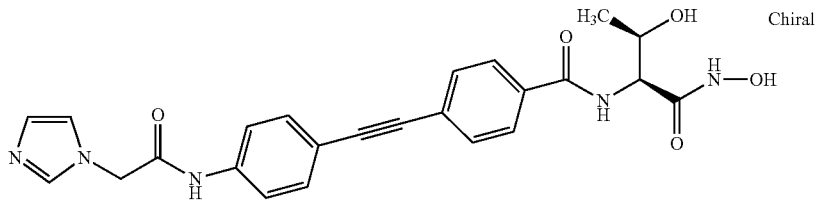 |

TABLE 1-continued
577
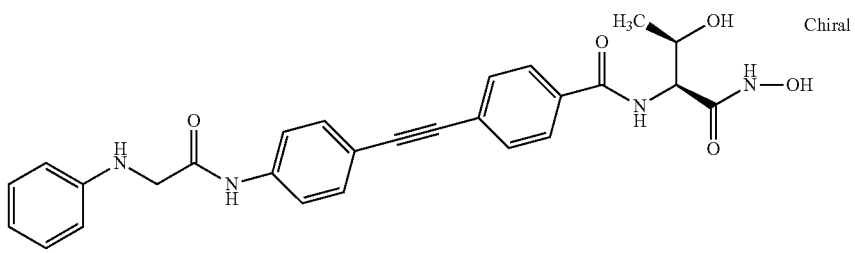
578
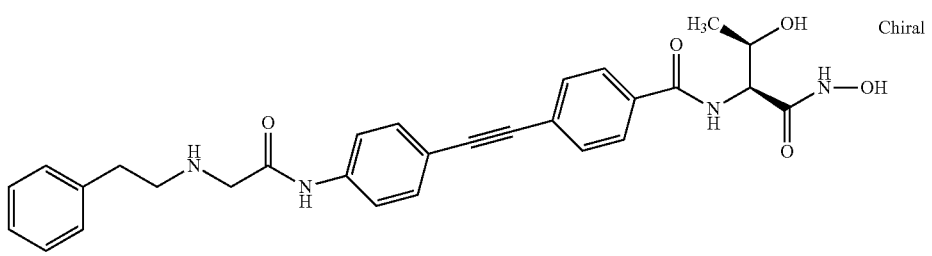
579
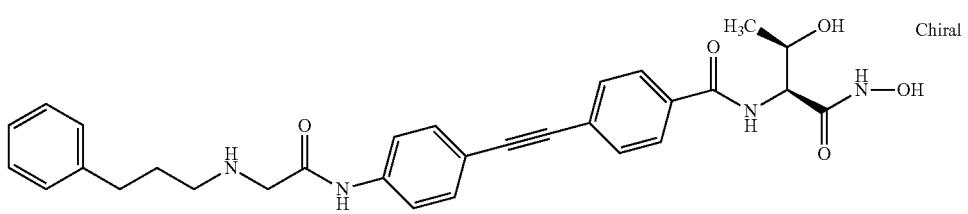
580
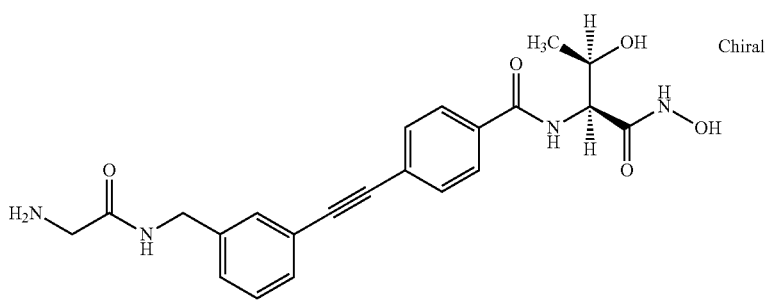
581
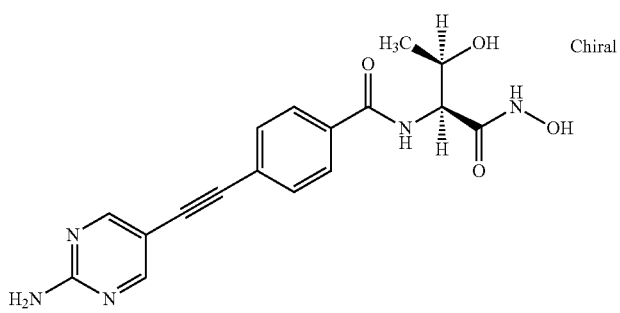

TABLE 1-continued
582
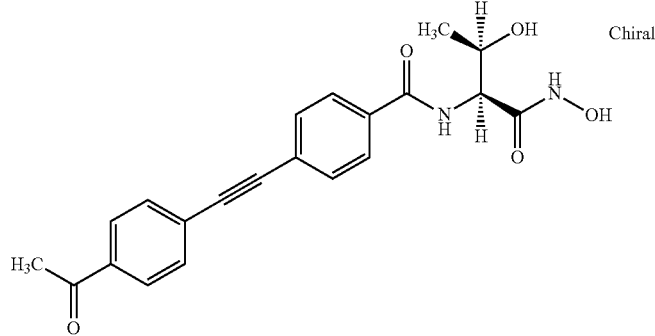
583
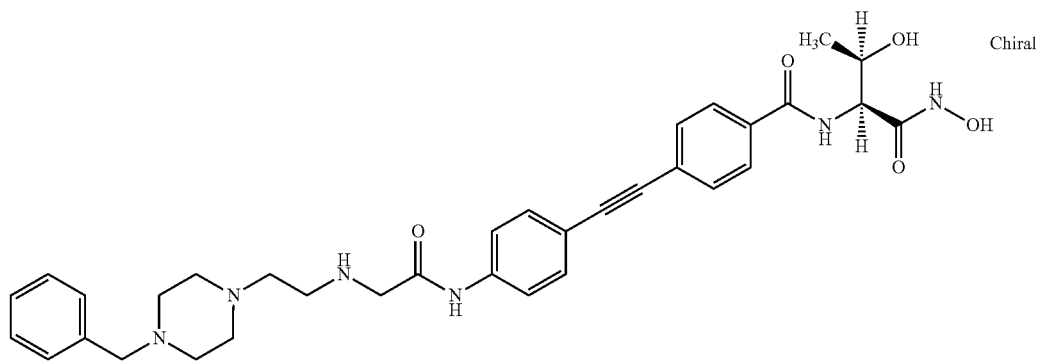
584
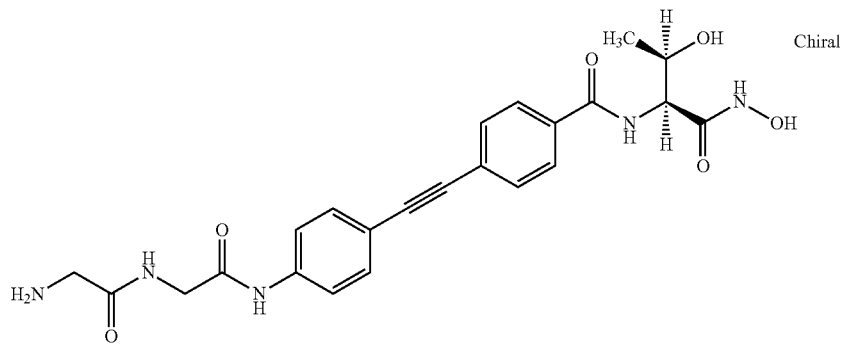
585
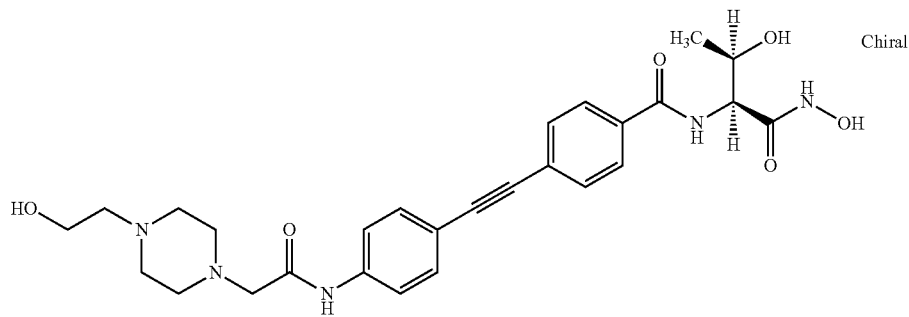

TABLE 1-continued
586 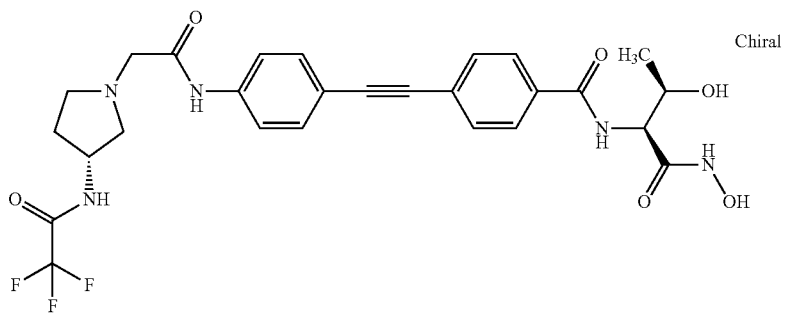
587 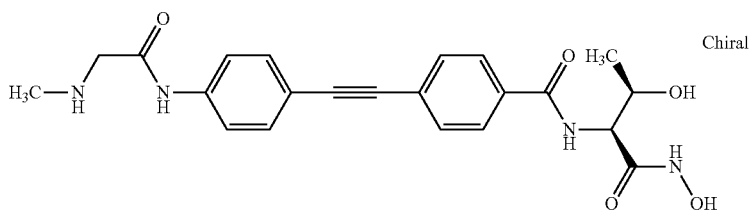
588 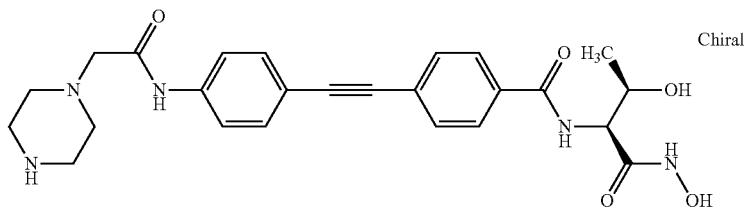
589 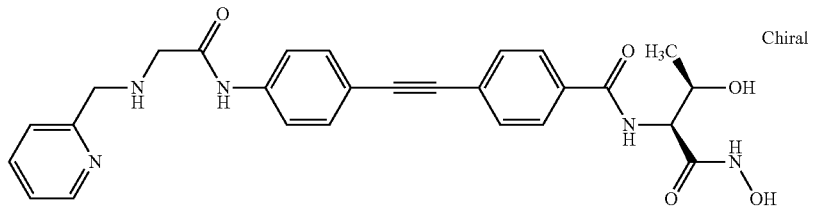
590 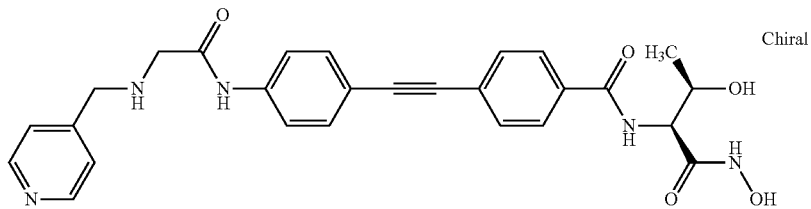
591 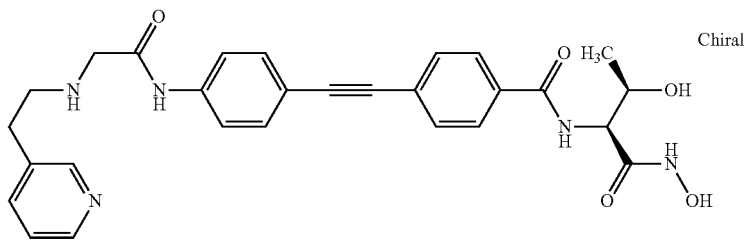

TABLE 1-continued
592 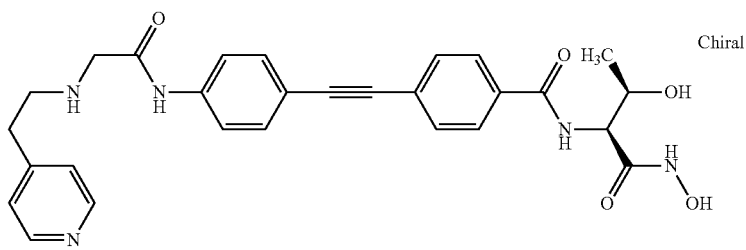
593 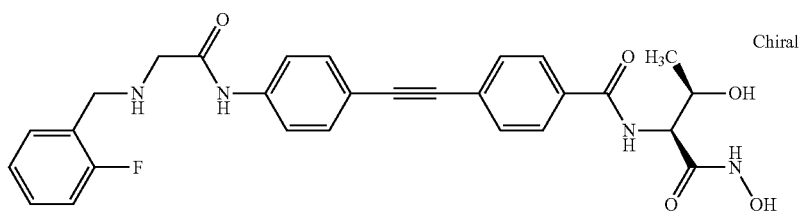
594 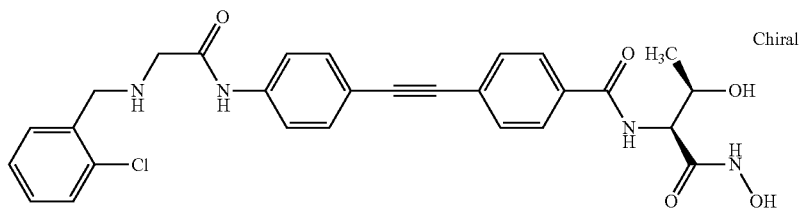
595 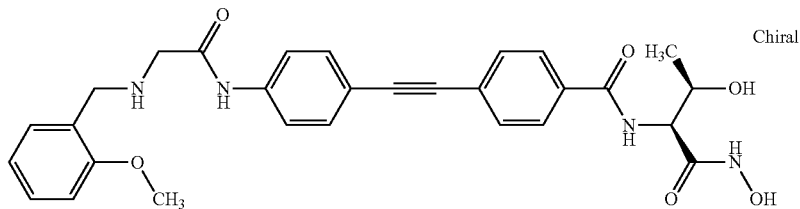
596 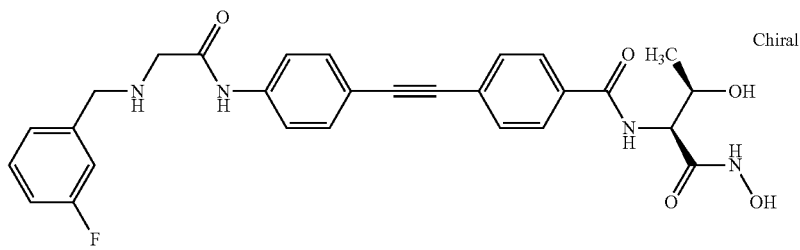
597 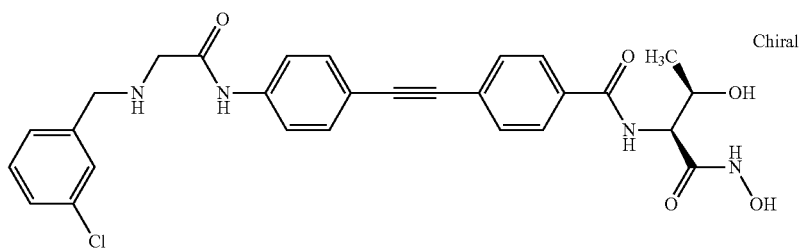

TABLE 1-continued
| 598 | 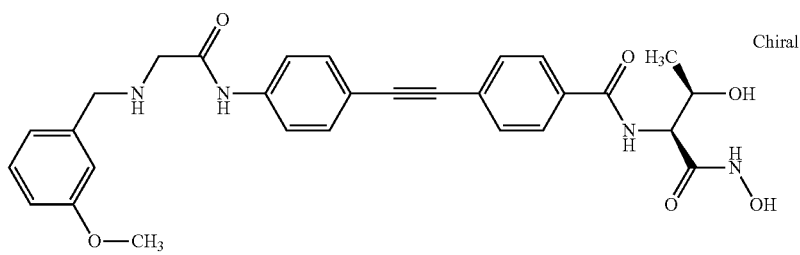 |
| 599 | 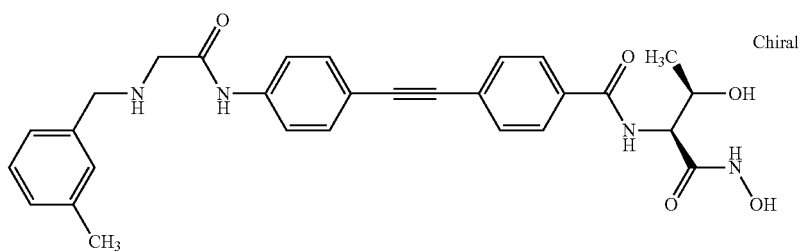 |
| 600 | 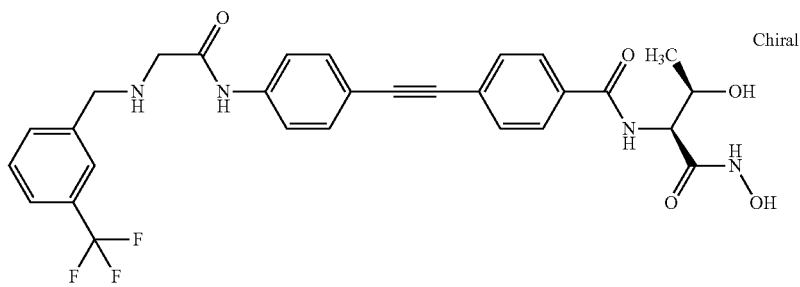 |
| 601 | 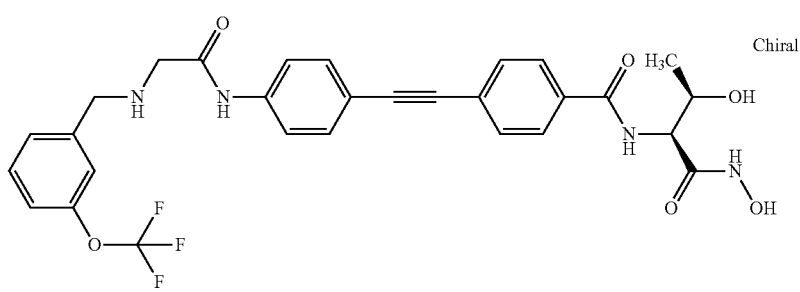 |
| 602 | 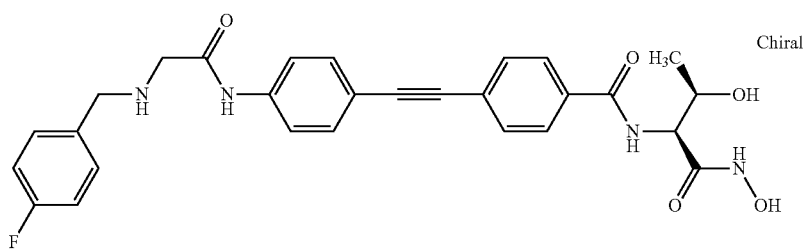 |
| 603 | 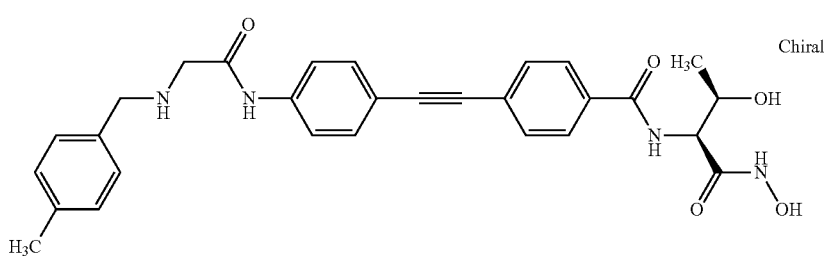 |

TABLE 1-continued
| 604 | 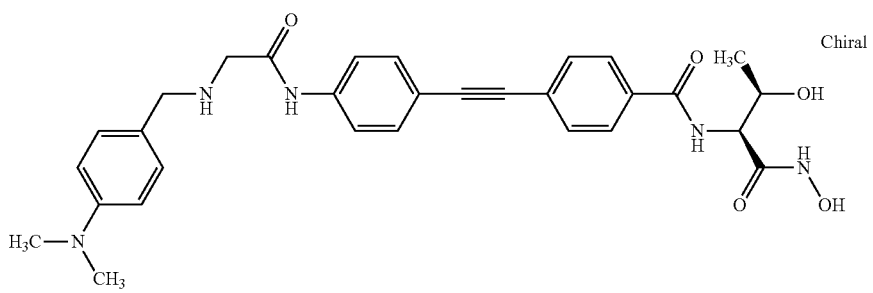 |
| 605 | 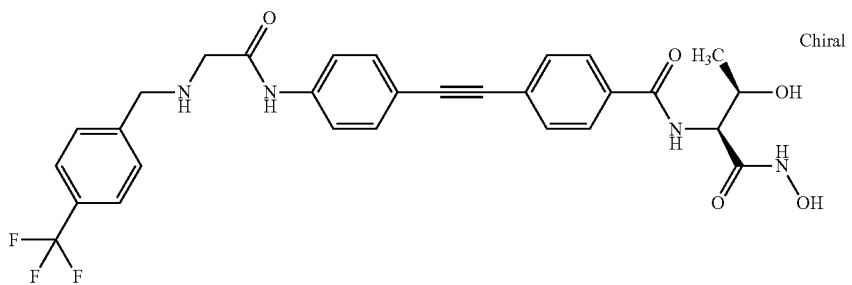 |
| 606 | 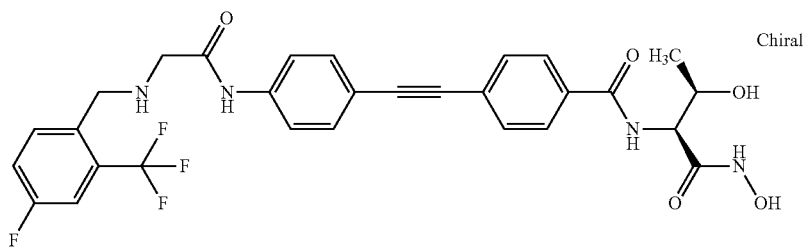 |
| 607 | 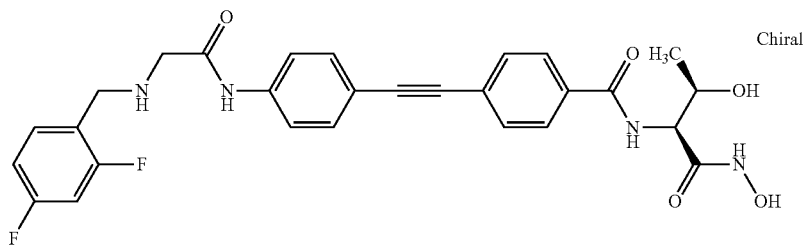 |
| 608 | 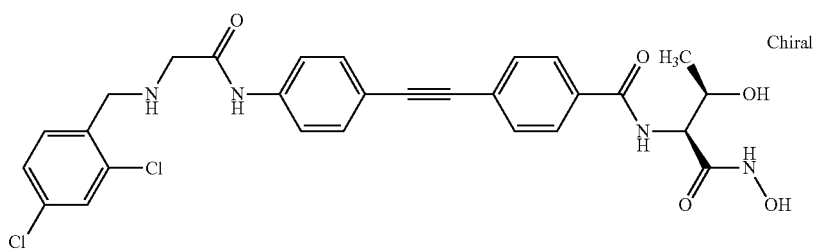 |
| 609 | 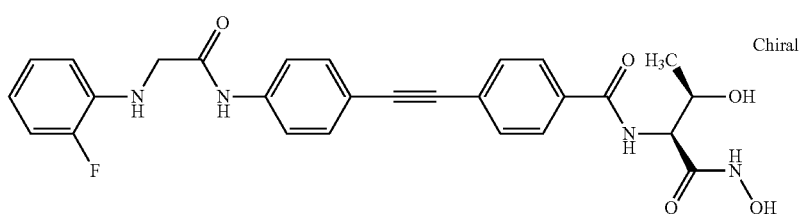 |

TABLE 1-continued
610 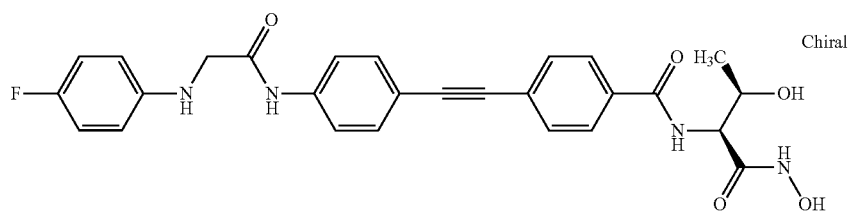
611 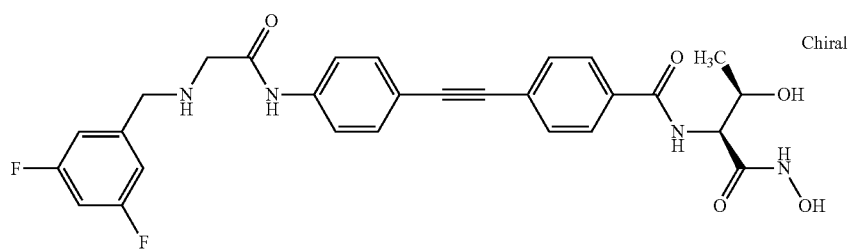
612 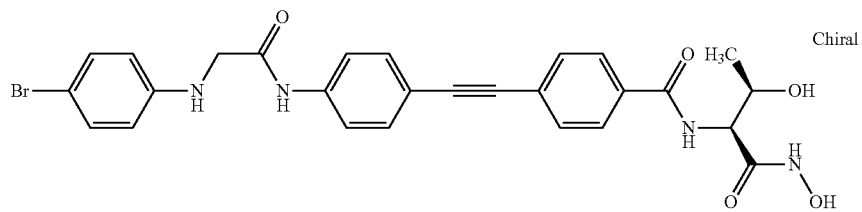
613 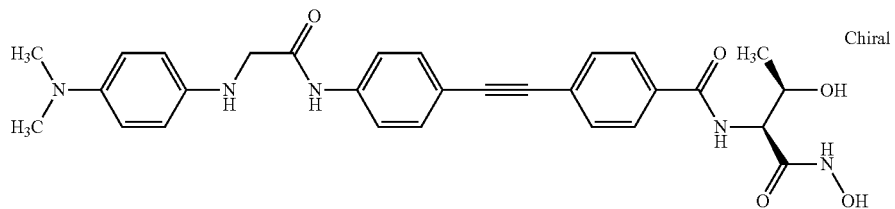
614 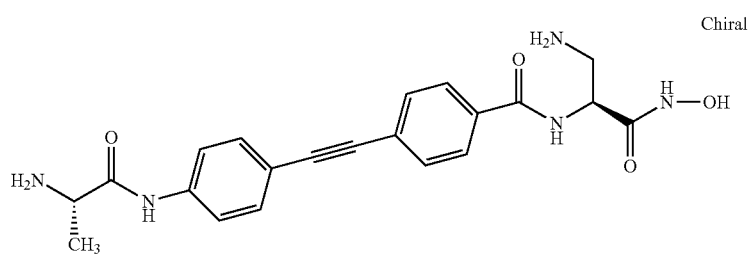
615 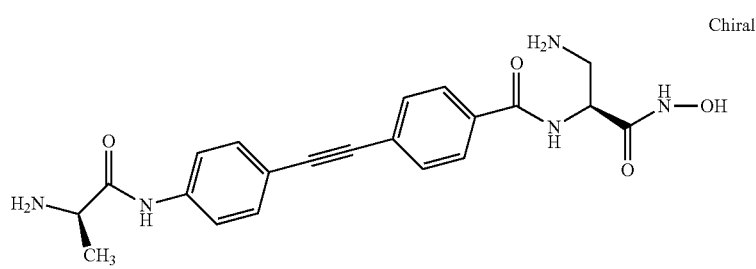

TABLE 1-continued
616 Chiral
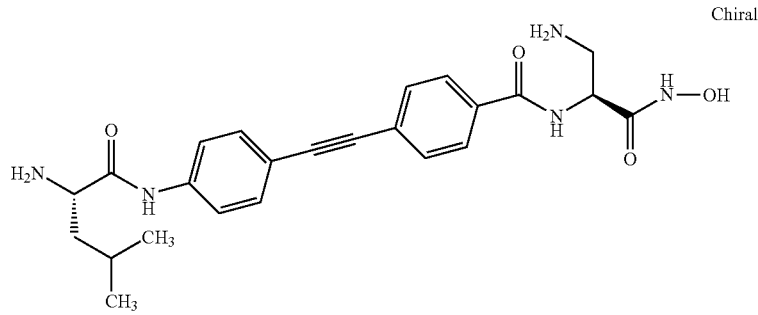
617 Chiral
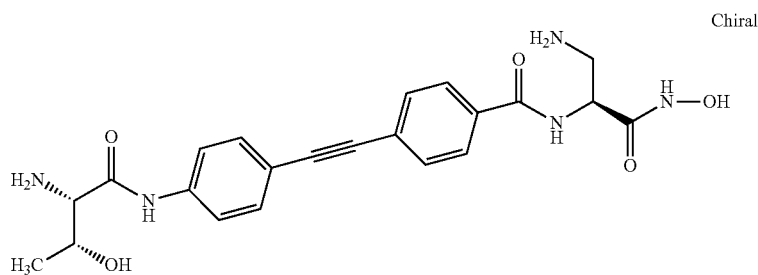
618 Chiral
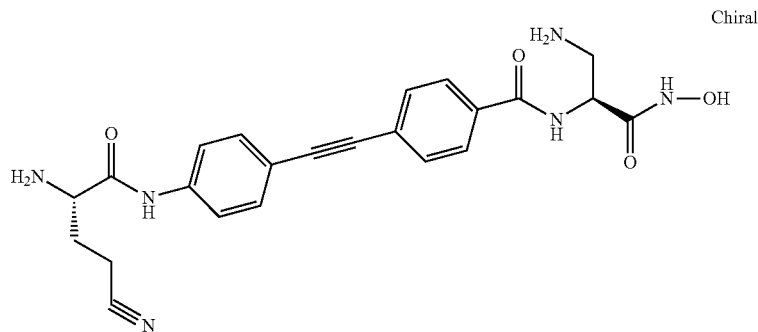
619 Chiral
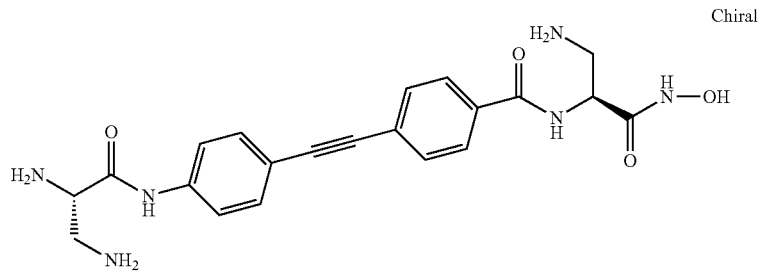
620 Chiral
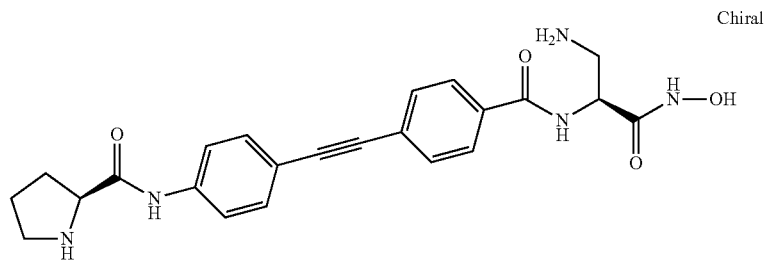

TABLE 1-continued
| 621 | 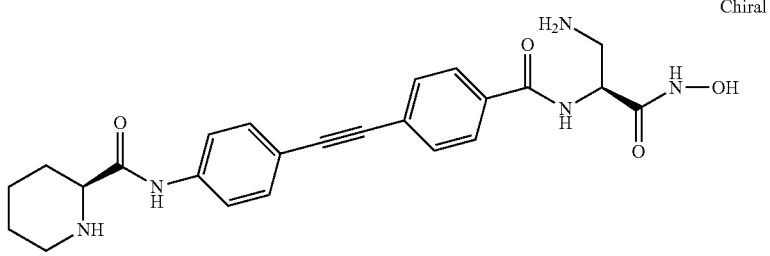 | Chiral |
| 622 | 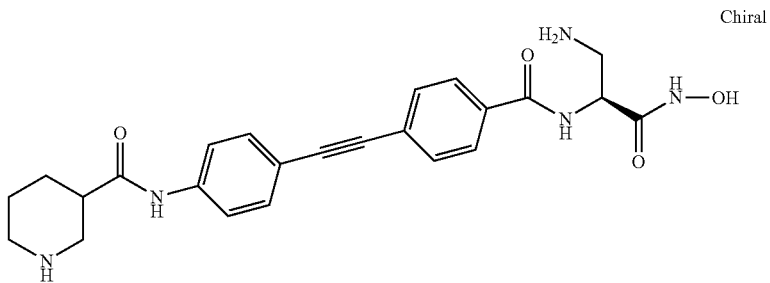 | Chiral |
| 623 | 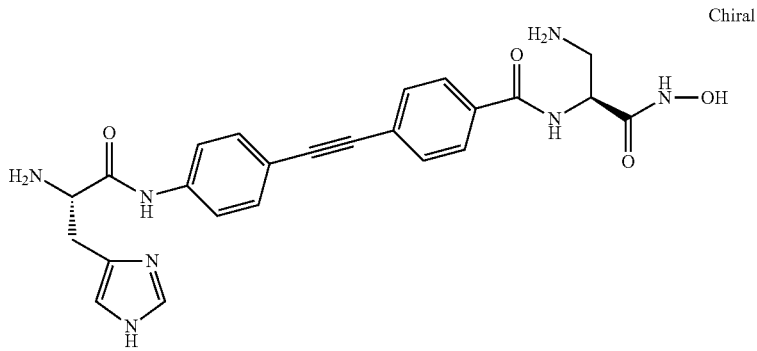 | Chiral |
| 624 | 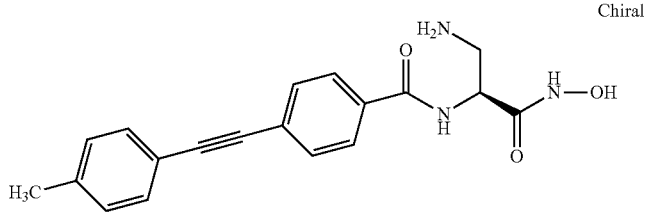 | Chiral |
| 625 | 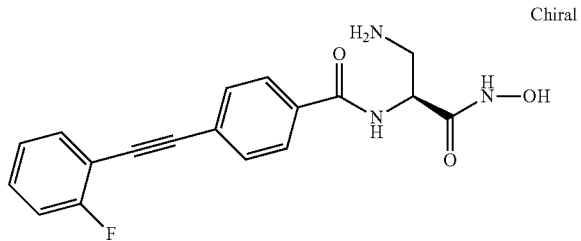 | Chiral |

TABLE 1-continued
626 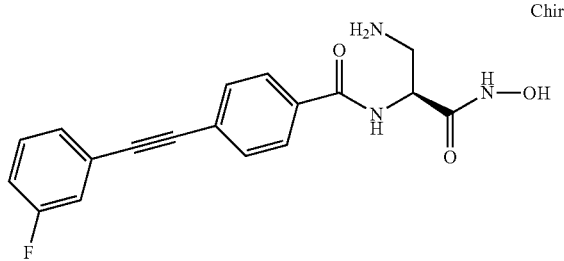
627 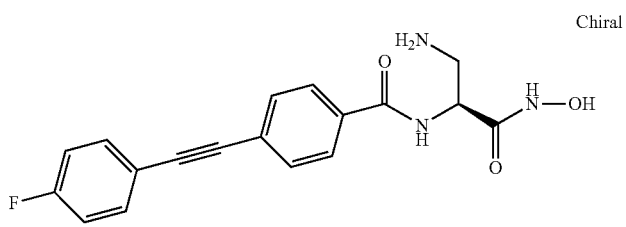
628 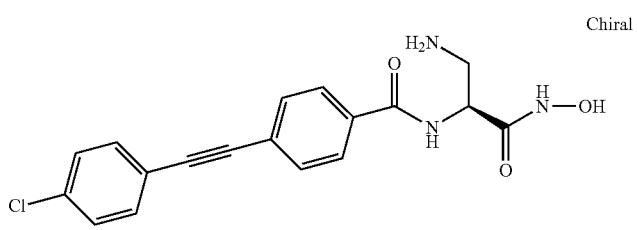
629 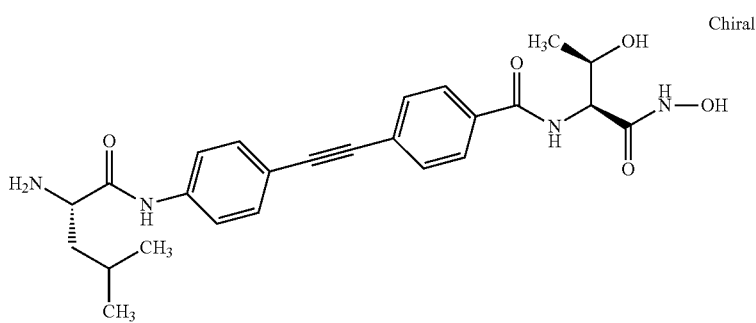
630 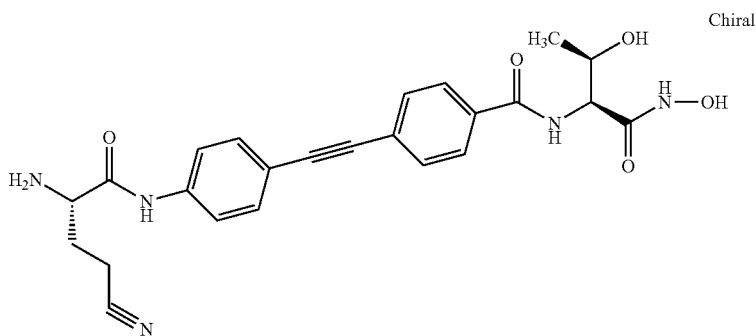

TABLE 1-continued
| 631 | 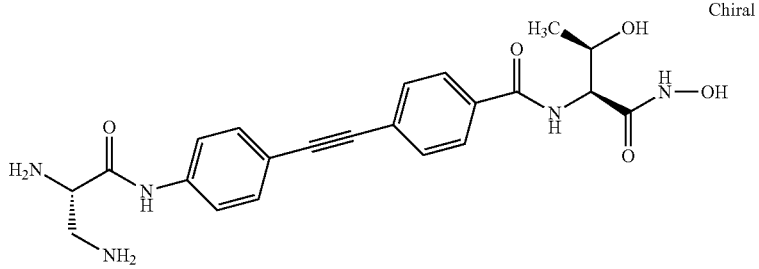 | Chiral |
| --- | --- | --- |
| 632 | 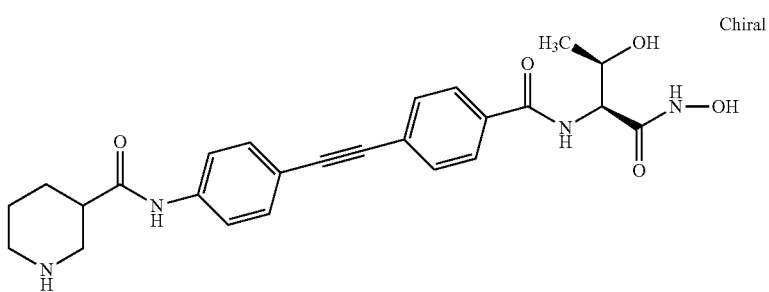 | Chiral |
| 633 | 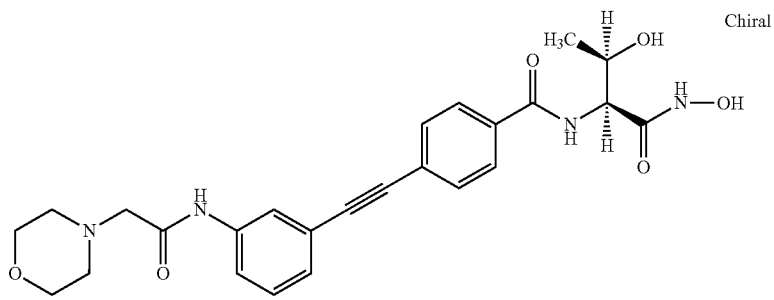 | Chiral |
| 634 | 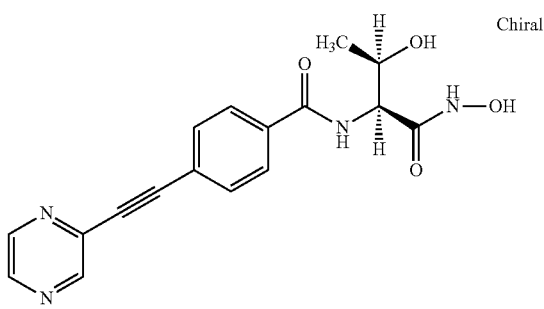 | Chiral |
| 635 | 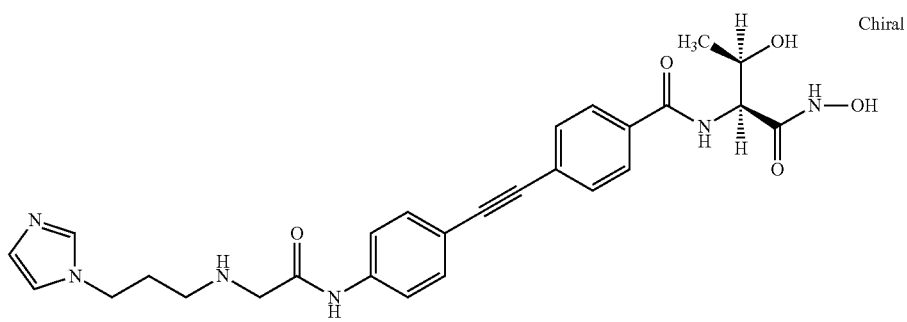 | Chiral |

TABLE 1-continued
| 636 | 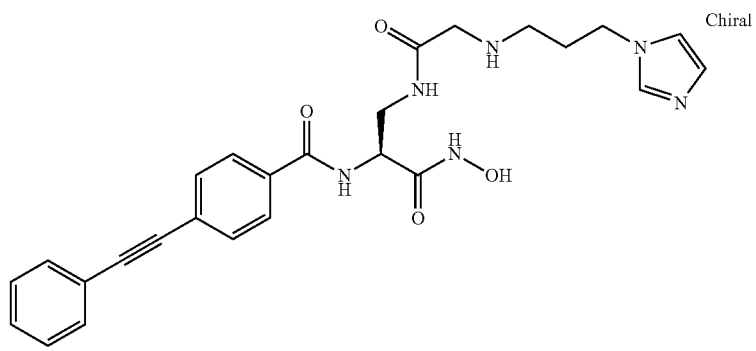 |
| --- | --- |
| 637 | 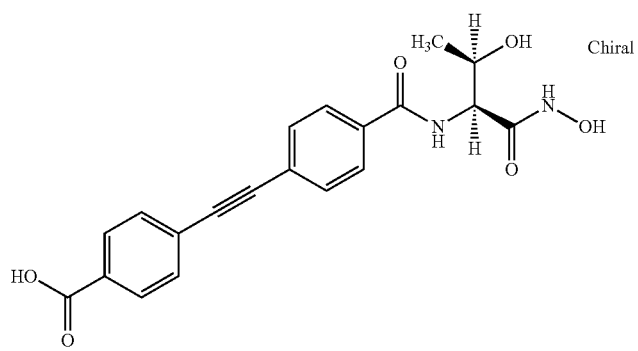 |
| 638 | 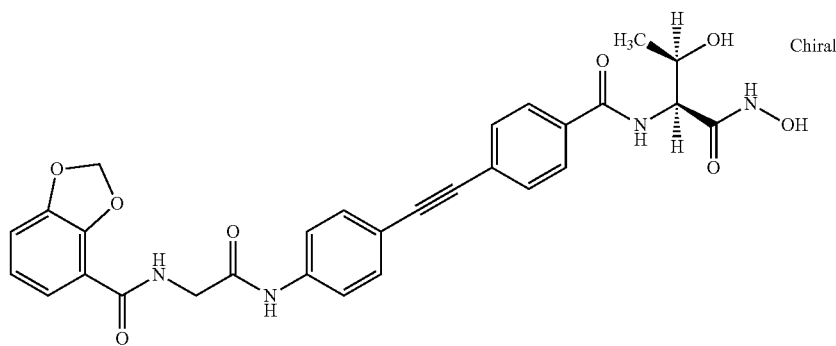 |
| 639 | 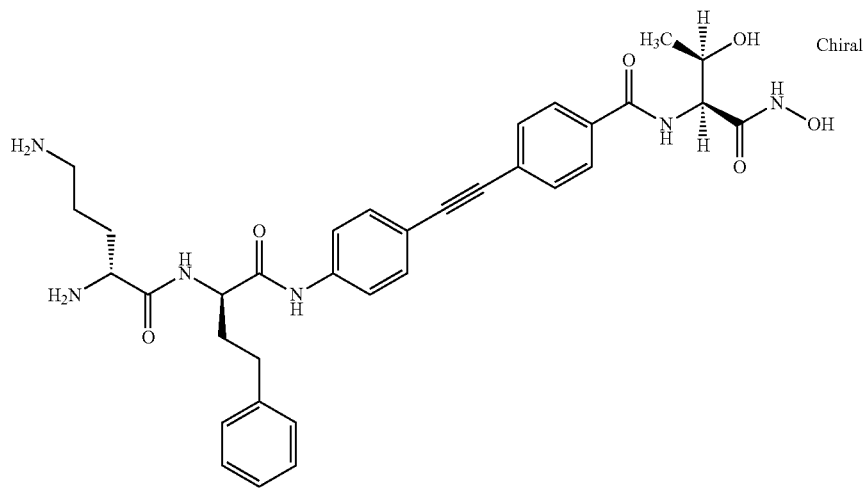 |

TABLE 1-continued
640
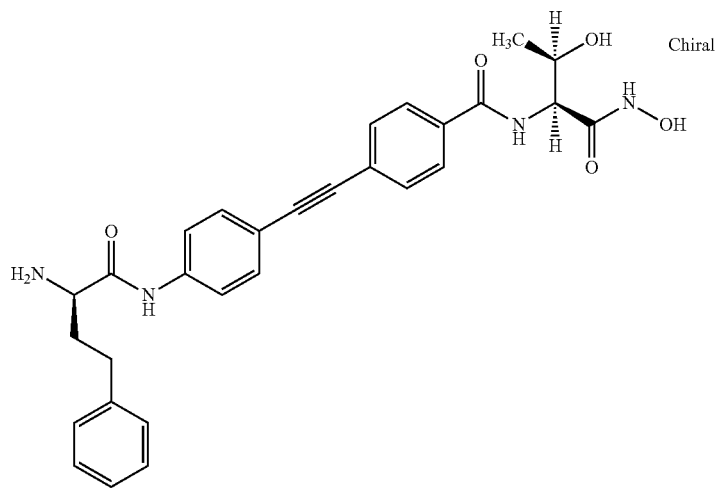
641
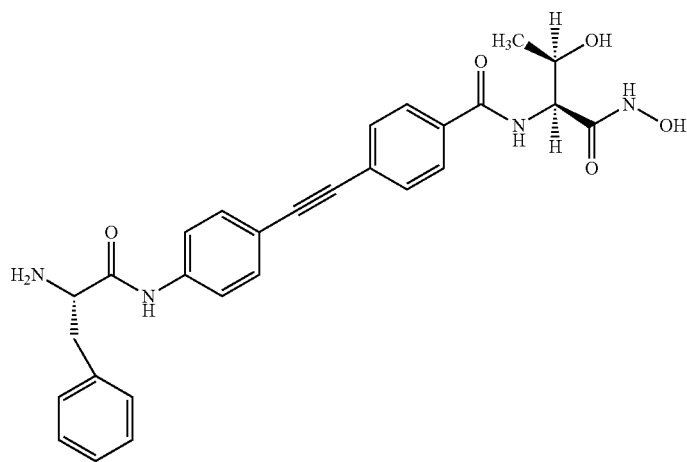
642
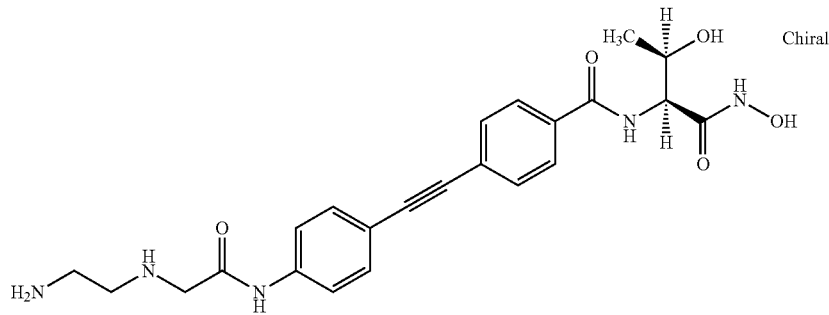
643
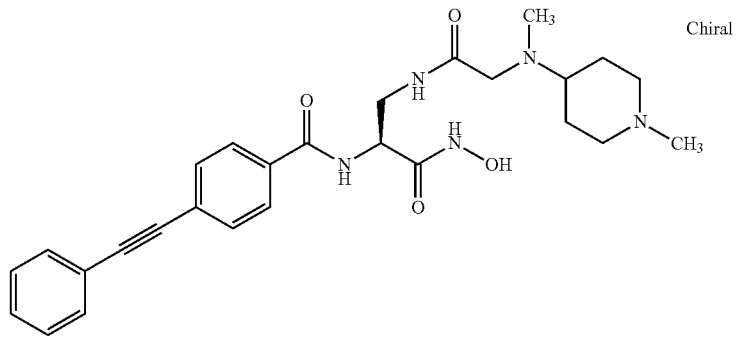

TABLE 1-continued
644 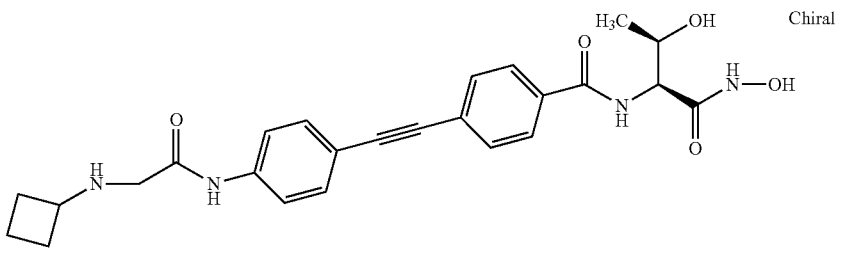
645 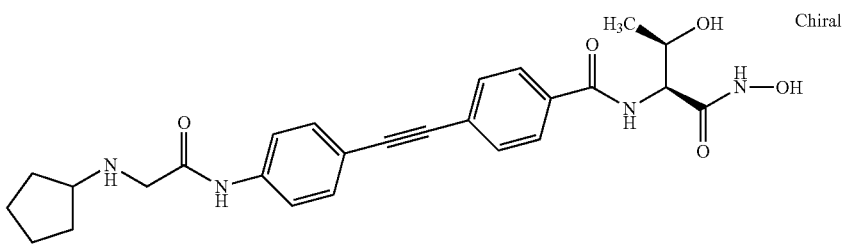
646 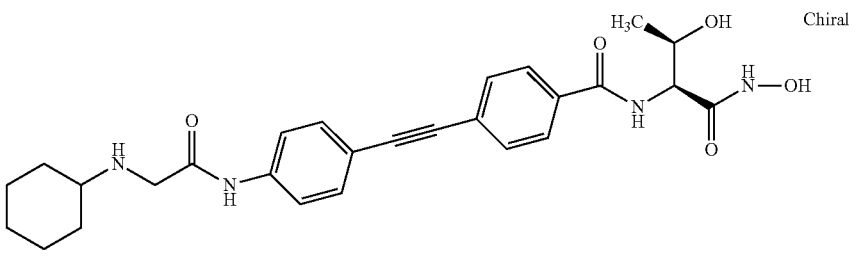
647 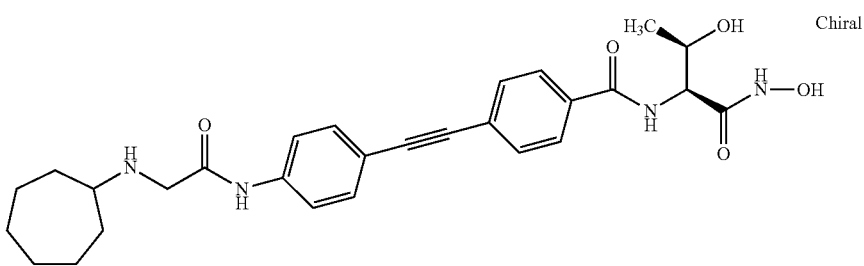
648 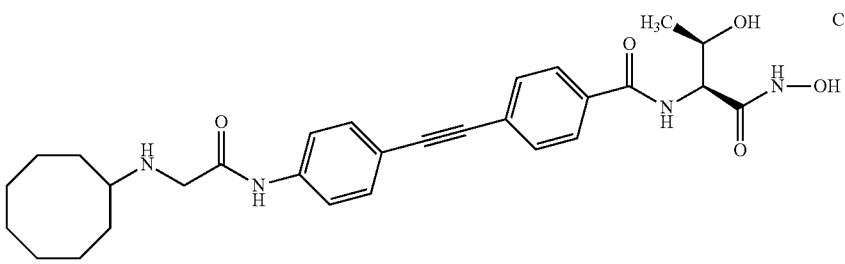
649 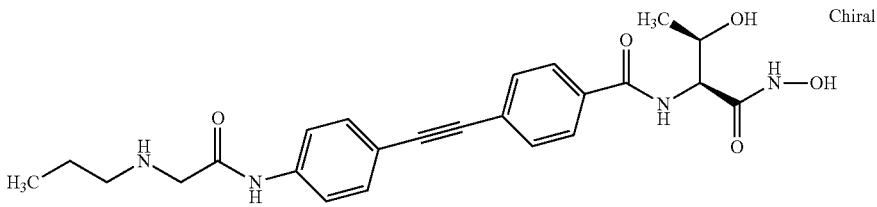

TABLE 1-continued
650 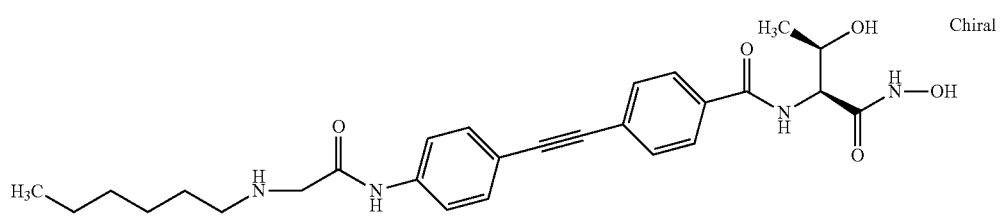
651 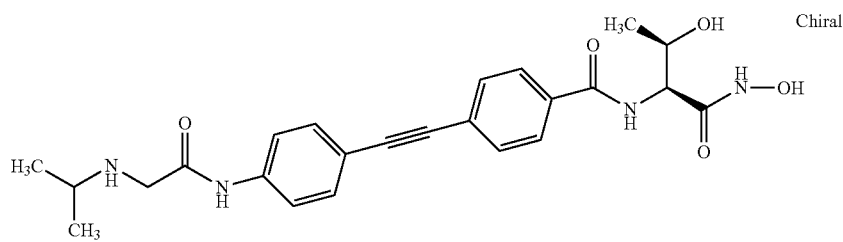
652 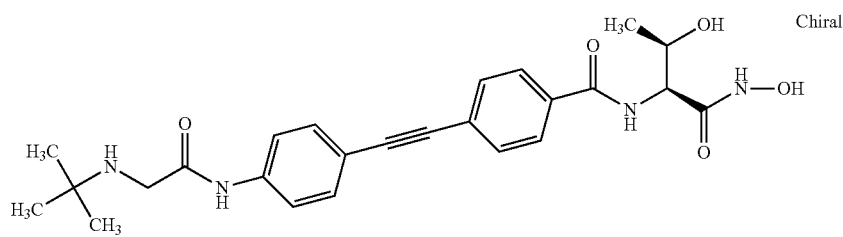
653 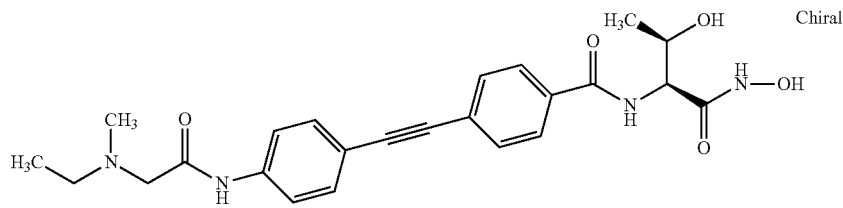
654 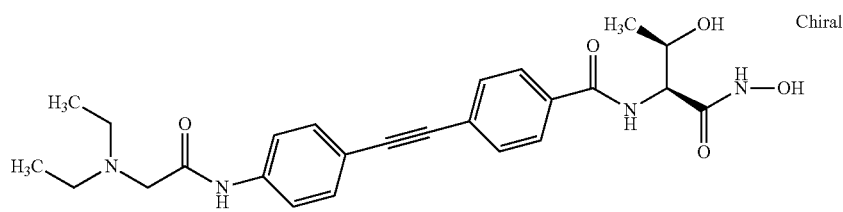
655 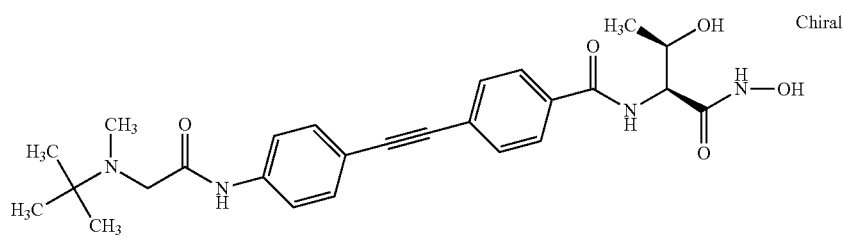

TABLE 1-continued
| 656 | 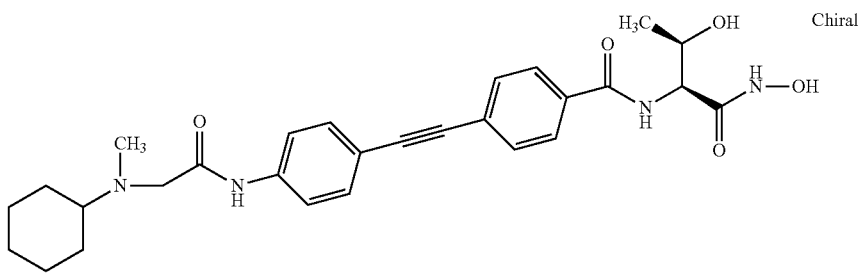 |
| 657 | 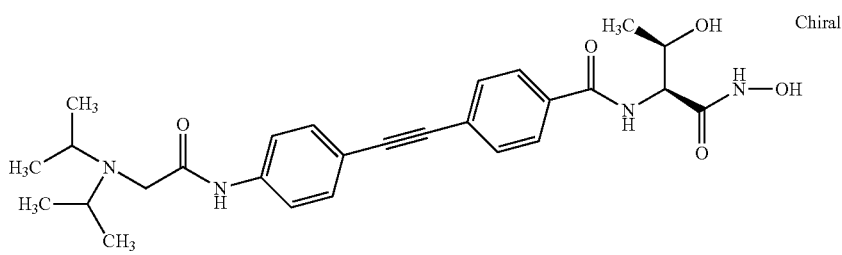 |
| 658 | 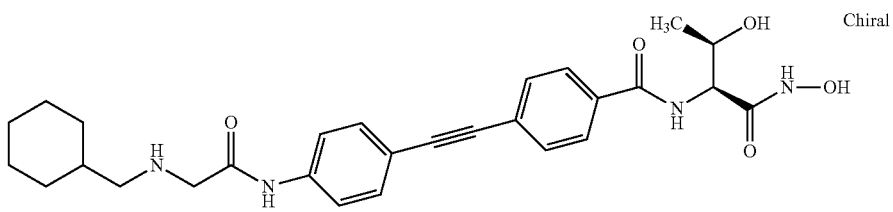 |
| 659 | 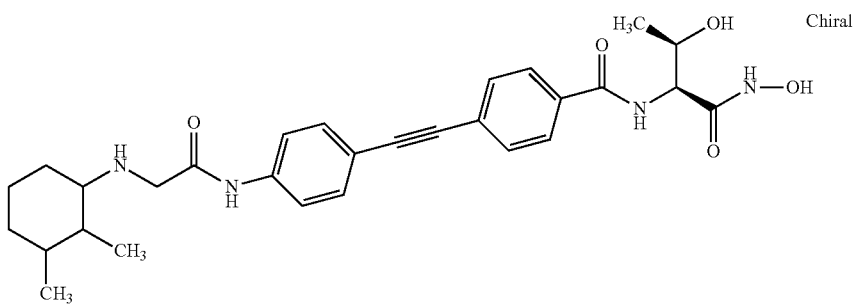 |
| 660 | 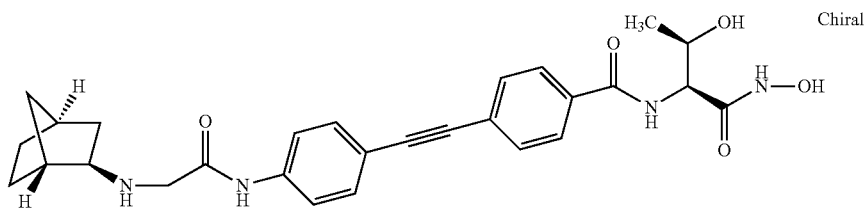 |
| 661 | 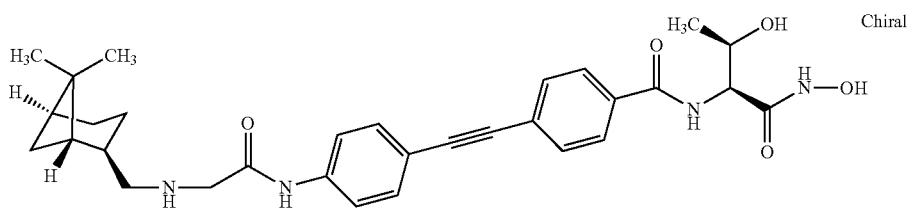 |

TABLE 1-continued
| 662 | 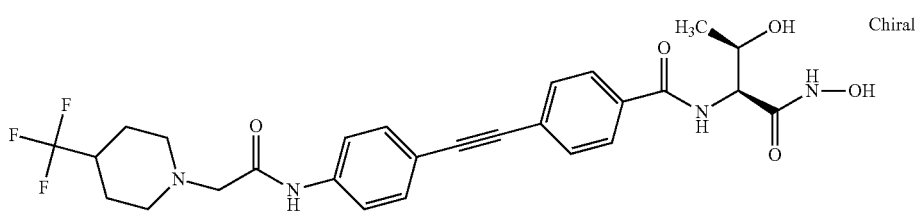 Chiral |
| 663 | 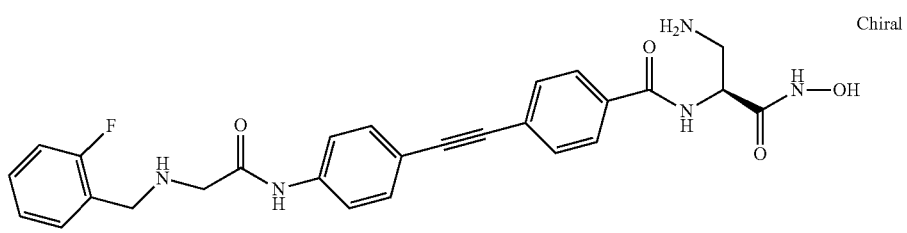 Chiral |
| 664 | 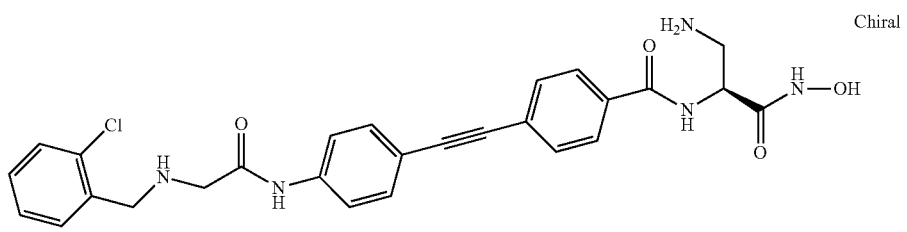 Chiral |
| 665 | 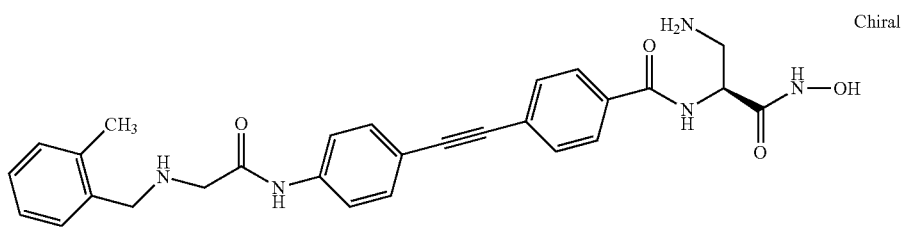 Chiral |
| 666 | 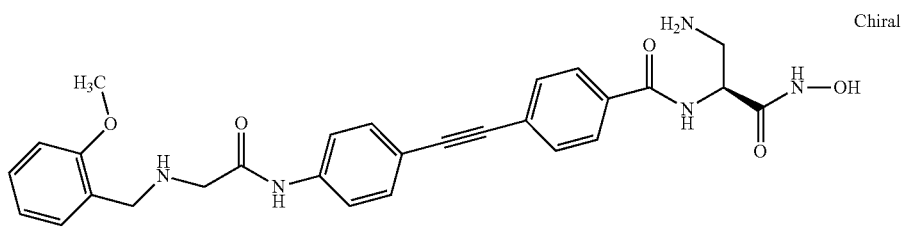 Chiral |
| 667 | 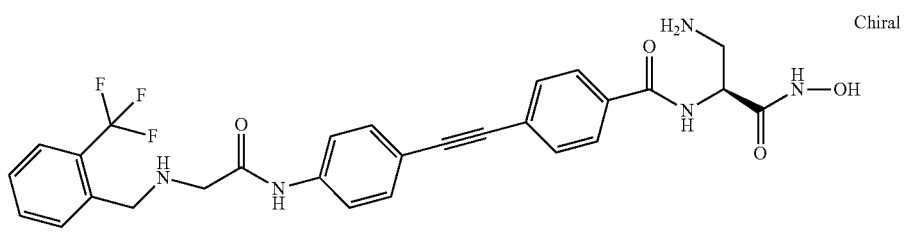 Chiral |
| 668 | 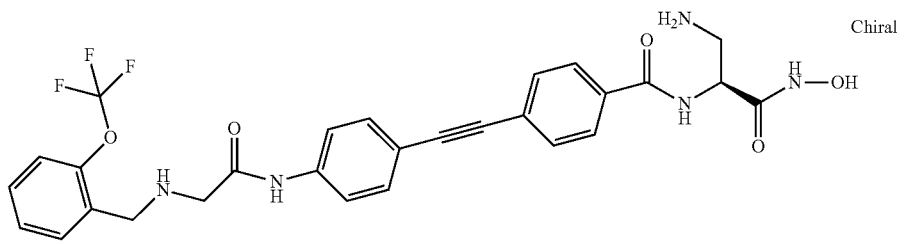 Chiral |

TABLE 1-continued
669
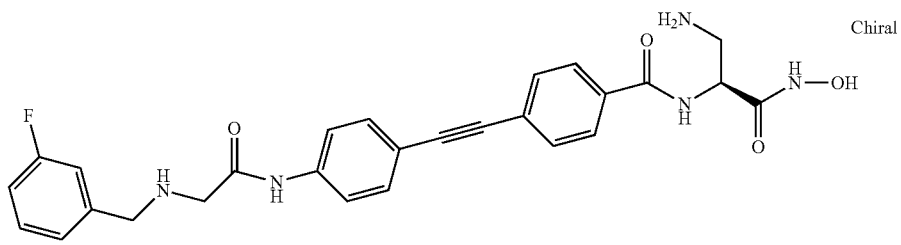
670
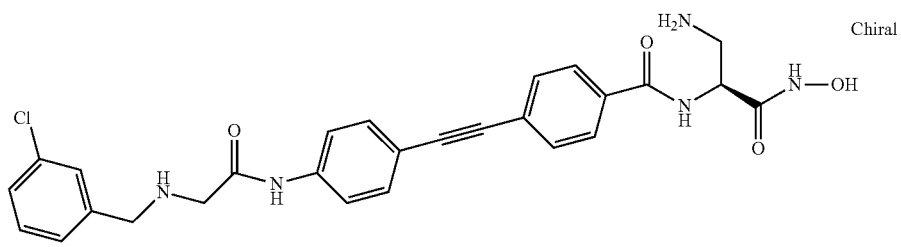
671
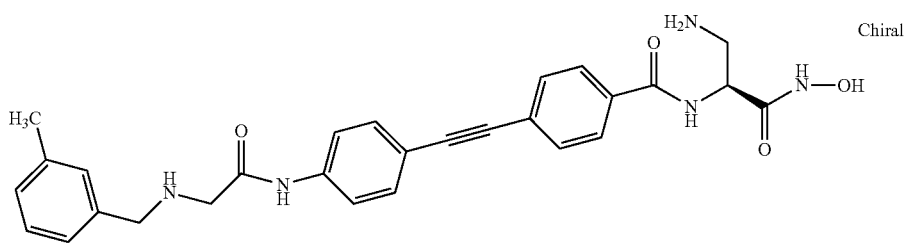
672
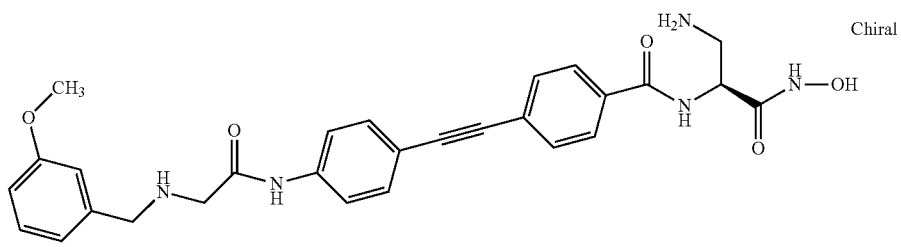
673
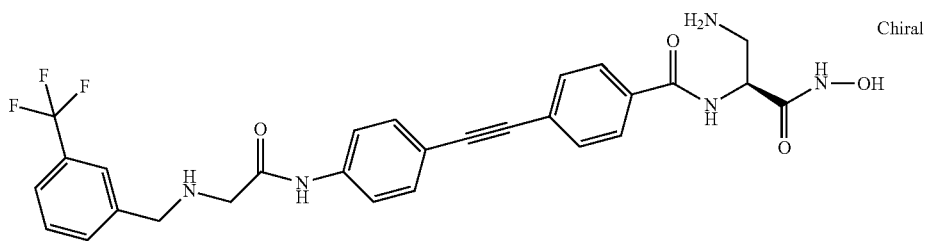
674
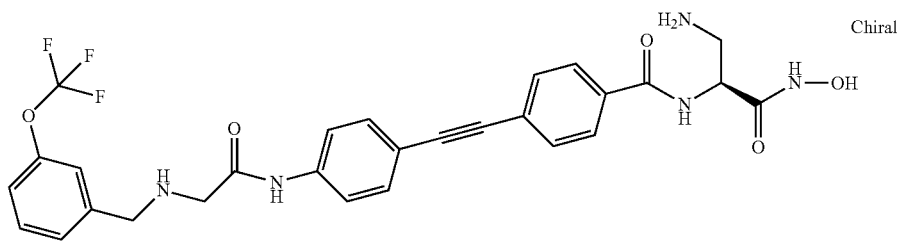

TABLE 1-continued
675 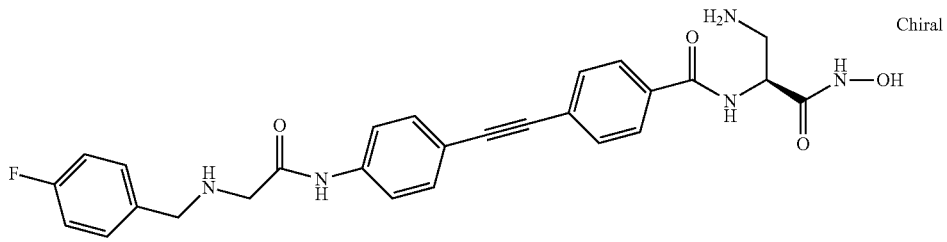
676 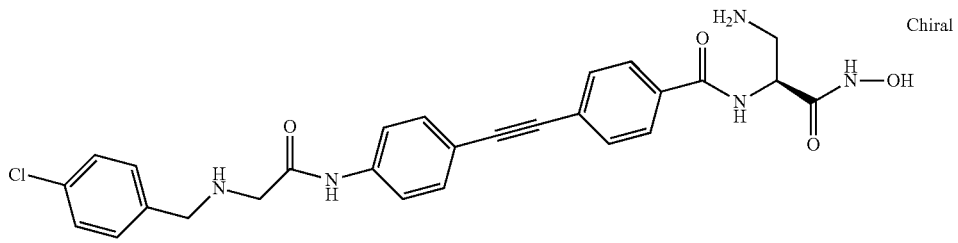
677 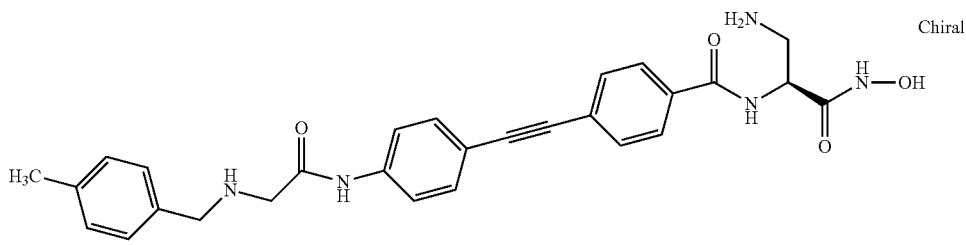
678 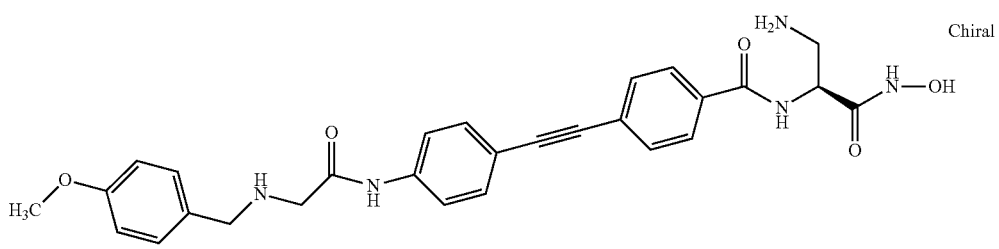
679 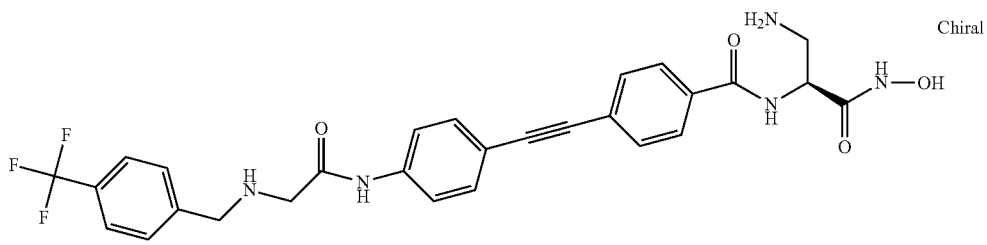
680 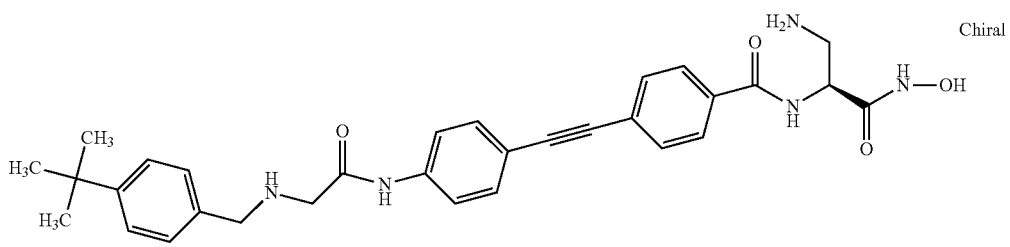

TABLE 1-continued
681
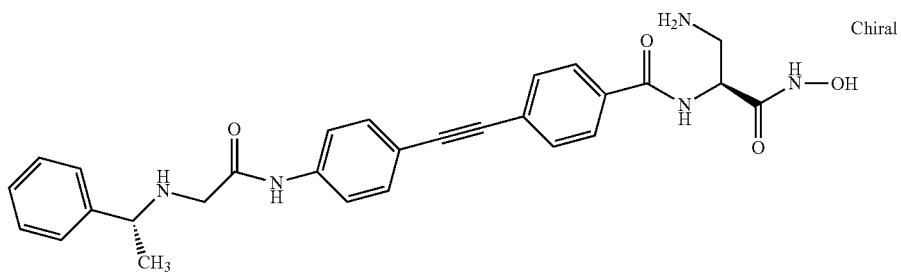
682
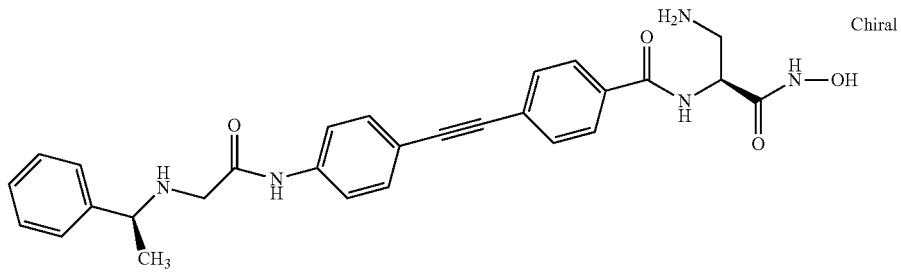
683
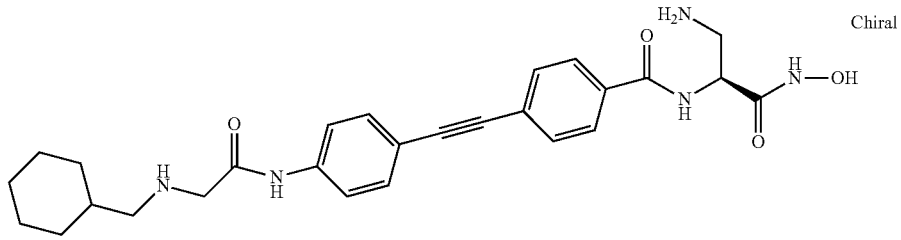
684
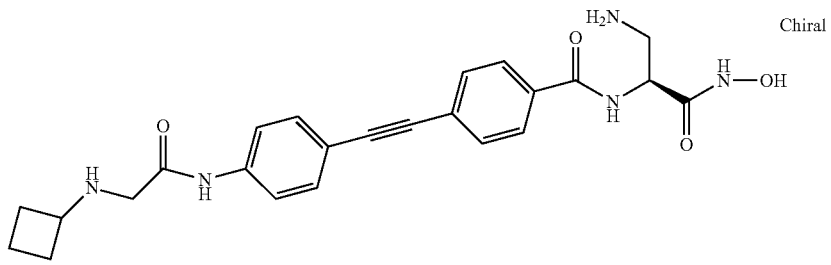
685
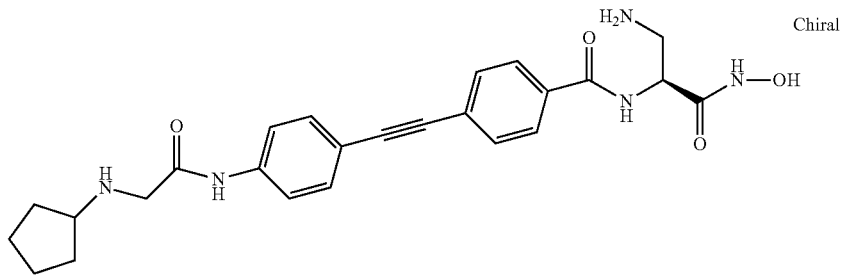
686
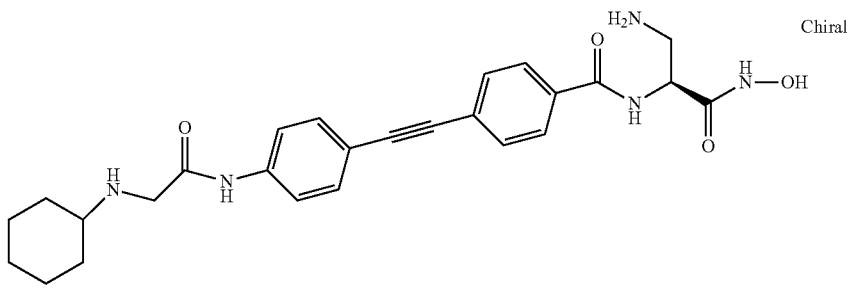

TABLE 1-continued
| 687 | 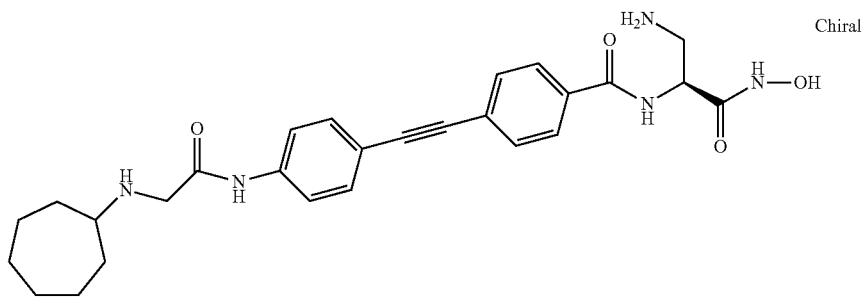 |
| 688 | 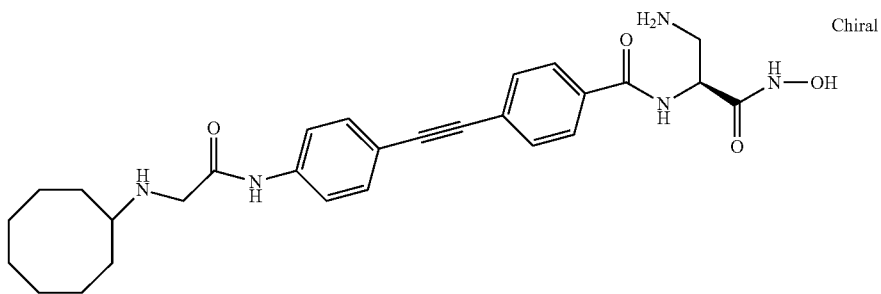 |
| 689 | 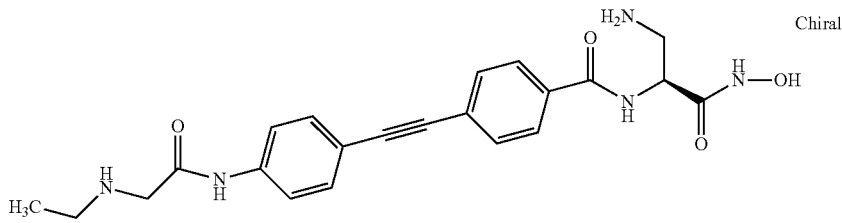 |
| 690 | 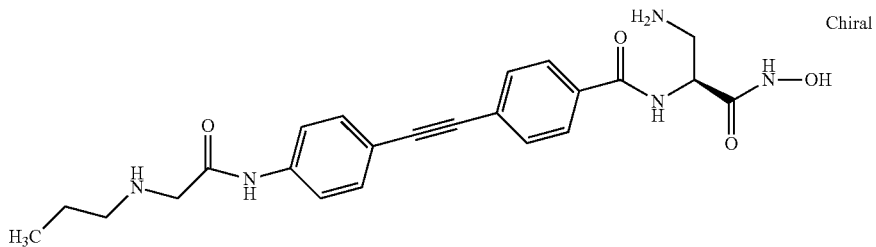 |
| 691 | 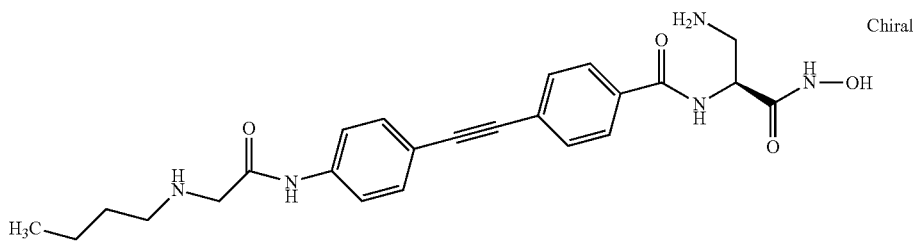 |
| 692 | 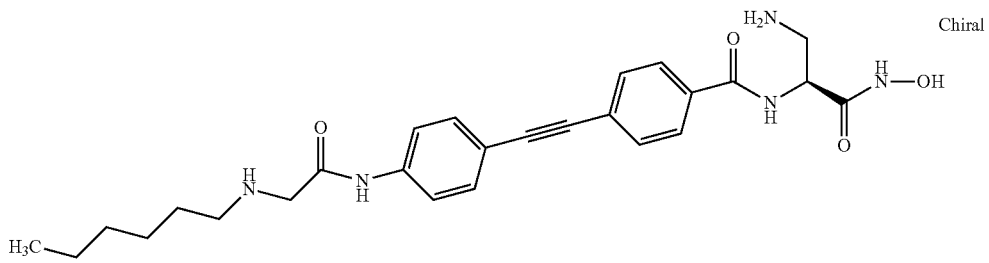 |

TABLE 1-continued
693 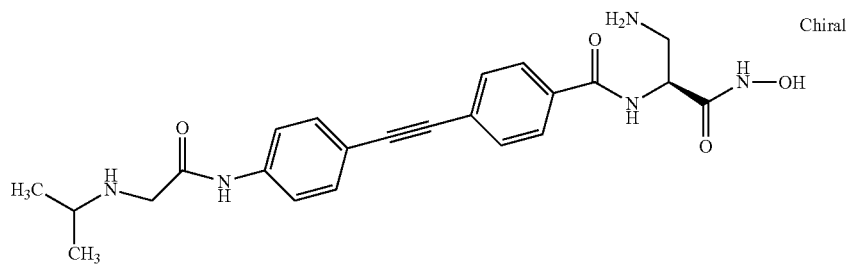 Chiral
694 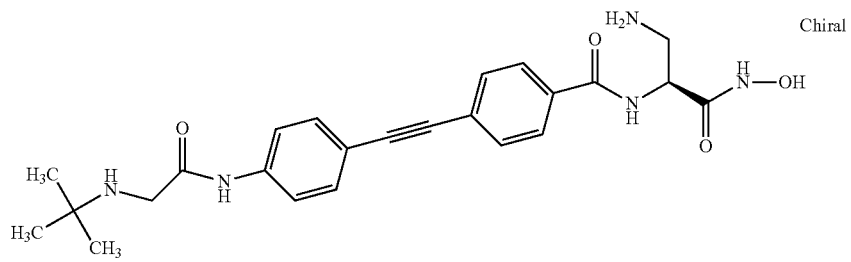 Chiral
695 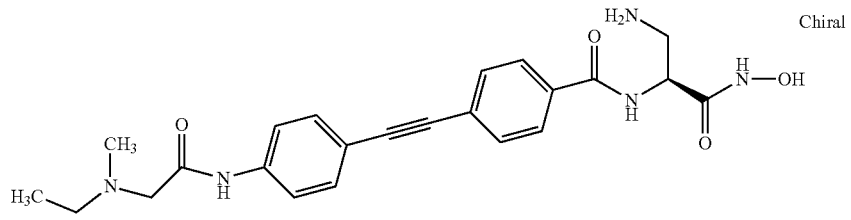 Chiral
696 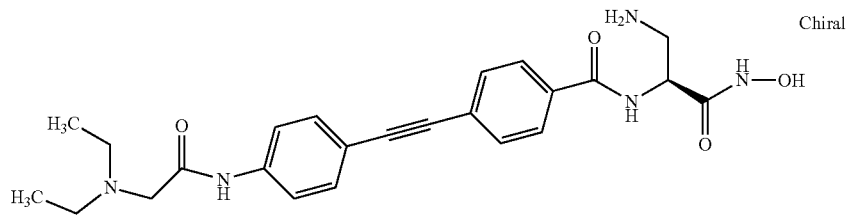 Chiral
697 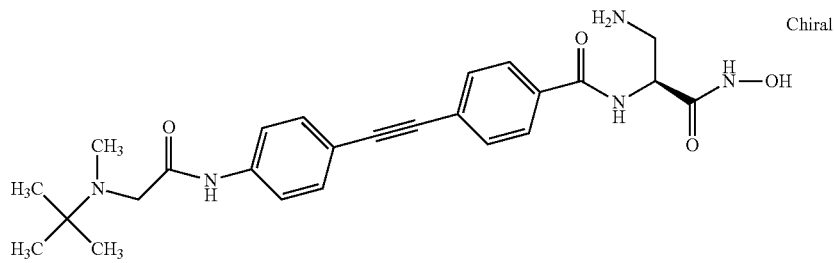 Chiral
698 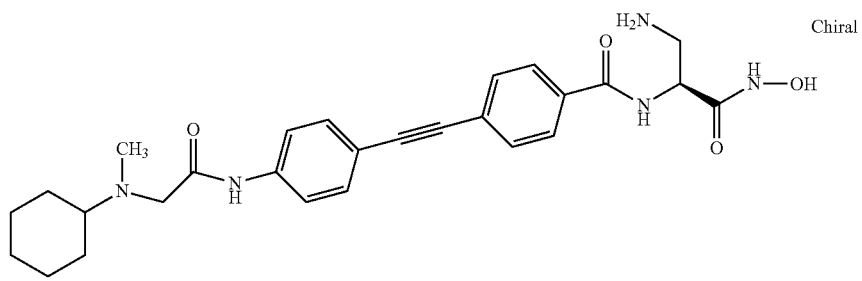 Chiral TABLE 1-continued
| 699 | 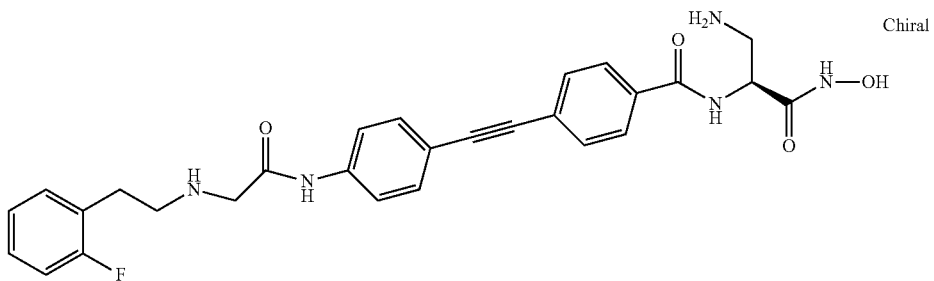 |
| 700 | 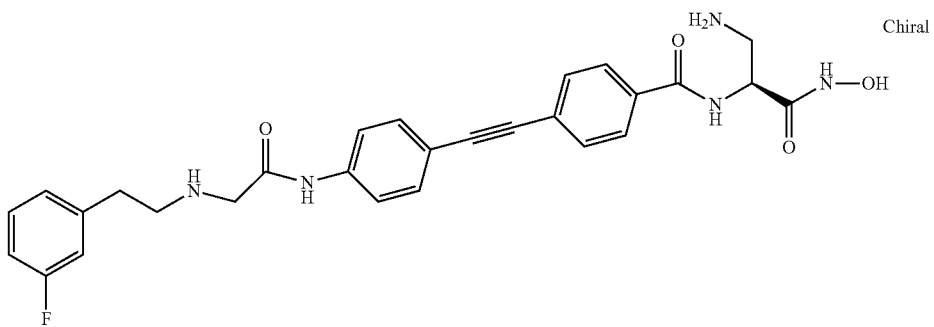 |
| 701 | 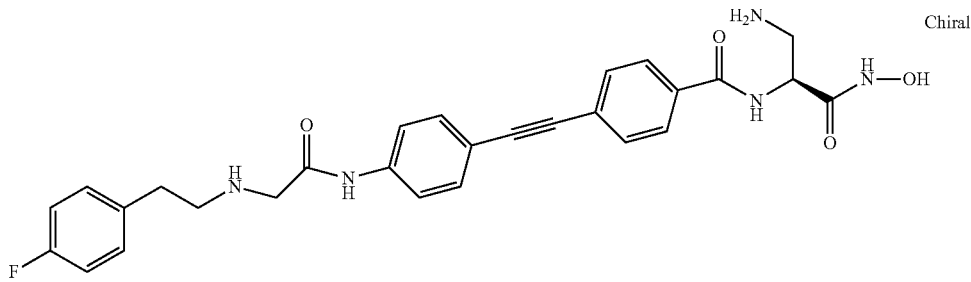 |
| 702 | 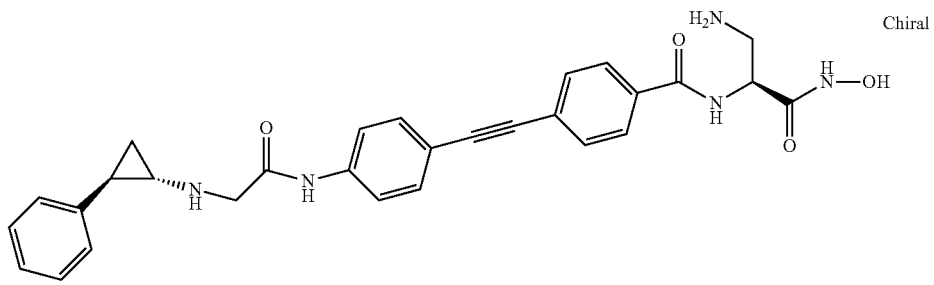 |
| 703 | 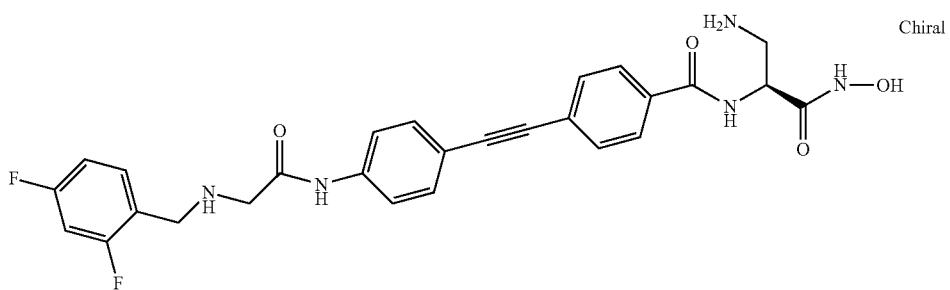 |

TABLE 1-continued
| 704 | 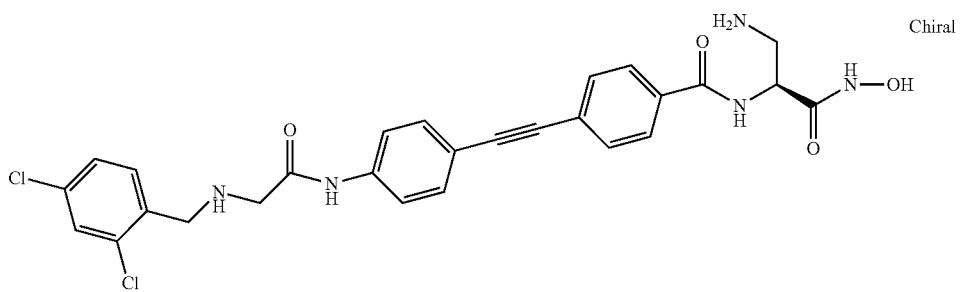 | Chiral |
| 705 | 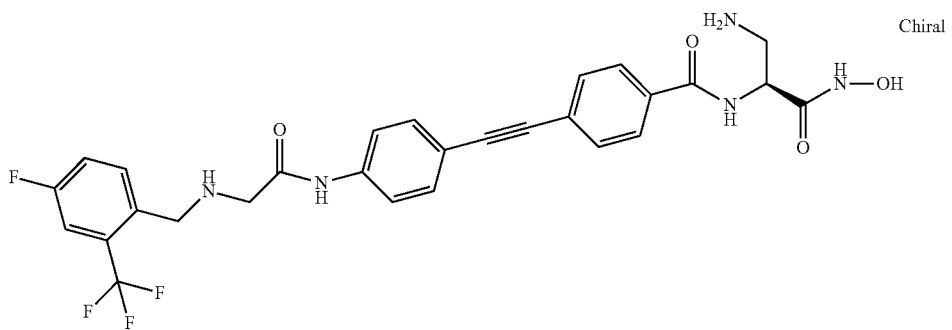 | Chiral |
| 706 | 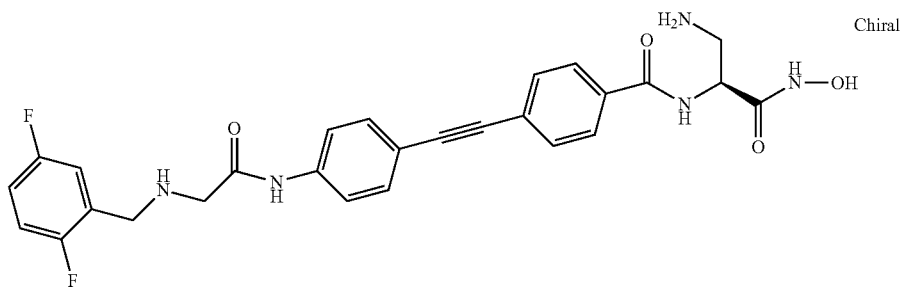 | Chiral |
| 707 | 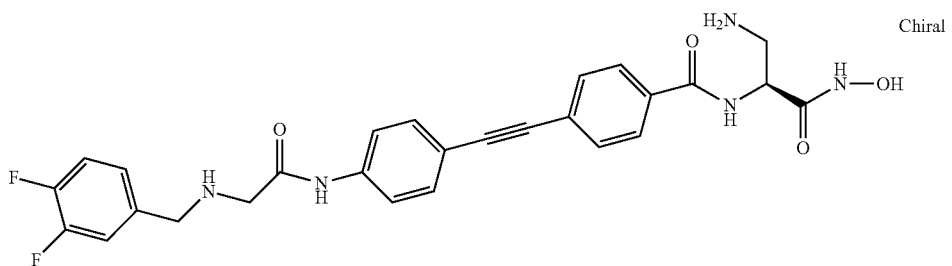 | Chiral |
| 708 | 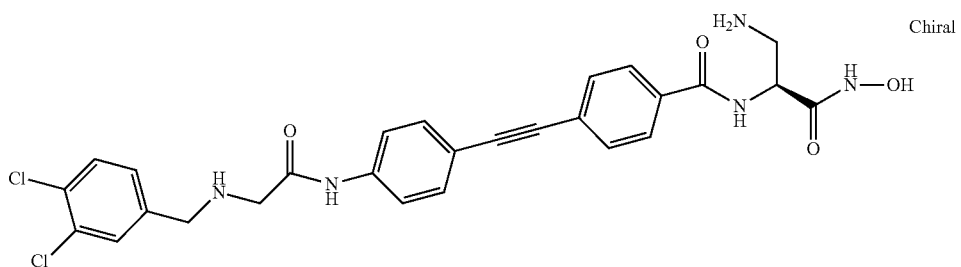 | Chiral |

TABLE 1-continued
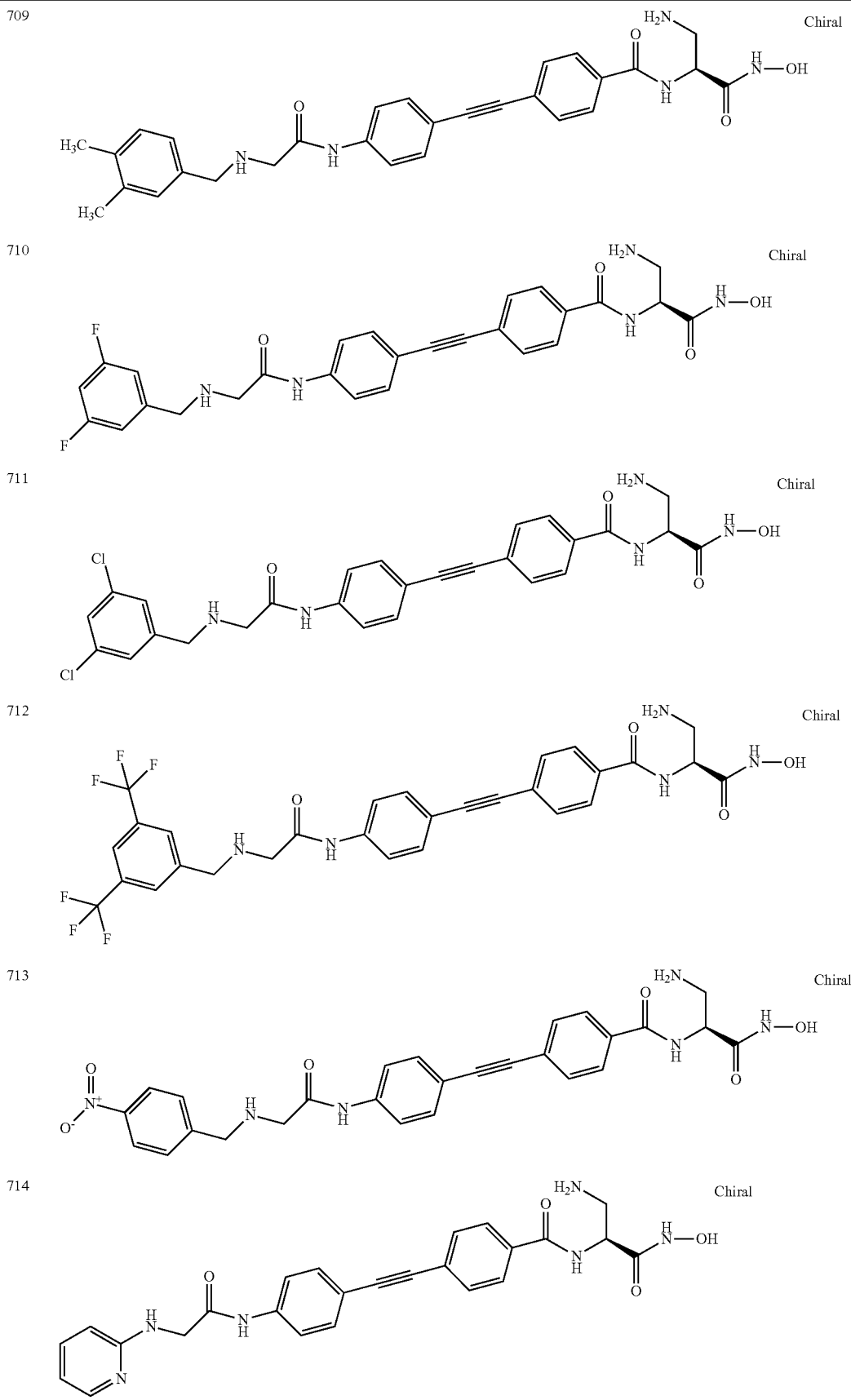

TABLE 1-continued
715
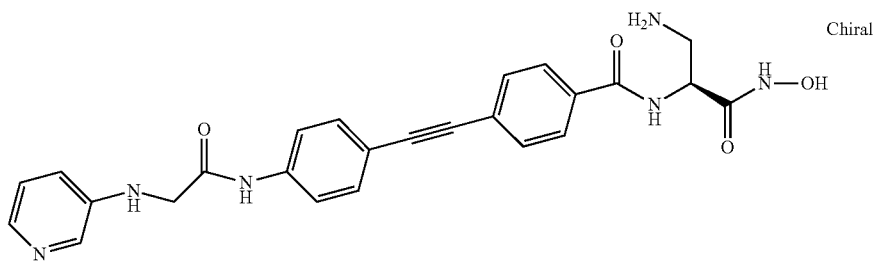
716
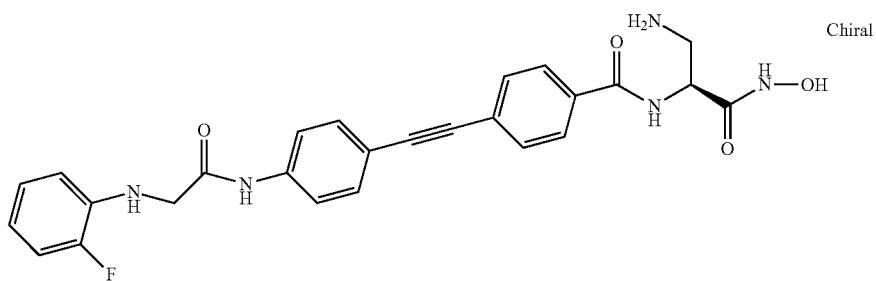
717
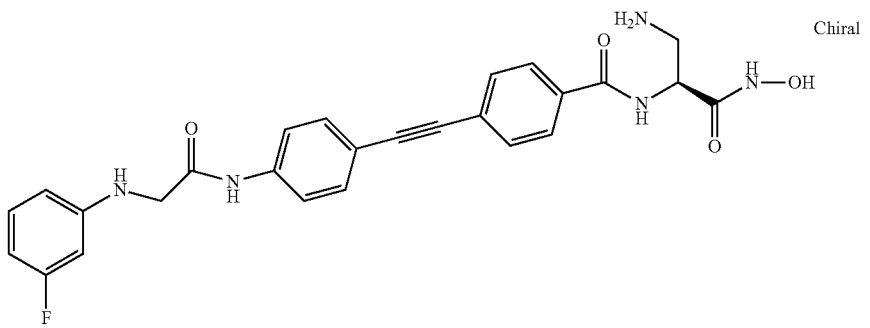
718
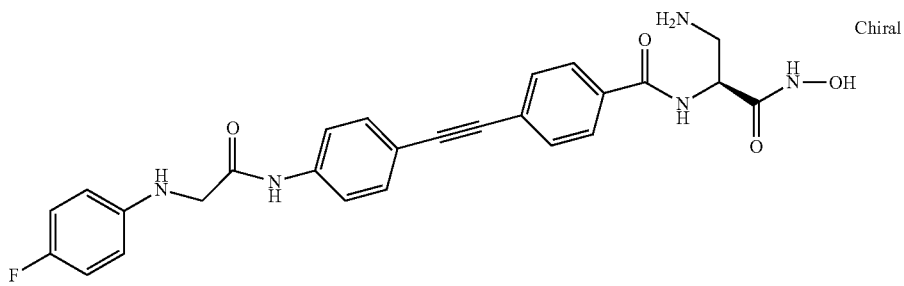
719
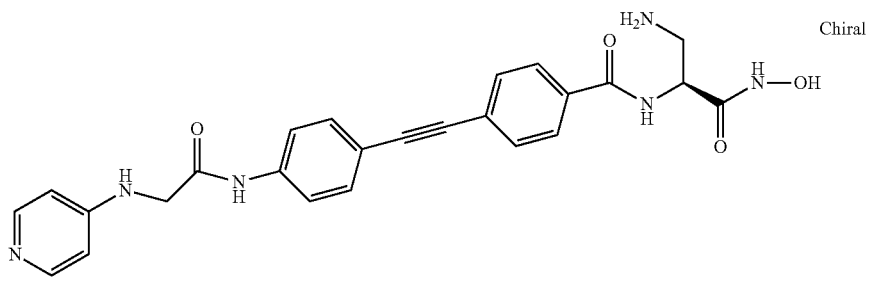

TABLE 1-continued
| 720 | 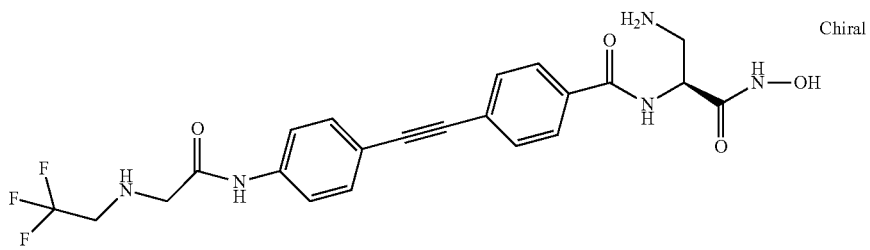 |
| --- | --- |
| 721 | 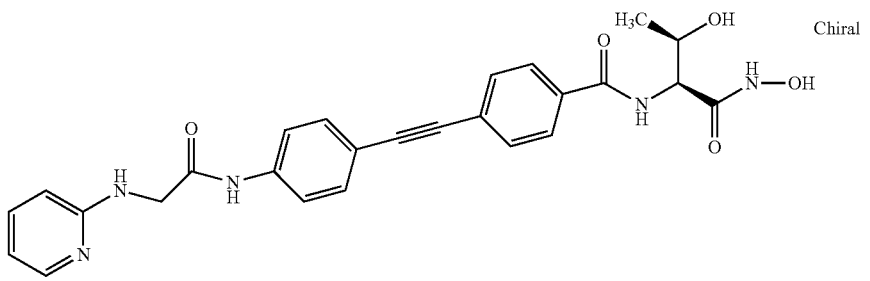 |
| 722 | 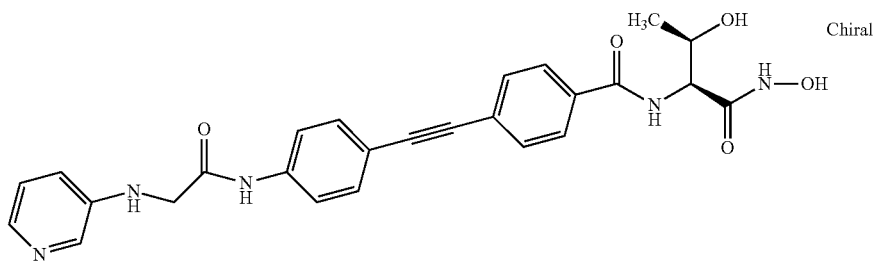 |
| 723 | 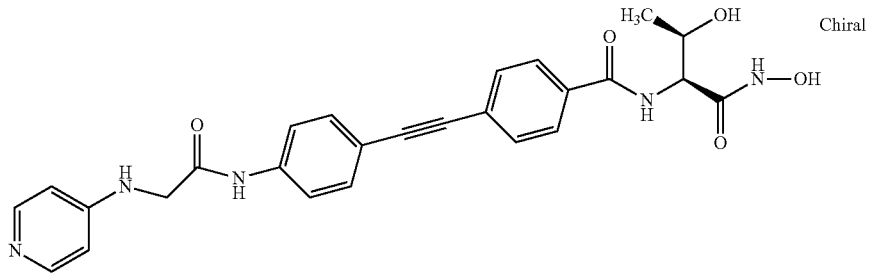 |
| 724 | 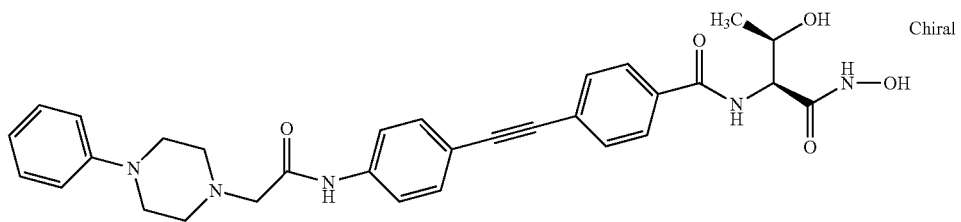 |
| 725 | 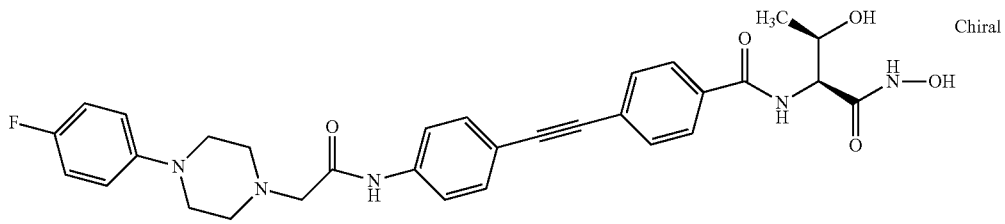 |

TABLE 1-continued
726
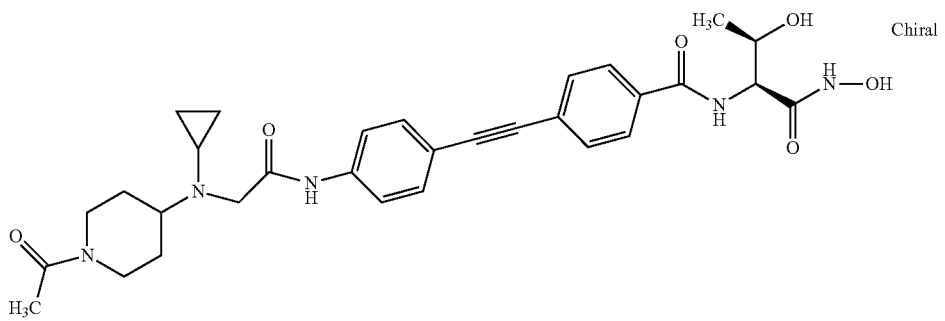
727
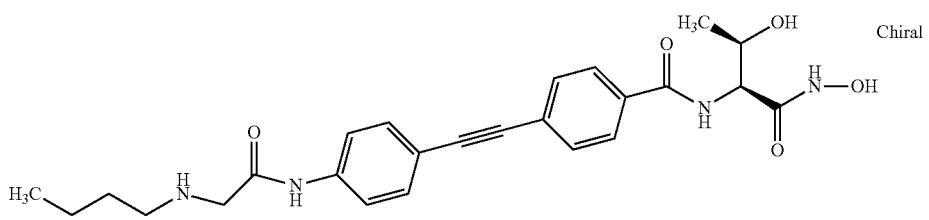
728
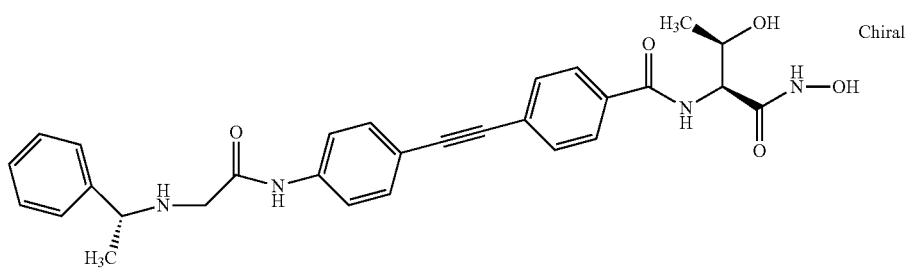
729
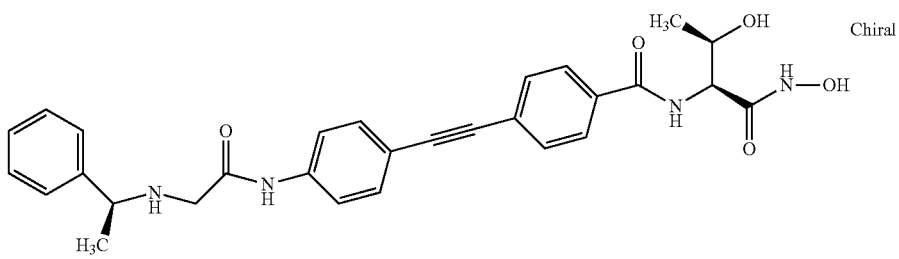
730
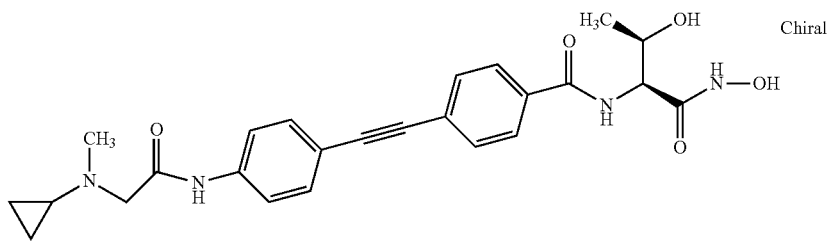
731
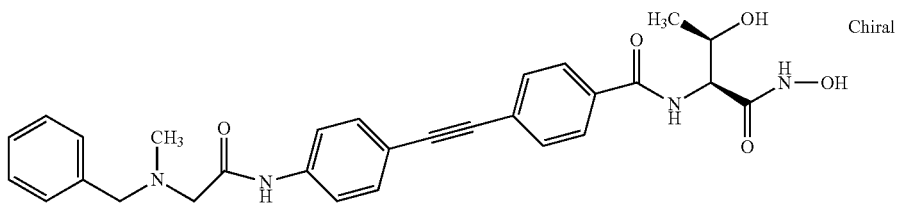

TABLE 1-continued
| 732 | 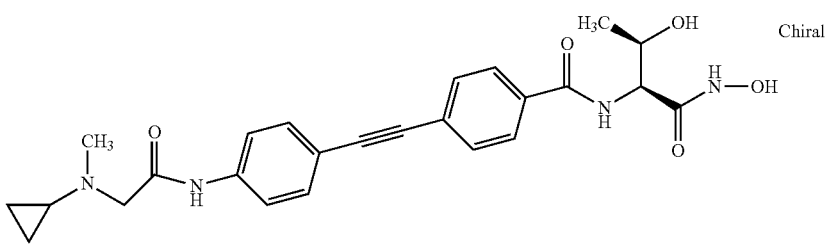 |
| --- | --- |
| 733 | 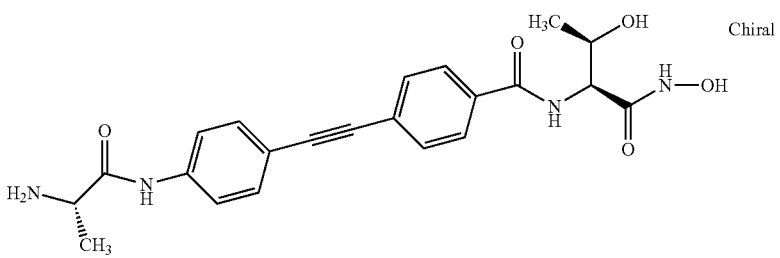 |
| 734 | 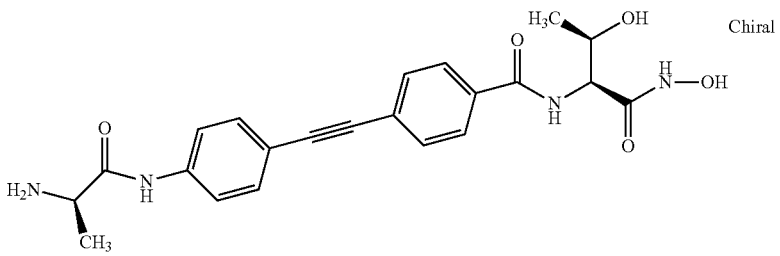 |
| 735 | 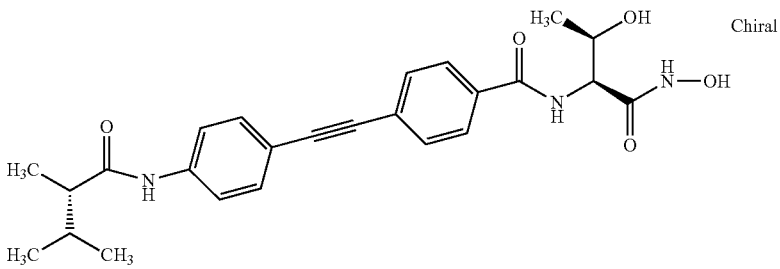 |
| 736 | 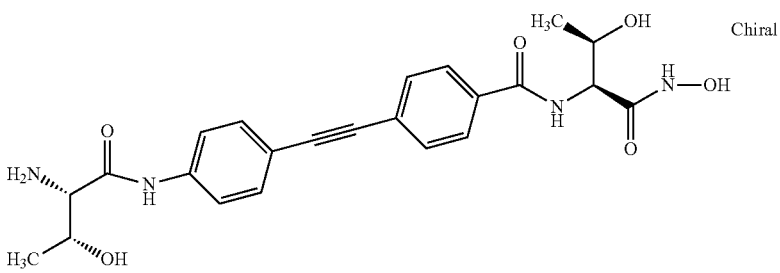 |
| 737 | 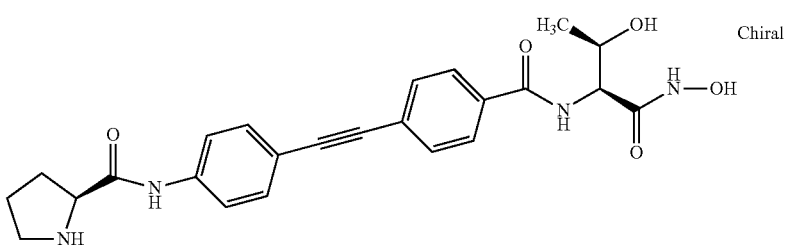 |

TABLE 1-continued
| 738 | 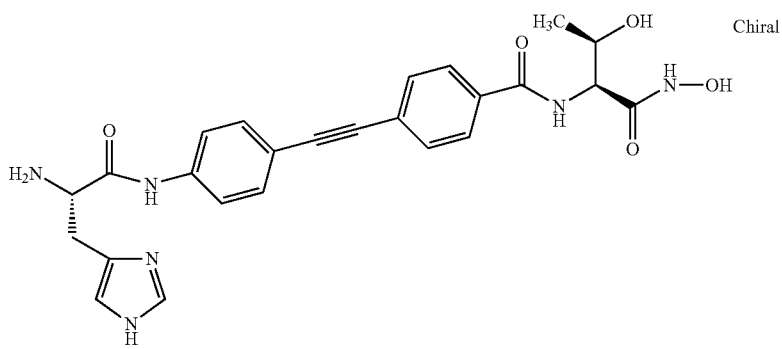 |
| --- | --- |
| 739 | 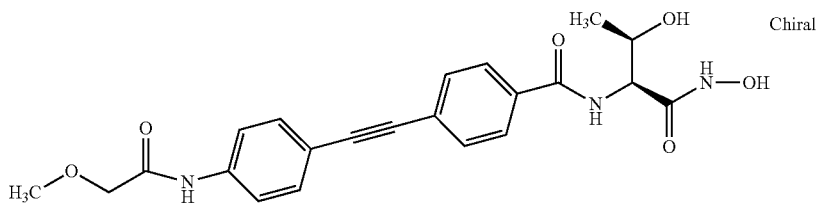 |
| 740 | 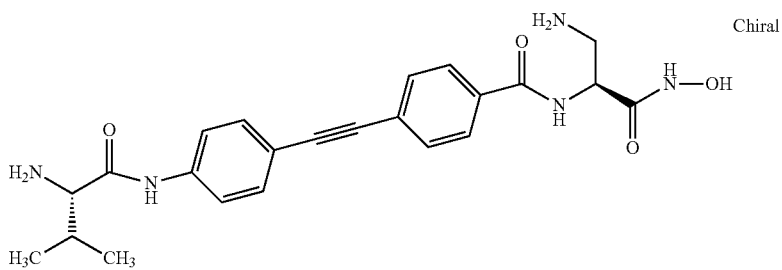 |
| 741 | 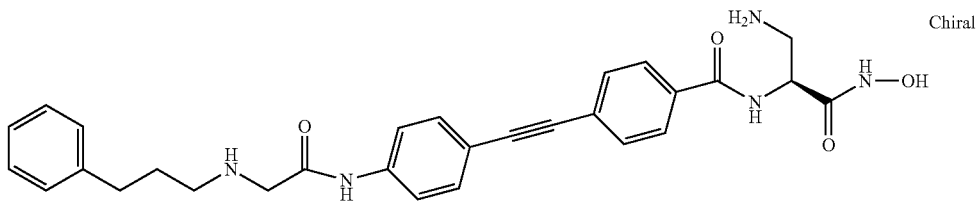 |
| 742 | 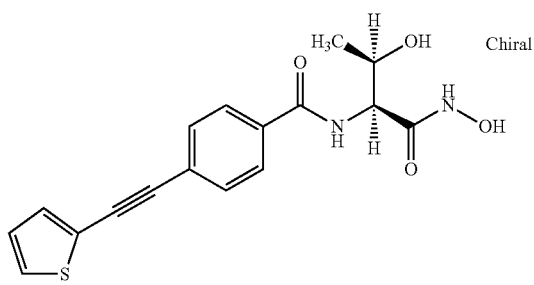 |

TABLE 1-continued
743
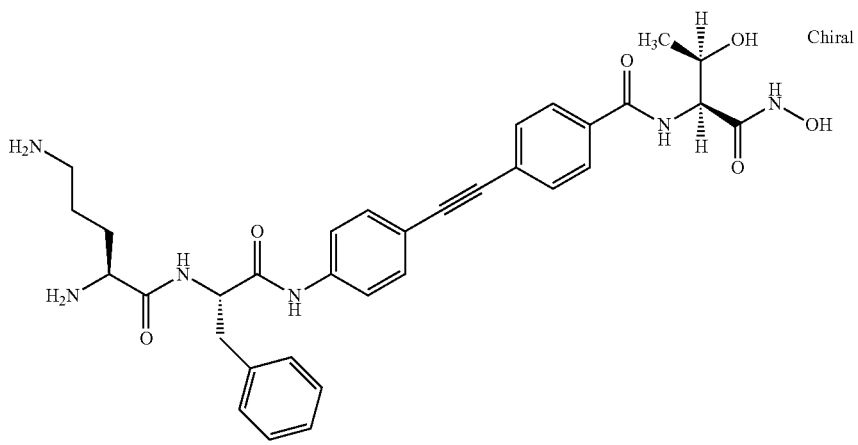
744
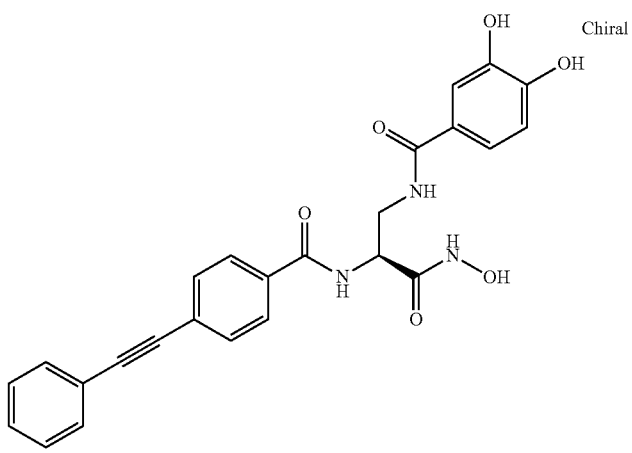
745
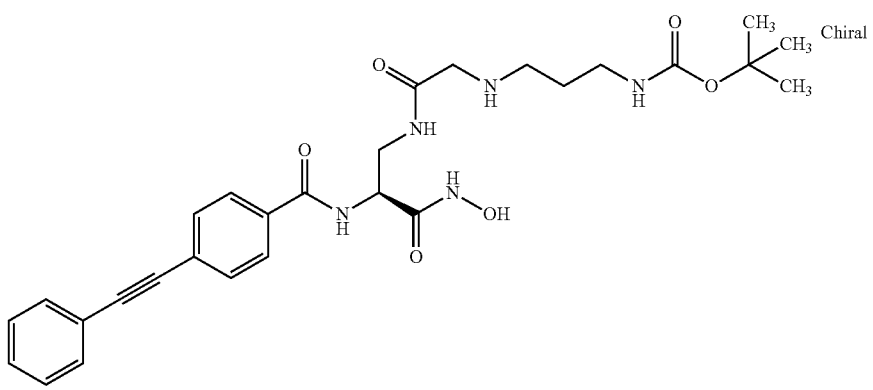
746
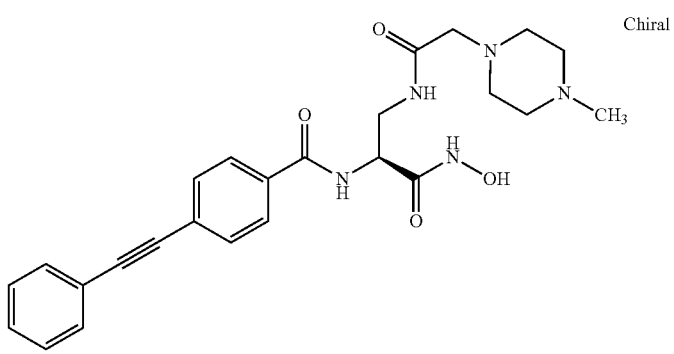

TABLE 1-continued
| 747 | 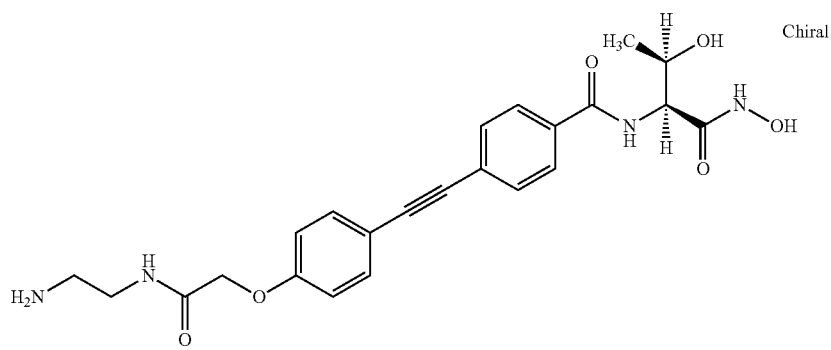 |
| 748 | 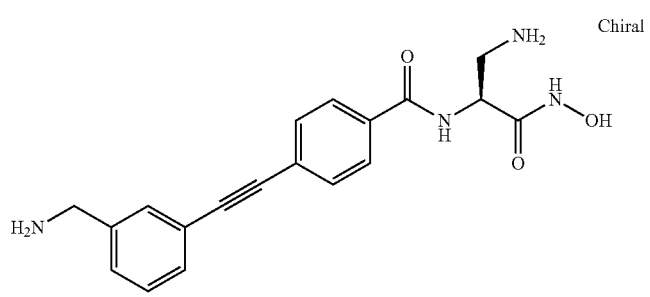 |
| 749 | 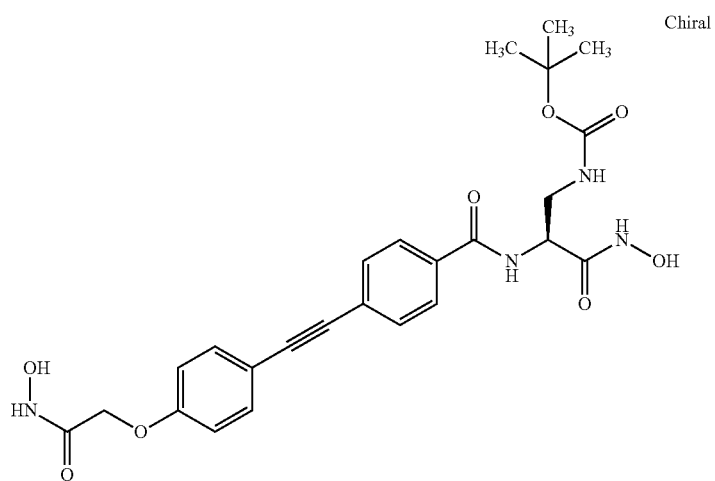 |
| 750 | 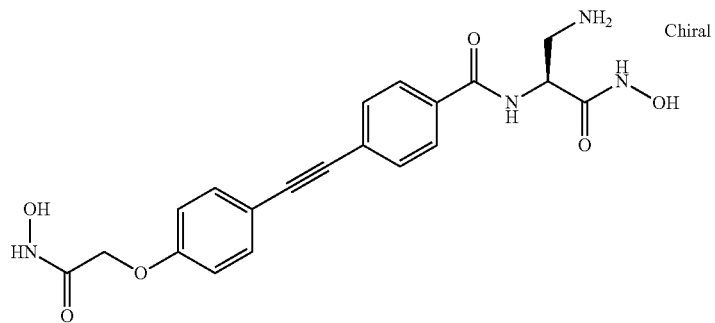 |

TABLE 1-continued
751
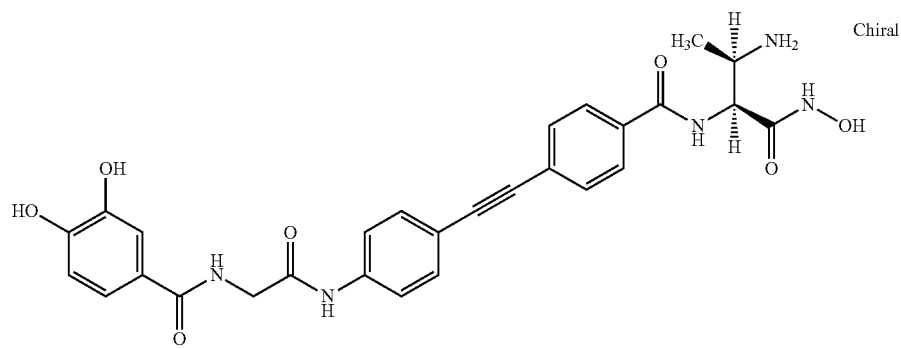
752
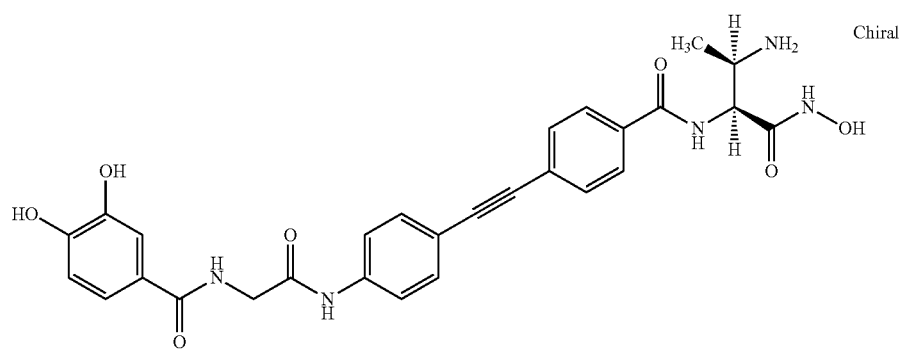
753
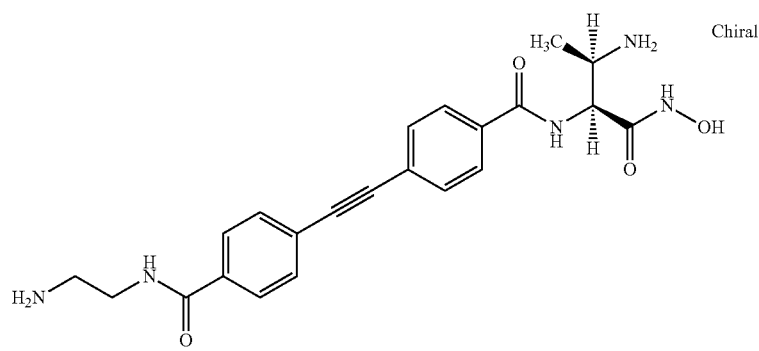
754
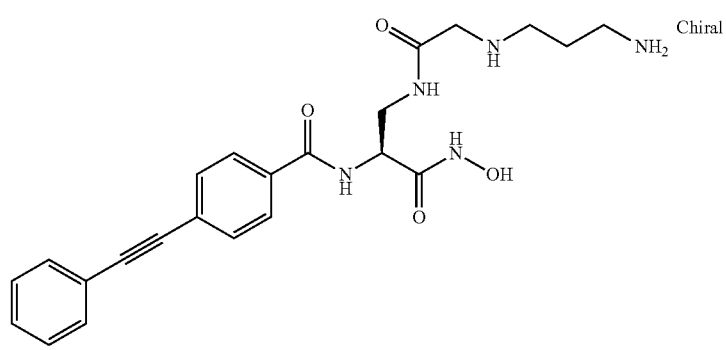

TABLE 1-continued
755 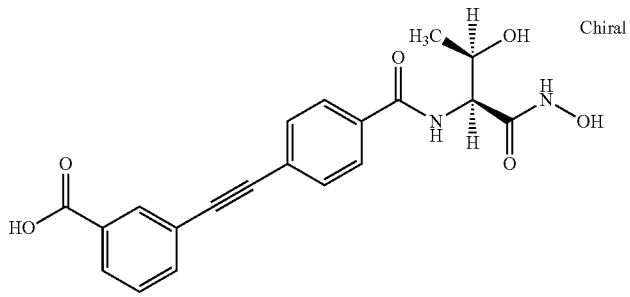
756 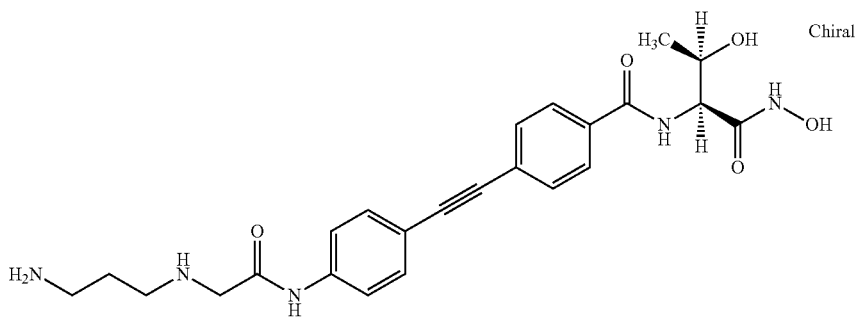
757 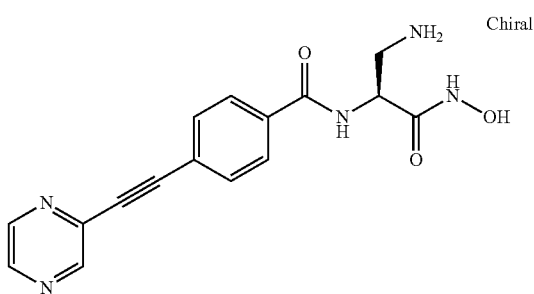
758 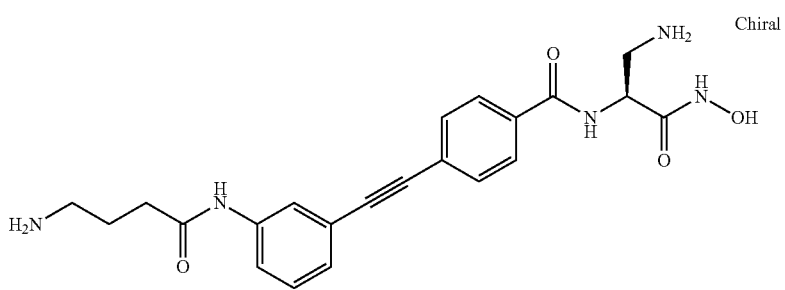
759 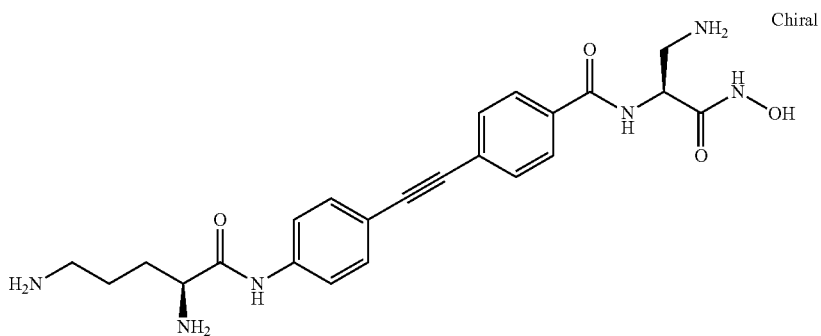

TABLE 1-continued
| 760 | 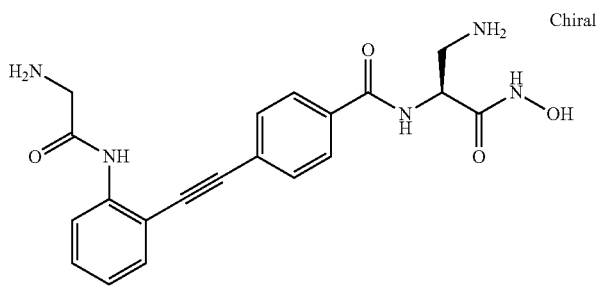 |
| 761 | 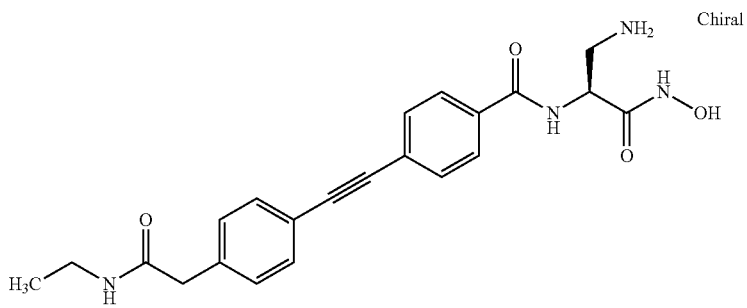 |
| 762 | 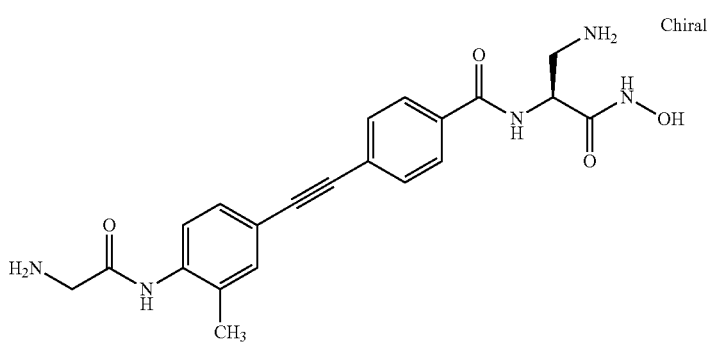 |
| 763 | 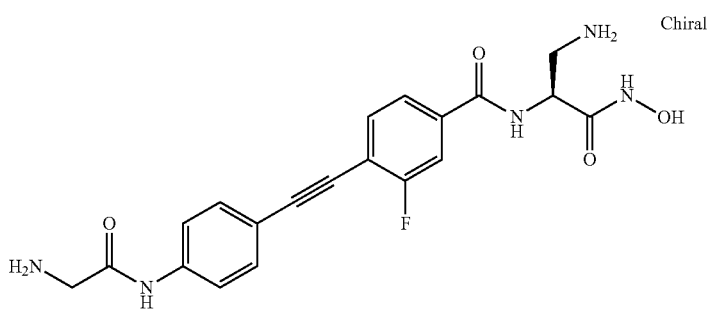 |
| 764 | 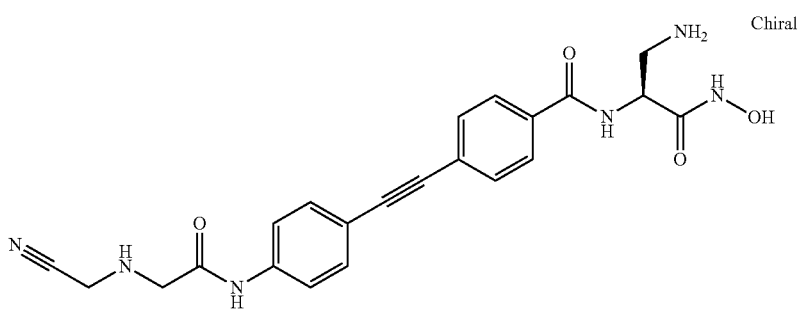 |

TABLE 1-continued
| 765 | 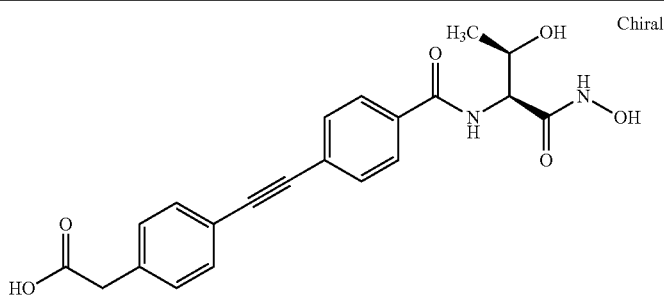 |
| --- | --- |
| 766 | 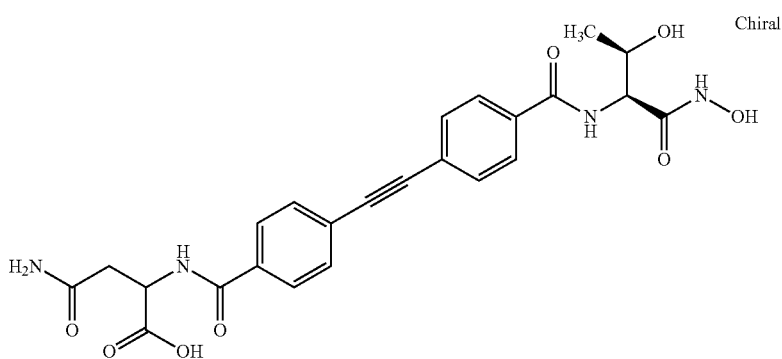 |
| 767 | 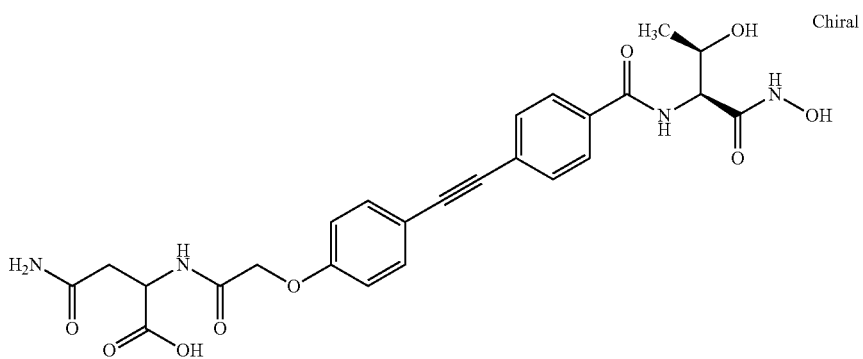 |
| 768 | 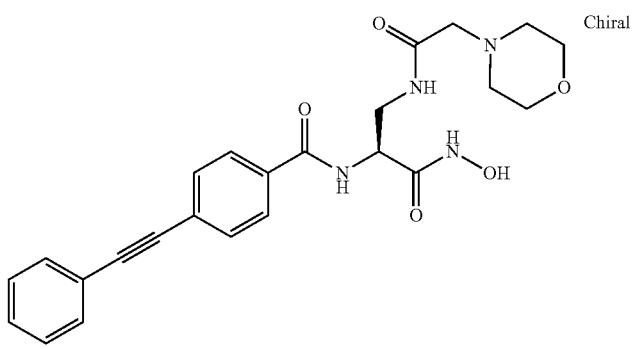 |

TABLE 1-continued
769 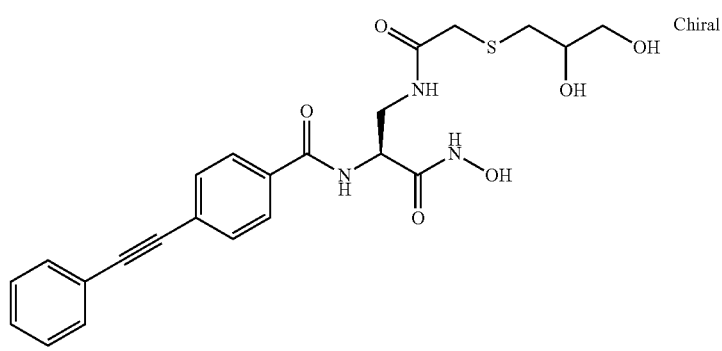
770 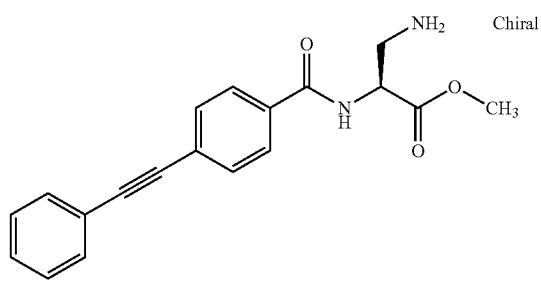
771 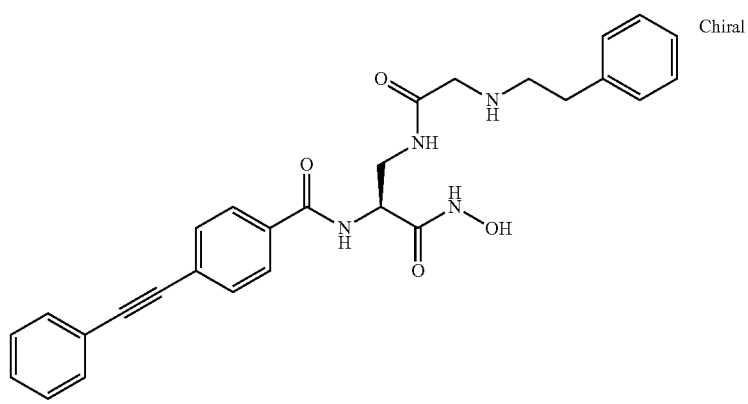
772 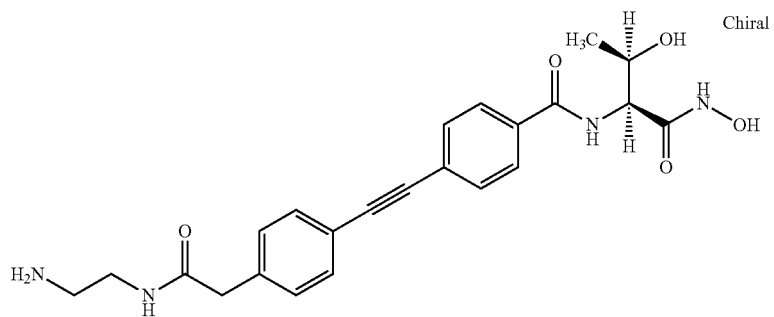

TABLE 1-continued
| 773 | 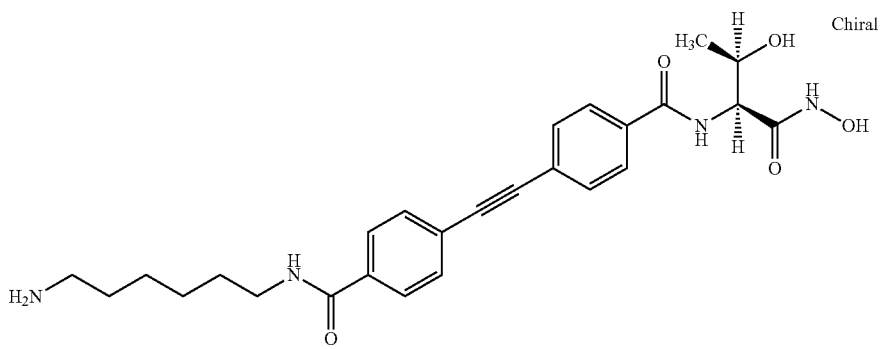 |
| --- | --- |
| 774 | 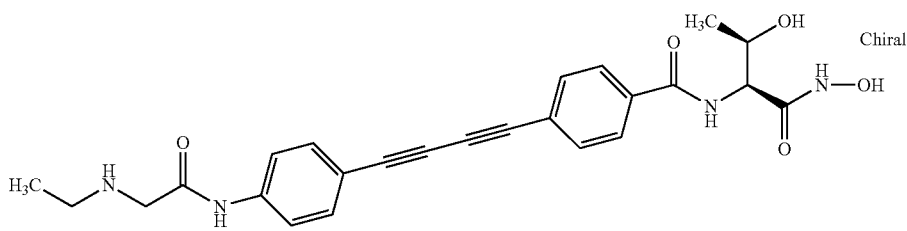 |
| 775 | 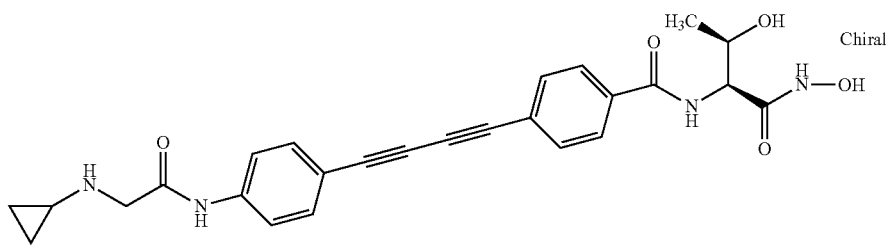 |
| 776 | 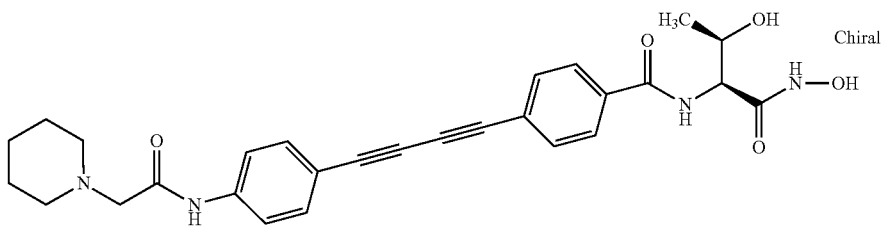 |
| 777 | 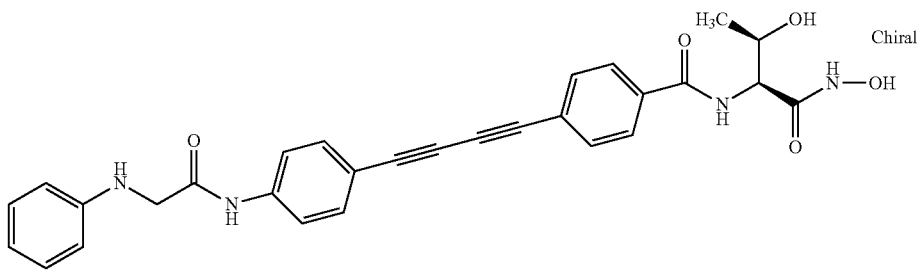 |
| 778 | 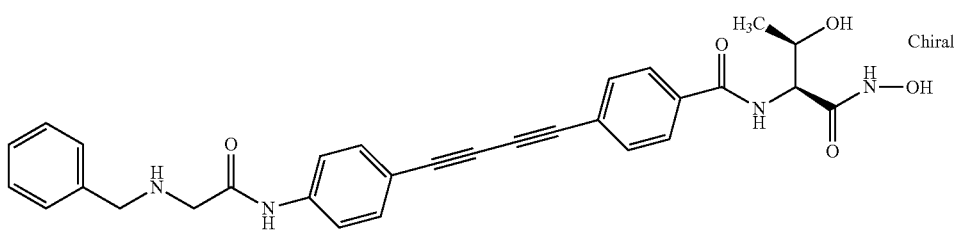 |

TABLE 1-continued
779 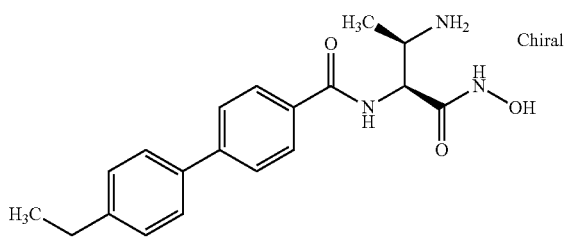
780 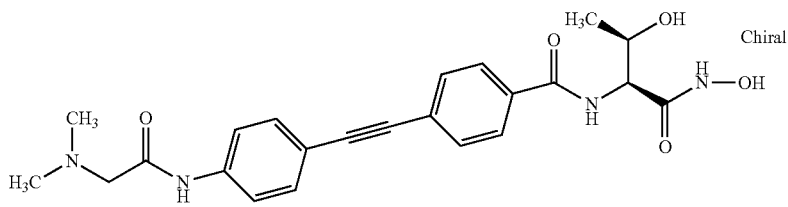
781 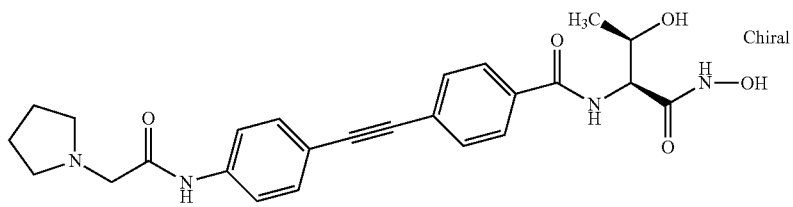
782 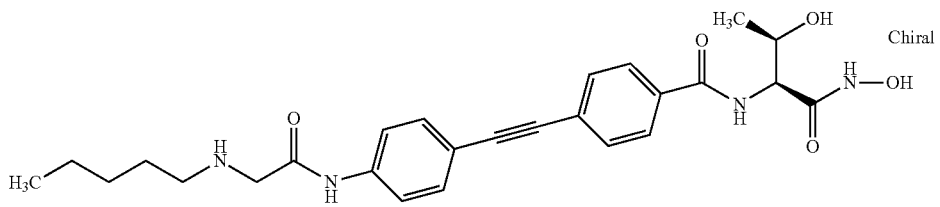
783 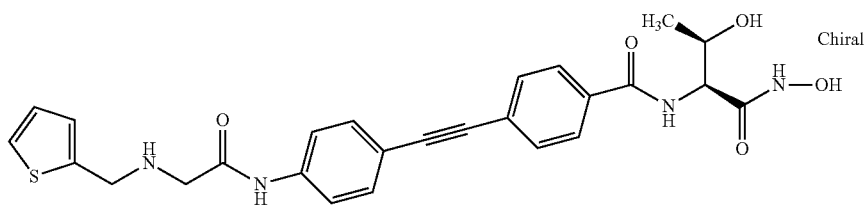
784 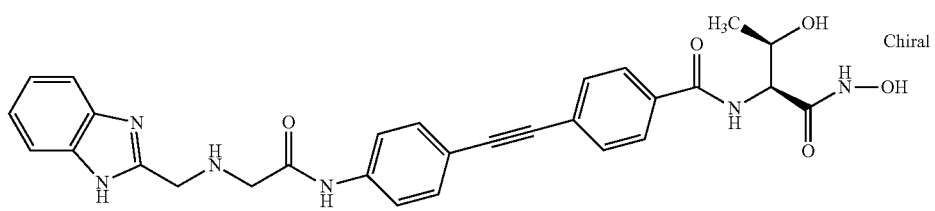
785 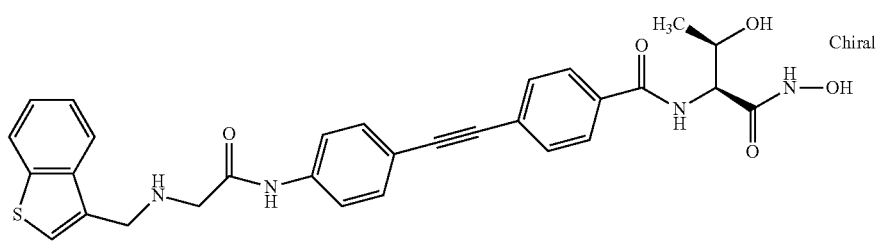

TABLE 1-continued
786
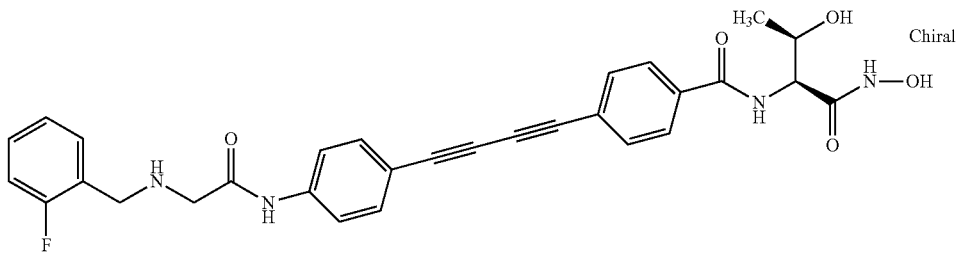
787
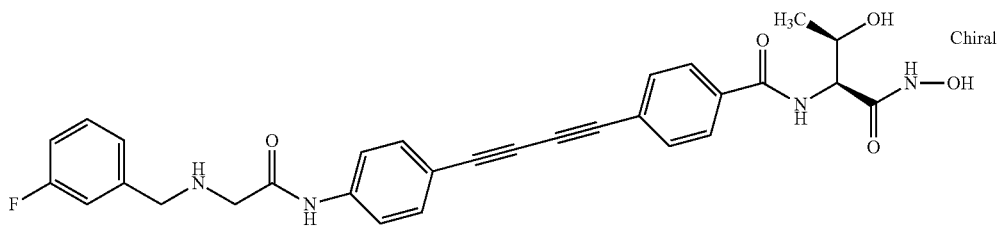
788
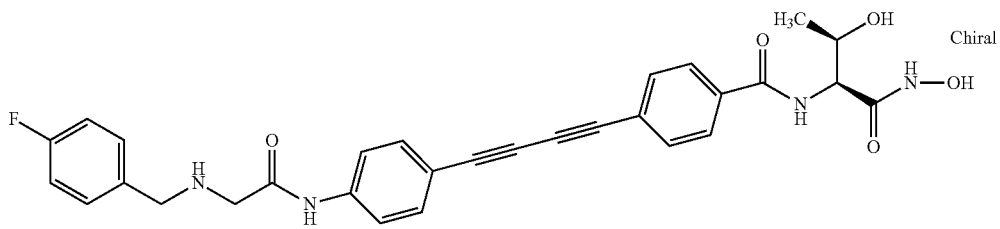
789
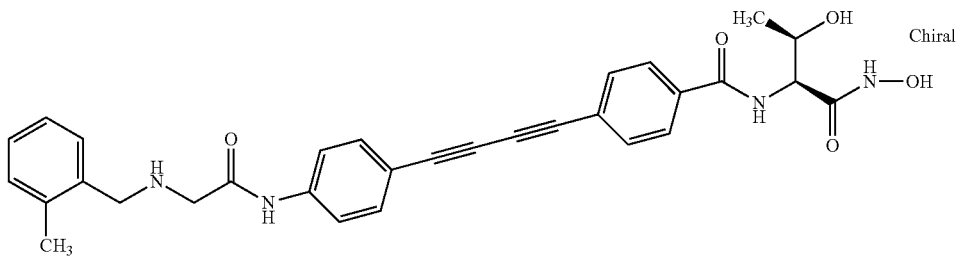
790
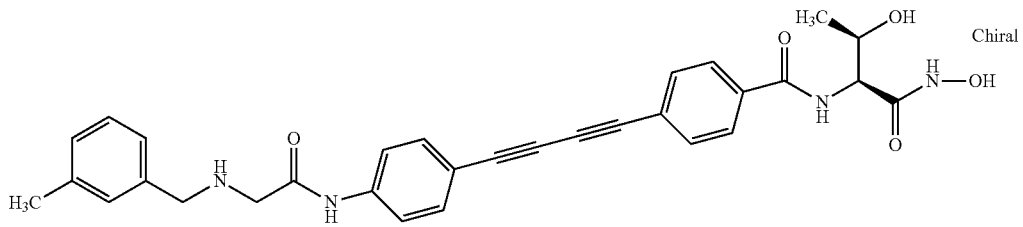
791
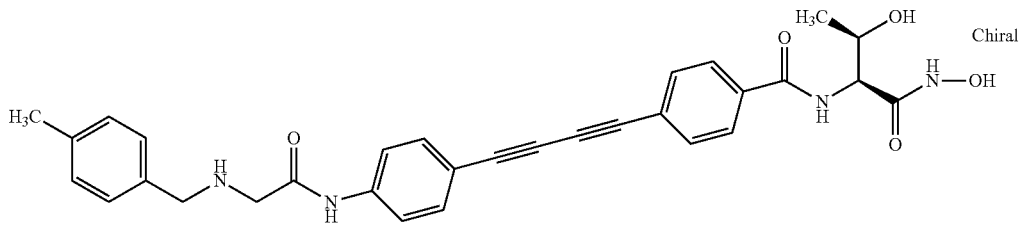

TABLE 1-continued
| 792 | 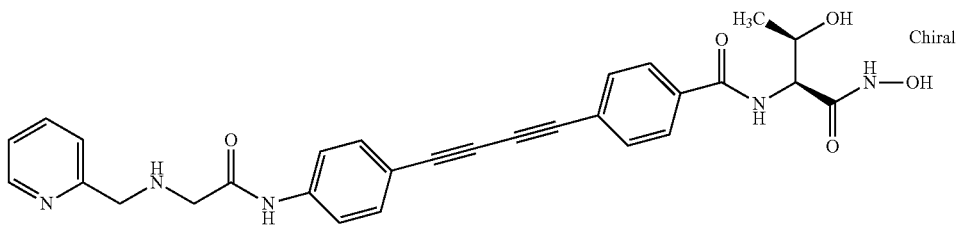 |
| --- | --- |
| 793 | 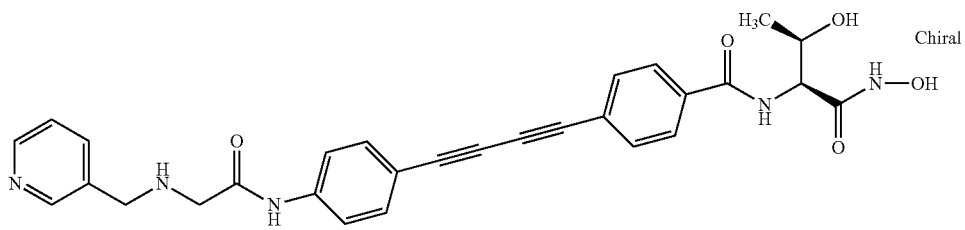 |
| 794 | 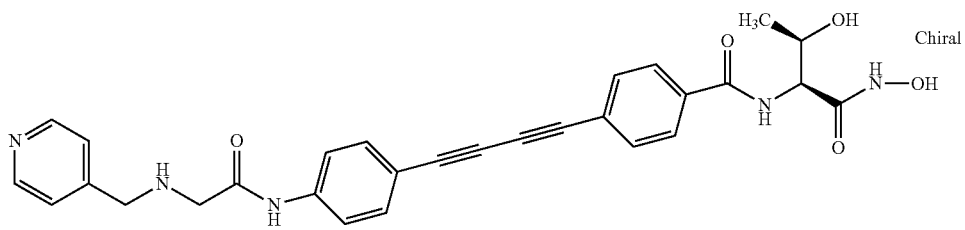 |
| 795 | 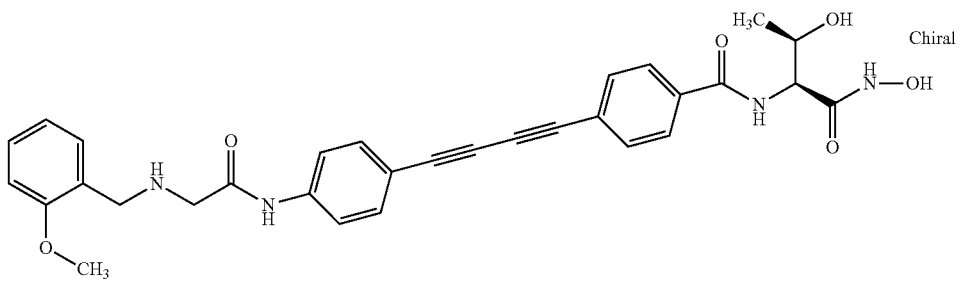 |
| 796 | 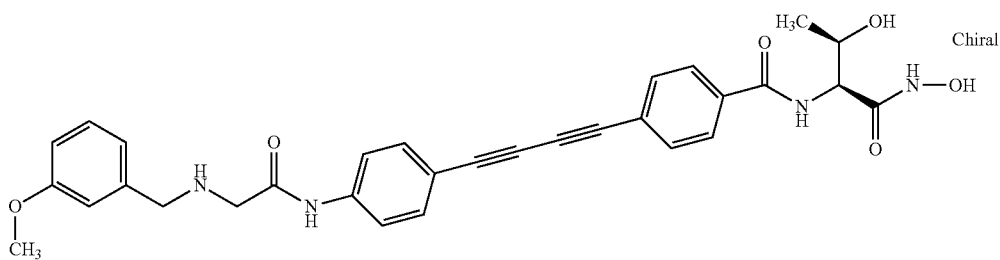 |
| 797 | 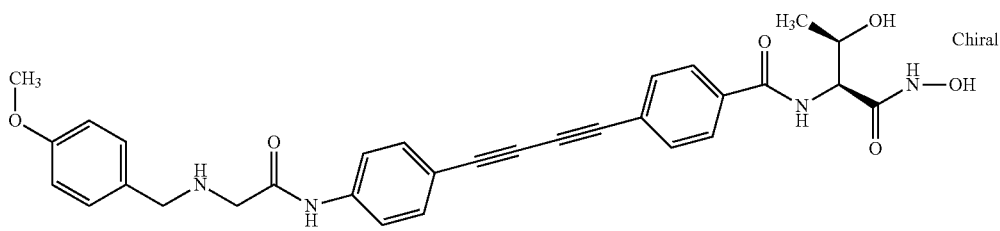 |

TABLE 1-continued
798 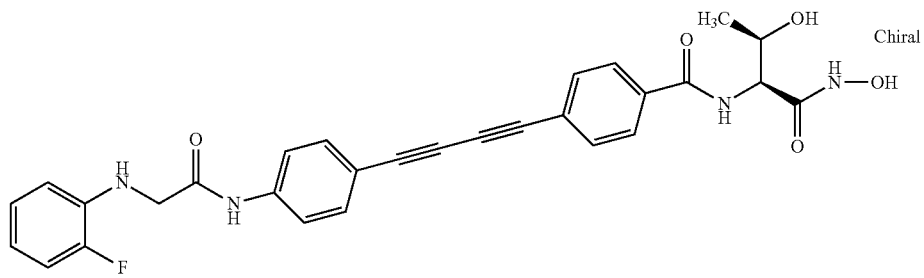
799 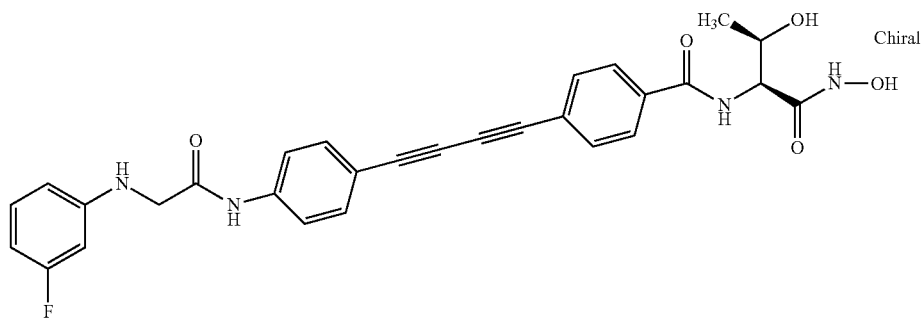
800 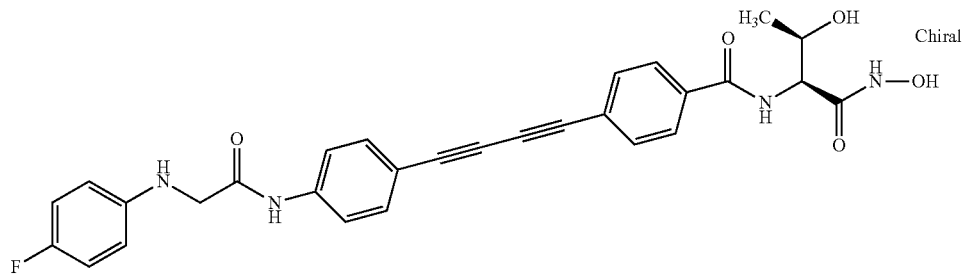
801 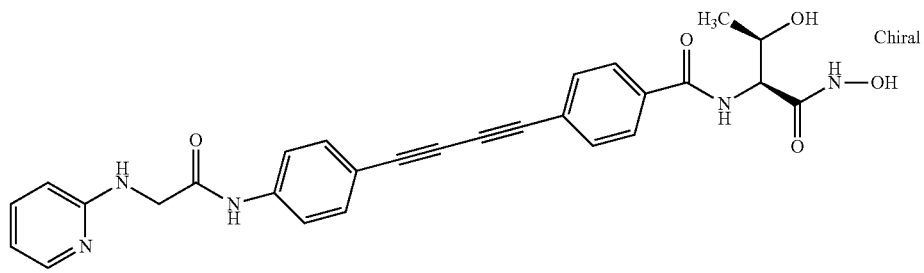
802 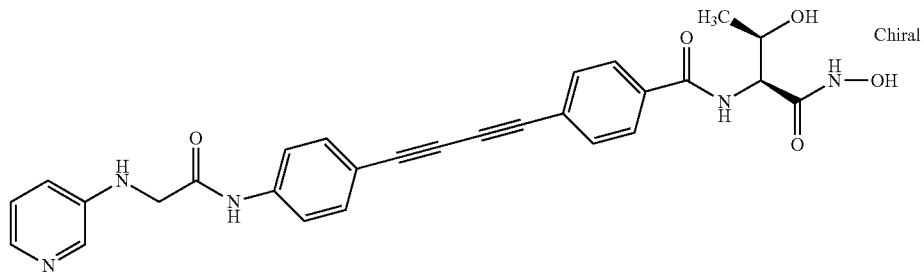

TABLE 1-continued
803 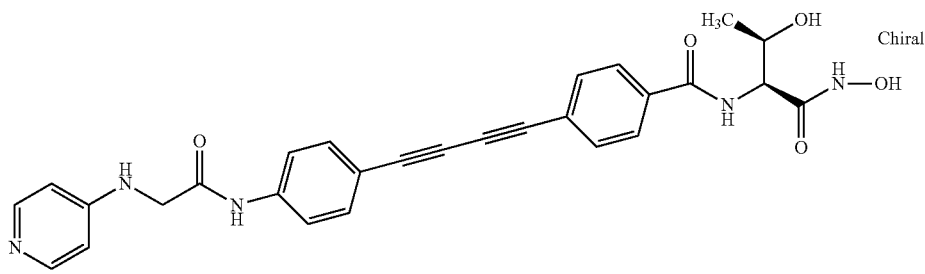
804 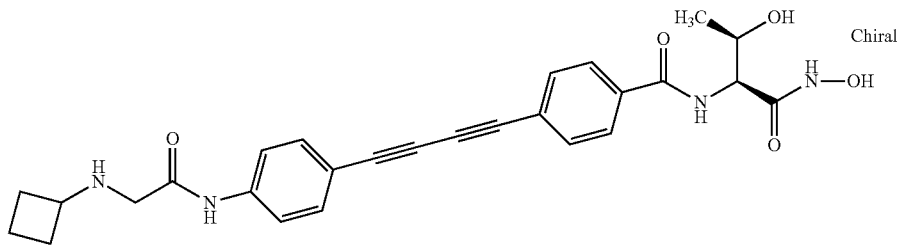
805 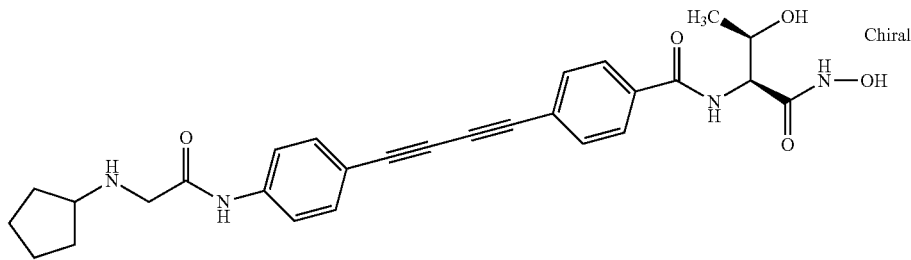
806 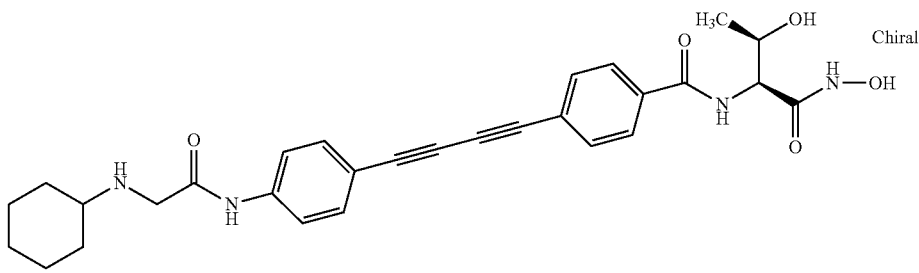
807 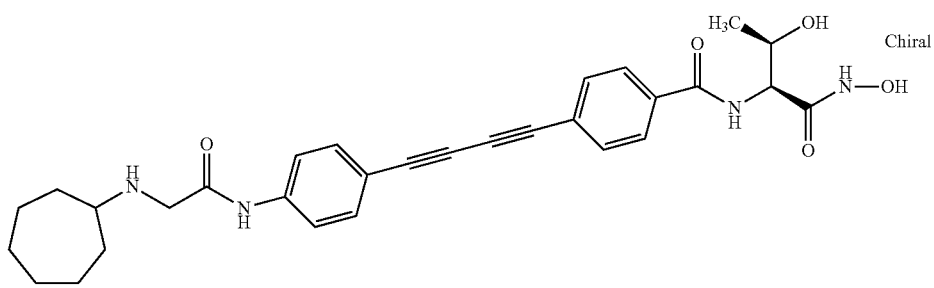
808 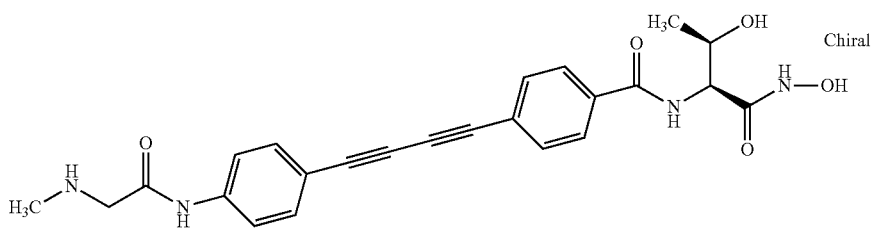

TABLE 1-continued
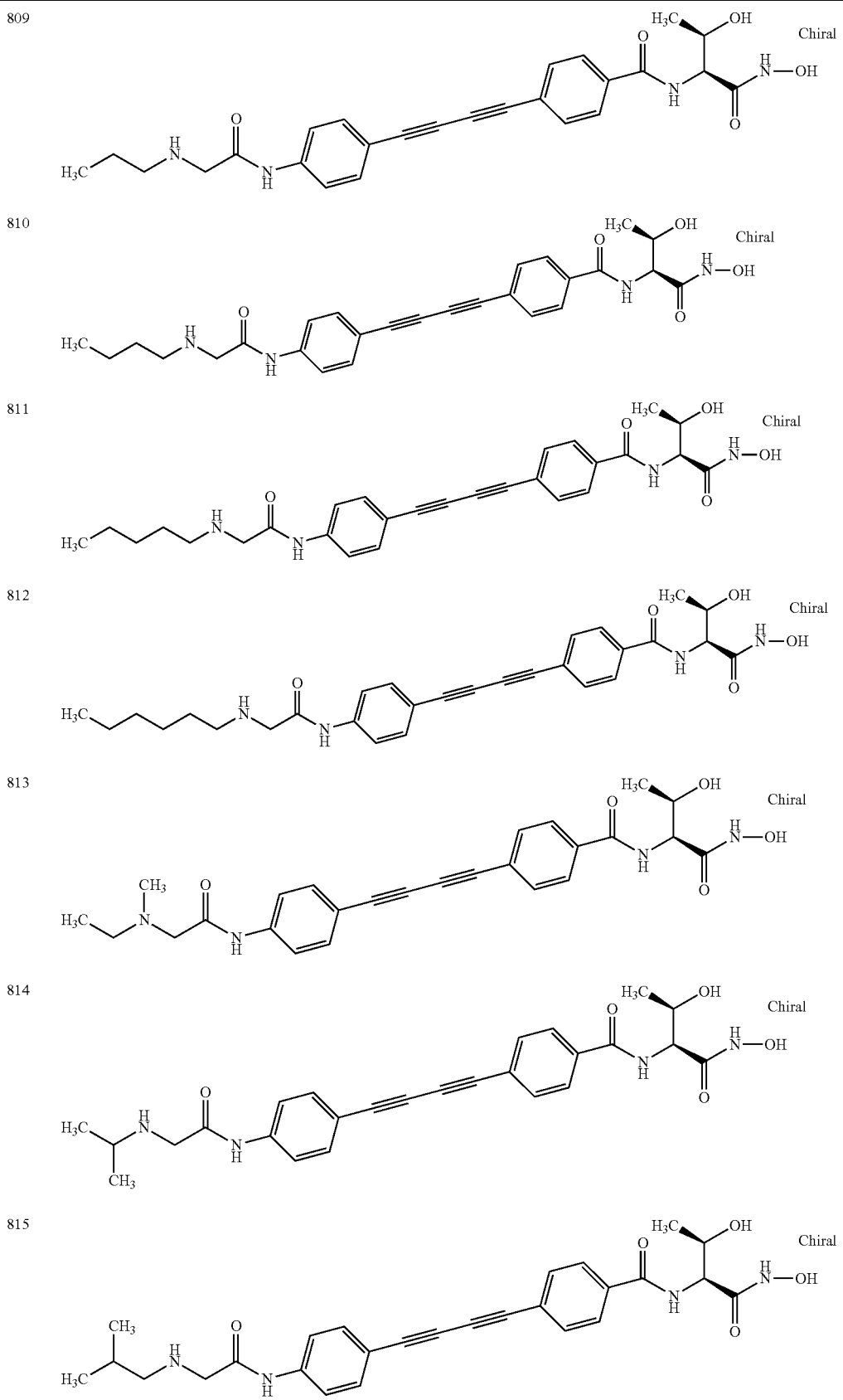

TABLE 1-continued
816 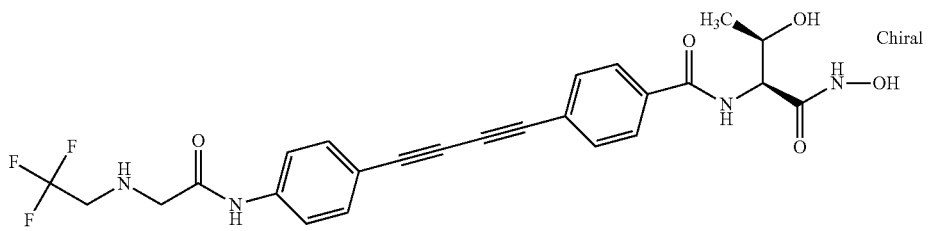
817 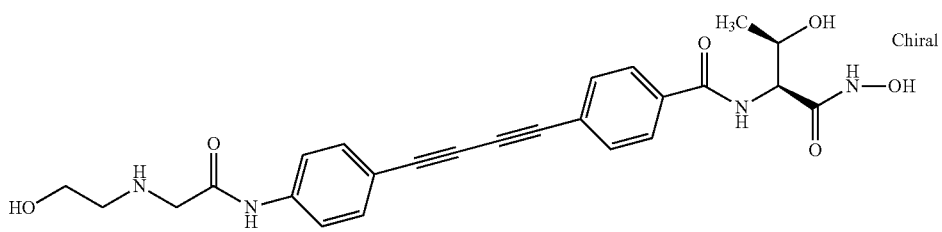
818 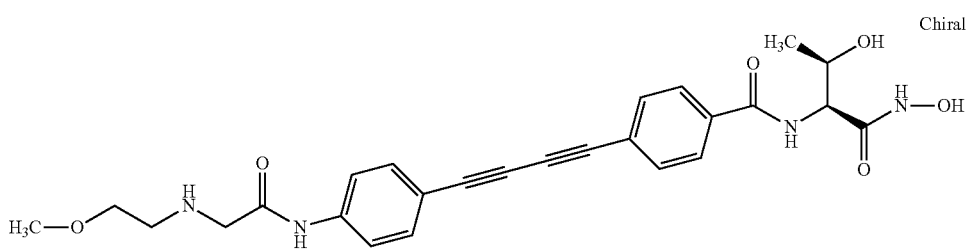
819 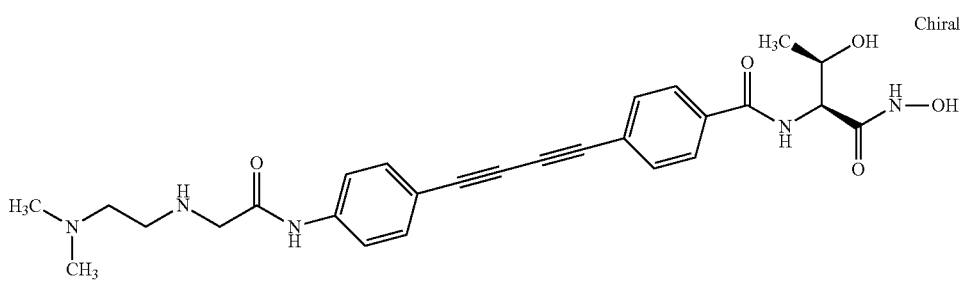
820 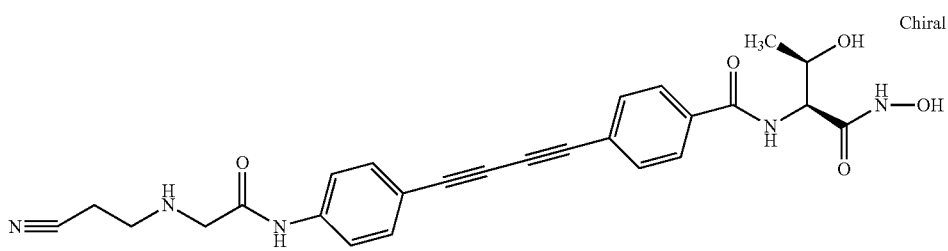
821 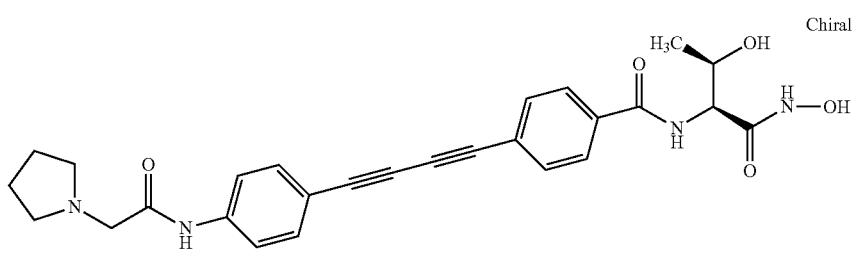

453 454
TABLE 1-continued
822 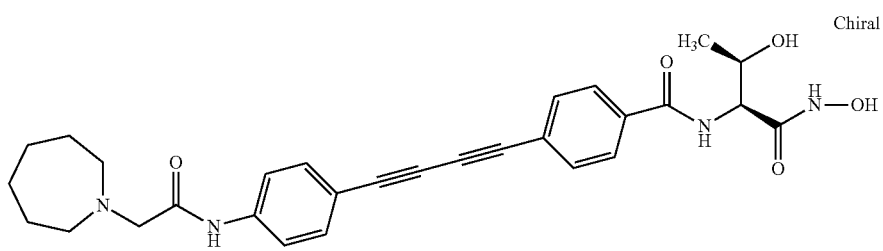
823 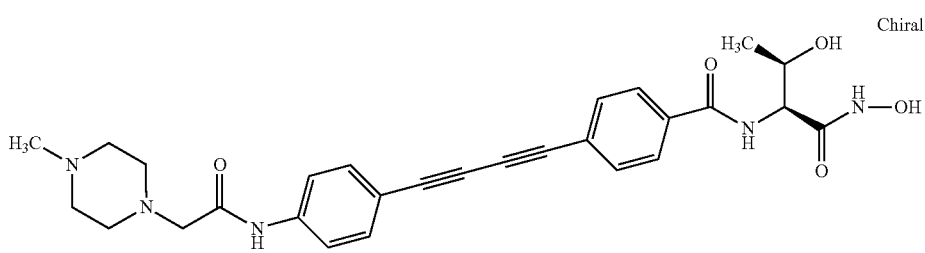
824 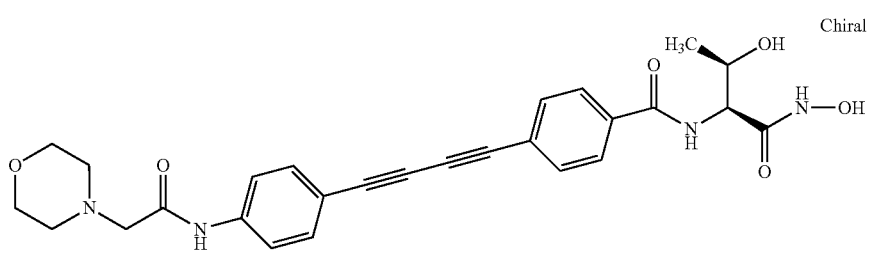
825 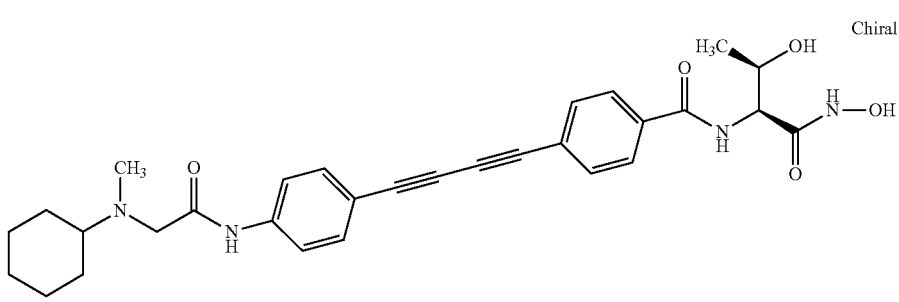
826 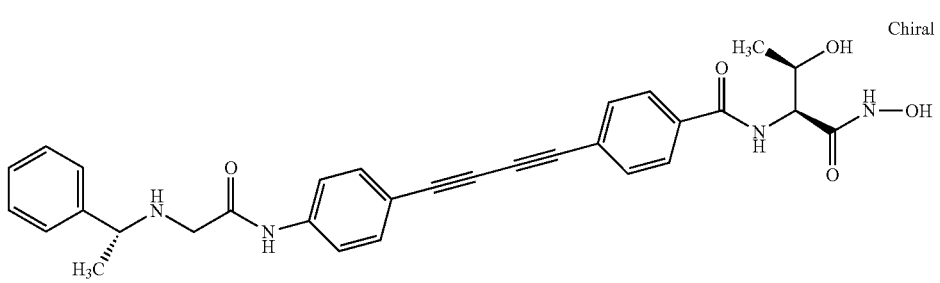
827 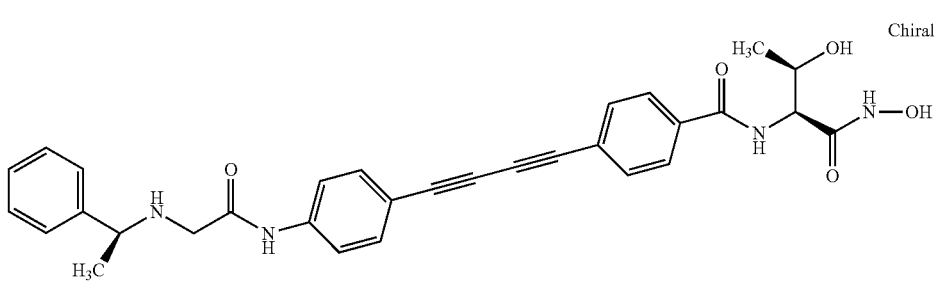

TABLE 1-continued
| 828 | 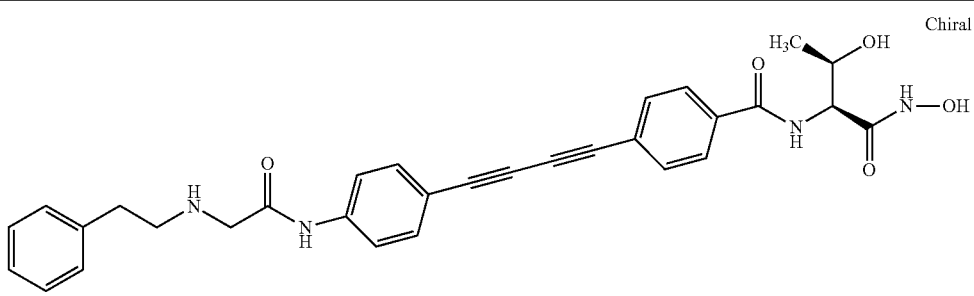 |
| --- | --- |
| 829 | 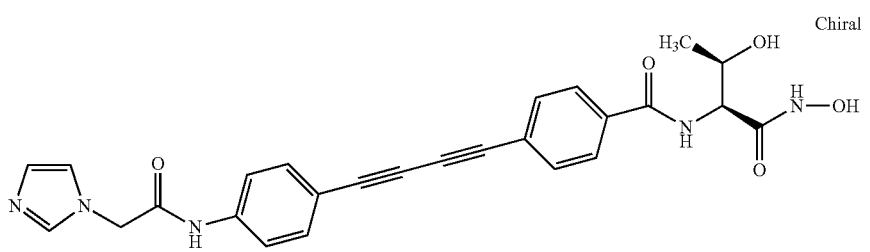 |
| 830 | 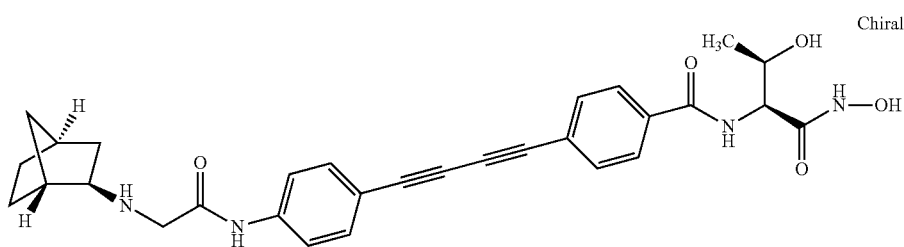 |
| 831 | 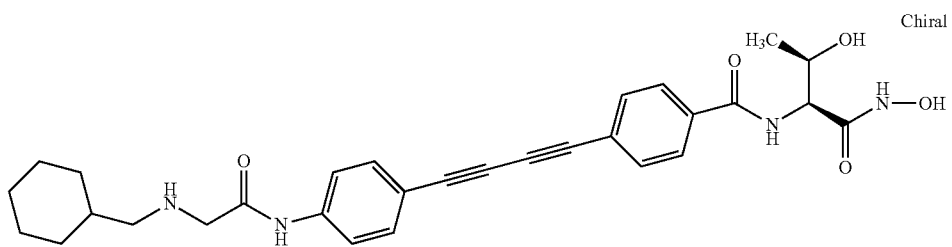 |
| 832 | 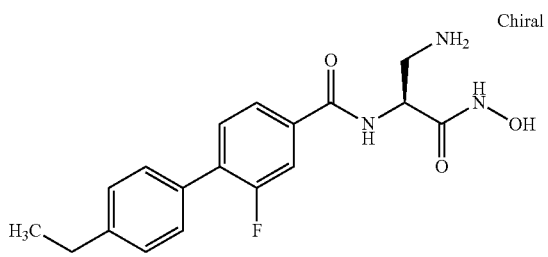 |
| 833 | 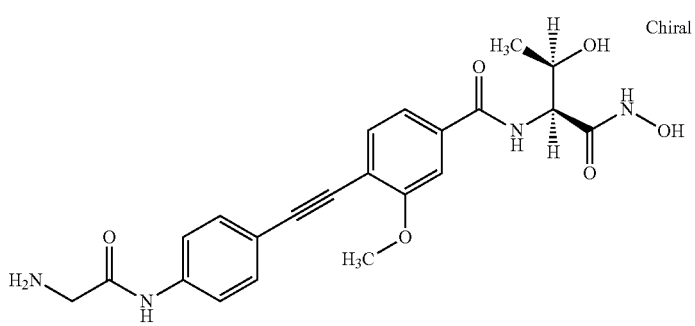 |

TABLE 1-continued
834 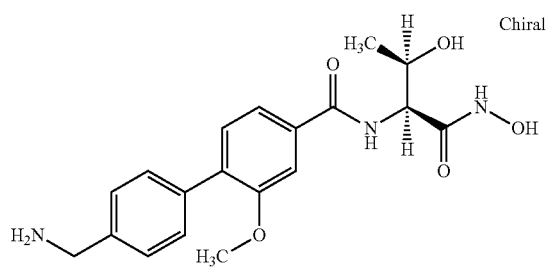
835 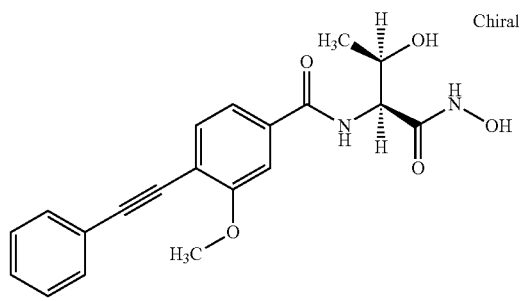
836 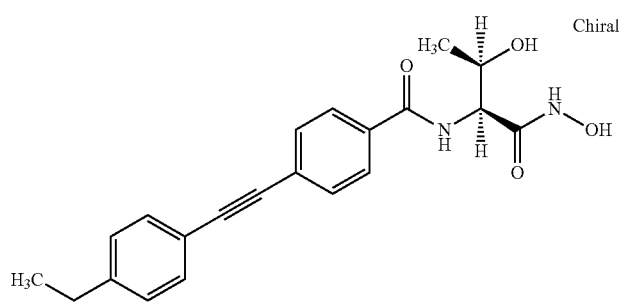
837 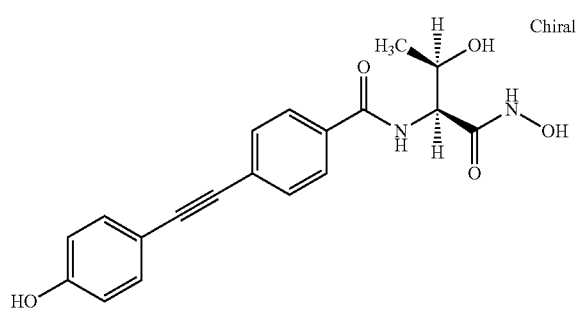
838 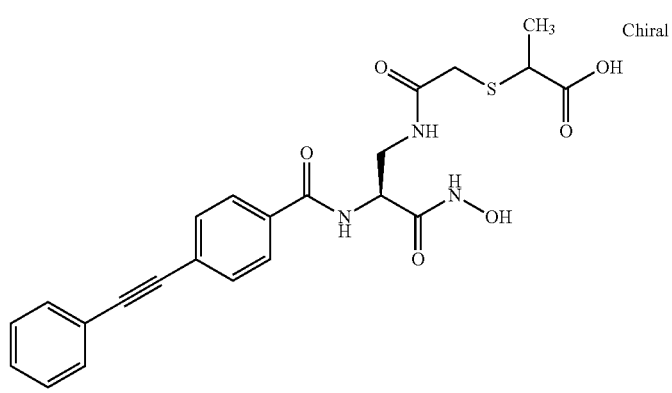

TABLE 1-continued
839
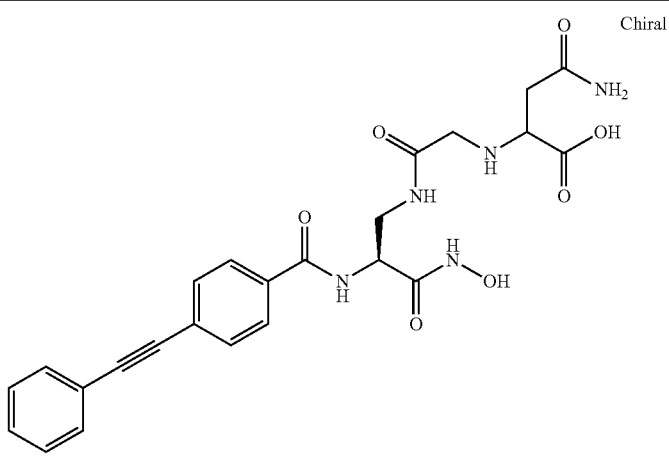
840
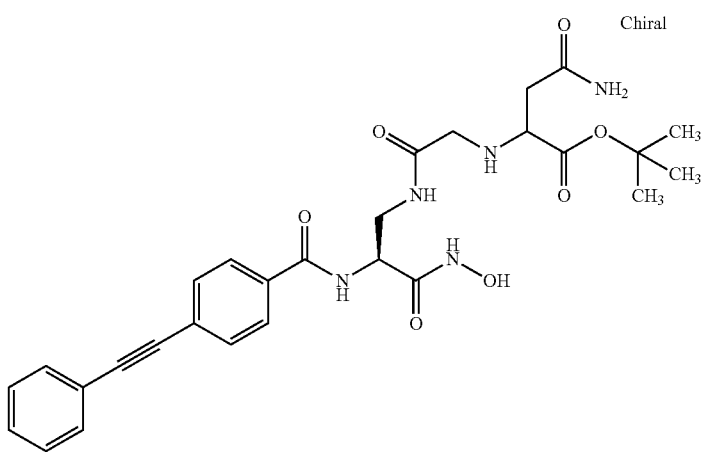
841
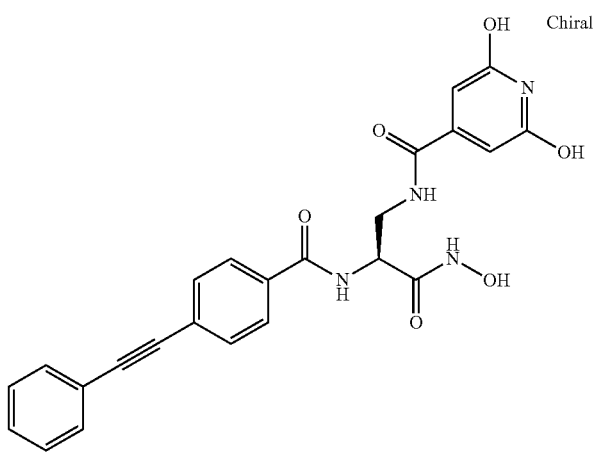
842
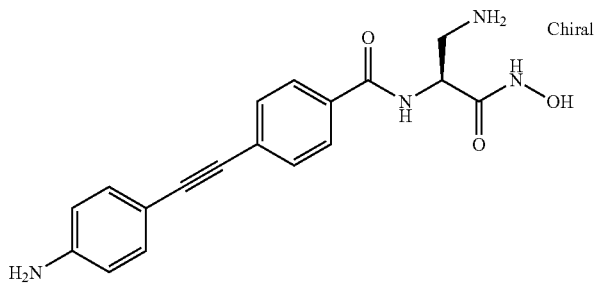

TABLE 1-continued
| 843 | 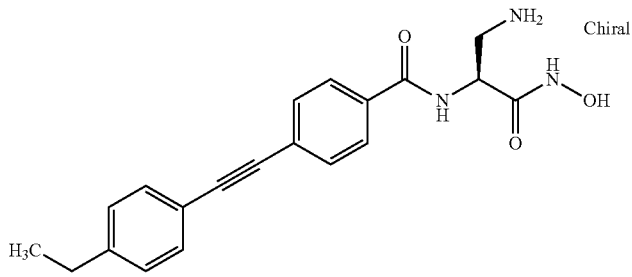 |
| --- | --- |
| 844 | 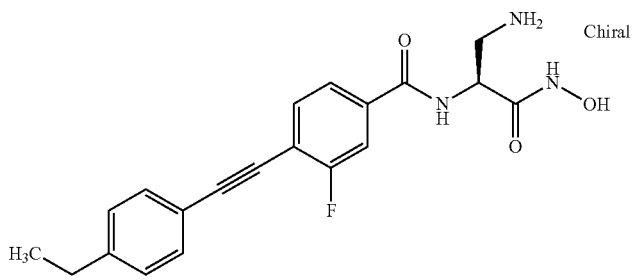 |
| 845 | 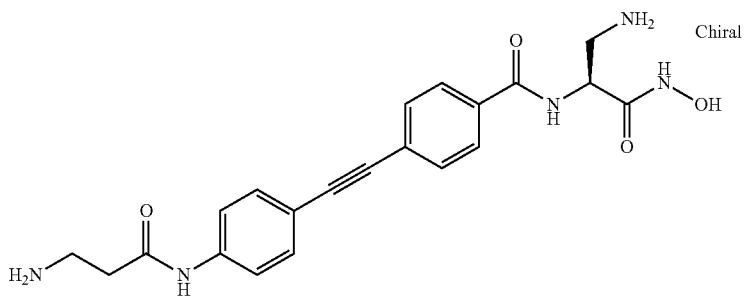 |
| 846 | 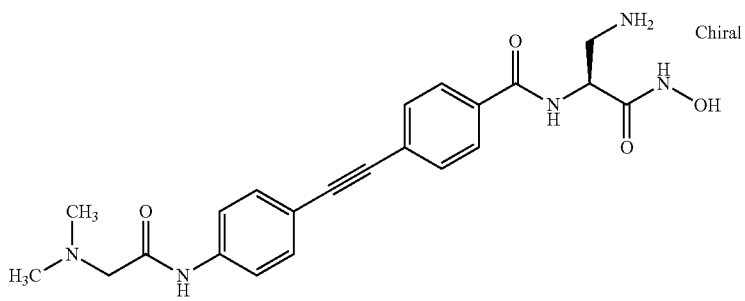 |
| 847 | 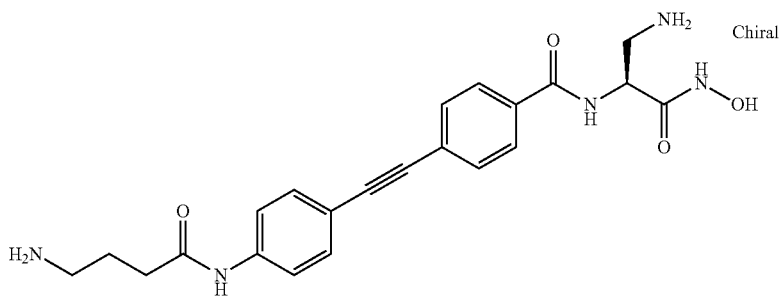 |

TABLE 1-continued
848 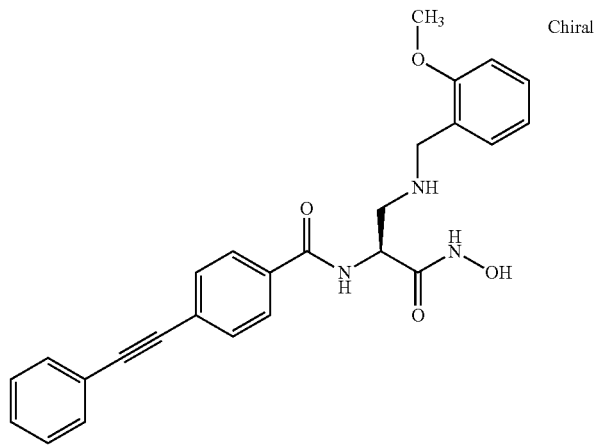
849 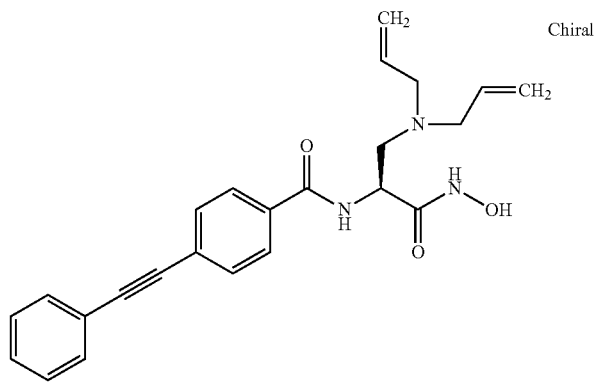
850 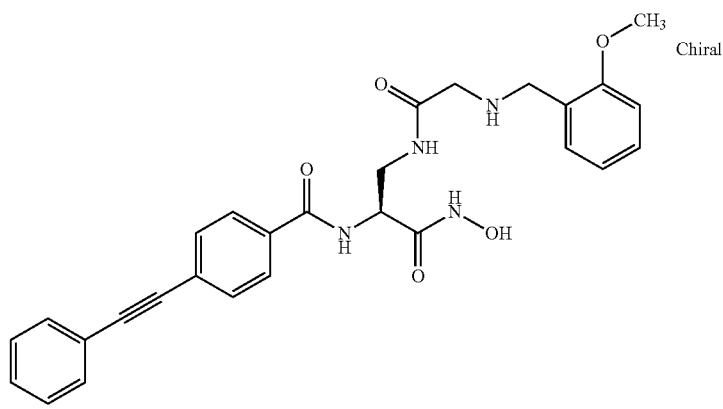
851 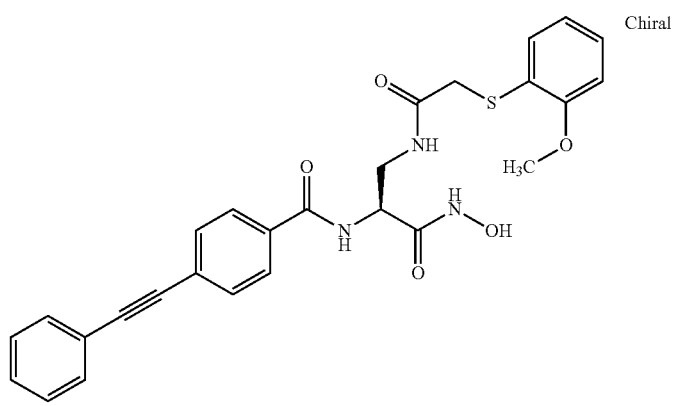

TABLE 1-continued
| 852 | 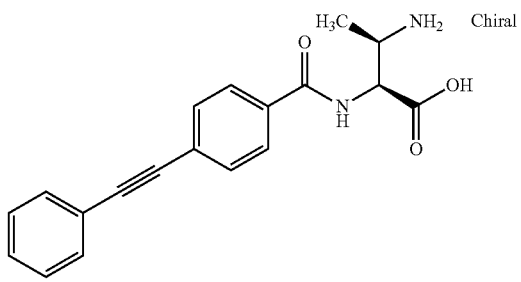 |
| 853 | 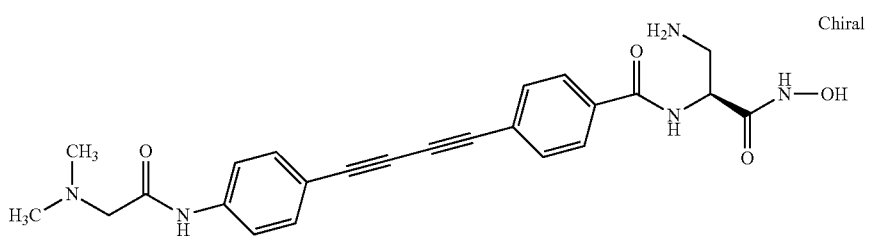 |
| 854 | 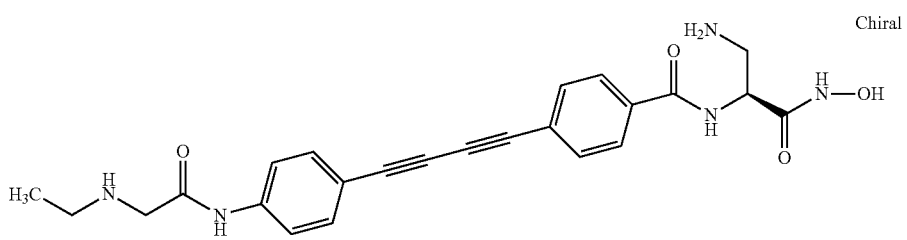 |
| 855 | 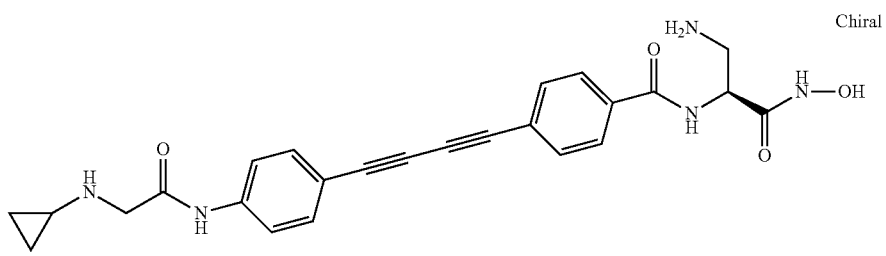 |
| 856 | 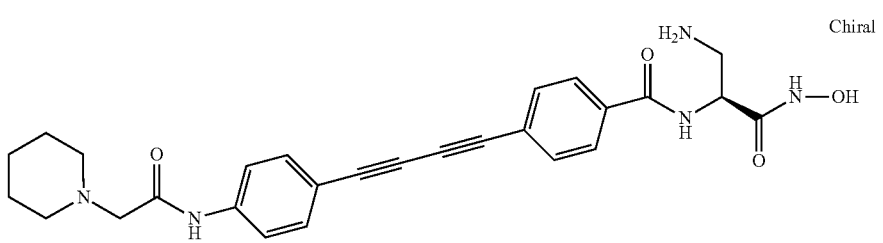 |
| 857 | 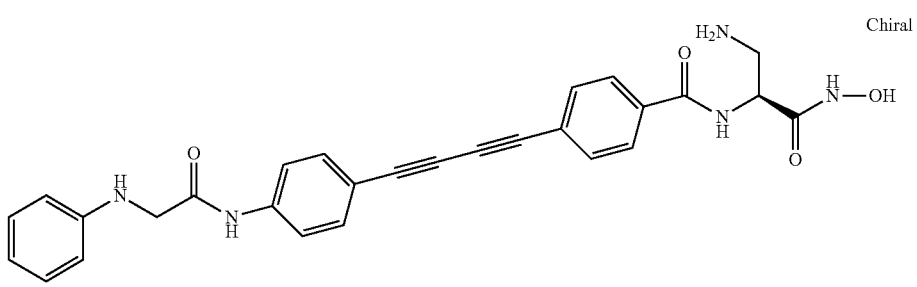 |

TABLE 1-continued
| 858 | 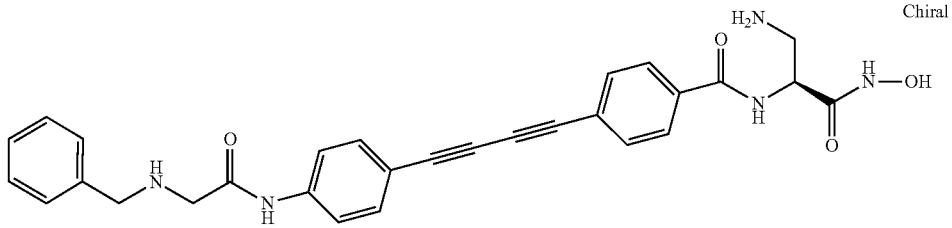 |
| 859 | 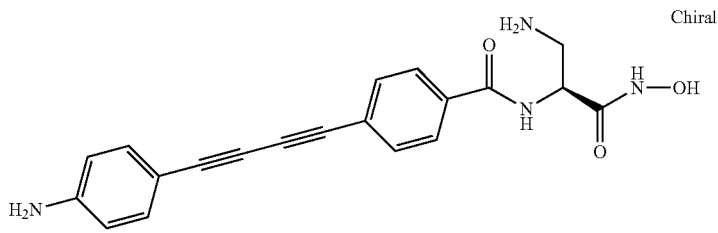 |
| 860 | 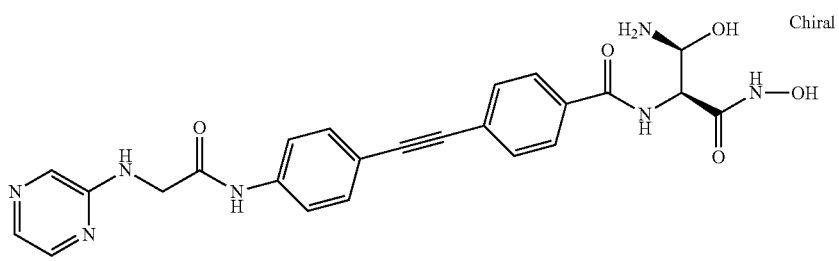 |
| 861 | 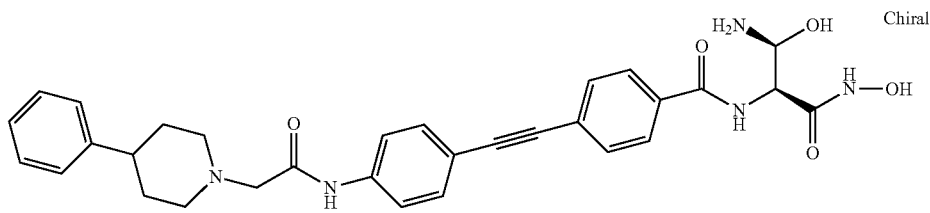 |
| 862 | 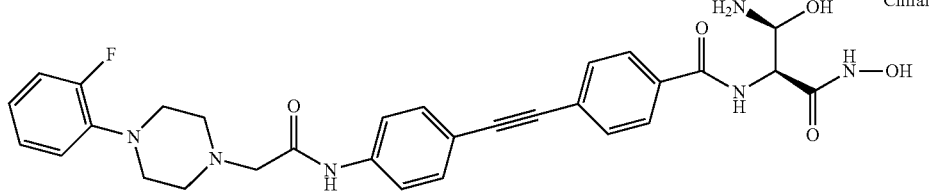 |
| 863 | 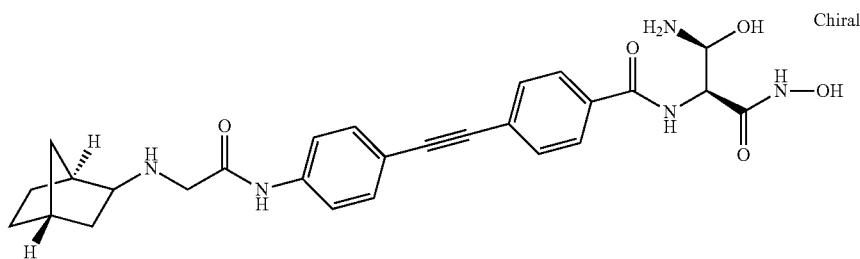 |

TABLE 1-continued
864 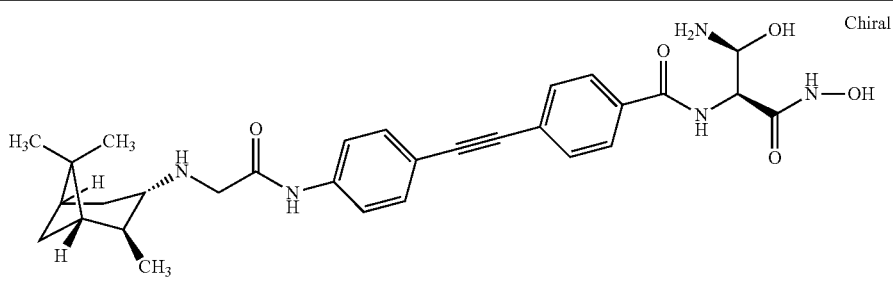
865 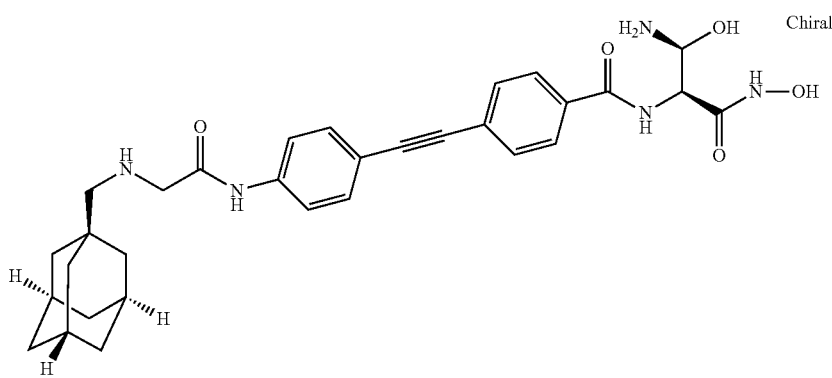
866 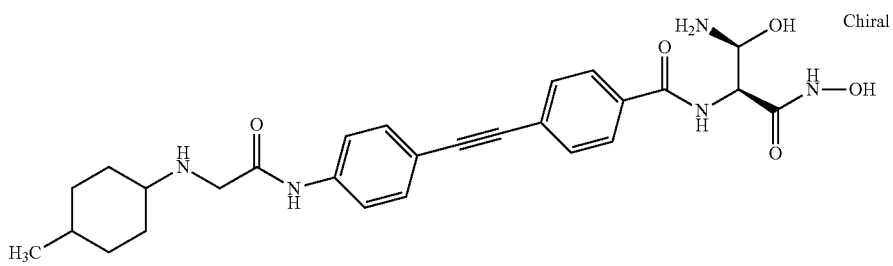
867 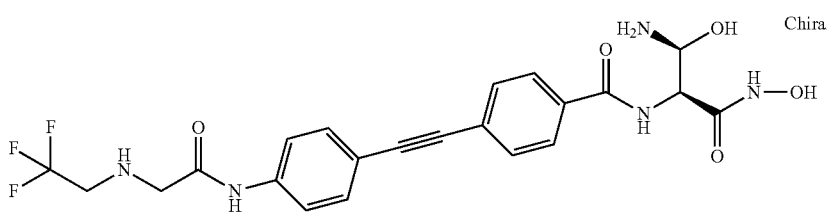
868 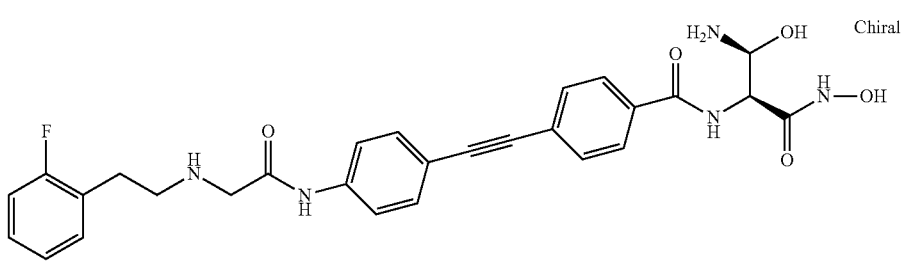

TABLE 1-continued
| 869 | 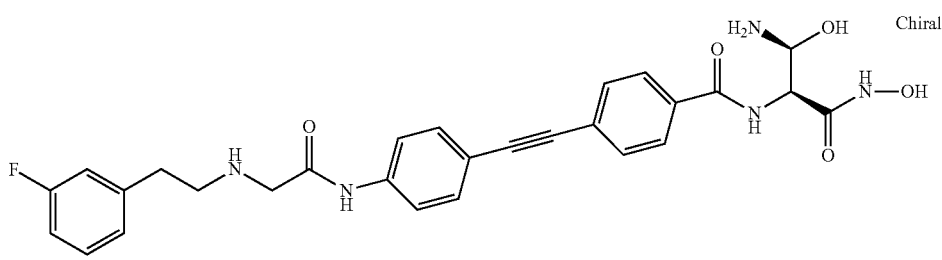 |
| 870 | 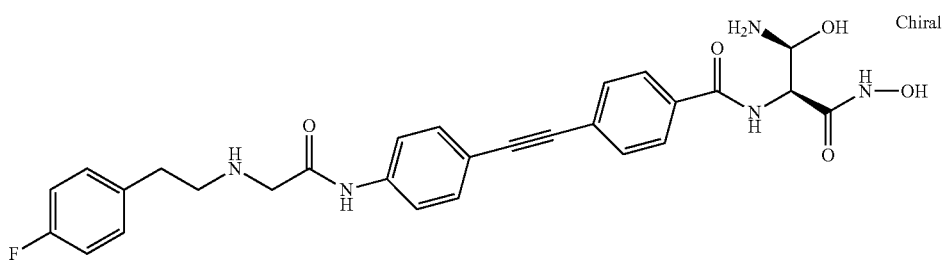 |
| 871 | 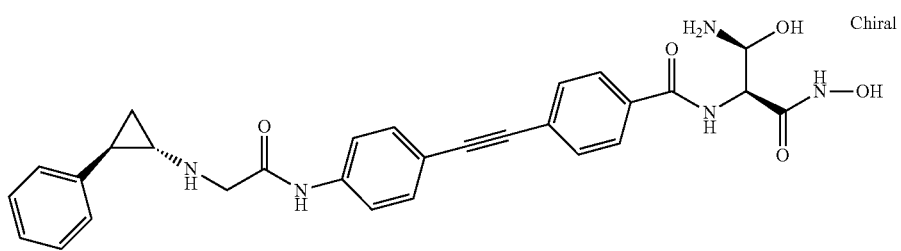 |
| 872 | 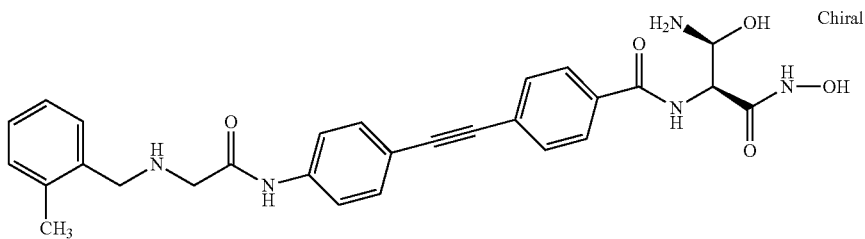 |
| 873 | 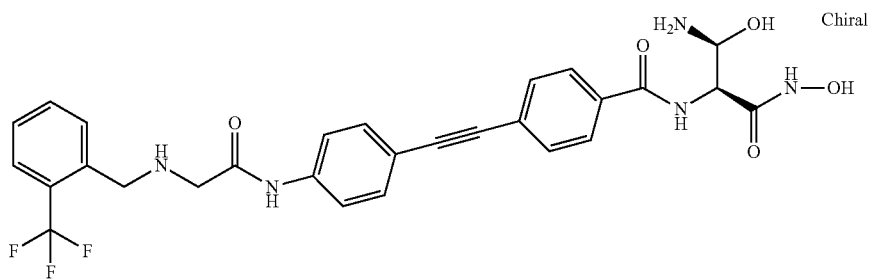 |
| 874 | 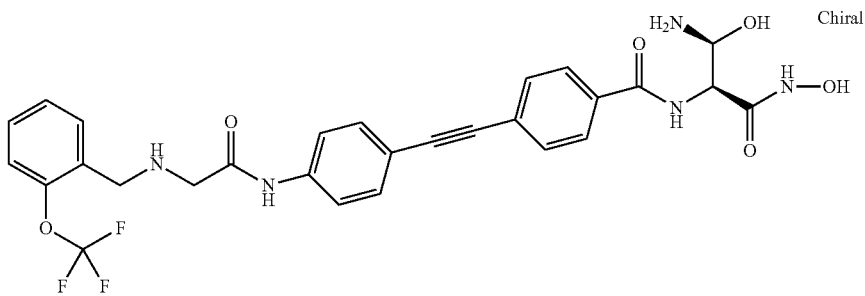 |

TABLE 1-continued
| 875 | 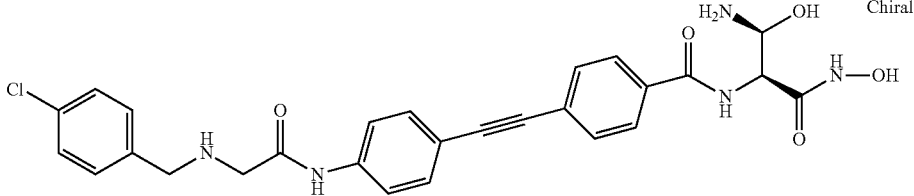 |
| 876 | 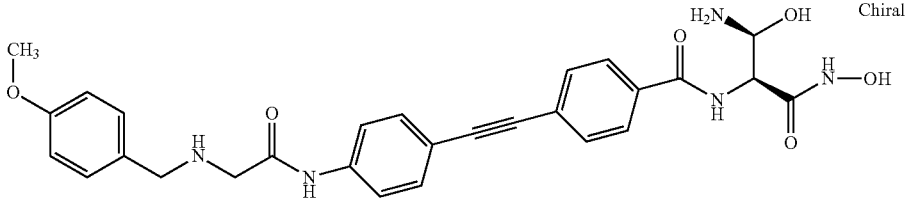 |
| 877 | 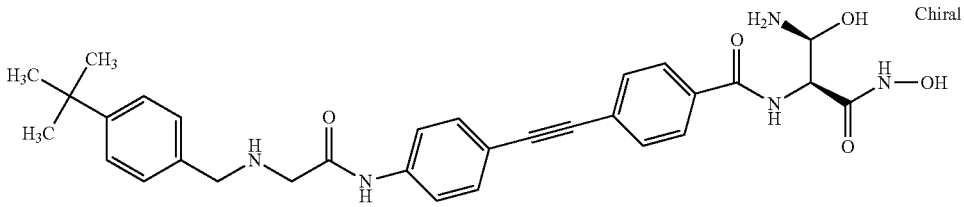 |
| 878 | 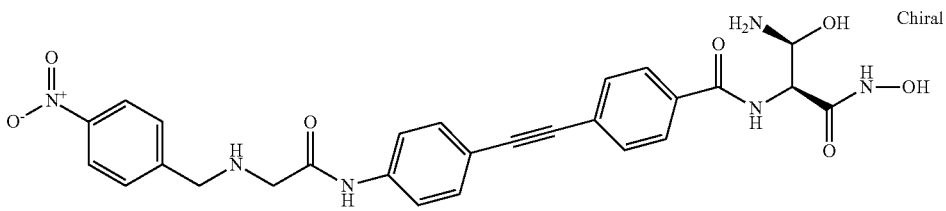 |
| 879 | 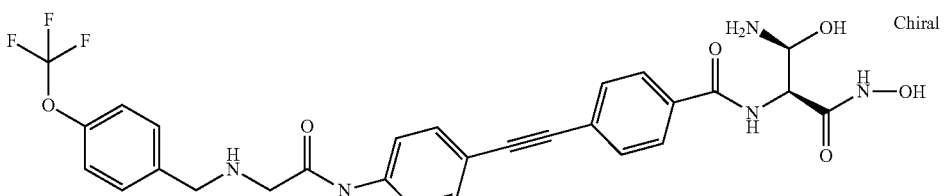 |
| 880 | 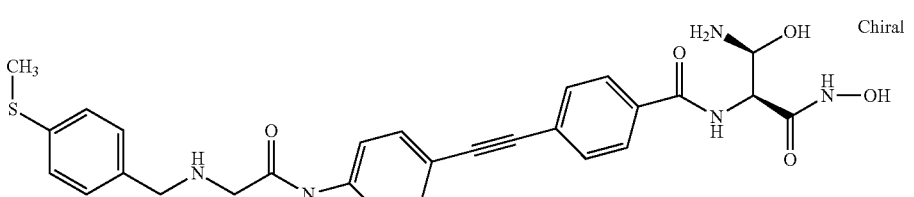 |
| 881 | 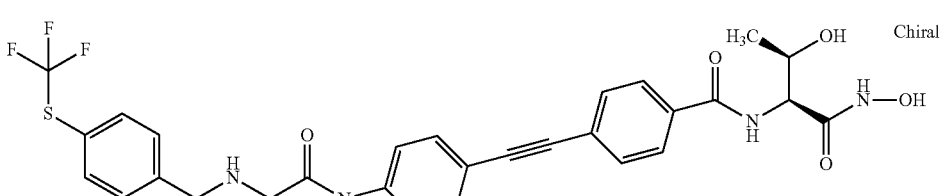 |

TABLE 1-continued
882 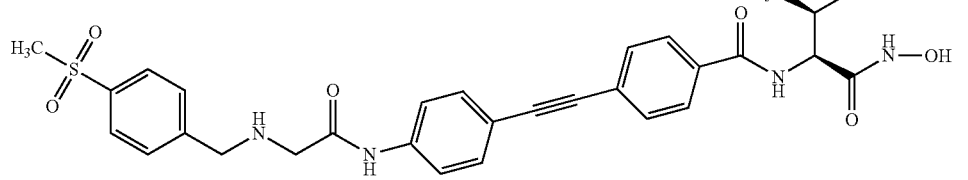
883 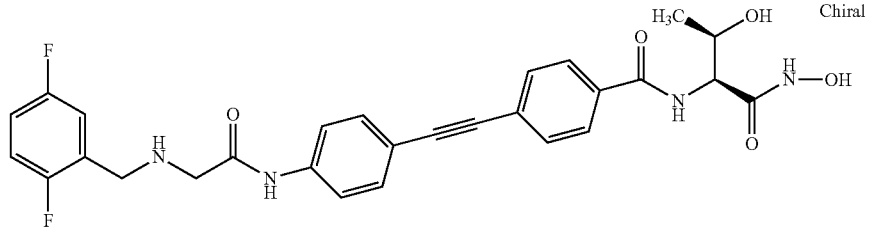
884 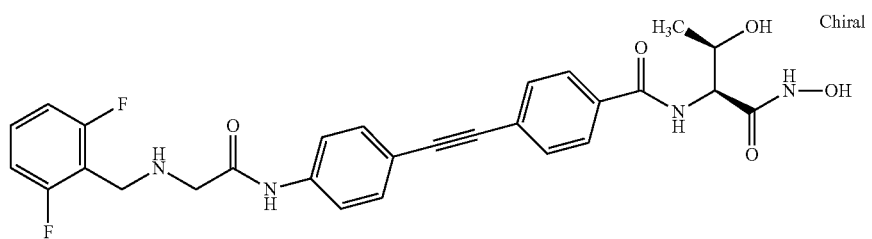
885 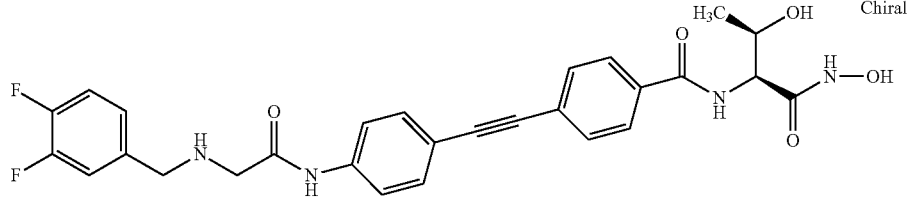
886 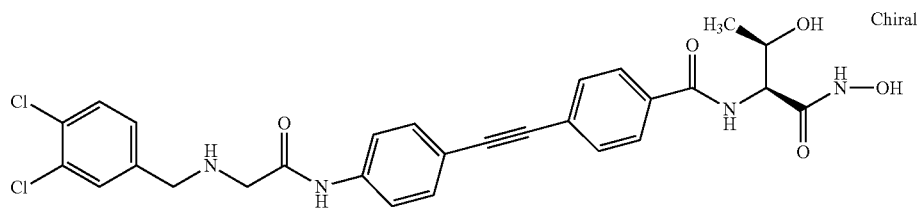
887 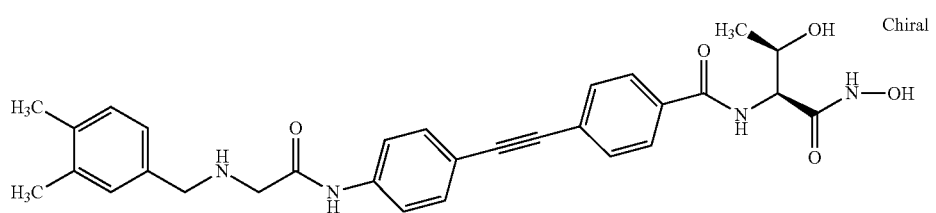
888 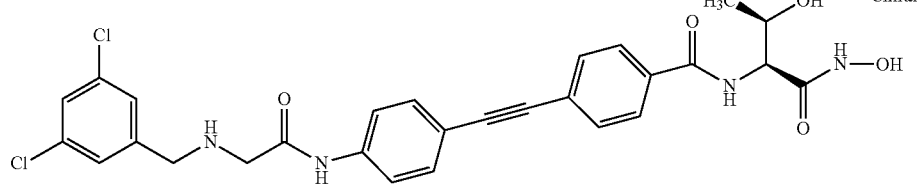

TABLE 1-continued
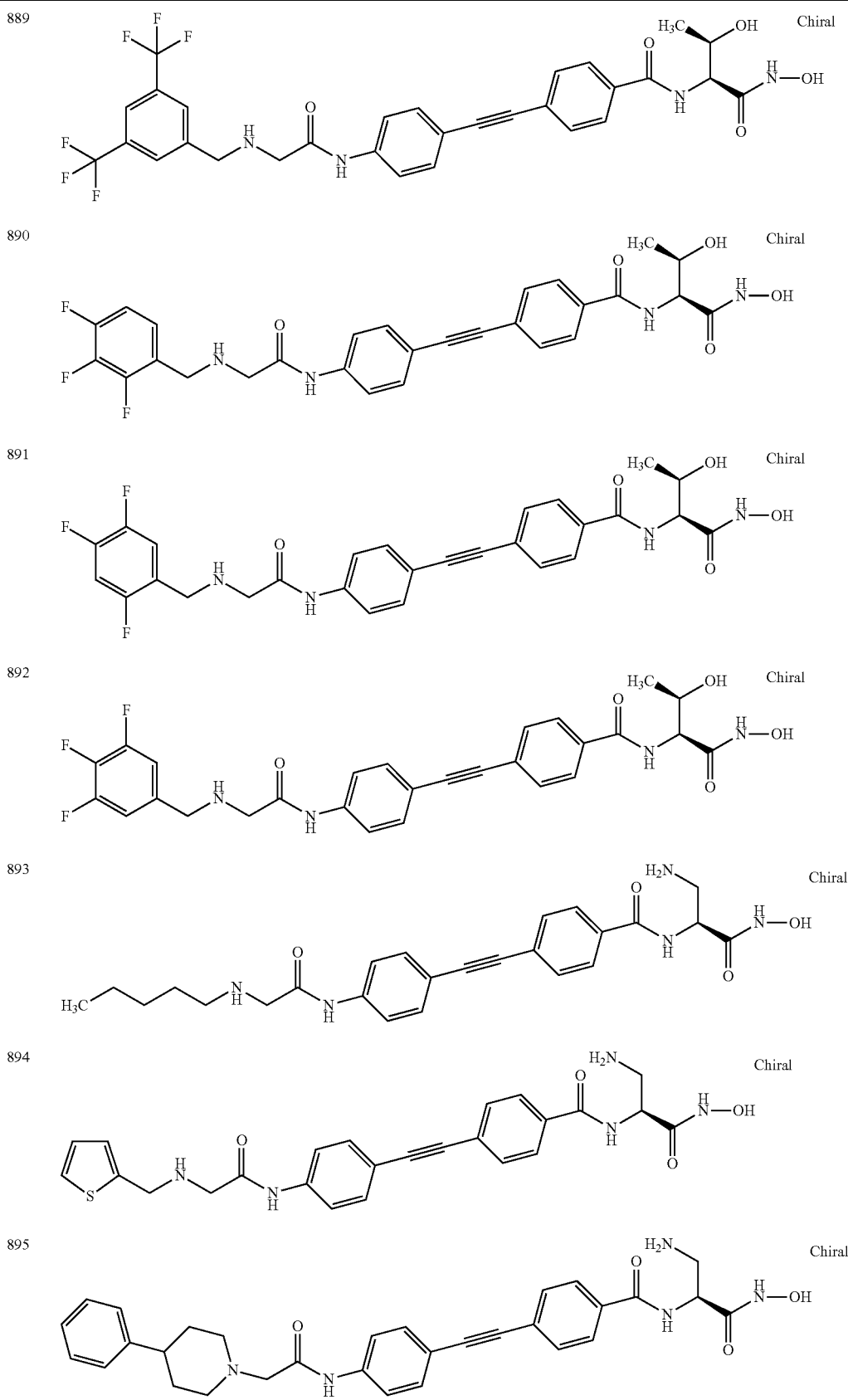

TABLE 1-continued
896 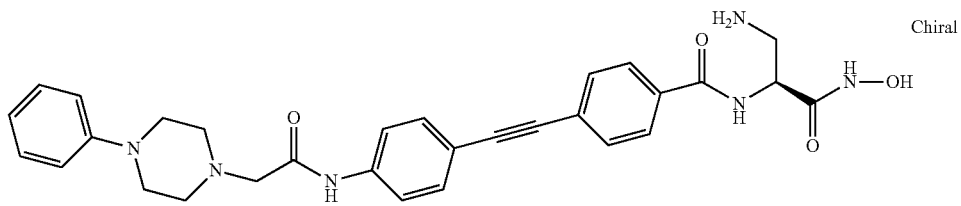
897 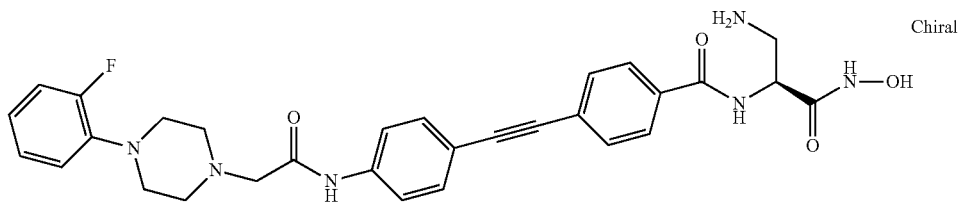
898 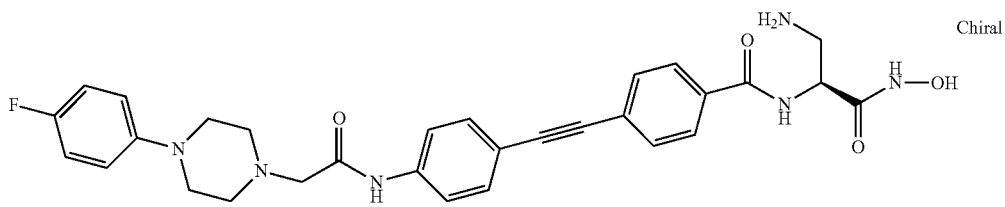
899 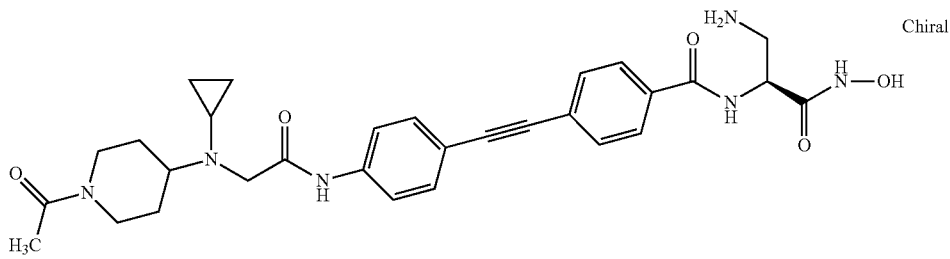
900 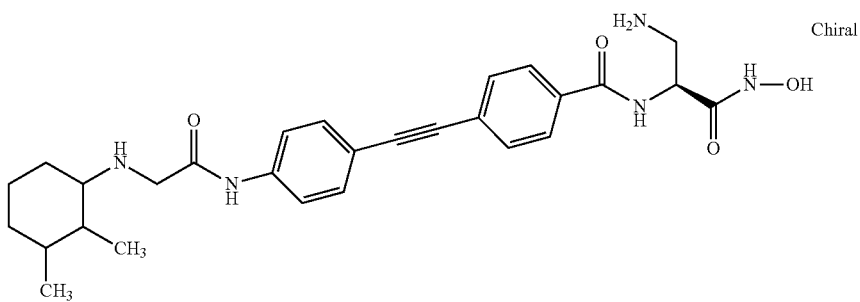
901 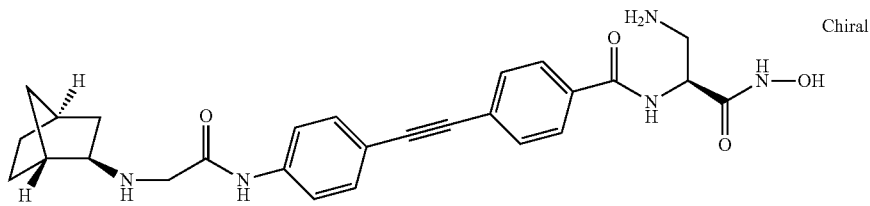
902 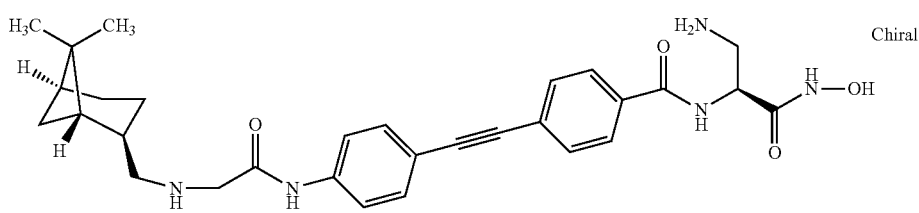

TABLE 1-continued
903
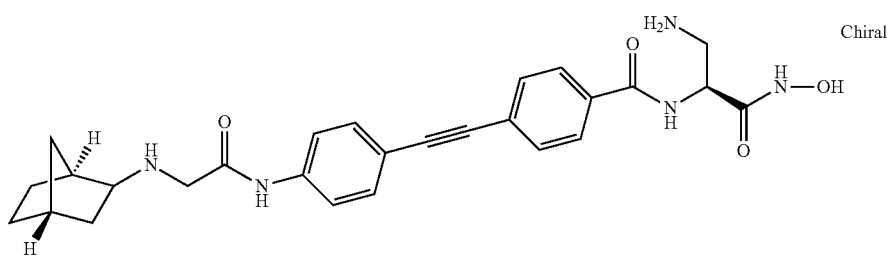
904
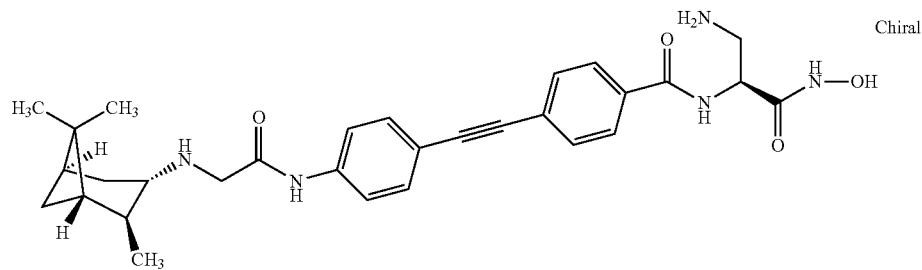
905
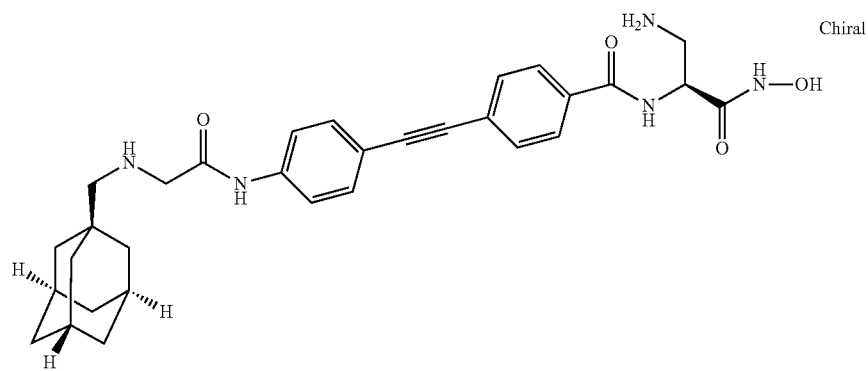
906
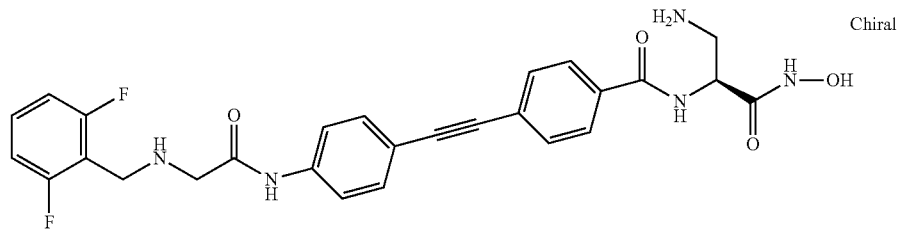
907
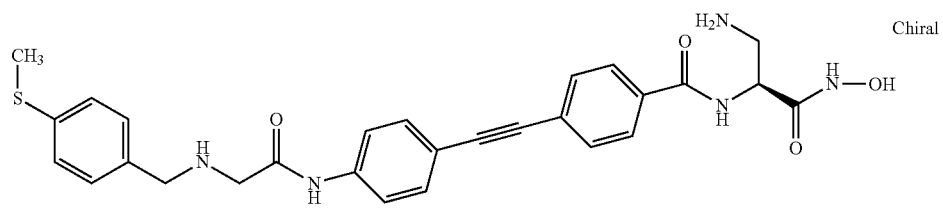
908
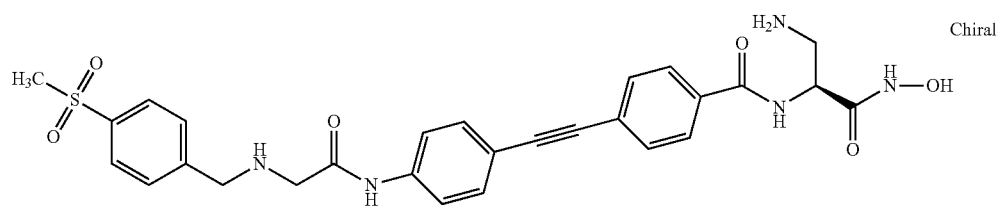

TABLE 1-continued
| 909 | 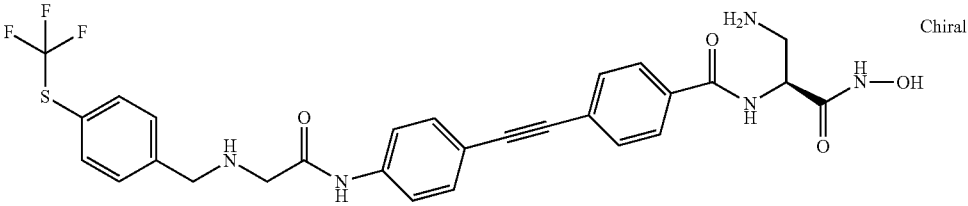 |
| 910 | 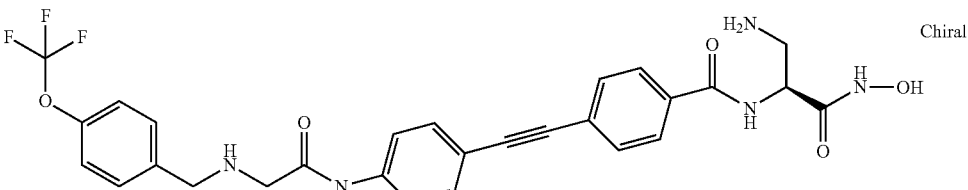 |
| 911 | 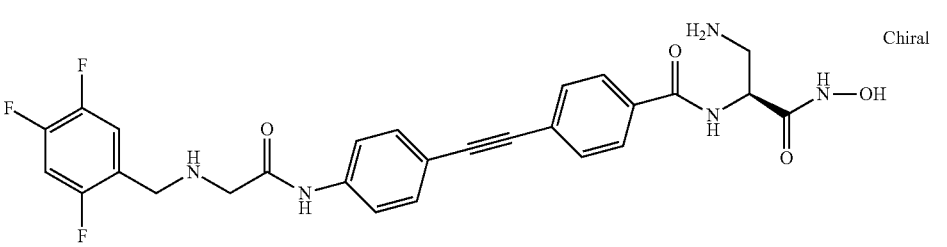 |
| 912 | 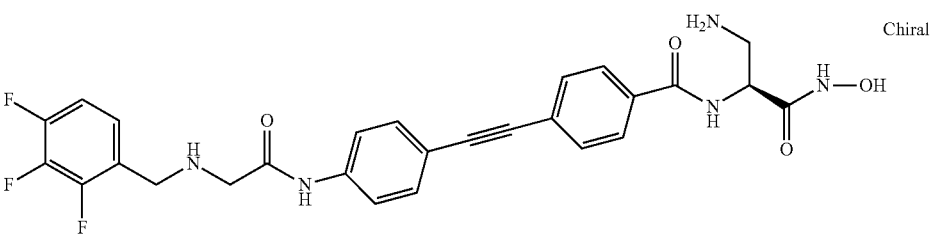 |
| 913 | 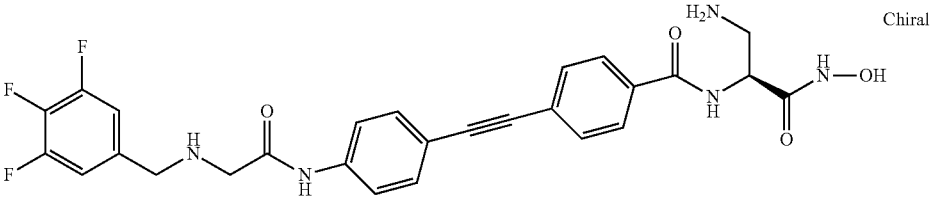 |
| 914 | 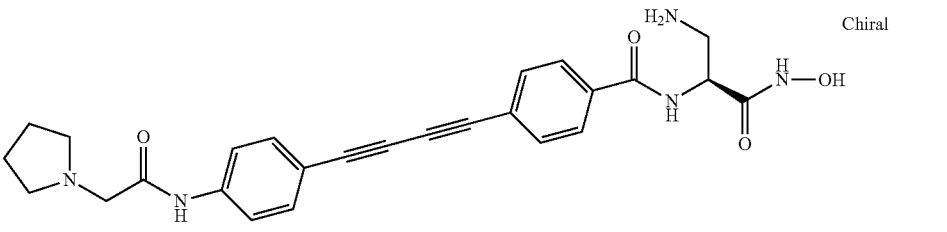 |
| 915 | 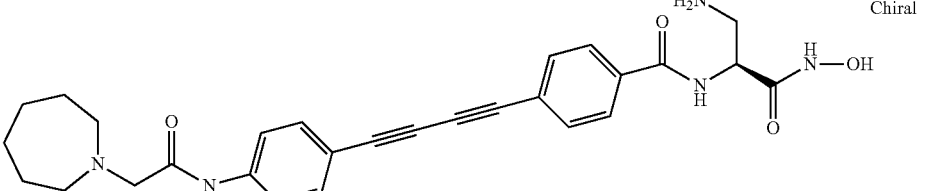 |

TABLE 1-continued
| 916 | 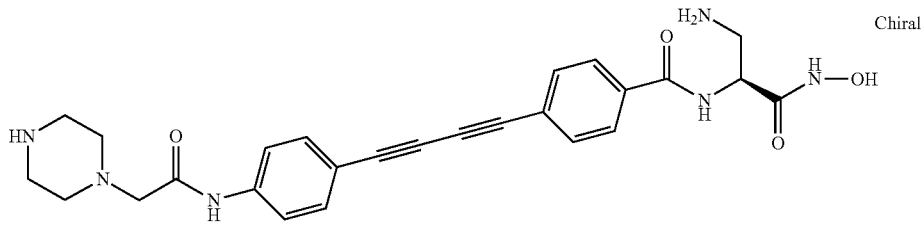 Chiral |
| 917 | 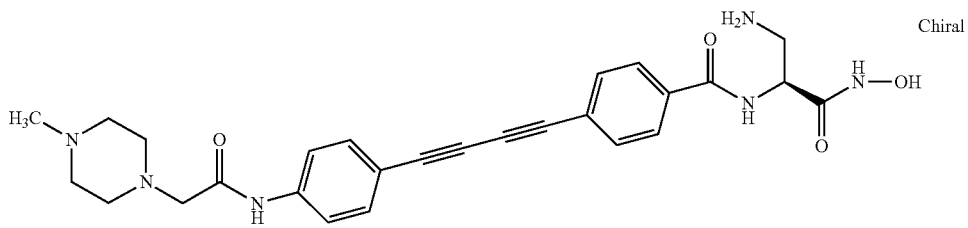 Chiral |
| 918 | 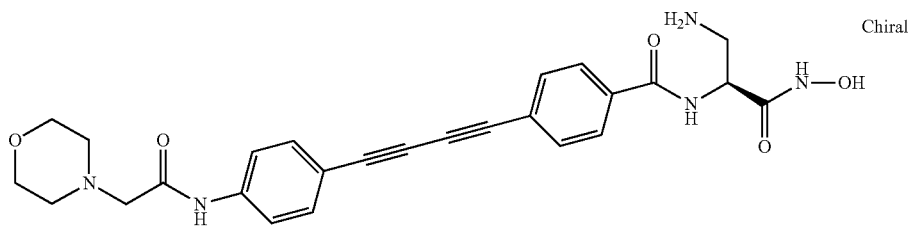 Chiral |
| 919 | 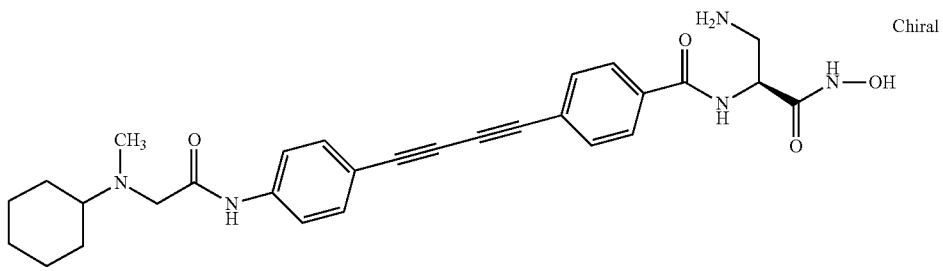 Chiral |
| 920 | 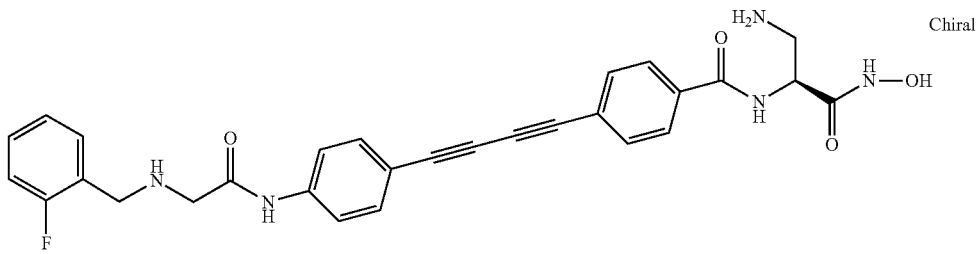 Chiral |
| 921 | 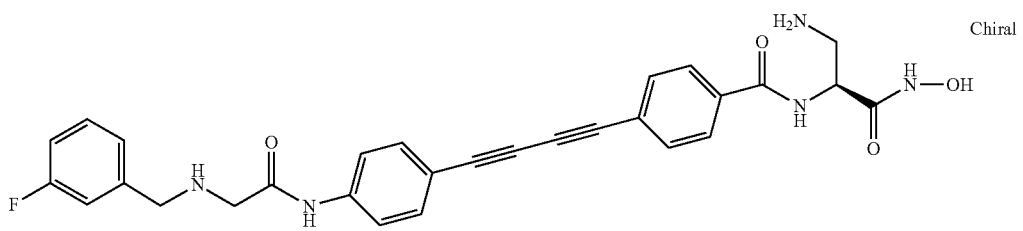 Chiral |

US 8,101,640 B2
TABLE 1-continued
922 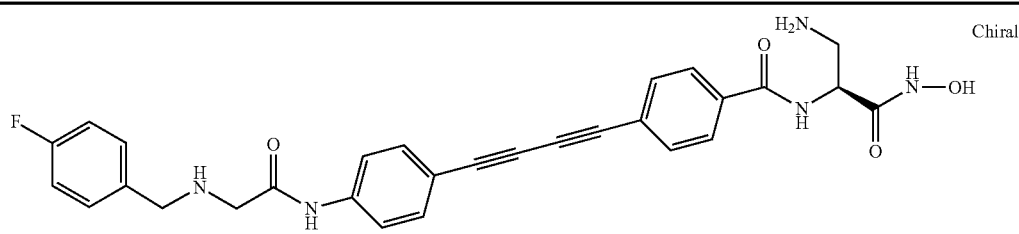
923 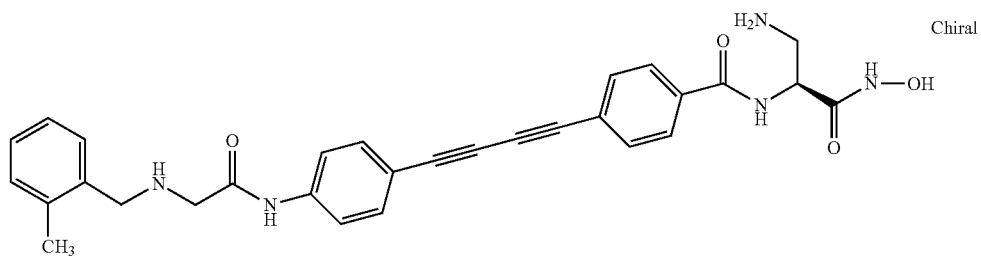
924 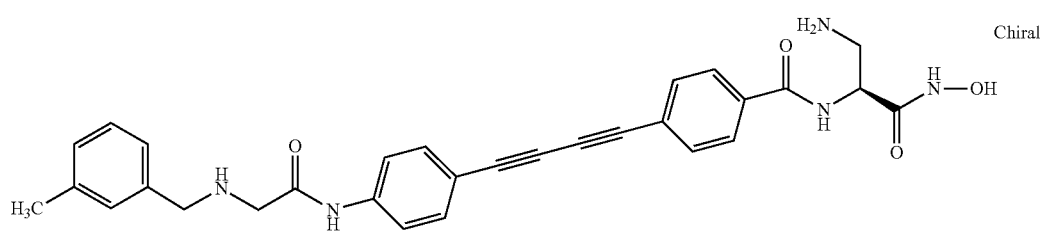
925 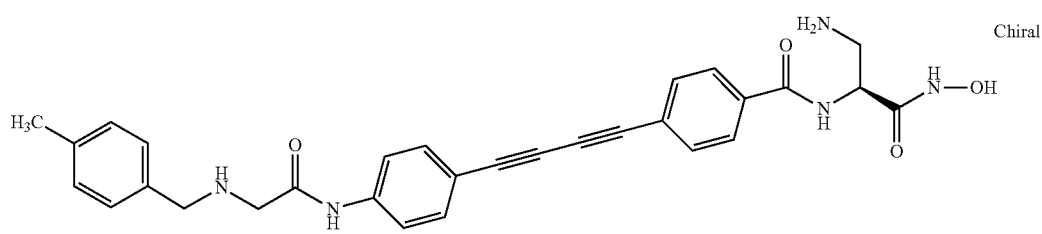
926 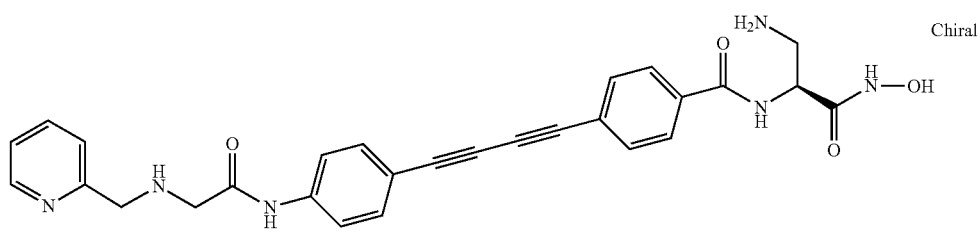
927 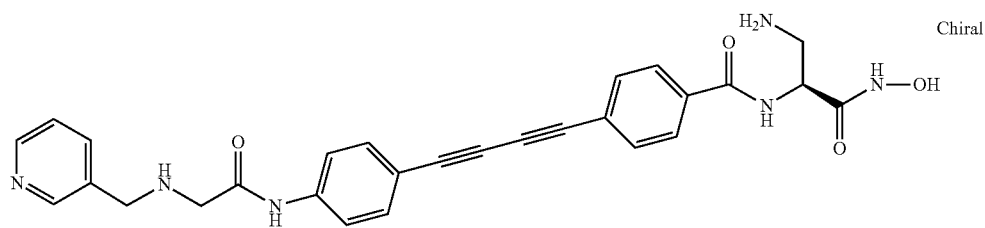
928 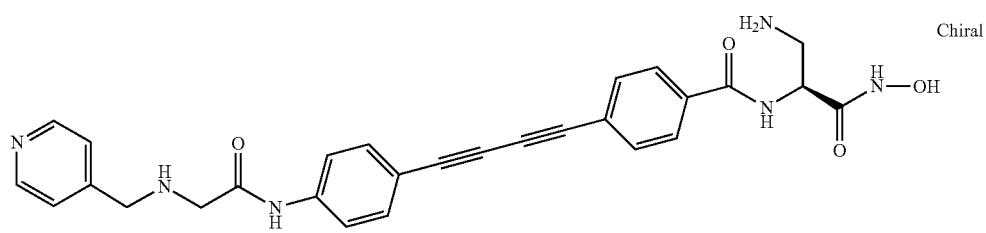

TABLE 1-continued
929
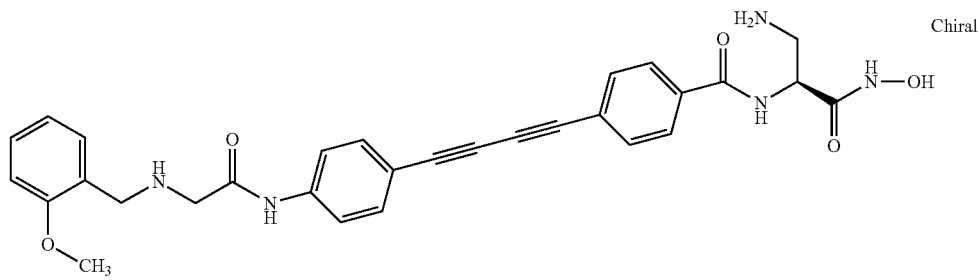
930
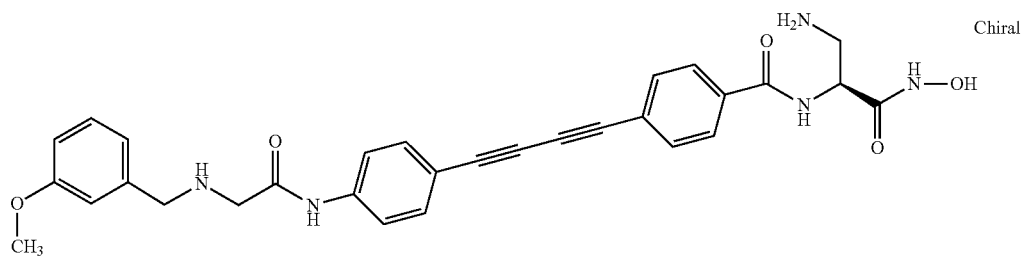
931
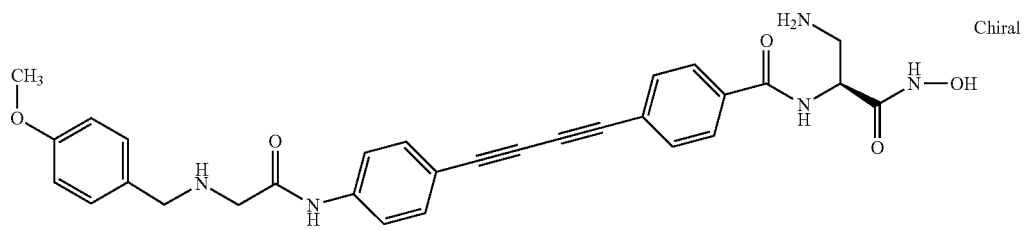
932
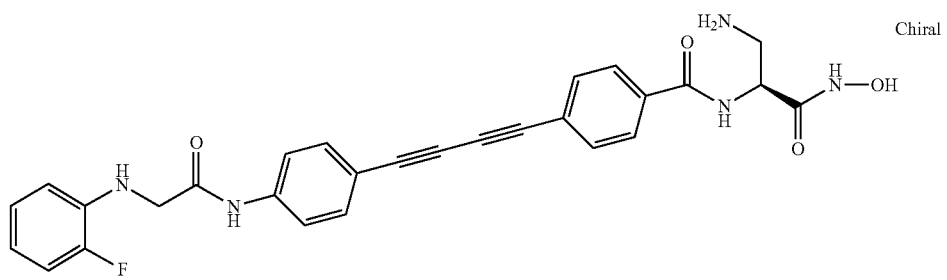
933
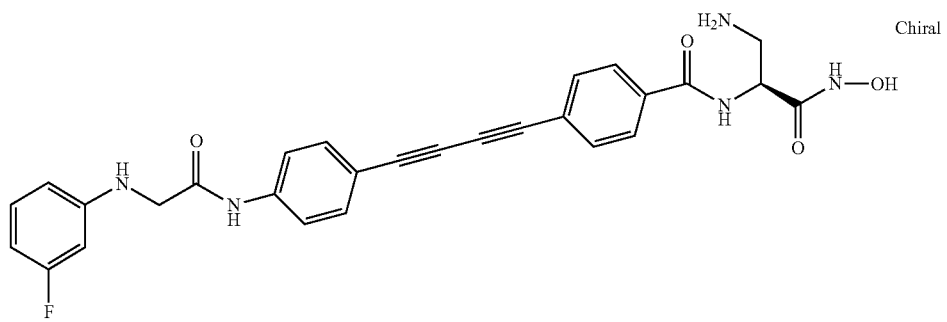

TABLE 1-continued
934
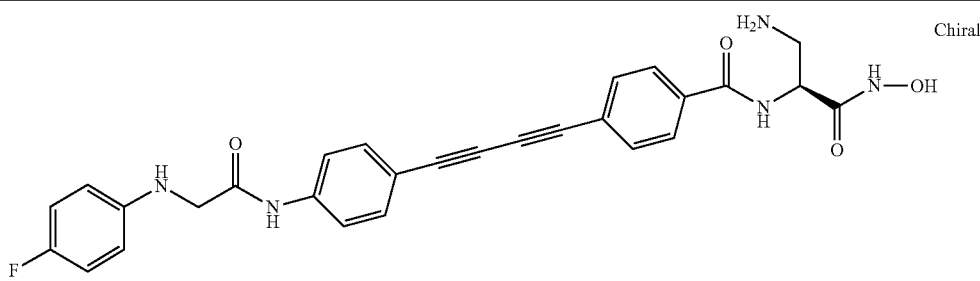
935
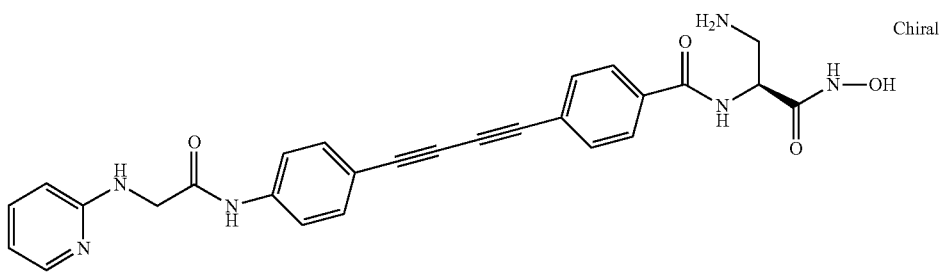
936
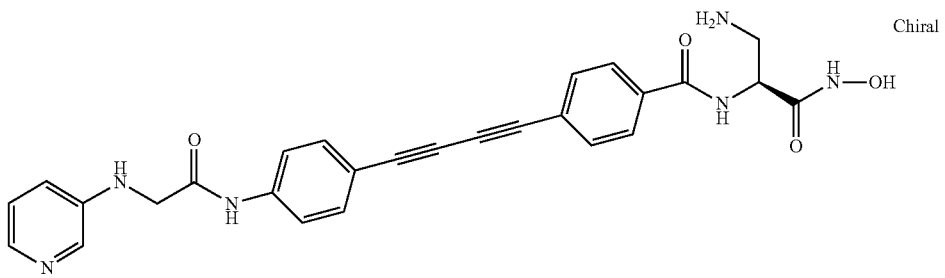
937
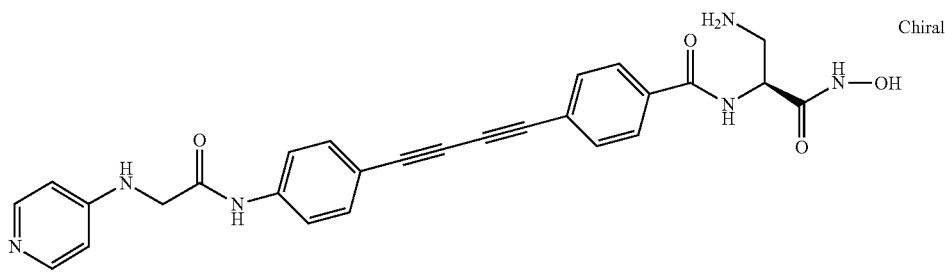
938
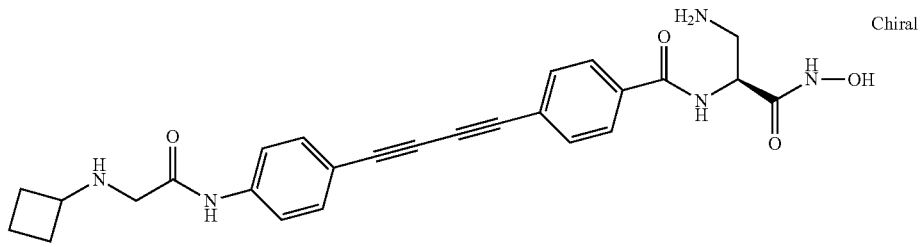
939
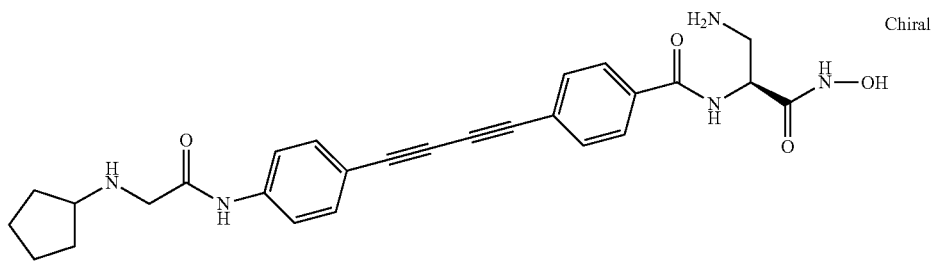

TABLE 1-continued
940 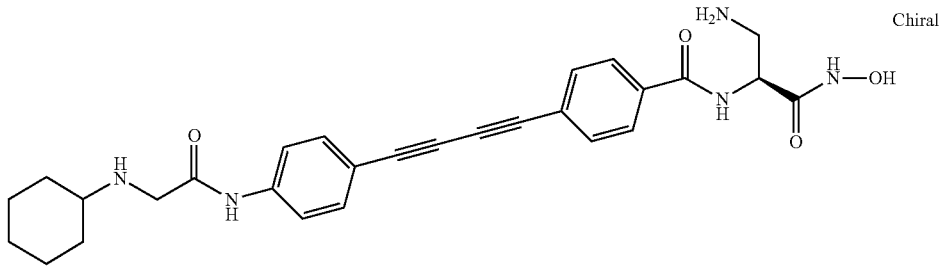
941 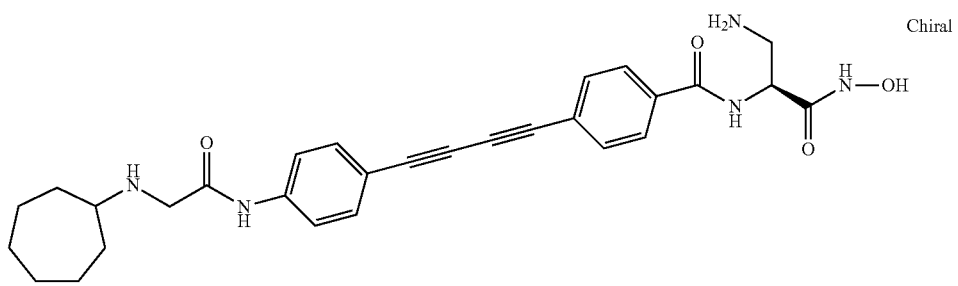
942 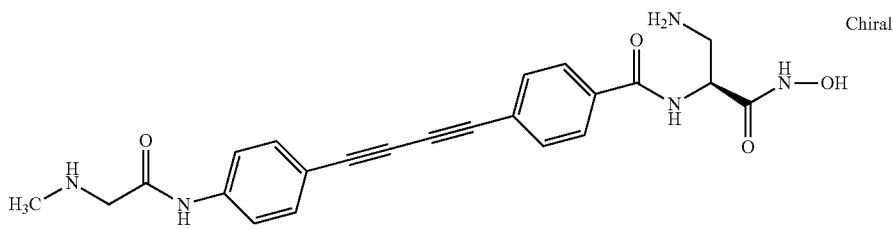
943 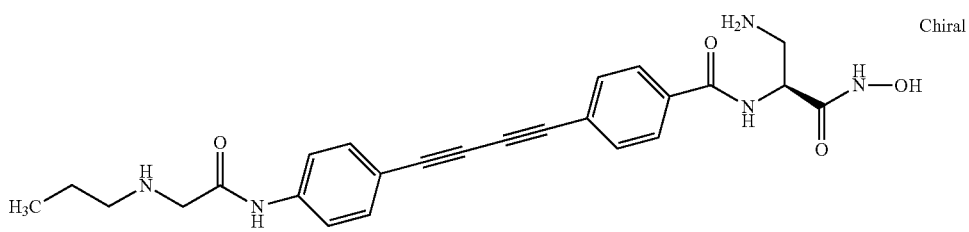
944 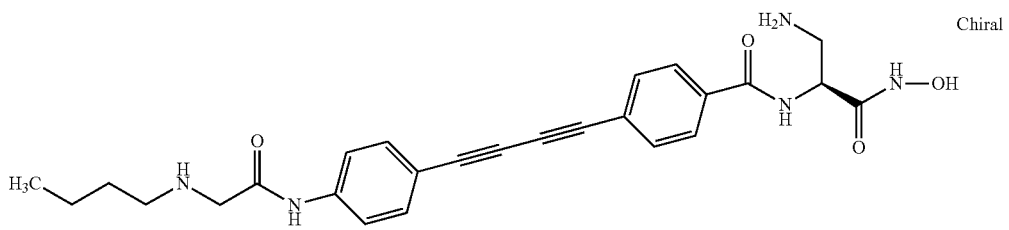
945 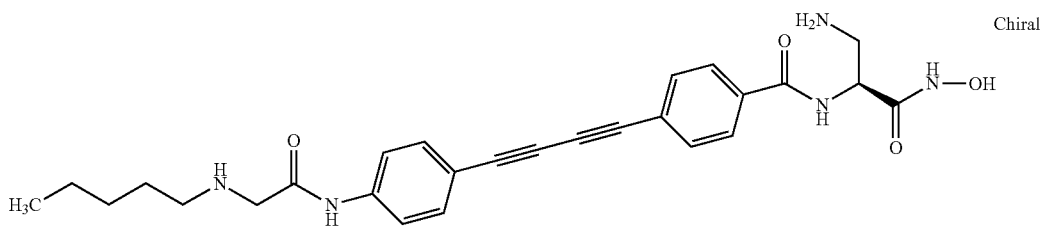

TABLE 1-continued
946 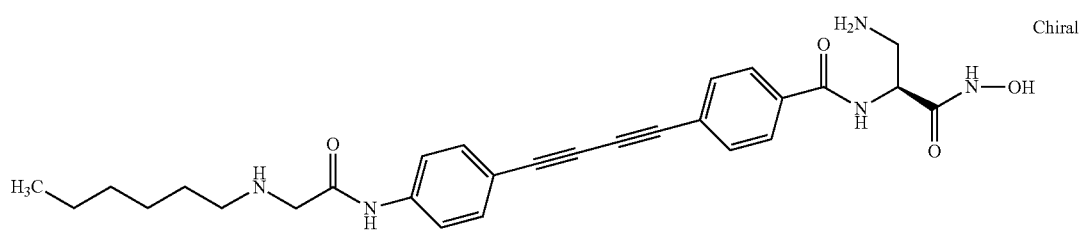
947 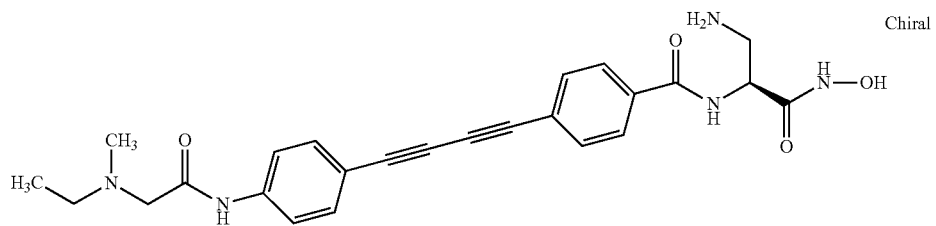
948 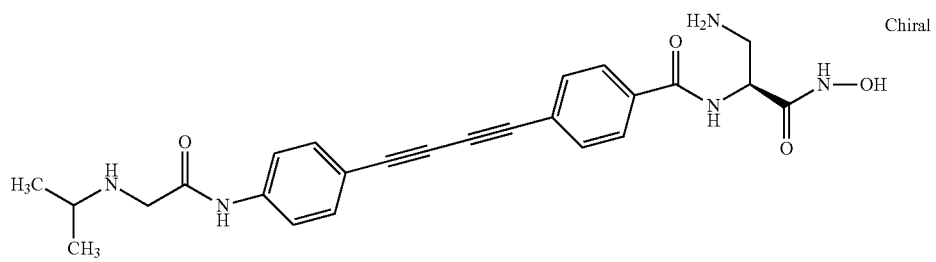
949 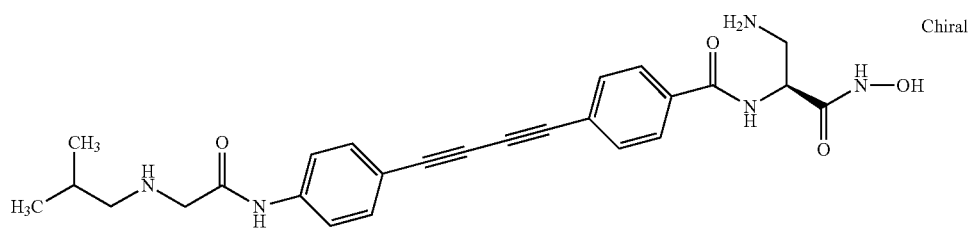
950 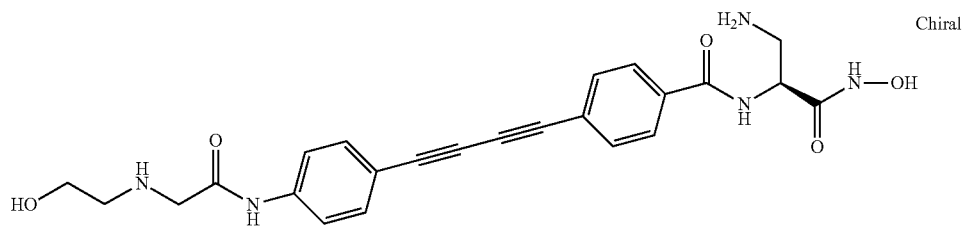
951 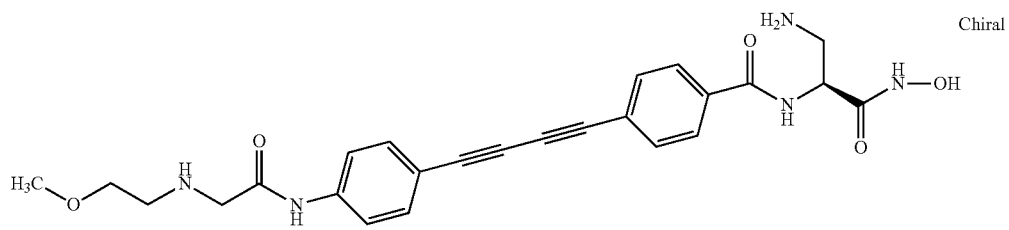

TABLE 1-continued
952 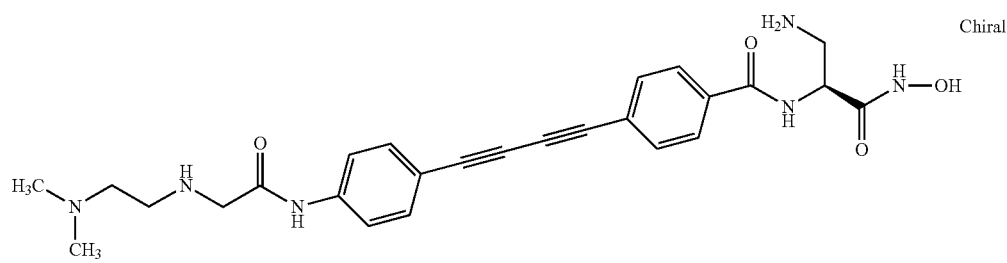
953 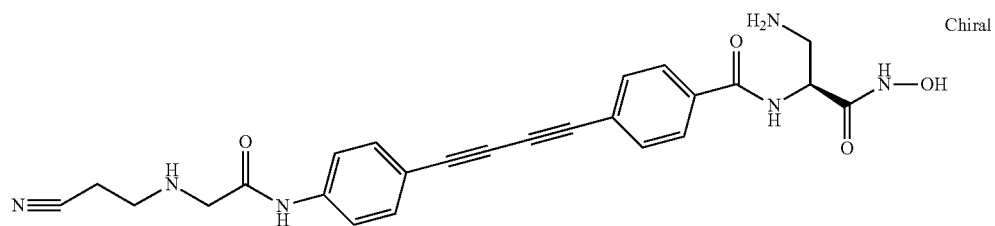
954 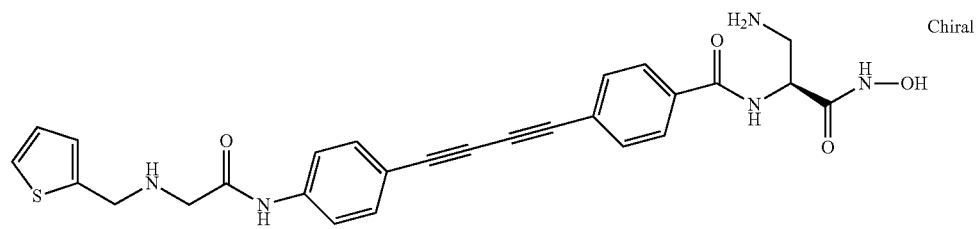
955 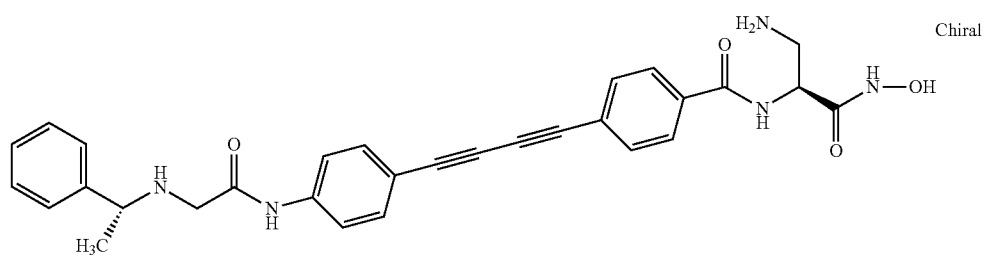
956 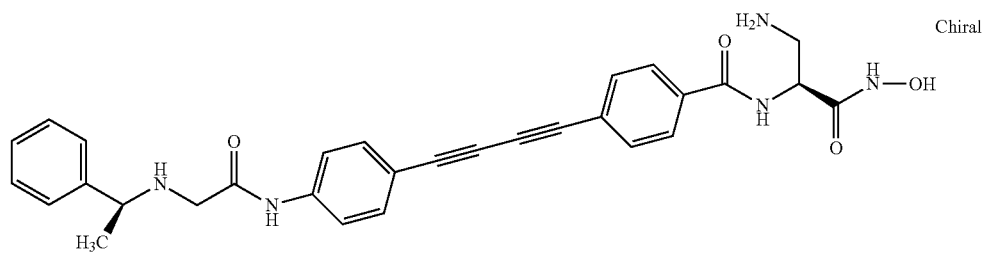
957 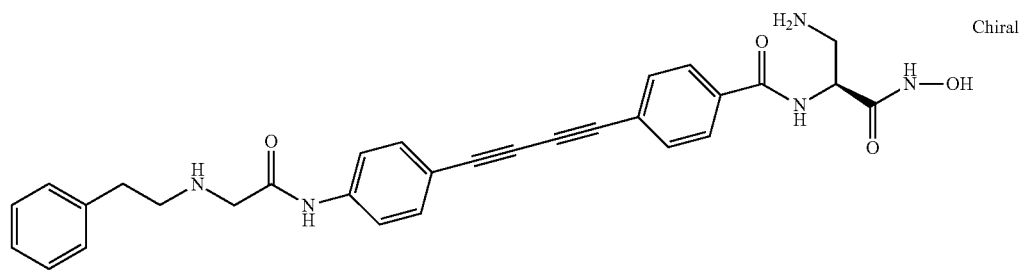

TABLE 1-continued
958 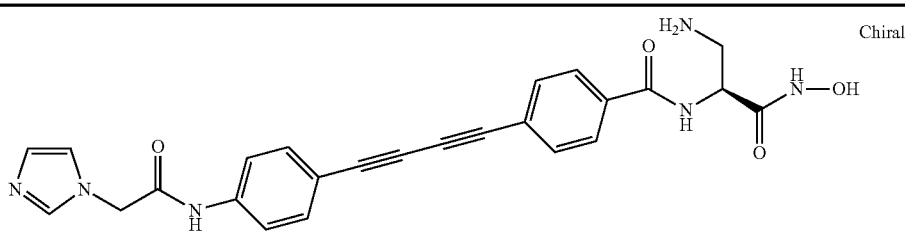
959 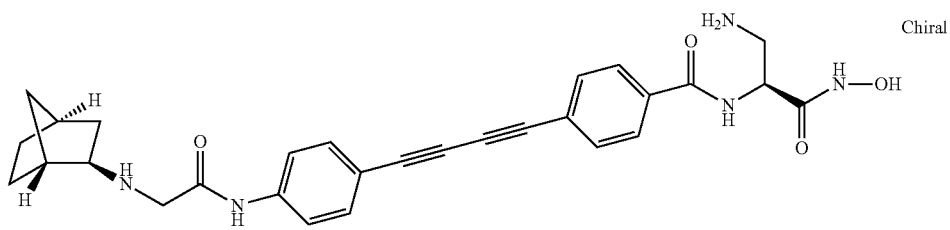
960 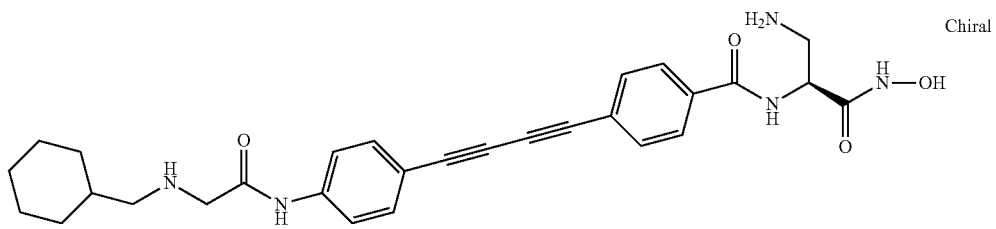
961 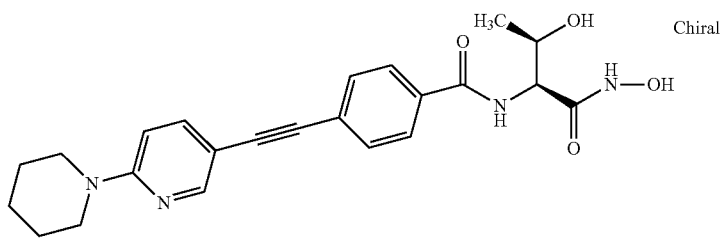
962 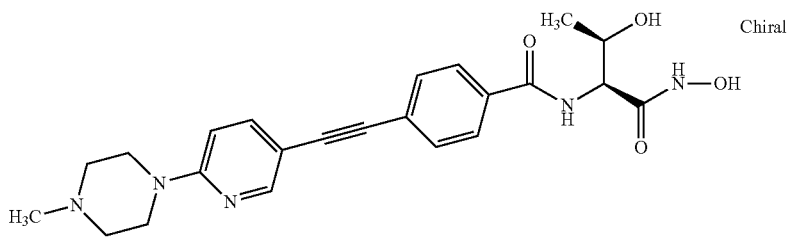
963 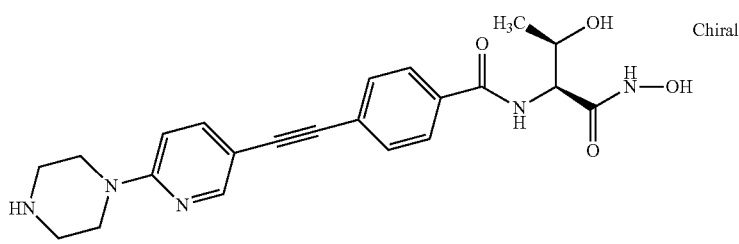

TABLE 1-continued
| 964 | 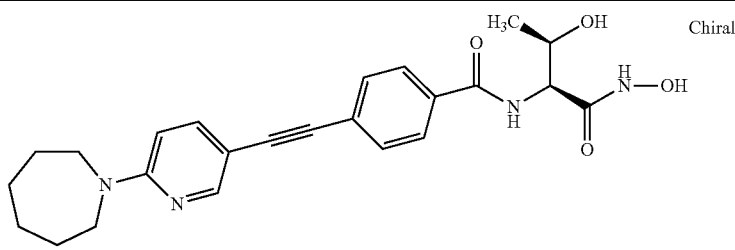 |
| 965 | 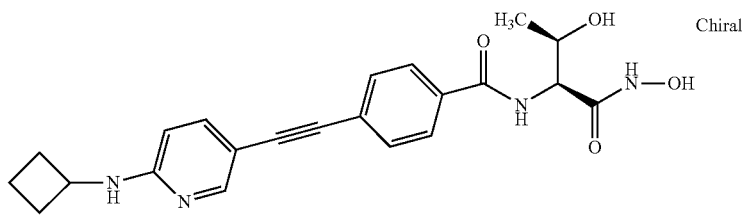 |
| 966 | 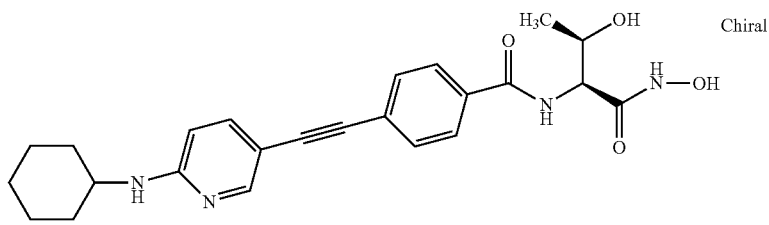 |
| 967 | 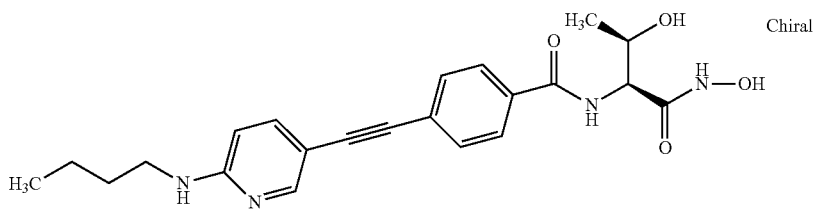 |
| 968 | 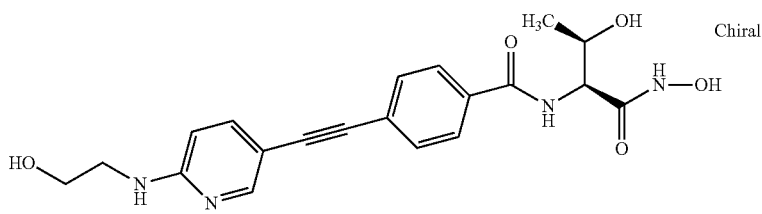 |
| 969 | 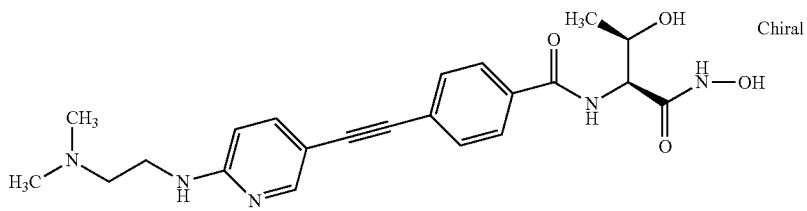 |
| 970 | 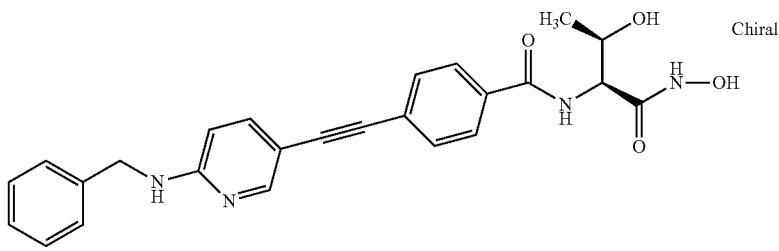 |

TABLE 1-continued
| 971 | 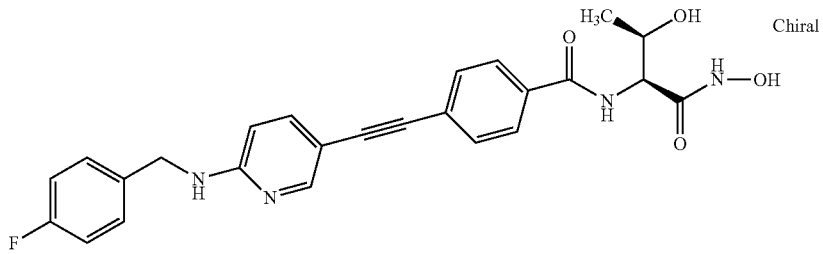 |
| --- | --- |
| 972 | 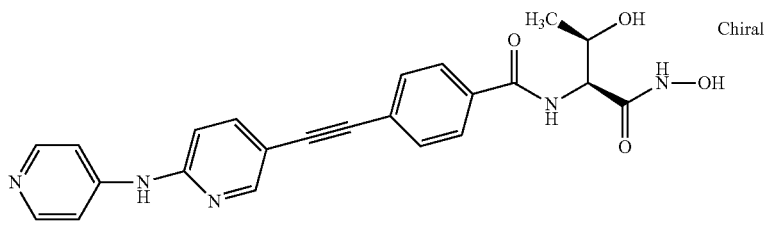 |
| 973 | 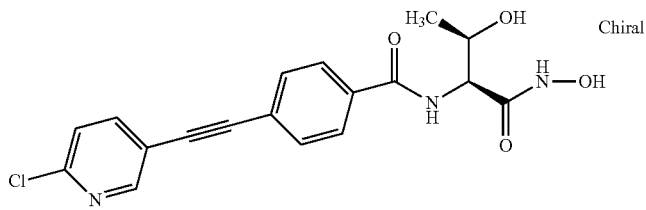 |
| 974 | 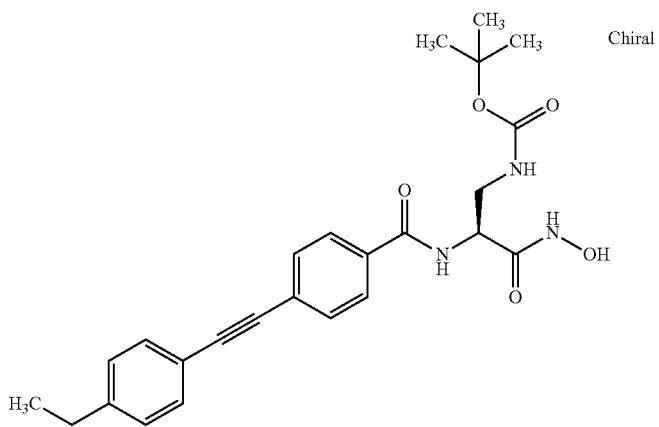 |
| 975 | 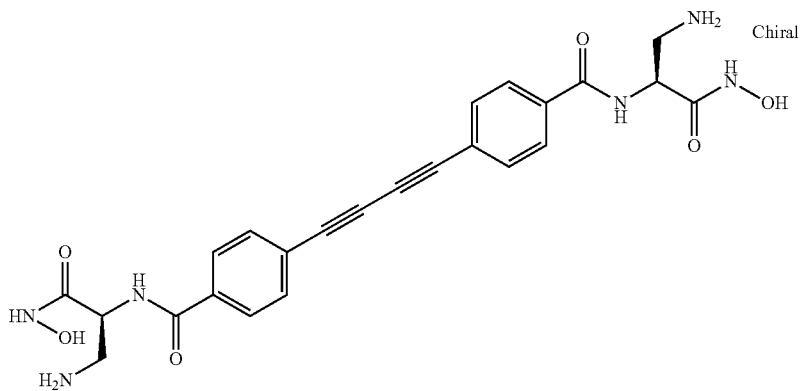 |

TABLE 1-continued
| 976 | 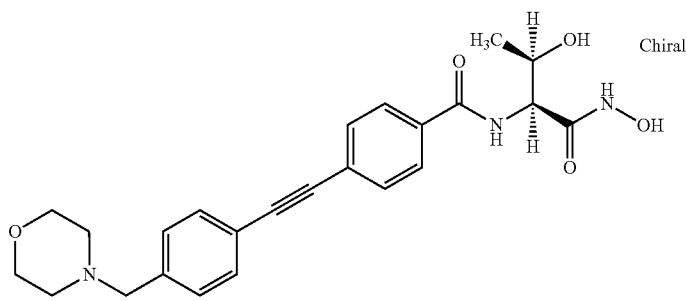 |
| 977 | 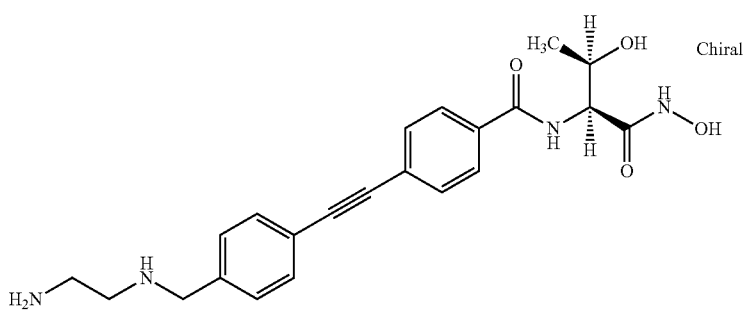 |
| 978 | 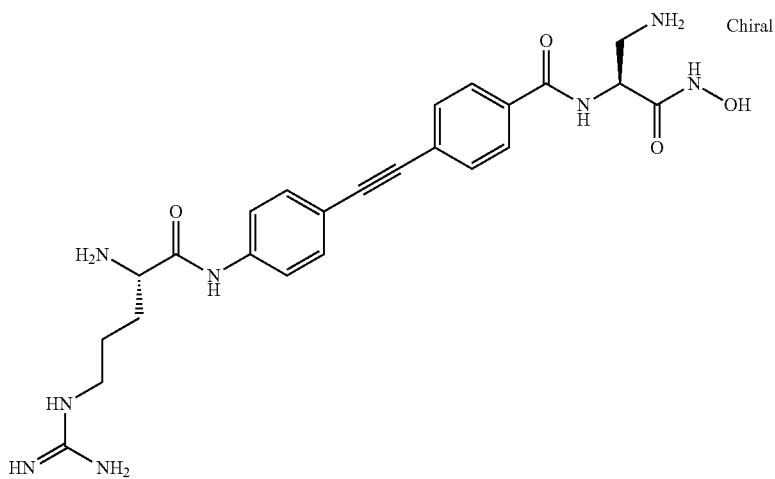 |
| 979 | 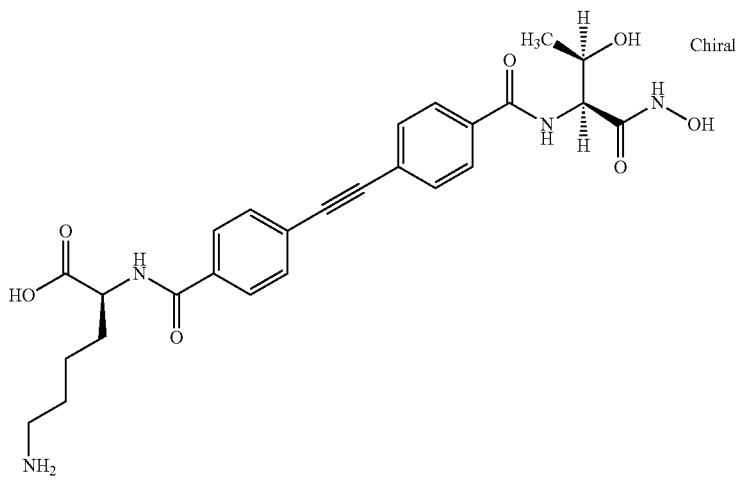 |

TABLE 1-continued
| 980 | 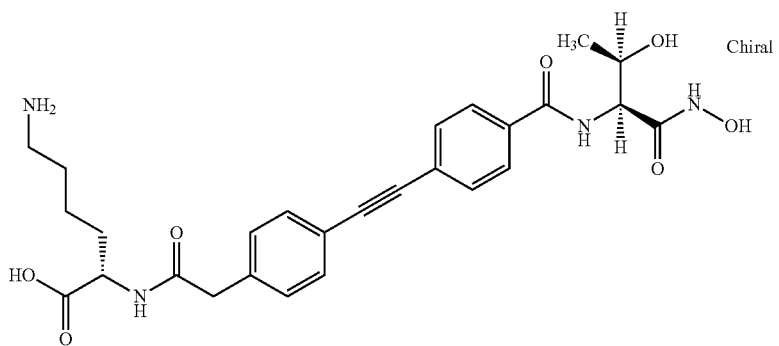 |
| --- | --- |
| 981 | 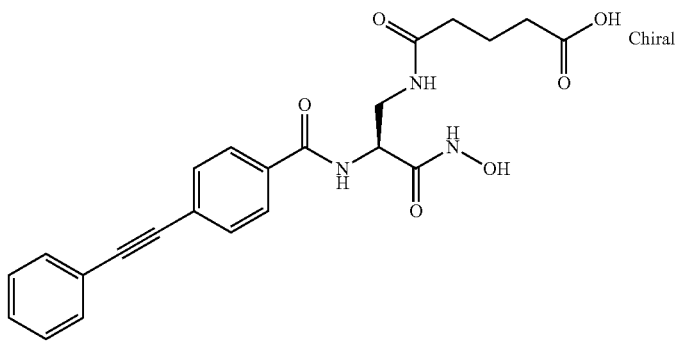 |
| 982 | 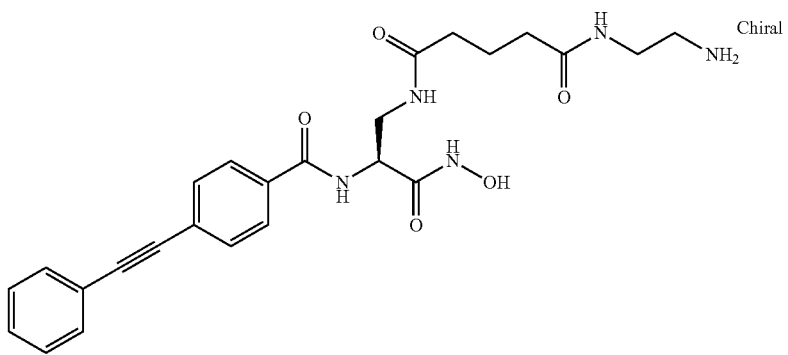 |
| 983 | 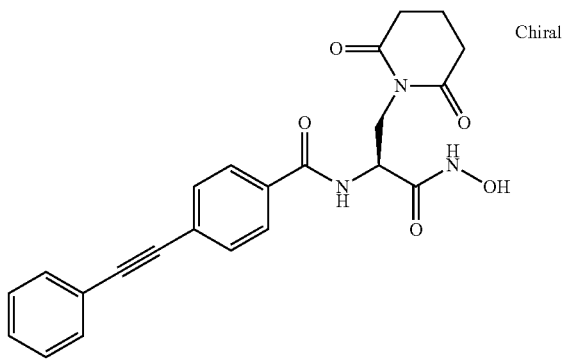 |

TABLE 1-continued
| 984 | 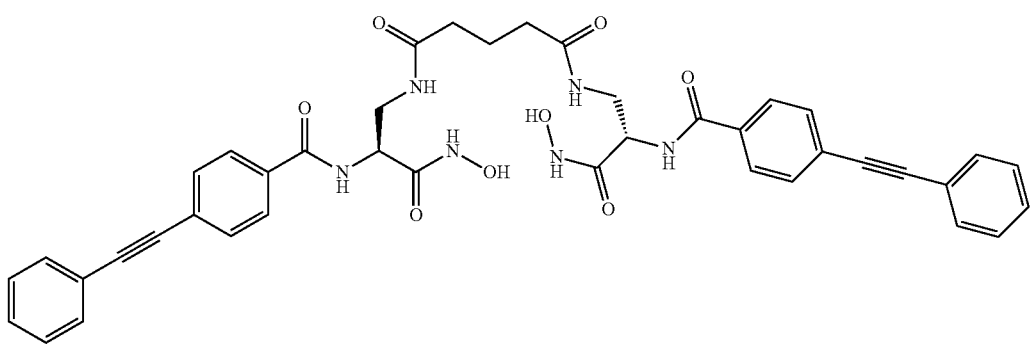 Chiral |
| 985 | 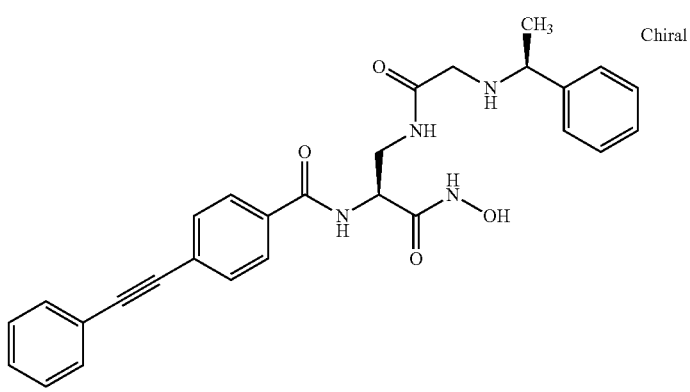 Chiral |
| 986 | 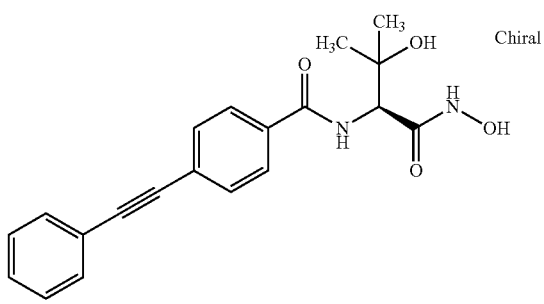 Chiral |
| 987 | 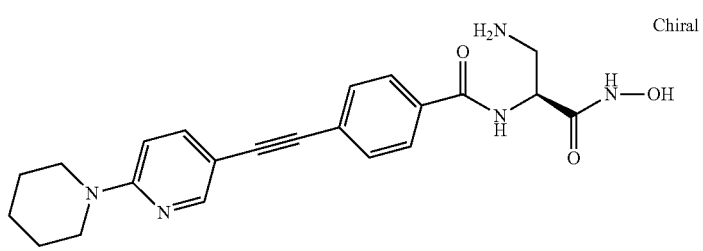 Chiral |
| 988 | 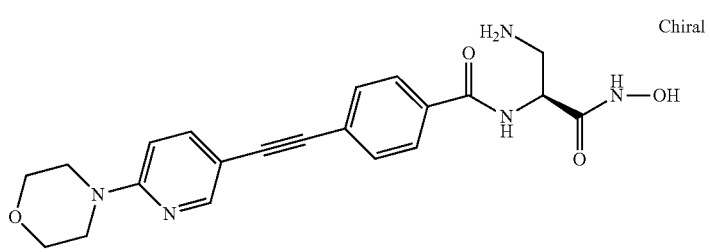 Chiral |

//  
US 8,101,640 B2  
511  512  
TABLE 1-continued
989 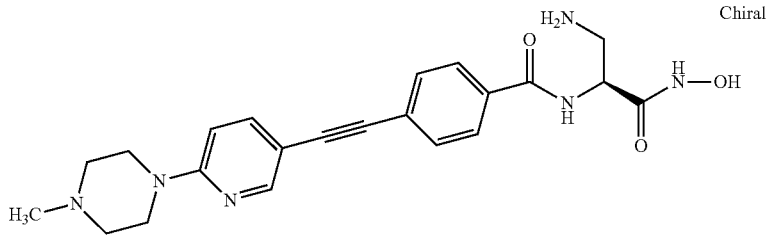
990 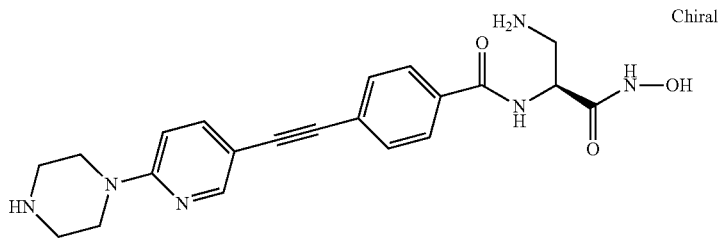
991 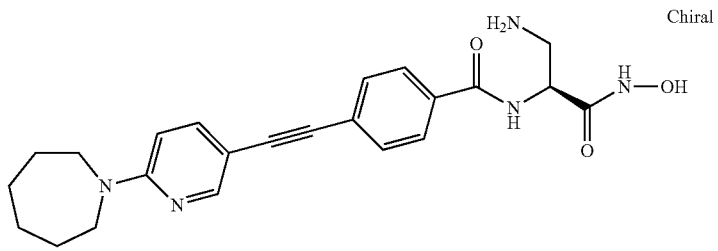
992 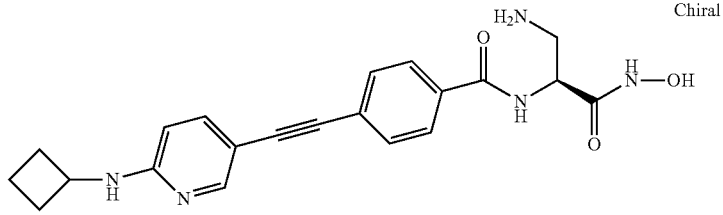
993 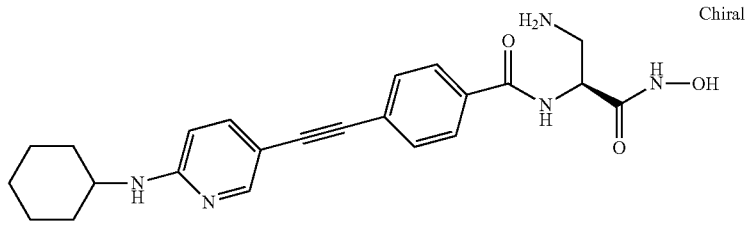
994 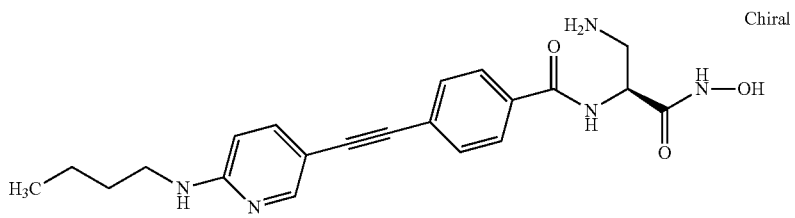

TABLE 1-continued
| 995 | 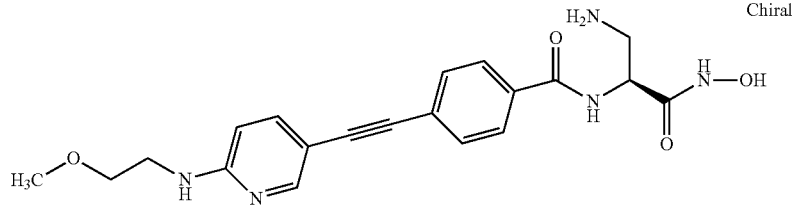 |
| --- | --- |
| 996 | 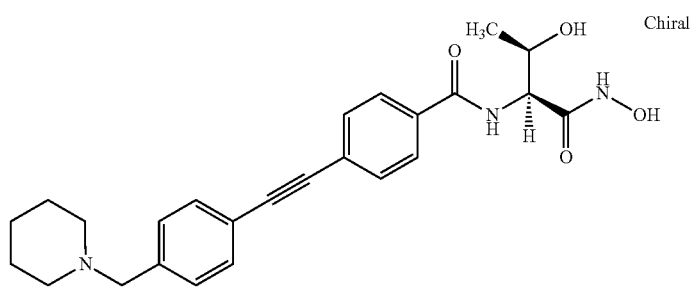 |
| 997 | 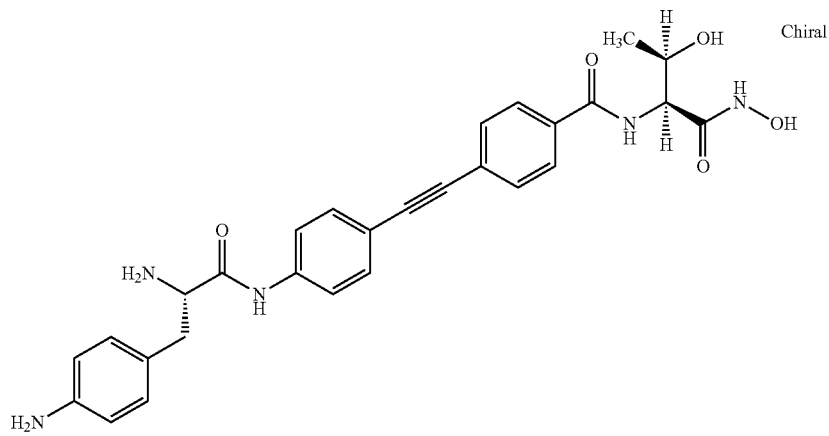 |
| 998 | 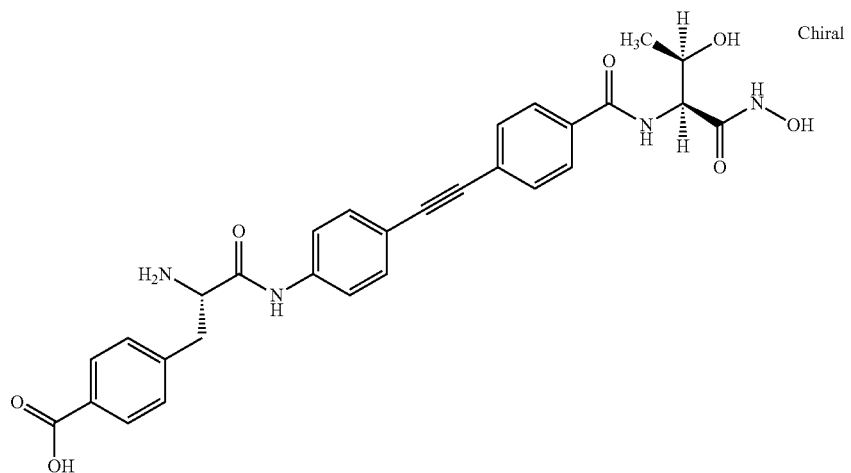 |

TABLE 1-continued
999
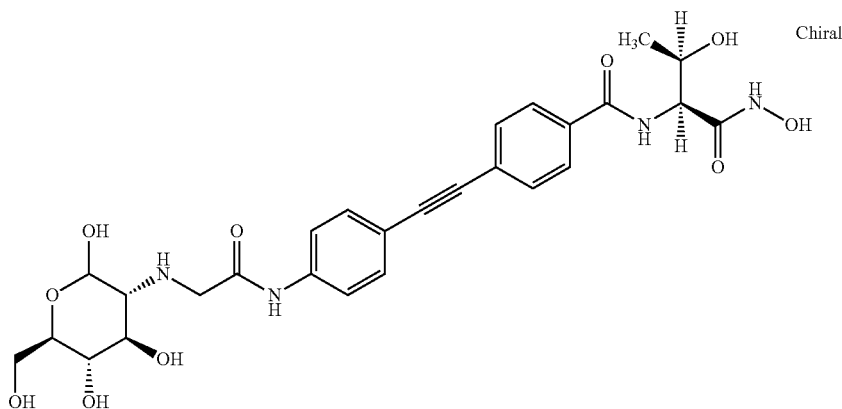
1000
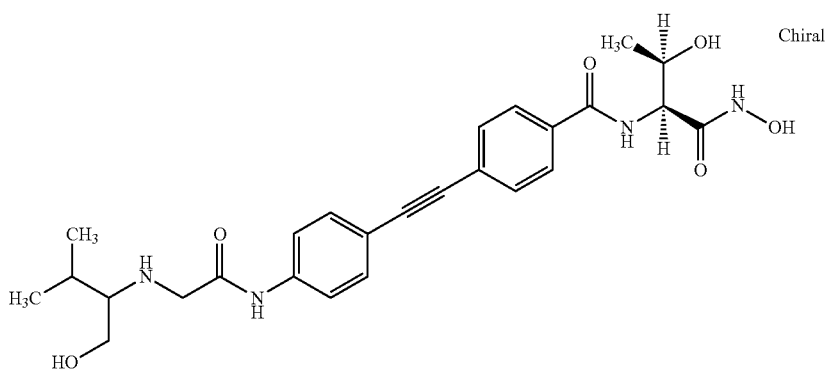
1001
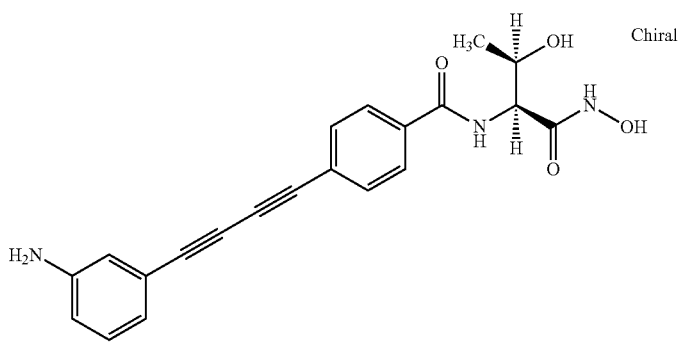
1002
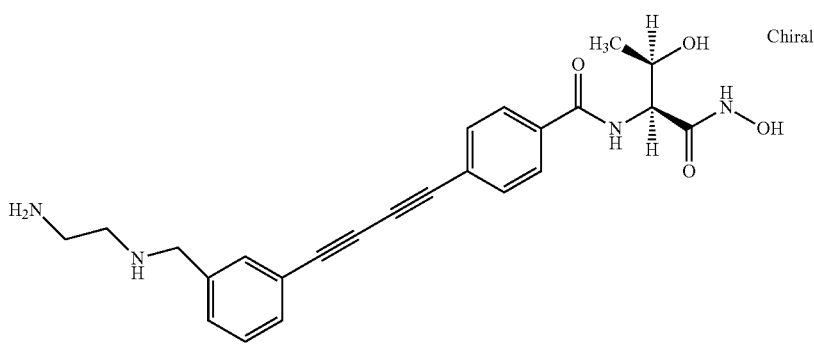

US 8,101,640 B2
TABLE 1-continued
1003 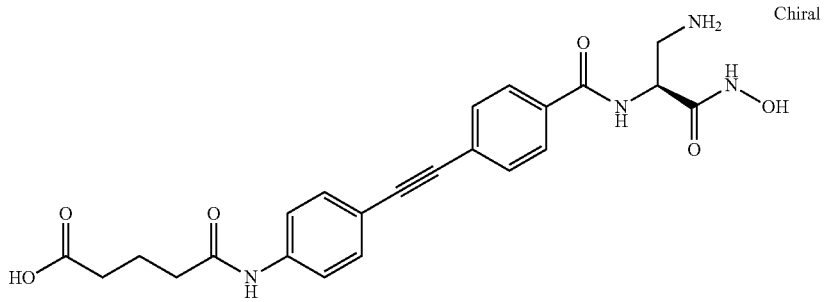
1004 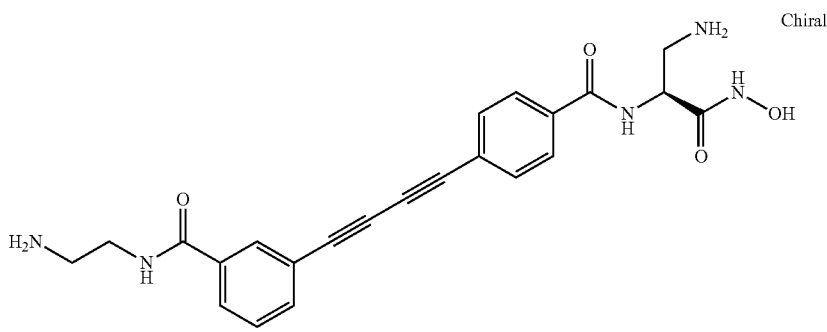
1005 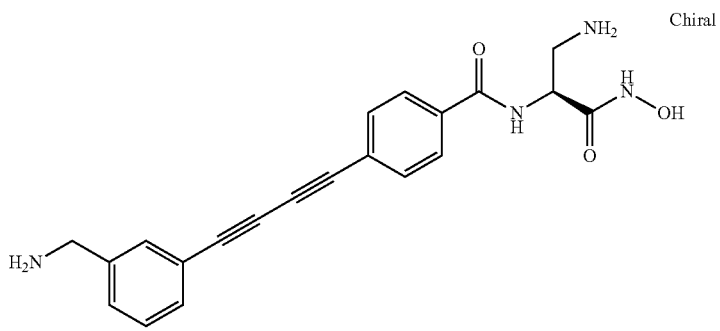
1006 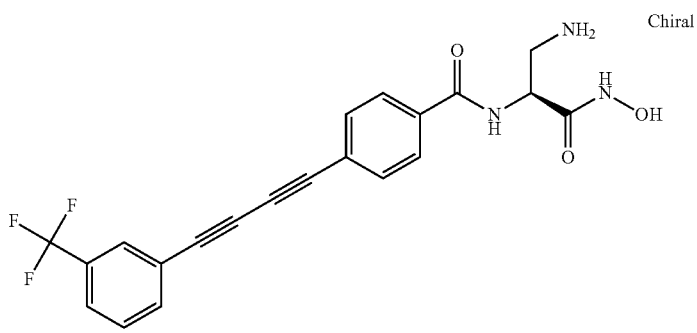
1007 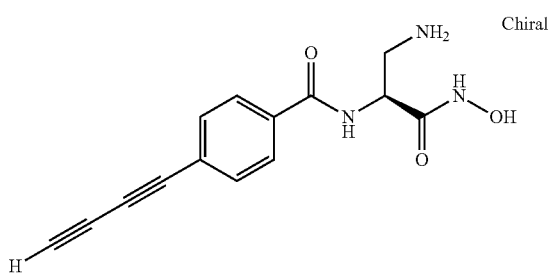

TABLE 1-continued
1008 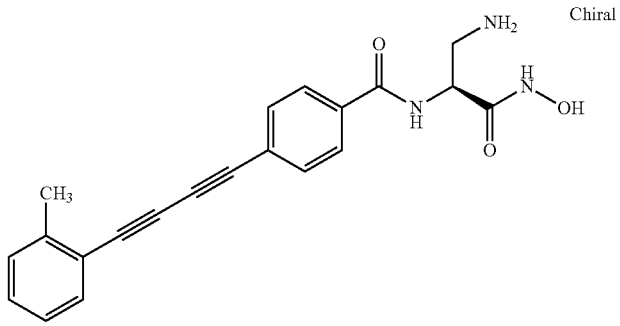
1009 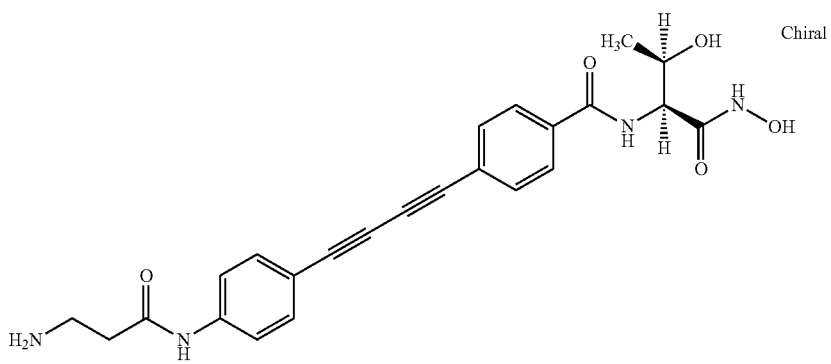
1010 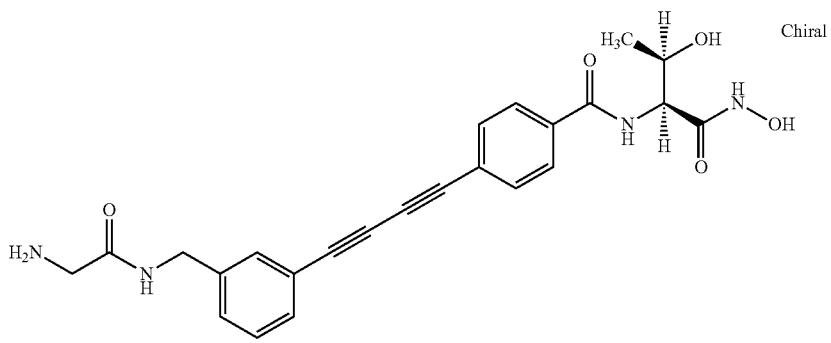
1011 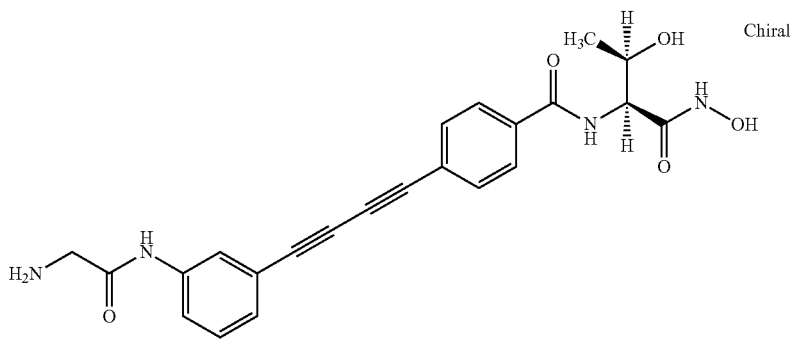

TABLE 1-continued
| 1012 | 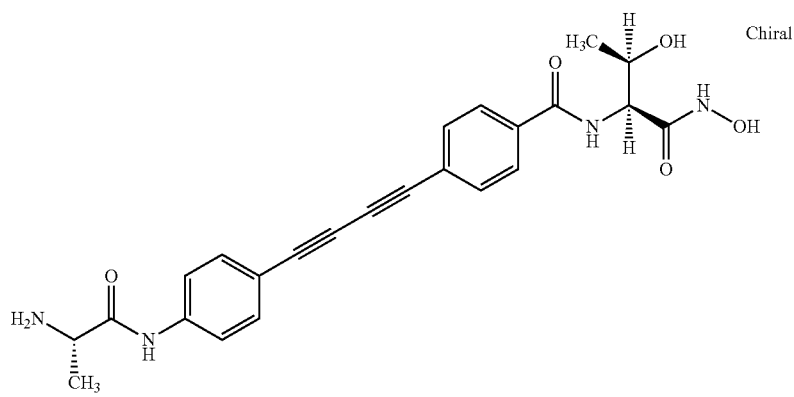 | Chiral |
| 1013 | 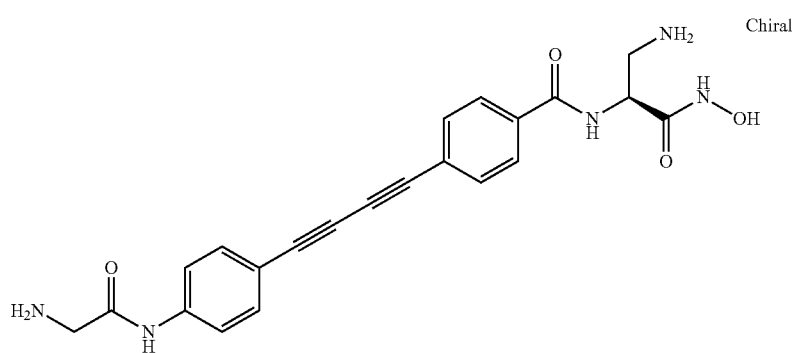 | Chiral |
| 1014 | 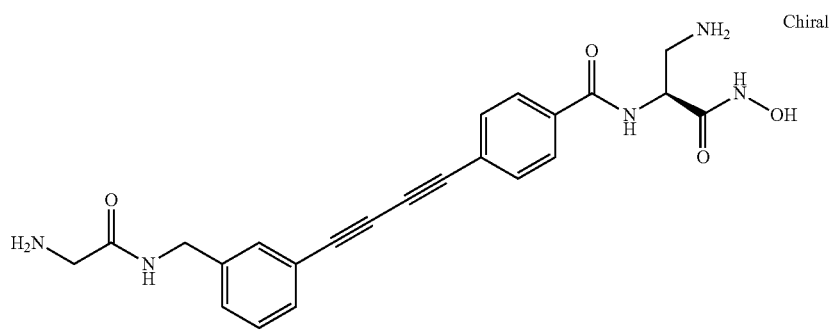 | Chiral |
| 1015 | 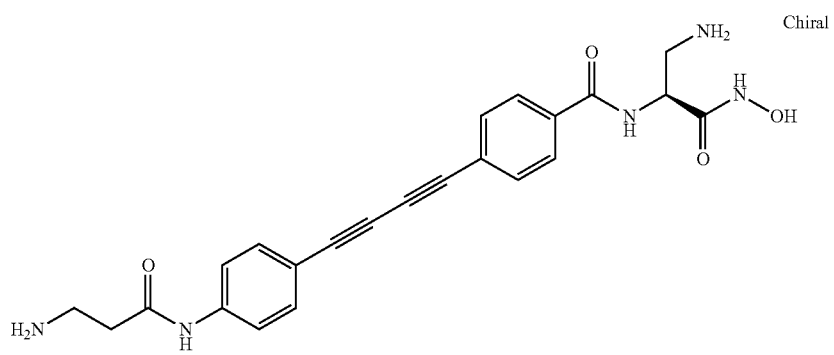 | Chiral |

TABLE 1-continued
1016 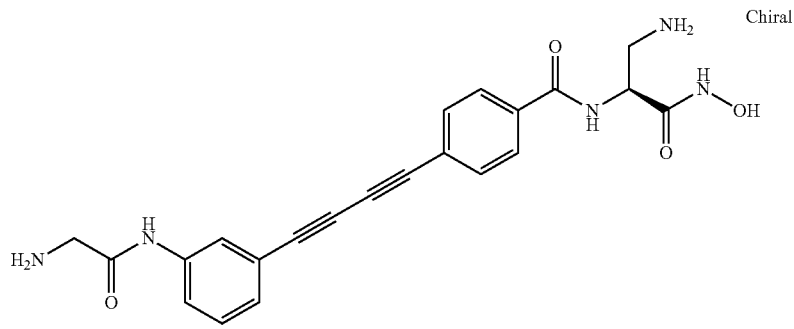
1017 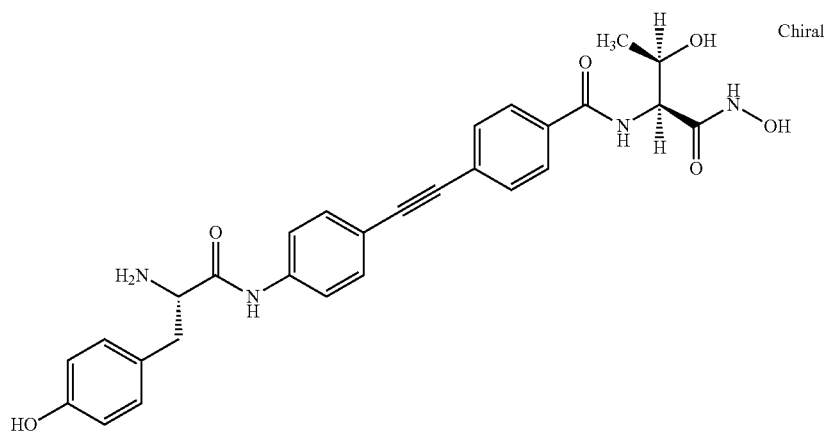
1018 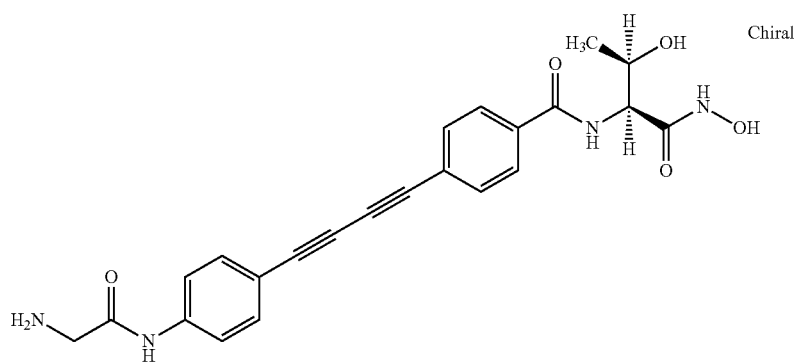
1019 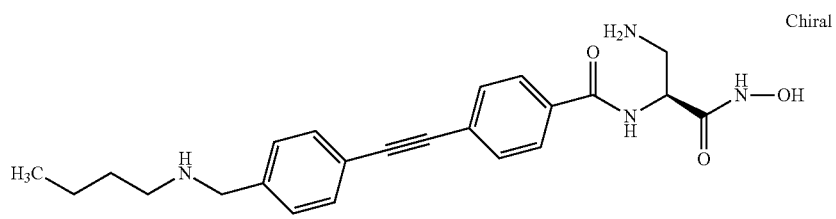
1020 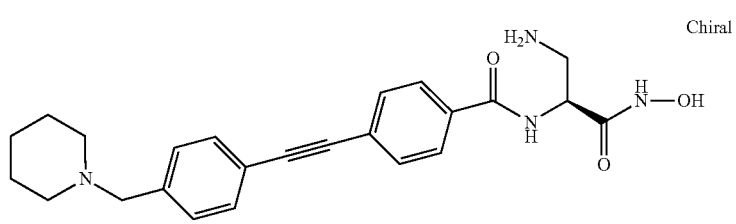

TABLE 1-continued
1021 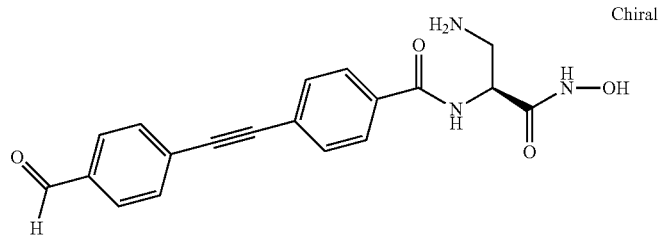
1022 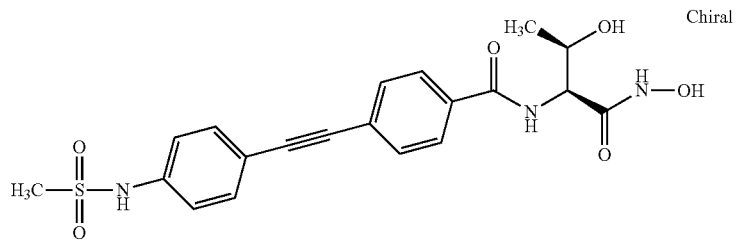
1023 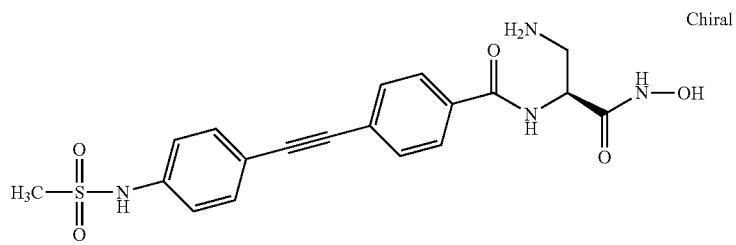
1024 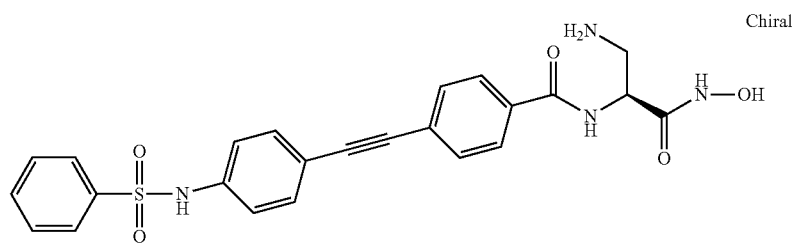
1025 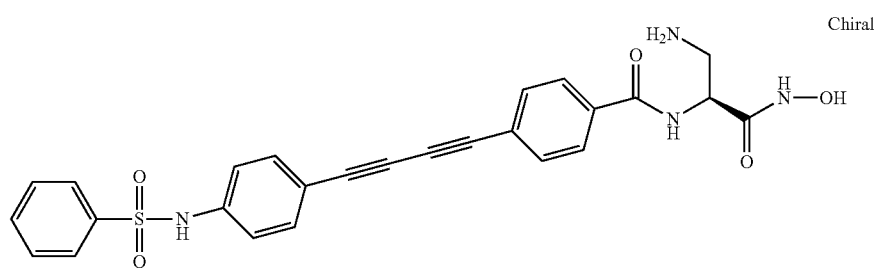
1026 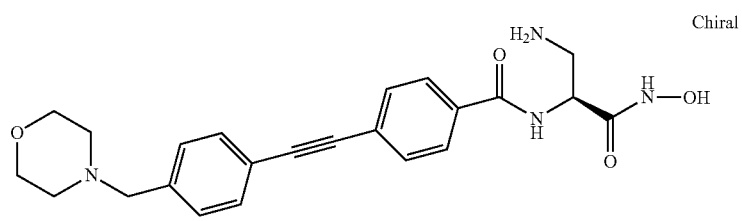

TABLE 1-continued
1027 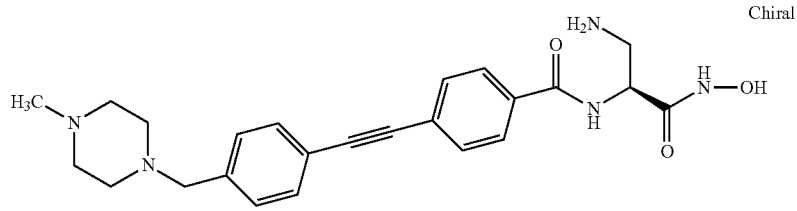
1028 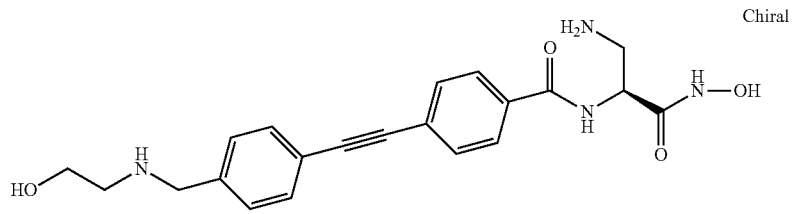
1029 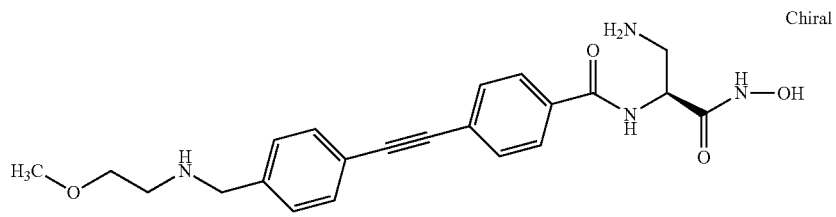
1030 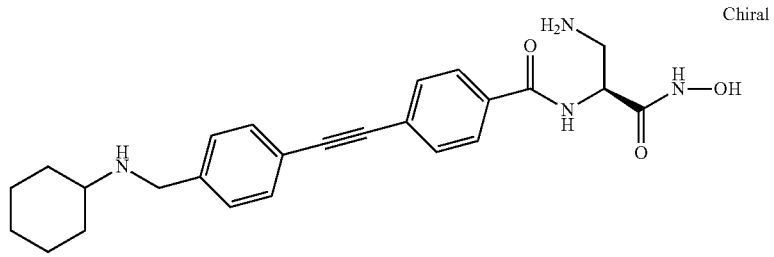
1031 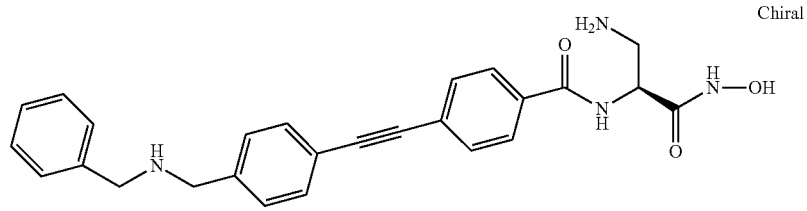
1032 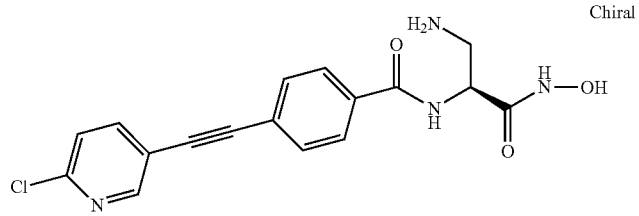

TABLE 1-continued
1033 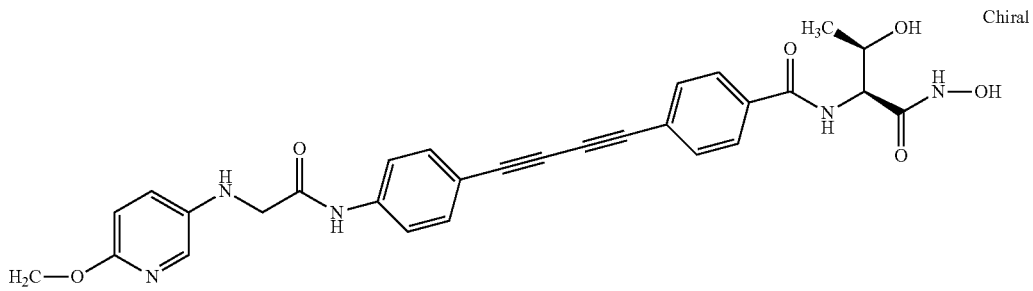
1034 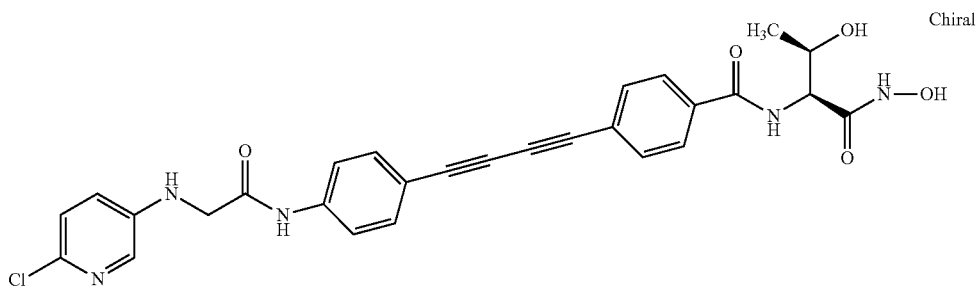
1035 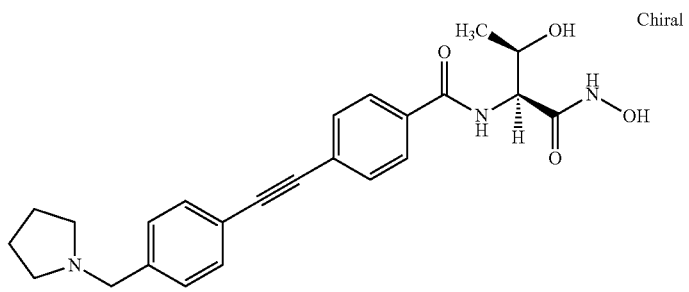
1036 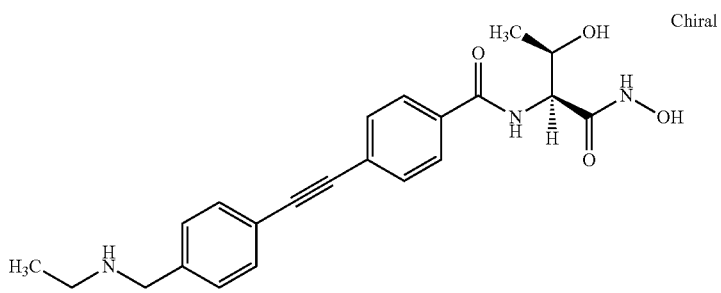
1037 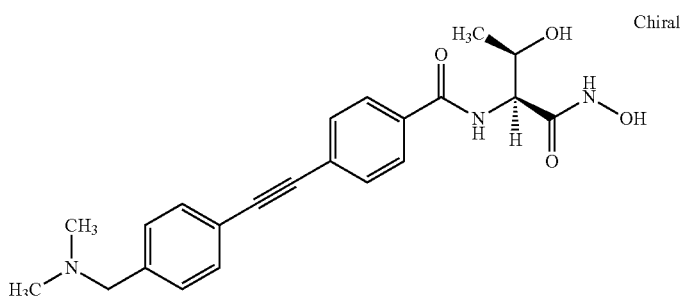

TABLE 1-continued
1038
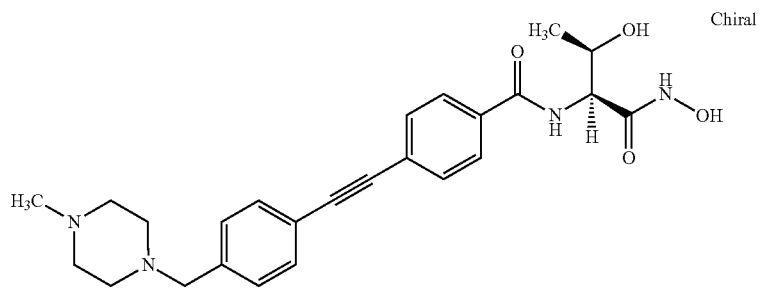
1039
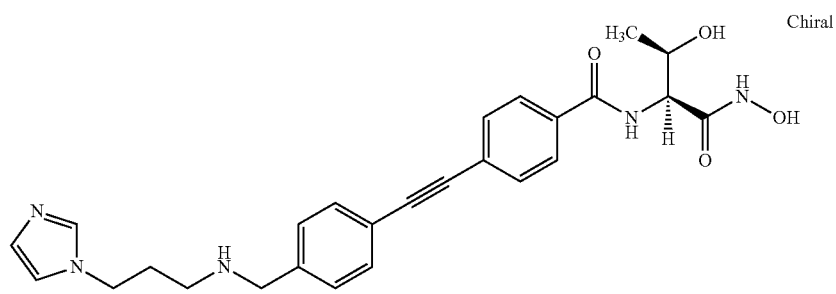
1040
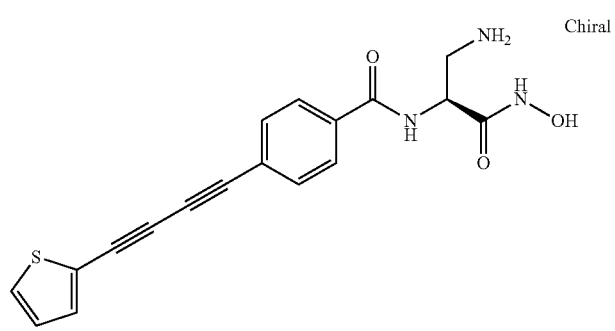
1041
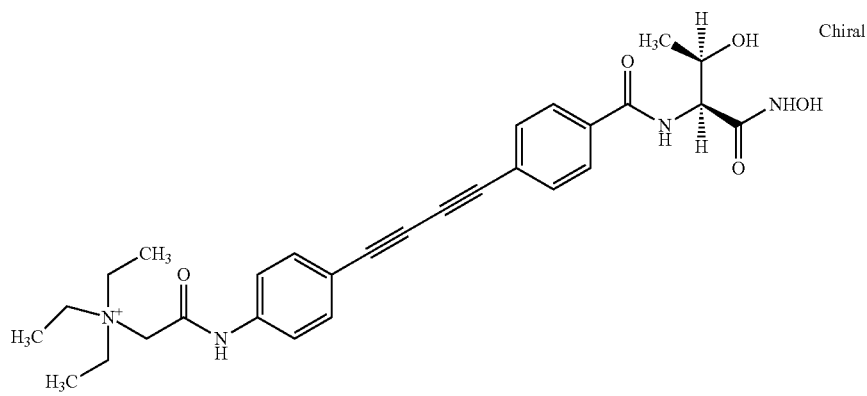
1042
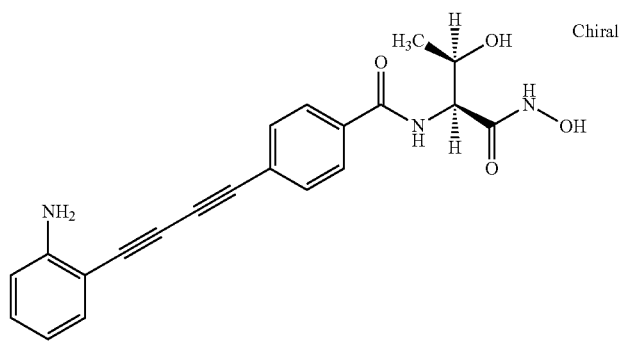

TABLE 1-continued
1043 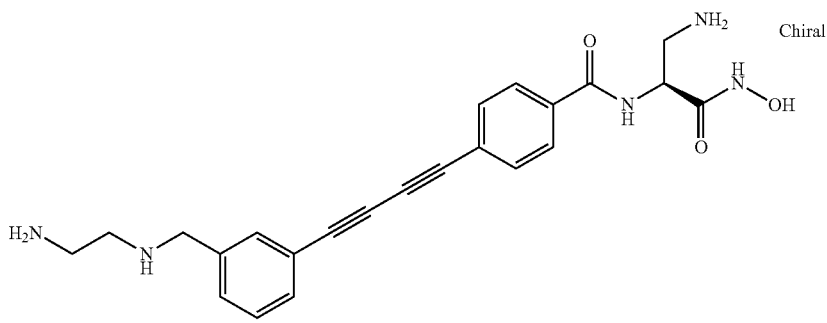
1044 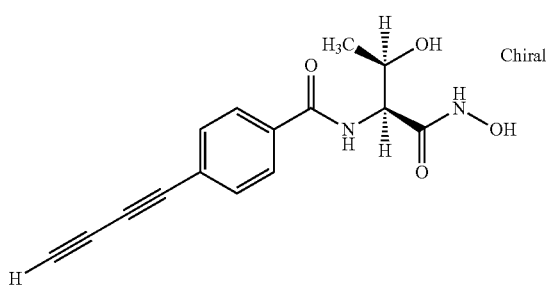
1045 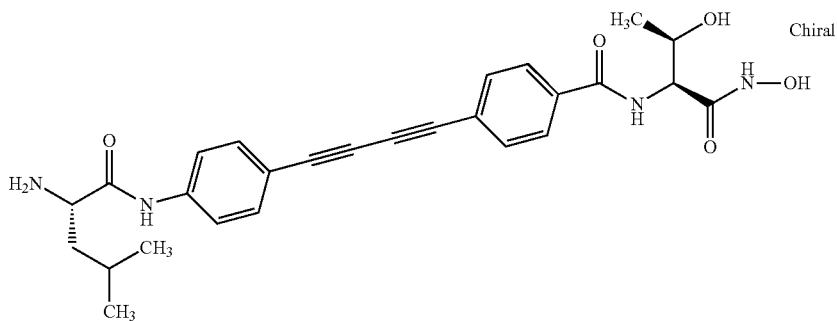
1046 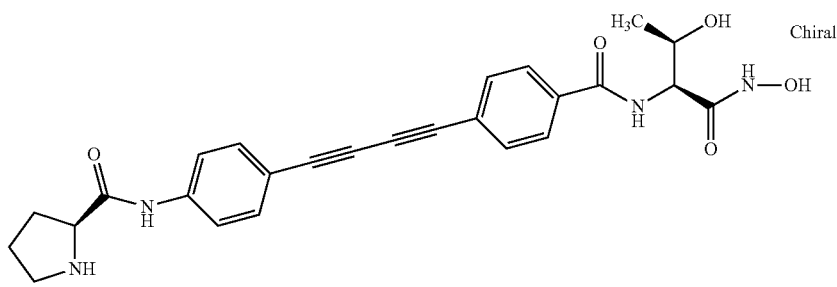
1047 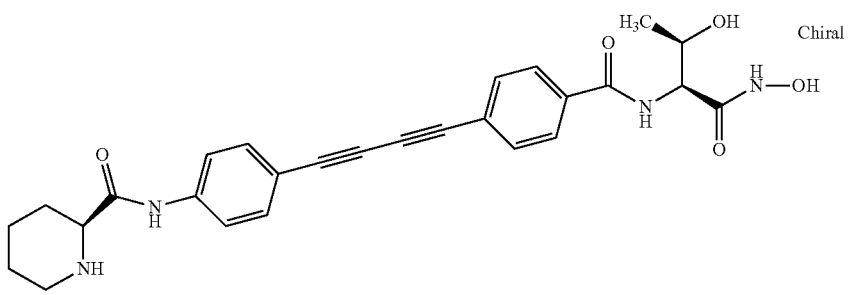

TABLE 1-continued
1048
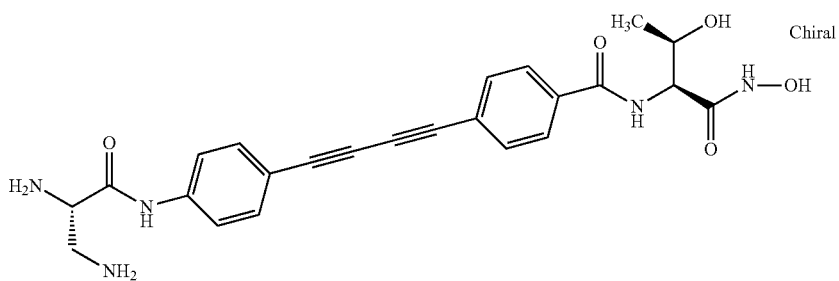
1049
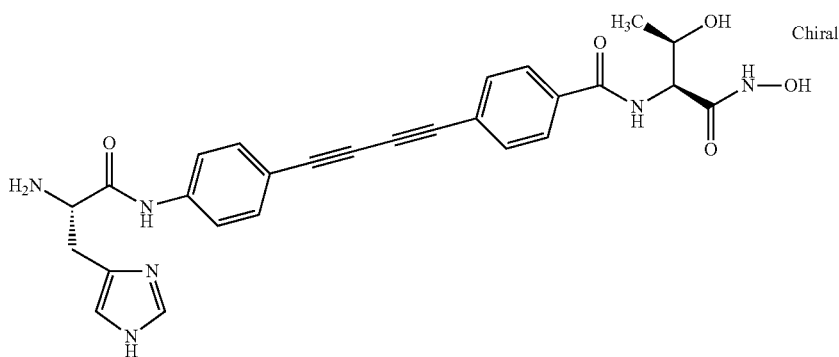
1050
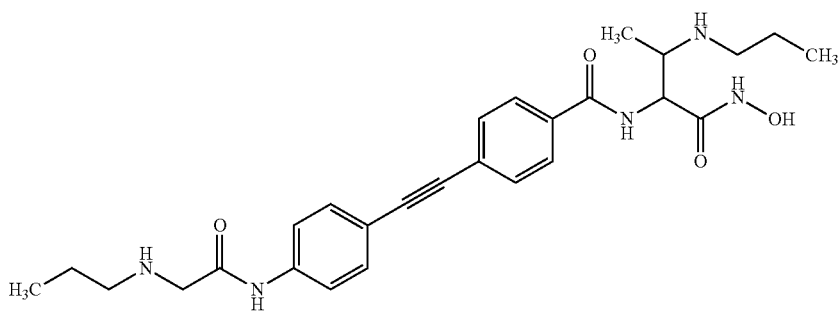
1051
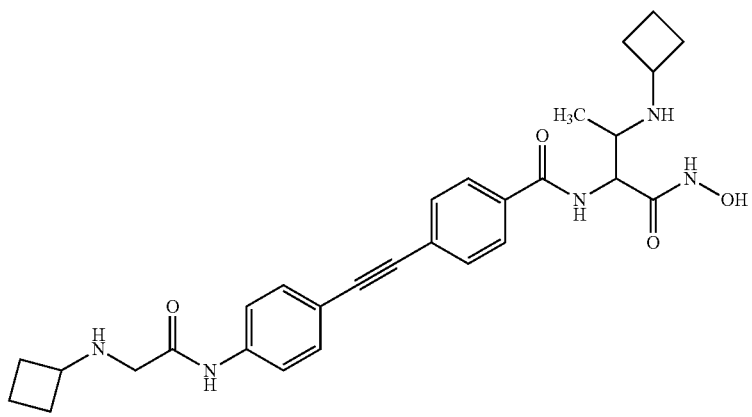

TABLE 1-continued
| 1052 | 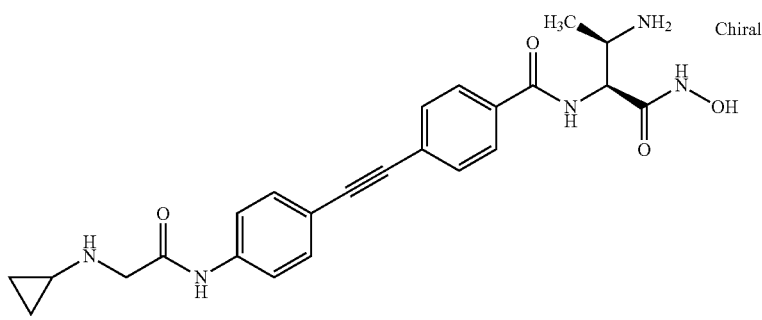 |
| 1053 | 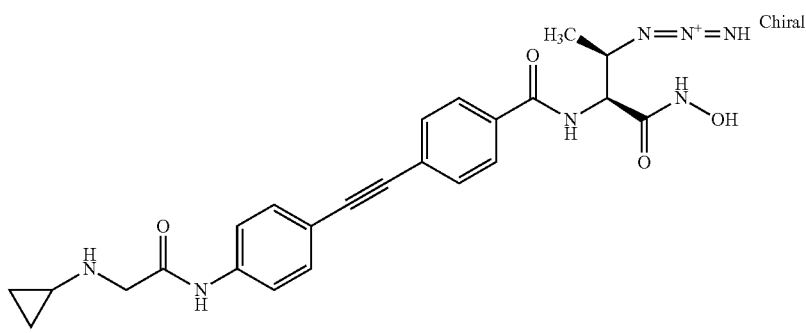 |
| 1054 | 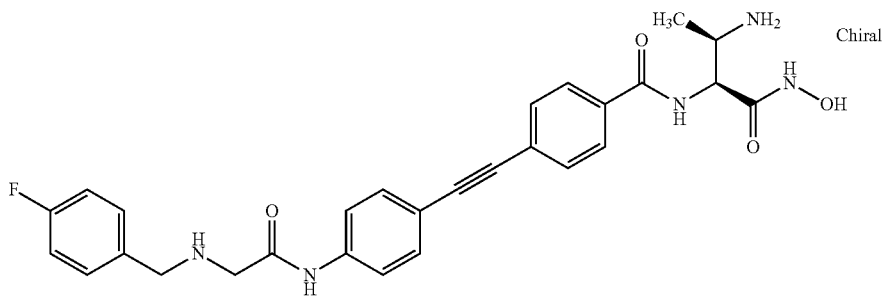 |
| 1055 | 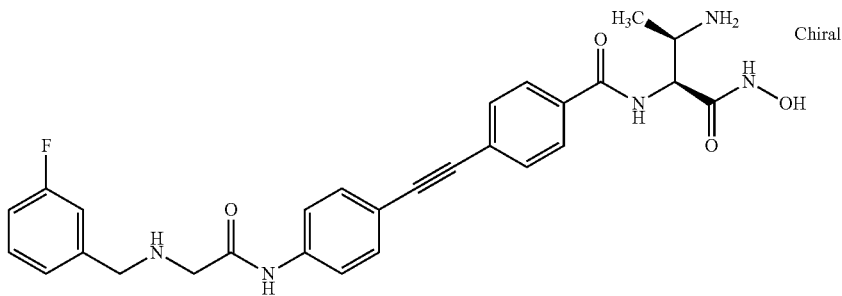 |
| 1056 | 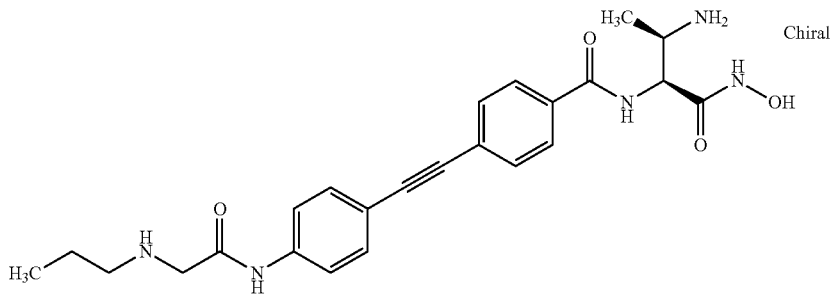 |

TABLE 1-continued
| 1057 | 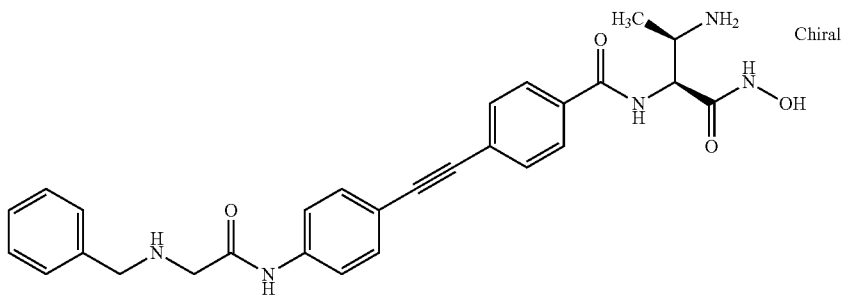 |
| --- | --- |
| 1058 | 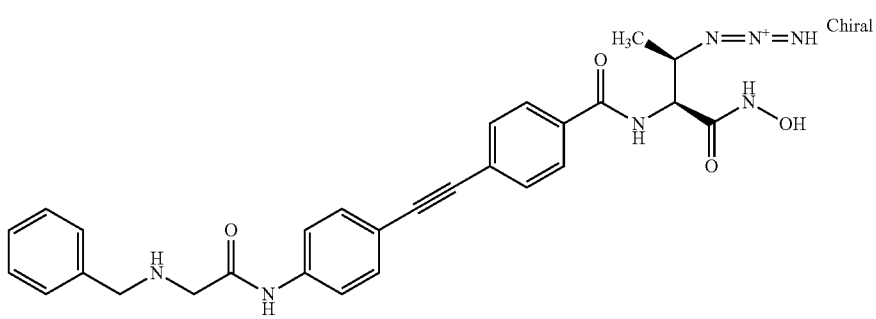 |
| 1059 | 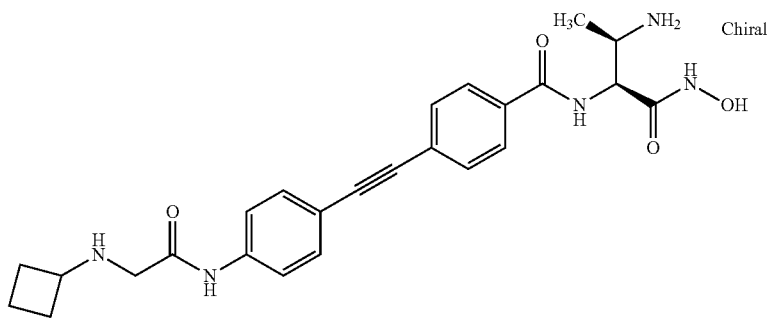 |
| 1060 | 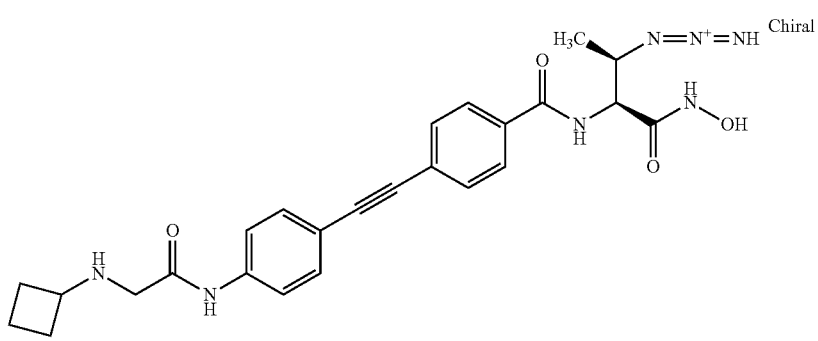 |
| 1061 | 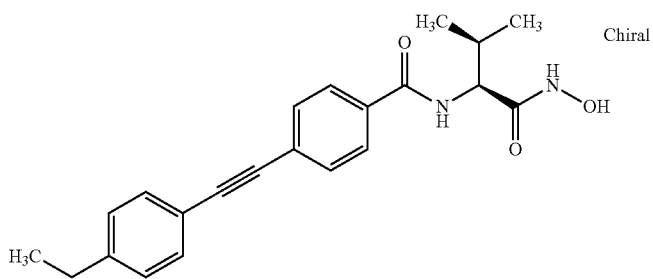 |

TABLE 1-continued
1062 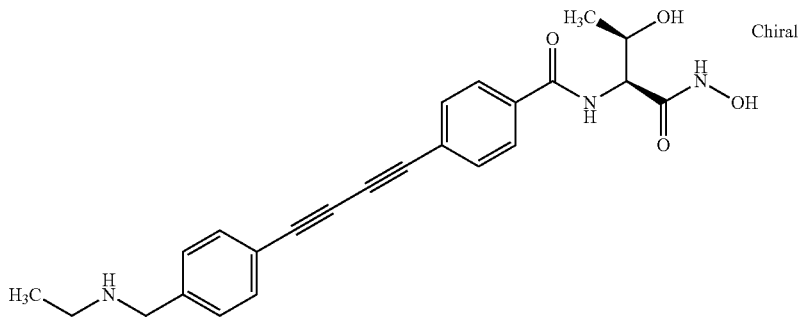
1063 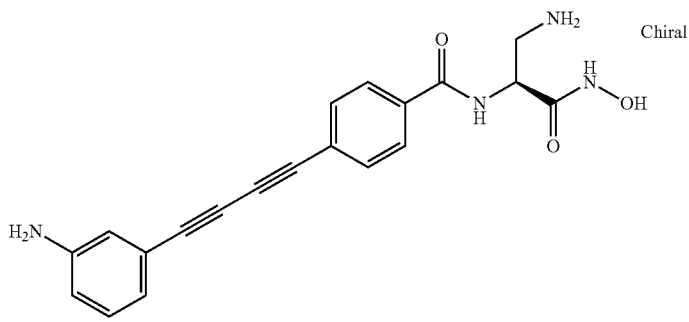
1064 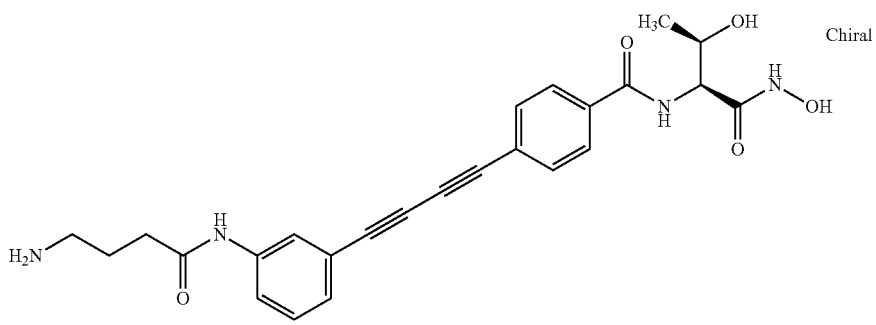
1065 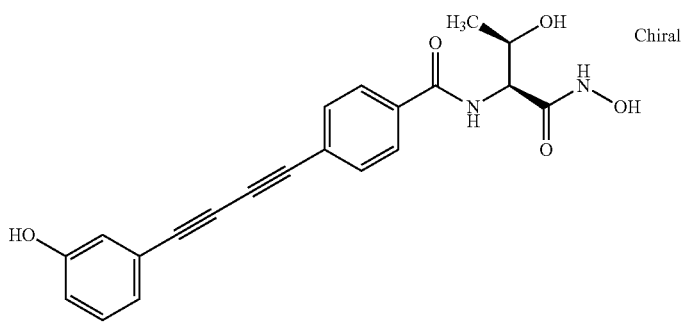
1066 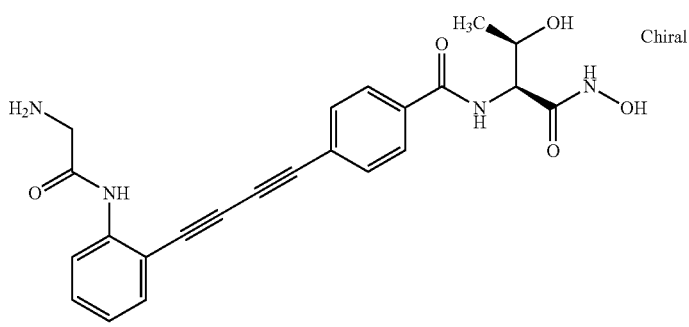

TABLE 1-continued
1067 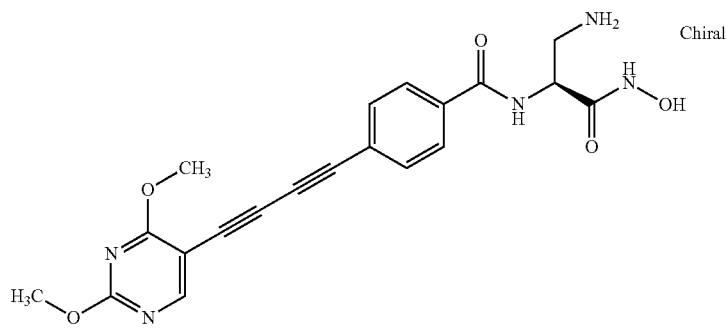
1068 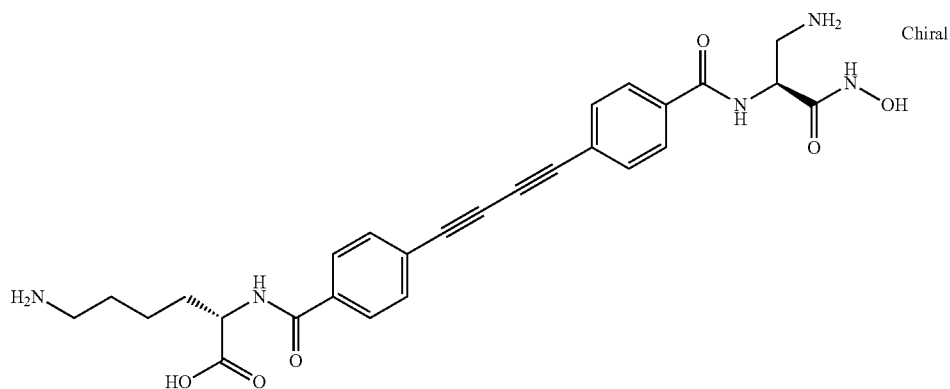
1069 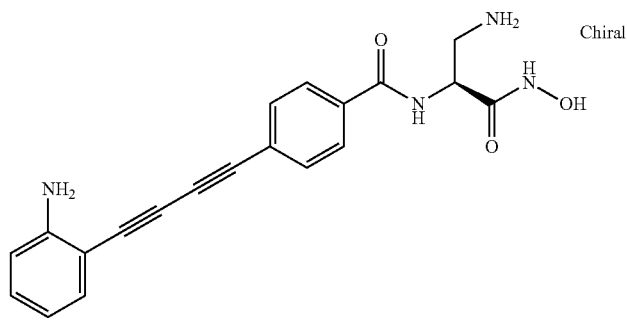
1070 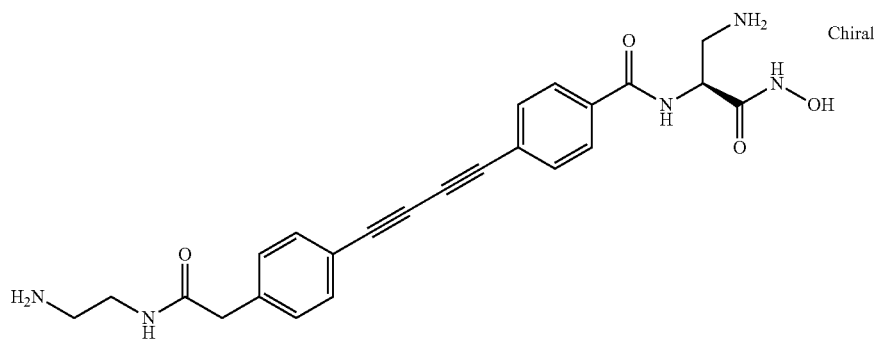

TABLE 1-continued
1071 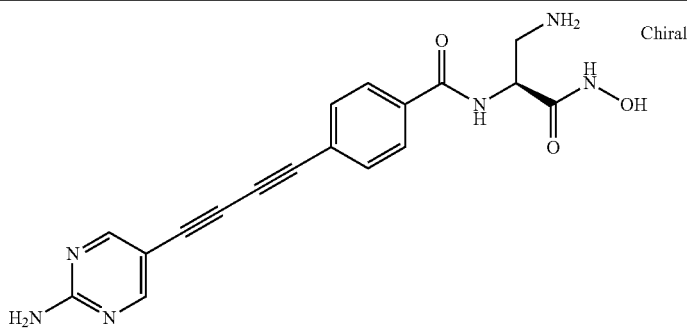
1072 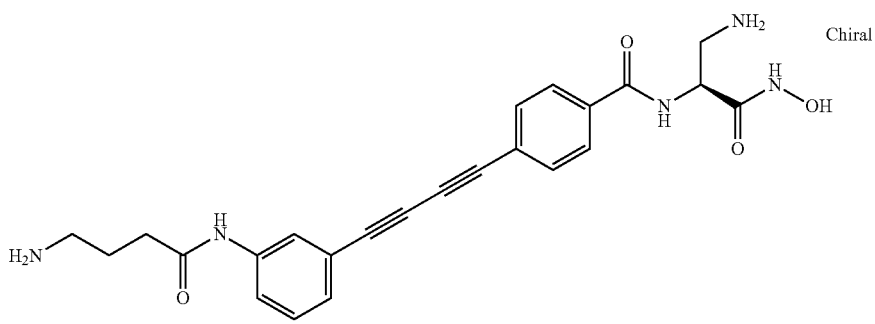
1073 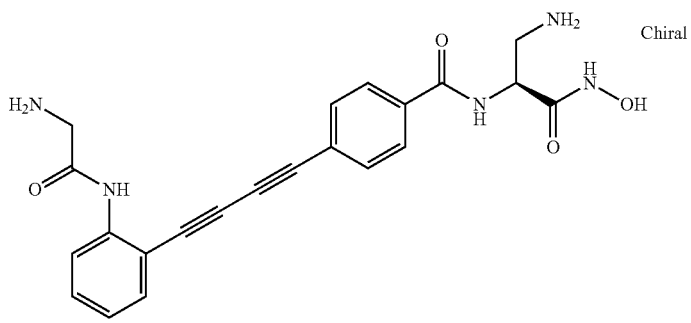
1074 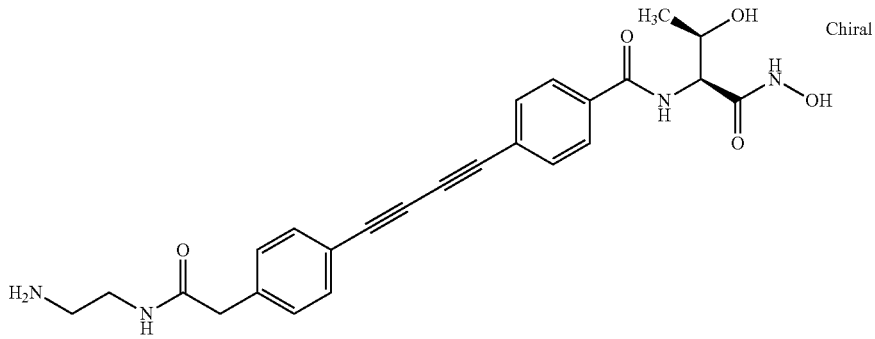
1075 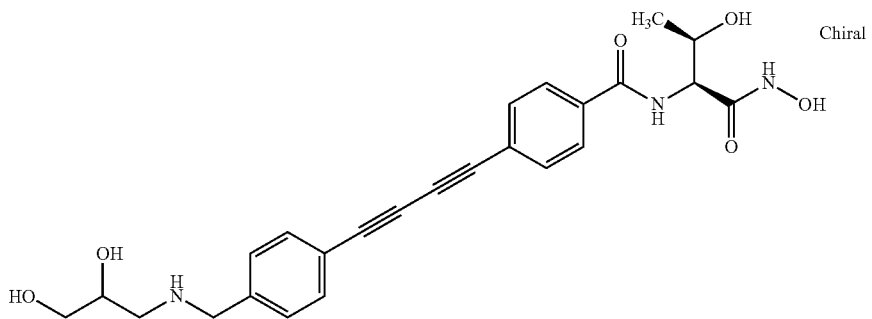

TABLE 1-continued
| 1076 | 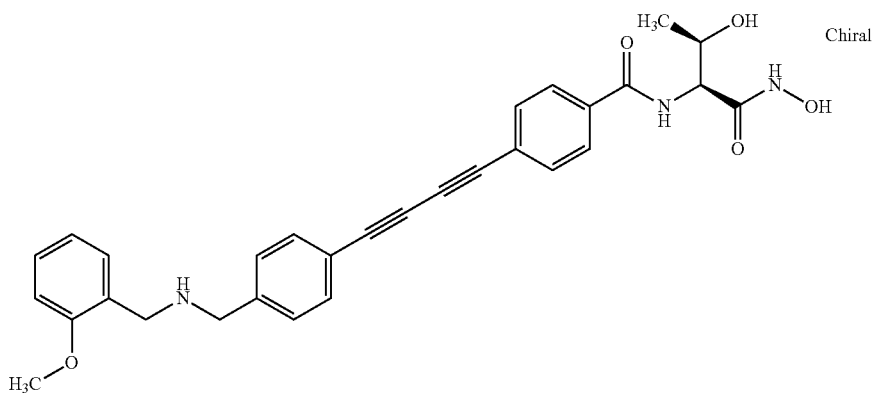 |
| --- | --- |
| 1077 | 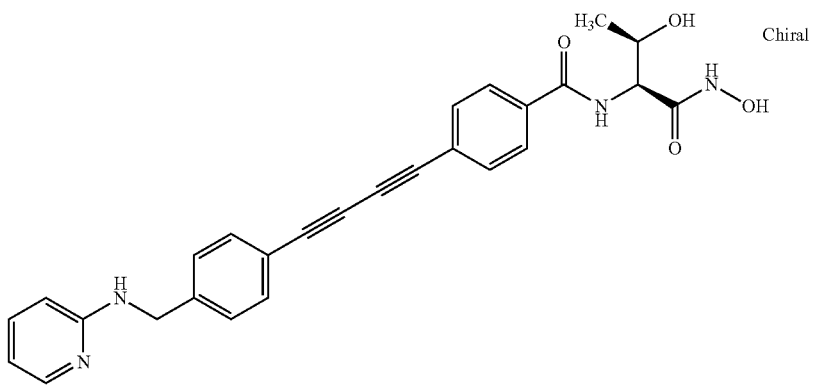 |
| 1078 | 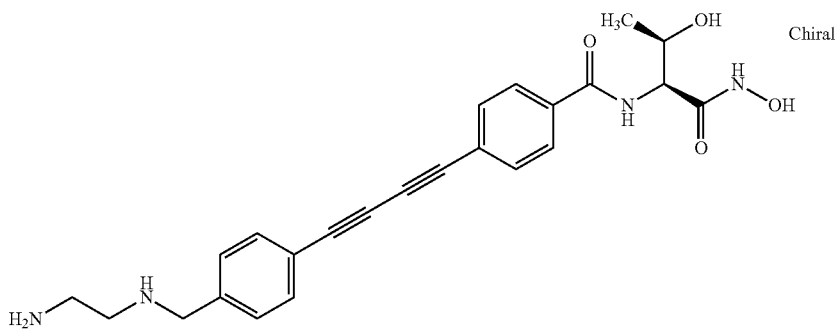 |
| 1079 | 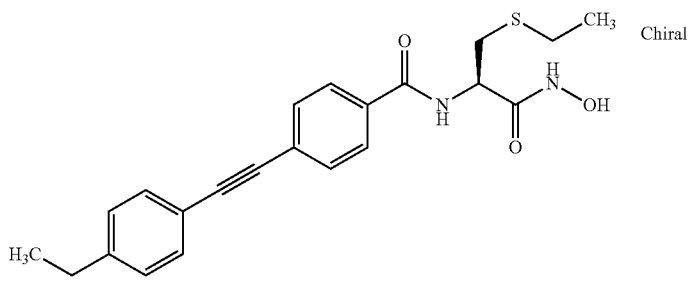 |

TABLE 1-continued
| 1080 | 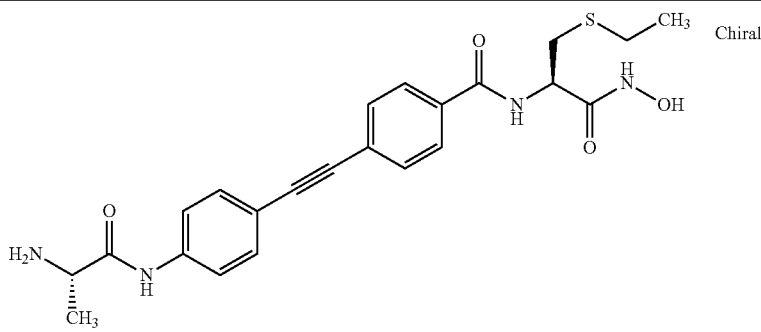 |
| --- | --- |
| 1081 | 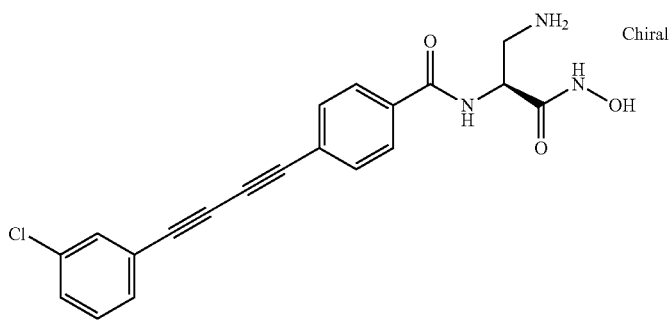 |
| 1082 | 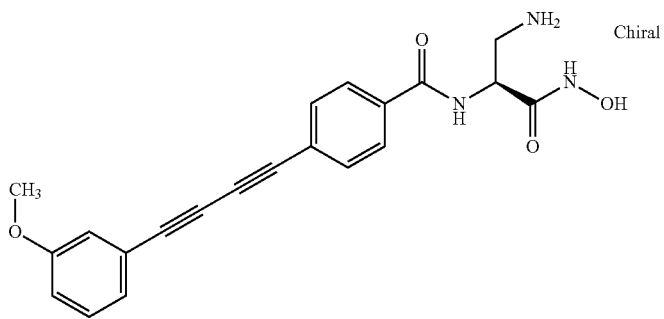 |
| 1083 | 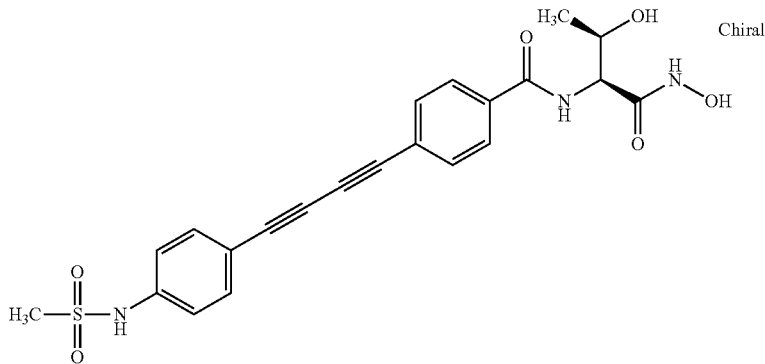 |
| 1084 | 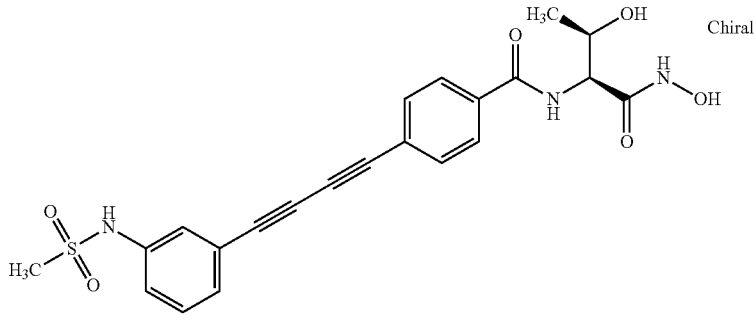 |

TABLE 1-continued
| 1085 | 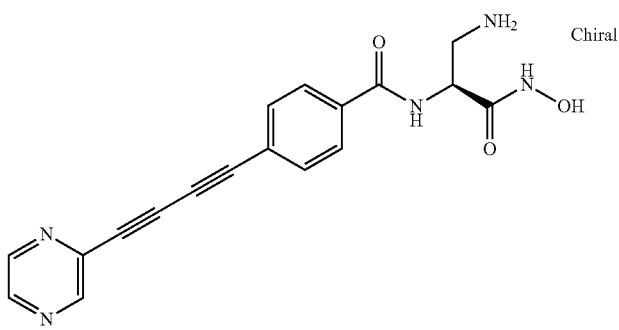 |
| 1086 | 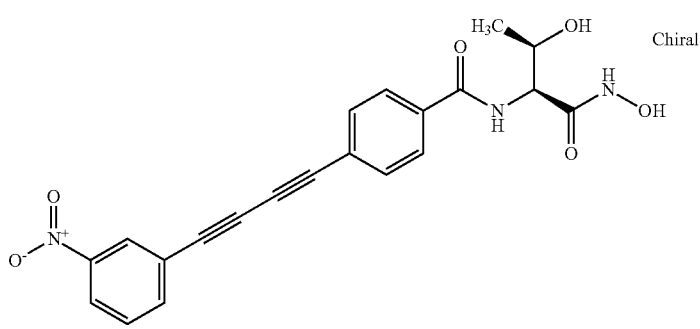 |
| 1087 | 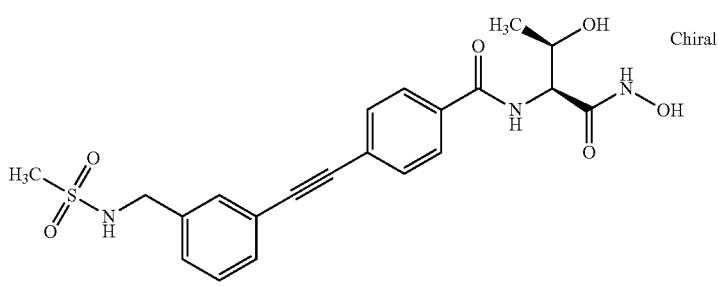 |
| 1088 | 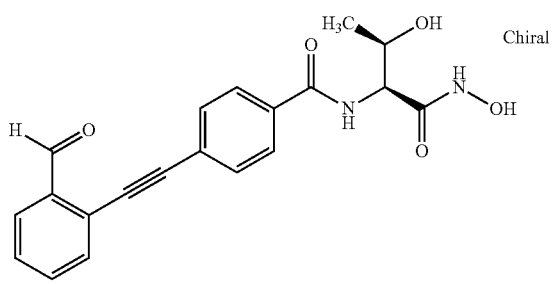 |
| 1089 | 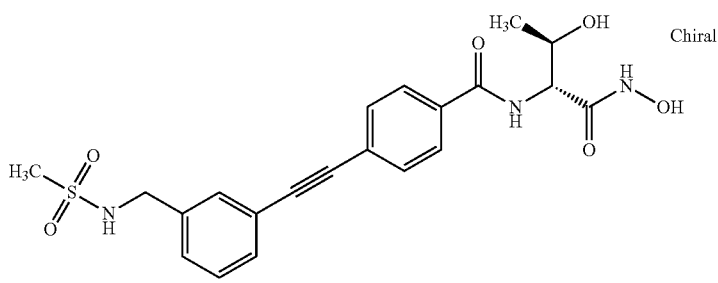 |

TABLE 1-continued

| 1090 | (structure: H₂N-CH₂-C(O)-NH-[phenyl]-C≡C-[phenyl]-C(O)-NH-CH(CH(OH)CH₃)-C(O)-NH-OH, Chiral) |
| 1091 | (structure: morpholine-CH₂-[phenyl]-C≡C-C≡C-[phenyl]-C(O)-NH-CH(CH(OH)CH₃)-C(O)-NH-OH, Chiral) |
| 1092 | (structure: H₃C-NH-CH₂-[phenyl]-C≡C-[phenyl]-C(O)-NH-CH(CH₂NH₂)-C(O)-NH-OH, Chiral) |
| 1093 | (structure: H₃C-CH₂-NH-CH₂-[phenyl]-C≡C-[phenyl]-C(O)-NH-CH(CH₂NH₂)-C(O)-NH-OH, Chiral) |
| 1094 | (structure: H₃C-(CH₂)₂-NH-CH₂-[phenyl]-C≡C-[phenyl]-C(O)-NH-CH(CH₂NH₂)-C(O)-NH-OH, Chiral) |
| 1095 | (structure: H₃C-(CH₂)₃-NH-CH₂-[phenyl]-C≡C-[phenyl]-C(O)-NH-CH(CH₂NH₂)-C(O)-NH-OH, Chiral) |
| 1096 | (structure: H₃C-(CH₂)₄-NH-CH₂-[phenyl]-C≡C-[phenyl]-C(O)-NH-CH(CH₂NH₂)-C(O)-NH-OH, Chiral) |

TABLE 1-continued
| 1097 | 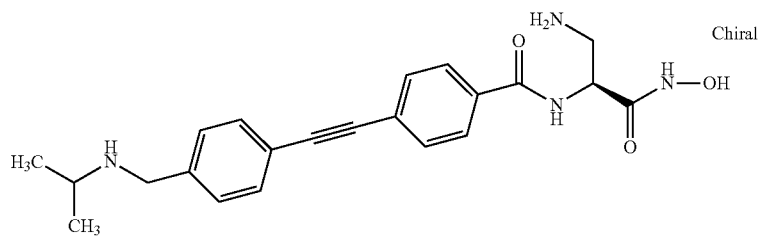 |
| --- | --- |
| 1098 | 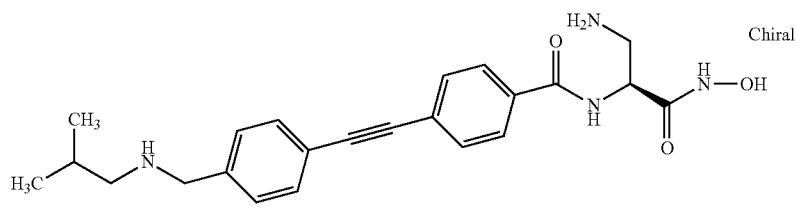 |
| 1099 | 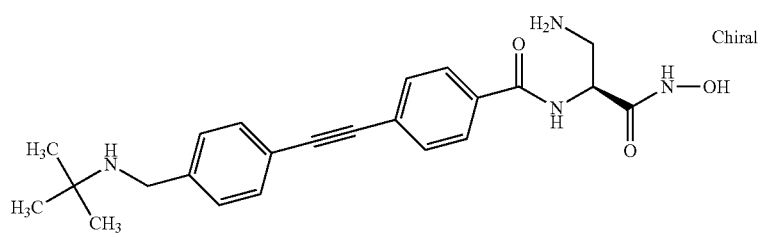 |
| 1100 | 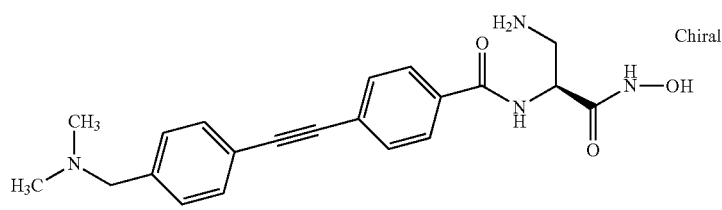 |
| 1101 | 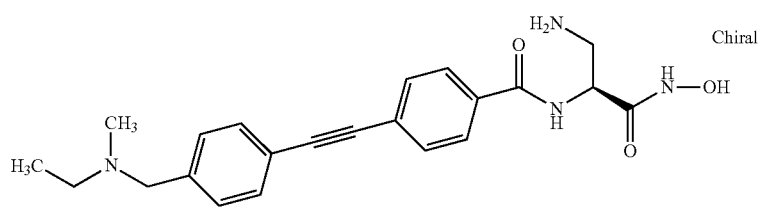 |
| 1102 | 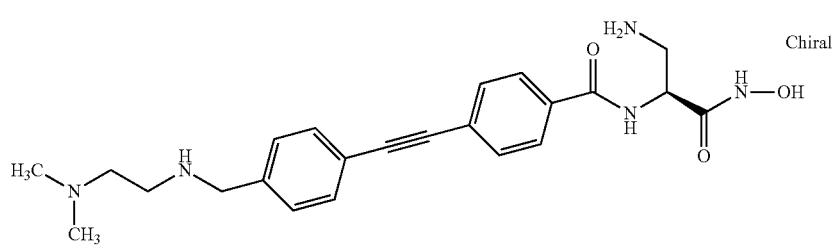 |
| 1103 | 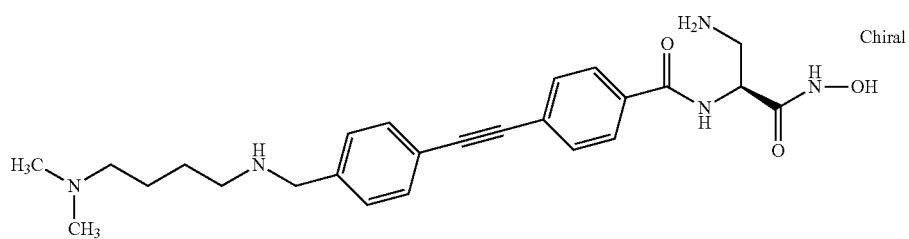 |

TABLE 1-continued
1104 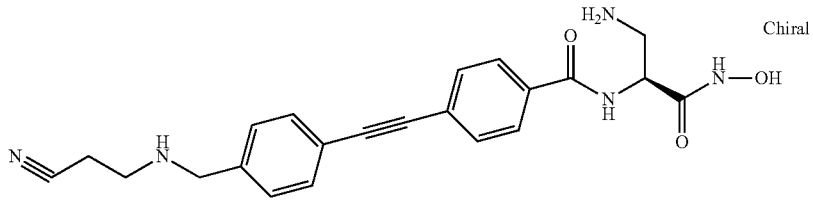
1105 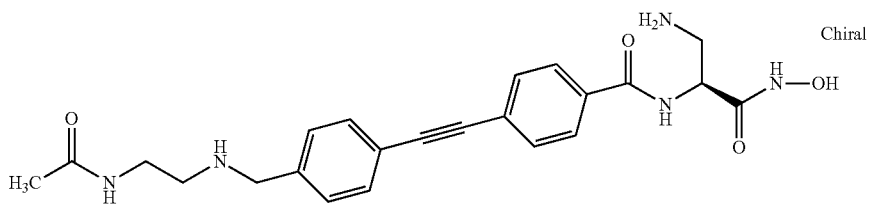
1106 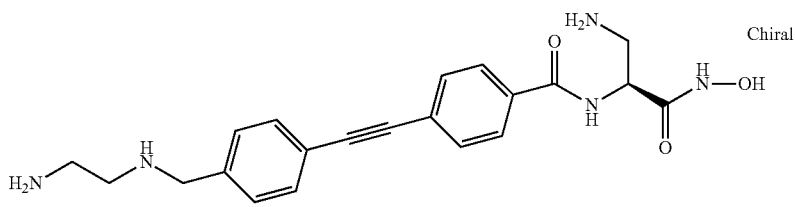
1107 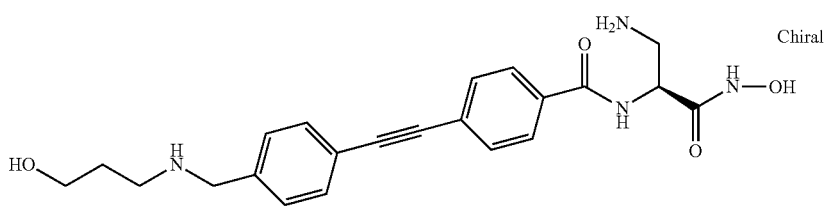
1108 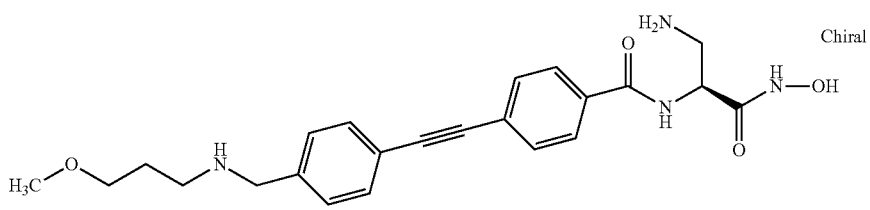
1109 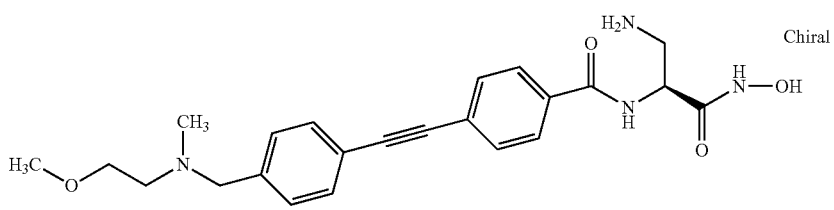
1110 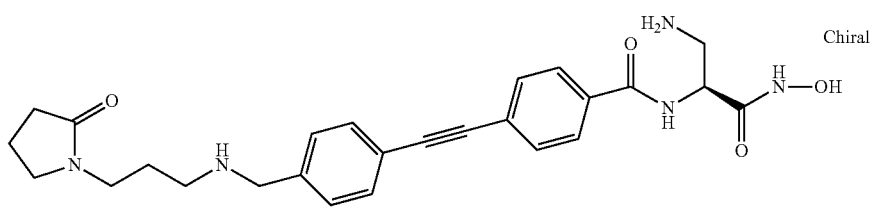

TABLE 1-continued
1111 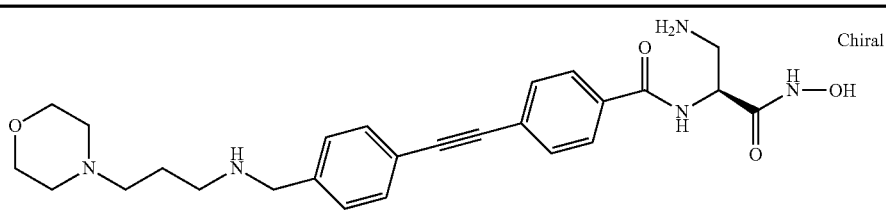
1112 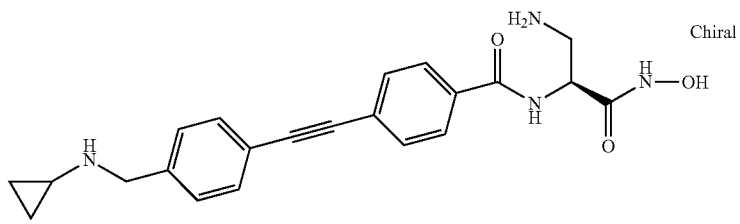
1113 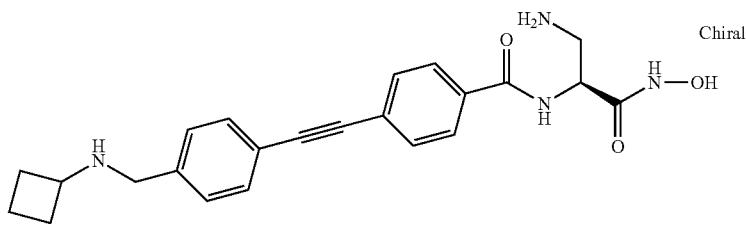
1114 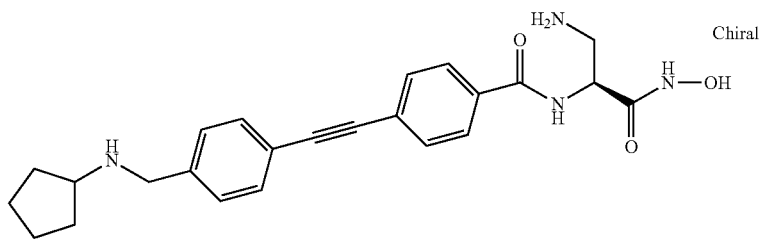
1115 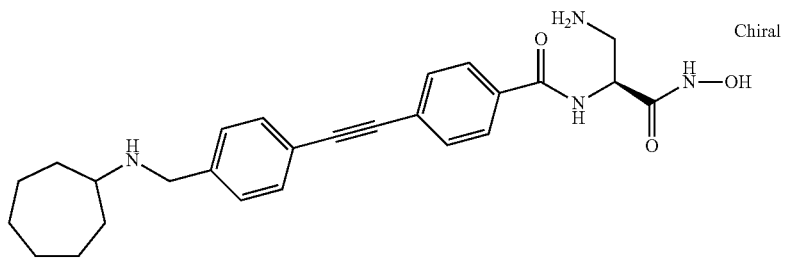
1116 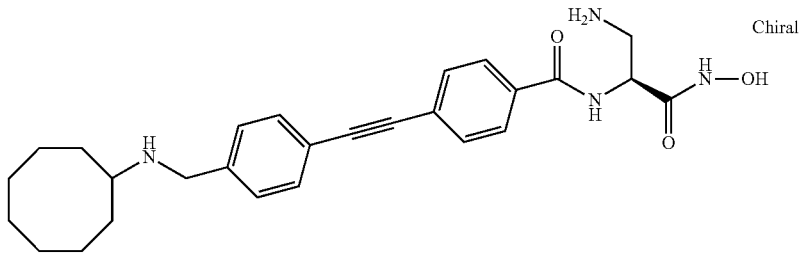
1117 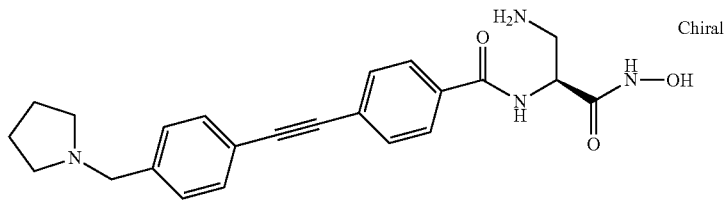

| | |
|---|---|
| 1118 | 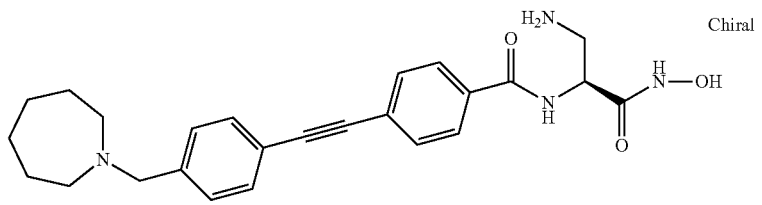 |
| 1119 | 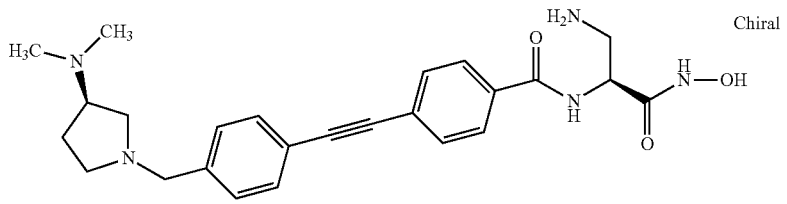 |
| 1120 | 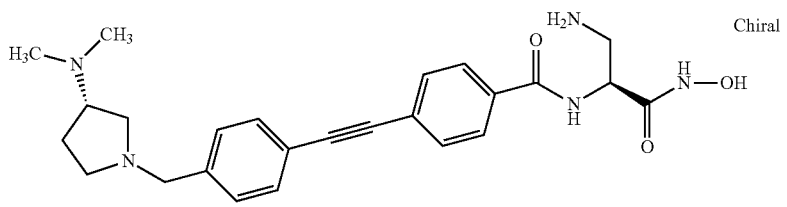 |
| 1121 | 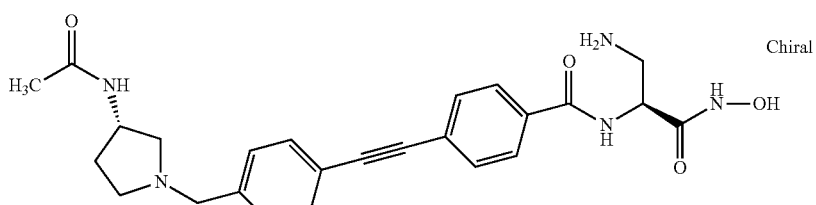 |
| 1122 | 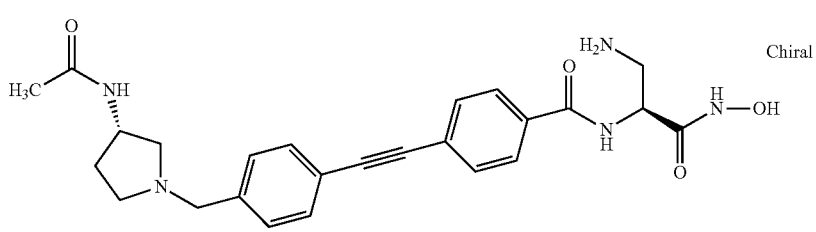 |
| 1123 | 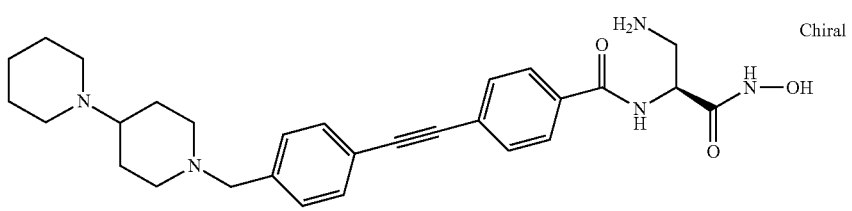 |
| 1124 | 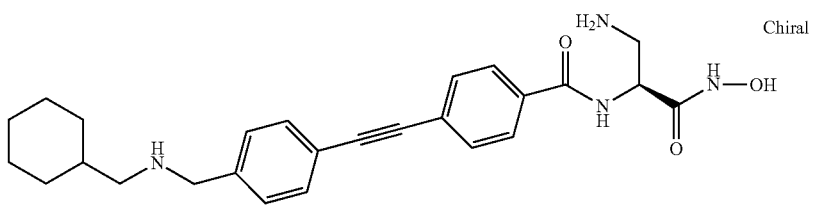 |

TABLE 1-continued
| 1125 | 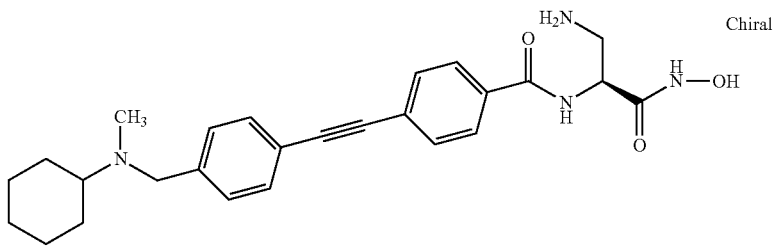 |
| 1126 | 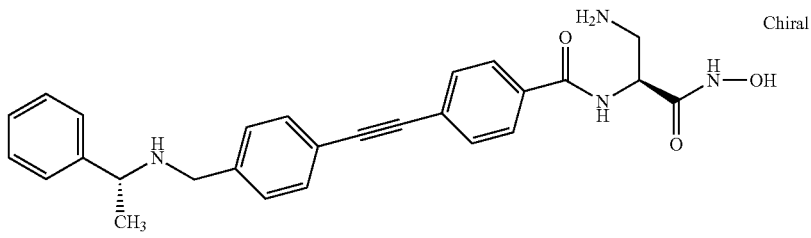 |
| 1127 | 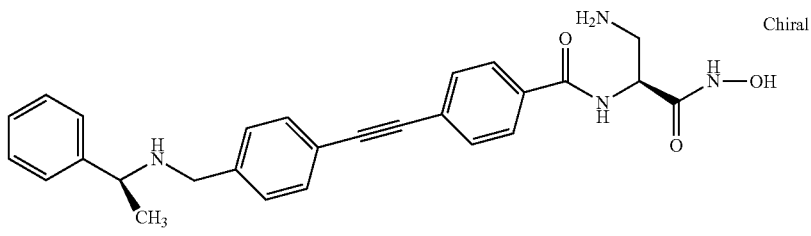 |
| 1128 | 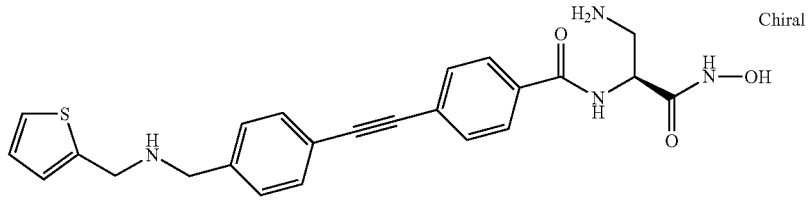 |
| 1129 | 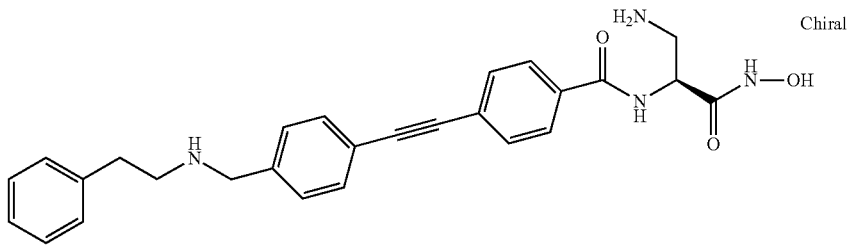 |
| 1130 | 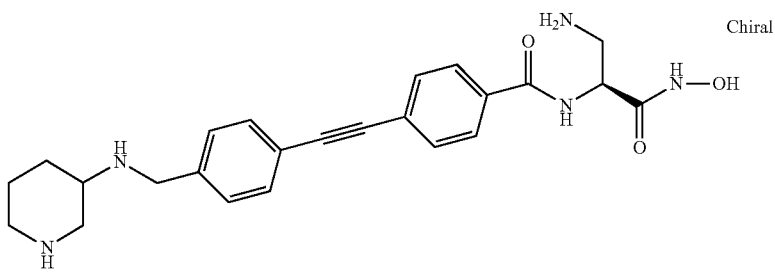 |

TABLE 1-continued
| 1131 | 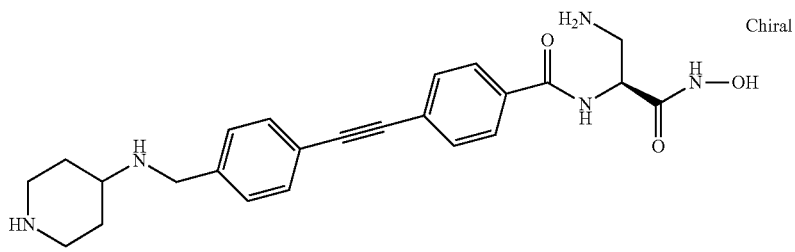 |
| 1132 | 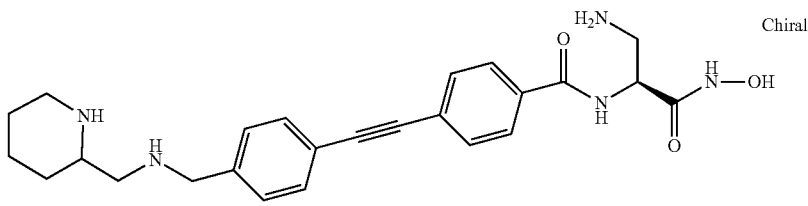 |
| 1133 | 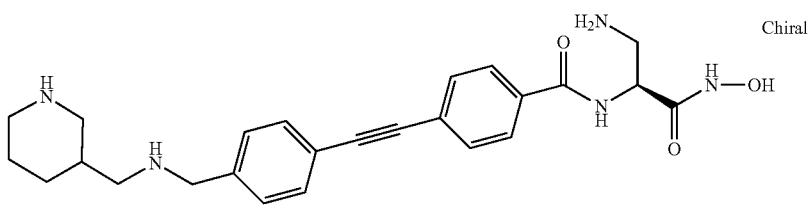 |
| 1134 | 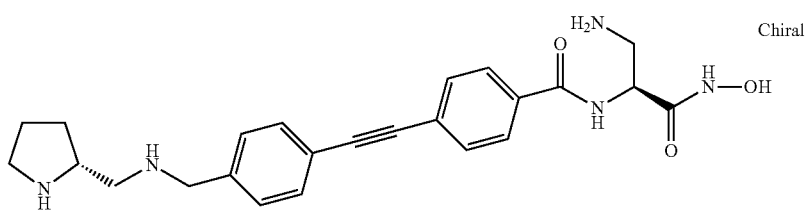 |
| 1135 | 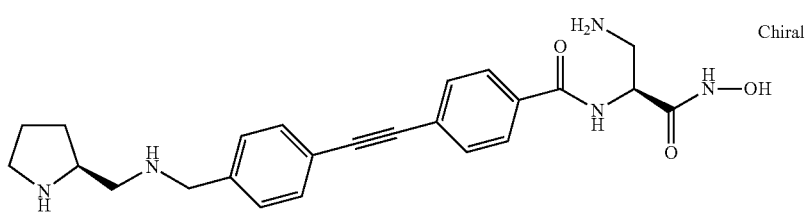 |
| 1136 | 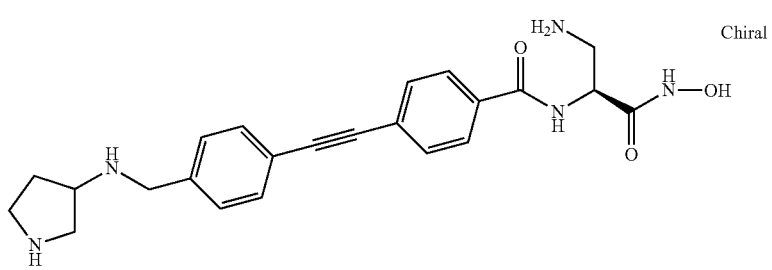 |
| 1137 | 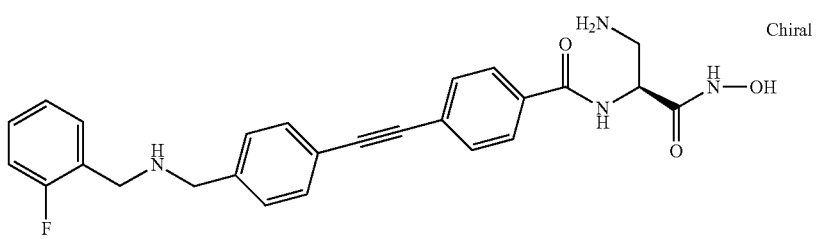 |

TABLE 1-continued
1138 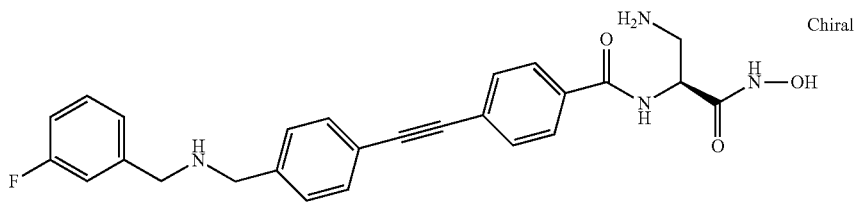
1139 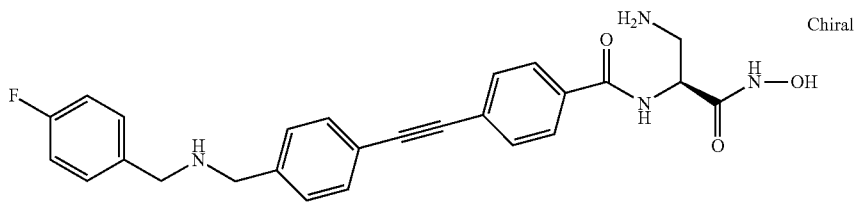
1140 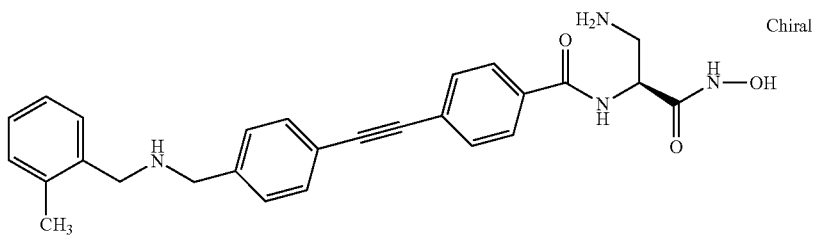
1141 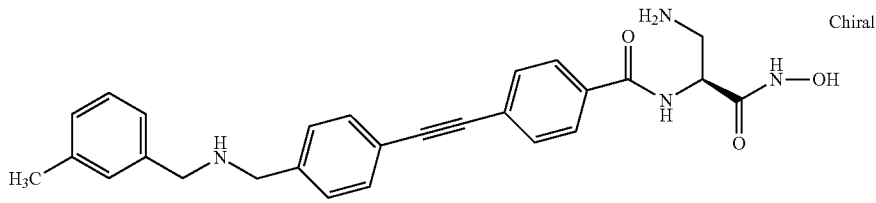
1142 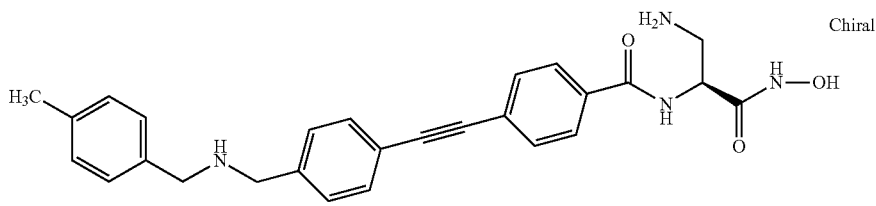
1143 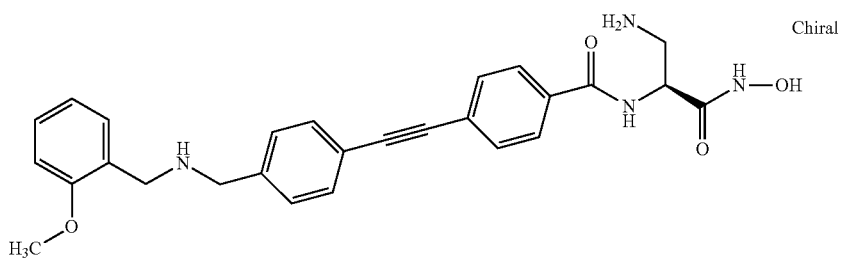
1144 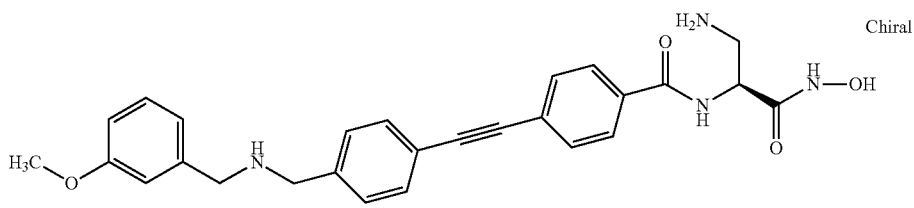

| | | |
|---|---|---|
| 1145 | 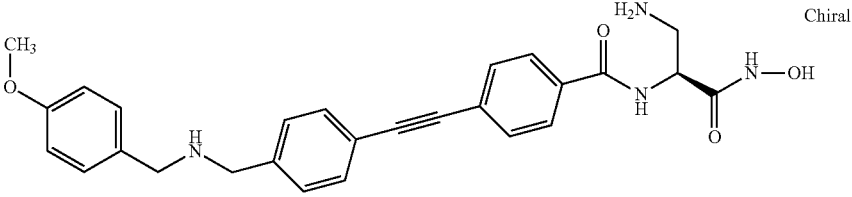 | Chiral |
| 1146 | 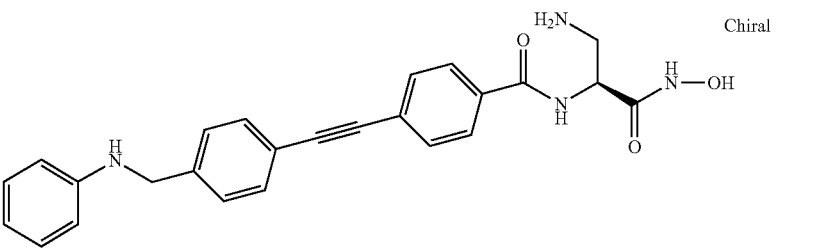 | Chiral |
| 1147 | 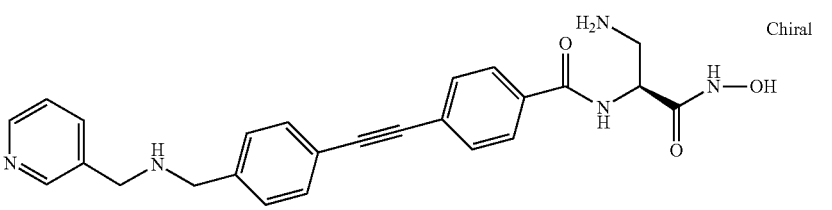 | Chiral |
| 1148 | 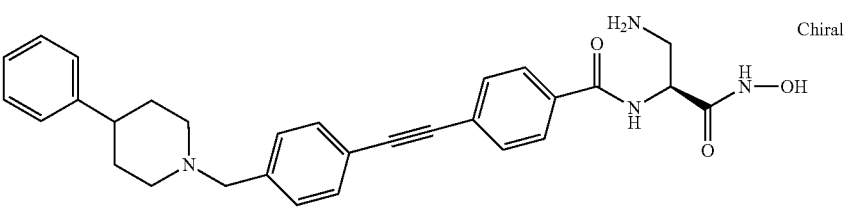 | Chiral |
| 1149 | 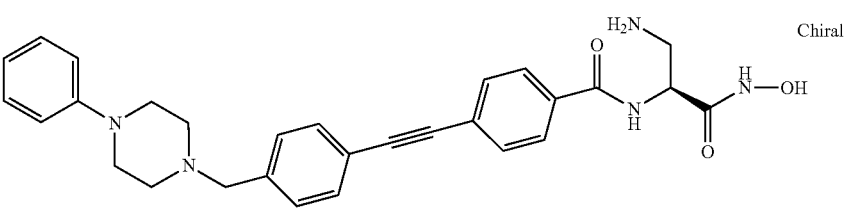 | Chiral |
| 1150 | 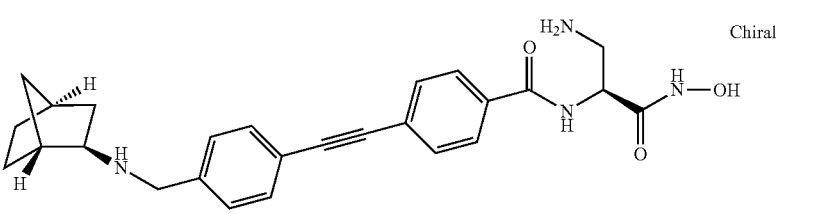 | Chiral |
| 1151 | 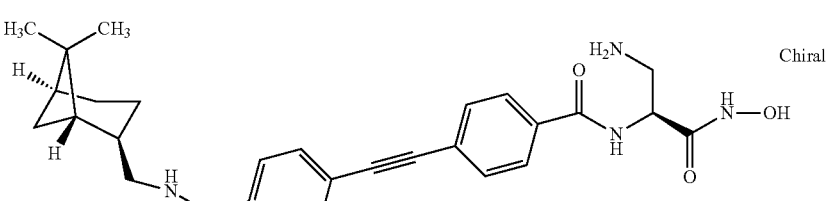 | Chiral |

TABLE 1-continued
| 1152 | 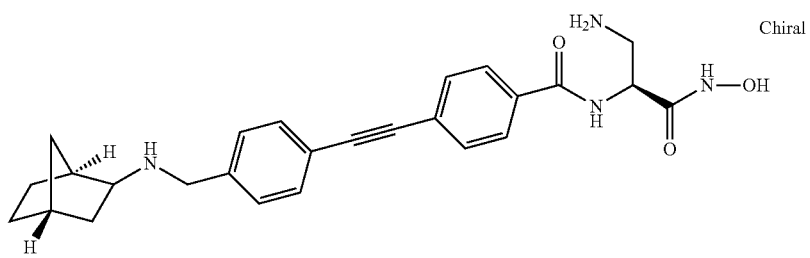 |
| --- | --- |
| 1153 | 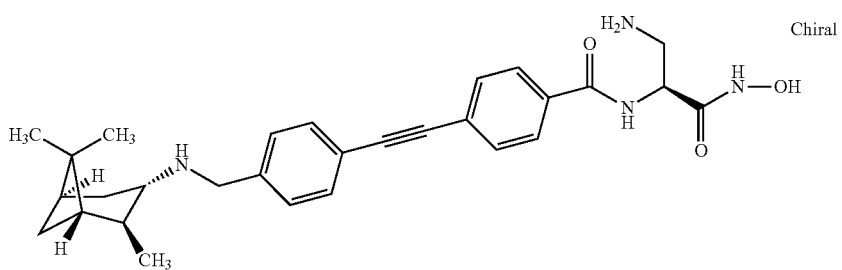 |
| 1154 | 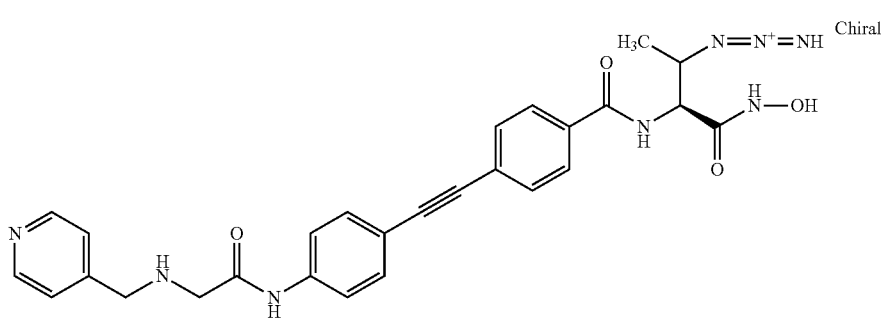 |
| 1155 | 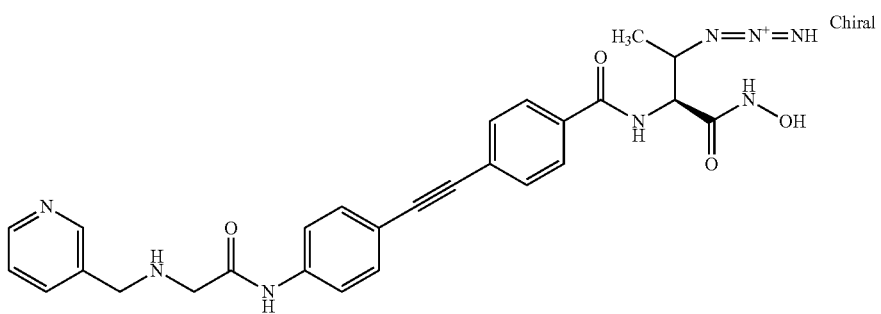 |
| 1156 | 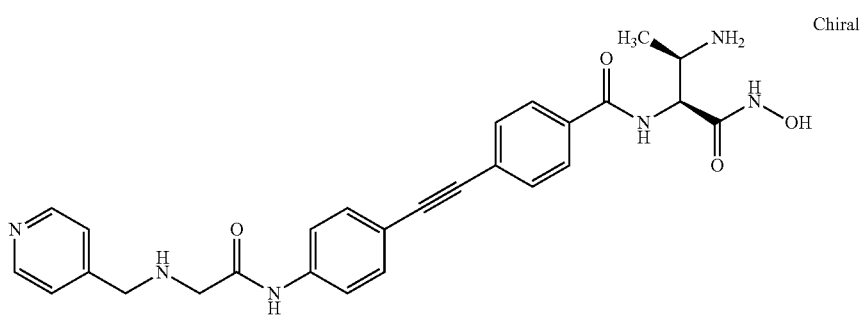 |

TABLE 1-continued
1157 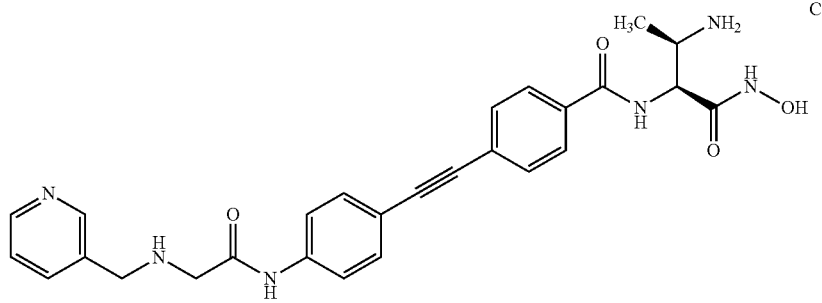 Chiral
1158 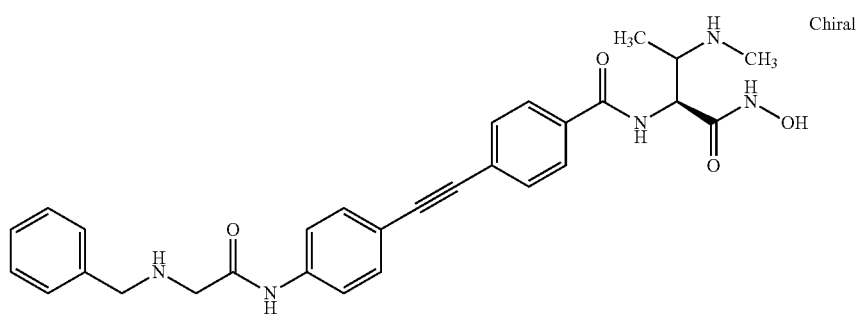 Chiral
1159 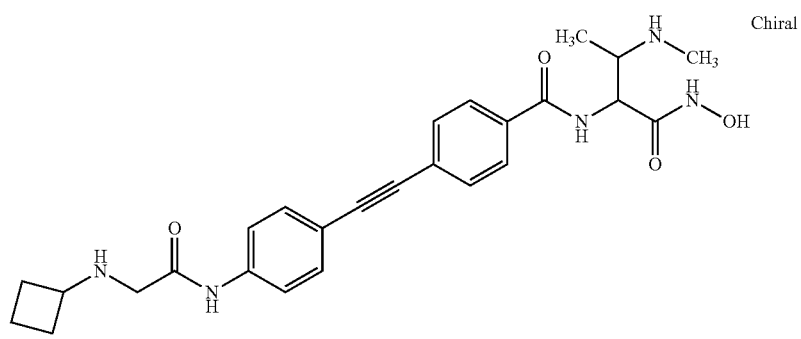 Chiral
1160 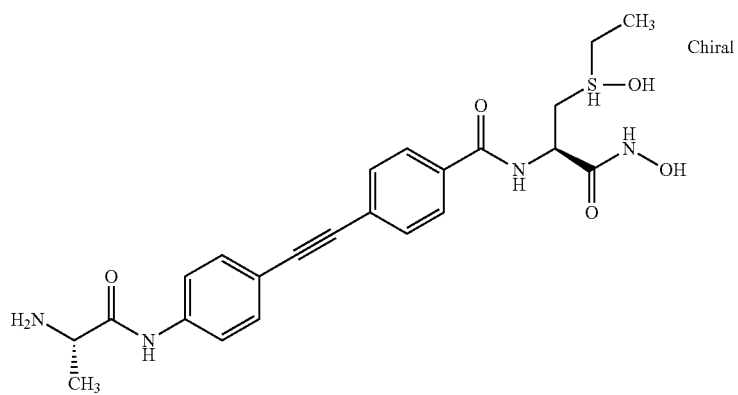 Chiral
1161 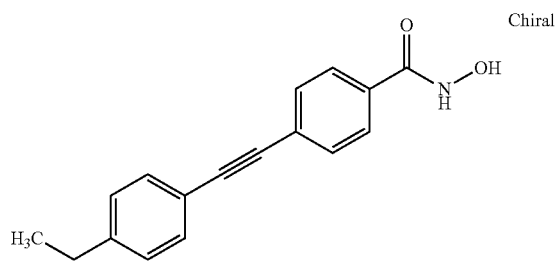 Chiral TABLE 1-continued
| 1162 | 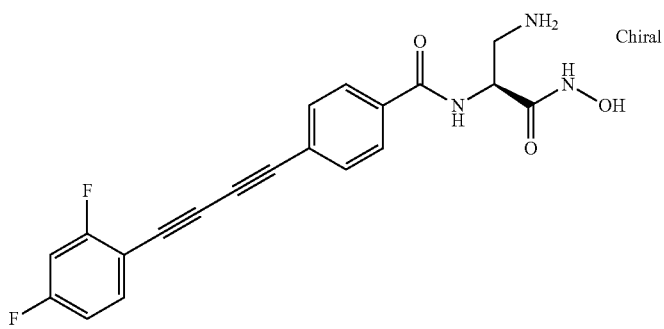 |
| --- | --- |
| 1163 | 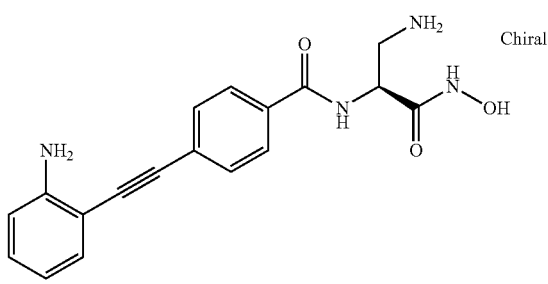 |
| 1164 | 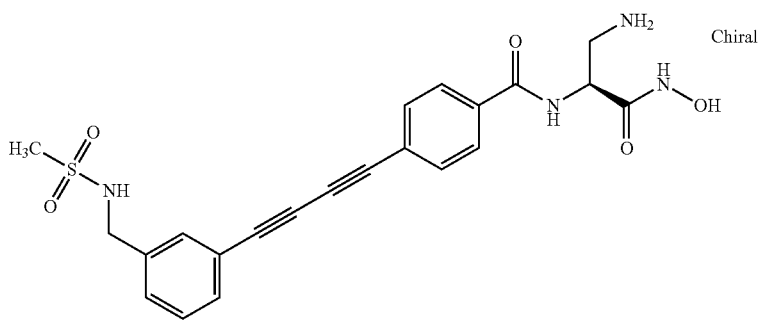 |
| 1165 | 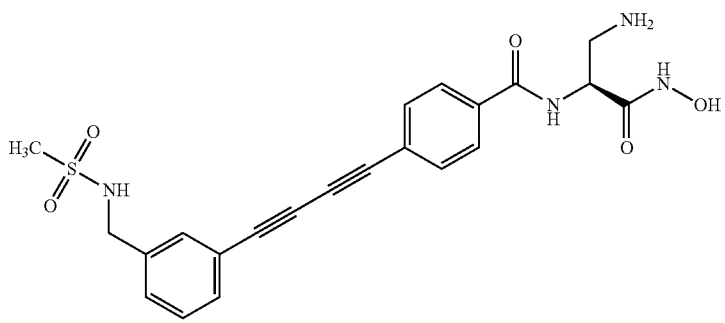 |
| 1166 | 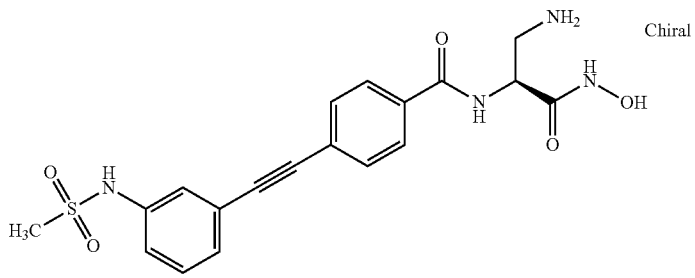 |

TABLE 1-continued
1167 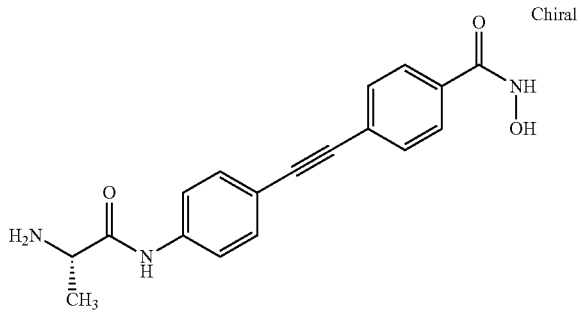
1168 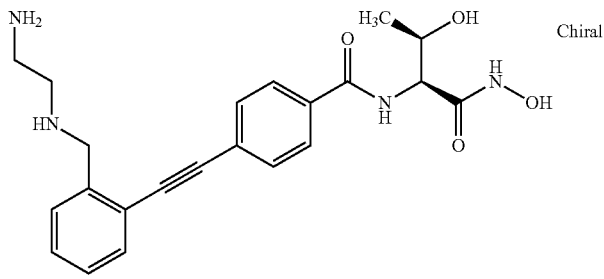
1169 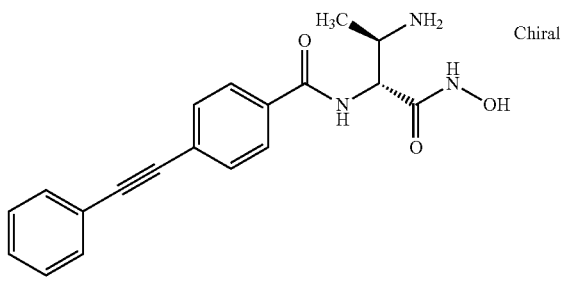
1170 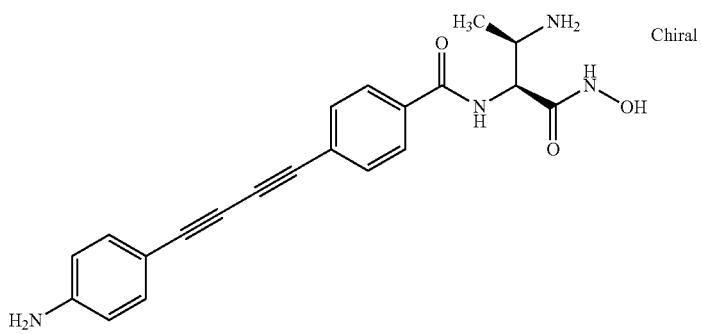
1171 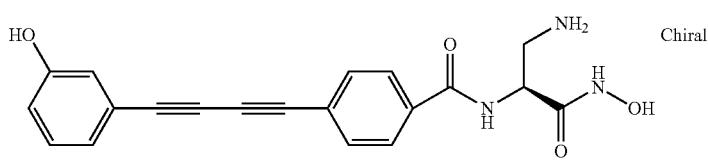
1172 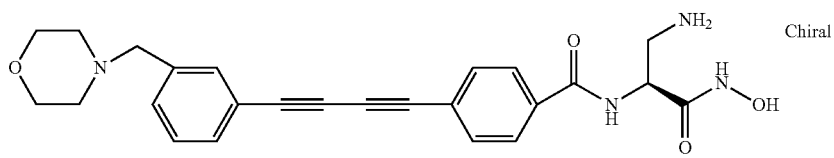

TABLE 1-continued

| 1173 | (structure) |
| 1174 | (structure) |
| 1175 | (structure) |
| 1176 | (structure) |
| 1177 | (structure) |
| 1178 | (structure) |
| 1179 | (structure) |
| 1180 | (structure) |

TABLE 1-continued
| 1181 | 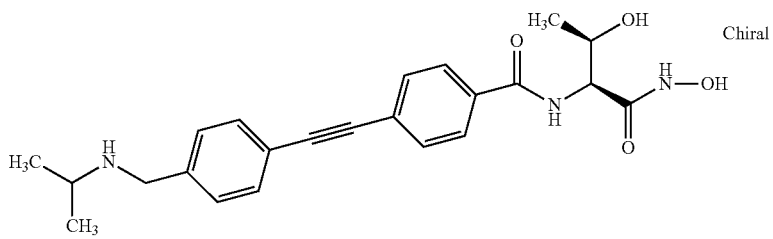 |
| --- | --- |
| 1182 | 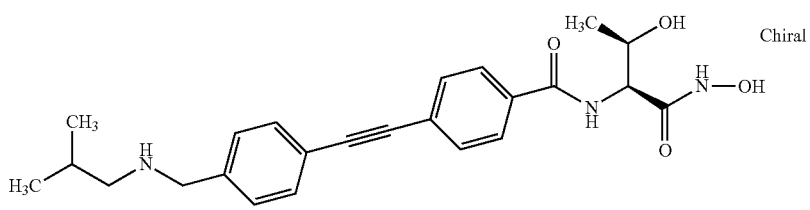 |
| 1183 | 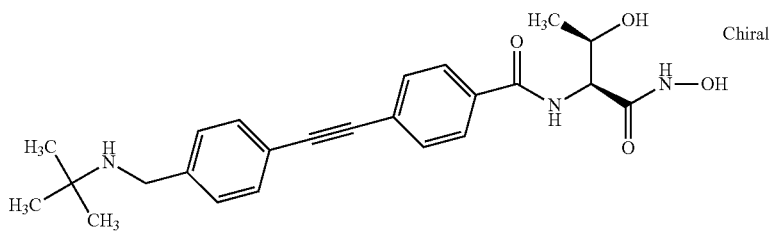 |
| 1184 | 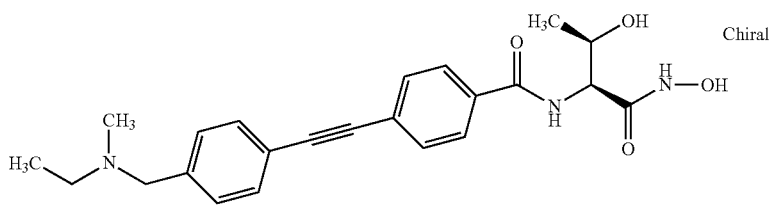 |
| 1185 | 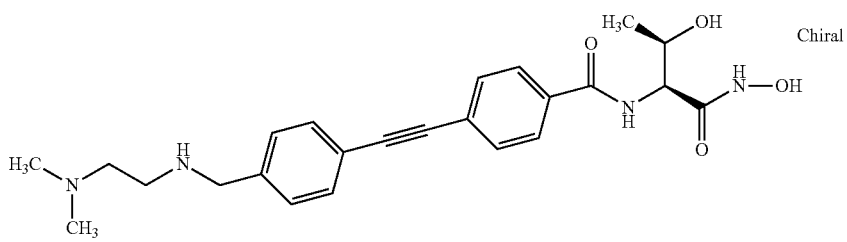 |
| 1186 | 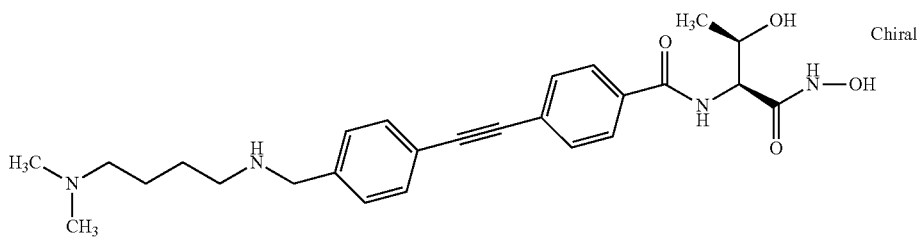 |
| 1187 | 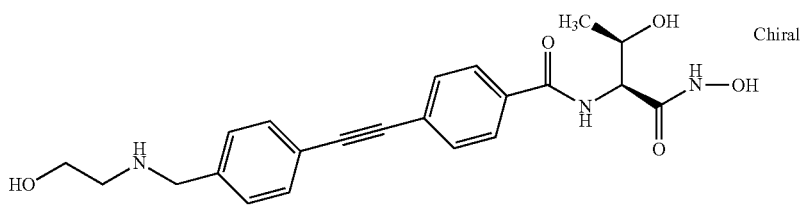 |

TABLE 1-continued
1188 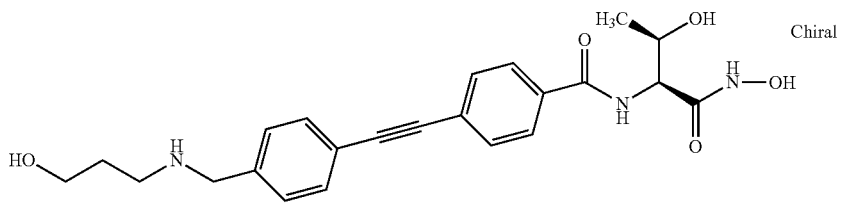
1189 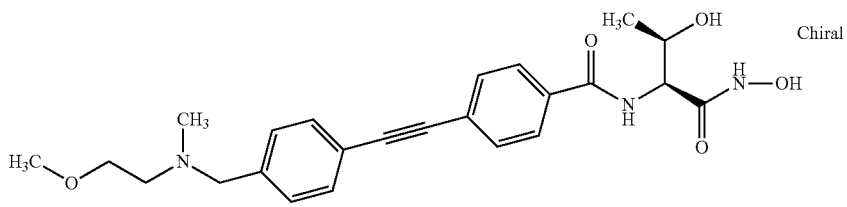
1190 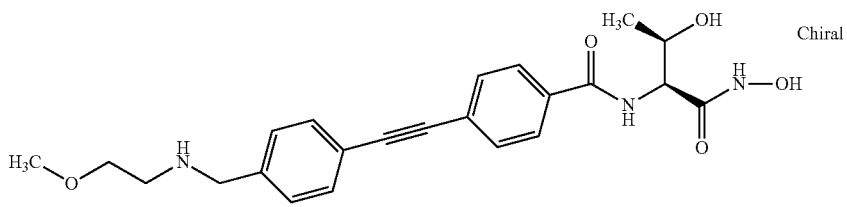
1191 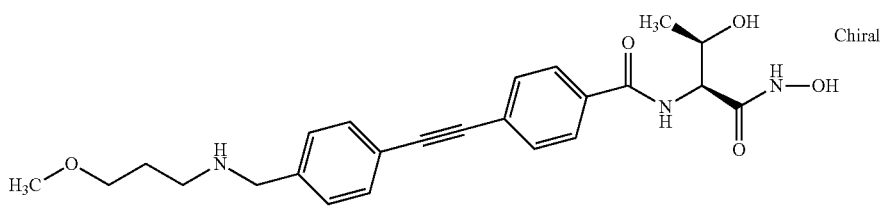
1192 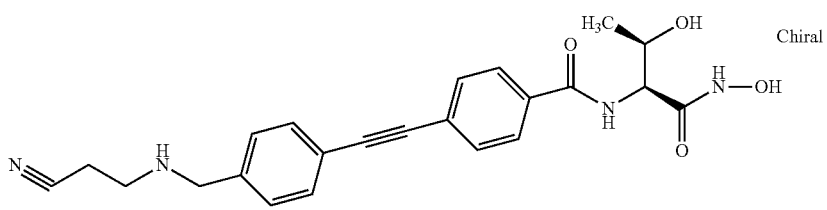
1193 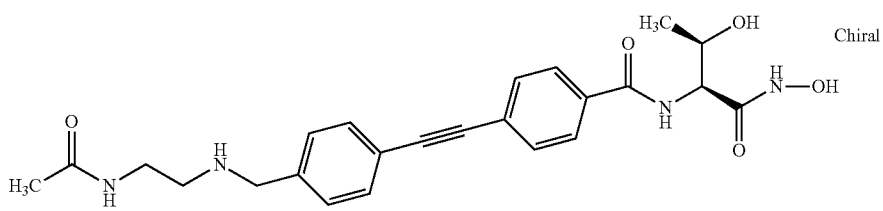
1194 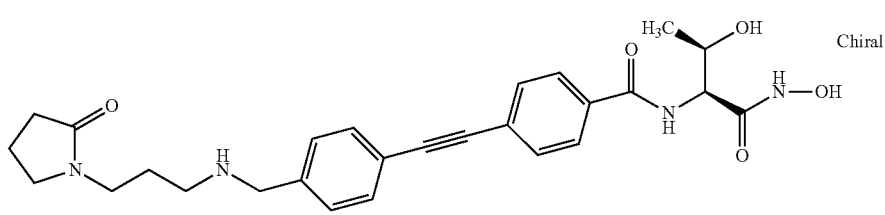

TABLE 1-continued
1195 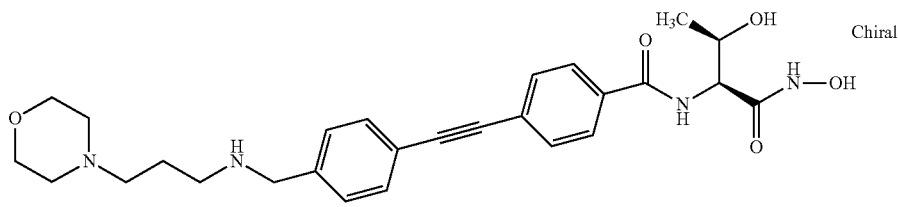
1196 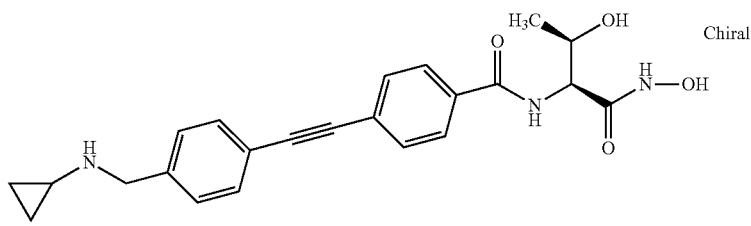
1197 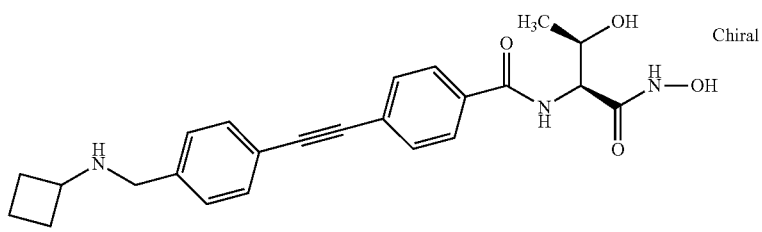
1198 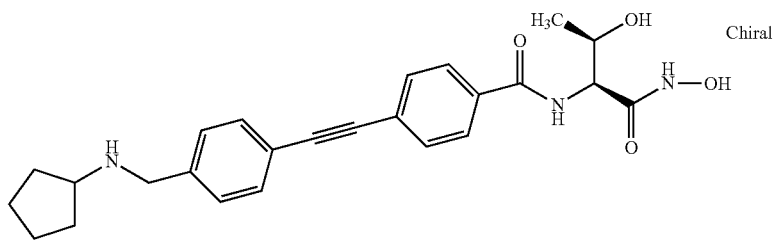
1199 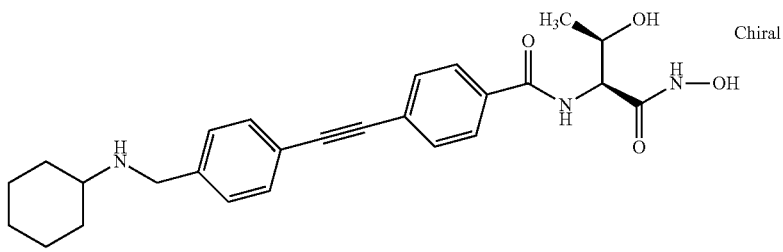
1200 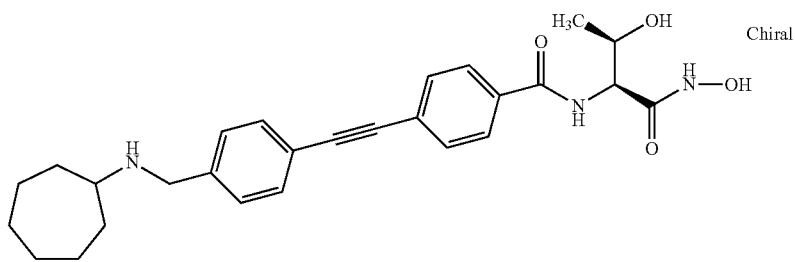

TABLE 1-continued
| 1201 | 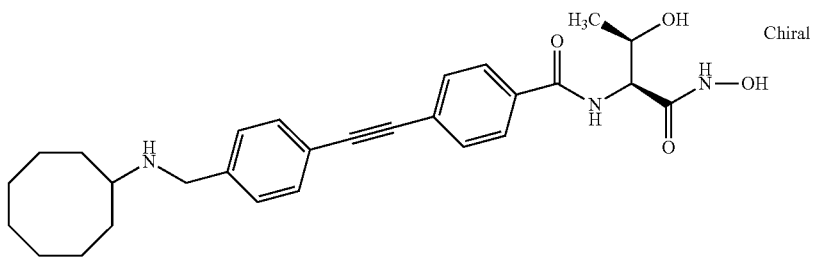 |
| 1202 | 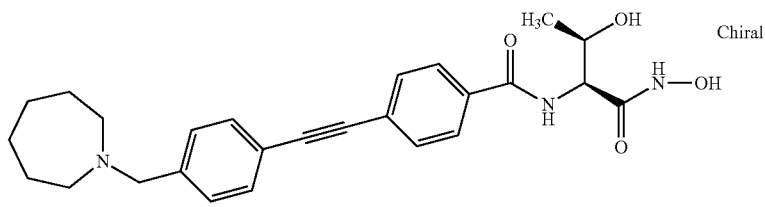 |
| 1203 | 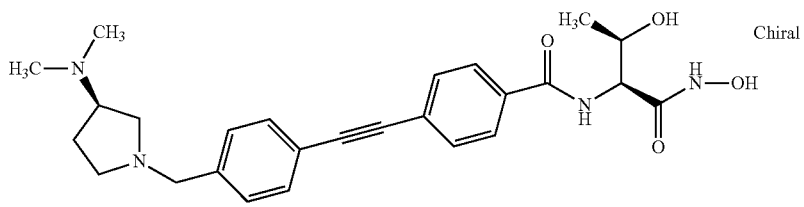 |
| 1204 | 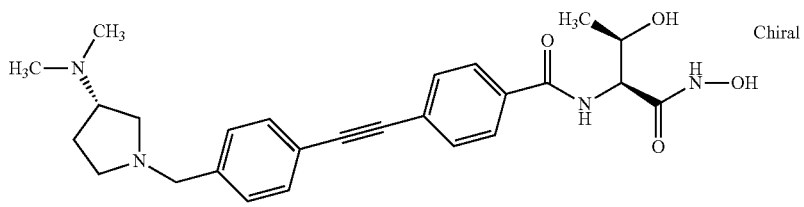 |
| 1205 | 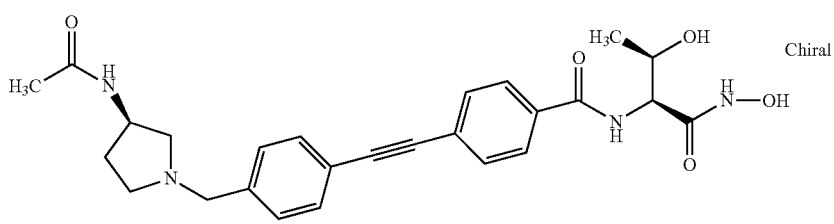 |
| 1206 | 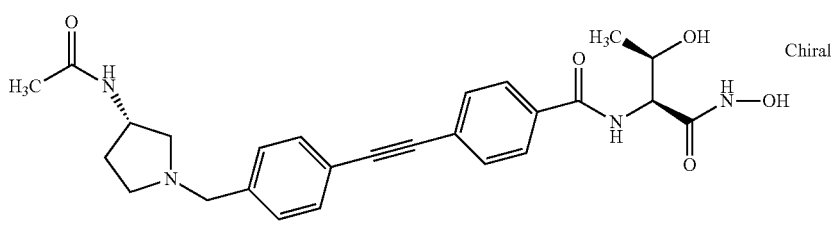 |
| 1207 | 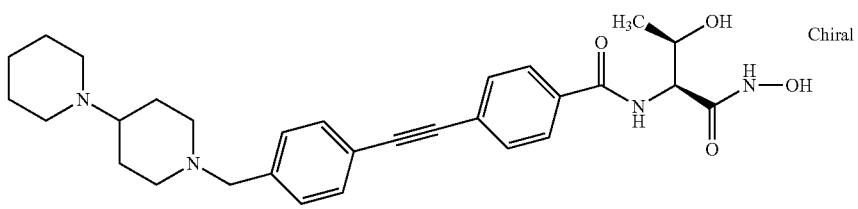 |

US 8,101,640 B2
TABLE 1-continued
| 1208 | 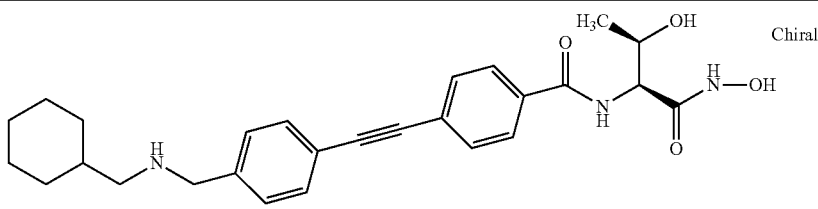 |
| 1209 | 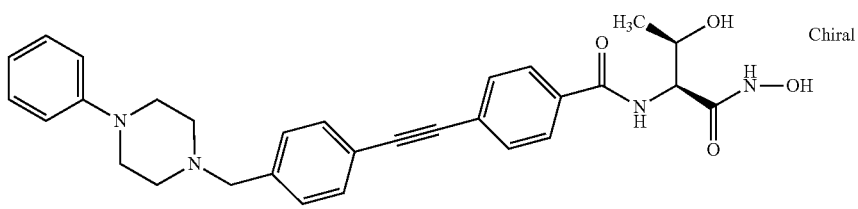 |
| 1210 | 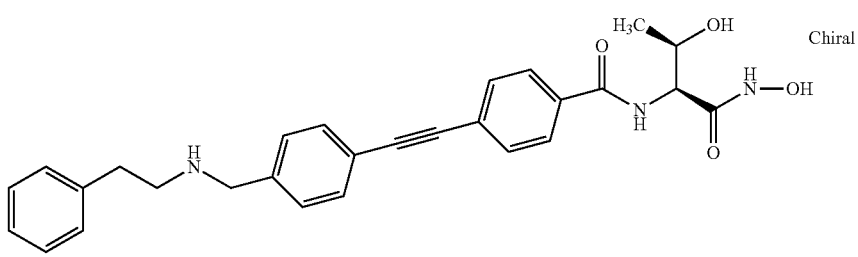 |
| 1211 | 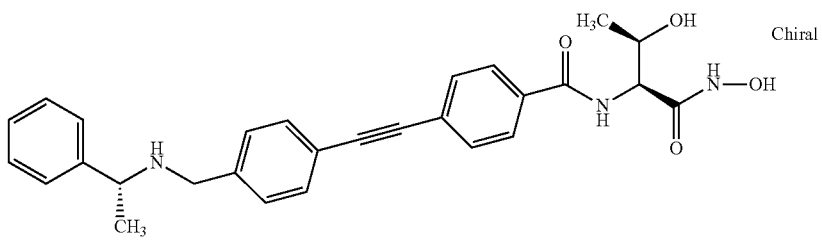 |
| 1212 | 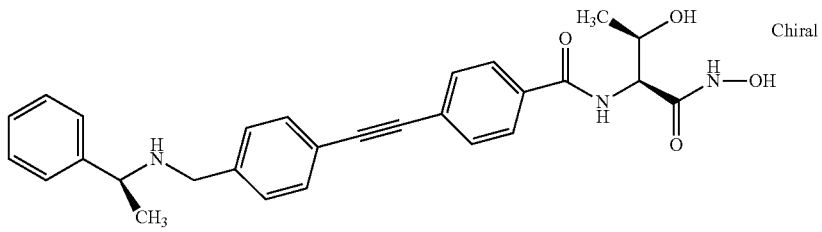 |
| 1213 | 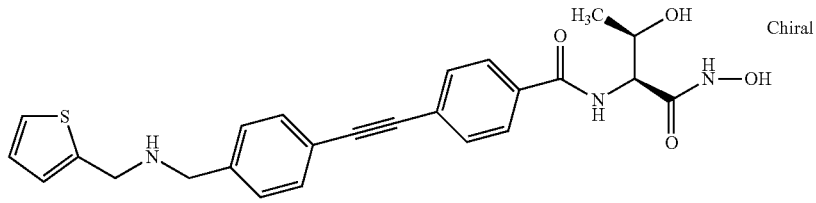 |
| 1214 | 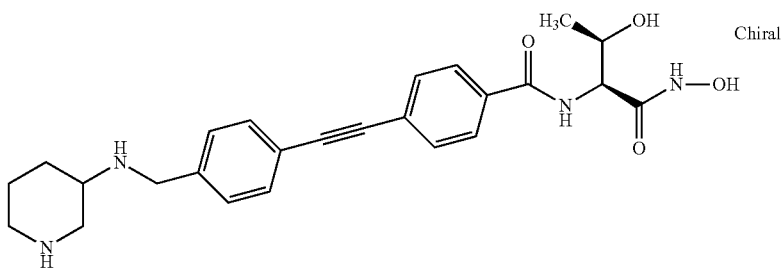 |

TABLE 1-continued
| 1215 | 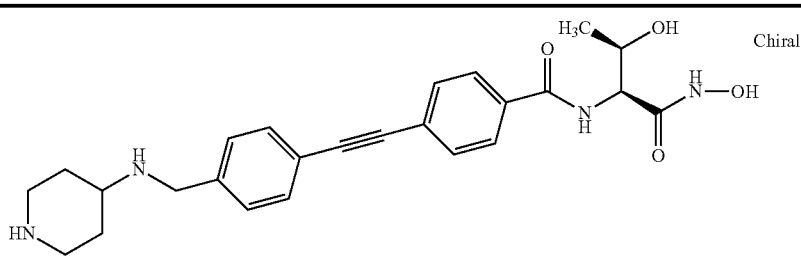 |
| 1216 | 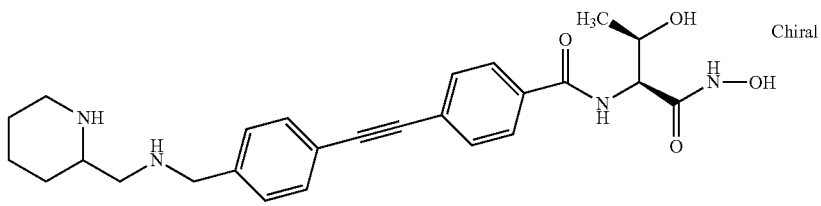 |
| 1217 | 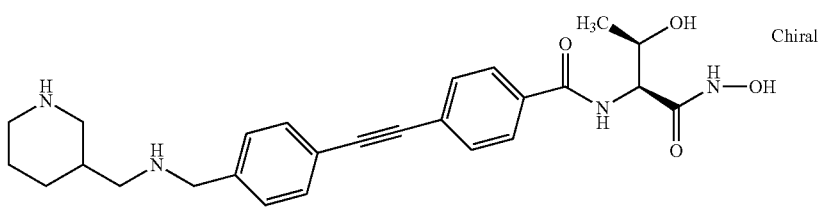 |
| 1218 | 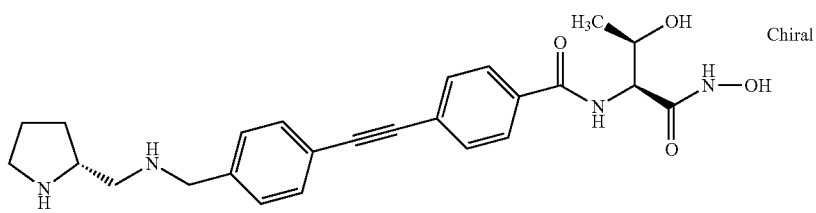 |
| 1219 | 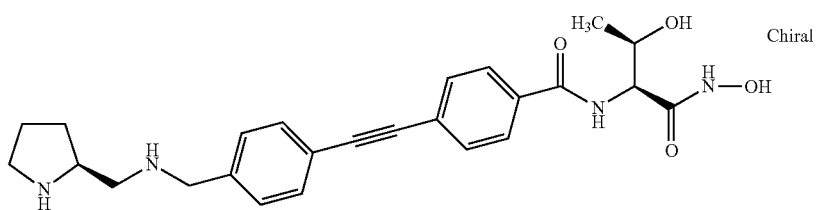 |
| 1220 | 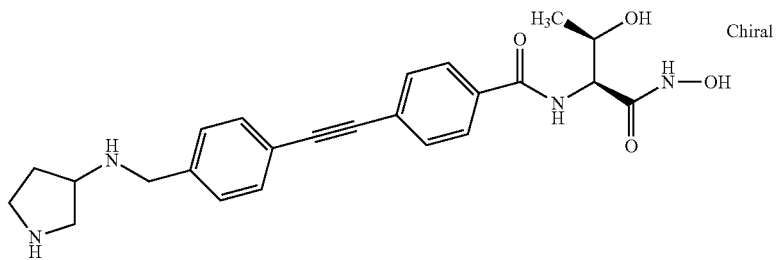 |
| 1221 | 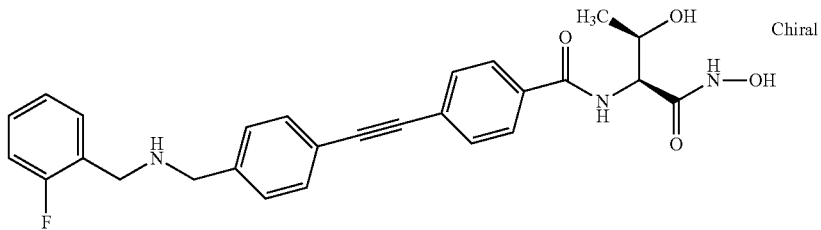 |

TABLE 1-continued
1222 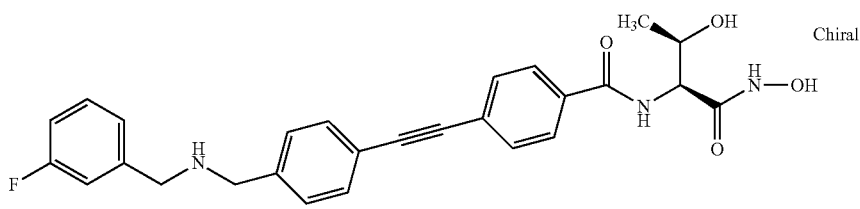
1223 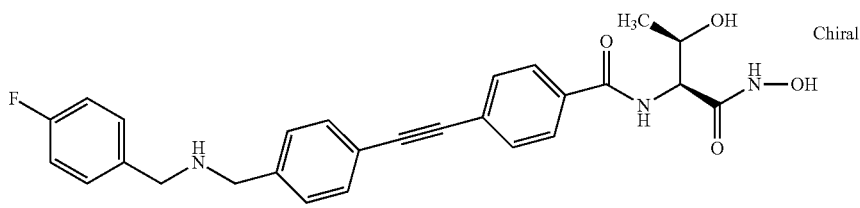
1224 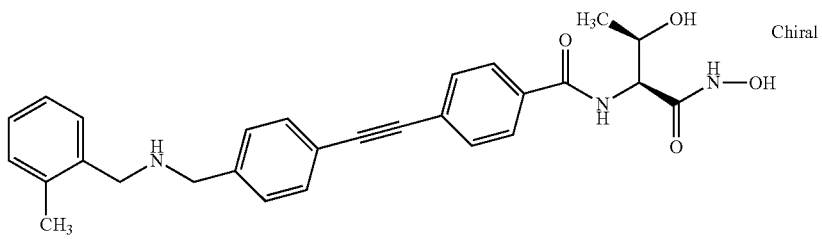
1225 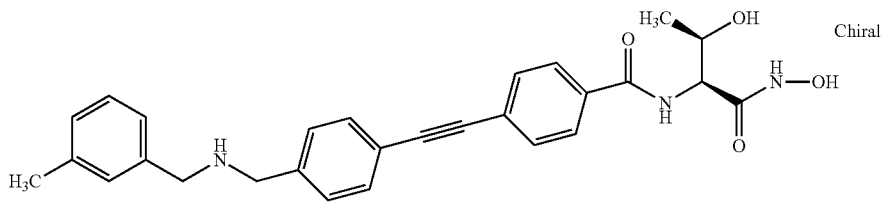
1226 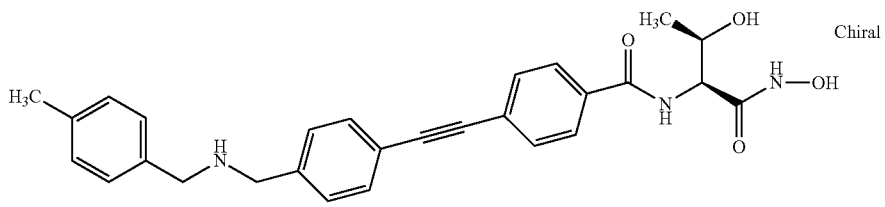
1227 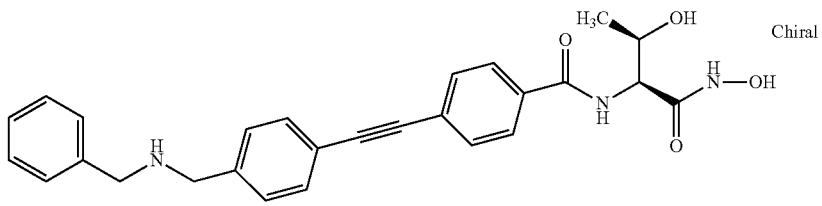
1228 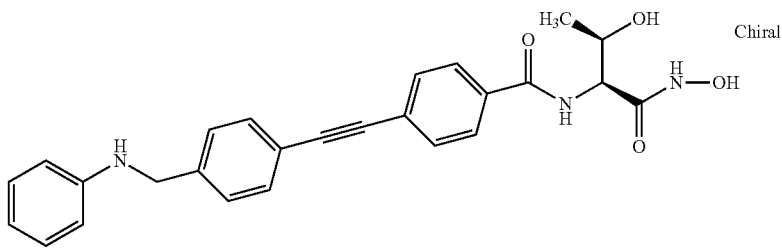

TABLE 1-continued
1229 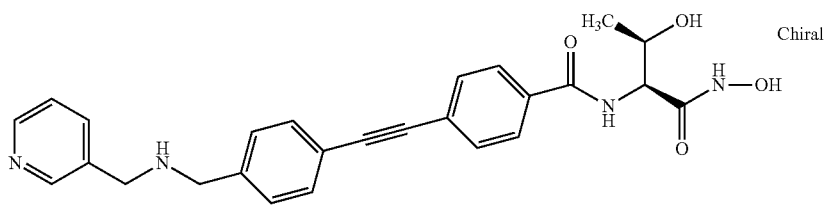
1230 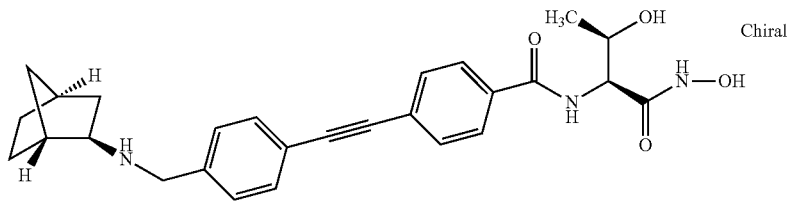
1231 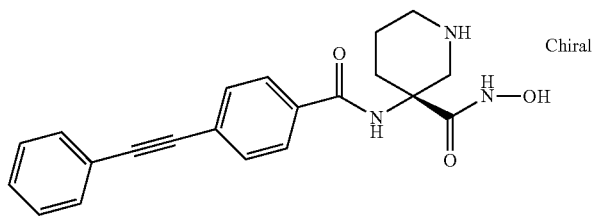
1232 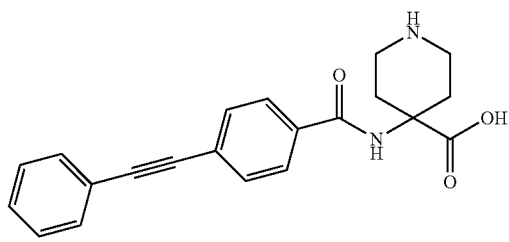
1233 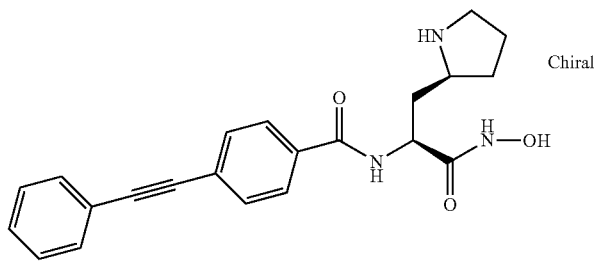
1234 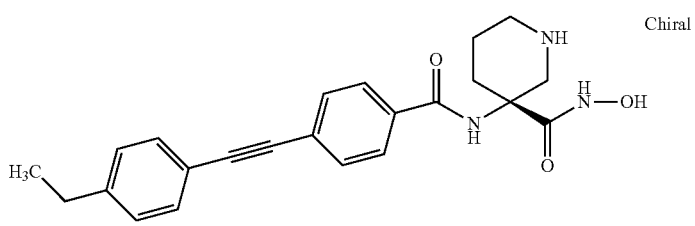

TABLE 1-continued
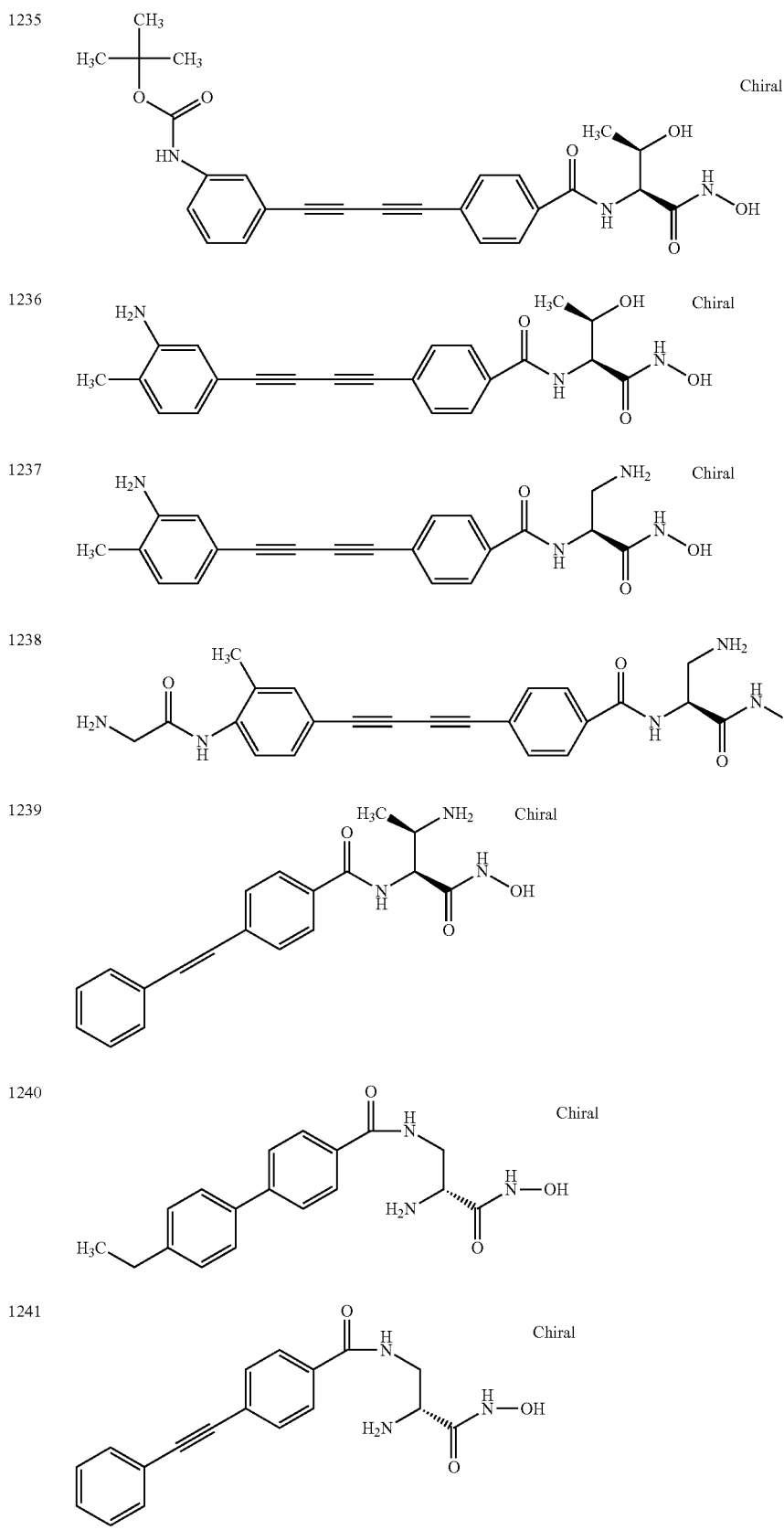

TABLE 1-continued
| 1242 | 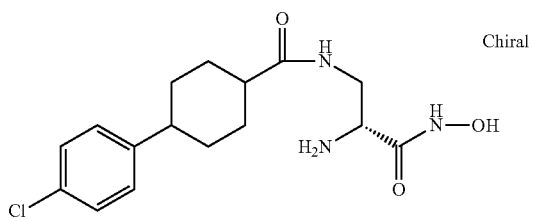 |
| --- | --- |
| 1243 | 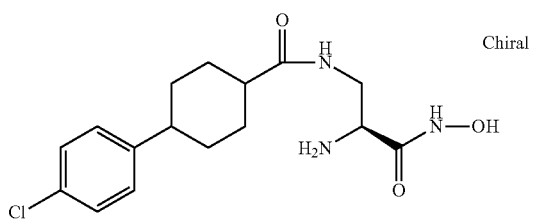 |
| 1244 | 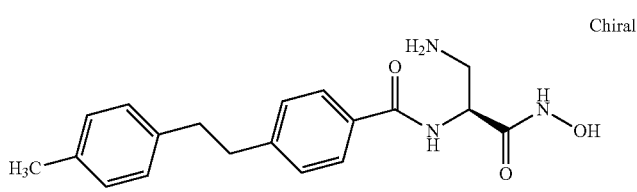 |
| 1245 | 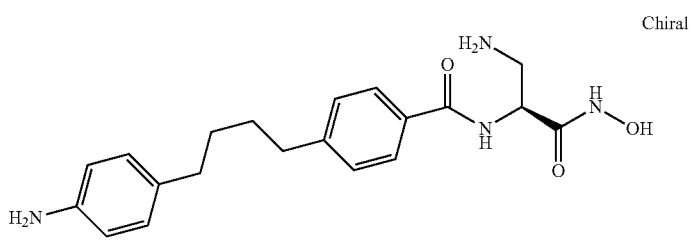 |
| 1246 | 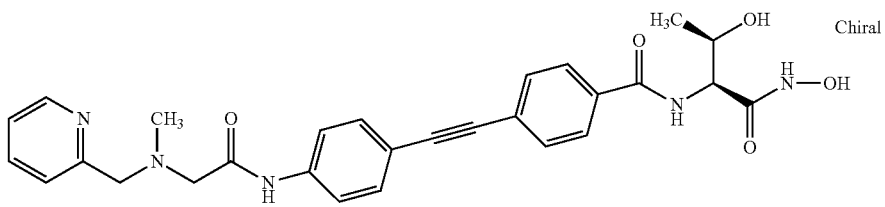 |
| 1247 | 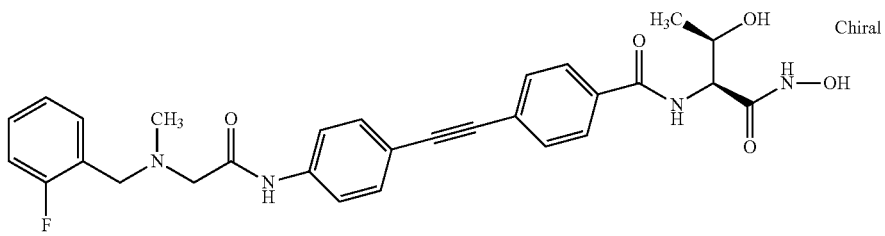 |
| 1248 | 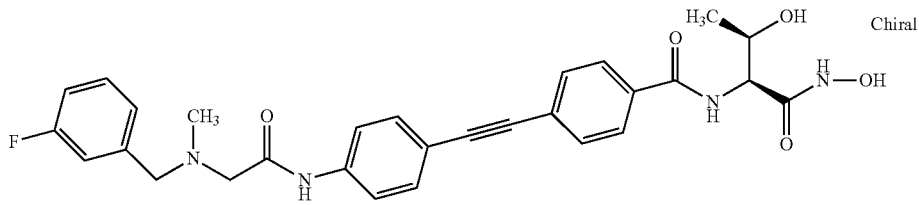 |

TABLE 1-continued

| 1249 | (structure) |
| 1250 | (structure) |
| 1251 | (structure) |
| 1252 | (structure) |
| 1253 | (structure) |
| 1254 | (structure) |
| 1255 | (structure) |

TABLE 1-continued
| 1256 | 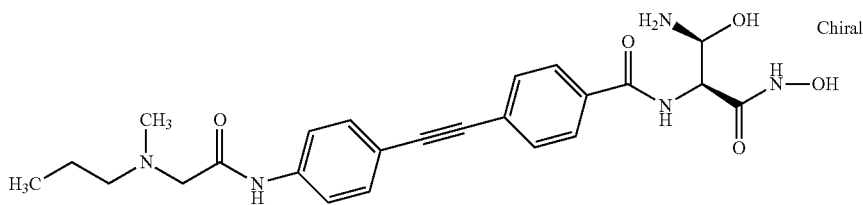 |
| 1257 | 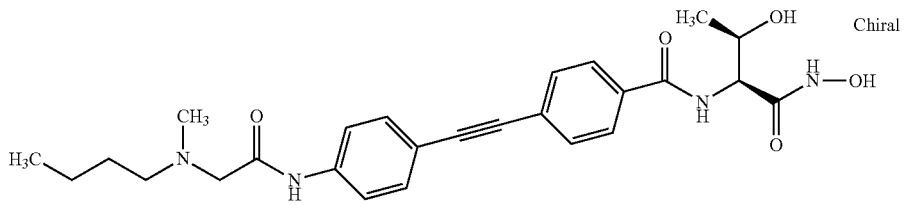 |
| 1258 | 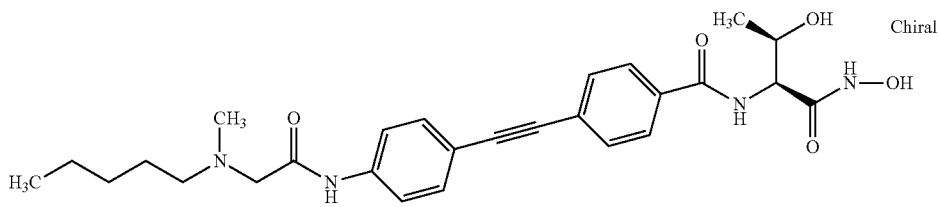 |
| 1259 | 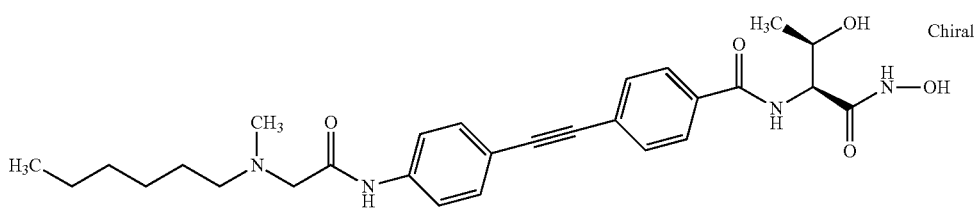 |
| 1260 | 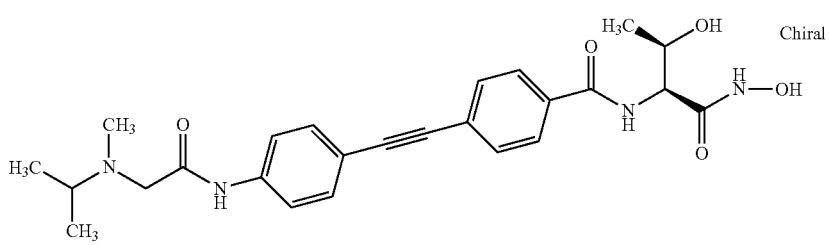 |
| 1261 | 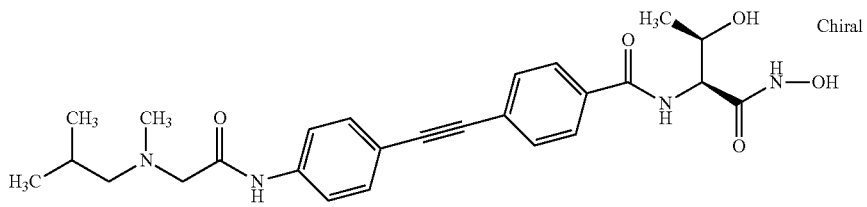 |
| 1262 | 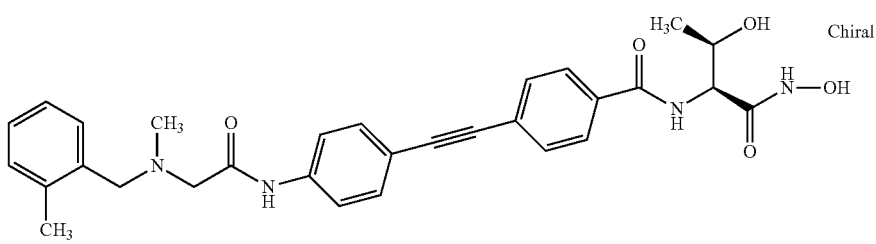 |

TABLE 1-continued
1263 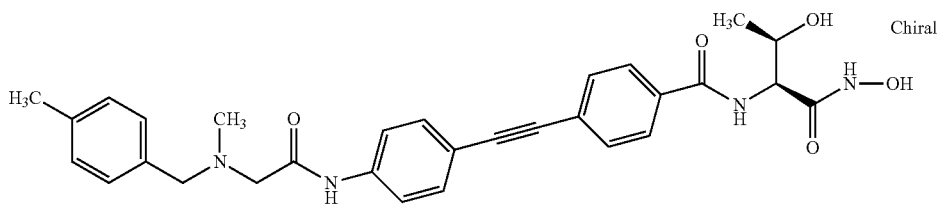
1264 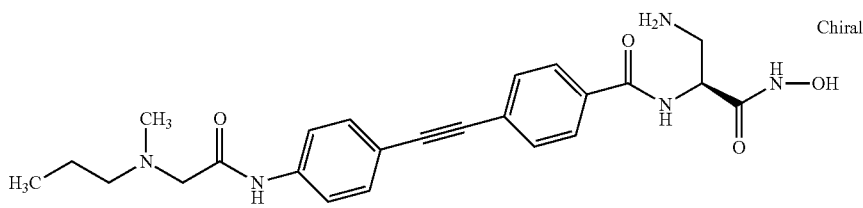
1265 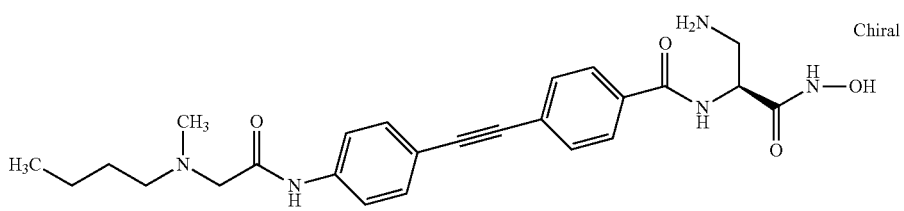
1266 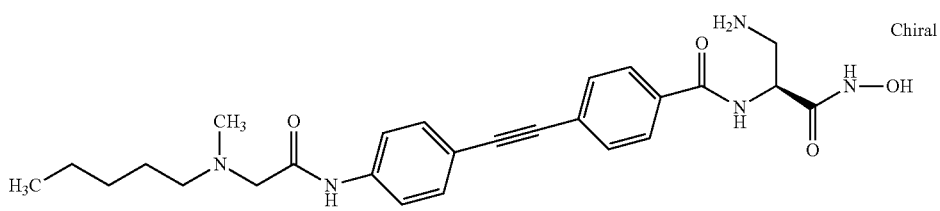
1267 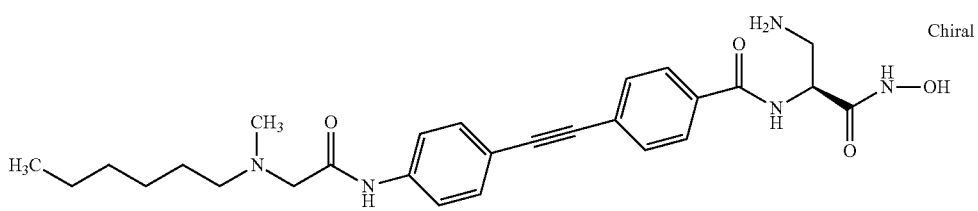
1268 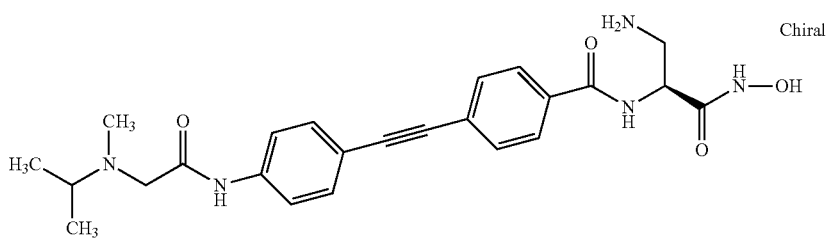
1269 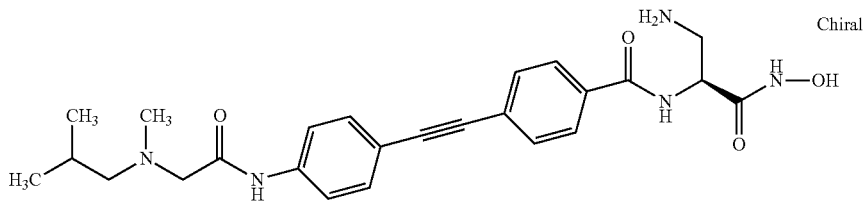

TABLE 1-continued
| 1270 | 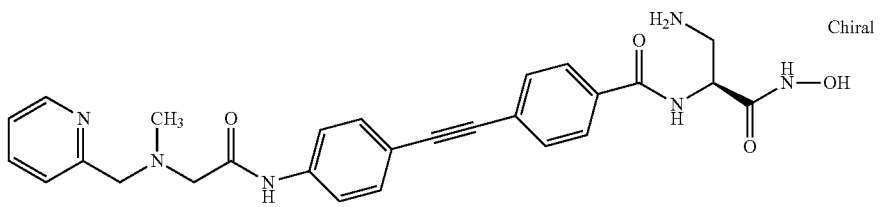 | Chiral |
| --- | --- | --- |
| 1271 | 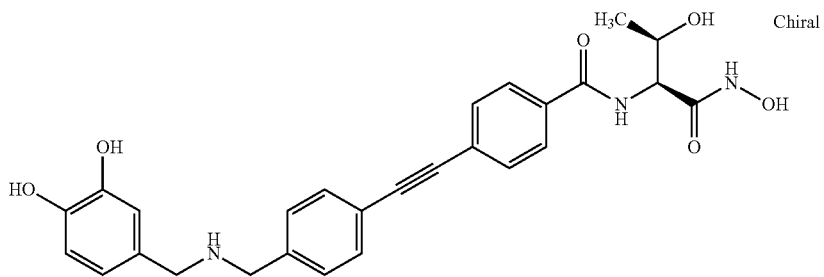 | Chiral |
| 1272 | 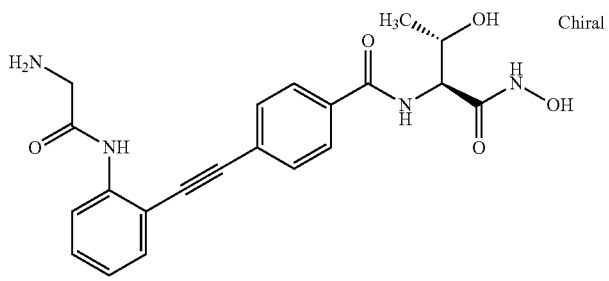 | Chiral |
| 1273 | 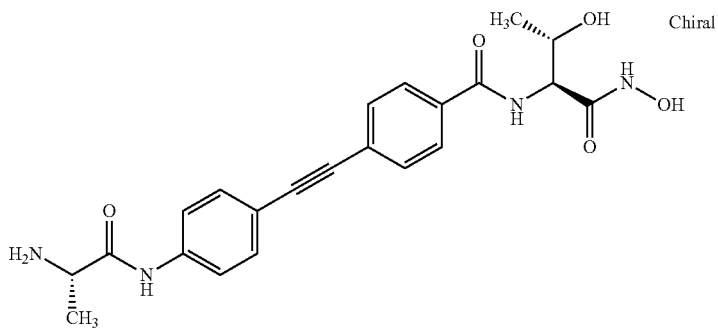 | Chiral |
| 1274 | 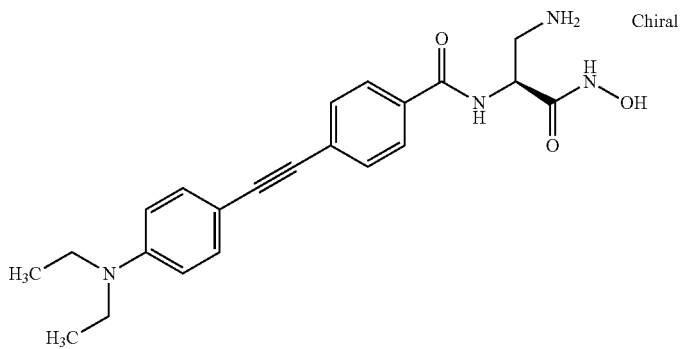 | Chiral |

TABLE 1-continued
1275 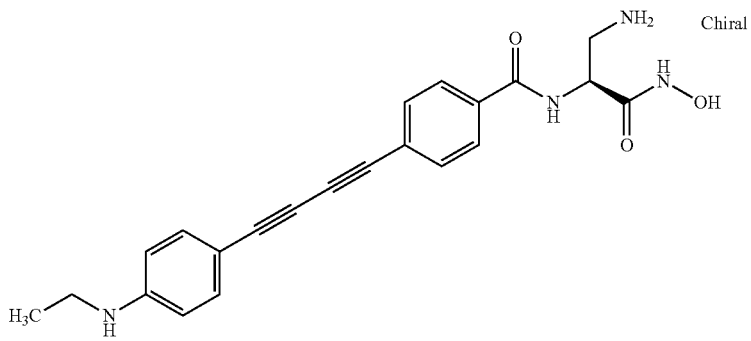 Chiral
1276 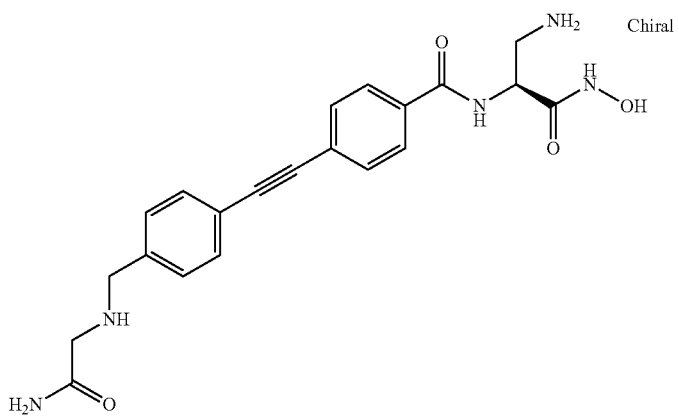 Chiral
1277 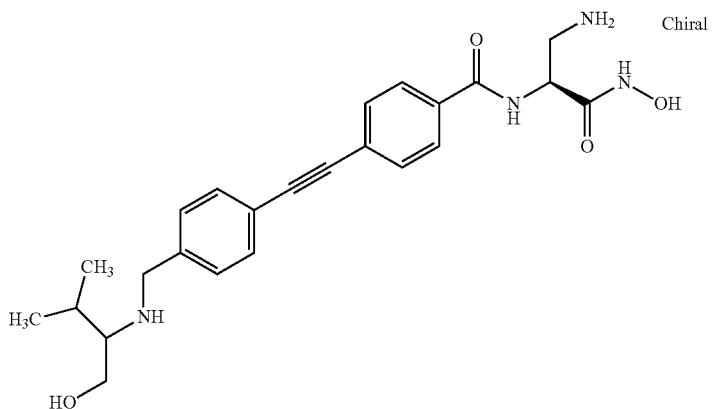 Chiral
1278 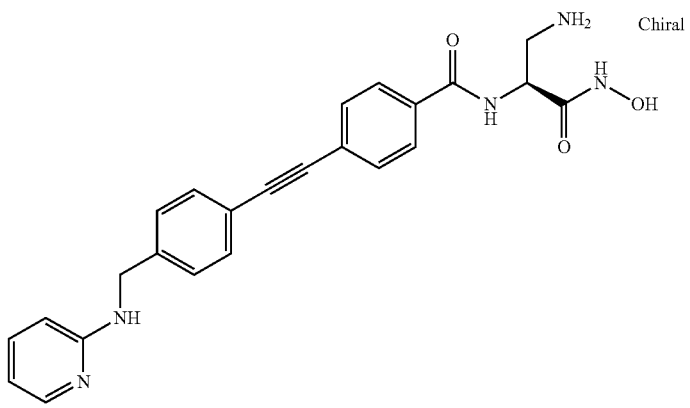 Chiral TABLE 1-continued
1279 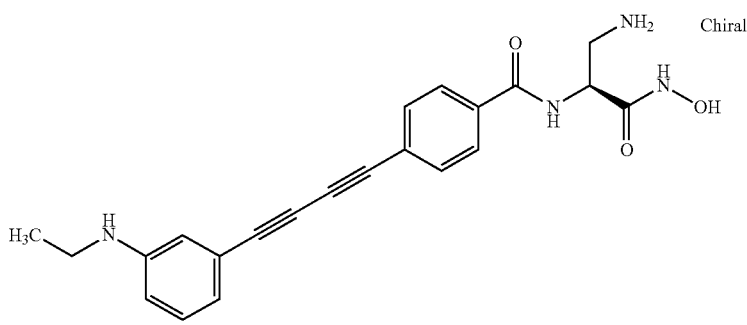
1280 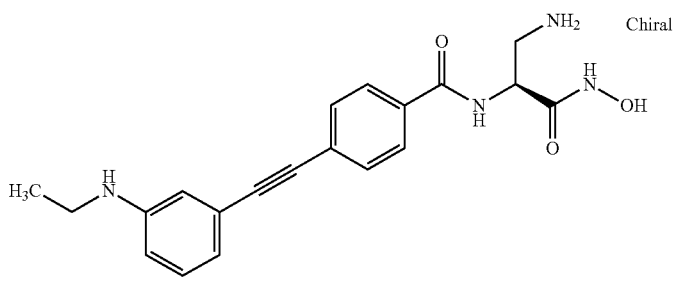
1281 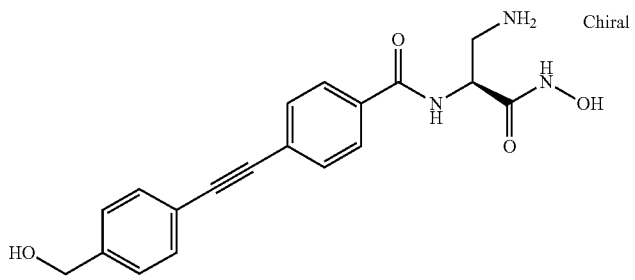
1282 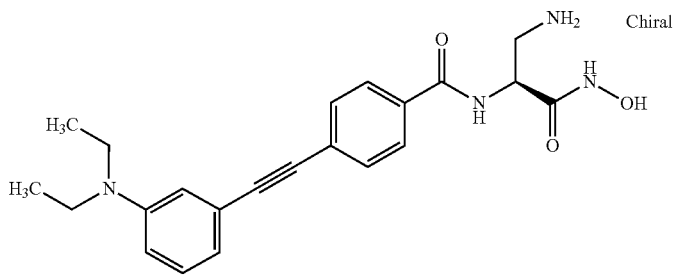
1283 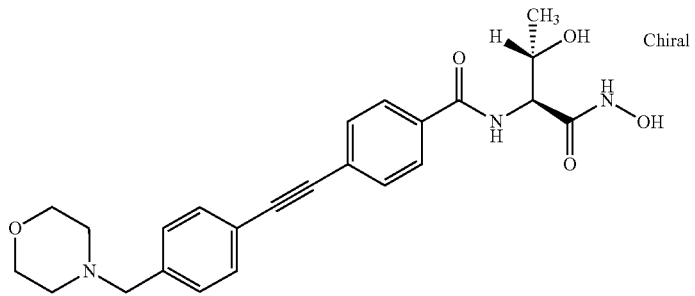

TABLE 1-continued
1284
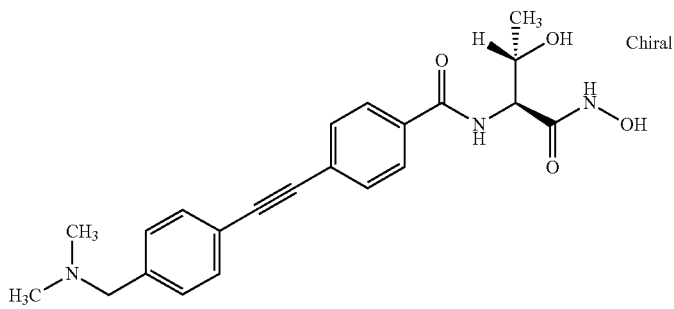
1285
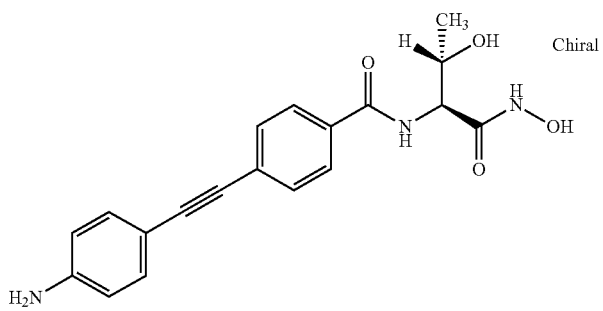
1286
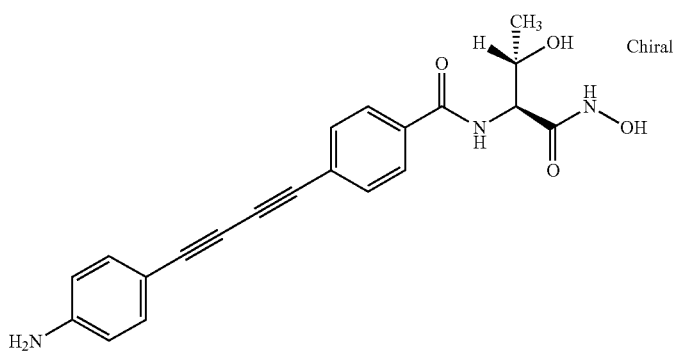
1287
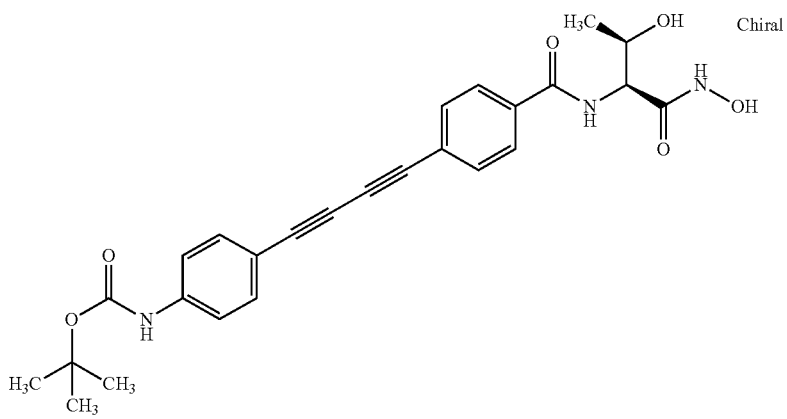

TABLE 1-continued
| 1288 | 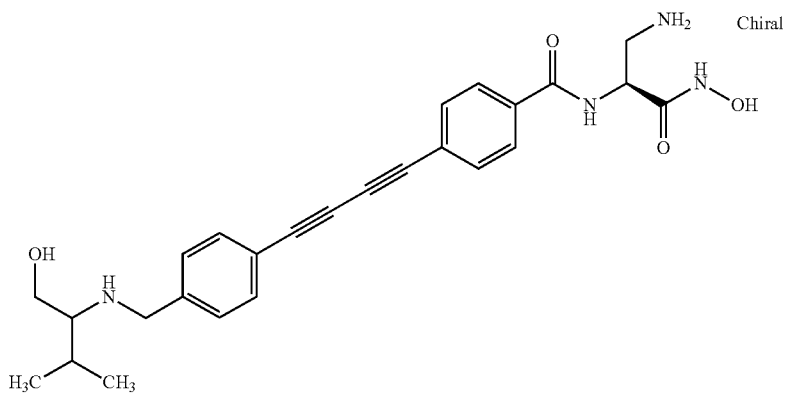 |
| --- | --- |
| 1289 | 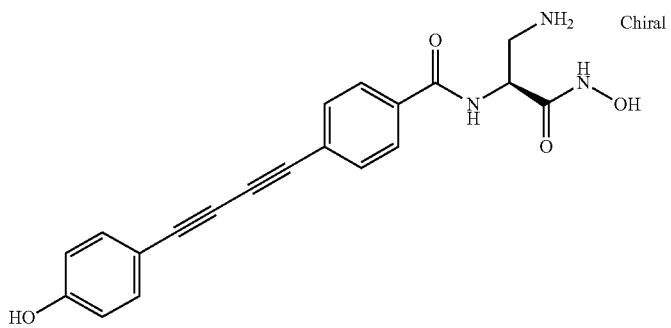 |
| 1290 | 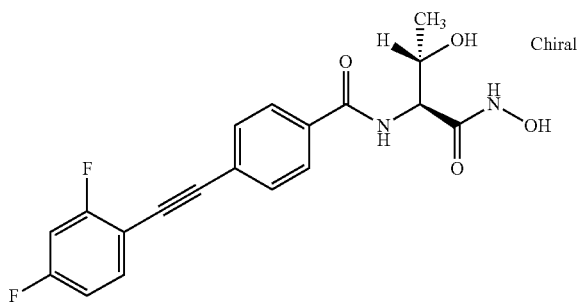 |
| 1291 | 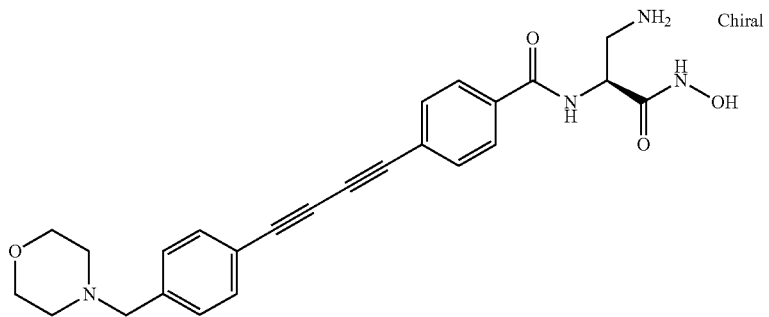 |

TABLE 1-continued
1292 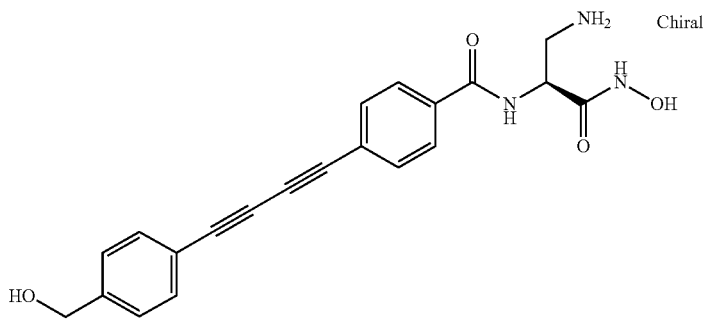
1293 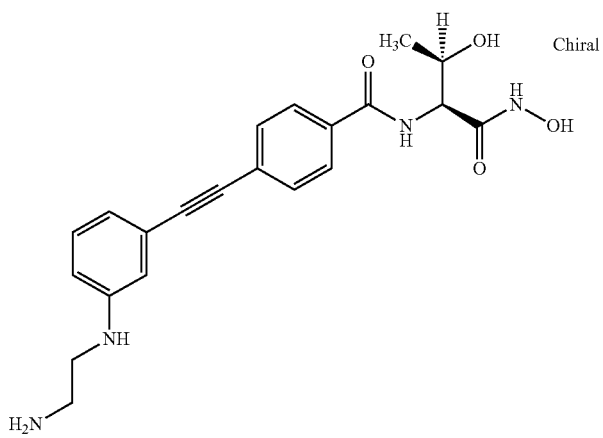
1294 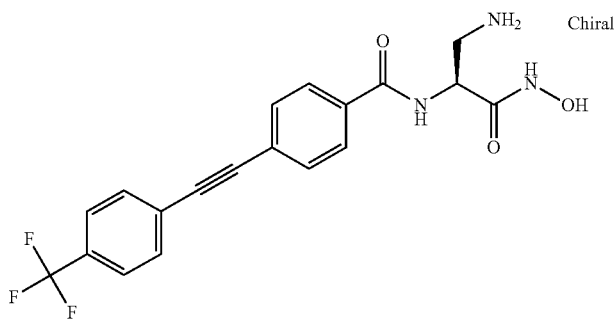
1295 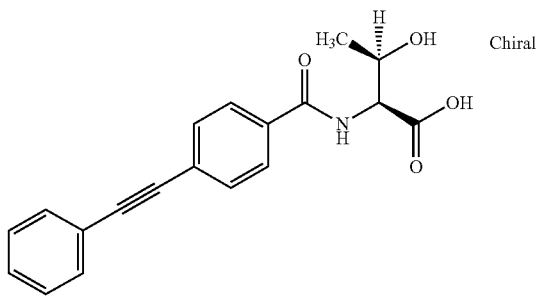

TABLE 1-continued
1296 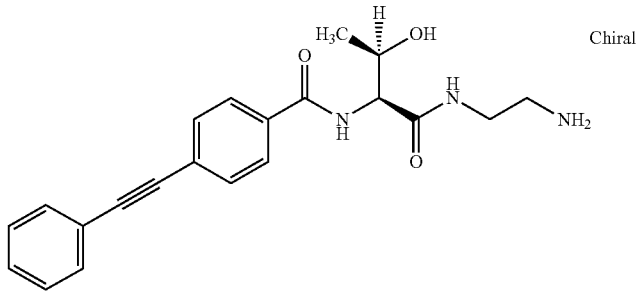
1297 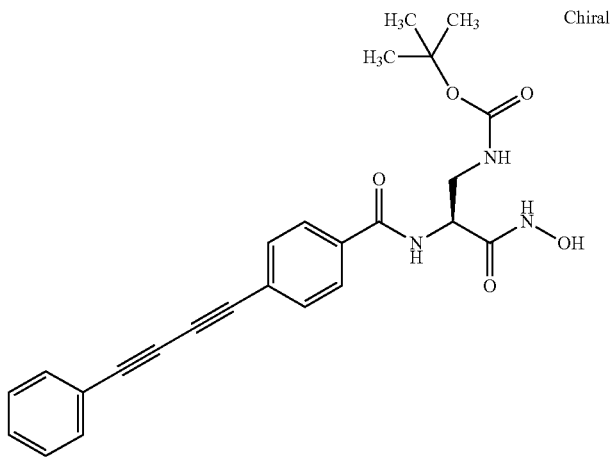
1298 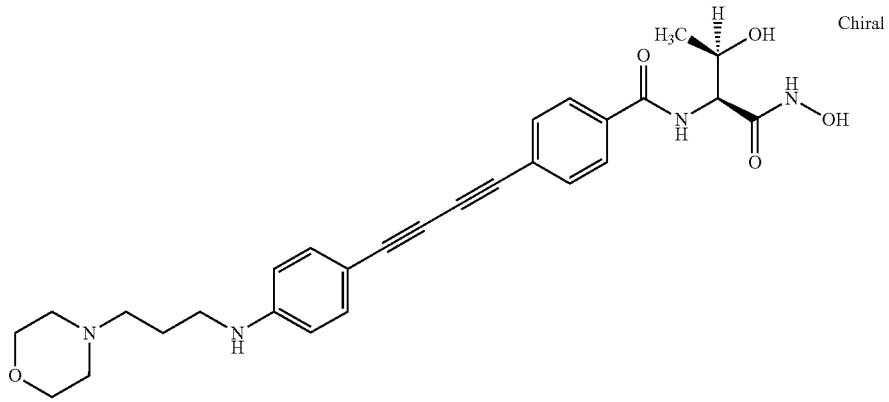
1299 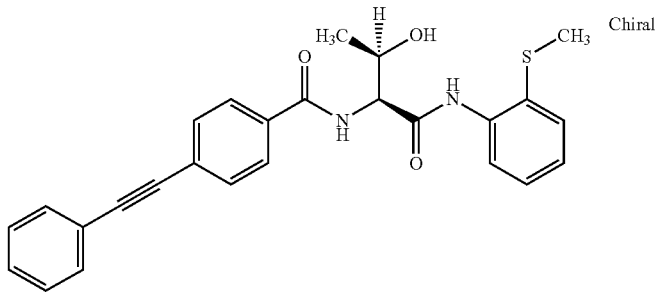

TABLE 1-continued
1300 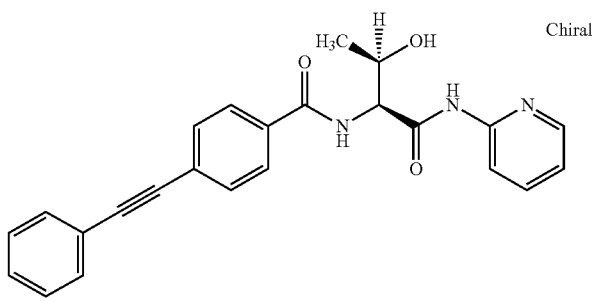
1301 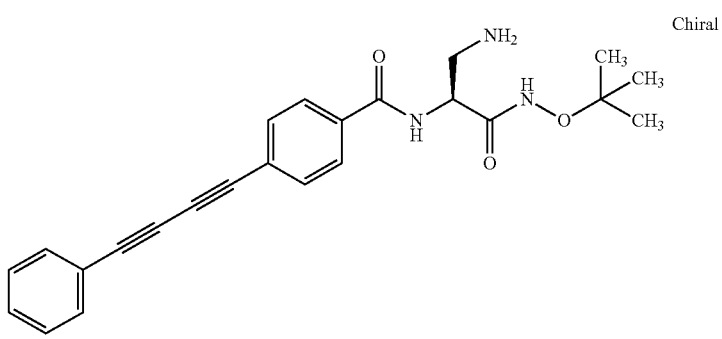
1302 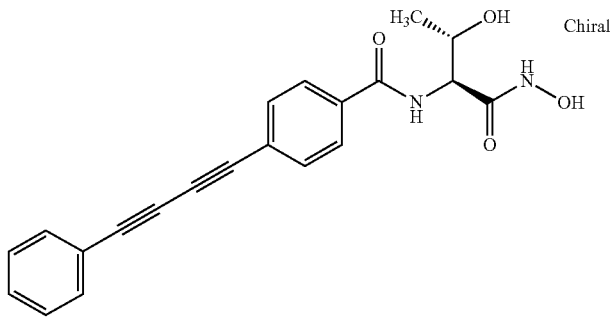
1303 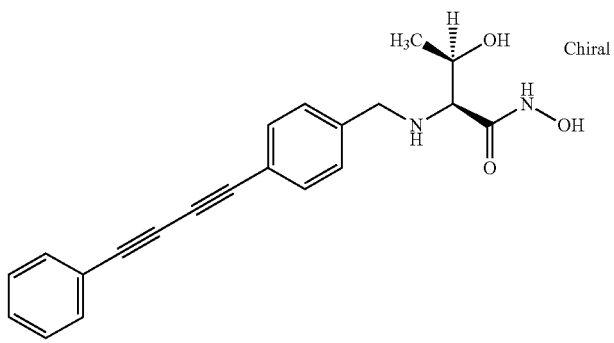

TABLE 1-continued

1304 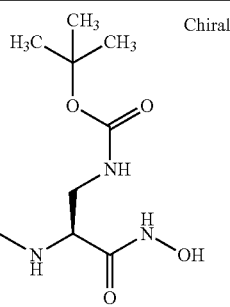

1305 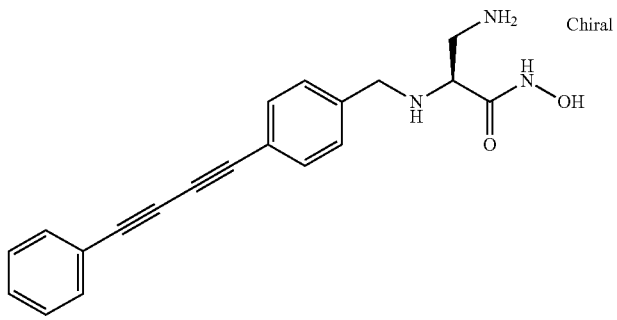

1306 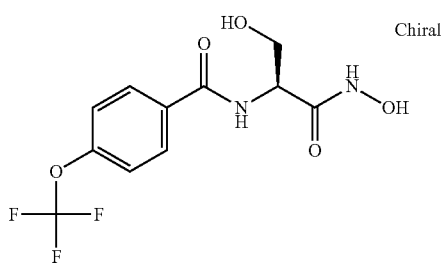

1307 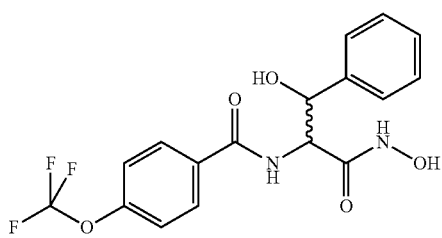

| Example | Name | MH+ |
|---|---|---|
| 30 | 3,4-difluoro-N-{(1S,2R)-2-hydroxy-1-[(hydroxyamino)carbonyl]propyl}benzamide | 275.2 |
| 31 | (2S,3R)-N,3-dihydroxy-2-[(4-phenylbutanoyl)amino]butanamide | 281.3 |
| 32 | (2S,3R)-N,3-dihydroxy-2-({4-[4-(methyloxy)phenyl]butanoyl}amino)butanamide | 311.3 |
| 33 | N-{(1S,2R)-2-hydroxy-1-[(hydroxyamino)carbonyl]propyl}-5-phenylpentanamide | 295.3 |
| 34 | (2E,4E)-N-{(1S,2R)-2-hydroxy-1-[(hydroxyamino)carbonyl]propyl}-5-phenylpenta-2,4-dienamide | 291.3 |
| 35 | (2E)-N-{(1S,2R)-2-hydroxy-1-[(hydroxyamino)carbonyl]propyl}-3-phenylprop-2-enamide | 265.3 |

TABLE 1-continued

| | | |
|---|---|---|
| 36 | (2S,3R)-3-hydroxy-2-({(2E)-3-[4-(methyloxy)phenyl]prop-2-enoyl}amino)butanoic acid | 280.3 |
| 37 | (3R)-3-amino-N-{(1S,2R)-2-hydroxy-1-[(hydroxyamino)carbonyl]propyl}-5-phenylpentanamide | 310.4 |
| 38 | (2E)-3-(4-fluorophenyl)-N-{(1S,2R)-2-hydroxy-1-[(hydroxyamino)carbonyl]propyl}prop-2-enamide | 283.3 |
| 39 | (2E)-3-(3-bromophenyl)-N-{(1S,2R)-2-hydroxy-1-[(hydroxyamino)carbonyl]propyl}prop-2-enamide | 344.2 |
| 40 | N-{(1S,2R)-2-hydroxy-1-[(hydroxyamino)carbonyl]propyl}-4-{[(2-phenylethyl)amino]methyl}benzamide | 372.4 |
| 41 | N-{(1S,2R)-2-hydroxy-1-[(hydroxyamino)carbonyl]propyl}-4-{[(4-phenylbutyl)amino]methyl}benzamide | 400.5 |
| 42 | 4-[(cyclopropylamino)methyl]-N-{(1S,2R)-2-hydroxy-1-[(hydroxyamino)carbonyl]propyl}benzamide | 308.3 |
| 43 | 4-[(hexylamino)methyl]-N-{(1S,2R)-2-hydroxy-1-[(hydroxyamino)carbonyl]propyl}benzamide | 352.4 |
| 44 | N-{(1S,2R)-2-hydroxy-1-[(hydroxyamino)carbonyl]propyl}-4-{[(2-pyridin-2-ylethyl)amino]methyl}benzamide | 373.4 |
| 45 | N-{(1S,2R)-2-hydroxy-1-[(hydroxyamino)carbonyl]propyl}-4-(4-methylpiperazin-1-yl)benzamide | 377.4 |
| 46 | N-{((1S,2R)-2-hydroxy-1-[(hydroxyamino)carbonyl]propyl}-4-(piperidin-1-ylmethyl)benzamide | 366.4 |
| 47 | N-{(1S,2R)-2-hydroxy-1-[hydroxyamino)carbonyl]propyl}-4-(morpholin-4-ylmethyl)benzamide | 338.4 |
| 48 | N-{(1S,2R)-2-hydroxy-1-[(hydroxyamino)carbonyl]propyl}-4-({[3-(2-oxopyrrolidin-1-yl)propyl]amino}methyl)benzamide | 393.5 |
| 49 | N-{(1S,2R)-2-hydroxy-1-[(hydroxyamino)carbonyl]propyl}-4-{[(3-phenylpropyl)amino]methyl}benzamide | 386.5 |
| 50 | (2S,5R)-N-{(1S,2R)-2-hydroxy-1-[(hydroxyamino)carbonyl]propyl-5-phenylpyrrolidine-2-carboxamide | 308.3 |
| 51 | (2R,5S)-N-{(1S,2R)-2-hydroxy-1-[(hydroxyamino)carbonyl]propyl}-5-phenylpyrrolidine-2-carboxamide | 308.3 |
| 52 | (2S,3R)-2-{[(3S)-3-amino-4-phenylbutanoyl]amino}-N,3-dihydroxybutanamide | 296.3 |
| 53 | (2S,3R){[(2S)-2-amino-4-phenylbutanoyl]amino}-N,3-dihydroxybutanamide | 296.3 |
| 54 | N-{(1S,2R)-2-hydroxy-1-[(hydroxyamino)carbonyl]propyl}-6-(2-pyrrolidin-1-ylethyl)pyridine-3-carboxamide | 337.4 |
| 55 | 2-{[(4'-ethyl-1,1'-biphenyl-4-yl)carbonyl]amino}-3-hydroxy-3-methylbutanoic acid | 342.4 |
| 56 | 2-{[4-(4-ethylphenyl)phenyl]carbonylamino}-3-hydroxy-4-methylpentanoic acid | 356.4 |
| 57 | {[(4'-ethyl-1,1'-biphenyl-4-yl)carbonyl]amino}(thien-2-yl)acetic acid | 366.5 |
| 58 | N-(2-{[(1,1-dimethylethyl)oxy]amino}-2-oxo-1-thien-2-ylethyl)-4'-ethyl-1,1'-biphenyl-4-carboxamide | 437.6 |
| 59 | 3-(dimethylamino)-2-{[(4'-ethyl-1,1'-biphenyl-4-yl)carbonyl]amino}propanoic acid | 341.4 |
| 60 | 4'-ethyl-N-{(1S)-1-[({(1S,2R)-2-hydroxy-1-[(hydroxyamino)carbonyl]propyl}amino)carbonyl]-3-methylbutyl1-1,1'-biphenyl-4-carboxamide | 456.6 |
| 61 | 4'-ethyl-N-[(1S)-2-({(1S,2R)-2-hydroxy-1-[(hydroxyamino)carbonyl]propyl}amino)-2-oxo-1-(phenylmethyl)ethyl]-1,1'-biphenyl-4-carboxamide | 490.6 |
| 62 | (2S)-1-[(4'-ethyl-1,1'-biphenyl-4-yl)carbonyl]-N-{(1S,2R)-2-hydroxy-1-[(hydroxyamino)carbonyl]propyl}pyrrolidine-2-carboxamide | 440.5 |

TABLE 1-continued

| | | |
|---|---|---|
| 63 | 4'-ethyl-N-[(1S)-2-({(1S,2R)-2-hydroxy-1-[(hydroxyamino)carbonyl]propyl}amino)-1-(1H-imidazol-4-ylmethyl)-2-oxoethyl]-1,1'-biphenyl-4-carboxamide | 480.5 |
| 64 | (3S)-2-[(4'-ethyl-1,1'-biphenyl-4-yl)carbonyl]-N-{(1S,2R)-2-hydroxy-1-[(hydroxyamino)carbonyl]propyl}-1,2,3,4-tetrahydroisoquinoline-3-carboxamide | 502.6 |
| 65 | (2S)-2-[(1,1'-biphenyl-4-ylacetyl)amine]-N-{(1S,2R)-2-hydroxy-1-[(hydroxyamino)carbonyl]propyl}-4-methylpentanamide | 442.5 |
| 66 | (2S,3R)-2-({(2S)-2-[(1,1'-biphenyl-4-ylacetyl)amino]-3-phenylpropanoyl}amino)-N,3-dihydroxybutanamide | 478.5 |
| 67 | (2S,3R)-2-{[(2S)-2-[(1,1'-biphenyl-4-ylacetyl)amino]-3-(4-hydroxyphenyl)propanoyl]amino}-N,3-dihydroxybutanamide | 492.5 |
| 68 | (2S)-1-(1,1'-biphenyl-4-ylacetyl)-N-{(1S,2R)-2-hydroxy-1-[(hydroxyamino)carbonyl]propyl}pyrrolidine-2-carboxamide | 426.5 |
| 69 | (2S,3R)-2-{[(2S)-2-[(1,1'-biphenyl-4-ylacetyamino]-3-(1H-imidazol-4-yl)propanoyl]amino}-N,3-dihydroxybutanamide | 466.5 |
| 70 | (2S)-2-[(1,1'-biphenyl-4-ylacetyl)amino]-N~1~{(1S,2R)-2-hydroxy-1-[(hydroxyamino)carbonyl]propyl}pentanediamide | 457.5 |
| 71 | (3S)-3-[(1,1'-biphenyl-4-ylacetyl)amino]-4-({(1S,2R)-2-hydroxy-1-[(hydroxyamino)carbonyl]propyl}amino)-4-oxobutanoic acid | 444.5 |
| 72 | (2S,4R)-1-[(4'-ethyl-1,1'-biphenyl-4-yl)carbonyl]-4-hydroxy-N-{(1S,2R)-2-hydroxy 1-[(hydroxyamino)carbonyl]propyl}pyrrolidine-2-carboxamide | 456.5 |
| 73 | N-[(1S)-1-(aminomethyl)-2-({(1S,2R)-2-hydroxy-1-[(hydroxyamino)carbonyl]propyl}amino)-2-oxoethyl]-4'-ethyl-1,1'-biphenyl-4-carboxamide | 429.5 |
| 74 | 4'-ethyl-N-{(1S)-1-[({(1S,2R)-2-hydroxy-1-[(hydroxyamino)carbonyl]propyl}amino)carbonyl]but-3-ynyl}-1,1'-biphenyl-4-carboxamide | 438.5 |
| 75 | (2S,3R)-2-({(2S)-2-[(1,1'-biphenyl-4-ylacetyl)amino]propanoyl}amino)-N,3-dihydroxybutanamide | 400.4 |
| 76 | (2S,4R)-1-(1,1'-biphenyl-4-ylacetyl)-4-hydroxy-N-{(1S,2R)-2-hydroxy-1-[(hydroxyamino)carbonyl]propyl}pyrrolidine-2-carboxamide | 442.5 |
| 77 | 4'-ethyl-N-{(1R,2R)-2-hydroxy-1-(hydroxy{[(2-hydroxyethyl)amino]carbonyl}amino)methyl]propy}-1,1'-biphenyl-4-carboxamide | 416.5 |
| 78 | N-((2R,3R)-2-{[(4'-ethyl-1,1'-biphenyl-4-yl)carbonyl]amino}-3-hydroxybutyl)-N-hydroxymorpholine-4-carboxamide | 442.5 |
| 79 | N-((2R,3R)-2-{[(4'-ethyl-1,1'-biphenyl-4-yl)carbonyl]amino}-3-hydroxybutyl)-N-hydroxy-4-methylpiperazine-1-carboxamide | 455.6 |
| 80 | N-((1R,2R)-1-{[[(cyclopropylamino)(carbonyl](hydroxy)amino]methyl}-2-hydroxypropyl)-4'-ethyl-1,1'-biphenyl-4-carboxamide | 412.5 |
| 81 | 4'-ethyl-N-{(1R,2R)-2-hydroxy-1-[(hydroxy{[(pyridin-3-ylmethyl)amino]carbonyl}amino)methyl]propyl}-1,1'-biphenyl-4-carboxamide | 463.5 |
| 82 | 4'-ethyl-N-{(1R,2R)-2-hydroxy-1-[(hydroxy{[(2-pyridin-2-ylethyl)amino]carbonyl}amino)methyl]propyl}1,1'-biphenyl-4-carboxamide | 477.6 |
| 83 | 4'-ethyl-N-{(1R,2R)-2-hydroxy-1-[(hydroxy{[(4-morpholin-4-ylphenyl)amino]carbonyl}amino)methyl]propyl}-1,1'-biphenyl-4-carboxamide | 533.6 |
| 84 | N~1~-((2R,3R)-2-{[(4'-ethyl-1,1'-biphenyl-4-yl)carbonyl]amino}-3-hydroxybutyl)-N~1~-hydroxypiperidine-1,4-dicarboxamide | 483.6 |

TABLE 1-continued

| | | |
|---|---|---|
| 85 | 4'-ethyl-N-[2-(hydroxyamino)ethyl]-1,1'-biphenyl-4-carboxamide | 285.4 |
| 86 | N-{2-[(aminocarbonyl)(hydroxy)amino]ethyl}-4'-ethyl-1,1'-biphenyl-4-carboxamide | 328.4 |
| 87 | N-{2-[(aminocarbonothioyl)(hydroxy)amino]ethyl}-4-ethyl-1,1'-biphenyl-4-carboxamide | 344.4 |
| 88 | N-{2-[({2-(dimethylamino)ethyl]amino}carbonyl)(hydroxy)amino]ethyl}-4'-ethyl-1,1'-biphenyl-4-carboxamide | 399.5 |
| 89 | N-{2-[{[(2-cyanoethyl)amino]carbonyl}(hydroxy)amino]ethyl}-4'-ethyl-1,1'-biphenyl-4-carboxamide | 381.4 |
| 90 | 4'-ethyl-N-[2-(hydroxy{[(2-hydroxyethyl)amino]carbonyl}amino)ethyl]-1,1'-biphenyl-4-carboxamide | 372.4 |
| 91 | N-(2-{[(4'-ethyl-1,1'-biphenyl-4-yl)carbonyl]amino}ethyl)-N-hydroxymorpholine-4-carboxamide | 398.5 |
| 92 | N-(2-{[(4'-ethyl-1,1'-biphenyl-4-yl)carbonyl]amino}ethyl)-N-hydroxy-4-methylpiperazine-1-carboxamide | 411.5 |
| 93 | N~1~-(2-{[(4'-ethyl-1,1'-biphenyl-4-yl)carbonyl]amino}ethyl)-N~1~-hydroxypiperidine-1,4-dicarboxamide | 439.5 |
| 94 | N-(2-{[(4'-ethyl-1,1'-biphenyl-4-yl)carbonyl]amino}ethyl)-N-hydroxypyrrolidine-1-carboxamide | 382.5 |
| 95 | N-{2-[[(cyclopropylamino)carbonyl](hydroxy)amino]ethyl}-4'-ethyl-1,1'-biphenyl-4-carboxamide | 368.4 |
| 96 | 4'-ethyl-N-{2-[hydroxy({[2-(methyloxy)ethyl]amino}carbonyl)amino]-1,1'-biphenyl-4-carboxamide | 386.5 |
| 97 | N-{2-[({[2-(acetylamino)ethyl]amino}carbonyl)(hydroxy)amino]ethyl}-4'-ethyl-1,1'-biphenyl-4-carboxamide | 413.5 |
| 98 | 4'-ethyl-N-{2-[hydroxy({[3-(2-oxopyrrolidin-1-yl)propyl]amino}carbonyl)amino]ethyl}-1,1'-biphenyl-4-carboxamide | 453.6 |
| 99 | 4'-ethyl-N-[2-(hydroxy{[(3-hydroxypropyl)amino]carbonyl}amino)ethyl]-1,1'-biphenyl-4-carboxamide | 386.5 |
| 100 | 4'-ethyl-N-{2-[hydroxy({[3-(methyloxy)propyl]amino}carbonyl)amino]ethyl}-1,1'-biphenyl-4-carboxamide | 400.5 |
| 101 | N-(2-{[(4'-ethy]-1,1'-biphenyl-4-yl)carbonyl]amino}ethyl)-N-hydroxy-1,4'-bipiperidine-1'-carboxamide | 479.6 |
| 102 | 4'-ethyl-N-[2-(hydroxy{[(2-pyridin-2-yl)ethyl]amino]carbonyl}amino)ethyl]-1,1'-biphenyl-4-carboxamide | 433.5 |
| 103 | 4'-ethyl-N-[2-(hydroxy{[(pyridin-3-ylmethyl)amino]carbonyl}amino)ethyl]-1,1'-biphenyl-4-carboxamide | 419.5 |
| 104 | 4'-ethyl-N-[2-(hydroxy{[(4-morpholin-4-ylphenyl)amino]carbonyl}amino)ethyl]-1,1'-biphenyl-4-carboxamide | 489.6 |
| 105 | N-(2-{[(4'-ethyl-1,1'-biphenyl-4-yl)carbonyl]amino}ethyl)-N,3-dihydroxypiperidine-1-carboxamide | 412.5 |
| 106 | N-{2-[{[(3-aminocyclohexyl)amino]carbonyl}(hydroxy)amino]ethyl}-4'-ethyl-1,1'-biphenyl-4-carboxamide | 425.5 |
| 107 | N-{2-[{[(2-aminoethyl)amino]carbonyl}(hydroxy)amino]ethyl}-4'-ethyl-1,1'-biphenyl-4-carboxamide | 371.4 |
| 108 | N-{2-[{[(3-aminopropyl)amino]carbonyl}(hydroxy)amino]ethyl}-4'-ethyl-1,1'-biphenyl-4-carboxamide | 385.5 |
| 109 | 1,1-dimethylethyl 3-({[(2-{[(4'-ethyl-1,1'-biphenyl-4-yl)carbonyl]amino}ethyl)(hydroxy)amino]carbonyl}amino)propylcarbamate | 485.6 |
| 110 | 4'-ethyl-N-{2-[({[(4-fluorophenyl)methyl]amino}carbonyl)(hydroxy)amino]ethyl}-1,1'-biphenyl-4-carboxamide | 436.5 |
| 111 | N-(2-{[(4'-ethyl-1,1'-biphenyl-4-yl)carbonyl]amino}ethyl)-N-hydroxy-3-[(trifluoroacetyl)amino]pyrrolidine-1-carboxamide | 493.5 |

TABLE 1-continued

| | | | |
|---|---|---|---|
| 112 | N-{2-[{[(4-aminothien-3-yl)amino]carbonyl}(hydroxy)amino]ethyl}-4'-ethyl-1,1'-biphenyl-4-carboxamide | 425.5 |
| 113 | 4'-ethyl-N-(2-{hydroxy[(piperidin-3-ylamino)carbonyl]amino}ethyl)-1,1'-biphenyl-4-carboxamide | 411.5 |
| 114 | 4'-ethyl-N-(2-{hydroxy[(piperidin-4-ylamino)carbonyl]amino}ethyl)-1,1'-biphenyl-4-carboxamide | 411.5 |
| 115 | 4'-ethyl-N-[2-(hydroxy{[(piperidin-2-ylmethyl)amino]carbonyl}amino)ethyl]-1,1'-biphenyl-4-carboxamide | 425.5 |
| 116 | 4'-ethyl-N-[2-(hydroxy{[(piperidin-3-ylmethyl)amino]carbonyl}amino)ethyl]-1,1-biphenyl-4-carboxamide | 425.5 |
| 117 | 3-amino-N-(2-{[(4'-ethyl-1,1'-biphenyl-4-yl)carbonyl]amino}ethyl)-N-hydroxypyrrolidine-1-carboxamide | 397.5 |
| 118 | 1,1-dimethylethyl 3-[({[(2-{[(4'-ethyl-1,1'-biphenyl-4-yl)carbonyl]amino}ethyl)(hydroxy)amino]carbonyl}amino)methyl]piperidine-1-carboxylate | 525.7 |
| 119 | 1,1-dimethylethyl 1-{[(2-{[(4'-ethyl-1,1'-biphenyl-4-yl)carbonyl]amino}ethyl)(hydroxy)amino]carbonyl}pyrrolidin-3-ylcarbamate | 497.6 |
| 120 | 4'-ethyl-N-[(1S,2R)-2-hydroxy-1-({[2-(hydroxyamino)ethyl]amino}carbonyl)propyl]-1,1'-biphenyl-4-carboxamide | 386.5 |
| 121 | N-{(1S,2R)-1-[({2-[(aminocarbonyl)(hydroxy)amino]ethyl}amino)carbonyl]-2-hydroxypropyl}-4'-ethyl-1,1'-biphenyl-4-carboxamide | 429.5 |
| 122 | N-{(1S,2R)-1-[({2-[(aminocarbonothioyl)(hydroxy)amino]ethyl}amino)carbonyl]-2-hydroxypropyl}-4'-ethyl-1,1'-biphenyl-4-carboxamide | 445.6 |
| 123 | 4'-ethyl-N-[(1S,2R)-2-hydroxy-1-({[2-(hydroxy{[(2-hydroxyethyl)amino]carbonyl}amino)ethyl]amino}carbonyl)propyl]-1,1'-biphenyl-4-carboxamide | 473.5 |
| 124 | 4'-ethyl-N-{(1S)-6-hydroxy-1-[(1R)-1-hydroxyethyl]-2,7-dioxo-11-oxa-3,6,8-triazadodec-1-yl}-1,1'-biphenyl-4-carboxamide | 487.6 |
| 125 | 4'-ethyl-N-{(1S)-6-hydroxy-1-[(1R)-1-hydroxyethyl]-11-methyl-2,7-dioxo-3,6,8,11-tetraazadodec-1-yl}-1,1'-bipheny]-4-carboxamide | 500.6 |
| 126 | 4'-ethyl-N-{(1S)-6-hydroxy-1-[(1R)-1-hydroxyethyl]-2,7,12-trioxo-3,6,8,11-tetraazatridec-1-yl}-1,1'-biphenyl-4-carboxamide | 514.6 |
| 127 | 4'-ethyl-N-{(1S,2R)-2-hydroxy-1-[({2-[hydroxy({[3-(2-oxopyrrolidin-1-yl)propyl]amino}carbonyl)amino]ethyl}amino)carbonyl]propyl}-1,1'-biphenyl-4-carboxamide | 554.7 |
| 128 | N-{(1S,2R)-1-[({2-[{[(2-cyanoethyl)amino]carbonyl}(hydroxy)amino]ethyl}amino)carbonyl]-2-hydroxypropyl}-4'-ethyl-1,1'-biphenyl-4-carboxamide | 482.6 |
| 129 | N-{(1S,2R)-1-[({2-[[(cyclopropylamino)carbonyl](hydroxy)amino]ethyl}amino)carbonyl]-2-hydroxypropyl}-4'-ethyl-1,1'-biphenyl-4-carboxamide | 469.6 |
| 130 | N-{2-[((2S,3R)-2-{[(4'-ethyl-1,1'-biphenyl-4-yl)carbonyl]amino}-3-hydroxybutanoyl)amino]ethyl}-N-hydroxypyrrolidine-1-carboxamide | 483.6 |
| 131 | N-{2-[((2S,3R)-2-{[(4'-ethyl-1,1'-biphenyl-4-yl)carbonyl]amino}-3-hydroxybutanoyl)amino]ethyl}-N-hydroxymorpholine-4-carboxamide | 499.6 |
| 132 | N-{2-[((2S,3R)-2-{[(4-ethyl-1,1'-biphenyl-4-yl)carbonyl]amino}-3-hydroxybutanoyl)amino]ethyl}-N-hydroxy-4-methylpiperazine-1-carboxamide | 512.6 |
| 133 | 4'-ethyl-N-[(1S,2R)-2-hydroxy-1-({[2-(hydroxy{[(pyridin-3-ylmethyl)amino]carbonyl}amino)ethyl]amino}carbonyl)propyl]-1,1'-biphenyl-4-carboxamide | 520.6 |

TABLE 1-continued

| | | |
|---|---|---|
| 134 | 4'-ethyl-N-[(1S,2R)-2-hydroxy-1-({[2-(hydroxy{[(2-pyridin-2-ylethyl)amino]carbonyl}amino)ethyl]amino}carbonyl)propyl]-1,1'-biphenyl-4-carboxamide | 534.6 |
| 135 | 3-chloro-N-{(1S,2S)-2-hydroxy-1-[(hydroxyamino)carbonyl]propyl}-4-[(trifluoromethyl)oxy]benzamide | 357.7 |
| 136 | N-{(1S,2R)-2-hydroxy-1-[(hydroxyamino)carbonyl]propyl}-4-{[(3-nitrophenyl)methyl]oxy}benzamide | 390.4 |
| 137 | (4R)-2-(4-fluoro-3-prop-2-enylphenyl)-N-hydroxy-4,5-dihydro-1,3-oxazole-4-carboxamide | 265.3 |
| 138 | 3-fluoro-N-{(1S,2R)-2-hydroxy-1-[(hydroxyamino)carbonyl]propyl}-4-(methyloxy)benzamide | 287.3 |
| 139 | 4-(but-3-enyloxy)-N-{(1S,2R)-2-hydroxy-1-[(hydroxyamino)carbonyl]propyl}benzamide | 309.3 |
| 140 | 3-bromo-5-fluoro-N-{(1S,2R)-2-hydroxy-1-[(hydroxyamino)carbonyl]propyl}-4-(prop-2-enyloxy)benzamide | 392.2 |
| 141 | 4-fluoro-N-{(1S,2S)-2-hydroxy-1-[(hydroxyamino)carbonyl]propyl}-3-prop-2-enylbenzamide | 297.3 |
| 142 | N-{(1S,2R)-2-hydroxy-1-[(hydroxyamino)carbonyl]propyl}-4-(prop-2-enyloxy)-3-(trifluoromethyl)benzamide | 363.3 |
| 143 | N-{(1S,2R)-2-hydroxy-1-[(hydroxyamino)carbonyl]propyl}-4-(methyloxy)benzamide | 269.3 |
| 144 | N-{(1S,2R)-2-hydroxy-1-[(hydroxyamino)carbonyl]propyl}-3-(phenyloxy)benzamide | 331.3 |
| 145 | N-{(1S,2R)-2-hydroxy-1-[(hydroxyamino)carbonyl]propyl}-4-(methyloxy)-3-[(trifluoromethyl)oxy]benzamide | 353.3 |
| 146 | N-{(1S,2S)-2-hydroxy-1-[(hydroxyamino)carbonyl]propyl}-4-[(trifluoromethyl)oxy]benzamide | 323.2 |
| 147 | N-{(1S,2R)-2-hydroxy-1-[(hydroxyamino)carbonyl]propyl}-4-[(trifluoromethyl)oxy]benzamide | 323.2 |
| 148 | N-{(1S,2R)-2-hydroxy-1-[(hydroxyamino)carbonyl]propyl}-4-(trifluoromethyl)benzamide | 307.2 |
| 149 | 3,4-difluoro-N-{(2R)-2-hydroxy-1-[(hydroxyamino)carbonyl]propyl}benzamide | 275.2 |
| 150 | N-{(1S,2S)-2-hydroxy-1-[(hydroxyamino)carbonyl]propyl}-4-(methyloxy)benzamide | 269.3 |
| 151 | N-{(1S,2R)-2-hydroxy-1-[(hydroxyamino)carbonyl]propyl}-4'-propyl-1,1'-biphenyl-4-carboxamide | 357.4 |
| 152 | N-{(1S,2R)-2-hydroxy-1-[(hydroxyamino)carbonyl]propyl}-4'-propyl-1,1'-biphenyl-4-carboxamide | 357.4 |
| 153 | N-{(1S,2R)-2-hydroxy-1-[(hydroxyamino)carbonyl]propyl}-4-[trifluoro(methylidene)-lambda~6~-sulfanyl]benzamide | 341.3 |
| 154 | N-{(1S,2R)-2-hydroxy-1-[(hydroxyamino)carbonyl]propyl}benzamide | 239.2 |
| 155 | N-{(1S,2R)-2-hydroxy-1-[(hydroxyamino)carbonyl]propyl}-1,1'-biphenyl-4-carboxamide | 315.3 |
| 156 | 3-bromo-N-{(1S,2R)-2-hydroxy-1-[(hydroxyamino)carbonyl]propyl}-4-(methyloxy)benzamide | 348.2 |
| 157 | 4-fluoro-N-{(1S,2R)-2-hydroxy-1-[(hydroxyamino)carbonyl]propyl}-3-(prop-2-enyloxy)benzamide | 313.3 |
| 158 | 2,3,5,6-tetrafluoro-N-{(1S,2R)-2-hydroxy-1-[(hydroxyamino)carbonyl]propyl}-4-prop-2-enylbenzamide | 351.3 |
| 159 | 3-fluoro-N-{(1S,2R)-2-hydroxy-1-[(hydroxyamino)carbonyl]propyl}-5-(trifluoromethyl)benzamide | 325.2 |
| 160 | 4-bromo-2-fluoro-N-{(1S,2R)-2-hydroxy-1-[(hydroxyamino)carbonyl]propyl}benzamide | 336.1 |
| 161 | N-{(1S,2R)-2-hydroxy-1-[(hydroxyamino)carbonyl]propyl}-4-(phenyloxy)benzamide | 331.3 |

TABLE 1-continued

| | | |
|---|---|---|
| 162 | 4-(dimethylamino)-N-{(1S,2R)-2-hydroxy-1-[(hydroxyamino)carbonyl]propyl}benzamide | 282.3 |
| 163 | 2-[3-fluoro-4-(methyloxy)-5-prop-2-enylphenyl]-N-hydroxy-4,5-dihydro-1,3-oxazole-4-carboxamide | 295.3 |
| 164 | N-{(1S,2R)-2-hydroxy-1-[(hydroxyamino)carbonyl]propyl}-5-[3-(trifluoromethyl)phenyl]furan-2-carboxamide | 373.3 |
| 165 | 4-{[(1E)-1,2-difluorobuta-1,3-dienyl]oxy}-N-{(1S,2R)-2-hydroxy-1-[(hydroxyamino)carbonyl]propyl}benzamide | 343.3 |
| 166 | N-{(1S,2R)-2-hydroxy-1-[(hydroxyamino)carbonyl]propyl}quinoline-2-carboxamide | 290.3 |
| 167 | N-[2-(hydroxyamino)-1-(hydroxymethyl)-2-oxoethyl]-1,1'-biphenyl-4-carboxamide | 301.3 |
| 168 | N-{(1S,2S)-2-hydroxy-1-[(hydroxyamino)carbonyl]propyl}-1,1'-biphenyl-4-carboxamide | 315.3 |
| 169 | N-{(1S,2R)-2-hydroxy-1-[(hydroxyamino)carbonyl]propyl}-2'-methyl-1,1'-biphenyl-4-carboxamide | 329.4 |
| 170 | N-{(1S,2S)-2-hydroxy-1-[(hydroxyamino)carbonyl]propyl}-4-(trifluoromethyl)benzamide | 307.2 |
| 171 | 4-fluoro-N-{(1S,2R)-2-hydroxy-1-[(hydroxyamino)carbonyl]propyl}-3-(trifluoromethyl)benzamide | 325.2 |
| 172 | N-{(1S,2R)-2-hydroxy-1-[(hydroxyamino)carbonyl]propyl}-4-{[(3-nitrophenyl)oxy]methyl}benzamide | 390.4 |
| 173 | N-[(1R)-2-(hydroxyamino)-1-(mercaptomethyl)-2-oxoethyl]-4-[(trifluoromethyl)oxy]benzamide | 325.3 |
| 174 | N-{(1S,2R)-2-hydroxy-1-[(hydroxyamino)carbonyl]propyl}-1,3-benzodioxole-5-carboxamide | 283.3 |
| 175 | N-{(1S,2R)-2-hydroxy-1-[(hydroxyamino)carbonyl]propyl}-6-(trifluoromethyl)pyridine-3-carboxamide | 308.2 |
| 176 | N-{3-hydroxy-1-[(hydroxyamino)carbonyl]propyl}-4-[(trifluoromethyl)oxy]benzamide | 323.2 |
| 177 | N-{3-hydroxy-1-[(hydroxyamino)carbonyl]propyl}-1,1'-biphenyl-4-carboxamide | 315.3 |
| 178 | N-{(1S,2R)-2-hydroxy-1-[(hydroxyamino)carbonyl]propyl}-4-[hydroxy(phenyl)methyl]benzamide | 345.4 |
| 179 | N-{(1S,2R)-2-hydroxy-1-[(hydroxyamino)carbonyl]propyl}-4-[({4-[(trifluoromethyl)oxy]phenyl}oxy)methyl]benzamide | 429.4 |
| 180 | 4-[({4-bromo-2-[(trifluoromethyl)oxy]phenyl}oxy)methyl]-N-{(1S,2R)-2-hydroxy-1-[(hydroxyamino)carbonyl]propyl}benzamide | 508.3 |
| 181 | N-{(1S,2R)-2-hydroxy-1-[(hydroxyamino)carbonyl]propyl}-3'-nitro-1,1'-biphenyl-4-carboxamide | 360.3 |
| 182 | 4-bromo-N-{(1S,2R)-2-hydroxy-1-[(hydroxyamino)carbonyl]propyl}benzamide | 318.1 |
| 183 | N-{(1S,2R)-2-hydroxy-1-[(hydroxyamino)carbonyl]propyl}-4-(methyloxy)-1,1'-biphenyl-4-carboxamide | 345.4 |
| 184 | N-{(1S,2R)-2-hydroxy-1-[(hydroxyamino)carbonyl]propyl}-4'-[(trifluoromethyl)oxy]-1,1'-biphenyl-4-carboxamide | 399.3 |
| 185 | 4'-(ethyloxy)-N-{(1S,2R)-2-hydroxy-1-[(hydroxyamino)carbonyl]propyl}-1,1'-biphenyl-4-carboxamide | 359.4 |
| 186 | N-{(1S,2R)-2-hydroxy-1-[(hydroxyamino)carbonyl]propyl}-4-{5-[(Z)-(hydroxyimino)methyl]thien-2-yl}benzamide | 364.4 |
| 187 | 3'-(ethyloxy)-N-{(1S,2R)-2-hydroxy-1-[(hydroxyamino)carbonyl]propyl}-1,1'-biphenyl-4-carboxamide | 359.4 |
| 188 | (2R,3R)-N,3-dihydroxy-1-({4-[(trifluoromethyl)oxy]phenyl}carbonyl)pyrrolidine-2-carboxamide | 335.2 |
| 189 | N-[2-(hydroxyamino)-1-(hydroxymethyl)-2-oxoethyl]-3-(1-methylethyl)-4-(methyloxy)benzamide | 297.3 |

TABLE 1-continued

| | | |
|---|---|---|
| 190 | N-[2-(hydroxyamino)-1-(hydroxymethyl)-2-oxoethyl]-3-(1-methylethyl)-4-(prop-2-enyloxy)benzamide | 323.4 |
| 191 | N-[2-(hydroxyamino)-1-(hydroxymethyl)-2-oxoethyl]-4-(methyloxy)-3-propylbenzamide | 297.3 |
| 192 | N-{(1S,2R)-2-hydroxy-1-[(hydroxyamino)carbonyl]propyl}-4-(methylthio)-1,1'-biphenyl-4-carboxamide | 361.4 |
| 193 | 5-bromo-N-{(1S,2R)-2-hydroxy-1-[(hydroxyamino)carbonyl]propyl}thiophene-2-carboxamide | 324.2 |
| 194 | N-{(1S,2R)-2-hydroxy-1-[(hydroxyamino)carbonyl]propyl}-5-{4-[(trifluoromethyl)oxy]phenyl}thiophene-2-carboxamide | 405.4 |
| 195 | N-{(1S,2R)-2-hydroxy-1-[(hydroxyamino)carbonyl]propyl}-1-benzofuran-2-carboxamide | 279.3 |
| 196 | N-{(1S,2R)-2-hydroxy-1-[(hydroxyamino)carbonyl]propyl}-5-phenylthiophene-2-carboxamide | 321.4 |
| 197 | 4'-(dimethylamino)-N-{(1S,2R)-2-hydroxy-1-[(hydroxyamino)carbonyl]propyl}-1,1'-biphenyl-4-carboxamide | 358.4 |
| 198 | (2S,3R)-N,3-dihydroxy-2-[({2-[(trifluoromethyl)oxy]phenyl}acetyl)amino]butanamide | 337.3 |
| 199 | 5-[4-(ethyloxy)phenyl]-N-{(1S,2R)-2-hydroxy-1-[(hydroxyamino)carbonyl]propyl}thiophene-2-carboxamide | 365.4 |
| 200 | 5-[3-(ethyloxy)phenyl]-N-{(1S,2R)-2-hydroxy-1-[(hydroxyamino)carbonyl]propyl}thiophene-2-carboxamide | 365.4 |
| 201 | (4R)-N-hydroxy-2-{2'-[(trifluoromethyl)oxy]-1,1'-biphenyl-4-yl}-4,5-dihydro-1,3-oxazole-4-carboxamide | 367.3 |
| 202 | N-{(1S,2R)-2-hydroxy-1-[(hydroxyamino)carbonyl]propyl}-4-(hydroxymethyl)-1,1'-biphenyl-4-carboxamide | 345.4 |
| 203 | N-{(1S,2R)-2-hydroxy-1-[(hydroxyamino)carbonyl]propyl}-4-{5-[(4-methylpiperazin-1-yl)methyl]thien-2-yl}benzamide | 433.5 |
| 204 | N-{(1S,2R)-2-hydroxy-1-[(hydroxyamino)carbonyl]propyl}-4-{[4-(methyloxy)phenyl]carbonyl}benzamide | 373.4 |
| 205 | N-{(1S,2R)-2-hydroxy-1-[(hydroxyamino)carbonyl]propyl}-4-[(E)-phenyldiazenyl]benzamide | 343.4 |
| 206 | (4R)-N-hydroxy-2-{4-(methyloxy)-3-[(trifluoromethyl)oxy]phenyl}-dihydro-1,3-oxazole-4-carboxamide | 321.2 |
| 207 | 4'-ethyl-N-{(1S,2R)-2-hydroxy-1-[(hydroxyamino)carbonyl]propyl}-1,1'-biphenyl-4-carboxamide | 343.4 |
| 208 | N-{(1S,2R)-2-hydroxy-1-[(hydroxyamino)carbonyl]propyl}-4'-(trifluoromethyl)-1,1'-biphenyl-4-carboxamide | 383.3 |
| 209 | 5-(4-ethylphenyl)-N-{(1S,2R)-2-hydroxy-1-[(hydroxyamino)carbonyl]propyl}thiophene-2-carboxamide | 349.4 |
| 210 | N-{(1S,2R)-2-hydroxy-1-[(hydroxyamino)carbonyl]propyl}-5-[4-(methyloxy)phenyl]thiophene-2-carboxamide | 351.4 |
| 211 | N-{(1S,2R)-2-hydroxy-1-[(hydroxyamino)carbonyl]propyl}-5-[4-(methylthio)phenyl]thiophene-2-carboxamide | 367.5 |
| 212 | N-{(1S,2R)-2-hydroxy-1-[(hydroxyamino)carbonyl]propyl}-5-(3-nitrophenyl)thiophene-2-carboxamide | 366.4 |
| 213 | N-{(1S,2R)-2-hydroxy-1-[(hydroxyamino)carbonyl]propyl}-4-oxo-4H-chromene-2-carboxamide | 307.3 |
| 214 | N-[1-[(hydroxyamino)carbonyl]-1-(hydroxymethyl)-2-methylpropyl]-4-[(trifluoromethyl)oxy]benzamide | 351.3 |
| 215 | N-[2-hydroxy-3-(hydroxyamino)-3-oxopropyl]-1,1'-biphenyl-4-carboxamide | 301.3 |
| 216 | N-{(1S,2R)-2-hydroxy-1-[(hydroxyamino)carbonyl]propyl}-4-[(E)-2-phenylethenyl]benzamide | 341.4 |
| 217 | N-{(1S,2R)-2-hydroxy-1-[(hydroxyamino)carbonyl]propyl}-9H-fluorene-2-carboxamide | 327.4 |

TABLE 1-continued

| | | |
|---|---|---|
| 218 | 4'-[({(1S,2R)-2-hydroxy-1-[(hydroxyamino)carbonyl]propyl}amino)carbonyl]-1,1'-biphenyl-4-carboxylic acid | 359.3 |
| 219 | N-[2-(hydroxyamino)-1-(hydroxymethyl)-2-oxoethyl]-4-(prop-2-enyloxy)-3-propylbenzamide | |
| 220 | N-{(1S,2R)-2-hydroxy-1-[(hydroxyamino)carbonyl]propyl}-4-iodobenzamide | 365.1 |
| 221 | 4'-hydroxy-N-{(1S,2R)-2-hydroxy-1-[(hydroxyamino)carbonyl]propyl}-1,1'-biphenyl-4-carboxamide | 331.3 |
| 222 | 6-bromo-N-{(1S,2R)-2-hydroxy-1-[(hydroxyamino)carbonyl]propyl}pyridine-2-carboxamide | 319.1 |
| 223 | N-{(1S,2R)-2-hydroxy-1-[(hydroxyamino)carbonyl]propyl}-6-phenylpyridine-2-carboxamide | 316.3 |
| 224 | 4'-butyl-N-{(1S,2R)-2-hydroxy-1-[(hydroxyamino)carbonyl]propyl}-1,1'-biphenyl-4-carboxamide | 371.4 |
| 225 | 4'-(1,1-dimethylethyl)-N-{(1S,2R)-2-hydroxy-1-[(hydroxyamino)carbonyl]propyl}-1,1'-biphenyl-4-carboxamide | 371.4 |
| 226 | N-{(1S,2R)-2-hydroxy-1-[(hydroxyamino)carbonyl]propyl}-5-[3-(methyloxy)phenyl]thiophene-2-carboxamide | 351.4 |
| 227 | 4'-[({(1S,2R)-2-hydroxy-1-[(hydroxyamino)carbonyl]propyl}amino)carbonyl]-1,1'-biphenyl-4-yl dihydrogen phosphate | 411.3 |
| 228 | N-ethyl-N'-{(1S,2R)-2-hydroxy-1-[(hydroxyamino)carbonyl]propyl}-1,1'-biphenyl-4,4'-dicarboxamide | 386.4 |
| 229 | N-[(1S,2R)-1-(hydrazinocarbonyl)-2-hydroxypropyl]-4'-propyl-1,1'-biphenyl-4-carboxamide | 356.4 |
| 230 | N-{(1S,2R)-2-hydroxy-1-[(methylamino)carbonyl]propyl}-4'-propyl-1,1'-biphenyl-4-carboxamide | 355.4 |
| 231 | N-[(1S,2R)-1-(hydrazinocarbonyl)-2-hydroxypropyl]-4-(methyloxy)benzamide | 268.3 |
| 232 | (2S,3R)-2-[(1,1'-biphenyl-4-ylsulfonyl)amino]-N,3-dihydroxybutanamide | 351.4 |
| 233 | 4-hydroxy-N-{(1S,2R)-2-hydroxy-1-[(hydroxyamino)carbonyl]propyl}benzamide | 255.2 |
| 234 | 3'-cyano-N-{(1S,2R)-2-hydroxy-1-[(hydroxyamino)carbonyl]propyl}-1,1'-biphenyl-4-carboxamide | 340.3 |
| 235 | 1,1-dimethylethyl({4-[({(1S,2R)-2-hydroxy-1-[(hydroxyamino)carbonyl]propyl}amino)carbonyl]phenyl}oxy)acetate | 369.4 |
| 236 | (2S,3R)-2-[(1,1'-biphenyl-4-ylsulfonyl)(methyl)amino]-N,3-dihydroxybutanamide | 365.4 |
| 237 | N-{(1S,2R)-2-hydroxy-1-[(hydroxyamino)carbonyl]propyl}-3'-[(Z)-(hydroxyimino)methyl]-4'-(methyloxy)-1,1'-biphenyl-4-carboxamide | 388.4 |
| 238 | N-{(1S,2R)-2-hydroxy-1-[(hydroxyamino)carbonyl]propyl}-4-[(phenylcarbonyl)amino]benzamide | 358.4 |
| 239 | N-hydroxy-2-[3-(1-methylethyl)-4-(prop-2-enyloxy)phenyl]-4,5-dihydro-1,3-oxazole-4-carboxamide | 305.3 |
| 240 | 4'-butyl-N-{(1S,2R)-2-hydroxy-1-[(methylamino)carbonyl]propyl}-1,1'-biphenyl-4-carboxamide | 369.5 |
| 241 | N-{(1S,2R)-2-hydroxy-1-[(hydroxyamino)carbonyl]propyl}-4-(5-methylpyridin-2-yl)benzamide | 330.4 |
| 242 | 5-bromo-N-{(1S,2R)-2-hydroxy-1-[(hydroxyamino)carbonyl]propyl}pyridine-3-carboxamide | 319.1 |
| 243 | N-{(1S,2R)-2-hydroxy-1-[(hydroxyamino)carbonyl]propyl}-4-pyridin-3-ylbenzamide | 316.3 |
| 244 | N-{(1R,2R)-2-hydroxy-1-[(hydroxyamino)carbonyl]propyl}-N'-{(1S,2R)-2-hydroxy-1-[(hydroxyamino)carbonyl]propyl}-1,1'-biphenyl-4,4'-dicarboxamide | 475.5 |
| 245 | (2S,3R)-N,3-dihydroxy-2-[({4-[(E)-2-phenylethenyl]phenyl}methyl)amino]butanamide | 327.4 |

TABLE 1-continued

| | | |
|---|---|---|
| 246 | 4-{[(4-bromophenyl)sulfonyl]amino}-N-{(1S,2R)-2-hydroxy-1-[(hydroxyamino)carbonyl]propyl}benzamide | 473.3 |
| 247 | 1,1-dimethylethyl 4-({4-[({(1S,2R)-2-hydroxy-1-[(hydroxyamino)carbonyl]propyl}amino)carbonyl]phenyl}amino)-4-oxobutylcarbamate | 439.5 |
| 248 | 4-[(4-aminobutanoyl)amino]-N-{(1S,2R)-2-hydroxy-1-[(hydroxyamino)carbonyl]propyl}benzamide | 339.4 |
| 249 | 1,1-dimethylethyl{4'-[({(1S,2R)-2-hydroxy-1-[(hydroxyamino)carbonyl]propyl}amino)methyl]-1,1'-biphenyl-4-yl}methylcarbamate | 430.5 |
| 250 | N-{(1S,2R)-2-hydroxy-1-[(hydroxyamino)carbonyl]propyl}-4-pyrimidin 5-ylbenzamide | 317.3 |
| 251 | 1,1-dimethylethyl 5-{4-[({(1S,2R)-2-hydroxy-1-[(hydroxyamino)carbonyl]propyl}amino)carbonyl]phenyl}pyridine-3-carboxylate | 416.4 |
| 252 | 5-{4-[({(1S,2R)-2-hydroxy-1-[(hydroxyamino)carbonyl]propyl}amino)carbonyl]phenyl}pyridine-3-carboxylic acid | 360.3 |
| 253 | (4S)-N-hydroxy-2-{4-(methyloxy)-3-[(trifluoromethyl)oxy]phenyl}-4,5-dihydro-1,3-oxazole-4-carboxamide | 321.2 |
| 254 | (2S,3R)-2-({[4'-(aminomethyl)-1,1'-biphenyl-4-yl]methyl}amino)-N,3-dihydroxybutanamide | 330.4 |
| 255 | (3S)-1-hydroxy-3-[(1R)-1-hydroxyethyl]-4-({4-[(E)-2-phenylethenyl]phenyl}methyl)piperazine-2,6-dione | 367.4 |
| 256 | (2S,3R)-N,3-dihydroxy-2-({[4-(phenylethynyl)phenyl]methyl}amino)butanamide | 325.4 |
| 257 | N-(3-aminopropyl)-N'-{(1S,2R)-2-hydroxy-1-[(hydroxyamino)carbonyl]propyl}benzene-1,4-dicarboxamide | 339.4 |
| 258 | N-{(1S,2R)-2-hydroxy-1-[(hydroxyamino)carbonyl]propyl}-4-(propanoylamino)benzamide | 310.3 |
| 259 | 1,1-dimethylethyl 3-[({4-[({(1S,2R)-2-hydroxy-1-[(hydroxyamino)carbonyl]propyl}amino)carbonyl]phenyl}carbonyl)amino]propylcarbamate | 439.5 |
| 260 | N-{(1S,2R)-2-hydroxy-1-[(hydroxyamino)carbonyl]propyl}-4'-(phenyloxy)-1,1'-biphenyl-4-carboxamide | 407.4 |
| 261 | N-[(1S,2R)-1-({[cyano(phenyl)methyl]amino}carbonyl)-2-hydroxypropyl]-4'-hydroxy-1,1'-biphenyl-4-carboxamide | 430.5 |
| 262 | 4'-{[2-(hydroxyamino)-2-oxoethyl]oxy}-N-{(1S,2R)-2-hydroxy-1-[(hydroxyamino)carbonyl]propyl}-1,1'-biphenyl-4-carboxamide | 404.4 |
| 263 | 4'-({[(1S,2R)-1-{[(cyanomethyl)amino]carbonyl}-2-(propanoyloxy)propyl]amino}carbonyl)-1,1'-biphenyl-4-yl propanoate | 466.5 |
| 264 | 4'-({[(1S,2R)-1-{[(cyanomethyl)(propanoyl)amino]carbonyl}-2-(propanoyloxy)propyl]amino}carbonyl)-1,1'-biphenyl-4-yl propanoate | 522.6 |
| 265 | N-((1S,2R)-1-{[(cyanomethyl)amino]carbonyl}-2-hydroxypropyl)-4'-hydroxy-1,1'-biphenyl-4-carboxamide | 354.4 |
| 266 | (2S,3S)-2-[(1,1',-biphenyl-4-ylmethyl)amino]-N,3-dihydroxybutanamide | 301.4 |
| 267 | N-{2-hydroxy-1-[(hydroxyamino)carbonyl]-2-phenylethyl}-1,1'-biphenyl-4-carboxamide | 377.4 |
| 268 | (2S,3R)-2-[(diphenylacetyl)amino]-N,3-dihydroxybutanamide | 329.4 |
| 269 | N-{(1S,2R)-2-hydroxy-1-[(hydroxyamino)carbonyl]propyl}-6-[(phenylmethyl)thio]pyridine-3-carboxamide | 362.4 |
| 270 | N,3-dihydroxy-2-({[4-(phenyloxy)phenyl]methyl}amino)butanamide | 317.4 |
| 271 | N-{(1S,2R)-2-hydroxy-1-[(hydroxyamino)carbonyl]propyl}-2'-[(trifluoromethyl)oxy]-1,1'-biphenyl-4-carboxamide | 399.3 |
| 272 | (2R,3S)-2-[(1,1'-biphenyl-4-ylmethyl)amino]-N,3-dihydroxybutanamide | 301.4 |

TABLE 1-continued

| | | |
|---|---|---|
| 273 | 4-[({(1S,2R)-2-hydroxy-1-[(hydroxyamino)carbonyl]propyl}amino)carbonyl]benzoic acid | 283.3 |
| 274 | 1,1-dimethylethyl 4-[({(1S,2R)-2-hydroxy-1-[(hydroxyamino)carbonyl]propyl}amino)carbonyl]benzoate | 339.4 |
| 275 | (4R)-4-{[(4'-ethyl-1,1'-biphenyl-4-yl)carbonyl]amino}-5-(hydroxyamino)-5-oxopentanoic acid | 371.4 |
| 276 | 4'-ethyl-N-[(1R)-2-(hydroxyamino)-1-(hydroxymethyl)-2-oxoethyl]-1,1'-biphenyl-4-carboxamide | 329.4 |
| 277 | 4'-ethyl-N-[(1S)-2-(hydroxyamino)-1-(hydroxymethyl)-2-oxoethyl]-1,1'-biphenyl-4-carboxamide | 329.4 |
| 278 | (2S)-1-[(4'-ethyl-1,1'-biphenyl-4-yl)carbonyl]-N,4-dihydroxypyrrolidine-2-carboxamide | 355.4 |
| 279 | 4'-ethyl-N-{(1S)-1-[(hydroxyamino)carbonyl]but-3-ynyl}-1,1'-biphenyl-4-carboxamide | 337.4 |
| 280 | N-[(1S)-1-(aminomethyl)-2-(hydroxyamino)-2-oxoethyl]-4'-ethyl-1,1'-biphenyl-4-carboxamide | 328.4 |
| 281 | N-{(1S)-1-[(hydroxyamino)carbonyl]-2-methylpropyl}-1,1'-biphenyl-4-carboxamide | 313.4 |
| 282 | N-{(1S,2R)-2-hydroxy-1-[(hydroxyamino)carbonyl]propyl}-N-methyl 1,1'-biphenyl-4-carboxamide | 329.4 |
| 283 | 4-ethynyl-N-{(1S,2R)-2-hydroxy-1-[(hydroxyamino)carbonyl]propyl}benzamide | 263.3 |
| 284 | 4-(1,3-benzodioxol-5-yl)-N-{(1S,2R)-2-hydroxy-1-[(hydroxyamino)carbonyl]propyl}benzamide | 359.3 |
| 285 | N-{(1R,2S)-2-hydroxy-1-[(hydroxyamino)carbonyl]propyl}-4'-propyl-1,1'-biphenyl-4-carboxamide | 357.4 |
| 286 | 2-({[3'-(ethyloxy)-1,1'-biphenyl-4-yl]methyl}amino)-N,3-dihydroxybutanamide | 345.4 |
| 287 | N-{(1S,2R)-2-hydroxy-1-[(hydroxyamino)carbonyl]propyl}-3',4-bis(methyloxy)-1,1'-biphenyl-4-carboxamide | 375.4 |
| 288 | 3'-formyl-N-{(1S,2R)-2-hydroxy-1-[(hydroxyamino)carbonyl]propyl}-4'-(methyloxy)-1,1'-biphenyl-4-carboxamide | 373.4 |
| 289 | N-{(1S,2R)-2-hydroxy-1-[(hydroxyamino)carbonyl]propyl}-4-(4-{4-[({(1S,2R)-2-hydroxy-1-[(hydroxyamino)carbonyl]propyl}amino)carbonyl]phenyl}buta-1,3-diynyl)benzamide | 523.5 |
| 290 | (2S,3R)-2-({[4'-(ethyloxy)-1,1'-biphenyl-4-yl]methyl}amino)-N,3-dihydroxybutanamide | 345.4 |
| 291 | 3'-chloro-N-{(1S,2R)-2-hydroxy-1-[(hydroxyamino)carbonyl]propyl}-4'-(methyloxy)-1,1'-biphenyl-4-carboxamide | 379.8 |
| 292 | (1R,2R)-N-{(1S,2R)-2-hydroxy-1-[(hydroxyamino)carbonyl]propyl}-2-phenylcyclopropanecarboxamide | 279.3 |
| 293 | N-{(1S,2R)-2-hydroxy-1-[(hydroxyamino)carbonyl]propyl}-4-(1H-pyrrol-1-yl)benzamide | 304.3 |
| 294 | N-{(1S,2R)-2-hydroxy-1-[(hydroxyamino)carbonyl]propyl}-4-propylbenzamide | 281.3 |
| 295 | N-{(1S,2R)-2-hydroxy-1-[(hydroxyamino)carbonyl]propyl}-4-pentylbenzamide | 309.4 |
| 296 | N-{(1S,2R)-2-hydroxy-1-[(hydroxyamino)carbonyl]propyl}-4-octylbenzamide | 351.5 |
| 297 | (2E)-N-{(1S,2R)-2-hydroxy-1-[(hydroxyamino)carbonyl]propyl}-3-(4-methylphenyl)prop-2-enamide | 279.3 |
| 298 | (2E)-N-{(1S,2R)-2-hydroxy-1-[(hydroxyamino)carbonyl]propyl}-3-[4-(trifluoromethyl)phenyl]prop-2-enamide | 333.3 |
| 299 | (2E)-3-(1,1'-biphenyl-4-yl)-N-{(1S,2R)-2-hydroxy-1-[(hydroxyamino)carbonyl]propyl}prop-2-enamide | 329.4 |
| 300 | (2S,3R)-2-[(1,1'-biphenyl-4-ylacetyl)amino]-N,3-dihydroxybutanamide | 358.4 |
| 301 | (2S,3R)-2-{[(2S)-amino-3-(1,1'-biphenyl-4-yl)propanoyl]amino}-N,3-dihydroxybutanamide | 358.4 |

TABLE 1-continued

| | | |
|---|---|---|
| 302 | (2S,3R)-2-{[(2R)-2-amino-3-(1,1'-biphenyl-4-yl)propanoyl]amino}-N,3-dihydroxybutanamide | 310.4 |
| 303 | (3S)-3-amino-N-{(1S,2R)-2-hydroxy-1-[(hydroxyamino)carbonyl]propyl}-5-phenylpentanamide | 344.4 |
| 304 | N-{(1S,2R)-2-hydroxy-1-[(hydroxyamino)carbonyl]propyl}-4-[(phenylamino)methyl]benzamide | 358.4 |
| 305 | N-{(1S,2R)-2-hydroxy-1-[(hydroxyamino)carbonyl]propyl}-4-{[(phenylmethyl)amino]methyl}benzamide | 444.5 |
| 306 | 4'-ethyl-N-{(1S,2R)-2-hydroxy-1-[({(1S,2R)-2-hydroxy-1-[(hydroxyamino)carbonyl]propyl}amino)carbonyl]propyl}-1,1'-biphenyl-4-carboxamide | 430.5 |
| 307 | (2S,3R)-2-[(1,1'-biphenyl-4-ylacetyl)amino]-3-hydroxy-N-{(1S,2R)-2-hydroxy-1-[(hydroxyamino)carbonyl]propyl}butanamide | 355.8 |
| 308 | 4-(4-chlorophenyl)-N-{(1S,2R)-2-hydroxy-1-[(hydroxyamino)carbonyl]propyl}cyclohexanecarboxamide | 305.3 |
| 309 | N-{(1S,2R)-2-hydroxy-1-[(hydroxyamino)carbonyl]propyl}-4-(1H-pyrazol-1-yl)benzamide | 324.3 |
| 310 | N-{(1S,2R)-2-hydroxy-1-[(hydroxyamino)carbonyl]propyl}-4-morpholin-4-ylbenzamide | 323.3 |
| 311 | N-{(1S,2R)-2-hydroxy-1-[(hydroxyamino)carbonyl]propyl}-4-(1,2,3-thiadiazol-4-yl)benzamide | 351.4 |
| 312 | N-{(1S,2R)-2-hydroxy-1-[(hydroxyamino)carbonyl]propyl}-4-[(4-methylpiperazin-1-yl)methyl]benzamide | 319.3 |
| 313 | N-{(1S,2R)-2-hydroxy-1-[(hydroxyamino)carbonyl]propyl}-4-(1H-imidazol-1-ylmethyl)benzamide | 308.3 |
| 314 | (2S,4S)-N-{(1S,2R)-2-hydroxy-1-[(hydroxyamino)carbonyl]propyl}-4-phenylpyrrolidine-2-carboxamide | 394.2 |
| 315 | 4'-bromo-N-{(1S,2R)-2-hydroxy-1-[(hydroxyamino)carbonyl]propyl}-1,1'-biphenyl-4-carboxamide | 394.2 |
| 316 | 4'-bromo-N-{(1S,2R)-2-hydroxy-1-[(hydroxyamino)carbonyl]propyl}-1,1-biphenyl-4-carboxamide | 394.2 |
| 317 | 4'-bromo-N-{(1S,2R)-2-hydroxy-1-[(hydroxyamino)carbonyl]propyl}-1,1'-biphenyl-4-carboxamide | 394.2 |
| 318 | (2R)-2-{[(4'-ethyl-1,1'-biphenyl-4-yl)carbonyl]amino}-N~1~-hydroxypentanediamide | 370.4 |
| 319 | (2S,3S)-1-[(4'-ethyl-1,1'-biphenyl-4-yl)carbonyl]-3-hydroxypyrrolidine-2-carboxylic acid | 340.4 |
| 320 | (2S,3S)-N-[(1,1-dimethylethyl)oxy]-1-[(4'-ethyl-1,1'-biphenyl-4-yl)carbonyl]-3-hydroxypyrrolidine-2-carboxamide | 411.5 |
| 321 | (2S,3S)-1-[(4'-ethyl-1,1'-biphenyl-4-yl)carbonyl]-N,3-dihydroxypyrrolidine-2-carboxamide | 355.4 |
| 322 | N-{(1S,2R)-2-hydroxy-1-[(hydroxyamino)carbonyl]propyl}-4-[(4-nitrophenyl)ethynyl]benzamide | 384.4 |
| 323 | N-{(1S,2R)-2-hydroxy-1-[(hydroxyamino)carbonyl]propyl}-4-{[4-(1H-pyrrol-1-yl)phenyl]ethynyl}benzamide | 404.4 |
| 324 | N-{(1S,2R)-2-hydroxy-1-[(hydroxyamino)carbonyl]propyl}-4'-nitro-1,1'-biphenyl-4-carboxamide | 360.3 |
| 325 | (2S,3R)-N,3-dihydroxy-2-({[4,-(methyloxy)-3'-propyl-1,1'-biphenyl-4-yl]methyl}amino)butanamide | 373.5 |
| 326 | 4'-cyano-N-{(1S,2R)-2-hydroxy-1-[(hydroxyamino)carbonyl]propyl}-1,1'-biphenyl-4-carboxamide | 340.3 |
| 327 | (2S,3R)-2-({[4'-(ethyloxy)-4-(methyloxy)-1,1'-biphenyl-3-yl]methyl}amino)-N,3-dihydroxybutanamide | 375.4 |
| 328 | 2',5'-difluoro-N-{(1S,2R)-2-hydroxy-1-[(hydroxyamino)carbonyl]propyl}-1,1-biphenyl-4-carboxamide | 351.3 |

TABLE 1-continued

| | | |
|---|---|---|
| 329 | N-[(1S)-1-[(acetylamino)methyl]-2-(hydroxyamino)-2-oxoethyl]-4'-ethyl-1,1'-biphenyl-4-carboxamide | 370.4 |
| 330 | N-{(1S)-4-amino-1-[(hydroxyamino)carbonyl]butyl}-4-ethyl-1,1'-biphenyl-4-carboxamide | 356.4 |
| 331 | 4'-ethyl-N-[(1S)-2-(hydroxyamino)-1-(1H-imidazol-5-ylmethyl)-2-oxoethyl]-1,1'-biphenyl-4-carboxamide | 379.4 |
| 332 | (2S,3R)-2-{[1-(1,1'-biphenyl-4-yl)ethyl]amino}-N,3-dihydroxybutanamide | 315.4 |
| 333 | (2S,3R)-2-{[1-(1,1'-biphenyl-4-yl)propyl]amino}-N,3-dihydroxybutanamide | 329.4 |
| 334 | (2S,3R)-2-{[1-(4'-bromo-1,1'-biphenyl-4-yl)ethyl]amino}-N,3-dihydroxybutanamide | 394.3 |
| 335 | (2S,3R)-N,3-dihydroxy-2-{[1-(4,-methyl-1,1'-biphenyl-4-yl)ethyl]amino}butanamide | 329.4 |
| 336 | N-[(S)-1-(aminomethyl)-2-(hydroxyamino)-2-oxoethyl]-1,1'-biphenyl-4-carboxamide | 300.3 |
| 337 | N-[(1S)-1-(aminomethy])-2-(hydroxyamino)-2 oxoethyl]-4-(1H-pyrrol-1-yl)benzamide | 289.3 |
| 338 | N-[(1S)-1-(aminomethyl)-2-(hydroxyamino)-2-oxoethyl]-4-(4-chlorophenyl)cyclohexanecarboxamide | 340.8 |
| 339 | N-[(1S)-1-(aminomethyl)-2-(hydroxyamino)-2 oxoethyl]-4-pentylbenzamide | 294.4 |
| 340 | (2E)-N-[(1S)-1-(aminomethyl)-2-(hydroxyamino)-2-oxoethyl]-3-(1,1'-biphenyl-4-yl)prop-2-enamide | 326.4 |
| 341 | (2S)-3-amino-2-{[(4'-ethyl-1,1'-biphenyl-4-yl)methyl]amino}-N-hydroxypropanamide | 314.4 |
| 342 | (2S)-3-amino-2-[(1,1'-biphenyl-4-ylmethyl)amino]-N-hydroxypropanamide | 286.3 |
| 343 | (2S)-3-amino-2-{[1-(4'-bromo-1,1'-biphenyl-4-yl)ethyl]amino}-N-hydroxypropanamide | 379.3 |
| 344 | (2S)-3-amino-N-hydroxy-2-{[l-(4'-methyl-1,1'-biphenyl-4-yl)ethyl]amino}propanamide | 314.4 |
| 345 | 4'-ethyl-N-[(1S)-2-({(1S,2R)-2-hydroxy-1-[(hydroxyamino)carbonyl]propyl}amino)-1-(hydroxymethyl)-2-oxoethyl]-1,1'-biphenyl-4-carboxamide | 430.5 |
| 346 | 4'-ethyl-N-{(1S)-2-({(1S,2R)-2-hydroxy-1-[(hydroxyamino)carbonyl]propyl}amino)-1-[(4-hydroxyphenyl)methyl]-2-oxoethyl}-1,1'-biphenyl-4-carboxamide | 506.6 |
| 347 | (2S)-2-{[(4'-ethyl-1,1'-biphenyl-4-yl)carbonyl]amino}-N~l~-{(1S,2R)-2-hydroxy-1-[(hydroxyamino)carbonyl]propyl}pentanediamide | 471.5 |
| 348 | (4S)-4-{[(4'-ethyl-1,1'-biphenyl-4-yl)carbonyl]amino}-5-({(1S,2R)-2-hydroxy-1-[(hydroxyamino)carbonyl]propyl}amino)-5-oxopentanoic acid | 472.5 |
| 349 | (3S)-3-{[(4'-ethyl-1,1'-biphenyl-4-yl)carbonyl]amino}-4-({(1S,2R)-2-hydroxy-1-[(hydroxyamino)carbonyl]propyl}amino)-4-oxobutanoic acid | 458.5 |
| 350 | (3S)-2-(1,1'-biphenyl-4-ylacetyl)-N-{(1S,2R)-2-hydroxy-1-[(hydroxyamino)carbonyl]propyl}-1,2,3,4-tetrahydroisoquinoline-3-carboxamide | 488.6 |
| 351 | 4'-ethyl-N-[(1S)-2-({(1S,2R)-2-hydroxy-1-[(hydroxyamino)carbonyl]propyl}amino)-1-methyl-2-oxoethy)]-1,1'-biphenyl-4-carboxamide | 414.5 |
| 352 | (2S,3R)-2-({(2S)-3-amino-2-[(1,1'-biphenyl-4-ylacetyl)amino]propanoyl}amino)-N,3-dihydroxybutanamide | 415.5 |
| 353 | (2S)-2-[(1,1'-biphenyl-4-ylacetyl)amino]-N-{(1S,2R)-2-hydroxy-1-[(hydroxyamino)carbonyl]propyl}pent-4-ynamide | 424.5 |
| 354 | (2S,3R)-2-{[(2S)-2-amino-2-(1,1'-biphenyl-4-yl)ethanoyl]amino}-N,3-dihydroxybutanamide | 344.4 |
| 355 | N-(3-aminopropyl)-4'-ethyl-N-[2-(hydroxyamino)-2-oxoethyl]-1,1'-biphenyl-4-carboxamide | 344.4 |
| 356 | N-(2-cyanoethyl)-4'-ethyl-N-[2-(hydroxyamino)-2-oxoethyl]-1,1'-biphenyl-4-carboxamide | 356.4 |
| 357 | N-[2-(acetylamino)ethyl]-4'-ethyl-N-[2-(hydroxyamino)-2-oxoethyl]-1,1'-biphenyl-4-carboxamide | 352.4 |

TABLE 1-continued

| | | |
|---|---|---|
| 358 | 4'-ethyl-N-[2-(hydroxyamino)-2-oxoethyl]-N-prop-2-ynyl-1,1'-biphenyl-4-carboxamide | 384.4 |
| 359 | 4-cyano-N-{(1S,2R)-2-hydroxy-1-[(hydroxyamino)carbonyl]propyl}benzamide | 337.4 |
| 360 | N-[(1S)-1-(aminomethyl)-2-(hydroxyamino)-2-oxoethyl]-4-cyanobenzamide | 264.3 |
| 361 | N-[(1S)-1-(aminomethyl)-2-(hydroxyamino)-2-oxoethyl]-4-cyanobenzamide | 249.2 |
| 362 | 1,1-dimethylethyl(2S)-2-{[(4-ethynylphenyl)carbonyl]amino}-3-(hydroxyamino)-3-oxopropylcarbamate | 348.4 |
| 363 | 1,1-dimethylethyl(2S)-3-(hydroxyamino)-3-oxo-2-[({4-[(E)-2-phenylethenyl]phenyl}methyl)amino]propylcarbamate | 412.5 |
| 364 | N-{(1R,2S)-2-hydroxy-1-[(hydroxyamino)carbonyl]propyl}-3'-(trifluoromethyl)-1,1'-biphenyl-4-carboxamide | 383.3 |
| 365 | (2S,3R)-2-[(1,1'-biphenyl-4-ylmethyl)amino]-3-hydroxybutanoic acid | 286.3 |
| 366 | N-[(1S)-1-(aminomethyl)-2-(hydroxyamino)-2-oxoethyl]-4-(phenylethynyl)benzamide | 324.4 |
| 367 | 1,1-dimethylethyl(2S)-3-(hydroxyamino)-3-oxo-2-({[4-(phenylethynyl)phenyl]carbonyl}amino)propyl carbamate | 424.5 |
| 368 | N-[(1S)-1-(aminomethyl)-2-(hydroxyamino)-2-oxoethyl]-4-ethynylbenzamide | 248.3 |
| 369 | N-[(1S)-1-(aminomethyl)-2-(hydroxyamino)-2-oxoethyl]-4-ethynylbenzamide | 248.3 |
| 370 | N-{(1S,2R)-2-hydroxy-1-[(hydroxyamino)carbonyl]propyl}-4-{[4-(methyloxy)phenyl]ethynyl}benzamide | 369.4 |
| 371 | (2S)-3-amino-N-hydroxy-2-[({4-[(E)-2-phenylethenyl]phenyl}methyl)amino]propanamide | 312.4 |
| 372 | 1,1-dimethylethyl 2-{4'-[({(1S,2R)-2-hydroxy-1-[(hydroxyamino)carbonyl]propyl}amino)carbonyl-1,1-biphenyl-4-yl]ethylcarbamate | 458.5 |
| 373 | (2S,3R)-N,3-dihydroxy-2-[({4,-[(2-pyrrolidin-1-ylethyl)oxy]-1,1'-biphenyl-4-yl}methyl)amino]butanamide | 414.5 |
| 374 | 1,1-dimethylethyl(1S)-4-({[(1,1-dimethylethyl)oxy]carbonyl}amino)-1-({[4-({4-[({(1S,2R)-2-hydroxy-1-[(hydroxyamino)carbonyl]propyl}amino)carbonyl]phenyl}ethynyl)phenyl]amino}carbonyl)butylcarbarnate | 668.8 |
| 375 | 4-(4-chlorophenyl)-N-[(1S)-2-({(1S,2R)-2-hydroxy-1-[(hydroxyamino)carbonyl]propyl}amino)-1-methyl-2-oxoethyl]cyclohexanecarboxamide | 426.9 |
| 376 | 4'-ethyl-N-[2-({(1S,2R)-2-hydroxy-1-[(hydroxyamino)carbonyl]propyl}amino)-2-oxoethyl]-1,1'-biphenyl-4-carboxamide | 400.4 |
| 377 | 4'-ethyl-N-[3-({(1S)2R)-2-hydroxy-1-[(hydroxyamino)carbonyl]propyl}amino)-3-oxopropyl]-1,1'-biphenyl-4-carboxamide | 414.5 |
| 378 | 4'-ethyl-N-[4-({(1S,2R)-2-hydroxy-1-[(hydroxyamino)carbonyl]propyl}amino)-4-oxobutyl]-1,1'-biphenyl-4-carboxamide | 428.5 |
| 379 | N-((1S)-2-{[(1S)-1-(aminomethyl)-2-(hydroxyamino)-2-oxoethyl]amino}-1-methyl-2-oxoethyl)-4'-ethyl-1,1'-biphenyl-4-carboxamide | 399.5 |
| 380 | N-(2-{[(1S)-1-(aminomethyl)-2-(hydroxyamino)-2-oxoethyl]amino}-2-oxoethyl)-4'-ethyl-1,1'-biphenyl-4-carboxamide | 385.4 |
| 381 | N-(3-{[(1S)-1-(aminomethyl)-2-(hydroxyamino)-2-oxoethyl]amino}-3-oxopropyl)-4'-ethyl-1,1'-biphenyl-4-carboxamide | 399.5 |
| 382 | N-(4-{[(1S)-1-(aminomethyl)-2-(hydroxyamino)-2-oxoethyl]amino}-4-oxobutyl)-4'-ethyl-1,1'-biphenyl-4-carboxamide | 413.5 |
| 383 | 4'-ethyl-N-[l-[(hydroxyamino)carbonyl]-2-(methyloxy)propyl]-1,1'-biphenyl-4-carboxamide | 357.4 |

TABLE 1-continued

| | | |
|---|---|---|
| 384 | 4'-ethyl-N-[(1S,2R)-1-[(hydroxyamino)carbonyl]-2-(methyloxy)propyl]-1,1'-biphenyl-4-carboxamide | 357.4 |
| 385 | N-[1-[(dimethylamino)methyl]-2-(hydroxyamino)-2-oxoethyl]-4'-ethy]-1,1'-biphenyl-4-carboxamide | 356.4 |
| 386 | N-{(1S)-3-cyano-1-[(hydroxyamino)carbonyl]propyl}-4'-ethyl-1,1'-biphenyl-4-carboxamide | 352.4 |
| 387 | N-{(1S)-5-amino-1-[(hydroxyamino)carbonyl]pentyl}-4'-ethyl-1,1'-biphenyl-4-carboxamide | 370.5 |
| 388 | N-{(1S)-3-amino-1-[(hydroxyamino)carbonyl]propyl}-4'-ethyl-1,1'-biphenyl-4-carboxamide | 342.4 |
| 389 | 4'-ethyl-N-hydroxy-1,1'-biphenyl-4-carboxamide | 242.3 |
| 390 | 4'-ethyl-N-{2-hydroxy-1-[(hydroxyamino)carbonyl]-2-methylpropyl}-1,1'-biphenyl-4-carboxamide | 357.4 |
| 391 | N-[(2S)-2-{[(4'-ethyl-1,1'-biphenyl-4-yl)carbonyl]amino}-3-(hydroxyamino)-3-oxopropyl]morpholine-4-carboxamide | 441.5 |
| 392 | N-[(1S)-1-{[(aminocarbonyl)amino]methyl}-2-(hydroxyamino)-2-oxoethyl]-4'-ethyl-1,1'-biphenyl-4-carboxamide | 371.4 |
| 393 | N-[(1S)-1-({[amino(imino)methyl]amino}methyl)-2-(hydroxyamino)-2-oxoethyl]-4'-ethyl-1,1'-biphenyl-4-carboxamide | 370.4 |
| 394 | N-[(2S)-2-amino-3-(hydroxyamino)-3-oxopropyl]-4'-ethyl-1,1'-biphenyl-4-carboxamide | 328.4 |
| 395 | 1-[(4'-ethyl-1,1'-biphenyl-4-yl)carbonyl]-N-hydroxypiperazine-2-carboxamide | 354.4 |
| 396 | N-[(2S)-2-amino-3-(hydroxyamino)-3-oxopropyl]-4-(phenylethynyl)benzamide | 324.4 |
| 397 | N-hydroxy-1-{[4-(phenylethynyl)phenyl]carbonyl}piperazine-2-carboxamide | 350.4 |
| 398 | N-{(1S,2R)-2-hydroxy-1-[(hydroxyamino)carbonyl]propyl}-4-[(4-pentylphenyl)ethynyl]benzamide | 369.4 |
| 399 | N-{(1S,2R)-2-hydroxy-1-[(hydroxyamino)carbonyl]propyl}-4-{[3-(methyloxy)phenyl]ethynyl}benzamide | 371.4 |
| 400 | 4-[(3-fluoro-4-methylphenyl)ethynyl]-N-{(1S,2R)-2-hydroxy-1-[(hydroxyamino)carbonyl]propyl}benzamide | 375.3 |
| 401 | 4-[(2,4-difluorophenyl)ethynyl]-N-{(1S,2R)-2-hydroxy-1-[(hydroxyamino)carbonyl]propyl}benzamide | 363.4 |
| 402 | methyl(2E)-3-(ethylamino)-2-({[4-(phenylethynyl)phenyl]carbonyl}amino)but-2-enoate | 509.6 |
| 403 | 1,1-dimethylethyl 4-{[(2S)-3-(hydroxyamino)-3-oxo-2-({[4-(phenylethynyl)phenyl]carbonyl}amino)propyl]amino}-4-oxobutylcarbamate | 371.4 |
| 404 | N-(1-(N-hydroxycarbamoyl)-2-hydroxy-3-methylbutyl)[4-(4-ethylphenyl)phenyl]carboxamide | 372.4 |
| 405 | N-((1R,2R)-1-{[(aminocarbonyl)(hydroxy)amino]methyl}-2-hydroxypropyl)-4'-ethyl-1,1'-biphenyl-4-carboxamide | 357.4 |
| 406 | 4'-ethy]-N-((1R,2R)-1-{[formyl(hydroxy)amino]methyl}-2-hydroxypropyl)-1,1'-biphenyl-4-carboxamide | 357.4 |
| 407 | N-{(1S,2R)-2-hydroxy-1-[(hydroxyamino)carbonyl]propyl}-4-{[4-(trifluoromethyl)phenyl]ethynyl}benzamide | 407.4 |
| 408 | 1,1-dimethylethyl 2-{[(2S)-3-(hydroxyamino)-3-oxo-2-({[4-(phenylethynyl)phenyl]carbonyl}amino)propyl]amino}-2-oxoethylcarbamate | 481.5 |
| 409 | N-[(S)-1-{[(aminoacetyl)amino]methyl}-2-(hydroxyamino)-2-oxoethyl]-4-(phenylethynyl)benzamide | 381.4 |
| 410 | N-[(1S)-1-{[(4-aminobutanoyl)amino]methyl}-2-(hydroxyamino)-2-oxoethyl]-4-(phenylethynyl)benzamide | 409.5 |

TABLE 1-continued

| | | |
|---|---|---|
| 411 | N-{(1S,2R)-2-hydroxy-1-[(hydroxyamino)carbonyl]propyl}-4-pent-1-ynylbenzamide | 305.3 |
| 412 | N-{(1S,2R)-2-[(1,1-dimethylethyl)oxy]-1-[(hydroxyamino)carbonyl]propyl}-4'-propyl-1,1'-biphenyl-4-carboxamide | 413.5 |
| 413 | 1,1-dimethylethyl (1S)-4-({[(1,1-dimethylethyl)oxy]carbonyl}amino)-1-{[(2-{4'-[({(1S,2R)-2-hydroxy-1-[(hydroxyamino)carbonyl]propyl}amino)carbonyl]-1,1'-biphenyl-4-yl}ethyl)amino]carbonyl}butylcarbamate | 672.8 |
| 414 | 4'-(2-aminoethyl)-N-{(1S, 2R)-2-hydroxy-1-[(hydroxyamino)carbonyl]propyl}-1,1'-biphenyl-4-carboxamide | 358.4 |
| 415 | 4'-(2-{[(2S)-2,5-diaminopentanoyl]amino}ethyl)-N-{(1S,2R)-2-hydroxy-1-[(hydroxyamino)carbonyl]propyl}-1,1'-biphenyl-4-carboxamide | 472.6 |
| 416 | 4-(cyclohex-1-en-1-ylethynyl)-N-{(1S,2R)-2-hydroxy-1-[(hydroxyamino)carbonyl]propyl}benzamide | 319.4 |
| 417 | 4-(3,3-dimethylbut-1-ynyl)-N-{(1S,2R)-2-hydroxy-1-[(hydroxyamino)carbonyl]propyl}benzamide | 728.8 |
| 418 | N-{(1S)- 1-{[(aminoacetyl)amino]methyl}-2-[(2-{[(2S)-3-(hydroxyamino)-3-oxo-2-({[4-(phenylethynyl)phenyl]carbonyl}amino)propyl]amino}-2-oxoethyl)amino]-2-oxoethyl}-4-(phenylethynyl)benzamide | 468.5 |
| 419 | 4-[(4-{[(2S)-2,5-diaminopentanoyl]amino}phenyl)ethynyl]-N-{(1S,2R)-2-hydroxy-1-[(hydroxyamino)carbonyl]propyl}benzamide | 340.4 |
| 420 | 4'-(2-aminoethyl)-N-{(1E)-1-[(hydroxyamino)carbonyl]prop-1-enyl}-1,1'-biphenyl-4-carboxamide | 351.3 |
| 421 | 2',4'-difluoro-N-{(1S,2R)-2-hydroxy-1-[(hydroxyamino)carbonyl]propyl}-1,1'-biphenyl-4-carboxamide | 308.4 |
| 422 | N-[(1E)-1-formylprop-1-enyl]-4'-propyl-1,1'-biphenyl-4-carboxamide | 239.2 |
| 423 | N-hydroxy-4-(pyridin-3-ylethynyl)benzamide | 363.4 |
| 424 | 4-(3-hydroxy-3,5-dimethylhex-1-ynyl)-N-{(1S,2R)-2-hydroxy-1-[(hydroxyamino)carbonyl]propyl}benzamide | 329.4 |
| 426 | 4'-ethyl-N-{(1R,2R)-2-hydroxy-1-[(hydroxyamino)methyl]propyl}-1,1'-biphenyl-4-carboxamide | 419.5 |
| 427 | 4'-ethyl-N-{(1R,2R)-1-[(hydroxyamino)methyl]-2-[(phenylmethyl)oxy]propyl}-1,1'-biphenyl-4-carboxamide | 355.4 |
| 428 | 4'-ethyl-N-[(5R,6R)-3-hydroxy-6-methyl-2-oxo-1,3-oxazinan-5-yl]-1,1'-biphenyl-4-carboxamide | 443.6 |
| 429 | N-((1R,2R)-1-{[({[2-(dimethylamino)ethyl]amino}carbonyl)(hydroxy)amino]methyl}-2-hydroxypropyl)-4'-ethyl-1,1'-biphenyl-4-carboxamide | 425.5 |
| 430 | N-((1R,2R)-1-{[{[(2-cyanoethyl)amino]carbonyl}(hydroxy)amino]methyl}-2-hydroxypropyl)-4'-ethyl-1,1'-biphenyl-4-carboxamide | 497.6 |
| 431 | 4'-ethyl-N-((1R,2R)-2-hydroxy-1-{[hydroxy({[3-(2-oxopyrrolidin-1-yl])propyl]amino}carbonyl)amino]methyl}propyl)-1,1'-biphenyl-4-carboxamide | 557.7 |
| 432 | (1R,2R)-3-[{[(2-cyanoethyl)amino]carbonyl}(hydroxy)amino]-2-{[(4'-ethyl-1,1'-biphenyl-4-yl)carbonyl]amino}-1-methylpropyl 2-cyanoethyl carbamate | 521.6 |
| 433 | N-{(1E)-1-[(E)-(hydroxyimino)methyl]prop-1-enyl}-4'-propyl-1,1'-biphenyl-4-carboxamide | 323.4 |
| 434 | N-{(1S,2R)-2-hydroxy-1-[(hydroxyamino)carbonyl]propyl}-4-(pyridin-3 ylethynyl)benzamide | 340.3 |
| 435 | N-{(1S,2R)-2-hydroxy-1-[(hydroxyamino)carbonyl] propyl}-4-[3 (methylamino)prop-1-ynyl]benzamide | 306.3 |

TABLE 1-continued

| | | |
|---|---|---|
| 436 | N-[(1S)-1-[(dimethylamino)methyl]-2-(hydroxyamino)-2-oxoethyl]-4'-ethyl-1,1'-biphenyl-4-carboxamide | 356.4 |
| 437 | N-[1-(N-hydroxycarbamoylmethyl)(1R,2R)-2-hydroxypropyl][4-(4-ethylphenyl)phenyl]carboxamide | 357.4 |
| 438 | N-[(1S)-1-[(diethylamino)methyl]-2-(hydroxyamino)-2-oxoethyl]-4'-ethyl-1,1'-biphenyl-4-carboxamide | 384.5 |
| 439 | 4-[(3-aminophenyl)ethynyl]-N-{(1S,2R)-2-hydroxy-1-[(hydroxyamino)carbonyl]propyl}benzamide | 354.4 |
| 440 | 4-[3-(dimethylamino)prop-1-ynyl]-N-{(1S,2R)-2-hydroxy-1-[(hydroxyamino)carbonyl]propyl}benzamide | 320.4 |
| 441 | 4-[3-(dimethylamino)prop-1-ynyl]-N-{(1S,2R)-2-hydroxy-1-[(hydroxyamino)carbonyl]propyl}benzamide | 320.4 |
| 442 | 4-({4-[(aminoacetyl)amino]phenyl}ethynyl)-N-{(1S,2R)-2-hydroxy-1-[(hydroxyamino)carbonyl]propyl}benzamide | 411.4 |
| 443 | 3'-fluoro-N-{(1S,2R)-2-hydroxy-1-[(hydroxyamino)carbonyl]propyl}-4'-methyl-1,1'-biphenyl-4-carboxamide | 347.4 |
| 444 | N-[(1S)-1-formyl-2-methylpropyl]-1,1'-biphenyl-4-carboxamide | 282.4 |
| 445 | N-{(1S)-1-[(E)-(hydroxyimino)methyl]-2-methylpropyl}-1,1'-biphenyl-4-carboxamide | 297.4 |
| 446 | N-((1E)-1-{(E)-[(aminocarbonyl)hydrazono]methyl}prop-1-enyl)-4'-propyl-1,1'-biphenyl-4-carboxamide | 365.4 |
| 447 | 4-[(4-aminophenyl)ethynyl]-N-{(1S,2R)-2-hydroxy-1-[(hydroxyamino)carbonyl]propyl}benzamide | 354.4 |
| 448 | 4-{3-(aminomethyl)phenyl]ethynyl}-N-{(1S,2R)-2-hydroxy-1-[(hydroxyamino)carbonyl]propyl}benzamide | 368.4 |
| 449 | N-(2-aminoethyl)-3-({4-[({(1S,2R)-2-hydroxy-1-[(hydroxyamino)carbonyl]propyl}amino)carbonyl]phenyl}ethynyl)benzamide | 425.5 |
| 450 | N-((1S)-1-{(E)-[(aminocarbonyl)hydrazono]methyl}-2-methylpropyl)-1,1'-biphenyl-4-carboxamide | 339.4 |
| 451 | N-{(1S,2R)-2-hydroxy-1-[(hydroxyamino)carbonyl]propyl}-4-{[3-(propanoylamino)phenyl]ethynyl}benzamide | 410.4 |
| 452 | N-{(1S,2R)-2-hydroxy-1-[(hydroxyamino)carbonyl]propyl}-4-{[3-(morpholin-4-ylmethyl)phenyl]ethynyl}benzamide | 438.5 |
| 453 | 4-[3-{[(2-aminoethyl)amino]methyl}phenyl]ethynyl]-N-{(1S,2R)-2-hydroxy-1-[(hydroxyamino)carbonyl]propyl}benzamide | 411.5 |
| 454 | N-[(1R)-2-(hydroxyamino)-1-(hydroxymethyl)-2-oxoethyl]-4'-propyl-1,1'-biphenyl-4-carboxamide | 343.4 |
| 455 | N-[1-(N-hydroxycarbamoylmethyl)(1R,2R)-2-hydroxypropyl][4-(2-phenylethynyl)phenyl]carboxamide | 353.4 |
| 456 | 4'-ethyl-N-[(1R,2R)-1-[(hydroxyamino)carbonyl]-2-(methyloxy)propyl]-1,1'-biphenyl-4-carboxamide | 357.4 |
| 457 | 4'-ethyl-N-[(1S)-1-[(ethylamino)methyl]-2-(hydroxyamino)-2-oxoethyl]-1,1'-biphenyl-4-carboxamide | 356.4 |
| 458 | 4'-ethyl-N-[(1S)-2-(hydroxyamino)-2-oxo-1-({[(2S)-pyrrolidin-2-ylmethyl]amino}methyl)ethyl]-1,1'-biphenyl-4-carboxamide | 411.5 |
| 459 | N-[(1S)-1-[(ethylamino)methyl]-2-(hydroxyamino)-2-oxoethyl]-4-(phenylethynyl)benzamide | 352.4 |
| 460 | N-[(1S)-2-(hydroxyamino)-2-oxo-1-({[(2S)-pyrrolidin-2-ylmethyl]amino}methyl)ethyl]-4-(phenylethynyl)benzamide | 407.5 |
| 461 | 4'-ethyl-N-((1S)-2-(hydroxyamino)-1-{[(1-methylethyl)amino]methyl}-2-oxoethyl)-1,1'-biphenyl-4-carboxamide | 370.5 |
| 462 | 4'-ethyl-N-[(1S)-2-(hydroxyamino)-1-({[2-(methylamino)ethyl]amino}methyl)-2-oxoethyl]-1,1'-biphenyl-4-carboxamide | 385.5 |

TABLE 1-continued

| | | |
|---|---|---|
| 463 | 4'-ethyl-N-((1S)-2-(hydroxyamino)-1-{[(1-methylpiperidin-4-yl)amino]methyl}-2-oxoethyl)-1,1'-biphenyl-4-carboxamide | 425.5 |
| 464 | N-((1S)-2-(hydroxyamino)-1-{[(1-methylethyl)amino]methyl}-2-oxoethyl)-4-(phenylethynyl)benzamide | 366.4 |
| 465 | N-[(1S)-2-(hydroxyamino)-1-({[2-(methylamino)ethyl]amino}methyl)-2-oxoethyl]-4-(phenylethynyl)benzamide | 381.4 |
| 466 | N-((1S)-2-(hydroxyamino)-1-{[(1-methylpiperidin-4-yl)amino]methyl}-2-oxoethyl)-4-(phenylethynyl)benzamide | 421.5 |
| 467 | N-[(1S)-1-{[(2-aminoethyl)amino]methyl}-2-(hydroxyamino)-2-oxoethyl]-4-(phenylethynyl)benzamide | 367.4 |
| 468 | N-[(1S)-1-{[bis(2-aminoethyl)amino]methyl}-2-(hydroxyamino)-2-oxoethyl]-4-(phenylethynyl)benzamide | 410.5 |
| 469 | N-{(1S,2R)-2-hydroxy-1-[(hydroxyamino)carbonyl]propyl}-4-({4-[(morpholin-4-ylacetyl)amino]phenyl}ethynyl)benzamide | 481.5 |
| 470 | N-{(1S,2R)-2-hydroxy-1-[(hydroxyamino)carbonyl]propyl}-4-{[4-(propanoylamino)phenyl]ethynyl}benzamide | 410.4 |
| 471 | N-{(1S,2R)-2-hydroxy-1-[(hydroxyamino)carbonyl]propyl}-4-({4-[(trifluoromethyl)oxy]phenyl}ethynyl)benzamide | 423.4 |
| 472 | 1,1-dimethylethyl (2S)-3-(hydroxyamino)-3-oxo-2-{[(4-{[3-(propanoylamino)phenyl]ethynyl}phenyl)carbonyl]amino}propylcarbamate | 495.5 |
| 473 | 1,1-dimethylethyl (2S)-3-(hydroxyamino)-3-oxo-2-{[(4-pent-1-ynylphenyl)carbonyl]amino}propylcarbamate | 390.4 |
| 474 | N-[(1S)-1-(aminomethyl)-2-(hydroxyamino)-2-oxoethyl]-4-{[3-(propanoylamino)phenyl]ethynyl}benzamide | 395.4 |
| 475 | N-[(1S)-1-(aminomethyl)-2-(hydroxyamino)-2-oxoethyl]-4-pent-1-ynylbenzamide | 290.3 |
| 476 | 4-(phenyloxy)benzaldehyde thiosemicarbazone | 272.3 |
| 477 | 4-(phenyloxy)benzaldehyde semicarbazone | 256.3 |
| 478 | 4-{[3-(trifluoromethyl)phenyl]oxy}benzaldehyde thiosemicarbazone | 340.3 |
| 479 | 4-[(3,4-difluorophenyl)ethynyl]-N-{(1S,2R)-2-hydroxy-1-[(hydroxyamino)carbonyl]propyl}benzamide | 375.3 |
| 480 | 4-[(2,4-dioxo-1,2,3,4-tetrahydropyrimidin-5-yl)ethynyl]-N-{(1S, 2R)-2-hydroxy-1-[(hydroxyamino)carbonyl]propyl}benzamide | 373.3 |
| 481 | N-[(1S)-1-(aminomethyl)-2-(hydroxyamino)-2-oxoethyl]-4-(4-phenylbuta-1,3-diynyl)benzamide | 348.4 |
| 482 | N-[(1S)-1-(aminomethyl)-2-(hydroxyamino)-2-oxoethyl]-4'-propyl-1,1'-biphenyl-4-carboxamide | 342.4 |
| 483 | N-[(1S)-1-(aminomethyl)-2-(hydroxyamino)-2-oxoethyl]-1,1':4',1''-terphenyl-4-carboxamide | 376.4 |
| 484 | N-{(1S,2R)-2-hydroxy-1-[(hydroxyamino)carbonyl]propyl}-1,1':4',1''-terphenyl-4-carboxamide | 391.4 |
| 485 | 1,1-dimethylethyl (2S)-2-[({4-[(4-{[({[(1,1-dimethylethyl)oxy]carbonyl}amino)acetyl]amino}phenyl)ethynyl]phenyl}carbonyl)amino]-3-(hydroxyamino)-3-oxopropylcarbamate | 596.6 |
| 486 | N-[(1S,2R)-1-(hydrazinocarbonyl)-2-hydroxypropyl]-4-(phenylethynyl)benzamide | 338.4 |
| 487 | 2-[(2S,3R)-3-hydroxy-2-({[4-(phenylethynyl)phenyl]carbonyl}amino)butanoyl]hydrazinecarboxamide | 381.4 |
| 488 | N-{(1S,2R)-2-hydroxy-1-[(hydroxyamino)carbonyl]propyl}-4-[(2-methylphenyl)ethynyl]benzamide | 353.4 |
| 489 | N-{(1S,2R)-2-hydroxy-1-[(hydroxyamino)carbonyl]propyl}-4-[(3-hydroxyphenyl)ethynyl]benzamide | 355.4 |
| 490 | 4-({3-[(aminoacetyl)amino]phenyl}ethynyl)-N-{(1S,2R)-2-hydroxy-1-[(hydroxyamino)carbonyl]propyl}benzamide | 411.4 |

TABLE 1-continued

| | | | |
|---|---|---|---|
| 491 | 4-{[4-({[(cyanomethyl)amino]acetyl}amino)phenyl]ethynyl}-N-{(1S,2R)-2-hydroxy-1-[(hydroxyamino)carbonyl]propyl}benzamide | 450.5 |
| 492 | 4'-ethyl-N-{(1S)-2-(hydroxyamino)-2-oxo-1-[(tetrahydro-2H-pyran-4-ylamino)methyl]ethyl}-1,1'-biphenyl-4-carboxamide | 412.5 |
| 493 | N-{(1S)-2-(hydroxyamino)-2-oxo-1-[(tetrahydro-2H-pyran-4-ylamino)methyl]ethyl}-4-(phenylethynyl)benzamide | 408.5 |
| 494 | 4-[(4-chlorophenyl)ethynyl]-N-{(1S,2R)-2-hydroxy-1-[(hydroxyamino)carbonyl]propyl}benzamide | 373.8 |
| 495 | N-{(1S,2R)-2-hydroxy-1-[(hydroxyamino)carbonyl]propyl}-4-[(4-methylphenyl)ethynyl]benzamide | 353.4 |
| 496 | 4-[(2-fluorophenyl)ethynyl]-N-{(1S,2R)-2-hydroxy-1-[(hydroxyamino)carbonyl]propyl}benzamide | 357.4 |
| 497 | 4-[(3-fluorophenyl)ethynyl]-N-{(1S,2R)-2-hydroxy-1-[(hydroxyamino)carbonyl]propyl}benzamide | 357.4 |
| 498 | 4-[(4-fluorophenyl)ethynyl]-N-{(1S,2R)-2-hydroxy-1-[(hydroxyamino)carbonyl]propyl}benzamide | 357.4 |
| 499 | 4-[(4-{[(cyclopropylamino)acetyl]amino}phenyl)ethynyl]-N-{(1S,2R)-2-hydroxy-1-[(hydroxyamino)carbonyl]propyl}benzamide | 451.5 |
| 500 | 4-({4-[({[2-(dimethylamino)ethyl]amino}acetyl)amino]phenyl}ethynyl)-N-{(1S,2R)-2-hydroxy-1-[(hydroxyamino)carbonyl]propyl}benzamide | 482.6 |
| 501 | 4-({4-[({[2-(acetylamino)ethyl]amino}acetyl)amino]phenyl}ethynyl)-N-{(1S,2R)-2-hydroxy-1-[(hydroxyamino)carbonyl]propyl}benzamide | 496.5 |
| 502 | N-{(1S,2R)-2-hydroxy-1-[(hydroxyamino)carbonyl]propyl}-4-({4-[({[3-(2-oxopyrrolidin-1-yl)propyl]amino}acetyl)amino]phenyl}ethynyl)benzamide | 536.6 |
| 503 | N-{(1S,2R)-2-hydroxy-1-[(hydroxyamino)carbonyl]propyl}-4-{[4-({[(pyridin-3-ylmethyl)amino]acetyl}amino)phenyl]ethynyl}benzamide | 502.5 |
| 504 | N-{(1S,2R)-2-hydroxy-1-[(hydroxyamino)carbonyl]propyl}-4-{4-({[(2-pyridin-2-ylethyl)amino]acetyl}amino)phenyl]ethynyl}benzamide | 516.6 |
| 505 | N-{(1S,2R)-2-hydroxy-1-[(hydroxyamino)carbonyl]propyl}-4-[(4-{[(4-methylpiperazin-1-yl)acetyl]amino}phenyl)ethynyl]benzamide | 494.6 |
| 506 | 4-({4-[(1,4'-bipiperidin-1'-ylacetyl)amino]phenyl}ethynyl)-N-{(1S,2R)-2-hydroxy-1-[(hydroxyamino)carbonyl]propyl}benzamide | 562.7 |
| 507 | 1-(2-{[4-({4-[({(1S,2R)-2-hydroxy-1-[(hydroxyamino)carbonyl]propyl}amino)carbonyl]phenyl}ethynyl)phenyl]amino}-2-oxoethyl)piperidine-4-carboxamide | 522.6 |
| 508 | N-{(1S,2R)-2-hydroxy-1-[(hydroxyamino)carbonyl]propyl}-4-[(4-{[(piperidin-3-ylamino)acetyl]amino}phenyl)ethynyl]benzamide | 494.6 |
| 509 | N-{(1S,2R)-2-hydroxy-1-[(hydroxyamino)carbonyl]propyl}-4-[(4-{[(piperidin-4-ylamino)acetyl]amino}phenyl)ethynyl]benzamide | 494.6 |
| 510 | N-{(1S,2R)-2-hydroxy-1-[(hydroxyamino)carbonyl]propyl}-4-{[4-({[(piperidin-2-ylmethyl)amino]acetyl}amino)phenyl]ethynyl}benzamide | 508.6 |

TABLE 1-continued

| | | |
|---|---|---|
| 511 | N-{(1S,2R)-2-hydroxy-1-[(hydroxyamino)carbonyl]propyl}-4-{[4-({[(piperidin-3-ylmethyl)amino]acetyl}amino)phenyl]ethynyl}benzamide | 508.6 |
| 512 | 4-[(4-{[(3-aminopyrrolidin-1-yl)acetyl]amino}phenyl)ethynyl]-N-{(1S,2R)-2-hydroxy-1-[(hydroxyamino)carbonyl]propyl}benzamide | 480.5 |
| 513 | 4-({4-[(azepan-1-ylacetyl)amino]phenyl}ethynyl)-N-{(1S,2R)-2-hydroxy-1-[(hydroxyamino)carbonyl]propyl}benzamide | 493.6 |
| 514 | N-{(1S,2R)-2-hydroxy-1-[(hydroxyamino)carbonyl]propyl}-4-{[4-({[(4-morpholin-4-ylphenyl)amino]acetyl}amino)phenyl]ethynyl}benzamide | 572.6 |
| 515 | N-[(1S)-1-(aminomethyl)-2-(hydroxyamino)-2-oxoethyl]-4-{[4-({[(2-hydroxyethyl)amino]acetyl}amino)phenyl]ethynyl}benzamide | 440.5 |
| 516 | N-[(1S)-1-(aminomethyl)-2-(hydroxyamino)-2-oxoethyl]-4-[4-{[(cyclopropylamino)acetyl]amino}phenyl)ethynyl]benzamide | 436.5 |
| 517 | N-[(1S)-1-(aminomethyl)-2-(hydroxyamino)-2-oxoethyl]-4-({4-[({[3-(2-oxopyrrolidin-1-yl)propyl]amino}acetyl)amino]phenyl}ethynyl)benzamide | 521.6 |
| 518 | N-[(1S)-1-(aminomethyl)-2-(hydroxyamino)-2-oxoethyl]-4-(4-{[[(4-methylpiperazin-1-yl)acetyl]amino}phenyl)ethynyl]benzamide | 479.6 |
| 519 | N-[(1S)-1-(aminomethyl)-2-(hydroxyamino)-2-oxoethyl]-4-{[4-({[(pyridin-3-ylmethyl)amino]acetyl}amino)phenyl]ethynyl}benzamide | 487.5 |
| 520 | N-[(1S)-1-(aminomethyl)-2-(hydroxyamino)-2-oxoethyl]-4-({4-[(piperidin-1-ylacetyl)amino]phenyl}ethynyl)benzamide | 464.5 |
| 521 | 4-{[4-({[(2-hydroxyethyl)amino]acetyl}amino)phenyl]ethynyl}-N-{(1S,2R)-2-hydroxy-1-[(hydroxyamino)carbonyl]propyl}benzamide | 455.5 |
| 522 | N-{(1S,2R)-2-hydroxy-1-[(hydroxyamino)carbonyl]propyl}-4-({4-[({[2-(methyloxy)ethyl]amino}acetyl)amino]phenyl}ethynyl)benzamide | 469.5 |
| 523 | N-{(1S,2R)-2-hydroxy-1-[(hydroxyamino)carbonyl]propyl}-4-({4-[({methyl[2-(methyloxy)ethyl]amino}acetyl)amino]phenyl}ethynyl)benzamide | 483.5 |
| 524 | 4-{[4-({[[2-(dimethylamino)ethyl](methyl)amino]acetyl}amino)phenyl]ethynyl}-N-{(1S)2R)-2-hydroxy-1-[(hydroxyamino)carbonyl]propyl}benzamide | 496.6 |
| 525 | 4-{[4-({[(3R)-3-(dimethylamino)pyrrolidin-1-yl]acetyl}amino)phenyl]ethynyl}-N-{(1S,2R)-2-hydroxy-1-[(hydroxyamino)carbonyl]propyl}benzamide | 508.6 |
| 526 | 4-{[4-({[(3S)-3-(dimethylamino)pyrrolidin-1-yl]acetyl}amino)phenyl]ethynyl}-N-{(1S,2R)-2-hydroxy-1-[(hydroxyamino)carbonyl]propyl}benzamide | 508.6 |
| 527 | 4-{[4-({[(3R)-3-(acetylamino)pyrrolidin-1-yl]acetyl}amino)phenyl]ethynyl}-N-{(1S,2R)-2-hydroxy-1-[(hydroxyamino)carbonyl]propyl}benzamide | 522.6 |
| 528 | 4-{[4-({[(3S)-3-(acetylamino)pyrrolidin-1-yl]acetyl}amino)phenyl]ethynyl}-N-{(1S,2R)-2-hydroxy-1-[(hydroxyamino)carbonyl]propyl}benzamide | 522.6 |
| 529 | 4-{[4-({[(3R)-1-azabicyclo[2.2.2]oct-3-ylamino]acetyl}amino)phenyl]ethynyl}-N-{(1S,2R)-2-hydroxy-1-[(hydroxyamino)carbonyl]propyl}benzamide | 520.6 |
| 530 | 4-{[4-({[(3S)-1-azabicyclo[2.2.2]oct-3-ylamino]acetyl}amino)phenyl]ethynyl}-N-{(1S,2R)-2-hydroxy-1-[(hydroxyamino)carbonyl]propyl}benzamide | 520.6 |

TABLE 1-continued

| | | |
|---|---|---|
| 531 | N-{(1S,2R)-2-hydroxy-1-[(hydroxyamino)carbonyl]propyl}-4-({4-[({[(2R)-pyrrolidin-2-ylmethyl]amino}acetyl)amino]phenyl}ethynyl)benzamide | 494.6 |
| 532 | N-{(1S,2R)-2-hydroxy-1-[(hydroxyamino)carbonyl]propyl}-4-({4-[({[(2S)-pyrrolidin-2-ylmethyl]amino}acetyl)amino]phenyl}ethynyl)benzamide | 494.6 |
| 533 | 4-{4-({[(3-aminocyclohexyl)amino]acetyl}amino)phenyl]ethynyl}-N-{(1S,2R)-2-hydroxy-1-[(hydroxyamino)carbonyl]propyl}benzamide | 508.6 |
| 534 | N-{(1S,2R)-2-hydroxy-1-[(hydroxyamino)carbonyl]propyl}-4-[(4-{[(3-hydroxypiperidin-1-yl)acetyl]amino}phenyl)ethynyl]benzamide | 495.5 |
| 535 | N-{(1S,2R)-2-hydroxy-1-[(hydroxyamino)carbonyl]propyl}-4-{4-({[(3-morpholin-4-ylpropyl)amino]acetyl}amino)phenyl]ethynyl}benzamide | 538.6 |
| 536 | N-{(1S,2R)-2-hydroxy-1-[(hydroxyamino)carbonyl]propyl}-4-{4-({[(2-methylpropyl)amino]acetyl}amino)phenyl]ethynyl}benzamide | 467.5 |
| 537 | 4-[(4-{[(ethylamino)acetyl]amino}phenyl)ethynyl]-N-{(1S,2R)-2-hydroxy-1-[(hydroxyamino)carbonyl]propyl}benzamide | 439.5 |
| 538 | N-{(1S,2R)-2-hydroxy-1-[(hydroxyamino)carbonyl]propyl}-4-({4-[(piperidin-1-ylacetyl)amino]phenyl}ethynyl)benzamide | 479.5 |
| 539 | N-{(1S,2R)-2-hydroxy-1-[(hydroxyamino)carbonyl]propyl}-4-{4-({[(3-hydroxypropyl)amino]acetyl}amino)phenyl]ethynyl}benzamide | 469.5 |
| 540 | N-{(1S,2R)-2-hydroxy-1-[(hydroxyamino)carbonyl]propyl}-4-({4-[({[3-(methyloxy)propyl]amino}acetyl)amino]phenyl}ethynyl)benzamide | 483.5 |
| 541 | 4-{4-({[(2-cyanoethyl)amino]acetyl}amino)phenyl]ethynyl}-N-{(1S,2R)-2-hydroxy-1-[(hydroxyamino)carbonyl]propyl}benzamide | 464.5 |
| 542 | N-{(1S,2R)-2-hydroxy-1-[(hydroxyamino)carbonyl]propyl}-4-{4-({[(2-pyrrolidin-1-ylethyl)amino]acetyl}amino)phenyl]ethynyl}benzamide | 508.6 |
| 543 | N-{(1S,2R)-2-hydroxy-1-[(hydroxyamino)carbonyl]propyl}-4-[(4-{[(2-methyl-1H-imidazol-1-yl)acetyl]amino}phenyl)ethynyl]benzamide | 476.5 |
| 544 | N-[(1S)-1-(aminomethyl)-2-(hydroxyamino)-2-oxoethyl]-4-[(4-{[(methylamino)acetyl]amino}phenyl)ethynyl]benzamide | 410.4 |
| 545 | N-[(1S)-1-(aminomethyl)-2-(hydroxyamino)-2-oxoethyl]-4-{4-({[(2-methylpropyl)amino]acetyl}amino)phenyl]ethynyl}benzamide | 452.5 |
| 546 | N-[(1S)-1-(aminomethyl)-2-(hydroxyamino)-2-oxoethyl]-4-({4-[({[2-(methyloxy)ethyl]amino}acetyl)amino]phenyl}ethynyl)benzamide | 454.5 |
| 547 | N-[(1S)-1-(aminomethyl)-2-(hydroxyamino)-2-oxoethyl]-4-({4-[({methyl[2-(methyloxy)ethyl]amino}acetyl)amino]phenyl}ethynyl)benzamide | 468.5 |
| 548 | N-[(1S)-1-(aminomethyl)-2-(hydroxyamino)-2-oxoethyl]-4-{4-({[(3-hydroxypropyl)amino]acetyl}amino)phenyl]ethynyl}benzamide | 454.5 |
| 549 | N-[(1S)-1-(aminomethyl)-2-(hydroxyamino)-2-oxoethyl]-4-({4-[({[3-(methyloxy)propyl]amino}acetyl)amino]phenyl}ethynyl)benzamide | 467.5 |

TABLE 1-continued

| | | |
|---|---|---|
| 550 | N-[(1S)-1-(aminomethyl)-2-(hydroxyamino)-2-oxoethyl]-4-({4-[({2-(dimethylamino)ethyl]amino}acetyl)amino]phenyl}ethynyl)benzamide | 481.6 |
| 551 | N-[(1S)-1-(aminomethyl)-2-(hydroxyamino)-2-oxoethyl]-4-{[4-({[[2-(dimethylamino)ethyl](methyl)amino]acetyl}amino)phenyl]ethynyl}benzamide | 481.5 |
| 552 | 4-({4-[({[2-(acetylamino)ethyl]amino}acetyl)amino]phenyl}ethynyl)-N-[(1S)-1-(aminomethyl)-2-(hydroxyamino)-2-oxoethyl]benzamide | 449.5 |
| 553 | N-[(1S)-1-(aminomethyl)-2-(hydroxyamino)-2-oxoethyl]-4-{[4-({[[(2-cyanoethyl)amino]acetyl}amino)phenyl]ethynyl}benzamide | 493.6 |
| 554 | N-[(1S)-1-(aminomethyl)-2-(hydroxyamino)-2-oxoethyl]-4-{[4-({[[(2-pyrrolidin-1-ylethyl)amino]acetyl}amino)phenyl]ethynyl}benzamide | 495.6 |
| 556 | N-[(1S)-1-(aminomethyl)-2-(hydroxyamino)-2-oxoethyl]-4-({4-[({[4-(dimethylamino)butyl]amino}acetyl])amino]phenyl}ethynyl)benzamide | 466.5 |
| 557 | N-[(1S)-1-(aminomethyl)-2-(hydroxyamino)-2-oxoethyl]-4-({4-[(azepan-1-ylacetyl)amino]phenyl}ethynyl)benzamide | 478.6 |
| 558 | N-[(1S)-1-(aminomethyl)-2-(hydroxyamino)-2-oxoethyl]-4-({4-[(pyrrolidin-1-ylacetyl)amino]phenyl}ethynyl)benzamide | 450.5 |
| 559 | 1-{2-[(4-{[4-({[(1S)-1-(aminomethy))-2-(hydroxyamino)-2-oxoethyl]amino}carbonyl)phenyl]ethynyl}phenyl)amino]-2-oxoethyl}piperidine-4-carboxamide | 507.6 |
| 560 | 4-{[4-({[(3R)-3-(acetylamino)pyrrolidin-1-yl]acetyl}amino)phenyl]ethynyl}-N-[(1S)-1-(aminomethyl)-2-(hydroxyamino)-2-oxoethyl]benzamide | 507.6 |
| 561 | N-[(1S)-1-(aminomethyl)-2-(hydroxyamino)-2-oxoethyl]-4-{[4-({[(3R)-3-(dimethylamino)pyrrolidin-1-yl]acetyl}amino)phenyl]ethynyl}benzamide | 493.6 |
| 562 | N-[(1S)-1-(aminomethyl)-2-(hydroxyamino)-2-oxoethyl]-4-[(4-{[(3-aminopyrrolidin-1-yl)acetyl]amino}phenyl)ethynyl]benzamide | 465.5 |
| 563 | N-[(1S)-1-(aminomethyl)-2-(hydroxyamino)-2-oxoethyl]-4-[(4-{[(piperidin-3-ylamino)acetyl]amino}phenyl)ethynyl]benzamide | 479.6 |
| 564 | N-[(1S)-1-(aminomethyl)-2-(hydroxyamino)-2-oxoethyl]-4-[(4-{[(piperidin-4-ylamino)acetyl]amino}phenyl)ethynyl]benzamide | 479.6 |
| 565 | N-[(1S)-1-(aminomethyl)-2-(hydroxyamino)-2-oxoethyl]-4-{[4-({[(piperidin-2-ylmethyl)amino]acetyl}amino)phenyl]ethynyl}benzamide | 493.6 |
| 566 | N-[(1S)-1-(aminomethyl)-2-(hydroxyamino)-2-oxoethyl]-4-{[4-({[(piperidin-3-ylmethyl)amino]acetyl}amino)phenyl]ethynyl}benzamide | 493.6 |
| 567 | N-[(1S)-1-(aminomethyl)-2-(hydroxyamino)-2-oxoethyl]-4-{[4-({[(pyridin-2-ylmethyl)amino]acetyl}amino)phenyl]ethynyl}benzamide | 487.5 |
| 568 | N-[(1S)-1-(aminomethyl)-2-(hydroxyamino)-2-oxoethyl]-4-{[4-({[(pyridin-4-ylmethyl)amino]acetyl}amino)phenyl]ethynyl}benzamide | 487.5 |
| 569 | N-[(1S)-1-(aminomethyl)-2-(hydroxyamino)-2-oxoethyl]-4-{[4-({[(2-pyridin-2-ylethyl)amino]acetyl}amino)phenyl]ethynyl}benzamide | 501.6 |
| 570 | N-[(1S)-1-(aminomethyl)-2-(hydroxyamino)-2-oxoethyl]-4-{[4-({[(2-pyridin-3-ylethyl)amino]acetyl}amino)phenyl]ethynyl}benzamide | 501.6 |
| 571 | N-[(1S)-1-(aminomethyl)-2-(hydroxyamino)-2-oxoethyl]-4-{[4-({[(2-pyridin-4-ylethyl)amino]acetyl}amino)phenyl]ethynyl}benzamide | 501.6 |

TABLE 1-continued

| | | |
|---|---|---|
| 572 | N-[(1S)-1-(aminomethyl)-2-(hydroxyamino)-2-oxoethyl]-4-[(4-{[(phenylamino)acetyl]amino}phenyl)ethynyl]benzamide | 472.5 |
| 573 | N-[(1S)-1-(aminomethyl)-2-(hydroxyamino)-2-oxoethyl]-4-{[4-({[(phenylmethyl)amino]acetyl}amino)phenyl]ethynyl}benzamide | 486.5 |
| 574 | N-[(1S)-1-(aminomethyl)-2-(hydroxyamino)-2-oxoethyl]-4-{[4-({[(2-phenylethyl)amino]acetyl}amino)phenyl]ethynyl]benzamide | 500.6 |
| 575 | N-[(1S)-1-(aminomethyl)-2-(hydroxyamino)-2-oxoethyl]-4-({4-[(1H-imidazol-1-ylacetyl)amino]phenyl}ethynyl)benzamide | 447.5 |
| 576 | N-{(1S,2R)-2-hydroxy-1-[(hydroxyamino)carbonyl]propyl}-4-({4-[(1H-imidazol-1-ylacetyl)amino]phenyl}ethynyl)benzamide | 462.5 |
| 577 | N-{(1S,2R)-2-hydroxy-1-[(hydroxyamino)carbonyl]propyl}-4-[(4-{[(phenylamino)acetyl]amino}phenyl)ethynyl]benzamide | 487.5 |
| 578 | N-{1S,2R)-2-hydroxy-1-[(hydroxyamino)carbonyl]propyl}-4-{[4-({[(2-phenylethyl)amino]acetyl}amino)phenyl]ethynyl}benzamide | 515.6 |
| 579 | N-{(1S,2R)-2-hydroxy-1-[(hydroxyamino)carbonyl]propyl}-4-{[4-({[(3-phenylpropyl)amino]acetyl}amino)phenyl]ethynyl}benzamide | 529.6 |
| 580 | 4-[(3-{[(aminoacetyl)amino]methyl}phenyl)ethynyl]-N-{(1S,2R)-2-hydroxy-1-[(hydroxyamino)carbonyl]propyl}benzamide | 425.5 |
| 581 | 4-[(2-aminopyrimidin-5-yl)ethynyl]-N-{(1S,2R)-2-hydroxy-1-[(hydroxyamino)carbonyl]propyl}benzamide | 356.4 |
| 582 | 4-[(4-acetylphenyl)ethynyl]-N-{(1S,2R)-2-hydroxy-1-[(hydroxyamino)carbonyl]propyl}benzamide | 381.4 |
| 583 | N-{(1S,2R)-2-hydroxy-1-[(hydroxyamino)carbonyl]propyl}-4-[(4-{[({2-[4-(phenylmethyl)piperazin-1-yl]ethyl}amino)acetyl]amino}phenyl)ethynyl]benzamide | 613.7 |
| 584 | 4-{[4-({[(aminoacetyl)amino]acetyl}amino)phenyl]ethyny}-N-{(1S,2R)-2-hydroxy-1-[(hydroxyamino)carbonyl]propyl}benzamide | 468.5 |
| 585 | 4-{[4-({[4-(2-hydroxyethyl)piperazin-1-yl]acetyl}amino)phenyl]ethynyl}-N-{(1S,2R)-2-hydroxy-1-[(hydroxyamino)carbonyl]propyl}benzamide | 524.6 |
| 586 | N-{(1S,2R)-2-hydroxy-1-[(hydroxyamino)carbonyl]propyl}-4-({4-[({(3R)-3-[(trifluoroacetyl)amino]pyrrolidin-1-yl}acetyl)amino]phenyl}ethynyl)benzamide | 576.5 |
| 587 | N-{(1S,2R)-2-hydroxy-1-[(hydroxyamino)carbonyl]propyl}-4-[(4-{[(methylamino)acetyl]amino}phenyl)ethynyl]benzamide | 425.5 |
| 588 | N-{(1S,2R)-2-hydroxy-1-[(hydroxyamino)carbonyl]propyl}-4-({4-[(piperazin-1-ylacetyl)amino]phenyl}ethyny)benzamide | 480.5 |
| 589 | N-{(1S,2R)-2-hydroxy-1-[(hydroxyamino)carbonyl]propyl}-4-{[4-({[(pyridin-2-ylmethyl)amino]acetyl}amino)phenyl]ethynyl}benzamide | 502.5 |
| 590 | N-{(1S,2R)-2-hydroxy-1-[(hydroxyamino)carbonyl]propyl}-4-{[4-({[(pyridin-4-ylmethyl)amino]acetyl}amino)phenyl]ethynyl}benzamide | 502.5 |
| 591 | N-{(1S,2R)-2-hydroxy-1-[(hydroxyamino)carbonyl]propyl}-4-{[4-({[(2-pyridin-3-ylethyl)amino]acetyl}amino)phenyl]ethynyl}benzamide | 516.6 |

TABLE 1-continued

| | | |
|---|---|---|
| 592 | N-{(1S,2R)-2-hydroxy-1-[(hydroxyamino)carbonyl]propyl}-4-{[4-({[(2-pyridin-4-ylethyl)amino]acetyl}amino)phenyl]ethynyl}benzamide | 516.6 |
| 593 | 4-({4-[({[(2-fluorophenyl)methyl]amino}acetyl)amino]phenyl}ethynyl)-N-{(1S,2R)-2-hydroxy-1-[(hydroxyamino)carbonyl]propyl}benzamide | 519.5 |
| 594 | 4-({4-[({[(2-chlorophenyl)methyl]amino}acetyl)amino]phenyl}ethynyl)-N-{(1S,2R)-2-hydroxy-1-[(hydroxyamino)carbonyl]propyl}benzamide | 536.0 |
| 595 | N-{(1S,2R)-2-hydroxy-1-[(hydroxyamino)carbonyl]propyl}-4-[(4-{[({[2-(methyloxy)phenyl]methyl}amino)acetyl]amino}phenyl)ethynyl]benzamide | 531.6 |
| 596 | 4-({4-[({[(3-fluorophenyl)methyl]amino}acetyl)amino]phenyl}ethynyl)-N-{(1S,2R)-2-hydroxy-1-[(hydroxyamino)carbonyl]propyl}benzamide | 519.5 |
| 597 | 4-({4-[({[(3-chlorophenyl)methyl]amino}acetyl)amino]phenyl}ethynyl)-N-{(1S,2R)-2-hydroxy-1-[(hydroxyamino)carbonyl]propyl}benzamide | 536.0 |
| 598 | N-{(1S,2R)-2-hydroxy-1-[(hydroxyamino)carbonyl]propyl}-4-[(4-{[({[3-(methyloxy)phenyl]methyl}amino)acetyl]amino}phenyl)ethynyl]benzamide | 531.6 |
| 599 | N-{(1S,2R)-2-hydroxy-1-[(hydroxyamino)carbonyl]propyl}-4-({4-[({[(3-methylpheny])methyl]amino}acetyl)amino]phenyl}ethynyl)benzamide | 515.6 |
| 600 | N-{(1S,2R)-2-hydroxy-1-[(hydroxyamino)carbonyl]propyl}-4-[(4-{[({[3-(trifluoromethyl)phenyl]methyl}amino)acetyl]amino}phenyl)ethynyl]benzamide | 569.5 |
| 601 | N-{(1S,2R)-2-hydroxy-1-[(hydroxyamino)carbonyl]propyl}-4-{[4-({[({3-[(trifluoromethyl)oxy]phenyl}methyl)amino]acetyl}amino)phenyl]ethynyl}benzamide | 585.5 |
| 602 | 4-({4-[({[(4-fluorophenyl)methyl]amino}acetyl)amino]phenyl}ethynyl)-N-{(1S,2R)-2-hydroxy-1-[(hydroxyamino)carbonyl]propyl}benzamide | 519.5 |
| 603 | N-{(1S,2R)-2-hydroxy-1-[(hydroxyamino)carbonyl]propyl}-4-({4-[({[(4 methylphenyl)methyl]amino}acetyl)amino]phenyl}ethynyl)benzamide | 515.6 |
| 604 | N-{(1S,2R)-2-hydroxy-1-[(hydroxyamino)carbonyl]propyl}-4-({4-[({[(4 methylphenyl)methyl]amino}acetyl)amino]phenyl}ethynyl)benzamide | 544.6 |
| 605 | N-{(1S,2R)-2-hydroxy-1-[(hydroxyamino)carbonyl]propyl}-4-[(4-{[({[4 (trifluoromethyl)phenyl]methyl}amino)acetyl]amino}phenyl)ethynyl]benzamide | 569.5 |
| 606 | 4-[(4-{[({[4-fluoro-2-(trifluoromethyl)phenyl]methyl}amino)acetyl]amino}phenyl)ethynyl]-N-{(1S,2R)-2-hydroxy-1-[(hydroxyamino)carbonyl]propyl}benzamide | 587.5 |
| 607 | 4-({4-[({[(2,4-difluorophenyl)methyl]amino}acetyl)amino]phenyl}ethynyl)-N-{(1S,2R)-2-hydroxy-1-[(hydroxyamino)carbonyl]propyl}benzamide | 537.5 |
| 608 | 4-({4-[({[(2,4-dichlorophenyl)methyl]amino}acetyl)amino]phenyl}ethynyl)-N-{(1S,2R)-2-hydroxy-1-[(hydroxyamino)carbonyl]propyl}benzamide | 570.4 |
| 609 | 4-{[4-({[(2-fluorophenyl)amino]acetyl}amino)phenyl]ethynyl}-N-{(1S,2R)-2-hydroxy-1-[(hydroxyamino)carbonyl]propyl}benzamide | 505.5 |
| 610 | 4-{[4-({[(4-fluorophenyl)amino]acetyl}amino)phenyl]ethynyl}-N-{(1S,2R)-2-hydroxy-1-[(hydroxyamino)carbonyl]propyl}benzamide | 505.5 |
| 611 | 4-({4-[({[(3,5-difluorophenyl)methyl]amino}acetyl)amino]phenyl}ethynyl)-N-{(1S,2R)-2-hydroxy-1-[(hydroxyamino)carbonyl]propyl}benzamide | 537.5 |

TABLE 1-continued

| | | |
|---|---|---|
| 612 | 4-{4-({[(4-bromophenyl)amino]acetyl}amino)phenyl]ethynyl}-N-{(1S,2R)-2-hydroxy-1-[(hydroxyamino)carbonyl]propyl}benzamide | 566.4 |
| 613 | 4-({4-[({[4-(dimethylaniino)phenyl]amino}acetyl)amino]phenyl}ethynyl)-N-{(1S,2R)-2-hydroxy-1-[(hydroxyamino)carbonyl]propyl}benzamide | 530.6 |
| 614 | N-[(1S)-1-(aminomethyl)-2-(hydroxyamino)-2-oxoethyl]-4-[(4-{[(2S)-2-aminopropanoyl]amino}phenyl)ethynyl]benzamide | 410.4 |
| 615 | N-[(1S)-1-(aminomethyl)-2-(hydroxyamino)-2-oxoethyl]-4-[(4-{[(2R)-2-aminopropanoyl]amino}phenyl)ethynyl]benzamide | 410.4 |
| 616 | N-[(1S)-1-(aminomethyl)-2-(hydroxyamino)-2-oxoethyl]-4-[(4-{[(2S)-2-amino-4-methylpentanoyl]amino}phenyl)ethynyl]benzamide | 452.5 |
| 617 | 4-[(4-{[(2S,3R)-2-amino-3-hydroxybutanoyl]amino}phenyl)ethynyl]-N-[(1S)-1-(aminomethyl)-2-(hydroxyamino)-2-oxoethyl]benzamide | 440.5 |
| 618 | 4-[(4-{[(2S)-2-amino-4-cyanobutanoyl]amino}phenyl)ethynyl]-N-[(1S)-1-(aminomethyl)-2-(hydroxyamino)-2-oxoethyl]benzamide | 449.5 |
| 619 | N-[(1S)-1-(aminomethyl)-2-(hydroxyamino)-2-oxoethyl]-4-[(4-{[(2S)-2,3-diaminopropanoyl]amino}phenyl)ethynyl]benzamide | 425.5 |
| 620 | (2S)-N-(4-{[4-({[(1S)-1-(aminomethyl)-2-(hydroxyamino)-2-oxoethyl]amino}carbonyl)phenyl]ethynyl}phenyl)pyrrolidine-2-carboxamide | 436.5 |
| 621 | (2S)-N-(4-{[4-({[(1S)-1-(aminomethyi)-2-(hydroxyamino)-2-oxoethyl]amino}carbonyl)phenyl]ethynyl}phenyl)piperidine-2-carboxamide | 450.5 |
| 622 | N-(4-{[4-({[(1S)-1-(aminomethyl)-2-(hydroxyamino)-2-oxoethyl]amino}carbonyl)phenyl]ethynyl}phenyl)piperidine-3-carboxamide | 450.5 |
| 623 | 4-[(4-{[(2S)-2-amino-3-(1H-imidazol-4-yl)propanoyl]amino}phenyl)ethynyl]-N-[(1S)-1-(aminomethyl)-2-(hydroxyamino)-2-oxoethyl]benzamide | 476.5 |
| 624 | N-[(1S)-1-(aminomethyl)-2-(hydroxyamino)-2-oxoethyl]-4-[(4-methylphenyl)ethynyl]benzamide | 338.4 |
| 625 | N-[(1S)-1-(aminomethyl)-2-(hydroxyamino)-2-oxoethyl]-4-[(2-fluorophenyl)ethynyl]benzamide | 342.3 |
| 626 | N-[(1S)-1-(aminomethyl)-2-(hydroxyamino)-2-oxoethyl]-4-[(3-fluorophenyl)ethynyl]benzamide | 342.3 |
| 627 | N-[(1S)-1-(aminomethyl)-2-(hydroxyamino)-2-oxoethyl]-4-[(4-fluorophenyl)ethynyl]benzamide | 342.3 |
| 628 | N-[(1S)-1-(aminomethyl)-2-(hydroxyamino)-2-oxoethyl]-4-[(4-chlorophenyl)ethynyl]benzamide | 358.8 |
| 629 | 4-[(4-{[(2S)-2-amino-4-methylpentanoyl]amino}phenyl)ethynyl]-N-{(1S,2R)-2-hydroxy-1-[(hydroxyamino)carbonyl]propyl}benzamide | 467.5 |
| 630 | 4-[(4-{[(2S)-2-amino-4-cyanobutanoyl]amino}phenyl)ethynyl]-N-{(1S,2R)-2-hydroxy-1-[(hydroxyamino)carbonyl]propyl}benzamide | 464.5 |
| 631 | 4-[(4-{[(2S)-2,3-diaminopropanoyl]amino}phenyl)ethynyl]-N-{(1S,2R)-2-hydroxy-1-[(hydroxyamino)carbonyl]propyl}benzamide | 440.5 |
| 632 | N-[4-({4-[({(1S,2R)-2-hydroxy-1-[(hydroxyamino)carbonyl]propyl}amino)carbonyl]phenyl}ethynyl)phenyl]piperidine-3-carboxamide | 465.5 |
| 633 | N-{(1S,2R)-2-hydroxy-1-[(hydroxyamino)carbonyl]propyl}-4-({3-[(morpholin-4-ylacetyl)amino]phenyl}ethynyl)benzamide | 481.5 |

TABLE 1-continued

| | | |
|---|---|---|
| 634 | N-{(1S,2R)-2-hydroxy-1-[(hydroxyamino)carbonyl]propyl}-4-(pyrazin-2-ylethynyl)benzamide | 341.3 |
| 635 | N-{(1S,2R)-2-hydroxy-1-[(hydroxyamino)carbonyl]propyl}-4-({4-[({3-(1H-imidazol-1-yl)propyl]amino}acetyl)amino]phenyl}ethynyl)benzamide | 519.6 |
| 636 | N-((1S)-2-(hydroxyamino)-1-{[({[3-(1H-imidazol-1-yl)propyl]amino}acetyl)amino]methy]}-2-oxoethyl)-4-(phenylethynyl)benzamide | |
| 637 | 4-({4-[({(1S,2R)-2-hydroxy-1-[(hydroxyamino)carbonyl]propyl}amino)carbonyl]phenyl}ethynyl)benzoic acid | 489.5 |
| 638 | N-(2-{[4-({4-[({(1S,2R)-2-hydroxy-1-[(hydroxyamino)carbonyl]propyl}amino)carbonyl]phenyl}ethynyl)phenyl]amino}-2-oxoethyl)-1,3-benzodioxole-4-carboxamide | 383.4 |
| 639 | 4-({4-[((2R)-2-{[(2R)-2,5-diaminopentanoyl]amino}-4-phenylbutanoyl]amino]phenyl}ethynyl)-N-{(1S,2R)-2-hydroxy-1-[(hydroxyamino)carbonyl]propyl}benzamide | 559.5 |
| 640 | 4-[(4-{[(2R)-2-amino-4-phenylbutanoyl]amino}phenyl)ethynyl]-N-{(1S,2R)-2-hydroxy-1-[(hydroxyamino)carbonyl]propyl}benzamide | 629.7 |
| 641 | 4-[(4-{[(2S)-2-amino-3-phenylpropanoyl]amino}phenyl)ethynyl]-N-{(1S,2R)-2-hydroxy-1-[(hydroxyamino)carbonyl]propyl}benzamide | 515.6 |
| 642 | 4-{[4-({[(2-aminoethyl)amino]acetyl}amino)phenyl]ethynyl}-N-{(1S,2R)-2-hydroxy-1-[(hydroxyamino)carbonyl]propyl}benzamide | 501.6 |
| 643 | N-{(1S)-2-(hydroxyamino)-1-[({[methyl(1-methylpiperidin-4-yl)amino]acetyl}amino)methyl]-2-oxoethyl}-4-(phenylethynyl)benzamide | 492.6 |
| 644 | 4-[(4-{[(cyclobutylamino)acetyl]amino}phenyl)ethynyl]-N-{(1S,2R)-2-hydroxy-1-[(hydroxyamino)carbonyl]propyl}benzamide | 465.5 |
| 645 | 4-[(4-{[(cyclopentylamino)acetyl]amino}phenyl)ethynyl]-N-{(1S,2R)-2-hydroxy-1-[(hydroxyamino)carbonyl]propyl}benzamide | 479.5 |
| 646 | 4-[(4-{[(cyclohexylamino)acetyl]amino}phenyl)ethynyl]-N-{(1S,2R)-2-hydroxy-1-[(hydroxyamino)carbonyl]propyl}benzamide | 493.6 |
| 647 | 4-[(4-{[(cycloheptylamino)acetyl]amino}phenyl)ethynyl]-N-{(1S,2R)-2-hydroxy-1-[(hydroxyamino)carbonyl]propyl}benzamide | 507.6 |
| 648 | 4-[(4-{[(cyclooctylamino)acetyl]amino}phenyl)ethynyl]-N-{(1S,2R)-2-hydroxy-1-[(hydroxyamino)carbonyl]propyl}benzamide | 521.6 |
| 649 | N-{(1S,2R)-2-hydroxy-1-[(hydroxyamino)carbonyl]propyl}-4-[(4-{[(propylamino)acetyl]amino}phenyl)ethynyl]benzamide | 453.5 |
| 650 | 4-[(4-{[(hexylamino)acetyl]amino}phenyl)ethynyl]-N-{(1S,2R)-2-hydroxy-1-[(hydroxyamino)carbonyl]propyl}benzamide | 495.6 |
| 651 | N-{(1S,2R)-2-hydroxy-1-[(hydroxyamino)carbonyl]propy!}-4-{4-({[(1-methylethyl)amino]acetyl}amino)phenyl]ethynyl}benzamide | 453.5 |
| 652 | 4-{[4-({[(1,1-dimethylethyl)amino]acetyl}amino)phenyl]ethyny]}-N-{(1S,2R)-2-hydroxy-1-[(hydroxyamino)carbonyl]propyl}benzamide | 467.5 |
| 653 | 4-{[4-({[ethyl(methyl)amino]acetyl}amino)phenyl]ethynyl}-N-{(1S,2R)-2-hydroxy-1-[(hydroxyamino)carbonyl]propyl}benzamide | 453.5 |

TABLE 1-continued

| | | |
|---|---|---|
| 654 | 4-[(4-{[(diethylamino)acetyl]amino}phenyl)ethynyl]-N-{(1S,2R)-2-hydroxy-1-[(hydroxyamino)carbonyl]propyl}benzamide | 467.5 |
| 655 | 4-{[4-({[(1,1-dimethylethyl)(methyl)amino]acetyl}amino)phenyl]ethynyl}-N-{(1S,2R)-2-hydroxy-1-[(hydroxyamino)carbonyl]propyl}benzamide | 481.6 |
| 656 | 4-{[4-({[cyclohexyl(methyl)amino]acetyl}amino)phenyl]ethynyl}-N-{(1S,2R)-2-hydroxy-1-[(hydroxyamino)carbonyl]propyl}benzamide | 507.6 |
| 657 | 4-{[4-({[bis(1-methylethyl)amino]acetyl}amino)phenyl]ethynyl}-N-{(1S,2R)-2-hydroxy-1-[(hydroxyamino)carbonyl]propyl}benzamide | 495.6 |
| 658 | 4-{[4-({[(cyclohexylmethyl)amino]acetyl}amino)phenyl]ethynyl]}-N-{(1S,2R)-2-hydroxy-1-[(hydroxyamino)carbonyl]propyl}benzamide | 507.6 |
| 659 | 4-{[4-({[(2,3-dimethylcyclohexyl)amino]acetyl}amino)phenyl]ethynyl}-N-{(1S,2R)-2-hydroxy-1-[(hydroxyamino)carbonyl]propyl}benzamide | 521.6 |
| 660 | 4-{[4-({[(1R,2R,4S)-bicyclo[2.2.1]hept-2-ylamino]acetyl}amino)phenyl]ethynyl}-N-{(1S,2R)-2-hydroxy-1-[(hydroxyamino)carbonyl]propyl}benzamide | 505.6 |
| 661 | 4-[(4-{[({[(1S,2R,5S)-6,6-dimethylbicyclo[3.1.1]hept-2-yl]methyl}amino)acetyl]amino}phenyl)ethynyl]-N-{(1S,2R)-2-hydroxy-1-[(hydroxyamino)carbonyl]propyl}benzamide | 547.7 |
| 662 | N-{(1S,2R)-2-hydroxy-1-[(hydroxyamino)carbonyl]propyl}-4-{[4-({[4-(trifluoromethyl)piperidin-1-yl]acetyl}amino)phenyl]ethynyl}benzamide | 547.5 |
| 663 | N-[(1S)-1-(aminomethyl)-2-(hydroxyamino)-2-oxoethyl]-4-({4-[({[(2-fluorophenyl)methyl]amino}acetyl)amino]phenyl}ethynyl)benzamide | 504.5 |
| 664 | N-[(1S)-1-(aminomethyl)-2-(hydroxyamino)-2-oxoethyl]-4-({4-[({[(2-chlorophenyl)methyl]amino}acetyl)amino]phenyl}ethynyl)benzamide | 521.0 |
| 665 | N-[(1S)-1-(aminomethyl)-2-(hydroxyamino)-2-oxoethyl]-4-({4-[({[(2-methylphenyl)methyl]amino}acetyl)amino]phenyl}ethynyl)benzamide | 500.6 |
| 666 | N-[(1S)-1-(aminomethyl)-2-(hydroxyamino)-2-oxoethyl]-4-[(4-{[({[2-(methyloxy)phenyl]methyl}amino)acetyl]amino}phenyl)ethynyl]benzamide | 516.6 |
| 667 | N-[(1S)-1-(aminomethyl)-2-(hydroxyamino)-2-oxoethyl]-4-[(4-{[({[2-(trifluoromethyl)phenyl]methyl}amino)acetyl]amino}phenyl)ethynyl]benzamide | 554.5 |
| 668 | N-[(1S)-1-(aminomethyl)-2-(hydroxyamino)-2-oxoethyl]-4-{[4-({[({2-[(trifluoromethyl)oxy]phenyl}methyl)amino]acetyl}amino)phenyl]ethynyl}benzamide | 570.5 |
| 669 | N-[(1S)-1-(aminomethyl)-2-(hydroxyamino)-2-oxoethyl]-4-({4-[({[(3-fluorophenyl)methyl]amino}acetyl)amino]phenyl}ethynyl)benzamide | 504.5 |
| 670 | N-[(1S)-1-(aminomethyl)-2-(hydroxyamino)-2-oxoethyl]-4-({4-[({[(3-chlorophenyl)methyl]amino}acetyl)amino]phenyl}ethynyl)benzamide | 521.0 |
| 671 | N-[(1S)-1-(aminomethyl)-2-(hydroxyamino)-2-oxoethyl]-4-({4-[({[(3-methylphenyl)methyl]amino}acetyl)amino]phenyl}ethynyl)benzamide | 500.6 |
| 672 | N-[(1S)-1-(aminomethyl)-2-(hydroxyamino)-2-oxoethyl]-4-[(4-{[({[3-(methyloxy)phenyl]methyl}amino)acetyl]amino}phenyl)ethynyl]benzamide | 516.6 |
| 673 | N-[(1S)-1-(aminomethyl)-2-(hydroxyamino)-2-oxoethyl]-4-[(4-{[({[3-(trifluoromethyl)phenyl]methyl}amino)acetyl]amino}phenyl)ethynyl]benzamide | 554.5 |

TABLE 1-continued

| | | |
|---|---|---|
| 674 | N-[(1S)-1-(aminomethyl)-2-(hydroxyamino)-2-oxoethyl]-4-{[4-({[({3-[(trifluoromethyl)oxy]phenyl]methyl)amino]acetyl}amino)phenyl]ethynyl}benzamide | 570.5 |
| 675 | N-[(1S)-1-(aminomethyl)-2-(hydroxyamino)-2-oxoethyl]-4-({4-[({[(4-fluorophenyl)methyl]amino}acetyl)amino]phenyl}ethynyl)benzamide | 504.5 |
| 676 | N-[(1S)-1-(aminomethyl)-2-(hydroxyamino)-2-oxoethyl]-4-({4-[({[(4-chlorophenyl)methyl]amino}acetyl)amino]phenyl}ethyny)benzamide | 521.0 |
| 677 | N-[(1S)-1-(aminomethyl)-2-(hydroxyamino)-2-oxoethyl]-4-({4-[({[(4-methylphenyl)methyl]amino}acetyl)amino]phenyl}ethynyl)benzamide | 500.6 |
| 678 | N-[(1S)-1-(aminomethyl)-2-(hydroxyamino)-2-oxoethyl]-4-[(4-{[({[4-(methyloxy)phenyl]methyl}amino)acetyl]amino}phenyl)ethynyl]benzamide | 516.6 |
| 679 | N-[(1S)-1-(aminomethyl)-2-(hydroxyamino)-2-oxoethyl]-4-[(4-{[({[4-(trifluoromethyl)phenyl]methyl}amino)acetyl]amino}phenyl)ethynyl]benzamide | 554.5 |
| 680 | N-[(1S)-1-(aminomethyl)-2-(hydroxyamino)-2-oxoethyl]-4-[(4-{[({[4-(1,1-dimethylethyl)phenyl]methyl}amino)acetyl]amino}phenyl)ethynyl]benzamide | 542.6 |
| 681 | N-[(1S)-1-(aminomethyl)-2-(hydroxyamino)-2-oxoethyl]-4-({4-[({[(1R)-1-phenylethyl]amino}acetyl)amino]phenyl}ethynyl)benzamide | 500.6 |
| 682 | N-[(1S)-1-(aminomethyl)-2-(hydroxyamino)-2-oxoethyl]-4-({4-[({[(1S)-1-phenylethyl]amino}acetyl)amino]phenyl}ethynyl)benzamide | 500.6 |
| 683 | N-[(1S)-1-(aminomethyl)-2-(hydroxyamino)-2-oxoethyl]-4-{[4-({[(cyclohexylmethyl)amino]acetyl}amino)phenyl]ethynyl}benzamide | 492.6 |
| 684 | N-[(1S)-1-(aminomethyl)-2-(hydroxyamino)-2-oxoethyl]-4-[(4-{[(cyclobutylamino)acetyl]amino}phenyl)ethynyl]benzamide | 450.5 |
| 685 | N-[(1S)-1-(aminomethyl)-2-(hydroxyamino)-2-oxoethyl]-4-[(4-{[(cyclopentylamino)acetyl]amino}phenyl)ethynyl]benzamide | 464.5 |
| 686 | N-[(1S)-1-(aminomethyl)-2-(hydroxyamino)-2-oxoethyl]-4-[(4-{[(cyclohexylamino)acetyl]amino}phenyl)ethynyl]benzamide | 478.6 |
| 687 | N-[(1S)-1-(aminomethyl)-2-(hydroxyamino)-2-oxoethyl]-4-[(4-{[(cycloheptylamino)acetyl]amino}phenyl)ethynyl]benzamide | 492.6 |
| 688 | N-[(1S)-1-(aminomethyl)-2-(hydroxyamino)-2-oxoethyl]-4-[(4-{[(cyclooctyiamino)acetyl]amino}pheny])ethynyl]benzamide | 506.6 |
| 689 | N-[(1S)-1-(aminomethyl)-2-(hydroxyamino)-2-oxoethyl]-4-[(4-{[(ethylamino)acetyl]amino}phenyl)ethynyl]benzamide | 424.6 |
| 690 | N-[(1S)-1-(aminomethyl)-2-(hydroxyamino)-2-oxoethyl]-4-[(4-{[(propylamino)acetyl]amino}phenyl)ethynyl]benzamidc | 438.5 |
| 691 | N-[(1S)-1-(aminomethyl)-2-(hydroxyamino)-2-oxoethyl]-4-[(4-{[(butylamino)acetyl]amino}phenyl)ethynyl]benzamide | 452.5 |
| 692 | N-[(1S)-1-(aminomethyl)-2-(hydroxyamino)-2-oxoethyl]-4-[(4-{[(hexylamino)acetyl]amino}phenyl)ethynyl}benzamide | 480.6 |
| 693 | N-[(1S)-1-(aminomethyl)-2-(hydroxyamino)-2-oxoethyl]-4-{[4-({[(1,1-methylethyl)amino]acetyl}amino)phenyl]ethynyl}benzamide | 438.5 |

TABLE 1-continued

| | | |
|---|---|---|
| 694 | N-[(1S)-1-(aminomethyl)-2-(hydroxyamino)-2-oxoethyl]-4-{[4-({[(1,1-dimethylethyl)amino]acetyl}amino)phenyl]ethynyl}benzamide | 452.5 |
| 695 | N-[(1S)-1-(aminomethyl)-2-(hydroxyamino)-2-oxoethyl]-4-{[4-({[ethyl(methyl)amino]acetyl}amino)phenyl]ethynyl}benzamide | 438.5 |
| 696 | N-[(1S)-1-(aminomethyl)-2-(hydroxyamino)-2-oxoethyl]-4-[(4-{[(diethylamino)acetyl]amino}phenyl)ethynyl]benzamide | 452.5 |
| 697 | N-[(1S)-1-(aminomethyl)-2-(hydroxyamino)-2-oxoethyl]-4-{[4-({[(1,1-dimethylethyl)(methyl)amino]acetyl}amino)phenyl]ethyny]}benzamide | 466.6 |
| 698 | N-[(1S)-1-(aminomethyl)-2-(hydroxyamino)-2-oxoethyl]-4-{[4-({[cyclohexyl(methy))amino]acetyl}amino)phenyl]ethynyl}benzamide | 492.6 |
| 699 | N-[(1S)-1-(aminomethyl)-2-(hydroxyamino)-2-oxoethyl]-4-({4-[({[2-(2-fluorophenyl)ethyl]amino}acetyl)amino]phenyl}ethynyl)benzamide | 518.6 |
| 700 | N-[(1S)-1-(aminomethyl)-2-(hydroxyamino)-2-oxoethyl]-4-({4-[({[2-(3-fluorophenyl)ethyl]amino}acetyl)amino]phenyl}ethynyl)benzamide | 518.6 |
| 701 | N-[(1S)-1-(aminomethyl)-2-(hydroxyamino)-2-oxoethyl]-4-({4-[({[2-(4-fluorophenyl)ethyl]amino}acetyl)amino]phenyl}ethynyl)benzamide | 518.6 |
| 702 | N-[(1S)-1-(aminomethyl)-2-(hydroxyamino)-2-oxoethyl]-4-({4-[({[(1S,2R)-2-phenylcyclopropyl]amino}acetyl)amino]phenyl}ethynyl)benzamide | 512.6 |
| 703 | N-[(1S)-1-(aminomethyl)-2-(hydroxyamino)-2-oxoethyl]-4-({4-[({[(2,4-difluorophenyl])methyl]amino}acetyl)amino]phenyl}ethynyl)benzamide | 522.5 |
| 704 | N-[(1S)-1-(aminomethyl)-2-(hydroxyamino)-2-oxoethyl]-4-({4-[({[(2,4-dichlorophenyl)methyl]amino}acetyl)amino]phenyl}ethynyl)benzamide | 555.4 |
| 705 | N-[(1S)-1-(aminomethyl)-2-(hydroxyamino)-2-oxoethyl]-4-(4-{[({[4-fluoro-2-(trifluoromethyl)phenyl]methyl}amino)acetyl]amino}phenyl)ethynyl]benzamide | 572.5 |
| 706 | N-[(1S)-1-(aminomethyl)-2-(hydroxyamino)-2-oxoethyl]-4-({4-[({[(2,5-difluorophenyl)methyl]amino}acetyl)amino]phenyl}ethynyl)benzamide | 522.5 |
| 707 | N-[(1S)-1-(aminomethyl)-2-(hydroxyamino)-2-oxoethyl]-4-({4-[({[(3,4-difluorophenyl)methyl]amino}acetyl)amino]phenyl}ethynyl)benzamide | 522.5 |
| 708 | N-[(1S)-1-(aminomethyl)-2-(hydroxyamino)-2-oxoethyl]-4-({4-[({[(3,4-dichlorophenyl)methyl]amino}acetyl)amino]phenyl}ethynyl)benzamide | 555.4 |
| 709 | N-[(1S)-1-(aminomethyl)-2-(hydroxyamino)-2-oxoethyl]-4-({4-[({[(3,4-dimethylphenyl)methyl]amino}acety])amino]phenyl}ethynyl)benzamide | 514.6 |
| 710 | N-[(1S)-1-(aminomethyl)-2-(hydroxyamino)-2-oxoethyl]-4-({4-[({[(3,5-difluorophenyl)methyl]amino}acetyl)amino]phenyl}ethynyl)benzamide | 522.5 |
| 711 | N-[(1S)-1-(aminomethyl)-2-(hydroxyamino)-2-oxoethyl]-4-({4-[({[(3,5-dichlorophenyl)methyl]amino}acetyl)amino]phenyl}ethynyl)benzamide | 555.4 |
| 712 | N-[(1S)-1-(aminomethyl)-2-(hydroxyamino)-2-oxoethyl]-4-[(4-{[({[3,5-bis(trifluoromethyl)phenyl]methyl}amino)acetyl]amino}phenyl)ethynyl]benzamide | 622.5 |
| 713 | N-[(1S)-1-(aminomethyl)-2-(hydroxyamino)-2-oxoethyl]-4-({4-[({[(4-nitrophenyl)methyl]amino}acetyl)amino]phenyl}ethynyl)benzamide | 531.5 |

TABLE 1-continued

| | | | |
|---|---|---|---|
| | 714 | N-[(1S)-1-(aminomethyl)-2-(hydroxyamino)-2-oxoethyl]-4-[(4-{[(pyridin-2-ylamino)acetyl]amino}phenyl)ethynyl]benzamide | 473.5 |
| | 715 | N-[(1S)-1-(aminomethyl)-2-(hydroxyamino)-2-oxoethyl]-4-[(4-{[(pyridin-3-ylamino)acetyl]amino}phenyl)ethynyl]benzamide | 473.5 |
| | 716 | N-[(1S)-1-(aminomethyl)-2-(hydroxyamino)-2-oxoethyl]-4-{[4-({[(2-fluorophenyl)amino]acetyl]}amino)phenyl]ethynyl}benzamide | 490.5 |
| | 717 | N-[(1S)-1-(aminomethyl)-2-(hydroxyamino)-2-oxoethyl]-4-{[4-({[(3-fluorophenyl)amino]acetyl}amino)phenyl]ethynyl}benzamide | 490.5 |
| | 718 | N~[(1S)-1-(aminomethyl)-2-(hydroxyamino)-2-oxoethyl]-4-{[4-({[(4-fluorophenyl)amino]acetyl}amino)phenyl]ethynyl}benzamide | 490.5 |
| | 719 | N-[(1S)-1-(aminomethyl)-2-(hydroxyamino)-2-oxoethyl]-4-[(4-{[(pyridin-4-ylamino)acetyl]amino}phenyl)ethynyl]benzamide | 473.5 |
| | 720 | N-[(1S)-1-(aminomethyl)-2-(hydroxyamino)-2-oxoethyl]-4-{[4-({[(2,2,2-trifluoroethyl)amino]acetyl}amino)phenyl]ethynyl}benzamide | 478.4 |
| | 721 | N-{(1S,2R)-2-hydroxy-1-[(hydroxyamino)carbonyl]propyl}-4-[(4-{[(pyridin-2-ylamino)acetyl]amino}phenyl)ethynyl]benzamide | 488.5 |
| | 722 | N-{(1S,2R)-2-hydroxy-1-[(hydroxyamino)carbonyl]propyl}-4-[(4-{[(pyridin-3-ylamino)acetyl]amino}phenyl)ethynyl]benzamide | 488.5 |
| | 723 | N-{(1S,2R)-2-hydroxy-1-[(hydroxyamino)carbonyl]propyl}-4-[(4-{[(pyridin-4-ylamino)acetyl]amino}phenyl)ethynyl]benzamide | 488.5 |
| | 724 | N-{(1S,2R)-2-hydroxy-1-[(hydroxyamino)carbonyl]propyl}-4-[(4-{[(4-phenylpiperazin-1-yl)acetyl]amino}phenyl)ethynyl]benzamide | 556.6 |
| | 725 | 4-{[4-({[4-(4-fluorophenyl)piperazin-1-yl]acetyl}amino)phenyl]ethynyl}-N-{(1S,2R)-2-hydroxy-1-[(hydroxyamino)carbonyl]propyl}benzamide | 574.6 |
| | 726 | 4-{[4-({[(l-acetylpiperidin-4-yl)(cyclopropyl)amino]acetyl}amino)phenyl]ethynyl}-N-{(1S,2R)-2-hydroxy-1-[(hydroxyamino)carbonyl]propyl}benzamide | 576.7 |
| | 727 | 4-[(4-{[(butylamino)acetyl]amino}phenyl)ethynyl]-N-{(1S,2R)-2-hydroxy-1-[(hydroxyamino)carbonyl]propyl}benzamide | 467.5 |
| | 728 | N-{(1S,2R)-2-hydroxy-1-[(hydroxyamino)carbonyl]propyl}-4-({4-[({[(1R)-1-phenylethyl]amino}acetyl)amino]phenyl}ethynyl)benzamide | 515.6 |
| | 729 | N-{(1S,2R)-2-hydroxy-1-[(hydroxyamino)carbonyl]propyl}-4-({4-[({[(1S)-1-phenylethyl]amino}acetyl)amino]phenyl}ethynyl)benzamide | 515.6 |
| | 730 | 4-{[4-({[cyclopropyl(methyl)amino]acetyl}amino)phenyl]ethynyl}-N-{(1S,2R)-2-hydroxy-1-[(hydroxyamino)carbonyl]propyl}benzamide | 465.5 |
| | 731 | N-{(1S,2R)-2-hydroxy-1-[(hydroxyamino)carbonyl]propyl}-4-[4-({[methyl(phenylmethyl)amino]acetyl}amino)phenyl]ethynyl]benzamide | 515.6 |
| | 732 | N-[(1S)-1-(aminomethyl)-2-(hydroxyamino)-2-oxoethyl]-4-{[4-({[cyclopropyl(methyl)amino]acetyl}amino)phenyl]ethyny]}benzamide | 450.5 |

TABLE 1-continued

| | | |
|---|---|---|
| 733 | 4-[(4-{[(2S)-2-aminopropanoyl]amino}phenyl)ethynyl]-N-{(1S,2R)-2-hydroxy-1-[(hydroxyamino)carbonyl]propyl}benzamide | 425.5 |
| 734 | 4-[(4-{[(2R)-2-aminopropanoyl]amino}phenyl)ethynyl]-N-{(1S,2R)-2-hydroxy-1-[(hydroxyamino)carbonyl]propyl}benzamide | 425.5 |
| 735 | 4-[(4-{[(2S)-2-amino-3-methylbutanoyl]amino}phenyl)ethynyl]-N-{(1S,2R)-2-hydroxy-1-[(hydroxyamino)carbonyl]propyl}benzamide | 453.5 |
| 736 | 4-[(4-{[(2S,3R)-2-amino-3-hydroxybutanoyl]amino}phenyl)ethynyl]-N-{(1S,2R)-2-hydroxy-1-[(hydroxyamino)carbonyl]propyl}benzamide | 455.5 |
| 737 | (2S)-N-[4-({4-[({(1S,2R)-2-hydroxy-1-[(hydroxyamino)carbonyl]propyl}amino)carbonyl]phenyl}ethynyl)phenyl]pyrrolidine-2-carboxamide | 451.5 |
| 738 | 4-[(4-{[(2S)-2-amino-3-(1H-imidazol-4-yl)propanoyl]amino}phenyl)ethynyl]-N-{(1S,2R)-2-hydroxy-1-[(hydroxyamino)carbonyl]propyl}benzamide | 491.5 |
| 739 | N-{(1S,2R)-2-hydroxy-1-[(hydroxyamino)carbonyl]propyl}-4-[(4-{[(methyloxy)acetyl]amino}phenyl)ethynyl]benzamide | 426.4 |
| 740 | 4-[(4-{[(2S)-2-amino-3-methylbutanoyl]amino}phenyl)ethynyl]-N-[(1S)-1-(aminomethyl)-2-(hydroxyamino)-2-oxoethyl]benzamide | 438.5 |
| 741 | N-[(1S)-1-(aminomethyl)-2-(hydroxyamino)-2-oxoethyl]-4-{[4-({[(3-phenylpropyl)amino]acetyl}amino)phenyl]ethynyl}benzamide | 514.6 |
| 742 | N-{(1S,2R)-2-hydroxy-1-[(hydroxyamino)carbonyl]propyl}-4-(thien-2-ylethynyl)benzamide | 345.4 |
| 743 | 4-({4-[((2S)-2-{[(2S)-2,5-diaminopentanoyl]amino}-3-phenylpropanoyl)amino]phenyl}ethynyl)-N-{(1S,2R)-2-hydroxy-1-[(hydroxyamino)carbonyl]propyl}benzamide | 615.7 |
| 744 | 3,4-dihydroxy-N-[(2S)-3-(hydroxyamino)-3-oxo-2-({[4-(phenylethynyl)phenyl]carbonyl}amino)propyl]benzamide | 460.5 |
| 745 | 1,1-dimethylethyl 3-[(2-{[(2S)-3-(hydroxyamino)-3-oxo-2-({[4-(phenylethynyl)phenyl]carbonyl}amino)propyl]amino}-2-oxoethyl)amino]propylcarbamate | 538.6 |
| 746 | N-[(1S)-2-(hydroxyamino)-1-({[(4-methylpiperazin-1-yl)acetyl]amino}methyl)-2-oxoethyl]-4-(phenylethynyl)benzamide | 464.5 |
| 747 | 4-{[4-({2-[(2-aminoethyl)amino]-2-oxoethyl}oxy)phenyl]ethynyl}-N-{(1S,2R)-2-hydroxy-1-[(hydroxyamino)carbonyl]propyl}benzamide | 455.5 |
| 748 | N-[(1S)-1-(aminomethyl)-2-(hydroxyamino)-2-oxoethyl]-4-{[3-(aminomethyl)phenyl]ethynyl}benzamide | 353.4 |
| 749 | 1,1-dimethylethyl (2S)-3-(hydroxyamino)-2-[({4-[(4-{2-(hydroxyamino)-2-oxoethyl]oxy}phenyl)ethynyl]phenyl}carbonyl)amino]-3-oxopropylcarbamate | 513.5 |
| 750 | N-[(1S)-1-(aminomethyl)-2-(hydroxyamino)-2-oxoethyl]-4-[(4-{[2-(hydroxyamino)-2-oxoethyl]oxy}phenyl)ethynyl]benzamide | 413.4 |
| 751 | 3,4-dihydroxy-N-(2-{[4-({4-[({(1S,2R)-2-hydroxy-1-[(hydroxyamino)carbonyl]propyl}amino)carbonyl]phenyl}ethynyl)phenyl]amino}-2-oxoethyl)benzamide | 547.5 |
| 752 | 4-({4-[({[(2S)-2,5-diaminopentanoyl]amino}acetyl)amino]phenyl}ethynyl)-N-(1S,2R)-2-hydroxy-1-[(hydroxyamino)carbonyl]propyl}benzamide | 525.6 |
| 753 | 4-[(4-{[(2-aminoethyl)amino]carbonyl}phenyl)ethynyl]-N-{(1S,2R)-2-hydroxy-1-[(hydroxyamino)carbonyl]propyl}benzamide | 425.5 |

TABLE 1-continued

| | | |
|---|---|---|
| 754 | N-[(1S)-1-[({[(3-aminopropyl)amino]acetyl}amino)methyl]-2-(hydroxyamino)-2-oxoethyl]-4-(phenylethynyl)benzamide | 438.5 |
| 755 | 3-({4-[({(1S,2R)-2-hydroxy-1-[(hydroxyamino)carbonyl]propyl}amino)carbonyl]phenyl}ethynyl)benzoic acid | 383.4 |
| 756 | 4-{[4-({[(3-aminopropyl)amino]acetyl}amino)phenyl]ethynyl}-N-{(1S,2R)-2-hydroxy-1-[(hydroxyamino)carbonyl]propyl}benzamide | 468.5 |
| 757 | N-[(1S)-1-(aminomethyl)-2-(hydroxyamino)-2-oxoethyl]-4-(pyrazin-2-ylethynyl)benzamide | 326.3 |
| 758 | 4-({3-[(4-aminobutanoyl)amino]phenyl}-ethynyl)-N-[(1S)-1-(aminomethyl)-2-(hydroxyamino)-2-oxoethyl]benzamide | 424.5 |
| 759 | N-[(1S)-1-(aminomethyl)-2-(hydroxyamino)-2-oxoethyl]-4-[(4-{[(2S)-2,5-diaminopentanoyl]amino}phenyl)ethynyl]benzamide | 453.5 |
| 760 | 4-({2-[(aminoacetyl)amino]phenyl}ethynyl)-N-[(1S)-1-(aminomethyl)-2-(hydroxyamino)-2-oxoethyl]benzamide | 396.4 |
| 761 | N-[(1S)-1-(aminomethyl)-2-(hydroxyamino)-2-oxoethyl]-4-({4-[2-(ethylamino)-2-oxoethyl]phenyl}ethynyl)benzamide | 409.5 |
| 762 | 4-({4-[(aminoacetyl)amino]-3-methylphenyl}ethyny])-N-[(1S)-1-(aminomethyl)-2-(hydroxyamino)-2-oxoethyl]benzamide | 410.4 |
| 763 | 4-({4-[(aminoacetyl)amino]phenyl}ethynyl)-N-[(1S)-1-(aminomethyl)-2-(hydroxyamino)-2-oxoethyl]-3-fluorobenzamide | 414.4 |
| 764 | N-[(1S)-1-(aminomethyl)-2-(hydroxyamino)-2-oxoethyl]-4-{[4-({[(cyanomethyl)amino]acetyl}amino)phenyl]ethynyl}benzamide | 435.5 |
| 765 | [4-({4-[({(1S,2R)-2-hydroxy-1-[(hydroxyamino)carbonyl]propyl}amino)carbonyl]phenyl}ethynyl)phenyl]acetic acid | 397.4 |
| 766 | 4-amino-2-({[4-({4-[({(1S,2R)-2-hydroxy-1-[(hydroxyamino)carbonyl]propyl}amino)carbonyl]phenyl}ethynyl)phenyl]carbonyl}amino)-4-oxobutanoic acid | 497.5 |
| 767 | 4-amino-2-[({[4-({4-[({(1S,2R)-2-hydroxy-1-[(hydroxyamino)carbonyl]propyl}amino)carbonyl]phenyl}ethynyl)phenyl]oxy}acetyl)amino]-4-oxobutanoic acid | 527.5 |
| 768 | N-((1S)-2-(hydroxyamino)-1-{[(morpholin-4-ylacetyl)amino]methyl}-2-oxoethyl)-4-(phenylethynyl)benzamide | 451.5 |
| 769 | N-[(1S)-1-[({[(2,3-dihydroxypropyl)thio]acetyl}amino)methyl]-2-(hydroxyamino)-2-oxoethyl]-4-(phenylethynyl)benzamide | 472.5 |
| 770 | methyl (2S)-3-amino-2-({[4-(phenylethynyl)phenyl]carbonyl}amino)propanoate | 323.4 |
| 771 | N-{(1S)-2-(hydroxyamino)-2-oxo-1-[({[(2-phenylethyl)amino]acetyl}amino)methyl]ethyl}-4-(phenylethynyl)benzamide | 485.6 |
| 772 | 4-[(4-{2-[(2-aminoethyl)amino]-2-oxoethyl}phenyl)ethynyl]-N-{(1S,2R)-2-hydroxy-1-[(hydroxyamino)carbonyl]propyl}benzamide | 439.5 |
| 773 | 4-[4-{[(6-aminohexyl)amino]carbonyl}phenyl]ethynyl]-N-{(1S,2R)-2-hydroxy-1-[(hydroxyamino)carbonyl]propyl}benzamide | 481.6 |
| 774 | 4-[4-(4-{[(ethylamino)acetyl]amino}phenyl)buta-1,3-diynyl]-N-{(1S,2R)-2-hydroxy-1-[(hydroxyamino)carbonyl]propyl}benzamide | 463.5 |
| 775 | 4-[4-(4-{[(cyclopropylamino)acetyl]amino}phenyl)buta-1,3-diynyl]-N-{(1S,2R)-2-hydroxy-1-[(hydroxyamino)carbonyl]propyl}benzamide | 475.5 |
| 776 | N-{(1S,2R)-2-hydroxy-1-[(hydroxyamino)carbonyl]propyl}-4-(4-{4-[(piperidin-1-ylacetyl)amino]phenyl}buta-1,3-diynyl)benzamide | 503.6 |

TABLE 1-continued

| | | |
|---|---|---|
| 777 | N-{(1S,2R)-2-hydroxy-1-[(hydroxyamino)carbonyl]propyl}-4-[4-(4-{[(phenylamino)acetyl]amino}phenyl)buta-1,3-diynyl]benzamide | 511.5 |
| 778 | N-{(1S,2R)-2-hydroxy-1-[(hydroxyamino)carbonyl]propyl}-4-{4-[4-({[(phenylmethyl)amino]acetyl}amino)phenyl]buta-1,3-diynyl}benzamide | 525.6 |
| 779 | N-{(1S,2R)-2-amino-1-[(hydroxyamino)carbonyl]propyl}-4'-ethyl-1,1'-biphenyl-4-carboxamide | 342.4 |
| 780 | 4-[(4-{[(dimethylamino)acetyl]amino}phenyl)ethynyl]-N-{(1S,2R)-2-hydroxy-1-[(hydroxyamino)carbonyl]propyl}benzamide | 439.5 |
| 781 | N-{(1S,2R)-2-hydroxy-1-[(hydroxyamino)carbonyl]propyl}-4-({4-[(pyrrolidin-1-ylacetyl)amino]phenyl}ethynyl)benzamide | 465.5 |
| 782 | N-{(1S,2R)-2-hydroxy-1-[(hydroxyamino)carbonyl]propyl}-4-[(4-{[(pentylamino)acetyl]amino}pheny])ethynyl]benzamide | 481.6 |
| 783 | N-{(1S,2R)-2-hydroxy-1-[(hydroxyamino)carbonyl]propyl}-4-{[4-({[(thien-2-ylmethyl)amino]acetyl}amino)phenyl]ethynyl}benzamide | 507.6 |
| 784 | 4-{[4-({[(1H-benzimidazol-2-ylmethyl)amino]acetyl}amino)phenyl]ethynyl}-N-{(1S,2R)-2-hydroxy-1-[(hydroxyamino)carbonyl]propyl}benzamide | 541.6 |
| 785 | 4-{[4-({[(l-benzothien-3-ylmethyl)amino]acetyl}amino)phenyl]ethynyl}-N-{(1S,2R)-2-hydroxy-1-[(hydroxyamino)carbonyl]propyl}benzamide | 557.6 |
| 786 | 4-(4-{4-[({[(2-fluorophenyl)methyl]amino}acetyl)amino]phenyl}buta-1,3-diynyl)-N-{(1S,2R)-2-hydroxy-1-[(hydroxyamino)carbonyl]propyl}benzamide | 543.6 |
| 787 | 4-(4-{4-[({[(3-fluorophenyl)methyl]amino}acetyl)amino]pheny]}buta-1,3-diynyl)-N-{(1S,2R)-2-hydroxy-1-[(hydroxyamino)carbonyl]propyl}benzamide | 543.6 |
| 788 | 4-(4-{4-[({[(4-fluorophenyl)methyl]amino}acetyl)amino]phenyl}buta-1,3-diynyl)-N-{(1S,2R)-2-hydroxy-1-[(hydroxyamino)carbonyl]propyl}benzamide | 543.6 |
| 789 | N-{(1S,2R)-2-hydroxy-1-[(hydroxyamino)carbonyl]propyl}-4-(4-{4-[({[(2-methylphenyl)methyl]amino}acetyl)amino]phenyl}buta-1,3-diynyl)benzamide | 539.6 |
| 790 | N-{(1S,2R)-2-hydroxy-1-[(hydroxyamino)carbonyl]propyl}-4-(4-{4-[({[(3-methylphenyl)methyl]amino}acetyl)amino]phenyl}buta-1,3-diynyl)benzamide | 539.6 |
| 791 | N-{(1S,2R)-2-hydroxy-1-[(hydroxyamino)carbonyl]propyl}-4-(4-{4-[({[(4-methylphenyl)methyl]amino}acetyl)amino]phenyl}buta-1,3-diynyl)benzamide | 539.6 |
| 792 | N-{(1S,2R)-2-hydroxy-1-[(hydroxyamino)carbonyl]propy)}-4-{4-[4-({[(pyridin-2-ylmethyl)amino]acetyl}amino)phenyl]buta-1,3-diynyl}benzamide | 526.6 |
| 793 | N-{(1S,2R)-2-hydroxy-1-[(hydroxyamino)carbonyl]propyl}-4-{4-[4-({[(pyridin-3-ylmethyi)amino]acetyl}amino)phenyl]buta-l,3 diynyl}benzamide | 526.6 |
| 794 | N-{(1S,2R)-2-hydroxy-1-[(hydroxyamino)carbonyl]propyl}-4-{4-[4-({[(pyridin-4-ylmethyl)amino]acetyl}amino)phenyl]buta-1,3-diynyl}benzamide | 526.6 |
| 795 | N-{(1S,2R)-2-hydroxy-1-[(hydroxyamino)carbonyl]propyl}-4-[4-(4-{[({[2-(methyloxy)phenyl]methyl}amino)acetyl]amino}phenyl)buta-1,3-diynyl]benzamide | 555.6 |

TABLE 1-continued

| | | |
|---|---|---|
| 796 | N-{(1S,2R)-2-hydroxy-1-[(hydroxyamino)carbonyl]propyl}-4-[4-(4-{[({[3-(methyloxy)phenyl]methyl}amino)acetyl]amino}phenyl)buta-1,3-diynyl]benzamide | 555.6 |
| 797 | N-{(1S,2R)-2-hydroxy-1-[(hydroxyamino)carbonyl]propyl}-4-[4-(4-{[({[4-(methyloxy)phenyl]methyl}amino)acetyl]amino}phenyl)buta-1,3-diynyl]benzamide | 555.6 |
| 798 | 4-{4-[4-({[(2-fluorophenyl)amino]acetyl}amino)phenyl]buta-1,3-diynyl}-N-{(1S,2R)-2-hydroxy-1-[(hydroxyamino)carbonyl]propyl}benzamide | 529.5 |
| 799 | 4-{4-[4-({[(3-fluorophenyl)amino]acetyl}amino)phenyl]buta-1,3-diynyl}-N-{(1S,2R)-2-hydroxy-1-[(hydroxyamino)carbonyl]propyl}benzamide | 529.5 |
| 800 | 4-{4-[4-({[(4-fluorophenyl)amino]acetyl}amino)phenyl]buta-1,3-diyny}-N-{(1S,2R)-2-hydroxy-1-[(hydroxyamino)carbonyl]propyl}benzamide | 529.5 |
| 801 | N-{(1S,2R)-2-hydroxy-1-[(hydroxyamino)carbonyl]propyl}-4-[4-(4-{[(pyridin-2-ylamino)acetyl]amino}phenyl)buta-1,3-diynyl]benzamide | 512.5 |
| 802 | N-{(1S,2R)-2-hydroxy-1-[(hydroxyamino)carbonyl]propyl}-4-[4-(4-{[(pyridin-3-ylamino)acetyl]amino}pheny])buta-1,3-diynyl]benzamide | 512.5 |
| 803 | N-{(1S,2R)-2-hydroxy-1-[(hydroxyamino)carbonyl]propyl}-4-[4-(4-{[(pyridin-4-ylamino)acetyl]amino}phenyl)buta-1,3-diynyl]benzamide | 512.5 |
| 804 | 4-[4-(4-{[(cyclobutylamino)acetyl]amino}phenyl)buta-1,3-diynyl]-N-{(1S,2R)-2-hydroxy-1-[(hydroxyamino)carbonyl]propyl}benzamide | 489.5 |
| 805 | 4-[4-(4-{[(cyclopentylamino)acetyl]amino}phenyl)buta-1,3-diynyl]-N-{(1S,2R)-2-hydroxy-1-[(hydroxyamino)carbonyl]propyl}benzamide | 503.6 |
| 806 | 4-[4-(4-{[(cyclohexylamino)acetyl]amino}phenyl)buta-1,3-diynyl]-N-{1S,2R)-2-hydroxy-1-[(hydroxyamino)carbonyl]propyl}benzamide | 517.6 |
| 807 | 4-[4-(4-{[(cycloheptylamino)acetyl]amino}phenyl)buta-1,3-diynyl]-N-{(1S,2R)-2-hydroxy-1-[(hydroxyamino)carbonyl]propyl}benzamide | 531.6 |
| 808 | N-{(1S,2R)-2-hydroxy-1-[(hydroxyamino)carbonyl]propyl}-4-[4-(4-{[(methylamino)acetyl]amino}phenyl)buta-1,3-diynyl]benzamide | 449.5 |
| 809 | N-{(1S,2R)-2-hydroxy-1-[(hydroxyamino)carbonyl]propyl}-4-[4-(4-{[(propylamino)acetyl]amino}phenyl)buta-1,3-diynyl]benzamide | 477.5 |
| 810 | 4-[4-(4-{[(butylamino)acetyl]amino}phenyl)buta-1,3-diynyl]-N-{(1S,2R)-2-hydroxy-1-[(hydroxyamino)carbonyl]propyl}benzamide | 491.6 |
| 811 | N-{(1S,2R)-2-hydroxy-1-[(hydroxyamino)carbonyl]propyl}-4-[4-(4-{[(pentylamino)acetyl]amino}phenyl)buta-1,3-diynyl]benzamide | 505.6 |
| 812 | 4-[4-(4-{[(hexylamino)acetyl]amino}phenyl)buta-1,3-diynyl]-N-{(1S,2R)-2-hydroxy-1-[(hydroxyamino)carbonyl]propyl}benzamide | 519.6 |
| 813 | 4-{4-[4-({[ethyl(methyl)amino]acetyl}amino)phenyl]buta-1,3-diynyl}-N-{(1S,2R)-2-hydroxy-1-[(hydroxyamino)carbonyl]propyl}benzamide | 477.5 |
| 814 | N-{(1S,2R)-2-hydroxy-1-[(hydroxyamino)carbonyl]propyl}-4-{4-[4-({[(1-methylethyl)amino]acetyl}amino)phenyl]buta-1,3-diynyl}benzamide | 477.5 |

TABLE 1-continued

| | | |
|---|---|---|
| 815 | N-{(1S,2R)-2-hydroxy-1-[(hydroxyamino)carbonyl]propyl}-4-{4-[4-({[(2-methylpropyl)amino]acetyl}amino)phenyl]buta-1,3-diynyl}benzamide | 491.6 |
| 816 | N-{(1S,2R)-2-hydroxy-1-[(hydroxyamino)carbonyl]propyl}-4-{4-[4-({[(2,2,2-trifluoroethyl)amino]acetyl}amino)phenyl]buta-1,3-diynyl}benzamide | 517.5 |
| 817 | 4-{4-[4-({[(2-hydroxyethyl)amino]acetyl}amino)phenyl]buta-1,3-diynyl}-N-{(1S,2R)-2-hydroxy-1-[(hydroxyamino)carbonyl]propyl}benzamide | 479.5 |
| 818 | N-{(1S,2R)-2-hydroxy-1-[(hydroxyamino)carbonyl]propyl}-4-(4-{4-[({[2-(methyloxy)ethyl]amino}acetyl)amino]phenyl}buta-1,3-diynyl)benzamide | 493.5 |
| 819 | 4-(4-{4-[({[2-(dimethylamino)ethyl]amino}acetyl)amino]phenyl}buta-1,3-diynyl)-N-{(1S,2R)-2-hydroxy-1-[(hydroxyamino)carbonyl]propyl}benzamide | 506.6 |
| 820 | 4-{4-[4-({[(2-cyanoethyl)amino]acetyl}amino)phenyl]buta-1,3-diynyl}-N-{(1S,2R)-2-hydroxy-1-[(hydroxyamino)carbonyl]propyl}benzamide | 488.5 |
| 821 | N-{(1S,2R)-2-hydroxy-1-[(hydroxyamino)carbonyl]propyl}-4-(4-{4-[(pyrrolidin-1-ylacetyl)amino]phenyl}buta-1,3-diynyl)benzamide | 489.5 |
| 822 | 4-(4-{4-[(azepan-1-ylacetyl)amino]phenyl}buta-1,3-diynyl)-N-{(1S,2R)-2-hydroxy-1-[(hydroxyamino)carbonyl]propyl}benzamide | 517.6 |
| 823 | N-{(1S,2R)-2-hydroxy-1-[(hydroxyamino)carbonyl]propyl}-4-[4-(4-{[(4-methylpiperazin-1-yl)acetyl]amino}phenyl)buta-1,3-diynyl]benzamide | 518.6 |
| 824 | N-{(1S,2R)-2-hydroxy-1-[(hydroxyamino)carbonyl]propyl}-4-(4-{4-[(morpholin-4-ylacetyl)amino]phenyl}buta-1,3-diynyl)benzamide | 505.5 |
| 825 | 4-{4-[4-({[cyclohexyl(methyl)amino]acetyl}amino)phenyl]buta-1,3-diynyl}-N-{(1S,2R)-2-hydroxy-1-[(hydroxyamino)carbonyl]propyl}benzamide | 531.6 |
| 826 | N-{(1S,2R)-2-hydroxy-1-[(hydroxyamino)carbonyl]propyl}-4-(4-{4-[({[(1R)-1-phenylethyl]amino}acetyl)amino]phenyl}buta-1,3-diynyl)benzamide | 539.6 |
| 827 | N-{(1S,2R)-2-hydroxy-1-[(hydroxyamino)carbonyl]propyl}-4-(4-{4-[({[(1S)-1-phenylethyl]amino}acetyl)amino]phenyl}buta-1,3-diynyl)benzamide | 539.6 |
| 828 | N-{(1S,2R)-2-hydroxy-1-[(hydroxyamino)carbonyl]propyl}-4-{4-[4-({[(2-phenylethyl)amino]acetyl}amino)phenyl]buta-1,3-diynyl}benzamide | 539.6 |
| 829 | N-{(1S,2R)-2-hydroxy-1-[(hydroxyamino)carbonyl]propyl}-4-(4-{4-[(1H-imidazol-1-ylacetyl)amino]phenyl}buta-1,3-diynyl)benzamide | 486.5 |
| 830 | 4-{4-[4-({[(1R,2R,4S)-bicyclo[2.2.1]hept-2-ylamino]acetyl}amino)phenyl]buta-1,3-diynyl}-N-{(1S,2R)-2-hydroxy-1-[(hydroxyamino)carbonyl]propyl}benzamide | 529.6 |
| 831 | 4-{4-[4-[{[(cyclohexylmethyl)amino]acetyl}amino]phenyl]buta-1,3-diynyl}-N-{(1S,2R)-2-hydroxy-1-[(hydroxyamino)carbonyl]propyl}benzamide | 531.6 |
| 832 | N-[(1S)-1-(aminomethyl)-2-(hydroxyamino)-2-oxoethyl]-4'-ethyl-2-fluoro-1,1'-biphenyl-4-carboxamide | 346.4 |
| 833 | 4-({4-[(aminoacetyl)amino]phenyl}ethynyl)-N-{(1S,2R)-2-hydroxy-1-[(hydroxyamino)carbonyl]propyl}-3-(methyloxy)benzamide | 441.5 |

TABLE 1-continued

| | | |
|---|---|---|
| 834 | 4'-ethyl-N-{(1S,2R)-2-hydroxy-1-[(hydroxyamino)carbonyl]propyl}-2-(methyloxy)-1,1'-biphenyl-4-carboxamide | 373.4 |
| 835 | N-{(1S,2R)-2-hydroxy-1-[(hydroxyamino)carbonyl]propyl}-3-(methyloxy)-4-(phenylethynyl)benzamide | 369.4 |
| 836 | 4-[(4-ethylphenyl)ethynyl]-N-{(1S,2R)-2-hydroxy-1-[(hydroxyamino)carbonyl]propyl}benzamide | 367.4 |
| 837 | N-{(1S,2R)-2-hydroxy-1-[(hydroxyamino)carbonyl]propyl}-4-[(4-hydroxyphenyl)ethynyl]benzamide | 355.4 |
| 838 | 2-[(2-{[(2S)-3-(hydroxyamino)-3-oxo-2-({[4-(phenylethynyl)phenyl]carbonyl}amino)propyl]amino}-2-oxoethyl)thio]propanoic acid | 470.5 |
| 839 | 4-amino-2-[(2-{[(2S)-3-(hydroxyamino)-3-oxo-2-({[4-(phenylethynyl)phenyl]carbonyl}amino)propyl]amino}-2-oxoethyl)amino]-4-oxobutanoic acid | 496.5 |
| 840 | 1,1-dimethylethyl 4-amino-2-[(2-{[(2S)-3-(hydroxyamino)-3-oxo-2-({[4-(phenylethynyl)phenyl]carbonyl}amino)propyl]amino}-2-oxoethyl)amino]-4-oxobutanoate | 552.6 |
| 841 | 2,6-dihydroxy-N-[(2S)-3-(hydroxyamino)-3-oxo-2-({[4-(phenylethynyl)phenyl]carbonyl}amino)propyl]pyridine-4-carboxamide | 461.4 |
| 842 | N-[(1S)-1-(aminomethyl)-2-(hydroxyamino)-2-oxoethyl]-4-[(4-aminophenyl)ethynyl]benzamide | 339.4 |
| 843 | N-[(1S)-1-(aminomethyl)-2-(hydroxyamino)-2-oxoethyl]-4-[(4-ethylphenyl)ethynyl]benzamide | 352.4 |
| 844 | N-[(1S)-1-(aminomethyl)-2-(hydroxyamino)-2-oxoethyl]-4-[(4-ethylphenyl)ethynyl]-3-fluorobenzamide | 370.4 |
| 845 | N-[(1S)-1-(aminomethyl)-2-(hydroxyamino)-2-oxoethyl]-4-({4-[(3-aminopropanoyl)amino]phenyl}ethynyl)benzamide | 410.4 |
| 846 | N-[(1S)-1-(aminomethyl)-2-(hydroxyamino)-2-oxoethy)]-4-[(4-{[(dimethylamino)acetyl]amino}phenyl)ethynyl]benzamide | 424.5 |
| 847 | 4-({4-[(4-aminobutanoyl)amino]phenyl}ethynyl)-N-[(1S)-1-(aminomethyl)-2-(hydroxyamino)-2-oxoethyl]benzamide | 424.5 |
| 848 | N-{(1S)-2-(hydroxyamino)-1-[({[2-(methyloxy)phenyl]methyl}amino)methyl]-2-oxoethyl}-4-(phenylethynyl)benzamide | 444.5 |
| 849 | N-[(1S)-1-[(diprop-2-enylamino)methyl]-2-(hydroxyamino)-2-oxoethyl]-4-(phenylethynyl)benzamide | 404.5 |
| 850 | N-[(1S)-2-(hydroxyamino)-1-({[({[2-(methyloxy)phenyl]methyl}amino)acetyl]amino}methyl)-2-oxoethyl]-4-(phenylethynyl)benzamide | 501.6 |
| 851 | N-((1S)-2-(hydroxyamino)-l-{[({[2-(methyloxy)phenyl]thio}acetyl)amino]methyl}2-oxoethyl)-4-(phenylethynyl)benzamide | 504.6 |
| 852 | (2S,3R)-3-amino-2-({[4-(phenylethynyl)phenyl]carbonyl}amino)butanoic acid | 323.4 |
| 853 | N-[(1S)-1-(aminomethyl)-2-(hydroxyamino)-2-oxoethyl]-4-[4-(4-{[(dimethylamino)acetyl]amino}phenyl)buta-1,3-diynyl]benzamide | 448.5 |
| 854 | N-[(1S)-1-(aminomethyl)-2-(hydroxyamino)-2-oxoethyl]-4-[4-(4-{[(ethylamino)acetyl]amino}phenyl)buta-1,3-diynyl]benzamide | 448.5 |
| 855 | N-[(1S)-1-(aminomethyl)-2-(hydroxyamino)-2-oxoethyl]-4-[4-(4-{[(cyclopropylamino)acetyl]amino}phenyl)buta-1,3-diynyl]benzamide | 460.5 |
| 856 | N-[(1S)-1-(aminomethyl)-2-(hydroxyamino)-2-oxoethyl]-4-(4-{4-[(piperidin-1-ylacetyl)amino]phenyl}buta-1,3-diynyl)benzamide | 488.6 |

TABLE 1-continued

| | | |
|---|---|---|
| 857 | N-[(1S)-1-(aminomethyl)-2-(hydroxyamino)-2-oxoethyl]-4-[4-(4-{[(phenylamino)acetyl]amino}phenyl)buta-1,3-diynyl]benzamide | 496.5 |
| 858 | N-[(1S)-1-(aminomethyl)-2-(hydroxyamino)-2-oxoethyl]-4-{4-[4-({[(phenylmethyl)amino]acetyl}amino)phenyl]buta-1,3-diynyl} benzamide | 510.6 |
| 859 | N-[(1S)-1-(aminomethyl)-2-(hydroxyamino)-2-oxoethyl]-4-[4-(4-aminophenyl)buta-1,3-diynyl]benzamide | 363.4 |
| 860 | N-{(1S,2R)-2-hydroxy-1-[(hydroxyamino)carbonyl]propyl}-4-[(4-{[(pyrazin-2-ylamino)acetyl]amino}phenyl)ethynyl]benzamide | 489.5 |
| 861 | N-{(1S,2R)-2-hydroxy-1-[(hydroxyamino)carbonyl]propyl}-4-[(4-{[(4-phenylpiperidin-1-yl)acetyl]amino}phenyl)ethynyl]benzamide | 555.6 |
| 862 | 4-{[4-({[4-(2-fluorophenyl)piperazin-1-yl]acetyl}amino)phenyl]ethynyl}-N-{(1S,2R)-2-hydroxy-1-[(hydroxyamino)carbonyl]propyl}benzamide | 574.6 |
| 863 | 4-{[4-({[[(1S,4R)-bicyclo[2.2.1]hept-2-ylamino]acetyl}amino)phenyl]ethynyl}-N-{(1S,2R)-2-hydroxy-1-[(hydroxyamino)carbonyl] propyl}benzamide | 505.6 |
| 864 | N-{(1S,2R)-2-hydroxy-1-[(hydroxyamino)carbonyl]propyl}-4-({4-[({[(1S,2S,3S,5R)-2,6,6-trimethylbicyclo[3.1.1]hept-3-yl]amino}acetyl)amino]phenyl}ethynyl)benzamide | 547.7 |
| 865 | N-{(1S,2R)-2-hydroxy-1-[(hydroxyamino)carbonyl]propyl}-4-{[4-({[(tricyclo[3.3.1.1~3,7~]dec-1-ylmethyl)amino]acetyl}amino)phenyl]ethynyl}benzamide | 559.7 |
| 866 | N-{(1S,2R)-2-hydroxy-1-[(hydroxyamino)carbonyl]propyl}-4-{[4-({[(4-methylcyclohexyl)amino]acetyl}amino)phenyl]ethynyl}benzamide | 507.6 |
| 867 | N-{(1S,2R)-2-hydroxy-1-[(hydroxyamino)carbonyl]propyl}-4-{[4-({[(2,2,2-trifluoroethyl)amino]acetyl}amino)phenyl]ethynyl}benzamide | 493.5 |
| 868 | 4-({4-[({[2-(2-fluorophenyl)ethyl]amino}acetyl)amino]phenyl}ethynyl)-N-{(1S,2R)-2-hydroxy-1-[(hydroxyamino)carbonyl]propyl}benzamide | 533.6 |
| 869 | 4-({4-[({[2-(3-fluorophenyl)ethyl]amino}acetyl)amino]phenyl}ethynyl)-N-{(1S,2R)-2-hydroxy-1-[(hydroxyamino)carbonyl]propyl}benzamide | 533.6 |
| 870 | 4-({4-[({[2-(4-fluorophenyl)ethyl]amino}acetyl)amino]phenyl}ethynyl)-N-{(1S,2R)-2-hydroxy-1-[(hydroxyamino)carbonyl]propyl}benzamide | 533.6 |
| 871 | N-{(1S,2R)-2-hydroxy-1-[(hydroxyamino)carbonyl]propyl}-4-({4-[({[(1S,2R)-2-phenylcyclopropyl]amino}acetyl)amino]phenyl}ethynyl)benzamide | 527.6 |
| 872 | N-{(1S,2R)-2-hydroxy-1-[(hydroxyamino)carbonyl]propyl}-4-({4-[({[(2-methylphenyl)methyl]amino}acetyl)amino]phenyl}ethynyl)benzamide | 515.6 |
| 873 | N-{(1S,2R)-2-hydroxy-1-[(hydroxyamino)carbonyl]propyl}-4-[4-{[({[2-(trifluoromethyl)phenyl]methyl}amino)acetyl]amino}phenyl)ethynyl]benzamide | 569.5 |
| 874 | N-{(1S,2R)-2-hydroxy-1-[(hydroxyamino)carbonyl]propyl}-4-{[4-({[({2-[(trifluoromethyl)oxy]phenyl}methyl)amino]acetyl}amino)phenyl]ethynyl}benzamide | 585.5 |
| 875 | 4-({4-[({[(4-chlorophenyl)methyl]amino}acetyl)amino]phenyl}ethynyl)-N-{(1S,2R)-2-hydroxy-1-[(hydroxyamino)carbonyl]propyl}benzamide | 536.0 |

TABLE 1-continued

| | | |
|---|---|---|
| 876 | N-{(1S,2R)-2-hydroxy-1-[(hydroxyamino)carbonyl]propyl}-4-[(4-{[({[4-(methyloxy)phenyl]methyl}amino)acetyl]amino}phenyl)ethynyl]benzamide | 531.6 |
| 877 | 4-[4-{[({[4-(1,1-dimethylethyl)phenyl]methyl}amino)acetyl]amino}phenyl)ethynyl]-N-{(1S,2R)-2-hydroxy-1-[(hydroxyamino)carbonyl]propyl}benzamide | 557.7 |
| 878 | N-{(1S,2R)-2-hydroxy-1-[(hydroxyamino)carbonyl]propyl}-4-({4-[({[(4 nitrophenyl)methyl]amino)acetyl)amino]phenyl}ethynyl)benzamide | 546.5 |
| 879 | N-{(1S,2R)-2-hydroxy-1-[(hydroxyamino)carbonyl]propyl}-4-{[4-({[({4-[(trifluoromethyl)oxy]phenyl}methyl)amino]acetyl}amino)phenyl]ethynyl}benzamide | 585.5 |
| 880 | N-{(1S,2R)-2-hydroxy-1-[(hydroxyamino)carbonyl]propyl}-4-[(4-{[({[4 (methylthio)phenyl]methyl}amino)acetyl]amino}phenyl)ethynyl]benzamide | 547.6 |
| 881 | N-{(1S,2R)-2-hydroxy-1-[(hydroxyamino)carbonyl]propyl}-4-{[4-({[({4-[(trifluoromethyl)thio]phenyl}methyl)amino]acetyl}amino)phenyl]ethynyl}benzamide | 601.6 |
| 882 | N-{(1S,2R)-2-hydroxy-1-[(hydroxyamino)carbonyl]propyl}-4-[(4-{[({[4 (methylsulfonyl)phenyl]methyl}amino)acetyl]amino}phenyl)ethynyl]benzamide | 579.6 |
| 883 | 4-({4-[({[(2,5-difluorophenyl)methyl]amino)acetyl)amino]phenyl}ethyny))-N-{(1S,2R)-2-hydroxy-1-[(hydroxyamino)carbonyl]propyl}benzamide | 537.5 |
| 884 | 4-({4-[({[(2,6-difluorophenyl)methyl]amino)acetyl)amino]phenyl}ethynyl)-N-{(1S,2R)-2-hydroxy-1-[(hydroxyamino)carbonyl]propyl}benzamide | 537.5 |
| 885 | 4-({4-[({[(3,4-difluorophenyl)methyl]amino)acetyl)amino]phenyl}ethynyl)-N-{(1S,2R)-2-hydroxy-1-[(hydroxyamino)carbonyl]propyl}benzamide | 537.5 |
| 886 | 4-({4-[({[(3,4-dichlorophenyl)methyl]amino)acetyl)amino]phenyl}ethynyl)-N-{(1S,2R)-2-hydroxy-1-[(hydroxyamino)carbonyl]propyl}benzamide | 570.4 |
| 887 | 4-({4-[({[(3,4-dimethylphenyl)methy)]amino)acetyl)amino]phenyl}ethynyl)-N-{(1S,2R)-2-hydroxy-1-[(hydroxyamino)carbonyl]propyl}benzamide | 529.6 |
| 888 | 4-({4-[({[(3,5-dichlorophenyl)methyl]amino)acetyl)amino]phenyl}ethynyl)-N-{(1S,2R)-2-hydroxy-1-[(hydroxyamino)carbonyl]propyl}benzamide | 570.4 |
| 889 | 4-[(4-{[({[3,5-bis(trifluoromethyl)phenyl]methyl}amino)acetyl]amino}phenyl)ethynyl]-N-{(1S,2R)-2-hydroxy-1-[(hydroxyamino)carbonyl]propyl}benzamide | 637.5 |
| 890 | N-{(1S,2R)-2-hydroxy-1-[(hydroxyamino)carbonyl]propyl}-4-({4-[({[(2,3,4-trifluorophenyl)methy]]amino}acetyl)amino]phenyl}ethynyl)bcnzamide | 555.5 |
| 891 | N-{(1S,2R)-2-hydroxyl-[(hydroxyamino)carbonyl]propyl}-4-({4-[({[(2,4,5-trifluorophcnyl)methyl]amino}acetyl)amino]phenyl}ethynyl)benzamide | 555.5 |
| 892 | N-{(1S,2R)-2-hydroxy-1-[(hydroxyamino)carbonyl]propyl}-4-({4-[({[(3,4,5-trifluorophenyl)methyl]amino}acetyl)amino]phenyl}ethynyl)benzamide | 555.5 |
| 893 | N-[(1S)-1-(aminomethyl)-2-(hydroxyamino)-2-oxoethyl]-4-[(4-{[(pentylamino)acetyl]amino}pheny))ethynyl]benzamide | 466.6 |
| 894 | N-[(1S)-1-(aminomethyl)-2-(hydroxyamino)-2-oxoethyl]-4-{[4-({[(thien-2-ylmethyl)amino]acetyl}amino)phenyl]ethynyl}benzamide | 492.6 |

TABLE 1-continued

| | | |
|---|---|---|
| 895 | N-[(1S)-1-(aminomethyl)-2-(hydroxyamino)-2-oxoethyl]-4-[(4-{[(4-phenylpiperidin-1-yl)acetyl]amino}phenyl)ethynyl]benzamide | 540.6 |
| 896 | N-[(1S)-1-(aminomethyl)-2-(hydroxyamino)-2-oxoethyl]-4-[(4-{[(4-phenylpiperazin-1-yl)acetyl]amino}phenyl)ethynyl]benzamide | 541.6 |
| 897 | N-[(1S)-1-(aminomethyl)-2-(hydroxyamino)-2-oxoethyl]-4-{[4-({[4-(2-fluorophenyl)piperazin-1-yl]acetyl}amino)phenyl]ethynyl}benzamide | 559.6 |
| 898 | N-[(1S)-1-(aminomethyl)-2-(hydroxyamino)-2-oxoethyl]-4-{[4-({[4-(4-fluorophenyl)piperazin-1-yl]acetyl}amino)phenyl]ethynyl}benzamide | 559.6 |
| 899 | 4-{[4-({[(1-acetylpiperidin-4-yl)(cyclopropyl)amino]acetyl}amino)phenyl]ethynyl}-N-[(1S)-1-(aminomethyl)-2-(hydroxyamino)-2-oxoethyl]benzamide | 561.7 |
| 900 | N-[(1S)-1-(aminomethyl)-2-(hydroxyamino)-2-oxoethyl]-4-{[4-({[(2,3-dimethylcyclohexyl)amino]acetyl}amino)phenyl]ethynyl}benzamide | 506.6 |
| 901 | N-[(1S)-1-(aminomethyl)-2-(hydroxyamino)-2-oxoethyl]-4-{[4-({[(1R,2R,4S)-bicyclo[2.2.1]hept-2-ylamino]acetyl}amino)phenyl]ethynyl}benzamide | 490.6 |
| 902 | N-[(1S)-1-(aminomethyl)-2-(hydroxyamino)-2-oxoethyl]-4-[(4-{[({[(1S,2R,5S)-6,6-dimethylbicyclo[3.1.1]hept-2-yl]methyl}amino)acetyl]amino}phenyl)ethynyl]benzamide | 532.7 |
| 903 | N-[(1S)-1-(aminomethyl)-2-(hydroxyamino)-2-oxoethyl]-4-{[4-({[(1S,4R)-bicyclo[2.2.1]hept 2-ylamino]acetyl}amino)phenyl]ethynyl}benzamide | 490.6 |
| 904 | N-[(1S)-1-(aminomethyl)-2-(hydroxyamino)-2-oxoethyl]-4-({4-[({[(1S,2S,3S,5R)-2,6,6-trimethylbicyclo[3.1.1]hept-3-yl]amino}acetyl)amino]phenyl}ethynyl)benzamide | 532.7 |
| 905 | N-[(1S)-1-(aminomethy])-2-(hydroxyamino)-2-oxoethyl]-4-{[4-({[(tricyclo[3.3.1.1~3,7~]dec-1-ylmethyl)amino]acetyl}amino)phenyl]ethynyl}benzamide | 544.7 |
| 906 | N-[(1S)-1-(aminomethyl)-2-(hydroxyamino)-2-oxoethyl]-4-({4-[({[(2,6-difluorophenyl)methyl]amino}acetyl)amino]phenyl}ethynyl)benzamide | 522.5 |
| 907 | N-[(1S)-1-(aminomethyl)-2-(hydroxyamino)-2-oxoethyl]-4-{[4-{[({[4-(methylthio)phenyl]methyl}amino)acetyl]amino}phenyl]ethynyl]benzamide | 532.6 |
| 908 | N-[(1S)-1-(aminomethyl)-2-(hydroxyamino)-2-oxoethyl]-4-[(4-{[({[4-(methylsulfonyl)phenyl]methyl}amino)acetyl]amino}phenyl)ethynyl]benzamide | 564.6 |
| 909 | N-[(1S)-1-(aminomethyl)-2-(hydroxyamino)-2-oxoethyl]-4-{[4-({[({4-[(trifluoromethyl)thio]phenyl}methyl)amino]acetyl}amino)phenyl]ethynyl}benzamide | 586.6 |
| 910 | N-[(1S)-1-(aminomethyl)-2-(hydroxyamino)-2-oxoethyl]-4-{[4-({[({4-[(trifluoromethyl)oxy]phenyl}methyl)amino]acetyl}amino)phenyl]ethynyl}benzamide | 570.5 |
| 911 | N-[(1S)-1-(aminomethyl)-2-(hydroxyamino)-2-oxoethyl]-4-({4-[({[(2,4,5-trifluorophenyl)methyl]amino}acetyl)amino]phenyl}ethynyl)benzamide | 540.5 |
| 912 | N-[(1S)-1-(aminomethyl)-2-(hydroxyamino)-2-oxoethyl]-4-({4-[({[(2,3,4-trifluorophenyl)methyl]amino}acetyl)amino]phenyl}ethynyl)benzamide | 540.5 |
| 913 | N-[(1S)-1-(aminomethyl)-2-(hydroxyamino)-2-oxoethyl]-4-({4-[({[(3,4,5-trifluorophenyl)methyl]amino}acetyl)amino]phenyl}ethynyl)benzamide | 540.5 |
| 914 | N-[(1S)-1-(aminomethyl)-2-(hydroxyamino)-2-oxoethyl]-4-(4-{[(pyrrolidin-1-ylacetyl)amino]phenyl}buta-1,3-diynyl)benzamide | 474.5 |

TABLE 1-continued

| | | |
|---|---|---|
| 915 | N-[(1S)-1-(aminomethyl)-2-(hydroxyamino)-2-oxoethyl]-4-(4-{4-[(azepan-1-ylacetyl)amino]phenyl}buta-1,3-diynyl)benzamide | 502.6 |
| 916 | N-[(1S)-1-(aminomethyl)-2-(hydroxyamino)-2-oxoethyl]-4-(4-{4-[(piperazin-l-ylacetyl)amino]phenyl}buta-1,3-diynyl)benzamide | 489.5 |
| 917 | N-[(1S)-1-(aminomethyl)-2-(hydroxyamino)-2-oxoethyl]-4-(4-{[(4-methylpiperazin-1-yl)acetyl]amino}phenyl)buta-1,3-diynyl]benzamide | 503.6 |
| 918 | N-[(1S)-1-(aminomethyl)-2-(hydroxyamino)-2-oxoethyl]-4-(4-{4-[(morpholin-4-ylacetyl)amino]phenyl}buta-1,3-diynyl)benzamide | 490.5 |
| 919 | N-[(1S)-1-(aminomethyl)-2-(hydroxyamino)-2-oxoethyl]-4-{4-[4-({[cyclohexyl(methyl)amino]acetyl}amino)phenyl]buta-l,3-diynyl}benzamide | 516.6 |
| 920 | N-[(1S)-1-(aminomethyl)-2-(hydroxyamino)-2-oxoethyl]-4-(4-{4-[({[(2-fluorophenyl)methyl]amino}acetyl)amino]phenyl}buta-l,3-diynyl)benzamide | 528.6 |
| 921 | N-[(1S)-1-(aminomethyl)-2-(hydroxyamino)-2-oxoethyl]-4-(4-{4-[({[(3-fluorophenyl)methyl]amino}acetyl)amino]phenyl}buta-1,3-diynyl)benzamide | 528.6 |
| 922 | N-[(1S)-1-(aminomethyl)-2-(hydroxyamino)-2-oxoethyl]-4-(4-{4-[({[(4-fluorophenyl)methyl]amino}acetyl)amino]phenyl}buta-1,3-diynyl)benzamide | 528.6 |
| 923 | N-[(1S)-1-(aminomethyl)-2-(hydroxyamino)-2-oxoethyl]-4-(4-{4-[({[(2-methylphenyl)methyl]amino}acetyl)amino]phenyl}buta-1,3-diynyl)benzamide | 524.6 |
| 924 | N-[(1S)-1-(aminomethyl)-2-(hydroxyamino)-2-oxoethyl]-4-(4-{4-[({[(3-methylphenyl)methyl]amino}acetyl)amino]phenyl}buta-1,3-diynyl)benzamide | 524.6 |
| 925 | N-[(1S)-1-(aminomethyl)-2-(hydroxyamino)-2-oxoethyl]-4-(4-{4-[({[(4-methylphenyl)methyl]amino}acetyl)amino]phenyl}buta-l,3-diynyl)benzamide | 524.6 |
| 926 | N-[(1S)-1-(aminomethyl)-2-(hydroxyamino)-2-oxoethyl]-4-{4-[4-({[(pyridin-2-ylmethyl)amino]acetyl}amino)phenyl]buta-1,3-diynyl}benzamide | 511.6 |
| 927 | N-[(1S)-1-(aminomethyl)-2-(hydroxyamino)-2-oxoethyl]-4-{4-[4-({[(pyridin-3-ylmethyl)amino]acctyl}amino)phenyl]buta-1,3-diynyl}benzamide | 511.6 |
| 928 | N-[(1S)-1-(aminomethyl)-2-(hydroxyamino)-2-oxoethyl]-4-{4-[4-({[(pyridin-4-ylmethyl)amino]acetyl}amino)phenyl]buta-1,3-diynyl}benzamide | 511.6 |
| 929 | N-[(1S)-1-(aminomethyl)-2-(hydroxyamino)-2-oxoethyl]-4-[4-(4-{[({[2-(methyloxy)phenyl]methyl}amino)acetyl]amino}phenyl)buta-l,3-diynyl]benzamide | 540.6 |
| 930 | N-[(1S)-1-(aminomethyl)-2-(hydroxyamino)-2-oxoethyl]-4-[4-(4-{[({[3-(methyloxy)phenyl]methyl}amino)acetyl]amino}phenyl)buta-l,3-diynyl]benzamide | 540.6 |
| 931 | N-[(1S)-1-(aminomethyl)-2-(hydroxyamino)-2-oxoethyl]-4-[4-(4-{[({[4-(methyloxy)phenyl]methyl}amino)acetyl]amino}phenyl)buta-1,3-diynyl]benzamide | 540.6 |
| 932 | N-[(1S)-1-(aminomethyl)-2-(hydroxyamino)-2-oxoethyl]-4-{4-[4-({[(2-fluorophenyl)amino]acetyl}amino)phenyl]buta-1,3-diynyl}benzamide | 514.5 |
| 933 | N-[(1S)-1-(aminomethyl)-2-(hydroxyamino)-2-oxoethyl]-4-{4-[4-({[(3-fluorophenyl)amino]acetyl}amino)phenyl]buta-1,3-diynyl}benzamide | 514.5 |
| 934 | N-[(1S)-1-(aminomethyl)-2-(hydroxyamino)-2-oxoethyl]-4-{4-[4-({[(4-fluorophenyl)amino]acetyl}amino)phenyl]buta-1,3-diynyl}benzamide | 514.5 |

TABLE 1-continued

| | | |
|---|---|---|
| 935 | N-[(1S)-1-(aminomethyl)-2-(hydroxyamino)-2-oxoethyl]-4-[4-(4-{[(pyridin-2-ylamino)acetyl]amino}phenyl)buta-1,3-diynyl]benzamide | 497.5 |
| 936 | N-[(1S)-1-(aminomethyl)-2-(hydroxyamino)-2-oxoethyl]-4-[4-(4-{[(pyridin-3-ylamino)acetyl]amino}phenyl)buta-1,3-diynyl]benzamide | 497.5 |
| 937 | N-[(1S)-1-(aminomethyl)-2-(hydroxyamino)-2-oxoethyl]-4-[4-(4-{[(pyridin-4-ylamino)acetyl]amino}phenyl)buta-1,3-diynyl]benzamide | 497.5 |
| 938 | N-[(1S)-1-(aminomethyl)-2-(hydroxyamino)-2-oxoethyl]-4-[4-(4-{[(cyclobutylamino)acetyl]amino}phenyl)buta-1,3-diynyl]benzamide | 474.5 |
| 939 | N-[(1S)-1-(aminomethyl)-2-(hydroxyamino)-2-oxoethyl]-4-[4-(4-{[(cyclopentylamino)acetyl]amino}phenyl)buta-1,3-diynyl]benzamide | 488.6 |
| 940 | N-[(1S)-1-(aminomethyl)-2-(hydroxyamino)-2-oxoethyl]-4-[4-(4-{[(cyclohexylamino)acetyl]amino}phenyl)buta-1,3-diynyl]benzamide | 502.6 |
| 941 | N-[(1S)-1-(aminomethyl)-2-(hydroxyamino)-2-oxoethyl]-4-[4-(4-{[(cycloheptylamino)acetyl]amino}phenyl)buta-1,3-diynyl]benzamide | 516.6 |
| 942 | N-[(1S)-1-(aminomethyl)-2-(hydroxyamino)-2-oxoethyl]-4-[4-(4-{[(methylamino)acetyl]amino}phenyl)buta-1,3-diynyl]benzamide | 434.5 |
| 943 | N-[(1S)-1-(aminomethyl)-2-(hydroxyamino)-2-oxoethyl]-4-[4-(4-{[(propylamino)acetyl]amino}phenyl)buta-1,3-diynyl]benzamide | 462.5 |
| 944 | N-[(1S)-1-(aminomethyl)-2-(hydroxyamino)-2-oxoethyl]-4-[4-(4-{[(butylamino)acetyl]amino}phenyl)buta-1,3-diynyl]benzamide | 476.5 |
| 945 | N-[(1S)-1-(aminomethyl)-2-(hydroxyamino)-2-oxoethyl]-4-[4-(4-{[(pentylamino)acetyl]amino}phenyl)buta-1,3-diynyl]benzamide | 490.6 |
| 946 | N-[(1S)-1-(aminomethyl)-2-(hydroxyamino)-2-oxoethyl]-4-[4-(4-{[(hexylamino)acetyl]amino}phenyl)buta-1,3-diynyl]benzamide | 504.6 |
| 947 | N-[(1S)-1-(aminomethyl)-2-(hydroxyamino)-2-oxoethyl]-4-{4-[4-({[ethyl(methyl)amino]acetyl}amino)phenyl]buta-1,3-diynyl}benzamide | 462.5 |
| 948 | N-[(1S)-1-(aminomethyl)-2-(hydroxyamino)-2-oxoethyl]-4-{4-[4-({[(1-methylethyl)amino]acetyl}amino)phenyl]buta-1,3-diynyl}benzamide | 462.5 |
| 949 | N-[(1S)-1-(aminomethyl)-2-(hydroxyamino)-2-oxoethyl]-4-{4-[4-({[(2-methylpropyl)amino]acetyl}amino)phenyl]buta-1,3-diynyl}benzamide | 476.5 |
| 950 | N-[(1S)-1-(aminomethyl)-2-(hydroxyamino)-2-oxoethyl]-4-{4-[4-({[(2-hydroxyethyl)amino]acetyl}amino)phenyl]buta-1,3-diynyl}benzamide | 464.5 |
| 951 | N-[(1S)-1-(aminomethyl)-2-(hydroxyamino)-2-oxoethyl]-4-(4-{4-[({[2-(methyloxy)ethyl]amino}acetyl)amino]phenyl}buta-1,3-diynyl)benzamide | 478.5 |
| 952 | N-[(1S)-1-(aminomethyl)-2-(hydroxyamino)-2-oxoethyl]-4-(4-{4-[({[2-(dimethylamino)ethyl]amino}acetyl)amino]phenyl}buta-1,3-diynyl)benzamide | 491.6 |
| 953 | N-[(1S)-1-(aminomethyl)-2-(hydroxyamino)-2-oxoethyl]-4-{4-[4-({[(2-cyanoethyl)amino]acetyl}amino)phenyl]buta-1,3-diynyl}benzamide | 473.5 |
| 954 | N-[(1S)-1-(aminomethyl)-2-(hydroxyamino)-2-oxoethyl]-4-{4-[4-({[(thien-2-ylmethyl)amino]acetyl}amino)phenyl]buta-1,3-diynyl}benzamide | 516.6 |

TABLE 1-continued

| | | |
|---|---|---|
| 955 | N-[(1S)-1-(aminomethyl)-2-(hydroxyamino)-2-oxoethyl]-4-(4-{4-[({[(1R)-1-phenylethyl]amino}acetyl)amino]phenyl}buta-1,3-diynyl)benzamide | 524.6 |
| 956 | N-[(1S)-1-(aminomethyl)-2-(hydroxyamino)-2-oxoethyl]-4-(4-{4-[({[(1S)-1-phenylethyl]amino}acetyl)amino]phenyl}buta-1,3-diynyl)benzamide | 524.6 |
| 957 | N-[(1S)-1-(aminomethyl)-2-(hydroxyamino)-2-oxoethyl]-4-{4-[4-({[(2-phenylethyl)amino]acetyl}amino]phenyl]buta-1,3-diynyl}benzamide | 24.6 |
| 958 | N-[(1S)-1-(aminomethyl)-2-(hydroxyamino)-2-oxoethyl]-4-(4-{4-[(1H-imidazol-1-ylacetyl)amino]phenyl}buta-1,3-diynyl)benzamide | 471.5 |
| 959 | N-[(1S)-1-(aminomethyl)-2-(hydroxyamino)-2-oxoethyl]-4-{4-[4-({[(1R,2R,4S)-bicyclo[2.2.1]hept-2-ylamino]acetyl}amino)phenyl]buta-1,3-diynyl}benzamide | 14.6 |
| 960 | N-[(1S)-1-(aminomethyl)-2-(hydroxyamino)-2-oxoethyl]-4-{4-[4-({[(cyclohexylmethyl)amino]acetyl}amino)phenyl]buta-1,3-diynyl}benzamide | 516.6 |
| 961 | N-{(1S,2R)-2-hydroxy-1-[(hydroxyamino)carbonyl]propyl}-4-[(6-piperidin-1-ylpyridin-3-yl)ethynyl]benzamide | 423.5 |
| 962 | N-{(1S,2R)-2-hydroxy-1-[(hydroxyamino)carbonyl]propyl}-4-{[6-(4-methylpiperazin-1-yl)pyridin-3-yl]ethynyl}benzamide | 438.5 |
| 963 | N-{(1S,2R)-2-hydroxy-1-[(hydroxyamino)carbonyl]propyl}-4-[(6-piperazin-1-ylpyridin-3-yl)ethynyl]benzamide | 424.5 |
| 964 | 4-[(6-azepan-1-ylpyridin-3-yl)ethynyl]-N-{(1S,2R)-2-hydroxy-1-[(hydroxyamino)carbonyl]propyl}benzamide | 437.5 |
| 965 | 4-{[6-(cyclobutylamino)pyridin-3-yl]ethynyl}-N-{(1S,2R)-2-hydroxy-1-[(hydroxyamino)carbonyl]propyl}benzamide | 409.5 |
| 966 | 4-{[6-(cyclohexylamino)pyridin-3-yl]ethynyl}-N-{(1S,2R)-2-hydroxy-1-[(hydroxyamino)carbonyl]propyl}benzamide | 437.5 |
| 967 | 4-{[6-(butylamino)pyridin-3-yl]ethynyl}-N-{(1S,2R)-2-hydroxy-1-[(hydroxyamino)carbonyl]propyl}benzamide | 411.5 |
| 968 | 4-({6-[(2-hydroxyethyl)amino]pyridin-3-yl}ethynyl)-N-{(1S,2R)-2-hydroxy-1-[(hydroxyamino)carbonyl]propyl}benzamide | 399.4 |
| 969 | 4-[(6-{[2-(dimethylamino)ethyl]amino}pyridin-3-yl)ethynyl]-N-{(1S,2R)-2-hydroxy-1-[(hydroxyamino)carbonyl]propyl}benzamide | 426.5 |
| 970 | N-{(1S,2R)-2-hydroxy-1-[(hydroxyamino)carbonyl]propyl}-4-({6-[(phenylmethyl)amino]pyridin-3-yl}ethynyl)benzamide | 445.5 |
| 971 | 4-[(6-{[(4-fluorophenyl)methyl]amino}pyridin-3-yl)ethynyl]-N-{(1S,2R)-2-hydroxy-1-[(hydroxyamino)carbonyl]propyl}benzamide | 463.5 |
| 972 | N-{(1S,2R)-2-hydroxy-1-[(hydroxyamino)carbonyl]propyl}-4-{[6-(pyridin-4-ylamino)pyridin-3-yl]ethynyl}benzamide | 432.4 |
| 973 | 4-[(6-chloropyridin-3-yl)ethynyl]-N-{(1S,2R)-2-hydroxy-1-[(hydroxyamino)carbonyl]propyl}benzamide | 374.8 |
| 974 | 1,1-dimethylethyl (2S)-2-[({4-[(4-ethylphenyl)ethynyl]phenyl}carbonyl)amino]-3-(hydroxyamino)-3-oxopropylcarbamate | 452.5 |
| 975 | N-[(1S)-1-(aminomethyl)-2-(hydroxyamino)-2-oxoethyl]-4-{4-[4-({[(1S)-1-(aminomethyl)-2-(hydroxyamino)-2-oxoethyl]amino}carbonyl)phenyl]buta-1,3-diynyl}benzamide | 493.5 |
| 976 | N-{(1S,2R)-2-hydroxy-1-[(hydroxyamino)carbonyl]propyl}-4-{[4-(morpholin-4-ylmethyl)phenyl]ethynyl}benzamide | 438.5 |
| 977 | 4-[(4-{[(2-aminoethyl)amino]methyl}phenyl)ethynyl]-N-{(1S,2R)-2-hydroxy-1-[(hydroxyamino)carbonyl]propyl}benzamide | 411.5 |

TABLE 1-continued

| | | |
|---|---|---|
| 978 | 4-({4-[((2S)-2-amino-5-{[amino(imino)methyl]amino}pentanoyl)amino]phenyl}ethynyl)-N-[(1S)-1-(aminomethyl)-2-(hydroxyamino)-2-oxoethyl]benzamide | 495.6 |
| 979 | (2S)-6-amino-2-({[4-({4-[({(1S,2R)-2-hydroxy-1-[(hydroxyamino)carbonyl]propyl}amino)carbonyl]phenyl}ethynyl)phenyl]carbonyl}amino)hexanoic acid | 511.5 |
| 980 | (2S)-6-amino-2-({[4-({4-[({(1S,2R)-2-hydroxy-1-[(hydroxyamino)carbonyl]propyl}amino)carbonyl]phenyl}ethynyl)phenyl]acetyl}amino)hexanoic acid | 525.6 |
| 981 | 5-{[(2S)-3-(hydroxyamino)-3-oxo-2-({[4-(phenylethynyl)phenyl]carbonyl}amino)propyl]amino}-5-oxopentanoic acid | 438.4 |
| 982 | N-(2-aminoethyl)-N'-[(2S)-3-(hydroxyamino)-3-oxo-2-({[4-(phenylethynyl)phenyl]carbonyl}amino)propyl]pentanediamide | 480.5 |
| 983 | N-[(1S)-1-[(2,6-dioxopiperidin-1-yl)methy)]-2-(hydroxyamino)-2-oxoethyl]-4-(phenylethynyl)benzamide | 420.4 |
| 984 | N,N'-bis[(2S)-3-(hydroxyamino)-3-oxo-2-({[4-(phenylethynyl)phenyl]carbonyl}amino)propyl]pentanediamide | 743.8 |
| 985 | N-((1S)-2-(hydroxyamino)-2-oxo-1-{[({[(1S)-1-phenylethyl]amino}acetyl)amino]methyl}ethyl)-4-(phenylethynyl)benzamide | 485.6 |
| 986 | N-{(1S)-2-hydroxy-1-[(hydroxyamino)carbonyl]-2-methylpropyl}-4-(phenylethynyl)benzamide | 353.4 |
| 987 | N-[(1S)-1-(aminomethyl)-2-(hydroxyamino)-2-oxoethyl]-4-[(6-piperidin-1-ylpyridin-3-yl)ethynyl]benzamide | 408.5 |
| 988 | N-[(1S)-1-(aminomethyl)-2-(hydroxyamino)-2-oxoethyl]-4-[(6-morpholin-4-ylpyridin-3-yl)ethynyl]benzamide | 410.4 |
| 989 | N-[(1S)-1-(aminomethyl)-2-(hydroxyamino)-2-oxoethyl]-4-{[6-(4-methylpiperazin-1-yl)pyridin-3-yl]ethynyl}benzamide | 423.5 |
| 990 | N-[(1S)-1-(aminomethyl)-2-(hydroxyamino)-2-oxoethyl]-4-[(6-piperazin-1-ylpyridin-3-y))ethynyl]benzamide | 409.5 |
| 991 | N-[(1S)-1-(aminomethyl)-2-(hydroxyamino)-2-oxoethyl]-4-[(6-azepan-1-ylpyridin-3-yl)ethynyl]benzamide | 422.5 |
| 992 | N-[(1S)-1-(aminomethyl)-2-(hydroxyamino)-2-oxoethyl]-4-{[6-(cyclobutylamino)pyridin-3-yl]ethynyl}benzamide | 394.4 |
| 993 | N-[(1S)-1-(aminomethyl)-2-(hydroxyamino)-2-oxoethyl]-4-{[6-(cyclohexylamino)pyridin-3-yl]ethynyl}benzamide | 422.5 |
| 994 | N-[(1S)-1-(aminomethyl)-2-(hydroxyamino)-2-oxoethyl]-4-{[6-(butylamino)pyridin-3-yl]ethynyl}benzamide | 396.5 |
| 995 | N-[(1S)-1-(aminomethyl)-2-(hydroxyamino)-2-oxoethyl]-4-[(6-{[2-(methyloxy)ethyl]amino}pyridin-3-yl)ethynyl]benzamide | 398.4 |
| 996 | N-{(1S,2R)-2-hydroxy-1-[(hydroxyamino)carbonyl]propyl}-4-{[4-(piperidin-1-ylmethyl)phenyl]ethynyl}benzamide | 436.5 |
| 997 | 4-[4-{[(2S)-2-amino-3-(4-aminophenyl)propanoyl]amino}pheny])ethynyl]-N-{(1S,2R)-2-hydroxy-1-[(hydroxyamino)carbonyl]propyl}benzamide | 516.6 |
| 998 | 4-((2S)-2-amino-3-{[4-({4-[({(1S,2R)-2-hydroxy-1-[(hydroxyamino)carbonyl]propyl}amino)carbonyl]phenyl}ethynyl)phenyl]amino}-3-oxopropyl)benzoic acid | 545.6 |
| 999 | | 573.6 |
| 1000 | N-{(1S,2R)-2-hydroxy-1-[(hydroxyamino)carbony)]propyl}-4-({4-[({[1-(hydroxymethyl)-2-methylpropyl]amino}acetyl)amino]phenyl}ethynyl)benzamide | 497.6 |

TABLE 1-continued

| | | |
|---|---|---|
| 1001 | 4-[4-(3-aminophenyl)buta-1,3-diynyl]-N-{(1S,2R)-2-hydroxy-1-[(hydroxyamino)carbonyl]propyl}benzamide | 378.4 |
| 1002 | 4-[4-(3-{[(2-aminoethyl)amino]methyl}phenyl)buta-1,3-diynyl]-N-{(1S,2R)-2-hydroxy-1-[(hydroxyamino)carbonyl]propyl}benzamide | 435.5 |
| 1003 | 5-[(4-{[4-({[(1S)-1-(aminomethyl)-2-(hydroxyamino)-2-oxoethyl]amino}carbonyl)phenyl]ethynyl}phenyl)amino]-5-oxopentanoic acid | 453.5 |
| 1004 | N-(2-aminoethyl)-3-{4-[4-({[(1S)-1-(aminomethyl)-2-(hydroxyamino)-2-oxoethyl]amino}carbonyl)phenyl]buta-1,3-diynyl}benzamide | 434.5 |
| 1005 | N-[(1S)-1-(aminomethyl)-2-(hydroxyamino)-2-oxoethyl]-4-{4-[3-(aminomethyl)phenyl]buta-1,3-diynyl}benzamide | 377.4 |
| 1006 | N-[(1S)-1-(aminomethyl)-2-(hydroxyamino)-2-oxoethyl]-4-{4-[3-(trifluoromethyl)phenyl]buta-1,3-diynyl}benzamide | 416.4 |
| 1007 | N-[(1S)-1-(aminomethyl)-2-(hydroxyamino)-2-oxoethyl]-4-buta-1,3-diynylbenzamide | 272.3 |
| 1108 | N-[(1S)-1-(aminomethyl)-2-(hydroxyamino)-2-oxoethyl]-4-[4-(2-methylphenyl)buta-1,3-diynyl]benzamide | 362.4 |
| 1109 | 4-(4-{4-[(3-aminopropanoyl)amino]phenyl}buta-1,3-diynyl)-N-{(1S,2R)-2-hydroxy-1-[(hydroxyamino)carbonyl]propyl}benzamide | 449.5 |
| 1110 | 4-[4-(3-{[(aminoacetyl)amino]methyl}phenyl)buta-1,3-diynyl]-N-{(1S,2R)-2-hydroxy-1-[(hydroxyamino)carbonyl]propyl}benzamide | 449.5 |
| 1011 | 4-(4-{3-[(aminoacetyl)amino]phenyl}buta-1,3-diynyl)-N-{(1S,2R)-2-hydroxy-1-[(hydroxyamino)carbonyl]propyl}benzamide | 435.4 |
| 1012 | 4-[4-(4-{[(2S)-2-aminopropanoyl]amino}phenyl)buta-1,3-diynyl]-N-{(1S,2R)-2-hydroxy-1-[(hydroxyamino)carbonyl]propyl}benzamide | 449.5 |
| 1013 | 4-(4-{4-[(aminoacetyl)amino]phenyl}buta-1,3-diynyl)-N-[(1S)-1-(aminomethyl)-2-(hydroxyamino)-2-oxoethyl]benzamide | 420.4 |
| 1014 | 4-[4-(3-{[(aminoacetyl)amino]methyl}phenyl)buta-1,3-diynyl]-N-[(1S)-1-(aminomethyl)-2-(hydroxyamino)-2-oxoethyl]benzamide | 434.5 |
| 1015 | N-[(1S)-1-(aminomethyl)-2-(hydroxyamino)-2-oxoethyl]-4-(4-{4-[(3-aminopropanoyl)amino]phenyl}buta-1,3-diynyl)benzamide | 434.5 |
| 1016 | 4-(4-{3-[(aminoacetyl)amino]phenyl}buta-1,3-diynyl)-N-[(1S)-1-(aminomethyl)-2-(hydroxyamino)-2-oxoethyl]benzamide | 420.4 |
| 1017 | 4-[(4-{[(2S)-2-amino-3-(4-hydroxyphenyl)propanoyl]amino}phenyl)ethynyl]-N-{(1S,2R)-2-hydroxy-1-[(hydroxyamino)carbonyl]propyl}benzamide | 517.6 |
| 1018 | 4-(4-{4-[(aminoacetyl)amino]phenyl}buta-1,3-diynyl)-N-{(1S,2R)-2-hydroxy-1-[(hydroxyamino)carbonyl]propyl}benzamide | 435.4 |
| 1019 | N-[(1S)-1-(aminomethyl)-2-(hydroxyamino)-2-oxoethyl]-4-({4-[(butylamino)methyl]phenyl}ethynyl)benzamide | 409.5 |
| 1020 | N-[(1S)-1-(aminomethyl)-2-(hydroxyamino)-2-oxoethyl]-4-{[4-(piperidin-1-ylmethyl)phenyl]ethynyl}benzamide | 421.5 |
| 1021 | N-[(1S)-1-(aminomethyl)-2-(hydroxyamino)-2-oxoethyl]-4-[(4-formylphenyl)ethynyl]benzamide | 352.4 |
| 1022 | N-{(1S,2R)-2-hydroxy-1-[(hydroxyamino)carbonyl]propyl}-4-({4-[(methylsulfonyl)amino]phenyl}ethynyl)benzamide | 432.5 |
| 1023 | N-[(1S)-1-(aminomethyl)-2-(hydroxyamino)-2-oxoethyl]-4-({4-[(methylsulfonyl)amino]phenyl}ethynyl)benzamide | 417.5 |
| 1024 | N-[(1S)-1-(aminomethyl)-2-(hydroxyamino)-2-oxoethyl]-4-({4-[(phenylsulfonyl)amino]phenyl}ethynyl)benzamide | 479.5 |

TABLE 1-continued

| | | |
|---|---|---|
| 1025 | N-[(1S)-1-(aminomethyl)-2-(hydroxyamino)-2-oxoethyl]-4-(4-{4-[(phenylsulfonyl)amino]phenyl}buta-1,3-diynyl)benzamide | 503.5 |
| 1026 | N-[(1S)-1-(aminomethyl)-2-(hydroxyamino)-2-oxoethyl]-4-{[4-(morpholin-4-ylmethyl)phenyl]ethynyl}benzamide | 423.5 |
| 1027 | N-[(1S)-1-(aminomethyl)-2-(hydroxyamino)-2-oxoethyl]-4-({4-[(4-methylpiperazin-1-yl)methyl]phenyl}ethynyl)benzamide | 436.5 |
| 1028 | N-[(1S)-1-(aminomethyl)-2-(hydroxyamino)-2-oxoethyl]-4-[(4-{[(2-hydroxyethyl)amino]methyl}phenyl)ethynyl]benzamide | 397.4 |
| 1029 | N-[(1S)-1-(aminomethyl))-2-(hydroxyamino)-2-oxoethyl]-4-{[4-({[2-(methyloxy)ethyl]amino}methyl)phenyl]ethynyl]benzamide | 411.5 |
| 1030 | N-[(1S)-1-(aminomethyl)-2-(hydroxyamino)-2-oxoethyl]-4-({4-[(cyclohexylamino)methyl]phenyl}ethynyl)benzamide | 435.5 |
| 1031 | N-[(1S)-1-(aminomethyl)-2-(hydroxyamino)-2-oxoethyl]-4-[(4-{[(phenylmethyl)amino]methyl}phenyl)ethynyl]benzamide | 443.5 |
| 1032 | N-[(1S)-1-(aminomethyl)-2-(hydroxyamino)-2-oxoethyl]-4-[(6-chloropyridin-3-yl)ethynyl]benzamide | 359.8 |
| 1033 | N-{(1S,2R)-2-hydroxy-1-[(hydroxyamino)carbonyl]propyl}-4-(4-{4-[({[6-(methyloxy)pyridin-3-yl]amino}acetyl)amino]phenyl}buta-1,3-diynyl)benzamide | 542.6 |
| 1034 | 4-{4-[4-({[(6-chloropyridin-3-yl)amino]acetyl}amino)phenyl]buta-1,3-diynyl}-N-{(1S,2R)-2-hydroxy-1-[(hydroxyamino)carbonyl]propyl}benzamide | 547.0 |
| 1035 | N-{(1S,2R)-2-hydroxy-1-[(hydroxyamino)carbonyl]propyl}-4-{[4-(pyrrolidin-1-ylmethyl)phenyl]ethynyl}benzamide | 422.5 |
| 1036 | 4-({4-[(ethylamino)methyl]phenyl}ethynyl)-N-{(1S,2R)-2-hydroxy-1-[(hydroxyamino)carbonyl]propyl}benzamide | 396.5 |
| 1037 | 4-({4-[(dimethylamino)methyl]phenyl}ethynyl)-N-{(1S,2R)-2-hydroxy-1-[(hydroxyamino)carbonyl]propyl}benzamide | 396.5 |
| 1038 | N-{(1S,2R)-2-hydroxy-1-[(hydroxyamino)carbonyl]propyl}-4-({4-[(4-methylpiperazin-1-yl)methyl]phenyl}ethynyl)benzamide | 451.5 |
| 1039 | N-{(1S,2R)-2-hydroxy-1-[(hydroxyamino)carbonyl]propyl}-4-{[4-({[3-(1H-imidazol-1-yl)propyl]amino}methyl)phenyl]ethynyl}benzamide | 476.5 |
| 1040 | N-[(1S)-1-(aminomethyl)-2-(hydroxyamino)-2-oxoethyl]-4-(4-thien-2-ylbuta-1,3-diynyl)benzamide | 354.4 |
| 1041 | N,N,N-triethyl-2-{[4-(4-{4-[({(1S,2R)-2-hydroxy-1-[(hydroxyamino)carbonyl]propyl}amino)carbonyl]phenyl}buta-1,3-diynyl)phenyl]amino}-2-oxoethanaminium | 520.6 |
| 1042 | 4-[4-(2-aminophenyl)buta-1,3-diynyl]-N-{(1S,2R)-2-hydroxy-1-[(hydroxyamino)carbonyl]propyl}benzamide | 378.4 |
| 1043 | 4-[4-(3-{[(2-aminoethyl)amino]methyl}phenyl)buta-1,3-diynyl]-N-[(1S)-1-(aminomethyl)-2-(hydroxyamino)-2-oxoethyl]benzamide | 420.5 |
| 1044 | 4-buta-1,3-diynyl-N-{(1S,2R)-2-hydroxy-1-[(hydroxyamino)carbonyl]propyl}benzamide | 287.3 |
| 1045 | 4-[4-(4-{[(2S)-2-amino-4-methylpentanoyl]amino}phenyl)buta-1,3-diynyl]-N-{(1S,2R)-2-hydroxy-1-[(hydroxyamino)carbonyl]propyl}benzamide | 491.6 |
| 1046 | (2S)-N-[4-(4-{4-[({(1S,2R)-2-hydroxy-1-[(hydroxyamino)carbonyl]propyl}amino)carbonyl]phenyl}buta-1,3-diynyl)phenyl]pyrrolidine-2-carboxamide | 475.5 |

TABLE 1-continued

| | | |
|---|---|---|
| 1047 | (2S)-N-[4-(4-{4-[({(1S,2R)-2-hydroxy-1-[(hydroxyamino)carbonyl]propyl}amino)carbonyl]phenyl}buta-1,3-diynyl)phenyl]piperidine-2-carboxamide | 489.5 |
| 1048 | 4-[4-(4-{[(2S)-2,3-diaminopropanoyl]amino}phenyl)buta-1,3-diynyl]-N-{(1S,2R)-2-hydroxy-1-[(hydroxyamino)carbonyl]propyl}benzamide | 464.5 |
| 1049 | 4-[4-(4-{[(2S)-2-amino-3-(1H-imidazol-4-yl)propanoyl]amino}phenyl)buta-1,3-diynyl]-N-{(1S,2R)-2-hydroxy-1-[(hydroxyamino)carbonyl]propyl}benzamide | 515.5 |
| 1050 | N-[1-[(hydroxyamino)carbonyl]-2-(propylamino)propyl]-4-[(4-{[(propylamino)acetyl]amino}phenyl)ethynyl]benzamide | 494.6 |
| 1051 | 4-[(4-{[(cyclobutylamino)acetyl]amino}phenyl)ethynyl]-N-{2-(cyclobutylamino)-1-[(hydroxyamino)carbonyl]propyl}benzamide | 518.6 |
| 1052 | N-{(1S,2R)-2-amino-1-[(hydroxyamino)carbonyl]propyl}-4-[(4-{[(cyclopropylamino)acetyl]amino}phenyl)ethynyl]benzamide | 450.5 |
| 1053 | 1-[(1R,2S)-2-[({4-[(4-{[(cyclopropylamino)acetyl]amino}phenyl)ethynyl]phenyl}carbonyl)amino]-3-(hydroxyamino)-1-methyl-3-oxopropyl]triaza-1,2-dien-2-ium | 477.5 |
| 1054 | N-{(1S,2R)-2-amino-1-[(hydroxyamino)carbonyl]propyl}-4-({4-[({[(4-fluorophenyl)methyl]amino}acetyl)amino]phenyl}ethynyl)benzamide | 518.6 |
| 1055 | N-{(1S,2R)-2-amino-1-[(hydroxyamino)carbonyl]propyl}-4-({4-[({[(3-fluorophenyl)methyl]amino}acetyl)amino]phenyl}ethynyl)benzamide | 518.6 |
| 1056 | N-{(1S,2R)-2-amino-1-[(hydroxyamino)carbonyl]propyl}-4-[(4-{[(propylamino)acetyl]amino}phenyl)ethynyl]benzamide | 452.5 |
| 1057 | N-{(1S,2R)-2-amino-1-[(hydroxyamino)carbonyl]propyl}-4-{[4-({[(phenylmethyl)amino]acetyl}amino)phenyl]ethynyl}benzamide | 500.6 |
| 1058 | 1-((1R,2S)-3-(hydroxyamino)-1-methyl-3-oxo-2-{[(4-{[4-({[(phenylmethyl)amino]acetyl}amino)phenyl]ethynyl}phenyl)carbonyl]amino}propyl)triaza-1,2-dien-2-ium | 527.6 |
| 1059 | N-{(1S,2R)-2-amino-1-[(hydroxyamino)carbonyl]propyl}-4-[(4-{[(cyclobutylamino)acetyl]amino}phenyl)ethynyl]benzamide | 464.5 |
| 1060 | 1-[(1R,2S)-2-[({4-[(4-{[(cyclobutylamino)acetyl]amino}phenyl)ethynyl]phenyl}carbonyl)amino]-3-(hydroxyamino)-1-methyl-3-oxopropyl]triaza-1,2-dien-2-ium | 491.5 |
| 1061 | 4-[(4-ethylphenyl)ethynyl]-N-{(1S)-1-[(hydroxyamino)carbonyl]-2-methylpropyl}benzamide | 365.4 |
| 1062 | 4-(4-{4-[(ethylamino)methyl]phenyl}buta-1,3-diynyl)-N-{(1S,2R)-2-hydroxy-1-[(hydroxyamino)carbonyl]propyl}benzamide | 420.5 |
| 1063 | N-4(1S)-Maminomethyl)-2-(hydroxyamino)-2-oxoethyl]-4-[4-(3-aminophenyl)buta-1,3-diynyl]benzamide | 363.4 |
| 1064 | 4-(4-{3-[(4-aminobutanoyl)amino]phenyl}buta-1,3-diynyl)-N-{(1S,2R)-2-hydroxy-1-[(hydroxyamino)carbonyl]propyl}benzamide | 463.5 |
| 1065 | N-{(1S,2R)-2-hydroxy-1-[(hydroxyamino)carbonyl]propyl}-4-[4-(3-hydroxyphenyl)buta-1,3-diynyl]benzamide | 379.4 |
| 1066 | 4-(4-{2-[(aminoacetyl)amino]phenyl}buta-1,3-diynyl)-N-{(1S,2R)-2-hydroxy-1-[(hydroxyamino)carbonyl]propyl}benzamide | 435.4 |
| 1067 | N-[(1S)-1-(aminomethyl)-2-(hydroxyamino)-2-oxoethyl]-4-{4-[2,4-bis(methyloxy)pyrimidin-5-yl]buta-1,3-diynyl}benzamide | 410.4 |

TABLE 1-continued

| | | |
|---|---|---|
| 1068 | (2S)-6-amino-2-{[(4-{4-[4-({[(1S)-1-(aminomethyl)-2-(hydroxyamino)-2-oxoethyl]amino}carbonyl)phenyl]buta-1,3-diynyl}phenyl)carbonyl]amino}hexanoic acid | 520.6 |
| 1069 | N-[(1S)-1-(aminomethyl)-2-(hydroxyamino)-2-oxoethyl]-4-[4-(2-aminophenyl)buta-1,3-diynyl]benzamide | 363.4 |
| 1070 | 4-[4-(4-{2-[(2-aminoethyl)amino]-2-oxoethyl}phenyl)buta-1,3-diynyl]-N-[(1S)-1-(aminomethyl)-2-(hydroxyamino)-2-oxoethyl]benzamide | 448.5 |
| 1071 | N-[(1S)-1-(aminomethyl)-2-(hydroxyamino)-2-oxoethyl]-4-[4-(2-aminopyrimidin-5-yl)buta-1,3-diynyl]benzamide | 365.4 |
| 1072 | 4-(4-{3-[(4-aminobutanoyl)amino]phenyl}buta-1,3-diynyl)-N-[(1S)-1-(aminomethyl)-2-(hydroxyamino)-2-oxoethyl]benzamide | 448.5 |
| 1073 | 4-(4-{2-[(aminoacetyl)amino]phenyl}buta-1,3-diynyl)-N-[(1S)-1-(aminomethyl)-2-(hydroxyamino)-2-oxoethyl]benzamide | 420.4 |
| 1074 | 4-[4-(4-{2-[(2-aminoethyl)amino]-2-oxoethyl}phenyl)buta-1,3-diynyl]-N-{(1S,2R)-2-hydroxy-1-[(hydroxyamino)carbonyl]propyl}benzamide | 463.5 |
| 1075 | 4-[4-(4-{[(2,3-dihydroxypropyl)amino]methyl}phenyl)buta-1,3-diynyl]-N-{(1S,2R)-2-hydroxy-1-[(hydroxyamino)carbonyl]propyl}benzamide | 466.5 |
| 1076 | N-{(1S,2R)-2-hydroxy-1-[(hydroxyamino)carbonyl]propyl}-4-(4-{4-[({[2-(methyloxy)phenyl]methyl}amino)methyl]phenyl}buta-1,3-diynyl)benzamide | 512.6 |
| 1077 | N-{(1S,2R)-2-hydroxy-1-[(hydroxyamino)carbonyl]propyl}-4-(4-{4-[(pyridin-2-ylamino)methyl]phenyl}buta-1,3-diynyl)benzamide | 469.5 |
| 1078 | 4-[4-(4-{[(2-aminoethyl)amino]methyl}phenyl)buta-1,3-diynyl]-N-{(1S,2R)-2-hydroxy-1-[(hydroxyamino)carbonyl]propyl}benzamide | 435.5 |
| 1079 | 4-[(4-ethylphenyl)ethynyl]-N-[(1R)-1-[(ethylthio)methyl]-2-(hydroxyamino)-2-oxoethyl]benzamide | 397.5 |
| 1080 | 4-[(4-{[(2S)-2-aminopropanoyl]amino}phenyl)ethynyl]-N-[(1R)-1-[(ethylthio)methyl]-2-(hydroxyamino)-2-oxoethyl]benzamide | 455.5 |
| 1081 | N-[(1S)-1-(aminomethyl)-2-(hydroxyamino)-2-oxoethyl]-4-[4-(3-chlorophenyl)buta-1,3-diynyl]benzamide | 382.8 |
| 1082 | N-[(1S)-1-(aminomethyl)-2-(hydroxyamino)-2-oxoethyl]-4-{4-[3-(methyloxy)phenyl]buta-1,3-diynyl}benzamide | 378.4 |
| 1083 | N-{(1S,2R)-2-hydroxy-1-[(hydroxyamino)carbonyl]propyl}-4-(4-{4-[(methylsulfonyl)amino]phenyl}buta-1,3-diynyl)benzamide | 456.5 |
| 1084 | N-{(1S,2R)-2-hydroxy-1-[(hydroxyamino)carbonyl]propyl}-4-(4-{3-[(methylsulfonyl)amino]phenyl}buta-1,3-diynyl)benzamide | 456.5 |
| 1085 | N-[(1S)-1-(aminomethyl)-2-(hydroxyamino)-2-oxoethyl]-4-(4-pyrazin-2-ylbuta-1,3-diynyl)benzamide | 350.3 |
| 1086 | N-{(1S,2R)-2-hydroxy-1-[(hydroxyamino)carbonyl]propyl}-4-[4-(3-nitrophenyl)buta-1,3-diynyl]benzamide | 408.4 |
| 1087 | N-{(1S,2R)-2-hydroxy-1-[(hydroxyamino)carbonyl]propyl}-4-[(3-{[(methylsulfonyl)amino]methyl}phenyl)ethynyl]benzamide | 446.5 |
| 1088 | 4-[(2-formylphenyl)ethynyl]-N-{(1S,2R)-2-hydroxy-1-[(hydroxyamino)carbonyl]propyl}benzamide | 367.4 |
| 1089 | N-{(1R,2R)-2-hydroxy-1-[(hydroxyamino)carbonyl]propyl}-4-[(3-{[(methylsulfonyl)amino]methyl}phenyl)ethynyl]benzamide | 446.5 |
| 1090 | 4-({2-[(aminoacetyl)amino]phenyl}ethynyl)-N-{(1S,2R)-2-hydroxy-1-[(hydroxyamino)carbonyl]propyl}benzamide | 411.4 |

TABLE 1-continued

| | | |
|---|---|---|
| 1091 | N-{(1S)-2-hydroxy-1-[(hydroxyamino)carbonyl]propyl}-4-{4-[3-(morpholin-4-ylmethyl)phenyl]buta-1,3-diynyl}benzamide | 462.5 |
| 1092 | N-[(1S)-1-(aminomethyl)-2-(hydroxyamino)-2-oxoethyl]-4-({4-[(methylamino)methyl]phenyl}ethynyl)benzamide | 367.4 |
| 1093 | N-[(1S)-1-(aminomethyl)-2-(hydroxyamino)-2-oxoethyl]-4-({4-[(ethylamino)methyl]phenyl}ethynyl)benzamide | 381.4 |
| 1094 | N-[(1S)-1-(aminomethyl)-2-(hydroxyamino)-2-oxoethyl]-4-({4-[(propylamino)methyl]phenyl}ethynyl)benzamide | 395.5 |
| 1095 | N-[(1S)-1-(aminomethyl)-2-(hydroxyamino)-2-oxoethyl]-4-({4-[(pentylamino)methyl]phenyl}ethynyl)benzamide | 423.5 |
| 1096 | N-[(1S)-1-(aminomethyl)-2-(hydroxyamino)-2-oxoethyl]-4-({4-[(hexylamino)methyl]phenyl}ethynyl)benzamide | 437.6 |
| 1097 | N-[(1S)-1-(aminomethyl)-2-(hydroxyamino)-2-oxoethyl]-4-[(4-{[(1-methylethyl)amino]methyl}phenyl)ethynyl]benzamide | 395.5 |
| 1098 | N-[(1S)-1-(aminomethyl)-2-(hydroxyamino)-2-oxoethyl]-4-[(4-{[(2-methylpropyl)amino]methyl}phenyl)ethynyl]benzamide | 409.5 |
| 1099 | N-[(1S)-1-(aminomethyl)-2-(hydroxyamino)-2-oxoethyl]-4-[(4-{[(1,1-dimethylethyl)amino]methyl}phenyl)ethynyl]benzamide | 409.5 |
| 1100 | N-[(1S)-1-(aminomethyl)-2-(hydroxyamino)-2-oxoethyl]-4-({4-[(dimethylamino)methyl]phenyl}ethynyl)benzamide | 381.4 |
| 1101 | N-[(1S)-1-(aminomethyl)-2-(hydroxyamino)-2-oxoethyl]-4-[(4-{[ethyl(methyl)amino]methyl}phenyl)ethynyl]benzamide | 395.5 |
| 1102 | N-[(1S)-1-(aminomethyl)-2-(hydroxyamino)-2-oxoethyl]-4-{[4-({[2-(dimethylamino)ethyl]amino}methyl)phenyl]ethynyl}benzamide | 424.5 |
| 1103 | N-[(1S)-1-(aminomethyl)-2-(hydroxyamino)-2-oxoethyl]-4-{[4-({[4-(dimethylamino)butyl]amino}methyl)phenyl]ethynyl]benzamide | 452.6 |
| 1104 | N-[(1S)-1-(aminomethyl)-2-(hydroxyamino)-2-oxoethyl]-4-[(4-{[(2-cyanoethyl)amino]methyl}phenyl)ethynyl]benzamide | 406.5 |
| 1105 | 4-{[4-({[2-(acetylamino)ethyl]amino}methyl)phenyl]ethynyl}-N-[(1S)-1-(aminomethyl)-2-(hydroxyamino)-2-oxoethyl]benzamide | 438.5 |
| 1106 | 4-[(4-{[(2-aminoethyl)amino]methyl}phenyl)ethynyl]-N-[(1S)-1-(aminomethyl)-2-(hydroxyamino)-2-oxoethyl]benzamide | 396.5 |
| 1107 | N-[(1S)-1-(aminomethyl)-2-(hydroxyamino)-2-oxoethyl]-4-[(4-{[(3-hydroxypropyl)amino]methyl}phenyl)ethynyl]benzamide | 411.5 |
| 1108 | N-[(1S)-1-(aminomethyl)-2-(hydroxyamino)-2-oxoethyl]-4-{[4-({[3-(methyloxy)propyl]amino}methyl)phenyl]ethynyl}benzamide | 425.5 |
| 1109 | N-[(1S)-1-(aminomethyl)-2-(hydroxyamino)-2-oxoethyl]-4-{[4-({methyl[2-(methyloxy)ethyl]amino}methyl)phenyl]ethynyl}benzamide | 425.5 |
| 1110 | N-[(1S)-1-(aminomethyl)-2-(hydroxyamino)-2-oxoethyl]-4-{[4-({[3-(2-oxopyrrolidin-1-yl)propyl]amino}methyl)phenyl]ethynyl}benzamide | 478.6 |
| 1111 | N-[(1S)-1-(aminomethyl)-2-(hydroxyamino)-2-oxoethyl]-4-[(4-{[(3-morpholin-4-ylpropyl)amino]methyl}phenyl)ethynyl]benzamide | 480.6 |

TABLE 1-continued

| | | |
|---|---|---|
| 1112 | N-[(1S)-1-(aminomethyl)-2-(hydroxyamino)-2]-oxoethyl]-4-({4-[(cyclopropylamino)methyl]phenyl}ethynyl)benzamide | 393.5 |
| 1113 | N-[(1S)-1-(aminomethyl)-2-(hydroxyamino)-2-oxoethyl]-4-({4-[(cyclobutylamino)methyl]phenyl}ethynyl)benzamide | 407.5 |
| 1114 | N-[(1S)-1-(aminomethyl)-2-(hydroxyamino)-2-oxoethyl]-4-({4-[(cyclopentylamino)methyl]phenyl}ethynyl)benzamide | 421.5 |
| 1115 | N-[(1S)-1-(aminomethyl)-2-(hydroxyamino)-2-oxoethyl]-4-({4-[(cycloheptylamino)methyl]phenyl}ethynyl)benzamide | 449.6 |
| 1116 | N-[(1S)-1-(aminomethyl)-2-(hydroxyamino)-2-oxoethyl]-4-({4-[(cyclooctylamino)methyl]pheny]}ethynyl)benzamide | 463.6 |
| 1117 | N-[(1S)-1-(aminomethyl)-2-(hydroxyamino)-2-oxoethyl]-4-{[4-(pyrrolidin-1-ylmethyl)phenyl]ethynyl}benzamide | 407.5 |
| 1118 | N-[(1S)-1-(aminomethyl)-2-(hydroxyamino)-2-oxoethyl]-4-{[4-(azepan-1-ylmethyl)phenyl]ethynyl}benzamide | 435.5 |
| 1119 | N-[(1S)-1-(aminomethyl)-2-(hydroxyamino)-2-oxoethyl]-4-[(4-{[(3R)-3-(dimethylamino)pyrrolidin-1-yl]methyl}phenyl)ethynyl]benzamide | 450.6 |
| 1120 | N-[(1S)-1-(aminomethyl)-2-(hydroxyamino)-2-oxoethyl]-4-[(4-{[(3S)-3-(dimethylamino)pyrrolidin-1-yl]methyl}phenyl)ethynyl]benzamide | 450.6 |
| 1121 | 4-[(4-{[(3R)-3-(acetylamino)pyrrolidin-1-yl]methyl}phenyl)ethynyl]-N-[(1S)-1-(aminomethyl)-2-(hydroxyamino)-2-oxoethyl]benzamide | 464.5 |
| 1122 | 4-[(4-{[(3S)-3-(acetylamino)pyrrolidin-1-yl]methyl}phenyl)ethynyl]-N-[(1S)-1-(aminomethyl)-2-(hydroxyamino)-2-oxoethyl]benzamide | 464.5 |
| 1123 | N-[(1S)-1-(aminomethyl)-2-(hydroxyamino)-2-oxoethyl]-4-{[4-(1,4'-bipiperidin-1'-ylmethyl)phenyl]ethynyl}benzamide | 504.6 |
| 1124 | N-[(1S)-1-(aminomethyl)-2-(hydroxyamino)-2-oxoethyl]-4-[(4-{[(cyclohexylmethyl)amino]methyl}phenyl)ethynyl]benzamide | 449.6 |
| 1125 | N-[(1S)-1-(aminomethyl)-2-(hydroxyamino)-2-oxoethyl]-4-[(4-{[cyclohexyl(methyl)amino]methyl}phenyl)ethynyl]benzamide | 449.6 |
| 1126 | N-[(1S)-1-(aminomethyl)-2-(hydroxyamino)-2-oxoethyl]-4-{[4-({[(1R)-1-phenylethyl]amino}methyl)phenyl]ethynyl}benzamide | 457.5 |
| 1127 | N-[(1S)-1-(aminomethyl)-2-(hydroxyamino)-2-oxoethyl]-4-{[4-({[(1S)-1-phenylethyl]amino}methyl)phenyl]ethynyl}benzamide | 457.5 |
| 1128 | N-[(1S)-1-(aminomethyl)-2-(hydroxyamino)-2-oxoethyl]-4-[(4-{[(thien-2-ylmethyl)amino]methyl}phenyl)ethynyl]benzamide | 449.5 |
| 1129 | N-[(1S)-1-(aminomethyl)-2-(hydroxyamino)-2-oxoethyl]-4-[(4-{[(2-phenylethyl)amino]methyl}phenyl)ethynyl]benzamide | 457.5 |
| 1130 | N-[(1S)-1-(aminomethyl)-2-(hydroxyamino)-2-oxoethyl]-4-({4-[(piperidin-3-ylamino)methyl]phenyl}ethynyl)benzamide | 436.5 |
| 1131 | N-[(1S)-1-(aminomethyl)-2-(hydroxyamino)-2-oxoethyl]-4-({4-[(piperidin-4-ylamino)methyl]phenyl}ethynyl)benzamide | 436.5 |
| 1132 | N-[(1S)-1-(aminomethyl)-2-(hydroxyamino)-2-oxoethyl]-4-[(4-{[(piperidin-2-ylmethyl)amino]methyl}phenyl)ethynyl]benzamide | 450.6 |
| 1133 | N-[(1S)-1-(aminomethyl)-2-(hydroxyamino)-2-oxoethyl]-4-[(4-{[(piperidin-3-ylmethyl)amino]methyl}phenyl)ethynyl]benzamide | 450.6 |

TABLE 1-continued

| | | |
|---|---|---|
| 1134 | N-[(1S)-1-(aminomethyl)-2-(hydroxyamino)-2-oxoethyl]-4-{[4-({[(2R)-pyrrolidin-2-ylmethyl]amino}methyl)phenyl]ethynyl}benzamide | 436.5 |
| 1135 | N-[(1S)-1-(aminomethyl)-2-(hydroxyamino)-2-oxoethyl]-4-{[4-({[(2S)-pyrrolidin-2-ylmethyl]amino}methyl)phenyl]ethynyl}benzamide | 436.5 |
| 1136 | N-[(1S)-1-(aminomethyl)-2-(hydroxyamino)-2-oxoethyl]-4-({4-[(pyrrolidin-3-ylamino)methyl]phenyl}ethynyl)benzamide | 422.5 |
| 1137 | N-[(1S)-1-(aminomethyl)-2-(hydroxyamino)-2-oxoethyl]-4-{[4-({[(2-fluorophenyl)methyl]amino}methyl)phenyl]ethynyl}benzamide | 461.5 |
| 1138 | N-[(1S)-1-(aminomethyl)-2-(hydroxyamino)-2-oxoethyl]-4-{[4-({[(3-fluorophenyl)methyl]amino}methyl)phenyl]ethynyl}benzamide | 461.5 |
| 1139 | N-[(1S)-1-(aminomethyl)-2-(hydroxyamino)-2-oxoethyl]-4-{[4-({[(4-fluorophenyl)methyl]amino}methyl)phenyl]ethynyl}benzamide | 461.5 |
| 1140 | N-[(1S)-1-(aminomethyl)-2-(hydroxyamino)-2-oxoethyl]-4-{[4-({[(2-methylphenyl)methyl]amino}methyl)phenyl]ethynyl}benzamide | 457.5 |
| 1141 | N-[(1S)-1-(aminomethyl)-2-(hydroxyamino)-2-oxoethyl]-4-{[4-({[(3-methylphenyl)methyl]amino}methyl)phenyl]ethynyl}benzamide | 457.5 |
| 1142 | N-[(1S)-1-(aminomethyl))-2-(hydroxyamino)-2-oxoethyl]-4-{[4-({[(4-methylphenyl)methyl]amino}methyl)phenyl)]ethynyl]benzamide | 457.5 |
| 1143 | N-[(1S)-1-(aminomethyl)-2-(hydroxyamino)-2-oxoethyl]-4-({4-[({[2-(methyloxy)phenyl]methyl}amino)methyl]phenyl}ethynyl)benzamide | 473.5 |
| 1144 | N-[(1S)-1-(aminomethyl)-2-(hydroxyamino)-2-oxoethyl]-4-({4-[({[3-(methyloxy)phenyl]methyl}amino)methyl]phenyl}ethynyl)benzamide | 473.5 |
| 1145 | N-[(1S)-1-(aminomethyl)-2-(hydroxyamino)-2-oxoethyl]-4-{[4-({[(3-methylphenyl)methyl]amino}methyl)phenyl]ethynyl}benzamide | 473.5 |
| 1146 | N-[(1S)-1-(aminomethy))-2-(hydroxyamino)-2-oxoethyl]-4-{[4-({[(4-methylphenyl)methyl]amino}methyl)pheny)]ethynyl}benzamide | 429.5 |
| 1147 | N-[(1S)-1-(aminomethyl)-2-(hydroxyamino)-2-oxoethyl]-4-({4-[({[2-(methyloxy)phenyl]methyl}amino)methyl]phenyl}ethynyl)benzamide | 444.5 |
| 1148 | N-[(1S)-1-(aminomethyl)-2-(hydroxyamino)-2-oxoethyl]-4-({4-[({[3-(methyloxy)phenyl]methyl}amino)methyl]phenyl}ethynyl)benzamide | 497.6 |
| 1149 | N-[(1S)-1-(aminomethyl)-2-(hydroxyamino)-2-oxoethyl]-4-({4-[(4-phenylpiperazin-1-yl)methyl]phenyl}ethynyl)benzamide | 498.6 |
| 1150 | N-[(1S)-1-(aminomethyl)-2-(hydroxyamino)-2-oxoethyl]-4-[(4-{[(1R,2R,4S)-bicyclo[2.2.1]hept-2-ylamino]methyl}phenyl)ethynyl]benzamide | 447.5 |
| 1151 | N-[(1S)-1-(aminomethyl)-2-(hydroxyamino)-2-oxoethyl]-4-({4-[({[(1S,2R,5S)-6,6-dimethylbicyclo[3.1.1]hept-2-yl]methyl}amino)methyl]phenyl}ethynyl)benzamide | 489.6 |
| 1152 | N-[(1S)-1-(aminomethyl)-2-(hydroxyamino)-2-oxoethyl]-4-[(4-{[(1S,4R)-bicyclo[2.2.1]hept-2-ylamino]methyl}phenyl)ethynyl]benzamide | 447.5 |
| 1153 | N-[(1S)-1-(aminomethyl)-2-(hydroxyamino)-2-oxoethyl]-4-{[4-({[(1S,2S,3S,5R)-2,6,6-trimethylbicyclo[3.1.1]hept-3-yl]amino}methyl)phenyl]ethynyl}benzamide | 489.6 |
| 1154 | 1-((1R,2S)-3-(hydroxyamino)-1-methyl-3-oxo-2-{[(4-{[4-({[(pyridin-4-ylmethyl)amino]acetyl}amino)phenyl]ethynyl}phenyl)carbonyl]amino}propyl)triaza-1,2-dien 2-ium | 528.6 |

TABLE 1-continued

| | | |
|---|---|---|
| 1155 | 1-((1R,2S)-3-(hydroxyamino)-1-methyl-3-oxo-2-{[(4-{[4-({[(pyridin-3-ylmethyl)amino]acetyl}amino)phenyl]ethynyl}phenyl)carbonyl]amino}propyl)triaza-1,2-dien-2-ium | 528.6 |
| 1156 | N-{(1S,2R)-2-amino-1-[(hydroxyamino)carbonyl]propyl}-4-{[4-({[(pyridin-4-ylmethyl)amino]acetyl}amino)phenyl]ethynyl}benzamide | 501.6 |
| 1157 | N-{(1S,2R)-2-amino-1-[(hydroxyamino)carbonyl]propyl}-4-{[4-({[(pyridin-3-ylmethyl)amino]acetyl}amino)phenyl]ethynyl}benzamide | 501.6 |
| 1158 | N-[1-[(hydroxyamino)carbonyl]-2-(methylamino)propyl]-4-{[4-({[(phenylmethyl)amino]acetyl}amino)phenyl]ethynyl}benzamide | 514.6 |
| 1159 | 4-[(4-{[(cyclobutylamino)acetyl]amino}phenyl)ethynyl]-N-[1-[(hydroxyamino)carbonyl]-2-(methylamino)propyl]benzamide | 478.6 |
| 1160 | 4-[(4-{[(2S)-2-aminopropanoyl]amino}pheny)ethynyl]-N-[(1R)-1-{[ethyl(hydroxy)-lambda~4~-sulfanyl]methyl}-2-(hydroxyamino)-2-oxoethyl]benzamide | 473.6 |
| 1161 | 4-[(4-ethylphenyl)ethynyl]-N-hydroxybenzamide | 266.3 |
| 1162 | N-[(1S)-1-(aminomethyl)-2-(hydroxyamino)-2-oxoethyl]-4-[4-(2,4-difluorophenyl)buta-1,3-diynyl]benzamide | 384.4 |
| 1163 | N-[(1S)-1-(aminomethyl)-2-(hydroxyamino)-2-oxoethyl]-4-[(2-aminophenyl)ethynyl]benzamide | 339.4 |
| 1164 | N-[(1S)-1-(arninomethyl)-2-(hydroxyamino)-2-oxoethyl]-4-[4-(3-{[(methy)sulfonyl)amino]methyl}phenyl)buta-1,3-diynyl]benzamide | 455.5 |
| 1165 | N-[(1S)-1-(aminomethyl)-2-(hydroxyamino)-2-oxoethyl]-4-[4-(3-{[(methylsulfonyl)amino]methyl}phenyl)buta-1,3-diynyl]benzamide | 455.5 |
| 1166 | N-[(1S)-1-(aminomethyl)-2-(hydroxyamino)-2-oxoethyl]-4-({3-[(methylsulfonyl)amino]phenyl}ethynyl)benzamide | 417.5 |
| 1167 | 4-[(4-{[(2S)-2-aminopropanoyl]amino}phenyl)ethynyl]-N hydroxybenzamide | 324.4 |
| 1168 | 4-[(2-{[(2-aminoethyl)amino]methyl}phenyl)ethynyl]-N-{(1S,2R)-2-hydroxy-1-[(hydroxyamino)carbonyl]propyl}benzamide | 411.5 |
| 1169 | N-{(1R,2R)-2-amino-1-[(hydroxyamino)carbonyl]propyl}-4-(phenylethynyl)benzamide | 338.4 |
| 1170 | N-{(1S,2R)-2-amino-1-[(hydroxyamino)carbonyl]propyl}-4-[4-(4-aminophenyl)buta-1,3-diynyl]benzamide | 377.4 |
| 1171 | N-[(1S)-1-(aminomethyl)-2-(hydroxyamino)-2-oxoethyl]-4-[4-(3-hydroxyphenyl)buta-1,3-diynyl]benzamide | 364.4 |
| 1172 | N-[(1S)-1-(aminomethyl)-2-(hydroxyamino)-2-oxoethyl]-4-{4-[3-(morpholin-4-ylmethyl)phenyl]buta-1,3-diynyl}benzamide | 447.5 |
| 1173 | N-{(1S,2R)-2-hydroxy-1-[(hydroxyamino)carbonyl]propyl}-4-({4-[({[2-(methyloxy)phenyl]methyl}amino)methyl]phenyl}ethynyl)benzamide | 488.6 |
| 1174 | 4-[(4-{[(2,3-dihydroxypropyl)amino]methyl}phenyl)ethynyl]-N-{(1S,2R)-2-hydroxy-1-[(hydroxyamino)carbonyl]propyl}benzamide | 442.5 |
| 1175 | 4-({2-[(dimethylamino)methyl]phenyl}ethynyl)-N-{(1S,2R)-2-hydroxy-1-[(hydroxyamino)carbonyl]propyl}benzamide | 396.5 |
| 1176 | N-{(1S,2R)-2-hydroxy-1-[(hydroxyamino)carbonyl]propyl}-4-({4-[(methylamino)methyl]phenyl}ethynyl)benzamide | 382.4 |

TABLE 1-continued

| | | |
|---|---|---|
| 1177 | N-{(1S,2R)-2-hydroxy-1-[(hydroxyamino)carbonyl]propyl}-4-({4-[(propylamino)methyl]phenyl}ethynyl)benzamide | 410.5 |
| 1178 | 4-({4-[(butylamino)methyl]phenyl}ethynyl)-N-{(1S,2R)-2-hydroxy-1-[(hydroxyamino)carbonyl]propyl}benzamide | 424.5 |
| 1179 | N-{(1S,2R)-2-hydroxy-1-[(hydroxyamino)carbonyl]propyl}-4-({4-[(pentylamino)methyl]phenyl}ethynyl)benzamide | 438.5 |
| 1180 | 4-({4-[(hexylamino)methyl]phenyl}ethynyl)-N-{(1S,2R)-2-hydroxy-1-[(hydroxyamino)carbonyl]propyl}benzamide | 452.6 |
| 1181 | N-{(1S,2R)-2-hydroxy-1-[(hydroxyamino)carbonyl]propyl}-4-[(4-{[(1-methylethyl)amino]methyl}phenyl)ethynyl]benzamide | 410.5 |
| 1182 | N-{(1S,2R)-2-hydroxy-1-[(hydroxyamino)carbonyl]propyl}-4-[(4-{[(2-methylpropyl)amino]methyl}phenyl)ethynyl]benzamide | 424.5 |
| 1183 | 4-[(4-{[(1,1-dimethylethyl)amino]methyl}phenyl)ethynyl]-N-{(1S,2R)-2-hydroxy-1-[(hydroxyamino)carbonyl]propyl}benzamide | 424.5 |
| 1184 | 4-[(4-{[ethyl(methyl)amino]methyl}phenyl)ethynyl]-N-{(1S,2R)-2-hydroxy-1-[(hydroxyamino)carbonyl]propyl}benzamide | 410.5 |
| 1185 | 4-{[4-({[2-(dimethylamino)ethyl]amino}methyl)phenyl]ethynyl}-N-{(1S,2R)-2-hydroxy-1-[(hydroxyamino)carbonyl]propyl}benzamide | 439.5 |
| 1186 | 4-{[4-({[4-(dimethylamino)butyl]amino}methyl)phenyl]ethynyl}-N-{(1S,2R)-2-hydroxy-1-[(hydroxyamino)carbonyl]propyl}benzamide | 467.6 |
| 1187 | 4-[(4-{[(2-hydroxyethyl)amino]methyl}phenyl)ethynyl]-N-{(1S,2R)-2-hydroxy-1-[(hydroxyamino)carbonyl]propyl}benzamide | 412.5 |
| 1188 | N-{(1S,2R)-2-hydroxy-1-[(hydroxyamino)carbonyl]propyl}-4-[(4-{[(3-hydroxypropyl)amino]methyl}phenyl)ethynyl]benzamide | 426.5 |
| 1189 | N-{(1S,2R)-2-hydroxy-1-[(hydroxyamino)carbonyl]propyl}-4-{[4-({methyl[2-(methyloxy)ethyl]amino}methyl)phenyl]ethynyl}benzamide | 440.5 |
| 1190 | N-{(1S,2R)-2-hydroxy-1-[(hydroxyamino)carbonyl]propyl}-4-{[4-({[2-(methyloxy)ethyl]amino}methyl)phenyl]ethynyl}benzamide | 426.5 |
| 1191 | N-{(1S,2R)-2-hydroxy-1-[(hydroxyamino)carbonyl]propyl}-4-{[4-({[3-(methyloxy)propyl]amino}methyl)phenyl]ethynyl}benzamide | 440.5 |
| 1192 | 4-[(4-{[(2-cyanoethyl)amino]methyl}phenyl)ethynyl]-N-{(1S,2R)-2-hydroxy-1-[(hydroxyamino)carbonyl]propyl}benzamide | 421.5 |
| 1193 | 4-{[4-({[2-(acetylamino)ethyl]amino}methyl)phenyl]ethynyl}-N-{(1S,2R)-2-hydroxy-1-[(hydroxyamino)carbonyl]propyl}benzamide | 453.5 |
| 1194 | N-{(1S,2R)-2-hydroxy-1-[(hydroxyamino)carbonyl]propyl}-4-{[4-({[3-(2-oxopyrrolidin-1-yl)propyl]amino}methyl)phenyl]ethynyl}benzamide | 493.6 |
| 1195 | N-{(1S,2R)-2-hydroxy-1-[(hydroxyamino)carbonyl]propyl}-4-[(4-{[(3-morpholin-4-ylpropyl)amino]methyl}phenyl)ethynyl]benzamide | 495.6 |
| 1196 | 4-({4-[(cyclopropylamino)methyl]phenyl}ethynyl)-N-{(1S,2R)-2-hydroxy-1-[(hydroxyamino)carbonyl]propyl}benzamide | 408.5 |
| 1197 | 4-({4-[(cyclobutylamino)methyl]phenyl}ethynyl)-N-{(1S,2R)-2-hydroxy-1-[(hydroxyamino)carbonyl]propyl}benzamide | 422.5 |

TABLE 1-continued

| | | |
|---|---|---|
| 1198 | 4-({4-[(cyclopentylamino)methyl]phenyl}ethynyl)-N-{(1S,2R)-2-hydroxy-1-[(hydroxyamino)carbonyl]propyl}benzamide | 436.5 |
| 1199 | 4-({4-[(cyclohexylamino)methyl]phenyl}ethynyl)-N-{(1S,2R)-2-hydroxy-1-[(hydroxyamino)carbonyl]propyl}benzamide | 450.5 |
| 1200 | 4-({4-[(cycloheptylamino)methyl]phenyl}ethynyl)-N-{(1S,2R)-2-hydroxy-1-[(hydroxyamino)carbonyl]propyl}benzamide | 464.6 |
| 1201 | 4-({4-[(cyclooctylamino)methyl]phenyl}ethynyl)-N-{(1S,2R)-2-hydroxy-1-[(hydroxyamino)carbonyl]propyl}benzamide | 478.6 |
| 1202 | 4-{[4-(azepan-1-ylmethyl)phenyl]ethynyl}-N-{(1S,2R)-2-hydroxy-1-[(hydroxyamino)carbonyl]propyl}benzamide | 450.5 |
| 1203 | 4-[(4-{[(3R)-3-(dimethylamino)pyrrolidin-1-yl]methyl}phenyl)ethynyl]-N-{(1S,2R)-2-hydroxy-1-[(hydroxyamino)carbonyl]propyl}benzamide | 465.6 |
| 1204 | 4-[(4-{[(3S)-3-(dimethylamino)pyrrolidin-1-yl]methyl}phenyl)ethynyl]-N-{(1S,2R)-2-hydroxy-1-[(hydroxyamino)carbonyl]propyl}benzamide | 465.6 |
| 1205 | 4-[(4-{[(3R)-3-(acetylamino)pyrrolidin-1-yl]methyl}phenyl)ethynyl]-N-{(1S,2R)-2-hydroxy-1-[(hydroxyamino)carbonyl]propyl}benzamide | 479.5 |
| 1206 | 4-[(4-{[(3S)-3-(acetylamino)pyrrolidin-1-yl]]methyl}phenyl)ethynyl]-N-{(1S,2R)-2-hydroxy-1-[(hydroxyamino)carbonyl]propyl}benzamide | 479.5 |
| 1207 | 4-{[4-(1,4'-bipiperidin-1'-ylmethyl)phenyl]ethynyl}-N-{(1S,2R)-2-hydroxy-1-[(hydroxyamino)carbonyl]propyl}benzamide | 519.7 |
| 1208 | 4-[(4-{[(cyclohexylmethyl)amino]methyl}phenyl)ethynyl]-N-{(1S,2R)-2-hydroxy-1-[(hydroxyamino)carbonyl]propyl}benzamide | 464.6 |
| 1209 | N-{(1S,2R)-2-hydroxy-1-[(hydroxyamino)carbonyl]propyl}-4-({4-[(4-phenylpiperazin-1-yl)methyl]phenyl}ethynyl)benzamide | 513.6 |
| 1210 | N-{(1S,2R)-2-hydroxy-1-[(hydroxyamino)carbonyl]propyl}-4-[(4-{[(2-phenylethyl)amino]methyl}phenyl)ethynyl]benzamide | 472.6 |
| 1211 | N-{(1S,2R)-2-hydroxy-1-[(hydroxyamino)carbonyl]propyl}-4-{[4-({[(1R)-1-phenylethyl]amino}methyl)phenyl]ethynyl}benzamide | 472.6 |
| 1212 | N-{(1S,2R)-2-hydroxy-1-[(hydroxyamino)carbonyl]propyl}-4-{[4-({[(1S)-1-phenylethyl]amino}methyl)phenyl]ethynyl}benzamide | 472.6 |
| 1213 | N-{(1S,2R)-2-hydroxy-1-[(hydroxyamino)carbonyl]propyl}-4-[(4-{[(thien-2-ylmethyl)amino]methyl}phenyl)ethynyl]benzamide | 464.6 |
| 1214 | N-{(1S,2R)-2-hydroxy-1-[(hydroxyamino)carbonyl]propyl}-4-({4-[(piperidin-3-ylamino)methyl]phenyl}ethynyl)benzamide | 451.5 |
| 1215 | N-{(1S,2R)-2-hydroxy-1-[(hydroxyamino)carbonyl]propyl}-4-({4-[(piperidin-4-ylamino)methyl]phenyl}ethynyl)benzamide | 451.5 |
| 1216 | N-{(1S,2R)-2-hydroxy-1-[(hydroxyamino)carbonyl]propyl}-4-[(4-{[(piperidin-2-ylmethyl)amino]methyl}phenyl)ethynyl]benzamide | 465.6 |

TABLE 1-continued

| | | |
|---|---|---|
| 1217 | N-{(1S,2R)-2-hydroxy-1-[(hydroxyamino)carbonyl]propy)}-4-[(4-{[(piperidin-3-ylmethyl)amino]methyl}phenyl)ethynyl]benzamide | 465.6 |
| 1218 | N-(1S,2R)-2-hydroxy-1-[(hydroxyamino)carbonyl]propyl}-4-{[4-({[(2R)-pyrrolidin-2-ylmethyl]amino}methyl)phenyl]ethynyl}benzamide | 451.5 |
| 1219 | N-{(1S,2R)-2-hydroxy-1-[(hydroxyamino)carbonyl]propyl}-4-{[4-({[(2S)-pyrrolidin-2-ylmethyl]amino}methyl)phenyl]ethynyl}benzamide | 451.5 |
| 1220 | N-{(1S,2R)-2-hydroxy-1-[(hydroxyamino)carbonyl]propyl}-4-({4-[(pyrrolidin-3-ylamino)methyl]phenyl}ethynyl)benzamide | 437.5 |
| 1221 | 4-{[4-({[(2-fluorophenyl)methyl]amino}methyl)phenyl]ethynyl}-N-{(1S,2R)-2-hydroxy-1-[(hydroxyamino)carbonyl]propyl}benzamide | 476.5 |
| 1222 | 4-{[4-({[(3-fluorophenyl)methyl]amino}methyl)phenyl]ethynyl}-N-{(1S,2R)-2-hydroxy-1-[(hydroxyamino)carbonyl]propyl}benzamide | 476.5 |
| 1223 | 4-{[4-({[(4-fluorophenyl)methyl]amino}methyl)phenyl]ethynyl}-N-{(1S,2R)-2-hydroxy-1-[(hydroxyamino)carbonyl]propyl}benzamide | 476.5 |
| 1224 | N-{(1S,2R)-2-hydroxy-1-[(hydroxyamino)carbonyl]propyl}-4-{[4-({[(2-methylphenyl)methyl]amino}methyl)phenyl]ethynyl}benzamide | 472.6 |
| 1225 | N-{(1S,2R)-2-hydroxy-1-[(hydroxyamino)carbonyl]propyl}-4-{[4-({[(3-methylphenyl)methyl]amino}methyl)phenyl]ethynyl}benzamide | 472.6 |
| 1226 | N-{(1S,2R)-2-hydroxy-1-[(hydroxyamino)carbonyl]propyl}-4-{[4-({[(4-methylphenyl)methyl]amino}methyl)phenyl]ethynyl}benzamide | 472.6 |
| 1227 | N-{(1S,2R)-2-hydroxy-1-[(hydroxyamino)carbonyl]propyl}-4-[(4-{[(phenylmethyl)amino]methyl}phenyl)ethynyl]benzamide | 458.5 |
| 1228 | N-{(1S,2R)-2-hydroxy-1-[(hydroxyamino)carbonyl]propyl}-4-({4-[(phenylamino)methyl]phenyl}ethynyl)benzamide | 444.5 |
| 1229 | N-{(1S,2R)-2-hydroxy-1-[(hydroxyamino)carbonyl]propyl}-4-[(4-{[(pyridin-3-ylmethyl)amino]methyl}phenyl)ethynyl]benzamide | 459.5 |
| 1230 | 4-[(4-{[(1R,2R,4S)-bicyclo[2.2.1]hept-2-ylamino]methyl}phenyl)ethynyl]-N-{(1S,2R)-2-hydroxy-1-[(hydroxyamino)carbonyl]propyl}benzamide | 462.6 |
| 1231 | (3R)-N-hydroxy-3-({[4-(phenylethynyl)phenyl]carbonyl}amino)piperidine-3-carboxamide | 364.4 |
| 1232 | 4-({[4-(phenylethynyl)phenyl]carbonyl}amino)piperidine-4-carboxylic acid | 349.4 |
| 1233 | N-{(1S)-2-(hydroxyamino)-2-oxo-1-[(2S)-pyrrolidin-2-ylmethyl]ethyl}-4-(phenylethynyl)benzamide | 378.4 |
| 1234 | (3R)-3-{[(4'-ethyl-1,1'-biphenyl-4-yl)carbonyl]amino}-N-hydroxypiperidine-3-carboxamide | 368.4 |
| 1235 | 1,1-dimethylethyl 3-(4-{4-[({(1S,2R)-2-hydroxy-1-[(hydroxyamino)carbonyl]propy})amino]carbonyl}phenyl}buta-1,3-diynyl)phenylcarbamate | 478.5 |
| 1236 | 4-[4-(3-amino-4-methylphenyl)buta-1,3-diynyl]-N-{(1S,2R)-2-hydroxy-1-[(hydroxyamino)carbonyl]propyl}benzamide | 392.4 |
| 1237 | N-[(1S)-1-(aminomethyl)-2-(hydroxyamino)-2-oxoethyl]-4-[4-(3-amino-4-methylphenyl)buta-1,3-diynyl]benzamide | 377.4 |

TABLE 1-continued

| | | |
|---|---|---|
| 1238 | 4-(4-{4-[(aminoacetyl)amino]-3-methylphenyl}buta-1,3-diynyl)-N-[(1S)-1-(aminomethyl)-2-(hydroxyamino)-2-oxoethyl]benzamide | 434.5 |
| 1239 | N-{(1S,2R)-2-amino-1-[(hydroxyamino)carbonyl]propyl}-4-(2-phenylethenyl)benzamide | 340.4 |
| 1240 | N-[(2R)-2-amino-3-(hydroxyamino)-3-oxopropyl]-4-ethyl-1,1'-biphenyl-4-carboxamide | 328.4 |
| 1241 | N-[(2R)-2-amino-3-(hydroxyamino)-3-oxopropyl]-4-(phenylethynyl)benzamide | 324.4 |
| 1242 | N-[(2R)-2-amino-3-(hydroxyamino)-3-oxopropyl]-4-(4-chlorophenyl)cyclohexanecarboxamide | 340.8 |
| 1243 | N-[(2S)-2-amino-3-(hydroxyamino)-3-oxopropyl]-4-(4-chlorophenyl)cyclohexanecarboxamide | 340.8 |
| 1244 | N-[(1S)-1-(aminomethyl)-2-(hydroxyamino)-2-oxoethyl]-4-[2-(4-methylphenyl)ethyl]benzamide | 342.4 |
| 1245 | N-[(1S)-1-(aminomethyl)-2-(hydroxyamino)-2-oxoethyl]-4-[4-(4-aminophenyl)butyl]benzamide | 371.4 |
| 1246 | N-{(1S,2R)-2-hydroxy-1-[(hydroxyamino)carbonyl]propyl}-4-{[4-({[methyl(pyridin-2-ylmethyl)amino]acetyl}amino)phenyl]ethynyl}benzamide | 516.6 |
| 1247 | 4-{[4-({[[(2-fluorophenyl)methyl](methyl)amino]acetyl}amino)phenyl]ethynyl}-N-{(1S,2R)-2-hydroxy-1-[(hydroxyamino)carbonyl]propyl}benzamide | 533.6 |
| 1248 | 4-{[4-({[[(3-fluorophenyl)methyl](methyl)amino]acetyl}amino)phenyl]ethynyl}-N-{(1S,2R)-2-hydroxy-1-[(hydroxyamino)carbonyl]propyl}benzamide | 533.6 |
| 1249 | 4-{[4-({[[(4-fluorophenyl)methyl](methyl)amino]acetyl}amino)phenyl]ethynyl}-N-{(1S,2R)-2-hydroxy-1-[(hydroxyamino)carbonyl]propyl}benzamide | 533.6 |
| 1250 | N-[(1S)-1-(aminomethyl)-2-(hydroxyamino)-2-oxoethyl]-4-{[4-({[[(2-fluorophenyl)methyl](methyl)amino]acetyl}amino)phenyl]ethynyl}benzamide | 518.6 |
| 1251 | N-[(1S)-1-(aminomethyl)-2-(hydroxyamino)-2-oxoethyl]-4-{[4-({[[(3-fluorophenyl)methyl](methyl)amino]acetyl}amino)phenyl]ethynyl}benzamide | 518.6 |
| 1252 | N-[(1S)-1-(aminomethyl)-2-(hydroxyamino)-2-oxoethyl]-4-{[4-({[[(4-fluorophenyl)methyl](methyl)amino]acetyl}amino)phenyl]ethynyl}benzamide | 518.6 |
| 1253 | N-[(1S)-1-(aminomethyl)-2-(hydroxyamino)-2-oxoethyl]-4-({4-[({methyl[(2-methylphenyl)methyl]amino}acetyl)amino]phenyl}ethynyl)benzamide | 514.6 |
| 1254 | N-[(1S)-1-(aminomethyl)-2-(hydroxyamino)-2-oxoethyl]-4-({4-[({methyl[(4-methylphenyl)methyl]amino}acetyl)amino]phenyl}ethynyl)benzamide | 514.6 |
| 1255 | N-[(1S)-1-(aminomethyl)-2-(hydroxyamino)-2-oxoethyl]-4-{[4-({[methyl(phenylmethyl)amino]acetyl}amino)phenyl]ethynyl}benzamide | 500.6 |
| 1256 | N-{(1S,2R)-2-hydroxy-1-[(hydroxyamino)carbonyl]propyl}-4-{[4-({[methyl(propyl)amino]acetyl}amino)phenyl]ethynyl}benzamide | 467.5 |
| 1257 | 4-{[4-({[butyl(methyl)amino]acetyl}amino)phenyl]ethynyl}-N-{(1S,2R)-2-hydroxy-1-[(hydroxyamino)carbonyl]propyl}benzamide | 481.6 |
| 1258 | N-{(1S,2R)-2-hydroxy-1-[(hydroxyamino)carbonyl]propyl}-4-{[4-({[methyl(pentyl)amino]acetyl}amino)phenyl]ethynyl}benzamide | 495.6 |
| 1259 | 4-{[4-({[hexyl(methyl)amino]acetyl}amino)phenyl]ethynyl}-N-{(1S,2R)-2-hydroxy-1-[(hydroxyamino)carbonyl]propyl}benzamide | 509.6 |

TABLE 1-continued

| | | |
|---|---|---|
| 1260 | N-{(1S,2R)-2-hydroxy-1-[(hydroxyamino)carbonyl]propyl}-4-{[4-({[methyl(1-methylethyl)amino]acetyl}amino)phenyl]ethynyl}benzamide | 467.5 |
| 1261 | N-{(1S,2R)-2-hydroxy-1-[(hydroxyamino)carbonyl]propyl}-4-{[4-({[methyl(2-methylpropyl)amino]acetyl}amino)phenyl]ethynyl}benzamide | 481.6 |
| 1262 | N-{(1S,2R)-2-hydroxy-1-[(hydroxyamino)carbonyl]propyl}-4-({4-[({methyl[(2-methylphenyl)methyl]amino}acetyl)amino]phenyl}ethynyl)benzamide | 529.6 |
| 1263 | N-{(1S,2R)-2-hydroxy-1-[(hydroxyamino)carbonyl]propyl}-4-({4-[({methyl[(4-methylphenyl)methyl]amino}acetyl)amino]phenyl}ethynyl)benzamide | 529.6 |
| 1264 | N-[(1S)-1-(aminomethyl)-2-(hydroxyamino)-2-oxoethyl]-4-{[4-({[methyl(propyl)amino]acetyl}amino)phenyl]ethynyl}benzamide | 452.5 |
| 1265 | N-[(1S)-1-(aminomethyl)-2-(hydroxyamino)-2-oxoethyl]-4-{[4-({[butyl(methyl)amino]acetyl}amino)phenyl]ethynyl}benzamide | 466.6 |
| 1266 | N-[(1S)-1-(aminomethyl)-2-(hydroxyamino)-2-oxoethyl]-4-{[4-({[methyl(pentyl)amino]acetyl}amino)phenyl]ethynyl}benzamide | 480.6 |
| 1267 | N-[(1S)-1-(aminomethyl)-2-(hydroxyamino)-2-oxoethyl]-4-{[4-({[hexyl(methyl)amino]acetyl}amino)phenyl]ethynyl}benzamide | 494.6 |
| 1268 | N-[(1S)-1-(aminomethyl)-2-(hydroxyamino)-2-oxoethyl]-4-{[4-({[methyl(l-methylethyl)amino]acetyl}amino)phenyl]ethynyl}benzamide | 452.5 |
| 1269 | N-[(1S)-1-(aminomethyl)-2-(hydroxyamino)-2-oxoethyl]-4-{[4-({[methyl(2-methylpropyl)amino]acetyl}amino)phenyl]ethynyl}benzamide | 466.6 |
| 1270 | N-[(1S)-1-(aminomethyl)-2-(hydroxyamino)-2-oxoethyl]-4-{[4-({[methyl(pyridin-2-ylmethyl)amino]acetyl}amino)phenyl]ethynyl}benzamide | 501.6 |
| 1271 | 4-{[4-({[(3,4-dihydroxyphenyl)methyl]amino}methyl)phenyl]ethynyl}-N-{(1S,2R)-2-hydroxy-1-[(hydroxyamino)carbonyl]propyl}benzamide | 490.5 |
| 1272 | 4-({2-[(aminoacetyl)amino]phenyl}ethynyl)-N-{(1S,2S)-2-hydroxy-1-[(hydroxyamino)carbonyl]propyl}benzamide | 411.4 |
| 1273 | 4-[(4-{[(2S)-2-aminopropanoyl]amino}phenyl)ethynyl]-N-{(1S,2S)-2-hydroxy-1-[(hydroxyamino)carbonyl]propyl}benzamide | 425.5 |
| 1274 | N-[(1S)-1-(aminomethyl)-2-(hydroxyamino)-2-oxoethyl]-4-{[4-(diethylamino)phenyl]ethynyl}benzamide | 395.5 |
| 1275 | N-[(1S)-1-(aminomethyl)-2-(hydroxyamino)-2-oxoethyl]-4-{4-[4-(ethylamino)phenyl]buta-1,3-diynyl}benzamide | 391.4 |
| 1276 | N-[(1S)-1-(aminomethyl)-2-(hydroxyamino)-2-oxoethyl]-4-[(4-{[(2-amino-2-oxoethyl)amino]methyl}phenyl)ethynyl]benzamide | 410.4 |
| 1277 | N-[(1S)-1-(aminomethyl)-2-(hydroxyamino)-2-oxoethyl]-4-{[4-({[1-(hydroxymethyl)-2-methylpropyl]amino}methyl)phenyl]ethynyl}benzamide | 439.5 |
| 1278 | N-[(1S)-1-(aminomethyl)-2-(hydroxyamino)-2-oxoethyl]-4-({4-[(pyridin-2-ylamino)methyl]phenyl}ethynyl)benzamide | 430.5 |
| 1279 | N-[(1S)-1-(aminomethyl)-2-(hydroxyamino)-2-oxoethyl]-4-{4-[3-(ethylamino)phenyl]buta-1,3-diynyl}benzamide | 391.4 |
| 1280 | N-[(1S)-1-(aminomethyl)-2-(hydroxyamino)-2-oxoethyl]-4-{[3-(ethylamino)phenyl]ethynyl}benzamide | 367.4 |

TABLE 1-continued

| | | |
|---|---|---|
| 1281 | N-[(1S)-1-(aminomethyl)-2-(hydroxyamino)-2-oxoethyl]-4-{[4-(hydroxymethyl)phenyl]ethynyl}benzamide | 354.4 |
| 1282 | N-[(1S)-1-(aminomethyl)-2-(hydroxyamino)-2-oxoethyl]-4-{[3-(diethylamino)phenyl]ethynyl}benzamide | 395.5 |
| 1283 | N-{(1S,2S)-2-hydroxy-1-[(hydroxyamino)carbonyl]propyl}-4-{[4-(morpholin-4-ylmethyl)phenyl]ethynyl}benzamide | 438.5 |
| 1284 | 4-({4-[(dimethylamino)methyl]phenyl}ethynyl)-N-{(1S,2S)-2-hydroxy-1-[(hydroxyamino)carbonyl]propyl}benzamide | 396.5 |
| 1285 | 4-[(4-aminophenyl)ethynyl]-N-{(1S,2S)-2-hydroxy-1-[(hydroxyamino)carbonyl]propyl}benzamide | 354.4 |
| 1286 | 4-[4-(4-aminophenyl)buta-1,3-diynyl]-N-{(1S,2S)-2-hydroxy-1-[(hydroxyamino)carbonyl]propyl}benzamide | 378.4 |
| 1287 | 1,1-dimethylethyl 4-(4-{4-[({(1S,2R)-2-hydroxy-1-[(hydroxyamino)carbony]]propyl}amino carbonyl]phenyl}buta-1,3-diynyl)phenylcarbamate | 478.5 |
| 1288 | N-[(1S)-1-(aminomethyl)-2-(hydroxyamino)-2-oxoethyl]-4-{4-[4-({[1-(hydroxymethyl)-2-methylpropyl]amino}methyl)phenyl]buta-1,3-diynyl}benzamide | 463.5 |
| 1289 | N-[(1S)-1-(aminomethyl)-2-(hydroxyamino)-2-oxoethyl]-4-[4-(4-hydroxyphenyl)buta-1,3-diynyl]benzamide | 364.4 |
| 1290 | 4-[(2,4-difluorophenyl)ethynyl]-N-{(1S,2S)-2-hydroxy-1-[(hydroxyamino)carbonyl]propyl}benzamide | 375.3 |
| 1291 | N-[(1S)-1-(aminomethyl)-2-(hydroxyamino)-2-oxoethyl]-4-{4-[4-(morpholin-4-ylmethyl)phenyl]buta-1,3-diynyl}benzamide | 447.5 |
| 1292 | N-[(1S)-1-(aminomethyl)-2-(hydroxyamino)-2-oxoethyl]-4-{4-[4-(hydroxymethyl)phenyl]buta-1,3-diynyl}benzamide | 378.4 |
| 1293 | 4-({3-[(2-aminoethyl)amino]phenyl}ethynyl)-N-{(1S,2R)-2-hydroxy-1-[(hydroxyamino)carbonyl]propyl}benzamide | 397.4 |
| 1294 | N-[(1S)-1-(aminomethyl)-2-(hydroxyamino)-2-oxoethyl]-4-{[4-(trifluoromethyl)phenyl]ethynyl}benzamide | 392.3 |
| 1295 | (2S,3R)-3-hydroxy-2-({[4-(phenylethynyl)phenyl]carbonyl}amino)butanoic acid | 324.3 |
| 1296 | N-((1S,2R)-1-{[(2-aminoethyl)amino]carbonyl}-2-hydroxypropyl)-4-(phenylethynyl)benzamide | 366.4 |
| 1297 | 1,1-dimethylethy] (2S)-3-(hydroxyamino)-3-oxo-2-({[4-(4-phenylbuta-1,3-diynyl)phenyl]carbonyl}amino)propylcarbamate | 448.5 |
| 1298 | N-{(1S,2R)-2-hydroxy-1-[(hydroxyamino)carbonyl]propyl}-4-(4-{4-[(3-morpholin-4-ylpropyl)amino]phenyl}buta-1,3-diynyl)benzamide | 505.6 |
| 1299 | N-[(1S,2R)-2-hydroxy-1-({[2-(methylthio)phenyl]amino}carbonyl)propyl]-4-(phenylethynyl)benzamide | 445.6 |
| 1300 | N-{(1S,2R)-2-hydroxy-1-[(pyridin-2-ylamino)carbonyl]propyl}-4-(phenylethynyl)benzamide | 400.4 |
| 1301 | N-((1S)-1-(aminomethyl)-2-{[(1,1-dimethylethyl)oxy]amino}-2-oxoethyl)-4-(4-phenylbuta-1,3-diynyl)benzamide | 404.5 |
| 1302 | N-{(1S,2S)-2-hydroxy-1-[(hydroxyamino)carbonyl]propyl}-4-(4-phenylbuta-1,3-diynyl)benzamide | 363.4 |
| 1303 | (2S,3R)-N,3-dihydroxy-2-({[4-(4-phenylbuta-1,3-diynyl)phenyl]methyl}amino)butanamide | 349.4 |
| 1304 | 1,1-dimethylethyl (2S)-3-(hydroxyamino)-3-oxo-2-({[4-(4-phenylbuta-1,3-diynyl)phenyl]methyl}amino)propylcarbamate | 434.5 |
| 1305 | (2S)-3-amino-N-hydroxy-2-({[4-(4-phenylbuta-1,3-diynyl)phenyl]methyl}amino)propanamide | 334.4 |
| 1306 | N-[(1S)-2-(hydroxyamino)-1-(hydroxymethyl)-2-oxoethyl]-4-[(trifluoromethyl)oxy]benzamide | 309.2 |

TABLE 1-continued

| 1307 | N-{2-hydroxy-1-[(hydroxyamino)carbonyl]-2-phenylethyl}-4-[(trifluoromethyl)oxy]benzamide | 385.3 |

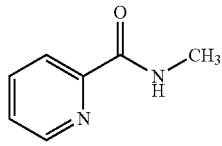

What is claimed is:

1. A compound having the formula XIII:

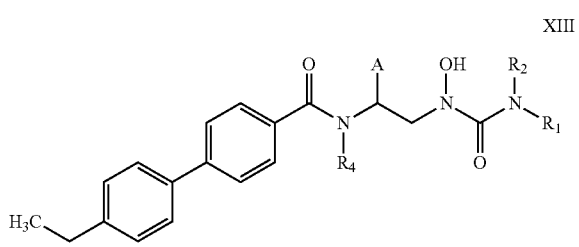

XIII or a stereoisomer, pharmaceutically acceptable salt, ester, or prodrug thereof, wherein $R_4$ is selected from the group consisting of
(1) H,
(2) substituted or unsubstituted $C_i$-$C_6$-alkyl,
(3) $C_1$-$C_6$-alkyl substituted with aryl,
(4) $C_1$-$C_6$-alkyl substituted with heterocyclyl, and
(5) $C_1$-$C_6$-alkyl substituted with heteroaryl;
A is H or —CH(CH$_3$)OH;
$R_1$ is H or substituted or unsubstituted $C_{1-6}$-alkyl;
$R_2$ is selected from the group consisting of
(1) H,
(2) substituted or unsubstituted $C_1$-$C_6$-alkyl,
(3) substituted or unsubstituted aryl,
(4) substituted or unsubstituted heterocyclyl,
(5) substituted or unsubstituted heteroaryl,
(6) $C_1$-$C_6$-alkyl substituted with aryl,
(7) $C_1$-$C_6$-alkyl substituted with heterocyclyl,
(8) $C_1$-$C_6$-alkyl substituted with heteroaryl,
or $R_1$ and $R_2$ together with the N atom to which they are attached can form a substituted or unsubstituted heterocyclic ring, having from 3 to 10 ring atoms, wherein 1-2 ring atoms of the heterocyclic ring system are selected from N, O and S.

2. The compound of claim 1, wherein $R_4$ is H.
3. The compound of claim 1, wherein A is —CH(CH$_3$)OH.
4. The compound of claim 1, wherein $R_1$ is H.
5. The compound of claim 1, wherein $R_1$ is H and $R_2$ is substituted or unsubstituted heterocyclyl or $C_1$-$C_6$-alkyl substituted with heterocyclyl, wherein the heterocyclyl group is selected from the group consisting of pyridine, pyrrolidine, thienyl and piperidine.
6. The compound of claim 1, wherein $R_1$ and $R_2$ together with the N atom to which they are attached can form a substituted or unsubstituted heterocyclic ring selected from the group consisting of morpholine, piperazine, piperidine and pyrrolidine.
7. A pharmaceutical composition comprising the compound of claim 1 and a pharmaceutically acceptable excipient.
8. A pharmaceutical composition comprising the compound of claim 1, a second agent, and a pharmaceutically acceptable excipient, wherein the second agent is an antibacterial agent, an antiendotoxin agent, or an inhaled non-antibacterial agent for the treatment of respiratory tract infection.
9. A method of inhibiting LpxC comprising administering to a patient in need thereof, an effective amount of the compound of claim 1.
10. A method of inhibiting LpxC comprising administering to a patient in need thereof, an effective amount of the compound of claim 1 and an effective amount of a second agent, wherein the second agent is an antibacterial agent, an antiendotoxin agent, or an inhaled non-antibacterial agent for the treatment of respiratory tract infection.

* * * * *